(12) United States Patent
Baker et al.

(10) Patent No.: US 7,838,224 B2
(45) Date of Patent: *Nov. 23, 2010

(54) GENE EXPRESSION PROFILING IN BIOPSIED TUMOR TISSUES

(75) Inventors: Joffre B. Baker, Montara, CA (US); Maureen T. Cronin, Los Altos, CA (US); Michael C. Kiefer, Clayton, CA (US); Steve Shak, Hillsborough, CA (US); Michael Graham Walker, Sunnyvale, CA (US)

(73) Assignee: Genomic Health, Inc., Redwood City, CA (US)

( * ) Notice: Subject to any disclaimer, the term of this patent is extended or adjusted under 35 U.S.C. 154(b) by 10 days.

This patent is subject to a terminal disclaimer.

(21) Appl. No.: 11/450,962

(22) Filed: Jun. 9, 2006

(65) Prior Publication Data

US 2007/0059737 A1    Mar. 15, 2007

Related U.S. Application Data

(63) Continuation of application No. 10/388,360, filed on Mar. 12, 2003, now Pat. No. 7,081,340.

(60) Provisional application No. 60/412,049, filed on Sep. 18, 2002.

(51) Int. Cl.
  C12Q 1/68       (2006.01)
  C07H 21/04      (2006.01)
  C12P 19/34      (2006.01)

(52) U.S. Cl. .................... 435/6; 536/24.3; 536/23.1; 435/91.2

(58) Field of Classification Search .................. None
See application file for complete search history.

(56) References Cited

U.S. PATENT DOCUMENTS

| | | | |
|---|---|---|---|
| 4,699,877 A | 10/1987 | Cline et al. | 435/6 |
| 5,015,568 A | 5/1991 | Tsujimoto et al. | 435/5 |
| 5,459,251 A | 10/1995 | Tsujimoto et al. | 536/23.5 |
| 5,563,035 A | 10/1996 | Weigel | |
| RE35,491 E | 4/1997 | Cline et al. | 435/6 |
| 5,858,678 A | 1/1999 | Chinnadurai | 435/7.1 |
| 5,952,179 A | 9/1999 | Chinnadurai | 435/6 |
| 5,985,553 A | 11/1999 | King et al. | 435/6 |
| 6,180,333 B1 | 1/2001 | Giordano | |
| 6,207,452 B1 | 3/2001 | Govindaswamy | 435/330 |
| 6,271,002 B1 | 8/2001 | Linsley et al. | 435/91.1 |
| 6,316,208 B1 | 11/2001 | Roberts et al. | |
| 6,322,986 B1 | 11/2001 | Ross | 435/6 |
| 6,331,396 B1 | 12/2001 | Silverman et al. | |
| 6,414,134 B1 | 7/2002 | Reed | 536/24.5 |
| 6,582,919 B2 | 6/2003 | Danenberg | 435/6 |
| 6,602,670 B2 | 8/2003 | Danenberg | 435/6 |
| 6,618,679 B2 | 9/2003 | Loehrlein et al. | 702/20 |
| 7,081,340 B2 * | 7/2006 | Baker et al. | 435/6 |
| 2002/0009736 A1 | 1/2002 | Wang | 435/6 |
| 2003/0073112 A1 | 4/2003 | Zhang et al. | 435/6 |
| 2003/0104499 A1 | 6/2003 | Pressman et al. | 435/7.23 |
| 2003/0165952 A1 | 9/2003 | Linnarsson et al. | 435/6 |
| 2003/0180791 A1 | 9/2003 | Chinnadurai | 435/6 |
| 2003/0198970 A1 | 10/2003 | Roberts | 435/6 |
| 2003/0225528 A1 * | 12/2003 | Baker et al. | 702/19 |
| 2004/0009489 A1 | 1/2004 | Golub et al. | 435/6 |
| 2004/0133352 A1 | 7/2004 | Bevilacqua et al. | 702/19 |
| 2004/0209290 A1 * | 10/2004 | Cobleigh et al. | 435/6 |
| 2006/0286565 A1 * | 12/2006 | Baker et al. | 435/6 |
| 2007/0059737 A1 * | 3/2007 | Baker et al. | 435/6 |
| 2007/0065845 A1 * | 3/2007 | Baker et al. | 435/6 |
| 2007/0141587 A1 * | 6/2007 | Baker et al. | 435/6 |
| 2007/0141588 A1 * | 6/2007 | Baker et al. | 435/6 |
| 2007/0141589 A1 * | 6/2007 | Baker et al. | 435/6 |

FOREIGN PATENT DOCUMENTS

| | | |
|---|---|---|
| EP | 0 108 564 B1 | 5/1988 |
| EP | 1 365 034 | 11/2003 |
| JP | 2003-576654 | 3/2010 |
| JP | 2006-40014 | 3/2010 |
| WO | WO 98/33450 | 8/1998 |
| WO | WO 99/02714 | 1/1999 |
| WO | WO 00/50595 | 8/2000 |
| WO | WO 00/55173 | 9/2000 |
| WO | WO 00/55629 A2 | 9/2000 |
| WO | WO 00/60076 | 10/2000 |
| WO | WO 01/04343 | 1/2001 |
| WO | WO 01/25250 | 4/2001 |
| WO | WO 01/40466 | 6/2001 |
| WO | WO 01/40517 A2 | 6/2001 |
| WO | WO 01/55320 | 8/2001 |
| WO | WO 01/70979 | 9/2001 |
| WO | WO 02/00677 | 1/2002 |
| WO | WO 02/06526 | 1/2002 |
| WO | WO 02/08228 | 1/2002 |
| WO | WO 02/08260 | 1/2002 |
| WO | WO 02/08261 | 1/2002 |
| WO | WO 02/08765 | 1/2002 |
| WO | WO 02/10436 | 2/2002 |

(Continued)

OTHER PUBLICATIONS

Lucentini, Jack. Gene Association Studies Typically Wrong. 2004. The Scientist vol. 18, pp. 1-3.*

(Continued)

Primary Examiner—Stephen Kapushoc
Assistant Examiner—Amanda Shaw
(74) Attorney, Agent, or Firm—James S. Keddie; Carol L. Francis; Bozicevic, Field & Francis LLP

(57) ABSTRACT

The invention concerns sensitive methods to measure mRNA levels in biopsied tumor tissues, including archived paraffin-embedded biopsy material. The invention also concerns breast cancer gene sets important in the diagnosis and treatment of breast cancer, and methods for assigning the most optimal treatment options to breast cancer patient based upon knowledge derived from gene expression studies.

19 Claims, 9 Drawing Sheets

FOREIGN PATENT DOCUMENTS

| WO | WO 02/46467 | 6/2002 |
|----|-------------|--------|
| WO | WO 02/17852 | 7/2002 |
| WO | WO 02/055988 | 7/2002 |
| WO | WO 02/059271 | 8/2002 |
| WO | WO 02/059377 | 8/2002 |
| WO | WO 02/068579 | 9/2002 |
| WO | WO 02/103320 | 12/2002 |
| WO | WO 03/011897 | 2/2003 |
| WO | WO 03/083096 | 10/2003 |

OTHER PUBLICATIONS

Wu, Thomas. Analyzing gene expression data from DNA microarrays to identify candidate genes. 2001. Journal of Pathology. vol. 195 pp. 53-65.*

Unger, Meredith et al. Characterization of adjacent breast tumors using oliognucleotide microarrays. 2001 Breast Cancer Research vol. 3 pp. 336-341.*

Specht, Katja et al. Quantitative gene expression analysis in microdissected archival fomalin fixed and paraffin embedded tumor tissue. 2001 American Journal of Pathology. vol. 158 pp. 419-429.*

Sorlie, Therese. Gene expression patterns of breast carcinomas distinguish tumor subclasses with clinical implications. 2001 PNAS vol. 98 pp. 10869-10874.*

The array finder at www.affymetrix.com accessed Jul. 23, 2008 demonstrates that probes of the ESR1 gene are one the HU95A array.*

The array finder at www.affymetrix.com accessed Jul. 23, 2008 demonstrates that probes of the BIRC5 gene are one the HU95A array.*

Nasu, Shunichi et al. Survivin mRNA expression in patients with breast cancer. 2002. Anticancer Research vol. 22 pp. 1839-1843.*

Chan, Eric. Integrating Transcriptomics and Proteomics. 2006. Genomics and Proteomics, avaliable online from www.genpromag.com, pp. 1-6.*

Schmittgen, Thomas, et al. Expression of prostate specific membrane antigen and three alternatively spliced variants of PSMA in prostate cancer patients. 2003 International Jouranl of Cancer. vol. 107 pp. 323-329.*

The Gene Card for ESR1 found online at http://www.genecards.org/cgi-bin/carddisp.pl?gene=ESR1&search=esr1 accessed Mar. 5, 2009.*

The Gene Card for BIRC5 found online at http://www.genecards.org/cgi-bin/carddisp.pl?gene=BIRC5&search=birc5 accessed Mar. 5, 2009.*

Affymetrix Inc.: "Affymetrix GeneChip Human Genome U95 Version 2 Set HG-U95A," GEO, XX, XX, 1-243 (2002).

Bhattacharjee et al., "Classification of human lung carcinomas by mRNA expression profiling reveals distinct adenocarcinoma subclasses", Proceedings of the National Academy of Sciences of USA, vol. 98, No. 24, pp. 13790-13795 (2001).

Chang, J. et al, "Biologic Markers as Predictors of Clinical Outcome from Systemic Therapy for Primary Operable Breast Cancer," Journal of Clinical Oncology: Official Journal of the American Society of Clinical Oncology, vol. 17:(10) 3058-3063 (1999).

Chen-Hsiang Yeang et al., "Molecular Classification of Multiple Tumor Types", Bioinformatics, vol. 37, Suppl. 1, pp. S316-S322 (2001).

Cox, G. et al., "Bcl-2 is an Independent Prognostic Factor and Adds to a Biological Model for Predicting Outcome in Operable Non-Small Cell Lung Cancer," Lung Cancer, vol. 34:(3) 417-426 (2001).

Dijkema, I.M. et al., "Influence of p53 and bcl-2 on Proliferative Activity and Treatment Outcome in head and Neck Cancer Patients," Oral Oncology, Elsevier Science, vol. 36:(1) 54-60 (2000).

Golub et al., "Molecular Classification of Cancer: Class Discovery and Class Prediction by Gene Expression Monitoring", Science, vol. 286, pp. 531-537 (1999).

Guerin, M. et al., "Structure and Expression of C-ERBB-2 and EGF Receptor Genes in Inflammatory and Non-Inflammatory Breast Cancer: Prognostic Significance," International Journal of Cancer, vol. 43 201-208 (1989).

Joensuu, H. et al., "Bcl-2 Protein Expression and Long-Term Survival in Breast Cancer," American Journal of Pathology, vol. 145:(5) 1191-1198 (1994).

Kymionis, G.D., et al., "Can Expression of Apoptosis Genes, bcl-2 and Bax, Predict Survival and Responsiveness to Chemotherapy in Node-Negative Breast Cancer Patients?" The Journal of Surgical Research, vol. 99:(2) 161-168 (2001).

Locker, A.P. et al., "Ki67 immunoreactivity in Breast Carcinoma: Relationships to prognostic Variable and Short time Survival," European Journal of Surgical Oncology, vol. 18:(3) 224-229 (1992).

Martin et al., "Linking Gene Expression Patterns to Therapeutic Groups in Breast Cancer", Cancer Research, vol. 60. pp. 2232-2238 (2000).

Murray, P.A. et al., "The Prognostic Significance of Transforming Growth Factors in Human Breast Cancer," British Journal of Cancer, vol. 67:(6) 1408-1412 (1993).

Perou et al., "Molecular portraits of human breast tumors", Nature, vol. 406, pp. 747-752 (2000).

Ramaswamy et al., "Multiclass cancer diagnosis using tumor gene expression signatures", Proceedings of the National Academy of Sciences of USA, vol. 98, No. 26, pp. 15149-15154 (2001).

Sens, Mary Ann et al.,"Metallothionein Isoform 3 Overexpression is Associated with Breast Cancers Having a Poor Prognosis," American Journal of Pathology, vol. 159:(1) 21-26 (2001).

Sorlie et al., "Gene Expression patterns of breast carcinomas distinguish tumor subclass with clinical implications", Proceedings of the National Academy of Sciences of USA, vol. 98, No. 19, pp. 10869-10874 (2001).

Specht K. et al., "Quantitative Gene Expression Analysis in Microdissected Archival Formalin-Fixed and Paraffin-Embedded Tumor Tissue," 158:(2) 419-429 (2001).

Steinbach, Daniel et al., "Clinical Implications of PRAME Gene Expression in Childhood Acute Myeloid Leukemia," Cancer Genetics and Cytogenetics, vol. 133:(2) 118-123 (2002).

Veer Van 'T.L.J. et al., "Gene Expression Profiling Predicts Clinical Outcome of Breast Cancer," Nature, Macmillan Journals Ltd., vol. 415:(6871) 530-536 (2002).

West et al., "Predicting the clinical status of human breast cancer by using gene expression profiles", Proceedings of the National Academy of Sciences of USA, vol. 98, No. 20, pp. 11462-11467 (2001).

Yan et al., "Dissecting Complex Epigenetic Alterations in Breast Cancer Using CpG Island Microarrays", Cancer Research, vol. 61, pp. 8375-7380 (2001).

Brabender, Jan, et al.; Epidermal Growth Factor Receptor and HER2-neu mRNA Expression in Non-Small Cell Lung Cancer Is Correlated with Survival, Clinical Cancer Research; vol. 7, Jul. 2001; pp. 1850-1855.

Ding, Chunming, et al.; A high-throughput gene expression analysis technique using competitive PCR and matrix-assisted laser desorption ionization time-of-flight MS, PNAS, vol. 100;6; Mar. 18, 2003; pp. 3059-3064.

Cambridge Healthtech Institute Conference Agenda; "Enabling Molecular Profiling With Cellular Resolution: Microgenomics Using Homogeneous Cell Samples"; Dec. 2002; 5 pgs.

Yang, Li, et al.; BADGE, BeadsArray for the Detection of Gene Expression, a High-Throughput Diagnostic Bioassay; Genome Research; vol. 11; 2001; pp. 1888-1898.

Dutta, A., et al., Proc. Natl. Acad. Sci. USA—92:5386-5390 (1995).

Winters, Z.E., et al., European Journal of Cancer—37(18):2405-2412 (2001).

Tanaka, K., et al. Expression of survivin and its relationship to loss of apoptosis in breast carcinomas. Clinical Cancer Research. 2000, vol. 6, pp. 127-134.

Span, P., et al. Survivin is an independent prognostic marker for risk stratification of breast cancer patients. Clinical Chemistry. 2004, vol. 50, pp. 1986-1993.

Yamashita, S., et al. Survivin expression predicts early recurrence in early-stage breast cancer. Anticancer Research. 2007, vol. 27, pp. 2803-2808.

Ambrosone, C., et al. Polymorphisms in glutathione S-Transferases (GSTM1 and GSTT1) and survival after treatment for breast cancer. Cancer Research. 2001, vol. 61, pp. 7130-7135.

Molino, A., et al. Ki-67 immunostaining in 322 primary breast cancers: Assocations with clinical and pathological variables and prognosis. International Journal of Cancer. 1997, vol. 74, pp. 433-437.

* cited by examiner

SEQUENCE LISTING

```
<160> NUMBER OF SEQ ID NOS: 384

<210> SEQ ID NO 1
<211> LENGTH: 18
<212> TYPE: DNA
<213> ORGANISM: Homo sapiens

<400> SEQUENCE: 1
gtcccaggag cccatcct                                                    18

<210> SEQ ID NO 2
<211> LENGTH: 19
<212> TYPE: DNA
<213> ORGANISM: Homo sapiens

<400> SEQUENCE: 2
cccggctgtt gtctccata                                                   19

<210> SEQ ID NO 3
<211> LENGTH: 68
<212> TYPE: DNA
<213> ORGANISM: Homo sapiens

<400> SEQUENCE: 3
gtcccaggag cccatcctgt ttgactgcag cattgctgag aacattgcct atggagacaa     60
cagccggg                                                              68

<210> SEQ ID NO 4
<211> LENGTH: 18
<212> TYPE: DNA
<213> ORGANISM: Homo sapiens

<400> SEQUENCE: 4
tcatggtgcc cgtcaatg                                                    18

<210> SEQ ID NO 5
<211> LENGTH: 23
<212> TYPE: DNA
<213> ORGANISM: Homo sapiens

<400> SEQUENCE: 5
cgattgtctt tgctcttcat gtg                                              23

<210> SEQ ID NO 6
<211> LENGTH: 79
<212> TYPE: DNA
<213> ORGANISM: Homo sapiens
```

```
<400> SEQUENCE: 6
tcatggtgcc cgtcaatgct gtgatggcga tgaagaccaa gacgtatcag gtggcccaca      60
tgaagagcaa agacaatcg                                                   79

<210> SEQ ID NO 7
<211> LENGTH: 20
<212> TYPE: DNA
<213> ORGANISM: Homo sapiens

<400> SEQUENCE: 7 agggatgac ttggacacat                                                   20

<210> SEQ ID NO 8
<211> LENGTH: 20
<212> TYPE: DNA
<213> ORGANISM: Homo sapiens

<400> SEQUENCE: 8
aaaactgcat ggctttgtca                                                  20

<210> SEQ ID NO 9
<211> LENGTH: 65
<212> TYPE: DNA
<213> ORGANISM: Homo sapiens

<400> SEQUENCE: 9 agggatgac ttggacacat ctgccattcg acatgactgc aattttgaca aagccatgca      60
gtttt                                                                  65

<210> SEQ ID NO 10
<211> LENGTH: 22
<212> TYPE: DNA
<213> ORGANISM: Homo sapiens

<400> SEQUENCE: 10
tcatcctggc gatctacttc ct                                               22

<210> SEQ ID NO 11
<211> LENGTH: 20
<212> TYPE: DNA
<213> ORGANISM: Homo sapiens

<400> SEQUENCE: 11
ccgttgagtg gaatcagcaa                                                  20

<210> SEQ ID NO 12
<211> LENGTH: 91
<212> TYPE: DNA
<213> ORGANISM: Homo sapiens

<400> SEQUENCE: 12
tcatcctggc gatctacttc ctctggcaga acctaggtcc ctctgtcctg gctggagtcg      60
ctttcatggt cttgctgatt ccactcaacg g                                     91

<210> SEQ ID NO 13
<211> LENGTH: 20
<212> TYPE: DNA
<213> ORGANISM: Homo sapiens

<400> SEQUENCE: 13
```
agcgcctgga atctacaact                                                      20

<210> SEQ ID NO 14
<211> LENGTH: 20
<212> TYPE: DNA
<213> ORGANISM: Homo sapiens

<400> SEQUENCE: 14
agagcccctg gagagaagat                                                      20

<210> SEQ ID NO 15
<211> LENGTH: 66
<212> TYPE: DNA
<213> ORGANISM: Homo sapiens

<400> SEQUENCE: 15
agcgcctgga atctacaact cggagtccag tgttttccca cttgtcatct tctctccagg          60
ggctct                                                                     66

<210> SEQ ID NO 16
<211> LENGTH: 24
<212> TYPE: DNA
<213> ORGANISM: Homo sapiens

<400> SEQUENCE: 16
gcccagagaa ggtctatgaa ctca                                                 24

<210> SEQ ID NO 17
<211> LENGTH: 22
<212> TYPE: DNA
<213> ORGANISM: Homo sapiens

<400> SEQUENCE: 17
gtttcaaagg cttggtggat tt                                                   22

<210> SEQ ID NO 18
<211> LENGTH: 94
<212> TYPE: DNA
<213> ORGANISM: Homo sapiens

<400> SEQUENCE: 18
gcccagagaa ggtctatgaa ctcatgcgag catgttggca gtggaatccc tctgaccggc          60
cctcctttgc tgaaatccac caagcctttg aaac                                      94

<210> SEQ ID NO 19
<211> LENGTH: 21
<212> TYPE: DNA
<213> ORGANISM: Homo sapiens

<400> SEQUENCE: 19
cgcagtgcag ctgagtatct g                                                    21

<210> SEQ ID NO 20
<211> LENGTH: 21
<212> TYPE: DNA
<213> ORGANISM: Homo sapiens

<400> SEQUENCE: 20
tgcccagggc tactctcact t                                                    21

<210> SEQ ID NO 21
<211> LENGTH: 80

<212> TYPE: DNA
<213> ORGANISM: Homo sapiens

<400> SEQUENCE: 21
cgcagtgcag ctgagtatct gctcagcagt ctaatcaatg gcagcttcct ggtgcgagaa        60
agtgagagta gccctgggca                                                    80

<210> SEQ ID NO 22
<211> LENGTH: 21
<212> TYPE: DNA
<213> ORGANISM: Homo sapiens

<400> SEQUENCE: 22
cagcagatgt ggatcagcaa g                                                  21

<210> SEQ ID NO 23
<211> LENGTH: 18
<212> TYPE: DNA
<213> ORGANISM: Homo sapiens

<400> SEQUENCE: 23
gcatttgcgg tggacgat                                                      18

<210> SEQ ID NO 24
<211> LENGTH: 66
<212> TYPE: DNA
<213> ORGANISM: Homo sapiens

<400> SEQUENCE: 24
cagcagatgt ggatcagcaa gcaggagtat gacgagtccg gcccctccat cgtccaccgc        60
aaatgc                                                                   66

<210> SEQ ID NO 25
<211> LENGTH: 20
<212> TYPE: DNA
<213> ORGANISM: Homo sapiens

<400> SEQUENCE: 25
cgcttctatg gcgctgagat                                                    20

<210> SEQ ID NO 26
<211> LENGTH: 20
<212> TYPE: DNA
<213> ORGANISM: Homo sapiens

<400> SEQUENCE: 26
tcccggtaca ccacgttctt                                                    20

<210> SEQ ID NO 27
<211> LENGTH: 71
<212> TYPE: DNA
<213> ORGANISM: Homo sapiens

<400> SEQUENCE: 27
cgcttctatg gcgctgagat tgtgtcagcc ctggactacc tgcactcgga gaagaacgtg        60
gtgtaccggg a                                                             71

<210> SEQ ID NO 28
<211> LENGTH: 25
<212> TYPE: DNA
<213> ORGANISM: Homo sapiens

<400> SEQUENCE: 28
ttgtctctgc cttggactat ctaca                                    25

<210> SEQ ID NO 29
<211> LENGTH: 24
<212> TYPE: DNA
<213> ORGANISM: Homo sapiens

<400> SEQUENCE: 29
ccagcattag attctccaac ttga                                     24

<210> SEQ ID NO 30
<211> LENGTH: 75
<212> TYPE: DNA
<213> ORGANISM: Homo sapiens

<400> SEQUENCE: 30
ttgtctctgc cttggactat ctacattccg gaaagattgt gtaccgtgat ctcaagttgg    60
agaatctaat gctgg                                               75

<210> SEQ ID NO 31
<211> LENGTH: 25
<212> TYPE: DNA
<213> ORGANISM: Homo sapiens

<400> SEQUENCE: 31
gaaggagata aggaggatgt tgaca                                    25

<210> SEQ ID NO 32
<211> LENGTH: 18
<212> TYPE: DNA
<213> ORGANISM: Homo sapiens

<400> SEQUENCE: 32
cgccacggag atccaatc                                            18

<210> SEQ ID NO 33
<211> LENGTH: 74
<212> TYPE: DNA
<213> ORGANISM: Homo sapiens

<400> SEQUENCE: 33
gaaggagata aggaggatgt tgacaaggca gtgaaggccg caagacaggc ttttcagatt    60
ggatctccgt ggcg                                                74

<210> SEQ ID NO 34
<211> LENGTH: 21
<212> TYPE: DNA
<213> ORGANISM: Homo sapiens

<400> SEQUENCE: 34
tggtgaacat tgtgccagga t                                        21

<210> SEQ ID NO 35
<211> LENGTH: 22
<212> TYPE: DNA
<213> ORGANISM: Homo sapiens

<400> SEQUENCE: 35
gaaggcgatc ttgttgatct ga                                       22

<210> SEQ ID NO 36
<211> LENGTH: 80
<212> TYPE: DNA
<213> ORGANISM: Homo sapiens

<400> SEQUENCE: 36
tggtgaacat tgtgccagga ttcgggccca cagtgggagc agcaatttct tctcaccctc    60
agatcaacaa gatcgccttc    80

<210> SEQ ID NO 37
<211> LENGTH: 20
<212> TYPE: DNA
<213> ORGANISM: Homo sapiens

<400> SEQUENCE: 37
ggacagcagg aatgtgtttc    20

<210> SEQ ID NO 38
<211> LENGTH: 20
<212> TYPE: DNA
<213> ORGANISM: Homo sapiens

<400> SEQUENCE: 38
acccactcga tttgtttctg    20

<210> SEQ ID NO 39
<211> LENGTH: 69
<212> TYPE: DNA
<213> ORGANISM: Homo sapiens

<400> SEQUENCE: 39
ggacagcagg aatgtgtttc tccatacagg tcacggggag ccaatggttc agaaacaaat    60
cgagtgggt    69

<210> SEQ ID NO 40
<211> LENGTH: 27
<212> TYPE: DNA
<213> ORGANISM: Homo sapiens

<400> SEQUENCE: 40
tgtgagtgaa atgccttcta gtagtga    27

<210> SEQ ID NO 41
<211> LENGTH: 27
<212> TYPE: DNA
<213> ORGANISM: Homo sapiens

<400> SEQUENCE: 41
ttgtggttcg ttatcatact cttctga    27

<210> SEQ ID NO 42
<211> LENGTH: 82
<212> TYPE: DNA
<213> ORGANISM: Homo sapiens

<400> SEQUENCE: 42
tgtgagtgaa atgccttcta gtagtgaacc gtcctcggga gccgactatg actactcaga    60
agagtatgat aacgaaccac aa    82

<210> SEQ ID NO 43
<211> LENGTH: 19
<212> TYPE: DNA

```
<213> ORGANISM: Homo sapiens

<400> SEQUENCE: 43
gtctcgctcc gtggcctta                                                   19

<210> SEQ ID NO 44
<211> LENGTH: 24
<212> TYPE: DNA
<213> ORGANISM: Homo sapiens

<400> SEQUENCE: 44
cgtgagtaaa cctgaatctt tgga                                             24

<210> SEQ ID NO 45
<211> LENGTH: 93
<212> TYPE: DNA
<213> ORGANISM: Homo sapiens

<400> SEQUENCE: 45
gtctcgctcc gtggccttag ctgtgctcgc gctactctct ctttctggcc tggaggctat      60
ccagcgtact ccaaagattc aggtttactc acg                                   93

<210> SEQ ID NO 46
<211> LENGTH: 20
<212> TYPE: DNA
<213> ORGANISM: Homo sapiens

<400> SEQUENCE: 46
ccattcccac cattctacct                                                  20

<210> SEQ ID NO 47
<211> LENGTH: 20
<212> TYPE: DNA
<213> ORGANISM: Homo sapiens

<400> SEQUENCE: 47
gggaacatag acccaccaat                                                  20

<210> SEQ ID NO 48
<211> LENGTH: 66
<212> TYPE: DNA
<213> ORGANISM: Homo sapiens

<400> SEQUENCE: 48
ccattcccac cattctacct gaggccagga cgtctggggt gtggggattg gtgggtctat      60
gttccc                                                                 66

<210> SEQ ID NO 49
<211> LENGTH: 18
<212> TYPE: DNA
<213> ORGANISM: Homo sapiens

<400> SEQUENCE: 49
ccgccgtgga cacagact                                                    18

<210> SEQ ID NO 50
<211> LENGTH: 21
<212> TYPE: DNA
<213> ORGANISM: Homo sapiens

<400> SEQUENCE: 50
ttgccgtcag aaaacatgtc a                                                21
```

<210> SEQ ID NO 51
<211> LENGTH: 70
<212> TYPE: DNA
<213> ORGANISM: Homo sapiens

<400> SEQUENCE: 51
ccgccgtgga cacagactcc ccccgagagg tcttttccg agtggcagct gacatgtttt    60
ctgacggcaa                                                          70

<210> SEQ ID NO 52
<211> LENGTH: 25
<212> TYPE: DNA
<213> ORGANISM: Homo sapiens

<400> SEQUENCE: 52
cagatggacc tagtacccac tgaga                                         25

<210> SEQ ID NO 53
<211> LENGTH: 24
<212> TYPE: DNA
<213> ORGANISM: Homo sapiens

<400> SEQUENCE: 53
cctatgattt aagggcattt ttcc                                          24

<210> SEQ ID NO 54
<211> LENGTH: 73
<212> TYPE: DNA
<213> ORGANISM: Homo sapiens

<400> SEQUENCE: 54
cagatggacc tagtacccac tgagatttcc acgccgaagg acagcgatgg gaaaaatgcc   60
cttaaatcat agg                                                      73

<210> SEQ ID NO 55
<211> LENGTH: 24
<212> TYPE: DNA
<213> ORGANISM: Homo sapiens

<400> SEQUENCE: 55
cttttgtgga actctatggg aaca                                          24

<210> SEQ ID NO 56
<211> LENGTH: 19
<212> TYPE: DNA
<213> ORGANISM: Homo sapiens

<400> SEQUENCE: 56
cagcggttga agcgttcct                                                19

<210> SEQ ID NO 57
<211> LENGTH: 70
<212> TYPE: DNA
<213> ORGANISM: Homo sapiens

<400> SEQUENCE: 57
cttttgtgga actctatggg aacaatgcag cagccgagag ccgaaagggc caggaacgct   60
tcaaccgctg                                                          70

<210> SEQ ID NO 58

```
<211> LENGTH: 24
<212> TYPE: DNA
<213> ORGANISM: Homo sapiens

<400> SEQUENCE: 58
ggatatttcc gtggctctta ttca                                              24

<210> SEQ ID NO 59
<211> LENGTH: 25
<212> TYPE: DNA
<213> ORGANISM: Homo sapiens

<400> SEQUENCE: 59
cttctcatca aggcagaaaa atctt                                             25

<210> SEQ ID NO 60
<211> LENGTH: 86
<212> TYPE: DNA
<213> ORGANISM: Homo sapiens

<400> SEQUENCE: 60
ggatatttcc gtggctctta ttcaaactct ccatcaaatc ctgtaaactc cagagcaaat       60
caagattttt ctgccttgat gagaag                                            86

<210> SEQ ID NO 61
<211> LENGTH: 23
<212> TYPE: DNA
<213> ORGANISM: Homo sapiens

<400> SEQUENCE: 61
gcagttggaa gacacaggaa agt                                               23

<210> SEQ ID NO 62
<211> LENGTH: 21
<212> TYPE: DNA
<213> ORGANISM: Homo sapiens

<400> SEQUENCE: 62
tgcgtggcac tattttcaag a                                                 21

<210> SEQ ID NO 63
<211> LENGTH: 77
<212> TYPE: DNA
<213> ORGANISM: Homo sapiens

<400> SEQUENCE: 63
gcagttggaa gacacaggaa agtatcccca aattgcagat ttatcaacgg cttttatctt       60
gaaaatagtg ccacgca                                                      77

<210> SEQ ID NO 64
<211> LENGTH: 20
<212> TYPE: DNA
<213> ORGANISM: Homo sapiens

<400> SEQUENCE: 64
tgttttgatt cccgggctta                                                   20

<210> SEQ ID NO 65
<211> LENGTH: 24
<212> TYPE: DNA
<213> ORGANISM: Homo sapiens

<400> SEQUENCE: 65
```

```
caaagctgtc agctctagca aaag                                              24

<210> SEQ ID NO 66
<211> LENGTH: 80
<212> TYPE: DNA
<213> ORGANISM: Homo sapiens

<400> SEQUENCE: 66
tgttttgatt cccgggctta ccaggtgaga agtgagggag gaagaaggca gtgtcccttt       60
tgctagagct gacagctttg                                                   80

<210> SEQ ID NO 67
<211> LENGTH: 20
<212> TYPE: DNA
<213> ORGANISM: Homo sapiens

<400> SEQUENCE: 67 tcaggggct agaaatctgt                                                    20

<210> SEQ ID NO 68
<211> LENGTH: 20
<212> TYPE: DNA
<213> ORGANISM: Homo sapiens

<400> SEQUENCE: 68
ccattccagt tgatctgtgg                                                   20

<210> SEQ ID NO 69
<211> LENGTH: 65
<212> TYPE: DNA
<213> ORGANISM: Homo sapiens

<400> SEQUENCE: 69 tcaggggct agaaatctgt tgctatgggc ccttcaccaa catgcccaca gatcaactgg       60
aatgg                                                                   65

<210> SEQ ID NO 70
<211> LENGTH: 20
<212> TYPE: DNA
<213> ORGANISM: Homo sapiens

<400> SEQUENCE: 70
agttcgtgct ttgcaagatg                                                   20

<210> SEQ ID NO 71
<211> LENGTH: 20
<212> TYPE: DNA
<213> ORGANISM: Homo sapiens

<400> SEQUENCE: 71
aaggtaagct gggtctgctg                                                   20

<210> SEQ ID NO 72
<211> LENGTH: 70
<212> TYPE: DNA
<213> ORGANISM: Homo sapiens

<400> SEQUENCE: 72
agttcgtgct ttgcaagatg gtgcagagct ttatgaagca gtgaagaatg cagcagaccc       60
agcttacctt                                                              70
```

```
<210> SEQ ID NO 73
<211> LENGTH: 21
<212> TYPE: DNA
<213> ORGANISM: Homo sapiens

<400> SEQUENCE: 73
gcatgttcgt ggcctctaag a                                              21

<210> SEQ ID NO 74
<211> LENGTH: 22
<212> TYPE: DNA
<213> ORGANISM: Homo sapiens

<400> SEQUENCE: 74
cggtgtagat gcacagcttc tc                                             22

<210> SEQ ID NO 75
<211> LENGTH: 69
<212> TYPE: DNA
<213> ORGANISM: Homo sapiens

<400> SEQUENCE: 75
gcatgttcgt ggcctctaag atgaaggaga ccatcccct gacggccgag aagctgtgca     60
tctacaccg                                                            69

<210> SEQ ID NO 76
<211> LENGTH: 20
<212> TYPE: DNA
<213> ORGANISM: Homo sapiens

<400> SEQUENCE: 76
agatgaagtg gaaggcgctt                                                20

<210> SEQ ID NO 77
<211> LENGTH: 21
<212> TYPE: DNA
<213> ORGANISM: Homo sapiens

<400> SEQUENCE: 77
tgcctctgta atcggcaact g                                              21

<210> SEQ ID NO 78
<211> LENGTH: 65
<212> TYPE: DNA
<213> ORGANISM: Homo sapiens

<400> SEQUENCE: 78
agatgaagtg gaaggcgctt ttcaccgcgg ccatcctgca ggcacagttg ccgattacag    60
aggca                                                                65

<210> SEQ ID NO 79
<211> LENGTH: 18
<212> TYPE: DNA
<213> ORGANISM: Homo sapiens

<400> SEQUENCE: 79
tggttcccag ccctgtgt                                                  18

<210> SEQ ID NO 80
<211> LENGTH: 19
<212> TYPE: DNA
<213> ORGANISM: Homo sapiens
```

<400> SEQUENCE: 80
ctcctccacc ctgggttgt                                            19

<210> SEQ ID NO 81
<211> LENGTH: 74
<212> TYPE: DNA
<213> ORGANISM: Homo sapiens

<400> SEQUENCE: 81
tggttcccag ccctgtgtcc acctccaagc ccagattcag attcgagtca tgtacacaac    60
ccagggtgga ggag                                                 74

<210> SEQ ID NO 82
<211> LENGTH: 20
<212> TYPE: DNA
<213> ORGANISM: Homo sapiens

<400> SEQUENCE: 82
tcttgctggc tacgcctctt                                           20

<210> SEQ ID NO 83
<211> LENGTH: 21
<212> TYPE: DNA
<213> ORGANISM: Homo sapiens

<400> SEQUENCE: 83
ctgcattgtg gcacagttct g                                         21

<210> SEQ ID NO 84
<211> LENGTH: 71
<212> TYPE: DNA
<213> ORGANISM: Homo sapiens

<400> SEQUENCE: 84
tcttgctggc tacgcctctt ctgtccctgt tagacgtcct ccgtccatat cagaactgtg    60
ccacaatgca g                                                    71

<210> SEQ ID NO 85
<211> LENGTH: 21
<212> TYPE: DNA
<213> ORGANISM: Homo sapiens

<400> SEQUENCE: 85
tgagtgtccc ccggtatctt c                                         21

<210> SEQ ID NO 86
<211> LENGTH: 21
<212> TYPE: DNA
<213> ORGANISM: Homo sapiens

<400> SEQUENCE: 86
cagccgcttt cagattttca t                                         21

<210> SEQ ID NO 87
<211> LENGTH: 81
<212> TYPE: DNA
<213> ORGANISM: Homo sapiens

<400> SEQUENCE: 87
tgagtgtccc ccggtatctt ccccgccctg ccaatcccga tgaaattgga aattttattg    60

```
atgaaaatct gaaagcggct g                                              81
```

<210> SEQ ID NO 88
<211> LENGTH: 21
<212> TYPE: DNA
<213> ORGANISM: Homo sapiens

<400> SEQUENCE: 88

```
tggagactct cagggtcgaa a                                              21
```

<210> SEQ ID NO 89
<211> LENGTH: 22
<212> TYPE: DNA
<213> ORGANISM: Homo sapiens

<400> SEQUENCE: 89

```
ggcgtttgga gtggtagaaa tc                                             22
```

<210> SEQ ID NO 90
<211> LENGTH: 65
<212> TYPE: DNA
<213> ORGANISM: Homo sapiens

<400> SEQUENCE: 90

```
tggagactct cagggtcgaa aacggcggca gaccagcatg acagatttct accactccaa    60
acgcc                                                                65
```

<210> SEQ ID NO 91
<211> LENGTH: 21
<212> TYPE: DNA
<213> ORGANISM: Homo sapiens

<400> SEQUENCE: 91

```
cggtggacca cgaagagtta a                                              21
```

<210> SEQ ID NO 92
<211> LENGTH: 19
<212> TYPE: DNA
<213> ORGANISM: Homo sapiens

<400> SEQUENCE: 92

```
ggctcgcctc ttccatgtc                                                 19
```

<210> SEQ ID NO 93
<211> LENGTH: 66
<212> TYPE: DNA
<213> ORGANISM: Homo sapiens

<400> SEQUENCE: 93

```
cggtggacca cgaagagtta acccgggact tggagaagca ctgcagagac atggaagagg    60
cgagcc                                                               66
```

<210> SEQ ID NO 94
<211> LENGTH: 19
<212> TYPE: DNA
<213> ORGANISM: Homo sapiens

<400> SEQUENCE: 94

```
gcggaaggtc cctcagaca                                                 19
```

<210> SEQ ID NO 95
<211> LENGTH: 23

```
<210> SEQ ID NO 95
<211> LENGTH: 23
<212> TYPE: DNA
<213> ORGANISM: Homo sapiens

<400> SEQUENCE: 95
tctaagtttc ccgaggtttc tca                                          23

<210> SEQ ID NO 96
<211> LENGTH: 70
<212> TYPE: DNA
<213> ORGANISM: Homo sapiens

<400> SEQUENCE: 96
gcggaaggtc cctcagacat ccccgattga agaaccaga gaggctctga gaaacctcgg    60
gaaacttaga                                                         70

<210> SEQ ID NO 97
<211> LENGTH: 22
<212> TYPE: DNA
<213> ORGANISM: Homo sapiens

<400> SEQUENCE: 97
ccagctttgt gcctgtcact at                                           22

<210> SEQ ID NO 98
<211> LENGTH: 20
<212> TYPE: DNA
<213> ORGANISM: Homo sapiens

<400> SEQUENCE: 98
gggaatgtgg tagcccaaga                                              20

<210> SEQ ID NO 99
<211> LENGTH: 71
<212> TYPE: DNA
<213> ORGANISM: Homo sapiens

<400> SEQUENCE: 99
ccagctttgt gcctgtcact attcctcatg ccaccactgc caacacctct gtcttgggct   60
accacattcc c                                                       71

<210> SEQ ID NO 100
<211> LENGTH: 27
<212> TYPE: DNA
<213> ORGANISM: Homo sapiens

<400> SEQUENCE: 100
ttgctataac taagtgcttc tccaaga                                      27

<210> SEQ ID NO 101
<211> LENGTH: 22
<212> TYPE: DNA
<213> ORGANISM: Homo sapiens

<400> SEQUENCE: 101
gtggaatggc agctcactgt ag                                           22

<210> SEQ ID NO 102
<211> LENGTH: 73
<212> TYPE: DNA
<213> ORGANISM: Homo sapiens

<400> SEQUENCE: 102
```

```
ttgctataac taagtgcttc tccaagaccc caactgagtc cccagcacct gctacagtga    60
gctgccattc cac                                                       73
```

<210> SEQ ID NO 103
<211> LENGTH: 19
<212> TYPE: DNA
<213> ORGANISM: Homo sapiens

<400> SEQUENCE: 103

```
aggacgcaag gagggtttg                                                 19
```

<210> SEQ ID NO 104
<211> LENGTH: 21
<212> TYPE: DNA
<213> ORGANISM: Homo sapiens

<400> SEQUENCE: 104

```
gatgtccgcc gagtccttac t                                              21
```

<210> SEQ ID NO 105
<211> LENGTH: 87
<212> TYPE: DNA
<213> ORGANISM: Homo sapiens

<400> SEQUENCE: 105

```
aggacgcaag gagggtttgt cactggcaga ctcgagactg taggcactgc catggcccct    60
gtgctcagta aggactcggc ggacatc                                        87
```

<210> SEQ ID NO 106
<211> LENGTH: 24
<212> TYPE: DNA
<213> ORGANISM: Homo sapiens

<400> SEQUENCE: 106

```
ctatatgcag ccagagatgt gaca                                           24
```

<210> SEQ ID NO 107
<211> LENGTH: 24
<212> TYPE: DNA
<213> ORGANISM: Homo sapiens

<400> SEQUENCE: 107

```
ccacgagttt cttactgaga atgg                                           24
```

<210> SEQ ID NO 108
<211> LENGTH: 82
<212> TYPE: DNA
<213> ORGANISM: Homo sapiens

<400> SEQUENCE: 108

```
ctatatgcag ccagagatgt gacagccacc gtggacagcc tgccactcat cacagcctcc    60
attctcagta agaaactcgt gg                                             82
```

<210> SEQ ID NO 109
<211> LENGTH: 20
<212> TYPE: DNA
<213> ORGANISM: Homo sapiens

<400> SEQUENCE: 109

```
tgtcgatgga cttccagaac                                                20
```

<210> SEQ ID NO 110
<211> LENGTH: 19
<212> TYPE: DNA
<213> ORGANISM: Homo sapiens

<400> SEQUENCE: 110
attgggacag cttggatca                                                    19

<210> SEQ ID NO 111
<211> LENGTH: 62
<212> TYPE: DNA
<213> ORGANISM: Homo sapiens

<400> SEQUENCE: 111
tgtcgatgga cttccagaac cacctgggca gctgccaaaa gtgtgatcca agctgtccca      60
at                                                                     62

<210> SEQ ID NO 112
<211> LENGTH: 23
<212> TYPE: DNA
<213> ORGANISM: Homo sapiens

<400> SEQUENCE: 112
gatctaagat ggcgactgtc gaa                                               23

<210> SEQ ID NO 113
<211> LENGTH: 25
<212> TYPE: DNA
<213> ORGANISM: Homo sapiens

<400> SEQUENCE: 113
ttagattccg ttttctcctc ttctg                                             25

<210> SEQ ID NO 114
<211> LENGTH: 82
<212> TYPE: DNA
<213> ORGANISM: Homo sapiens

<400> SEQUENCE: 114
gatctaagat ggcgactgtc gaaccggaaa ccacccctac tcctaatccc ccgactacag      60
aagaggagaa aacggaatct aa                                               82

<210> SEQ ID NO 115
<211> LENGTH: 20
<212> TYPE: DNA
<213> ORGANISM: Homo sapiens

<400> SEQUENCE: 115
cggtgtgaga agtgcagcaa                                                   20

<210> SEQ ID NO 116
<211> LENGTH: 19
<212> TYPE: DNA
<213> ORGANISM: Homo sapiens

<400> SEQUENCE: 116
cctctcgcaa gtgctccat                                                    19

<210> SEQ ID NO 117
<211> LENGTH: 70
<212> TYPE: DNA
<213> ORGANISM: Homo sapiens

<400> SEQUENCE: 117
cggtgtgaga agtgcagcaa gccctgtgcc cgagtgtgct atggtctggg catggagcac    60
ttgcgagagg                                                          70

<210> SEQ ID NO 118
<211> LENGTH: 23
<212> TYPE: DNA
<213> ORGANISM: Homo sapiens

<400> SEQUENCE: 118
cggttatgtc atgccagata cac                                           23

<210> SEQ ID NO 119
<211> LENGTH: 24
<212> TYPE: DNA
<213> ORGANISM: Homo sapiens

<400> SEQUENCE: 119
gaactgagac ccactgaaga aagg                                          24

<210> SEQ ID NO 120
<211> LENGTH: 81
<212> TYPE: DNA
<213> ORGANISM: Homo sapiens

<400> SEQUENCE: 120
cggttatgtc atgccagata cacacctcaa aggtactccc tcctcccggg aaggcaccct    60
ttcttcagtg ggtctcagtt c                                             81

<210> SEQ ID NO 121
<211> LENGTH: 19
<212> TYPE: DNA
<213> ORGANISM: Homo sapiens

<400> SEQUENCE: 121
cgtggtgccc ctctatgac                                                19

<210> SEQ ID NO 122
<211> LENGTH: 19
<212> TYPE: DNA
<213> ORGANISM: Homo sapiens

<400> SEQUENCE: 122
ggctagtggg cgcatgtag                                                19

<210> SEQ ID NO 123
<211> LENGTH: 68
<212> TYPE: DNA
<213> ORGANISM: Homo sapiens

<400> SEQUENCE: 123
cgtggtgccc ctctatgacc tgctgctgga gatgctggac gcccaccgcc tacatgcgcc    60
cactagcc                                                            68

<210> SEQ ID NO 124
<211> LENGTH: 20
<212> TYPE: DNA
<213> ORGANISM: Homo sapiens

<400> SEQUENCE: 124
tggtccatcg ccagttatca                                               20

<210> SEQ ID NO 125
<211> LENGTH: 23
<212> TYPE: DNA
<213> ORGANISM: Homo sapiens

<400> SEQUENCE: 125
tgttctagcg atcttgcttc aca                                           23

<210> SEQ ID NO 126
<211> LENGTH: 76
<212> TYPE: DNA
<213> ORGANISM: Homo sapiens

<400> SEQUENCE: 126
tggtccatcg ccagttatca catctgtatg cggaacctca aaagagtccc tggtgtgaag   60
caagatcgct agaaca                                                   76

<210> SEQ ID NO 127
<211> LENGTH: 24
<212> TYPE: DNA
<213> ORGANISM: Homo sapiens

<400> SEQUENCE: 127
catccatgac aactttggta tcgt                                          24

<210> SEQ ID NO 128
<211> LENGTH: 21
<212> TYPE: DNA
<213> ORGANISM: Homo sapiens

<400> SEQUENCE: 128
cagtcttctg ggtggcagtg a                                             21

<210> SEQ ID NO 129
<211> LENGTH: 74
<212> TYPE: DNA
<213> ORGANISM: Homo sapiens

<400> SEQUENCE: 129
catccatgac aactttggta tcgtggaagg actcatgacc acagtccatg ccatcactgc   60
cacccagaag actg                                                     74

<210> SEQ ID NO 130
<211> LENGTH: 23
<212> TYPE: DNA
<213> ORGANISM: Homo sapiens

<400> SEQUENCE: 130
caaaggagct cactgtggtg tct                                           23

<210> SEQ ID NO 131
<211> LENGTH: 26
<212> TYPE: DNA
<213> ORGANISM: Homo sapiens

<400> SEQUENCE: 131
gagtcagaat ggcttattca cagatg                                        26

<210> SEQ ID NO 132
<211> LENGTH: 75
<212> TYPE: DNA

<213> ORGANISM: Homo sapiens

<400> SEQUENCE: 132
caaaggagct cactgtggtg tctgtgttcc aaccactgaa tctggacccc atctgtgaat    60
aagccattct gactc                                                    75

<210> SEQ ID NO 133
<211> LENGTH: 20
<212> TYPE: DNA
<213> ORGANISM: Homo sapiens

<400> SEQUENCE: 133
ccatctgcat ccatcttgtt                                               20

<210> SEQ ID NO 134
<211> LENGTH: 20
<212> TYPE: DNA
<213> ORGANISM: Homo sapiens

<400> SEQUENCE: 134
ggccaccagg gtattatctg                                               20

<210> SEQ ID NO 135
<211> LENGTH: 67
<212> TYPE: DNA
<213> ORGANISM: Homo sapiens

<400> SEQUENCE: 135
ccatctgcat ccatcttgtt tgggctcccc acccttgaga agtgcctcag ataataccct    60
ggtggcc                                                             67

<210> SEQ ID NO 136
<211> LENGTH: 23
<212> TYPE: DNA
<213> ORGANISM: Homo sapiens

<400> SEQUENCE: 136
cgaaaagatg ctgaacagtg aca                                           23

<210> SEQ ID NO 137
<211> LENGTH: 20
<212> TYPE: DNA
<213> ORGANISM: Homo sapiens

<400> SEQUENCE: 137
tcaggaacag ccaccagtga                                               20

<210> SEQ ID NO 138
<211> LENGTH: 73
<212> TYPE: DNA
<213> ORGANISM: Homo sapiens

<400> SEQUENCE: 138
cgaaaagatg ctgaacagtg acaaatccaa ctgaccagaa gggaggagga agctcactgg    60
tggctgttcc tga                                                      73

<210> SEQ ID NO 139
<211> LENGTH: 20
<212> TYPE: DNA
<213> ORGANISM: Homo sapiens

<400> SEQUENCE: 139

```
gagaccctgc tgtcccagaa                                          20

<210> SEQ ID NO 140
<211> LENGTH: 23
<212> TYPE: DNA
<213> ORGANISM: Homo sapiens

<400> SEQUENCE: 140
ggttgtagtc agcgaaggag atc                                      23

<210> SEQ ID NO 141
<211> LENGTH: 76
<212> TYPE: DNA
<213> ORGANISM: Homo sapiens

<400> SEQUENCE: 141
gagaccctgc tgtcccagaa ccagggaggc aagaccttca ttgtgggaga ccagatctcc    60
ttcgctgact acaacc                                              76

<210> SEQ ID NO 142
<211> LENGTH: 20
<212> TYPE: DNA
<213> ORGANISM: Homo sapiens

<400> SEQUENCE: 142
cccactcagt agccaagtca                                          20

<210> SEQ ID NO 143
<211> LENGTH: 20
<212> TYPE: DNA
<213> ORGANISM: Homo sapiens

<400> SEQUENCE: 143
cacgcaggtg gtatcagtct                                          20

<210> SEQ ID NO 144
<211> LENGTH: 73
<212> TYPE: DNA
<213> ORGANISM: Homo sapiens

<400> SEQUENCE: 144
cccactcagt agccaagtca caatgtttgg aaaacagccc gtttacttga gcaagactga    60
taccacctgc gtg                                                 73

<210> SEQ ID NO 145
<211> LENGTH: 24
<212> TYPE: DNA
<213> ORGANISM: Homo sapiens

<400> SEQUENCE: 145
catcaaatgt cagccctgga gttc                                     24

<210> SEQ ID NO 146
<211> LENGTH: 26
<212> TYPE: DNA
<213> ORGANISM: Homo sapiens

<400> SEQUENCE: 146
ttcctgtagg tctttacccc gatagc                                   26

<210> SEQ ID NO 147
```

```
<211> LENGTH: 85
<212> TYPE: DNA
<213> ORGANISM: Homo sapiens

<400> SEQUENCE: 147
catcaaatgt cagccctgga gttccatgat accacacgaa cacagctttt tgccttcgag    60
ctatcggggt aaagacctac aggaa                                          85

<210> SEQ ID NO 148
<211> LENGTH: 24
<212> TYPE: DNA
<213> ORGANISM: Homo sapiens

<400> SEQUENCE: 148
tccaggatgt taggaactgt gaag                                           24

<210> SEQ ID NO 149
<211> LENGTH: 22
<212> TYPE: DNA
<213> ORGANISM: Homo sapiens

<400> SEQUENCE: 149
gcgtgtctgc gtagtagctg tt                                             22

<210> SEQ ID NO 150
<211> LENGTH: 73
<212> TYPE: DNA
<213> ORGANISM: Homo sapiens

<400> SEQUENCE: 150
tccaggatgt taggaactgt gaagatggaa gggcatgaaa ccagcgactg aacagctac     60 tacgcagaca cgc                                                       73

<210> SEQ ID NO 151
<211> LENGTH: 23
<212> TYPE: DNA
<213> ORGANISM: Homo sapiens

<400> SEQUENCE: 151
aacgactgct actccaagct caa                                            23

<210> SEQ ID NO 152
<211> LENGTH: 22
<212> TYPE: DNA
<213> ORGANISM: Homo sapiens

<400> SEQUENCE: 152
ggatttccat cttgctcacc tt                                             22

<210> SEQ ID NO 153
<211> LENGTH: 76
<212> TYPE: DNA
<213> ORGANISM: Homo sapiens

<400> SEQUENCE: 153
aacgactgct actccaagct caaggagctg gtgcccagca tcccccagaa caagaaggtg    60
agcaagatgg aaatcc                                                    76

<210> SEQ ID NO 154
<211> LENGTH: 21
<212> TYPE: DNA
<213> ORGANISM: Homo sapiens
```

<400> SEQUENCE: 154
tccggagctg tgatctaagg a                                          21

<210> SEQ ID NO 155
<211> LENGTH: 20
<212> TYPE: DNA
<213> ORGANISM: Homo sapiens

<400> SEQUENCE: 155
cggacagagc gagctgactt                                            20

<210> SEQ ID NO 156
<211> LENGTH: 76
<212> TYPE: DNA
<213> ORGANISM: Homo sapiens

<400> SEQUENCE: 156
tccggagctg tgatctaagg aggctggaga tgtattgcgc acccctcaag cctgccaagt   60
cagctcgctc tgtccg                                                76

<210> SEQ ID NO 157
<211> LENGTH: 17
<212> TYPE: DNA
<213> ORGANISM: Homo sapiens

<400> SEQUENCE: 157
acgcaccggg tgtctga                                               17

<210> SEQ ID NO 158
<211> LENGTH: 24
<212> TYPE: DNA
<213> ORGANISM: Homo sapiens

<400> SEQUENCE: 158
tgccctttct tgatgatgat tatc                                       24

<210> SEQ ID NO 159
<211> LENGTH: 68
<212> TYPE: DNA
<213> ORGANISM: Homo sapiens

<400> SEQUENCE: 159
acgcaccggg tgtctgatcc caagttccac cccctccatt caaagataat catcatcaag   60
aaagggca                                                         68

<210> SEQ ID NO 160
<211> LENGTH: 22
<212> TYPE: DNA
<213> ORGANISM: Homo sapiens

<400> SEQUENCE: 160
ccattcaccc tgtgtaacag ga                                         22

<210> SEQ ID NO 161
<211> LENGTH: 21
<212> TYPE: DNA
<213> ORGANISM: Homo sapiens

<400> SEQUENCE: 161
ccgaccctct aggttaaggc a                                          21

```
<210> SEQ ID NO 162
<211> LENGTH: 68
<212> TYPE: DNA
<213> ORGANISM: Homo sapiens

<400> SEQUENCE: 162
ccattcaccc tgtgtaacag gaccccaagg acctgcctcc ccggaagtgc cttaacctag    60
agggtcgg                                                              68

<210> SEQ ID NO 163
<211> LENGTH: 20
<212> TYPE: DNA
<213> ORGANISM: Homo sapiens

<400> SEQUENCE: 163
cgtcaggacc caccatgtct                                                 20

<210> SEQ ID NO 164
<211> LENGTH: 24
<212> TYPE: DNA
<213> ORGANISM: Homo sapiens

<400> SEQUENCE: 164
ggttaattgg tgacatcctc aaga                                            24

<210> SEQ ID NO 165
<211> LENGTH: 81
<212> TYPE: DNA
<213> ORGANISM: Homo sapiens

<400> SEQUENCE: 165
cgtcaggacc caccatgtct gccccatcac gcggccgaga catggcttgg ccacagctct    60
tgaggatgtc accaattaac c                                               81

<210> SEQ ID NO 166
<211> LENGTH: 23
<212> TYPE: DNA
<213> ORGANISM: Homo sapiens

<400> SEQUENCE: 166
caaacgctga catgtacggt cta                                             23

<210> SEQ ID NO 167
<211> LENGTH: 18
<212> TYPE: DNA
<213> ORGANISM: Homo sapiens

<400> SEQUENCE: 167
gctcgttggc gcactctt                                                   18

<210> SEQ ID NO 168
<211> LENGTH: 88
<212> TYPE: DNA
<213> ORGANISM: Homo sapiens

<400> SEQUENCE: 168
caaacgctga catgtacggt ctatgccatt cctccccgc atcacatcca ctggtattgg     60
cagttggagg aagagtgcgc caacgagc                                        88

<210> SEQ ID NO 169
<211> LENGTH: 25
```

<212> TYPE: DNA
<213> ORGANISM: Homo sapiens

<400> SEQUENCE: 169
gaggcaactg cttatggctt aatta                                            25

<210> SEQ ID NO 170
<211> LENGTH: 18
<212> TYPE: DNA
<213> ORGANISM: Homo sapiens

<400> SEQUENCE: 170
ggcactcggc ttgagcat                                                    18

<210> SEQ ID NO 171
<211> LENGTH: 75
<212> TYPE: DNA
<213> ORGANISM: Homo sapiens

<400> SEQUENCE: 171
gaggcaactg cttatggctt aattaagtca gatgcggcca tgactgtcgc tgtaaagatg      60
ctcaagccga gtgcc                                                       75

<210> SEQ ID NO 172
<211> LENGTH: 18
<212> TYPE: DNA
<213> ORGANISM: Homo sapiens

<400> SEQUENCE: 172
gtccccggga tggatgtt                                                    18

<210> SEQ ID NO 173
<211> LENGTH: 25
<212> TYPE: DNA
<213> ORGANISM: Homo sapiens

<400> SEQUENCE: 173
gatcagtcaa gctgtctgac aattg                                            25

<210> SEQ ID NO 174
<211> LENGTH: 79
<212> TYPE: DNA
<213> ORGANISM: Homo sapiens

<400> SEQUENCE: 174
gtccccggga tggatgtttt gccaagtcat tgttggataa gcgagatggt agtacaattg      60
tcagacagct tgactgatc                                                   79

<210> SEQ ID NO 175
<211> LENGTH: 21
<212> TYPE: DNA
<213> ORGANISM: Homo sapiens

<400> SEQUENCE: 175
cgaggattgg ttcttcagca a                                                21

<210> SEQ ID NO 176
<211> LENGTH: 22
<212> TYPE: DNA
<213> ORGANISM: Homo sapiens

<400> SEQUENCE: 176

```
actctgcacc agctcactgt tg                                            22
```

<210> SEQ ID NO 177
<211> LENGTH: 73
<212> TYPE: DNA
<213> ORGANISM: Homo sapiens

<400> SEQUENCE: 177

```
cgaggattgg ttcttcagca agacagagga actgaaccgc gaggtggcca ccaacagtga   60
gctggtgcag agt                                                      73
```

<210> SEQ ID NO 178
<211> LENGTH: 20
<212> TYPE: DNA
<213> ORGANISM: Homo sapiens

<400> SEQUENCE: 178

```
tcagtggaga aggagttgga                                               20
```

<210> SEQ ID NO 179
<211> LENGTH: 20
<212> TYPE: DNA
<213> ORGANISM: Homo sapiens

<400> SEQUENCE: 179

```
tgccatatcc agaggaaaca                                               20
```

<210> SEQ ID NO 180
<211> LENGTH: 69
<212> TYPE: DNA
<213> ORGANISM: Homo sapiens

<400> SEQUENCE: 180

```
tcagtggaga aggagttgga ccagtcaaca tctctgttgt cacaagcagt gtttcctctg   60
gatatggca                                                           69
```

<210> SEQ ID NO 181
<211> LENGTH: 26
<212> TYPE: DNA
<213> ORGANISM: Homo sapiens

<400> SEQUENCE: 181

```
gtacaagaga gaaccagact ccaatg                                        26
```

<210> SEQ ID NO 182
<211> LENGTH: 18
<212> TYPE: DNA
<213> ORGANISM: Homo sapiens

<400> SEQUENCE: 182

```
gtgtagcccg cggacact                                                 18
```

<210> SEQ ID NO 183
<211> LENGTH: 87
<212> TYPE: DNA
<213> ORGANISM: Homo sapiens

<400> SEQUENCE: 183

```
gtacaagaga gaaccagact ccaatgtcat tgtggtggac tggctgtcac gggctcagga   60
gcattaccca gtgtccgcgg gctacac                                       87
```

```
<210> SEQ ID NO 184
<211> LENGTH: 22
<212> TYPE: DNA
<213> ORGANISM: Homo sapiens

<400> SEQUENCE: 184
gacatttcca gtcctgcagt ca                                              22

<210> SEQ ID NO 185
<211> LENGTH: 20
<212> TYPE: DNA
<213> ORGANISM: Homo sapiens

<400> SEQUENCE: 185
ctccgatcgc acacatttgt                                                 20

<210> SEQ ID NO 186
<211> LENGTH: 86
<212> TYPE: DNA
<213> ORGANISM: Homo sapiens

<400> SEQUENCE: 186
gacatttcca gtcctgcagt caatgcctct ctgccccacc ctttgttcag tgtggctggt     60
gccacgacaa atgtgtgcga tcggag                                          86

<210> SEQ ID NO 187
<211> LENGTH: 24
<212> TYPE: DNA
<213> ORGANISM: Homo sapiens

<400> SEQUENCE: 187
gttttggagg aaatgtgttc ttca                                            24

<210> SEQ ID NO 188
<211> LENGTH: 26
<212> TYPE: DNA
<213> ORGANISM: Homo sapiens

<400> SEQUENCE: 188
ttctctaata cactgccgtc ttaagg                                          26

<210> SEQ ID NO 189
<211> LENGTH: 101
<212> TYPE: DNA
<213> ORGANISM: Homo sapiens

<400> SEQUENCE: 189
gttttggagg aaatgtgttc ttcagtgcac agaatgcagc aaaacagcca tctgataaat     60
gctctgcaag ccctccctta agacggcagt gtattagaga a                        101

<210> SEQ ID NO 190
<211> LENGTH: 22
<212> TYPE: DNA
<213> ORGANISM: Homo sapiens

<400> SEQUENCE: 190
acgagaacga gggcatctat gt                                              22

<210> SEQ ID NO 191
<211> LENGTH: 22
<212> TYPE: DNA
<213> ORGANISM: Homo sapiens
```

```
<400> SEQUENCE: 191
gcatgtaggt gcttccaatc ac                                                22

<210> SEQ ID NO 192
<211> LENGTH: 75
<212> TYPE: DNA
<213> ORGANISM: Homo sapiens

<400> SEQUENCE: 192
acgagaacga gggcatctat gtgcaggatg tcaagaccgg aaaggtgcgc gctgtgattg       60
gaagcaccta catgc                                                       75

<210> SEQ ID NO 193
<211> LENGTH: 21
<212> TYPE: DNA
<213> ORGANISM: Homo sapiens

<400> SEQUENCE: 193
tccctccact cggaaggact a                                                 21

<210> SEQ ID NO 194
<211> LENGTH: 22
<212> TYPE: DNA
<213> ORGANISM: Homo sapiens

<400> SEQUENCE: 194
cggttgttgc tgatctgtct ca                                                22

<210> SEQ ID NO 195
<211> LENGTH: 84
<212> TYPE: DNA
<213> ORGANISM: Homo sapiens

<400> SEQUENCE: 195
tccctccact cggaaggact atcctgctgc caagagggtc aagttggaca gtgtcagagt       60
cctgagacag atcagcaaca accg                                             84

<210> SEQ ID NO 196
<211> LENGTH: 19
<212> TYPE: DNA
<213> ORGANISM: Homo sapiens

<400> SEQUENCE: 196
ttgttggtgt gccctggtg                                                    19

<210> SEQ ID NO 197
<211> LENGTH: 21
<212> TYPE: DNA
<213> ORGANISM: Homo sapiens

<400> SEQUENCE: 197
tgggttctgt ccaaacactg g                                                 21

<210> SEQ ID NO 198
<211> LENGTH: 67
<212> TYPE: DNA
<213> ORGANISM: Homo sapiens

<400> SEQUENCE: 198
ttgttggtgt gccctggtgc cgtggtggcg gtcactccct ctgctgccag tgtttggaca       60
gaaccca                                                                67
```

<210> SEQ ID NO 199
<211> LENGTH: 20
<212> TYPE: DNA
<213> ORGANISM: Homo sapiens

<400> SEQUENCE: 199
actgaaggag acccttggag                                                      20

<210> SEQ ID NO 200
<211> LENGTH: 20
<212> TYPE: DNA
<213> ORGANISM: Homo sapiens

<400> SEQUENCE: 200
taaataaccc tgcccacaca                                                      20

<210> SEQ ID NO 201
<211> LENGTH: 62
<212> TYPE: DNA
<213> ORGANISM: Homo sapiens

<400> SEQUENCE: 201
actgaaggag acccttggag cctaggggca tcggcaggag agtgtgtggg cagggttatt          60
ta                                                                         62

<210> SEQ ID NO 202
<211> LENGTH: 28
<212> TYPE: DNA
<213> ORGANISM: Homo sapiens

<400> SEQUENCE: 202
agttactaaa aaataccacg aggtcctt                                             28

<210> SEQ ID NO 203
<211> LENGTH: 21
<212> TYPE: DNA
<213> ORGANISM: Homo sapiens

<400> SEQUENCE: 203
gtcggtgagt gatttgtgca a                                                    21

<210> SEQ ID NO 204
<211> LENGTH: 79
<212> TYPE: DNA
<213> ORGANISM: Homo sapiens

<400> SEQUENCE: 204
agttactaaa aaataccacg aggtccttca gttgagacca aagaccggtg tcagggggatt         60 gcacaaatca ctcaccgac                                                       79

<210> SEQ ID NO 205
<211> LENGTH: 20
<212> TYPE: DNA
<213> ORGANISM: Homo sapiens

<400> SEQUENCE: 205
gggagtttcc aagagatgga                                                      20

<210> SEQ ID NO 206
<211> LENGTH: 20
<212> TYPE: DNA

<213> ORGANISM: Homo sapiens

<400> SEQUENCE: 206
cttcaaccac cttcccaaac    20

<210> SEQ ID NO 207
<211> LENGTH: 72
<212> TYPE: DNA
<213> ORGANISM: Homo sapiens

<400> SEQUENCE: 207
gggagtttcc aagagatgga ctagtgcttg gtcgggtctt ggggtctgga gcgtttggga    60
aggtggttga ag    72

<210> SEQ ID NO 208
<211> LENGTH: 23
<212> TYPE: DNA
<213> ORGANISM: Homo sapiens

<400> SEQUENCE: 208
aggtgtcatc catcaacgtc tct    23

<210> SEQ ID NO 209
<211> LENGTH: 20
<212> TYPE: DNA
<213> ORGANISM: Homo sapiens

<400> SEQUENCE: 209
tcccgatcac aatgcacatg    20

<210> SEQ ID NO 210
<211> LENGTH: 90
<212> TYPE: DNA
<213> ORGANISM: Homo sapiens

<400> SEQUENCE: 210
aggtgtcatc catcaacgtc tctgtgaacg cagtgcagac tgtggtccgc cagggtgaga    60
acatcaccct catgtgcatt gtgatcggga    90

<210> SEQ ID NO 211
<211> LENGTH: 24
<212> TYPE: DNA
<213> ORGANISM: Homo sapiens

<400> SEQUENCE: 211
agagccagtt gctgtagaac tcaa    24

<210> SEQ ID NO 212
<211> LENGTH: 21
<212> TYPE: DNA
<213> ORGANISM: Homo sapiens

<400> SEQUENCE: 212
ctgggcctac acagtccttc a    21

<210> SEQ ID NO 213
<211> LENGTH: 74
<212> TYPE: DNA
<213> ORGANISM: Homo sapiens

<400> SEQUENCE: 213
agagccagtt gctgtagaac tcaaatctct gctgggcaag gatgttctgt tcttgaagga    60

```
ctgtgtaggc ccag                                                    74

<210> SEQ ID NO 214
<211> LENGTH: 26
<212> TYPE: DNA
<213> ORGANISM: Homo sapiens

<400> SEQUENCE: 214
gaaatgactg catcgttgat aaaatc                                       26

<210> SEQ ID NO 215
<211> LENGTH: 19
<212> TYPE: DNA
<213> ORGANISM: Homo sapiens

<400> SEQUENCE: 215
tgccagcctg acagcactt                                               19

<210> SEQ ID NO 216
<211> LENGTH: 78
<212> TYPE: DNA
<213> ORGANISM: Homo sapiens

<400> SEQUENCE: 216
gaaatgactg catcgttgat aaaatccgca gaaaaactg cccagcatgt cgccttagaa   60
agtgctgtca ggctggca                                                78

<210> SEQ ID NO 217
<211> LENGTH: 20
<212> TYPE: DNA
<213> ORGANISM: Homo sapiens

<400> SEQUENCE: 217
gatcaacggc tacatccaga                                              20

<210> SEQ ID NO 218
<211> LENGTH: 20
<212> TYPE: DNA
<213> ORGANISM: Homo sapiens

<400> SEQUENCE: 218
tgaactgtga ggccagagac                                              20

<210> SEQ ID NO 219
<211> LENGTH: 68
<212> TYPE: DNA
<213> ORGANISM: Homo sapiens

<400> SEQUENCE: 219
gatcaacggc tacatccaga agatcaagtc gggagaggag gactttgagt ctctggcctc  60
acagttca                                                           68

<210> SEQ ID NO 220
<211> LENGTH: 19
<212> TYPE: DNA
<213> ORGANISM: Homo sapiens

<400> SEQUENCE: 220
gtggatgtgc cctgaagga                                               19

<210> SEQ ID NO 221
```

```
<211> LENGTH: 20
<212> TYPE: DNA
<213> ORGANISM: Homo sapiens

<400> SEQUENCE: 221
ctgcggatcc agggtaagaa                                                    20

<210> SEQ ID NO 222
<211> LENGTH: 70
<212> TYPE: DNA
<213> ORGANISM: Homo sapiens

<400> SEQUENCE: 222
gtggatgtgc cctgaaggac aagccaggcg tctacacgag agtctcacac ttcttaccct        60
ggatccgcag                                                               70

<210> SEQ ID NO 223
<211> LENGTH: 27
<212> TYPE: DNA
<213> ORGANISM: Homo sapiens

<400> SEQUENCE: 223
tggacttcta gtgatgagaa agattga                                            27

<210> SEQ ID NO 224
<211> LENGTH: 22
<212> TYPE: DNA
<213> ORGANISM: Homo sapiens

<400> SEQUENCE: 224
cactgcgaga tcaccacagg ta                                                 22

<210> SEQ ID NO 225
<211> LENGTH: 84
<212> TYPE: DNA
<213> ORGANISM: Homo sapiens

<400> SEQUENCE: 225
tggacttcta gtgatgagaa agattgagaa tgttcccaca ggccccaaca ataagcccaa        60
gctacctgtg gtgatctcgc agtg                                               84

<210> SEQ ID NO 226
<211> LENGTH: 25
<212> TYPE: DNA
<213> ORGANISM: Homo sapiens

<400> SEQUENCE: 226
tggctaagtg aagatgacaa tcatg                                              25

<210> SEQ ID NO 227
<211> LENGTH: 25
<212> TYPE: DNA
<213> ORGANISM: Homo sapiens

<400> SEQUENCE: 227
tgcacatatc attacaccag ttcgt                                              25

<210> SEQ ID NO 228
<211> LENGTH: 81
<212> TYPE: DNA
<213> ORGANISM: Homo sapiens

<400> SEQUENCE: 228
```

-continued tggctaagtg aagatgacaa tcatgttgca gcaattcact gtaaagctgg aaagggacga    60
actggtgtaa tgatatgtgc a    81

<210> SEQ ID NO 229
<211> LENGTH: 23
<212> TYPE: DNA
<213> ORGANISM: Homo sapiens

<400> SEQUENCE: 229
tctgcagagt tggaagcact cta    23

<210> SEQ ID NO 230
<211> LENGTH: 21
<212> TYPE: DNA
<213> ORGANISM: Homo sapiens

<400> SEQUENCE: 230
gccgaggctt ttctaccaga a    21

<210> SEQ ID NO 231
<211> LENGTH: 79
<212> TYPE: DNA
<213> ORGANISM: Homo sapiens

<400> SEQUENCE: 231
tctgcagagt tggaagcact ctatggtgac atcgatgctg tggagctgta tcctgccctt    60
ctggtagaaa agcctcggc    79

<210> SEQ ID NO 232
<211> LENGTH: 24
<212> TYPE: DNA
<213> ORGANISM: Homo sapiens

<400> SEQUENCE: 232
acgacacgta tgccgtacag tact    24

<210> SEQ ID NO 233
<211> LENGTH: 18
<212> TYPE: DNA
<213> ORGANISM: Homo sapiens

<400> SEQUENCE: 233
ccgggaaaac acgaagga    18

<210> SEQ ID NO 234
<211> LENGTH: 86
<212> TYPE: DNA
<213> ORGANISM: Homo sapiens

<400> SEQUENCE: 234
acgacacgta tgccgtacag tactcctgcc gcctcctgaa cctcgatggc acctgtgctg    60
acagctactc cttcgtgttt tcccgg    86

<210> SEQ ID NO 235
<211> LENGTH: 19
<212> TYPE: DNA
<213> ORGANISM: Homo sapiens

<400> SEQUENCE: 235
ctgccgggat ggcttctat    19

```
<210> SEQ ID NO 236
<211> LENGTH: 22
<212> TYPE: DNA
<213> ORGANISM: Homo sapiens

<400> SEQUENCE: 236
ccaggttctg gaaactgtgg at                                              22

<210> SEQ ID NO 237
<211> LENGTH: 68
<212> TYPE: DNA
<213> ORGANISM: Homo sapiens

<400> SEQUENCE: 237
ctgccgggat ggcttctatg aggctgagct ctgcccggac cgctgcatcc acagtttcca    60
gaacctgg                                                             68

<210> SEQ ID NO 238
<211> LENGTH: 20
<212> TYPE: DNA
<213> ORGANISM: Homo sapiens

<400> SEQUENCE: 238
ccacaagctg aaggcagaca                                                20

<210> SEQ ID NO 239
<211> LENGTH: 21
<212> TYPE: DNA
<213> ORGANISM: Homo sapiens

<400> SEQUENCE: 239
gcgtgcttcc ttggtcttag a                                              21

<210> SEQ ID NO 240
<211> LENGTH: 85
<212> TYPE: DNA
<213> ORGANISM: Homo sapiens

<400> SEQUENCE: 240
ccacaagctg aaggcagaca aggcccgcaa gaagctcctg gctgaccagg ctgaggcccg    60
caggtctaag accaaggaag cacgc                                          85

<210> SEQ ID NO 241
<211> LENGTH: 24
<212> TYPE: DNA
<213> ORGANISM: Homo sapiens

<400> SEQUENCE: 241
ccattctatc atcaacgggt acaa                                           24

<210> SEQ ID NO 242
<211> LENGTH: 23
<212> TYPE: DNA
<213> ORGANISM: Homo sapiens

<400> SEQUENCE: 242
tcagcaagtg ggaaggtgta atc                                            23

<210> SEQ ID NO 243
<211> LENGTH: 75
<212> TYPE: DNA
<213> ORGANISM: Homo sapiens
```

<400> SEQUENCE: 243
ccattctatc atcaacgggt acaaacgagt cctggccttg tctgtggaga cggattacac    60
cttcccactt gctga    75

<210> SEQ ID NO 244
<211> LENGTH: 20
<212> TYPE: DNA
<213> ORGANISM: Homo sapiens

<400> SEQUENCE: 244
tatcgaggca ggtcatacca    20

<210> SEQ ID NO 245
<211> LENGTH: 20
<212> TYPE: DNA
<213> ORGANISM: Homo sapiens

<400> SEQUENCE: 245
taacgcttgg catcatcatt    20

<210> SEQ ID NO 246
<211> LENGTH: 74
<212> TYPE: DNA
<213> ORGANISM: Homo sapiens

<400> SEQUENCE: 246
tatcgaggca ggtcatacca tgaccggaag tcaaaagttg acctggatag gctcaatgat    60
gatgccaagc gtta    74

<210> SEQ ID NO 247
<211> LENGTH: 19
<212> TYPE: DNA
<213> ORGANISM: Homo sapiens

<400> SEQUENCE: 247
ccgcaacgtg gttttctca    19

<210> SEQ ID NO 248
<211> LENGTH: 21
<212> TYPE: DNA
<213> ORGANISM: Homo sapiens

<400> SEQUENCE: 248
tgctgggttt ctcctcctgt t    21

<210> SEQ ID NO 249
<211> LENGTH: 81
<212> TYPE: DNA
<213> ORGANISM: Homo sapiens

<400> SEQUENCE: 249
ccgcaacgtg gttttctcac cctatggggt ggcctcggtg ttggccatgc tccagctgac    60
aacaggagga gaaacccagc a    81

<210> SEQ ID NO 250
<211> LENGTH: 25
<212> TYPE: DNA
<213> ORGANISM: Homo sapiens

<400> SEQUENCE: 250
tcaagaccat catcactttc attgt   25

<210> SEQ ID NO 251
<211> LENGTH: 27
<212> TYPE: DNA
<213> ORGANISM: Homo sapiens

<400> SEQUENCE: 251
ggatcaggaa gtacacggag tataact   27

<210> SEQ ID NO 252
<211> LENGTH: 96
<212> TYPE: DNA
<213> ORGANISM: Homo sapiens

<400> SEQUENCE: 252
tcaagaccat catcactttc attgtctcgg acgtgcgggg cctgggcctc ccggtccgca   60
agcagttcca gttatactcc gtgtacttcc tgatcc   96

<210> SEQ ID NO 253
<211> LENGTH: 19
<212> TYPE: DNA
<213> ORGANISM: Homo sapiens

<400> SEQUENCE: 253
gcccgaaacg ccgaatata   19

<210> SEQ ID NO 254
<211> LENGTH: 23
<212> TYPE: DNA
<213> ORGANISM: Homo sapiens

<400> SEQUENCE: 254
cgtggctctc ttatcctcat gat   23

<210> SEQ ID NO 255
<211> LENGTH: 65
<212> TYPE: DNA
<213> ORGANISM: Homo sapiens

<400> SEQUENCE: 255
gcccgaaacg ccgaatataa tcccaagcgg tttgctgcgg taatcatgag gataagagag   60
ccacg   65

<210> SEQ ID NO 256
<211> LENGTH: 19
<212> TYPE: DNA
<213> ORGANISM: Homo sapiens

<400> SEQUENCE: 256
gccctcccag tgtgcaaat   19

<210> SEQ ID NO 257
<211> LENGTH: 25
<212> TYPE: DNA
<213> ORGANISM: Homo sapiens

<400> SEQUENCE: 257
cgtcgatggt attaggatag aagca   25

<210> SEQ ID NO 258
<211> LENGTH: 86

```
<212> TYPE: DNA
<213> ORGANISM: Homo sapiens

<400> SEQUENCE: 258
gccctcccag tgtgcaaata agggctgctg tttcgacgac accgttcgtg gggtccctg    60 gtgcttctat cctaatacca tcgacg                                        86

<210> SEQ ID NO 259
<211> LENGTH: 27
<212> TYPE: DNA
<213> ORGANISM: Homo sapiens

<400> SEQUENCE: 259
caagctagat cagcattctc taacttg                                       27

<210> SEQ ID NO 260
<211> LENGTH: 25
<212> TYPE: DNA
<213> ORGANISM: Homo sapiens

<400> SEQUENCE: 260
cacatgactg ttatcgccat ctact                                         25

<210> SEQ ID NO 261
<211> LENGTH: 99
<212> TYPE: DNA
<213> ORGANISM: Homo sapiens

<400> SEQUENCE: 261
caagctagat cagcattctc taacttgttt ggtggagaac cattgtcata tacccggttc   60
agcctggctc ggcaagtaga tggcgataac agtcatgtg                          99

<210> SEQ ID NO 262
<211> LENGTH: 22
<212> TYPE: DNA
<213> ORGANISM: Homo sapiens

<400> SEQUENCE: 262
cacaggaaca acagcatctt tc                                            22

<210> SEQ ID NO 263
<211> LENGTH: 20
<212> TYPE: DNA
<213> ORGANISM: Homo sapiens

<400> SEQUENCE: 263
agataagccc ctgggatcca                                               20

<210> SEQ ID NO 264
<211> LENGTH: 75
<212> TYPE: DNA
<213> ORGANISM: Homo sapiens

<400> SEQUENCE: 264
cacaggaaca acagcatctt tcaccaagat gggtggcacc aaccttgctg ggacttggat   60 cccagggct tatct                                                     75

<210> SEQ ID NO 265
<211> LENGTH: 21
<212> TYPE: DNA
<213> ORGANISM: Homo sapiens
```

```
<400> SEQUENCE: 265
ggattgctca acaaccatgc t                                          21

<210> SEQ ID NO 266
<211> LENGTH: 24
<212> TYPE: DNA
<213> ORGANISM: Homo sapiens

<400> SEQUENCE: 266
ggcattaaca cttttggacg ataa                                       24

<210> SEQ ID NO 267
<211> LENGTH: 91
<212> TYPE: DNA
<213> ORGANISM: Homo sapiens

<400> SEQUENCE: 267
ggattgctca acaaccatgc tgggcatctg gaccctccta cctctggttc ttacgtctgt  60
tgctagatta tcgtccaaaa gtgttaatgc c                                91

<210> SEQ ID NO 268
<211> LENGTH: 24
<212> TYPE: DNA
<213> ORGANISM: Homo sapiens

<400> SEQUENCE: 268
gcactttggg attctttcca ttat                                       24

<210> SEQ ID NO 269
<211> LENGTH: 24
<212> TYPE: DNA
<213> ORGANISM: Homo sapiens

<400> SEQUENCE: 269
gcatgtaaga agaccctcac tgaa                                       24

<210> SEQ ID NO 270
<211> LENGTH: 80
<212> TYPE: DNA
<213> ORGANISM: Homo sapiens

<400> SEQUENCE: 270
gcactttggg attctttcca ttatgattct ttgttacagg caccgagaat gttgtattca  60
gtgagggtct tcttacatgc                                             80

<210> SEQ ID NO 271
<211> LENGTH: 20
<212> TYPE: DNA
<213> ORGANISM: Homo sapiens

<400> SEQUENCE: 271
aatccaaggg ggagagtgat                                            20

<210> SEQ ID NO 272
<211> LENGTH: 20
<212> TYPE: DNA
<213> ORGANISM: Homo sapiens

<400> SEQUENCE: 272
gtacagattt tgcccgagga                                            20
```

```
<210> SEQ ID NO 273
<211> LENGTH: 72
<212> TYPE: DNA
<213> ORGANISM: Homo sapiens

<400> SEQUENCE: 273
aatccaaggg ggagagtgat gacttccata tggactttga ctcagctgtg gctcctcggg      60
caaaatctgt ac                                                         72

<210> SEQ ID NO 274
<211> LENGTH: 21
<212> TYPE: DNA
<213> ORGANISM: Homo sapiens

<400> SEQUENCE: 274
tgtggacatc ttcccctcag a                                               21

<210> SEQ ID NO 275
<211> LENGTH: 18
<212> TYPE: DNA
<213> ORGANISM: Homo sapiens

<400> SEQUENCE: 275
ctagcccgac cggttcgt                                                   18

<210> SEQ ID NO 276
<211> LENGTH: 66
<212> TYPE: DNA
<213> ORGANISM: Homo sapiens

<400> SEQUENCE: 276
tgtggacatc ttcccctcag acttccctac tgagccacct tctctgccac gaaccggtcg     60
ggctag                                                                66

<210> SEQ ID NO 277
<211> LENGTH: 20
<212> TYPE: DNA
<213> ORGANISM: Homo sapiens

<400> SEQUENCE: 277
ctttgaaccc ttgcttgcaa                                                 20

<210> SEQ ID NO 278
<211> LENGTH: 18
<212> TYPE: DNA
<213> ORGANISM: Homo sapiens

<400> SEQUENCE: 278
cccgggacaa agcaaatg                                                   18

<210> SEQ ID NO 279
<211> LENGTH: 68
<212> TYPE: DNA
<213> ORGANISM: Homo sapiens

<400> SEQUENCE: 279
ctttgaaccc ttgcttgcaa taggtgtgcg tcagaagcac ccaggacttc catttgcttt     60
gtcccggg                                                              68

<210> SEQ ID NO 280
<211> LENGTH: 18
<212> TYPE: DNA
```

<213> ORGANISM: Homo sapiens

<400> SEQUENCE: 280
gcctcggtgt gcctttca                                              18

<210> SEQ ID NO 281
<211> LENGTH: 19
<212> TYPE: DNA
<213> ORGANISM: Homo sapiens

<400> SEQUENCE: 281
cgtgatgtgc gcaatcatg                                             19

<210> SEQ ID NO 282
<211> LENGTH: 65
<212> TYPE: DNA
<213> ORGANISM: Homo sapiens

<400> SEQUENCE: 282
gcctcggtgt gcctttcaac atcgccagct acgccctgct cacgtacatg attgcgcaca    60
tcacg                                                              65

<210> SEQ ID NO 283
<211> LENGTH: 20
<212> TYPE: DNA
<213> ORGANISM: Homo sapiens

<400> SEQUENCE: 283
ctgctgtctt gggtgcattg                                              20

<210> SEQ ID NO 284
<211> LENGTH: 18
<212> TYPE: DNA
<213> ORGANISM: Homo sapiens

<400> SEQUENCE: 284
gcagcctggg accacttg                                                18

<210> SEQ ID NO 285
<211> LENGTH: 71
<212> TYPE: DNA
<213> ORGANISM: Homo sapiens

<400> SEQUENCE: 285
ctgctgtctt gggtgcattg gagccttgcc ttgctgctct acctccacca tgccaagtgg    60
tcccaggctg c                                                       71

<210> SEQ ID NO 286
<211> LENGTH: 1947
<212> TYPE: DNA
<213> ORGANISM: Homo sapiens

<400> SEQUENCE: 286
ttttccccag atatggggtt ctattcagcc atagataatc tagacagagg atttcagaat    60
gaaaggaaaa atgtgtggag attagtccta gttcattctg agggccgact aagtggctca   120
gccagcttct tactccatct gcagttcata ctgccaaaga gctcccactt ccaaatcccc   180
agtgacttta tggagaagat tctgcattaa attgtctttc gaatgatggg gaagcaaggc   240
ataatatgcg atgatgagga gaaagtagac cagtgaggtg attgcaagac taacaaggag   300
actcaatggg aagttttttct ttcttttaga tattgctttt gaagtagatg gtaaaatttt   360

-continued

```
tgtcatcctt cttgtatttt ttgtacccca agttacaatt tttcttcttc cttgtaaata      420
atttaaacag tatttatttt tgtaaggcat aactagaaac taaaatatat tctaaaaaat      480
tcattattct gaacaaagtg atcaaattag aatacatatt tttcaacagt ggtagagctt      540
ttaatatatg tttattgaaa gttatctata atacttgcac cagtgttgaa aaagttaac      600 atgtaggcaa gagcaatatg tttgtctcaa ggattttccc atggtttcct cagtgatggt      660
gtcctggaat tattcaggtg gtgaccatca ctggtctaag tttgtgtgca gggttttcag      720
acgtgttttt gtgaaacttg gtagaaccat ggctaataaa gaggacagtg ttgtcagggt      780
ccatctgccc tccatagaaa aatgtctctg gctcataaaa tgagactccc tcagggacta      840
aatatgaact gacagcagta actctgatac agaataatct aaattgcatc aaatggcctt      900
aattcagagt ttgttaggct tatcagtatg ttgcttttaa ttggggtggg aaagtagagg      960
gagagaaagc aagacattta ttaagcacct cgtatgtgcc aggcactatg ctaagcactt     1020
tacataagtt aggattaatc cctgcaagaa tcctataaag aatgttacta gcatttacac     1080
ttcccaaatg aaggtaccaa agctcaaacg caatgttgtg aagctgtttc cttcagattt     1140
aggttatgtg ggatgatgtg ggattgaaga ggaaagaaag gtgggattat cccctagga     1200 agactttcag gcctgacttc ataggaattc atccatctta tcatgtggag tttatctcac     1260
cctgctgttg caggatgcta tttgcatgtg tccccaggtg atgttttttc tttggggagt     1320
aggggtttgg cttcctcatt catccctctt gctaaaagag gagatagttg atgttgcatc     1380
taaagatgct ataagacaat gaaagtttga tgttgtacat acctacaagt accattttg      1440 tgcatgatta cactccactg acatcttcca agtactgcat gtgattgaat aagaaacaag     1500
aaagtgacca caccaaagcc tccctggctg gtgtacaggg atcaggtcca cagtggtaca     1560
gattcaacca ccacccaggg agtgcttgca gactctgcat agatgttgct gcatgcgtcc     1620
catgtgcctg tcagaatggc agtgtttaat tctcttgaaa gaaagttatt tgctcactat     1680
ccccagcctc aaggagccaa ggaagagtca ttcacatgga aggtccgggt ctggtcagcc     1740
actctgactt ttctaccaca ttaaattctc cattacatct cactattggt aatggcttaa     1800
gtgtaaagag ccatgatgtg tatattaagc tatgtgccac atatttattt ttagactctc     1860
cacagcattc atgtcaatat gggattaatg cctaaacttt gtaaatattg tacagtttgt     1920
aaatcaatga ataaaggttt tgagtgt                                         1947
```

<210> SEQ ID NO 287
<211> LENGTH: 1311
<212> TYPE: DNA
<213> ORGANISM: Homo sapiens

<400> SEQUENCE: 287

```
tagtcgggcg gggttgtgag acgccgcgct cagcttccat cgctgggcgg tcaacaagtg       60
cgggcctggc tcagcgcggg ggggcgcgga gaccgcgagg cgaccgggag cggctgggtt      120
cccggctgcg cgcccttcgg ccaggccggg agcgcgccca gtcggagccc ccggcccagc      180
gtggtccgcc tccctctcgg cgtccacctg cccggagtac tgccagcggg catgaccgac      240
ccaccagggg cgccgccgcc ggcgctcgca ggccgcggat gaagaagaaa acccggcgcc      300
gctcgacccg gagcgaggag ttgacccgga gcgaggagtt gaccctgagt gaggaagcga      360
cctggagtga agaggcgacc cagagtgagg aggcgaccca gggcgaagag atgaatcgga      420
gccaggaggt gacccgggac gaggagtcga cccggagcga ggaggtgacc agggaggaaa      480
```

```
tggcggcagc tgggctcacc gtgactgtca cccacagcaa tgagaagcac gaccttcatg    540
ttacctccca gcagggcagc agtgaaccag ttgtccaaga cctggcccag gttgttgaag    600
aggtcatagg ggttccacag tcttttcaga aactcatatt taagggaaaa tctctgaagg    660
aaatggaaac accgttgtca gcacttggaa tacaagatgt tgccgggtc atgttaattg     720 ggaaaaagaa cagtccacag gaagaggttg aactaaagaa gttgaaacat ttggagaagt    780
ctgtggagaa gatagctgac cagctggaag agttgaataa agagcttact ggaatccagc    840
agggttttct gcccaaggat ttgcaagctg aagctctctg caaacttgat aggagagtaa    900
aagccacaat agagcagttt atgaagatct tggaggagat tgacacactg atcctgccag    960
aaaatttcaa agacagtaga ttgaaaagga aaggcttggt aaaaaaggtt caggcattcc   1020
tagccgagtg tgacacagtg gagcagaaca tctgccagga gactgagcgg ctgcagtcta   1080
caaactttgc cctggccgag tgaggtgtag cagaaaaagg ctgtgctgcc tgaagaatg    1140 gcgccaccag ctctgccgtc tctggatcgg aatttacctg atttcttcag gctgctgggg   1200
ggcaactggc catttgccaa ttttcctact ctcacactgg ttctcaatga aaaatagtgt   1260
ctttgtgatt tgagtaaagc tcctattctg tttttcacaa aaaaaaaaaa a            1311

<210> SEQ ID NO 288
<211> LENGTH: 582
<212> TYPE: DNA
<213> ORGANISM: Homo sapiens

<400> SEQUENCE: 288
atggcccgcg cacgccagga gggcagctcc ccggagcccg tagagggcct ggcccgcgac     60
ggcccgcgcc ccttcccgct cggccgcctg gtgcccccgg cagtgtcctg cggcctctgc    120
gagcccggcc tggctgccgc cccgccgcc cccaccctgc tgcccgctgc ctacctctgc    180
gcccccaccg ccccacccgc cgtcaccgcc gccctggggg gttcccgctg gcctgggggt    240
ccccgcagcc ggccccgagg cccgcgcccg gacggtcctc agccctcgct ctcgctggcg    300
gagcagcacc tggagtcgcc cgtgcccagc gccccggggg ctctggcggg cggtcccacc    360
caggcggccc cgggagtccg cggggaggag gaacagtggg cccgggagat cggggcccag    420
ctgcggcgga tggcggacga cctcaacgca cagtacgagc ggcggagaca agaggagcag    480
cagcggcacc gccctcacc ctggagggtc ctgtacaatc tcatcatggg actcctgccc    540
ttacccaggg gccacagagc ccccgagatg gagcccaatt ag                       582

<210> SEQ ID NO 289
<211> LENGTH: 6030
<212> TYPE: DNA
<213> ORGANISM: Homo sapiens

<400> SEQUENCE: 289
gttggccccc gttactttc ctctgggaaa tatggcgcac gctgggagaa cagggtacga      60
taaccgggag atagtgatga agtacatcca ttataagctg tcgcagaggg gctacgagtg    120
ggatgcggga gatgtgggcg ccgcgccccc ggggccgcc ccgcgccgg gcatcttctc      180 ctcgcagccc gggcacacgc cccatacagc cgcatcccgg acccggtcg ccaggacctc     240 gccgctgcag accccggctg cccccggcgc cgccgcgggg cctgcgctca gcccggtgcc    300
acctgtggtc cacctgaccc tccgccaggc cggcgacgac ttctcccgcc gctaccgccg    360
cgacttcgcc gagatgtcca ggcagctgca cctgacgccc ttcaccgcgc ggggacgctt    420
tgccacggtg gtggaggagc tcttcaggga cggggtgaac tgggggagga ttgtggcctt    480
```

|  |  |
|---|---|
| ctttgagttc ggtggggtca tgtgtgtgga gagcgtcaac cgggagatgt cgccctggt | 540 |
| ggacaacatc gccctgtgga tgactgagta cctgaaccgg cacctgcaca cctggatcca | 600 |
| ggataacgga ggctgggatg cctttgtgga actgtacggc cccagcatgc ggcctctgtt | 660 |
| tgatttctcc tggctgtctc tgaagactct gctcagtttg ccctggtgg gagcttgcat | 720 |
| caccctgggt gcctatctgg gccacaagtg aagtcaacat gcctgcccca aacaaatatg | 780 |
| caaaaggttc actaaagcag tagaaataat atgcattgtc agtgatgttc catgaaacaa | 840 |
| agctgcaggc tgtttaagaa aaataacac acatataaac atcacacaca cagacagaca | 900 |
| cacacacaca caacaattaa cagtcttcag gcaaaacgtc gaatcagcta tttactgcca | 960 |
| aagggaaata tcatttattt tttacattat taagaaaaaa agatttattt atttaagaca | 1020 |
| gtcccatcaa aactcctgtc tttggaaatc cgaccactaa ttgccaagca ccgcttcgtg | 1080 |
| tggctccacc tggatgttct gtgcctgtaa acatagattc gctttccatg ttgttggccg | 1140 |
| gatcaccatc tgaagagcag acggatggaa aaaggacctg atcattgggg aagctggctt | 1200 |
| tctggctgct ggaggctggg gagaaggtgt tcattcactt gcatttcttt gccctggggg | 1260 |
| ctgtgatatt aacagaggga gggttcctgt gggggaagt ccatgcctcc ctggcctgaa | 1320 |
| gaagagactc tttgcatatg actcacatga tgcatacctg gtgggaggaa aagagttggg | 1380 |
| aacttcagat ggacctagta cccactgaga tttccacgcc gaaggacagc gatgggaaaa | 1440 |
| atgcccttaa atcataggaa agtatttttt taagctacca attgtgccga gaaaagcatt | 1500 |
| ttagcaattt atacaatatc atccagtacc ttaagccctg attgtgtata ttcatatatt | 1560 |
| ttggatacgc accccccaac tcccaatact ggctctgtct gagtaagaaa cagaatcctc | 1620 |
| tggaacttga ggaagtgaac atttcggtga cttccgcatc aggaaggcta gagttaccca | 1680 |
| gagcatcagg ccgccacaag tgcctgcttt taggagaccg aagtccgcag aacctgcctg | 1740 |
| tgtcccagct tggaggcctg gtcctggaac tgagccgggg ccctcactgg cctcctccag | 1800 |
| ggatgatcaa cagggcagtg tggtctccga atgtctggaa gctgatggag ctcagaattc | 1860 |
| cactgtcaag aaagagcagt agaggggtgt ggctgggcct gtcaccctgg ggccctccag | 1920 |
| gtaggcccgt tttcacgtgg agcatgggag ccacgaccct tcttaagaca tgtatcactg | 1980 |
| tagagggaag gaacagaggc cctgggccct tcctatcaga aggacatggt gaaggctggg | 2040 |
| aacgtgagga gaggcaatgg ccacggccca ttttggctgt agcacatggc acgttggctg | 2100 |
| tgtggccttg gcccacctgt gagtttaaag caaggcttta aatgactttg gagagggtca | 2160 |
| caaatcctaa agaagcatt gaagtgaggt gtcatggatt aattgacccc tgtctatgga | 2220 |
| attacatgta aaacattatc ttgtcactgt agtttggttt tatttgaaaa cctgacaaaa | 2280 |
| aaaaagttcc aggtgtggaa tatgggggtt atctgtacat cctgggggcat taaaaaaaaa | 2340 |
| atcaatggtg gggaactata aagaagtaac aaaagaagtg acatcttcag caaataaact | 2400 |
| aggaaatttt ttttcttcc agtttagaat cagccttgaa acattgatgg aataactctg | 2460 |
| tggcattatt gcattatata ccatttatct gtattaactt tggaatgtac tctgttcaat | 2520 |
| gtttaatgct gtggttgata tttcgaaagc tgctttaaaa aaatacatgc atctcagcgt | 2580 |
| ttttttgttt ttaattgtat ttagttatgg cctatacact atttgtgagc aaaggtgatc | 2640 |
| gttttctgtt tgagattttt atctcttgat tcttcaaaag cattctgaga aggtgagata | 2700 |
| agccctgagt ctcagctacc taagaaaaac ctggatgtca ctggccactg aggagctttg | 2760 |
| tttcaaccaa gtcatgtgca tttccacgtc aacagaattg tttattgtga cagttatatc | 2820 |

```
tgttgtccct tgaccttgt ttcttgaagg tttcctcgtc cctgggcaat tccgcattta    2880
attcatggta ttcaggatta catgcatgtt tggttaaacc catgagattc attcagttaa    2940
aaatccagat ggcaaatgac cagcagattc aaatctatgg tggtttgacc tttagagagt    3000
tgctttacgt ggcctgtttc aacacagacc cacccagagc cctcctgccc tccttccgcg    3060
ggggctttct catggctgtc cttcagggtc ttcctgaaat gcagtggtgc ttacgctcca    3120
ccaagaaagc aggaaacctg tggtatgaag ccagacctcc ccggcgggcc tcagggaaca    3180
gaatgatcag acctttgaat gattctaatt tttaagcaaa atattatttt atgaaaggtt    3240
tacattgtca aagtgatgaa tatggaatat ccaatcctgt gctgctatcc tgccaaaatc    3300
attttaatgg agtcagtttg cagtatgctc cacgtggtaa gatcctccaa gctgctttag    3360
aagtaacaat gaagaacgtg gacgctttta atataaagcc tgttttgtct tctgttgttg    3420
ttcaaacggg attcacagag tatttgaaaa atgtatatat attaagaggt cacgggggct    3480
aattgctggc tggctgcctt tgctgtgggg gttttgttac ctggttttaa taacagtaaa    3540
tgtgcccagc ctcttggccc cagaactgta cagtattgtg gctgcacttg ctctaagagt    3600
agttgatgtt gcattttcct tattgttaaa aacatgttag aagcaatgaa tgtatataaa    3660
agcctcaact agtcattttt ttctcctctt cttttttttc attatatcta attattttgc    3720
agttgggcaa cagagaacca tccctatttt gtattgaaga gggattcaca tctgcatctt    3780
aactgctctt tatgaatgaa aaaacagtcc tctgtatgta ctcctcttta cactggccag    3840
ggtcagagtg aaatagagta tatgcacttt ccaaatttggg gacaagggct ctaaaaaaag    3900
ccccaaaagg agaagaacat ctgagaacct cctcggcccct cccagtccct cgctgcacaa    3960
atactccgca agagaggcca gaatgacagc tgacagggtc tatggccatc gggtcgtctc    4020
cgaagatttg gcaggggcag aaaactctgg caggcttaag atttggaata aagtcacaga    4080
atcaaggaag cacctcaatt tagttcaaac aagacgccaa cattctctcc acagctcact    4140
tacctctctg tgttcagatg tggccttcca tttatatgtg atctttgttt tattagtaaa    4200
tgcttatcat ctaaagatgt agctctggcc cagtgggaaa aattaggaag tgattataaa    4260
tcgagaggag ttataataat caagattaaa tgtaaataat cagggcaatc ccaacacatg    4320
tctagctttc acctccagga tctattgagt gaacagaatt gcaaatagtc tctatttgta    4380
attgaactta tcctaaaaca aatagtttat aaatgtgaac ttaaactcta attaattcca    4440
actgtacttt taaggcagtg gctgttttta gactttctta tcacttatag ttagtaatgt    4500
acacctactc tatcagagaa aaacaggaaa ggctcgaaat acaagccatt ctaaggaaat    4560
tagggagtca gttgaaattc tattctgatc ttattctgtg gtgtcttttg cagcccagac    4620
aaaatgtggt acacactttt taagaaatac aattctacat tgtcaagctt atgaaggttc    4680
caatcagatc tttattgtta ttcaatttgg atctttcagg gattttttt ttaaattatt    4740
atgggacaaa ggacatttgt tggaggggtg ggagggagga acaattttta aatataaaac    4800
attcccaagt ttggatcagg gagttggaag ttttcagaat aaccagaact aagggtatga    4860
aggacctgta ttggggtcga tgtgatgcct ctgcgaagaa ccttgtgtga caatgagaaa    4920
acatttgaa gtttgtggta cgaccttttag attccagaga catcagcatg gctcaaagtg    4980
cagctccgtt tggcagtgca atggtataaa tttcaagctg gatatgtcta atgggtattt    5040
aaacaataaa tgtgcagttt taactaacag gatatttaat gacaaccttc tggttggtag    5100
ggacatctgt ttctaaatgt ttattatgta caatacagaa aaaaatttta taaaattaag    5160
caatgtgaaa ctgaattgga gagtgataat acaagtcctt tagtcttacc cagtgaatca    5220
```

-continued

| | | | | |
|---|---|---|---|---|
| ttctgttcca | tgtctttgga | caaccatgac | cttggacaat | catgaaatat | gcatctcact | 5280 |
| ggatgcaaag | aaaatcagat | ggagcatgaa | tggtactgta | ccggttcatc | tggactgccc | 5340 |
| cagaaaaata | acttcaagca | aacatcctat | caacaacaag | gttgttctgc | ataccaagct | 5400 |
| gagcacagaa | gatgggaaca | ctggtggagg | atggaaaggc | tcgctcaatc | aagaaaattc | 5460 |
| tgagactatt | aataaataag | actgtagtgt | agatactgag | taaatccatg | cacctaaacc | 5520 |
| ttttggaaaa | tctgccgtgg | gccctccaga | tagctcattt | cattaagttt | ttccctccaa | 5580 |
| ggtagaattt | gcaagagtga | cagtggattg | catttctttt | ggggaagctt | tcttttggtg | 5640 |
| gttttgttta | ttataccttc | ttaagttttc | aaccaaggtt | tgcttttgtt | ttgagttact | 5700 |
| ggggttattt | ttgttttaaa | taaaaataag | tgtacaataa | gtgtttttgt | attgaaagct | 5760 |
| tttgttatca | agattttcat | acttttacct | tccatggctc | ttttttaagat | tgatactttt | 5820 |
| aagaggtggc | tgatattctg | caacactgta | cacataaaaa | atacggtaag | gatactttac | 5880 |
| atggttaagg | taaagtaagt | ctccagttgg | ccaccattag | ctataatggc | actttgtttg | 5940 |
| tgttgttgga | aaaagtcaca | ttgccattaa | actttccttg | tctgtctagt | taatattgtg | 6000 |
| aagaaaaata | aagtacagtg | tgagatactg | | | | 6030 |

<210> SEQ ID NO 290
<211> LENGTH: 10987
<212> TYPE: DNA
<213> ORGANISM: Homo sapiens

<400> SEQUENCE: 290

| | | | | | | |
|---|---|---|---|---|---|---|
| ggtggcgcga | gcttctgaaa | ctaggcggca | gaggcggagc | cgctgtggca | ctgctgcgcc | 60 |
| tctgctgcgc | ctcgggtgtc | ttttgcgcg | gtgggtcgcc | gccgggagaa | gcgtgagggg | 120 |
| acagatttgt | gaccggcgcg | gttttttgtca | gcttactccg | gccaaaaaag | aactgcacct | 180 |
| ctggagcgga | cttatttacc | aagcattgga | ggaatatcgt | aggtaaaaat | gcctattgga | 240 |
| tccaaagaga | ggccaacatt | ttttgaaatt | tttaagacac | gctgcaacaa | agcagattta | 300 |
| ggaccaataa | gtcttaattg | gtttgaagaa | cttctcttcag | aagctccacc | ctataattct | 360 |
| gaacctgcag | aagaatctga | acataaaaac | aacaattacg | aaccaaacct | atttaaaact | 420 |
| ccacaaagga | aaccatctta | taatcagctg | gcttcaactc | caataatatt | caaagagcaa | 480 |
| gggctgactc | tgccgctgta | ccaatctcct | gtaaaagaat | tagataaatt | caaattagac | 540 |
| ttaggaagga | atgttcccaa | tagtagacat | aaaagtcttc | gcacagtgaa | aactaaaatg | 600 |
| gatcaagcag | atgatgtttc | ctgtccactt | ctaaattctt | gtcttagtga | aagtcctgtt | 660 |
| gttctacaat | gtacacatgt | aacaccacaa | agagataagt | cagtggtatg | tgggagtttg | 720 |
| tttcatacac | caaagtttgt | gaagggtcgt | cagacaccaa | acatatttc | tgaaagtcta | 780 |
| ggagctgagg | tggatcctga | tatgtcttgg | tcaagttctt | tagctacacc | acccacccctt | 840 |
| agttctactg | tgctcatagt | cagaaatgaa | gaagcatctg | aaactgtatt | tcctcatgat | 900 |
| actactgcta | atgtgaaaag | ctatttttcc | aatcatgatg | aaagtctgaa | gaaaaatgat | 960 |
| agatttatcg | cttctgtgac | agacagtgaa | aacacaaatc | aaagagaagc | tgcaagtcat | 1020 |
| ggatttggaa | aaacatcagg | gaattcattt | aaagtaaata | gctgcaaaga | ccacattgga | 1080 |
| aagtcaatgc | caaatgtcct | agaagatgaa | gtatatgaaa | cagttgtaga | tacctctgaa | 1140 |
| gaagatagtt | tttcattatg | ttttttctaaa | tgtagaacaa | aaaatctaca | aaaagtaaga | 1200 |
| actagcaaga | ctaggaaaaa | aattttccat | gaagcaaacg | ctgatgaatg | tgaaaaatct | 1260 |

```
aaaaaccaag tgaaagaaaa atactcattt gtatctgaag tggaaccaaa tgatactgat    1320
ccattagatt caaatgtagc acatcagaag ccctttgaga gtggaagtga caaaatctcc    1380
aaggaagttg taccgtcttt ggcctgtgaa tggtctcaac taacccttc aggtctaaat     1440 ggagcccaga tggagaaaat acccctattg catatttctt catgtgacca aaatatttca    1500 gaaaagacc tattagacac agagaacaaa agaaagaaag attttcttac ttcagagaat     1560
tctttgccac gtatttctag cctaccaaaa tcagagaagc cattaaatga ggaaacagtg    1620
gtaaataaga gagatgaaga gcagcatctt gaatctcata cagactgcat tcttgcagta    1680
aagcaggcaa tatctggaac ttctccagtg gcttcttcat ttcagggtat caaaaagtct    1740
atattcagaa taagagaatc acctaaagag actttcaatg caagttttc aggtcatatg     1800 actgatccaa actttaaaaa agaaactgaa gcctctgaaa gtggactgga aatacatact    1860
gtttgctcac agaaggagga ctccttatgt ccaaatttaa ttgataatgg aagctggcca    1920
gccaccacca cacagaattc tgtagctttg aagaatgcag gtttaatatc cacttttgaaa   1980 aagaaaacaa ataagtttat ttatgctata catgatgaaa cattttataa aggaaaaaaa    2040
ataccgaaag accaaaaatc agaactaatt aactgttcag cccagtttga agcaaatgct    2100
tttgaagcac cacttacatt tgcaaatgct gattcaggtt tattgcattc ttctgtgaaa    2160
agaagctgtt cacagaatga ttctgaagaa ccaactttgt ccttaactag ctcttttggg    2220
acaattctga ggaaatgttc tagaaatgaa acatgttcta ataatacagt aatctctcag    2280
gatcttgatt ataagaagc aaaatgtaat aaggaaaaac tacagttatt tattaccca      2340 gaagctgatt ctctgtcatg cctgcaggaa ggacagtgtg aaaatgatcc aaaaagcaaa    2400
aaagtttcag atataaaaga agaggtcttg gctgcagcat gtcacccagt acaacattca    2460
aaagtggaat acagtgatac tgactttcaa tcccagaaaa gtcttttata tgatcatgaa    2520
aatgccagca ctcttatttt aactcctact tccaaggatg ttctgtcaaa cctagtcatg    2580
atttctagag gcaaagaatc atacaaaatg tcagacaagc tcaaaggtaa caattatgaa    2640
tctgatgttg aattaaccaa aaatattccc atggaaaaga tcaagatgt atgtgcttta     2700 aatgaaaatt ataaaaacgt tgagctgttg ccacctgaaa aatacatgag agtagcatca    2760
ccttcaagaa aggtacaatt caaccaaaac acaaatctaa gagtaatcca aaaaaatcaa    2820
gaagaaacta cttcaatttc aaaaataact gtcaatccag actctgaaga acttttctca    2880
gacaatgaga ataattttgt cttccaagta gctaatgaaa ggaataatct tgctttagga    2940
aatactaagg aacttcatga acagacttg acttgtgtaa acgaacccat tttcaagaac     3000
tctaccatgg ttttatatgg agacacaggt gataaacaag caacccaagt gtcaattaaa    3060
aaagatttgg tttatgttct tgcagaggag aacaaaaata gtgtaaagca gcatataaaa    3120
atgactctag gtcaagattt aaaatcggac atctccttga atatagataa ataccagaa     3180 aaaaataatg attacatgaa caaatgggca ggactcttag gtccaatttc aaatcacagt    3240
tttggaggta gcttcagaac agcttcaaat aaggaaatca agctctctga acataacatt    3300
aagaagagca aaatgttctt caagatatt gaagaacaat atcctactag tttagcttgt    3360
gttgaaattg taaataccctt ggcattagat aatcaaaaga aactgagcaa gcctcagtca    3420
attaatactg tatctgcaca tttacagagt agtgtagttg tttctgattg taaaaatagt    3480
catataaccc ctcagatgtt attttccaag caggatttta attcaaacca taatttaaca    3540
cctagccaaa aggcagaaat tacagaactt tctactatat tagaagaatc aggaagtcag    3600
tttgaattta ctcagtttag aaaaccaagc tacatattgc agaagagtac atttgaagtg    3660
```

| | |
|---|---|
| cctgaaaacc agatgactat cttaaagacc acttctgagg aatgcagaga tgctgatctt | 3720 |
| catgtcataa tgaatgcccc atcgattggt caggtagaca gcagcaagca atttgaaggt | 3780 |
| acagttgaaa ttaaacggaa gtttgctggc ctgttgaaaa atgactgtaa caaaagtgct | 3840 |
| tctggttatt taacagatga aaatgaagtg gggtttaggg gcttttattc tgctcatggc | 3900 |
| acaaaactga atgtttctac tgaagctctg caaaaagctg tgaaactgtt tagtgatatt | 3960 |
| gagaatatta gtgaggaaac ttctgcagag gtacatccaa taagtttatc ttcaagtaaa | 4020 |
| tgtcatgatt ctgttgtttc aatgtttaag atagaaaatc ataatgataa aactgtaagt | 4080 |
| gaaaaaaata taaatgccca actgatatta caaataata ttgaaatgac tactggcact | 4140 |
| tttgttgaag aaattactga aaattacaag agaaatactg aaaatgaaga taacaaatat | 4200 |
| actgctgcca gtagaaattc tcataactta gaatttgatg gcagtgattc aagtaaaaat | 4260 |
| gatactgttt gtattcataa agatgaaacg gacttgctat ttactgatca gcacaacata | 4320 |
| tgtcttaaat tatctggcca gtttatgaag gagggaaaca ctcagattaa agaagatttg | 4380 |
| tcagatttaa cttttttgga agttgcgaaa gctcaagaag catgtcatgg taatacttca | 4440 |
| aataaagaac agttaactgc tactaaaacg gagcaaaata taaaagattt tgagacttct | 4500 |
| gatacatttt ttcagactgc aagtgggaaa aatattagtg tcgccaaaga gtcatttaat | 4560 |
| aaaattgtaa atttctttga tcagaaacca gaagaattgc ataacttttc cttaaattct | 4620 |
| gaattacatt ctgacataag aaagaacaaa atggacattc taagttatga ggaaacagac | 4680 |
| atagttaaac acaaaatact gaaagaaagt gtcccagttg gtactggaaa tcaactagtg | 4740 |
| accttccagg gacaacccga acgtgatgaa aagatcaaag aacctactct gttgggtttt | 4800 |
| catacagcta gcgggaaaaa agttaaaatt gcaaggaat ctttggacaa agtgaaaaac | 4860 |
| cttttttgatg aaaaagagca aggtactagt gaaatcacca gttttagcca tcaatgggca | 4920 |
| aagaccctaa agtacagaga ggcctgtaaa gaccttgaat tagcatgtga gaccattgag | 4980 |
| atcacagctg ccccaaagtg taaagaaatg cagaattctc tcaataatga taaaaacctt | 5040 |
| gtttctattg agactgtggt gccacctaag ctcttaagtg ataatttatg tagacaaact | 5100 |
| gaaaatctca aaacatcaaa agtatctttt tgaaagtta agtacatga aatgtagaa | 5160 |
| aaagaaacag caaaaagtcc tgcaacttgt tacacaaatc agtccccta ttcagtcatt | 5220 |
| gaaaattcag ccttagcttt ttacacaagt tgtagtagaa aaacttctgt gagtcagact | 5280 |
| tcattacttg aagcaaaaaa atggcttaga gaaggaatat tgatggtca accagaaaga | 5340 |
| ataaatactg cagattatgt aggaaattat ttgtatgaaa ataattcaaa cagtactata | 5400 |
| gctgaaaatg acaaaaatca tctctccgaa aaacaagata cttatttaag taacagtagc | 5460 |
| atgtctaaca gctattccta ccattctgat gaggtatata tgattcagg atatctctca | 5520 |
| aaaaataaac ttgattctgg tattgagcca gtattgaaga atgttgaaga tcaaaaaaac | 5580 |
| actagttttt ccaaagtaat atccaatgta aaagatgcaa atgcataccc acaaactgta | 5640 |
| aatgaagata tttgcgttga ggaacttgtg actagctctt caccctgcaa aaataaaaat | 5700 |
| gcagccatta aattgtccat atctaatagt aataattttg aggtagggcc acctgcattt | 5760 |
| aggatagcca gtggtaaaat cgtttgtgtt tcacatgaaa caattaaaaa agtgaaagac | 5820 |
| atatttacag acagtttcag taaagtaatt aaggaaaaca acgagaataa atcaaaaatt | 5880 |
| tgccaaacga aaattatggc aggttgttac gaggcattgg atgattcaga ggatattctt | 5940 |
| cataactctc tagataatga tgaatgtagc acgcattcac ataaggtttt tgctgacatt | 6000 |

```
cagagtgaag aaattttaca acataaccaa aatatgtctg gattggagaa agtttctaaa    6060
atatcacctt gtgatgttag tttggaaact tcagatatat gtaaatgtag tataggggaag   6120 cttcataagt cagtctcatc tgcaaatact tgtgggattt ttagcacagc aagtggaaaa    6180
tctgtccagg tatcagatgc ttcattacaa aacgcaagac aagtgttttc tgaaatagaa    6240
gatagtacca agcaagtctt ttccaaagta ttgtttaaaa gtaacgaaca ttcagaccag    6300
ctcacaagag aagaaaatac tgctatacgt actccagaac atttaatatc ccaaaaaggc    6360
tttccatata atgtggtaaa ttcatctgct ttctctggat ttagtacagc aagtggaaag    6420
caagtttcca ttttagaaag ttccttacac aaagttaagg gagtgttaga ggaatttgat    6480
ttaatcagaa ctgagcatag tcttcactat tcacctacgt ctagacaaaa tgtatcaaaa    6540
atacttcctc gtgttgataa agaaaaccca gagcactgtg taaactcaga aatggaaaaa    6600
acctgcagta aagaatttaa attatcaaat aacttaaatg ttgaaggtgg ttcttcagaa    6660
aataatcact ctattaaagt ttctccatat ctctctcaat ttcaacaaga caaacaacag    6720
ttggtattag gaaccaaagt ctcacttgtt gagaacattc atgttttggg aaaagaacag    6780
gcttcaccta aaaacgtaaa aatggaaatt ggtaaaactg aaacttttc tgatgttcct    6840 gtgaaaacaa atatagaagt ttgttctact tactccaaag attcagaaaa ctactttgaa    6900
acagaagcag tagaaattgc taaagctttt atggaagatg atgaactgac agattctaaa    6960
ctgccaagtc atgccacaca ttctctttt acatgtcccg aaaatgagga aatggttttg    7020
tcaaattcaa gaattggaaa aagaagagga gagccccta tcttagtggg agaaccctca    7080
atcaaaagaa acttattaaa tgaatttgac aggataatag aaaatcaaga aaaatccta    7140 aaggcttcaa aaagcactcc agatggcaca ataaaagatc gaagattgtt tatgcatcat    7200
gtttctttag agccgattac ctgtgtaccc tttcgcacaa ctaaggaacg tcaagagata    7260
cagaatccaa attttaccgc acctggtcaa gaatttctgt ctaaatctca tttgtatgaa    7320
catctgactt tggaaaaatc ttcaagcaat ttagcagttt caggacatcc atttatcaa    7380 gtttctgcta caagaaatga aaaaatgaga cacttgatta ctacaggcag accaaccaaa    7440
gtctttgttc caccttttaa aactaaatca catttttcaca gagttgaaca gtgtgttagg    7500
aatattaact tggaggaaaa cagacaaaag caaaacattg atggacatgg ctctgatgat    7560
agtaaaaata agattaatga caatgagatt catcagttta acaaaaacaa ctccaatcaa    7620
gcagcagctg taacttttcac aaagtgtgaa gaagaacctt tagatttaat tacaagtctt    7680
cagaatgcca gagatataca ggatatgcga attaagaaga acaaaggca acgcgtcttt    7740 ccacagccag gcagtctgta tcttgcaaaa acatccactc tgcctcgaat ctctctgaaa    7800
gcagcagtag gaggccaagt tccctctgcg tgttctcata acagctgta tacgtatggc    7860 gtttctaaac attgcataaa aattaacagc aaaaatgcag agtcttttca gtttcacact    7920
gaagattatt ttggtaagga aagtttatgg actggaaaag gaatacagtt ggctgatggt    7980
ggatggctca taccctccaa tgatggaaag gctggaaaag aagaatttta tagggctctg    8040
tgtgacactc caggtgtgga tccaaagctt atttctagaa tttgggttta taatcactat    8100
agatggatca tatggaaact ggcagctatg gaatgtgcct ttcctaagga atttgctaat    8160
agatgcctaa gcccagaaag ggtgcttctt caactaaaat acagatatga tacgaaatt    8220 gatagaagca agatcggc tataaaaaag ataatggaaa gggatgacac agctgcaaaa    8280
acacttgttc tctgtgtttc tgacataatt tcattgagcg caaatatatc tgaaacttct    8340
agcaataaaa ctagtagtgc agatacccaa aaagtggcca ttattgaact tacagatggg    8400
```

```
tggtatgctg ttaaggccca gttagatcct ccctcttag ctgtcttaaa gaatggcaga    8460
ctgacagttg gtcagaagat tattcttcat ggagcagaac tggtgggctc tcctgatgcc    8520
tgtacacctc ttgaagcccc agaatctctt atgttaaaga tttctgctaa cagtactcgg    8580
cctgctcgct ggtataccaa acttggattc tttcctgacc ctagacctt tcctctgccc    8640
ttatcatcgc ttttcagtga tggaggaaat gttggttgtg ttgatgtaat tattcaaaga    8700
gcataccta tacagtggat ggagaagaca tcatctggat tatacatatt tcgcaatgaa    8760
agagaggaag aaaaggaagc agcaaaatat gtggaggccc aacaaaagag actagaagcc    8820
ttattcacta aaattcagga ggaatttgaa gaacatgaag aaaacacaac aaaaccatat    8880
ttaccatcac gtgcactaac aagacagcaa gttcgtgctt tgcaagatgg tgcagagctt    8940
tatgaagcag tgaagaatgc agcagaccca gcttaccttg agggttattt cagtgaagag    9000
cagttaagag ccttgaataa tcacaggcaa atgttgaatg ataagaaaca agctcagatc    9060
cagttggaaa ttaggaaggc catggaatct gctgaacaaa aggaacaagg tttatcaagg    9120
gatgtcacaa ccgtgtggaa gttgcgtatt gtaagctatt caaaaaaaga aaagattca    9180
gttatactga gtatttggcg tccatcatca gatttatatt ctctgttaac agaaggaaag    9240
agatacagaa tttatcatct tgcaacttca aaatctaaaa gtaaatctga aagagctaac    9300
atacagttag cagcgacaaa aaaaactcag tatcaacaac taccggtttc agatgaaatt    9360
ttatttcaga tttaccagcc acgggagccc cttcacttca gcaaattttt agatccagac    9420
tttcagccat cttgttctga ggtggaccta ataggatttg tcgtttctgt tgtgaaaaaa    9480
acaggacttg cccctttcgt ctatttgtca gacgaatgtt acaatttact ggcaataaag    9540
ttttggatag accttaatga ggacattatt aagcctcata tgttaattgc tgcaagcaac    9600
ctccagtggc gaccagaatc caatcaggc cttcttactt tatttgctgg agattttct    9660
gtgttttctg ctagtccaaa agagggccac tttcaagaga cattcaacaa aatgaaaaat    9720
actgttgaga atattgacat actttgcaat gaagcagaaa acaagcttat gcatatactg    9780
catgcaaatg atcccaagtg gtccacccca actaaagact gtacttcagg gccgtacact    9840
gctcaaatca ttcctggtac aggaaacaag cttctgatgt cttctcctaa ttgtgagata    9900
tattatcaaa gtcctttatc actttgtatg gccaaaagga gtctgttttc cacacctgtc    9960
tcagcccaga tgacttcaaa gtcttgtaaa ggggagaaag agattgatga ccaaaagaac   10020
tgcaaaaaga gaagagcctt ggatttcttg agtagactgc cttaccctcc acctgttagt   10080
cccatttgta catttgttttc tccggctgca cagaaggcat ttcagccacc aaggagttgt   10140
ggcaccaaat acgaaacacc cataaagaaa aagaactga attctcctca gatgactcca   10200
tttaaaaat tcaatgaaat ttctcttttg gaaagtaatt caatagctga cgaagaactt   10260
gcattgataa atacccaagc tctttttgtct ggttcaacag gagaaaaaca atttatatct   10320
gtcagtgaat ccactaggac tgctcccacc agttcagaag attatctcag actgaaacga   10380
cgttgtacta catctctgat caaagaacag gagagttccc aggccagtac ggaagaatgt   10440
gagaaaaata agcaggacac aattacaact aaaaaatata tctaagcatt tgcaaaggcg   10500
acaataaatt attgacgctt aacctttcca gtttataaga ctggaatata atttcaaacc   10560
acacattagt acttatgttg cacaatgaga aaagaaatta gtttcaaatt tacctcagcg   10620
tttgtgtatc gggcaaaaat cgttttgccc gattccgtat tggtatactt ttgcttcagt   10680
tgcatatctt aaaactaaat gtaatttatt aactaatcaa gaaaaacatc tttggctgag   10740
```

```
ctcggtggct catgcctgta atcccaacac tttgagaagc tgaggtggga ggagtgcttg    10800
aggccaggag ttcaagacca gcctgggcaa catagggaga cccccatctt tacgaagaaa    10860
aaaaaaaagg ggaaaagaaa atcttttaaa tctttggatt tgatcactac aagtattatt    10920
ttacaatcaa caaaatggtc atccaaactc aaacttgaga aaatatcttg ctttcaaatt    10980
gacacta                                                              10987

<210> SEQ ID NO 291
<211> LENGTH: 1552
<212> TYPE: DNA
<213> ORGANISM: Homo sapiens

<400> SEQUENCE: 291
gcccgtacac accgtgtgct gggacacccc acagtcagcc gcatggctcc cctgtgcccc      60
agcccctggc tccctctgtt gatcccggcc cctgctccag gcctcactgt gcaactgctg     120
ctgtcactgc tgcttctgat gcctgtccat ccccagaggt tgcccccgga tgcaggaggat   180 tccccctggg gaggaggctc ttctggggaa gatgacccac tgggcgagga ggatctgccc     240
agtgaagagg attcacccag agaggaggat ccacccggag aggaggatct acctggagag     300
gaggatctac ctggagagga ggatctacct gaagttaagc ctaaatcaga agaagggc       360 tccctgaagt tagaggatct acctactgtt gaggctcctg gagatcctca gaaccccag      420 aataatgccc acaggacaa agaaggggat gaccagagtc attggcgcta tggaggcgac      480 ccgcctggc cccgggtgtc cccagcctgc gcggccgct tccagtcccc ggtggatatc       540
cgcccccagc tcgccgcctt ctgcccggcc ctgcgccccc tggaactcct gggcttccag      600
ctcccgccgc tccagaact gcgcctgcgc aacaatggcc acagtgtgca actgaccctg      660
cctcctgggc tagagatggc tctgggtccc gggcgggagt accgggctct gcagctgcat      720
ctgcactggg gggctgcagg tcgtccgggc tcggagcaca ctgtggaagg ccaccgtttc      780
cctgccgaga tccacgtggt tcacctcagc accgcctttg ccagagttga cgaggccttg      840
gggcgcccgg gaggcctggc cgtgttggcc gcctttctgg aggagggccc ggaagaaaac      900
agtgcctatg agcagttgct gtctcgcttg aagaaatcg ctgaggaagg ctcagagact       960
caggtcccag gactggacat atctgcactc ctgcccctg acttcagccg ctacttccaa      1020
tatgaggggt ctctgactac accgcccctgt gccagggtg tcatctggac tgtgtttaac     1080
cagacagtga tgctgagtgc taagcagctc cacaccctct ctgacaccct gtggggacct    1140
ggtgactctc ggctacagct gaacttccga gcgacgcagc ctttgaatgg gcgagtgatt     1200
gaggcctcct tccctgctgg agtggacagc agtcctcggg ctgctgagcc agtccagctg    1260
aattcctgcc tggctgctgg tgacatccta gccctggttt ttggcctcct ttttgctgtc   1320
accagcgtcg cgttccttgt gcagatgaga aggcagcaca aagggaac caaaggggt        1380 gtgagctacc gcccagcaga ggtagccgag actgagcct agaggctgga tcttggaaa     1440 tgtgagaagc cagccagagg catctgaggg ggagccggta actgtcctgt cctgctcatt    1500
atgccacttc cttttaactg ccaagaaatt ttttaaaata aatatttata at             1552

<210> SEQ ID NO 292
<211> LENGTH: 1578
<212> TYPE: DNA
<213> ORGANISM: Homo sapiens

<400> SEQUENCE: 292
acgaacaggc caataaggag ggagcagtgc ggggtttaaa tctgaggcta ggctggctct      60
```

```
tctcggcgtg ctgcggcgga acggctgttg gtttctgctg gttgtaggtc cttggctggt    120
cgggcctccg gtgttctgct tctccccgct gagctgctgc ctggtgaaga ggaagccatg    180
gcgctccgag tcaccaggaa ctcgaaaatt aatgctgaaa ataaggcgaa gatcaacatg    240
gcaggcgcaa agcgcgttcc tacggcccct gctgcaacct ccaagcccgg actgaggcca    300
agaacagctc ttggggacat tggtaacaaa gtcagtgaac aactgcaggc caaaatgcct    360
atgaagaagg aagcaaaacc ttcagctact ggaaaagtca ttgataaaaa actaccaaaa    420
cctcttgaaa aggtacctat gctggtgcca gtgccagtgt ctgagccagt gccagagcca    480
gaacctgagc cagaacctga gcctgttaaa gaagaaaaac tttcgcctga gcctattttg    540
gttgatactg cctctccaag cccaatggaa acatctggat gtgccctgc agaagaagac    600 ctgtgtcagg ctttctctga tgtaattctt gcagtaaatg atgtggatgc agaagatgga    660
gctgatccaa acctttgtag tgaatatgtg aaagatattt atgcttatct gagacaactt    720
gaggaagagc aagcagtcag accaaaatac ctactgggtc gggaagtcac tggaaacatg    780
agagccatcc taattgactg ctagtacag gttcaaatga aattcaggtt gttgcaggag    840
accatgtaca tgactgtctc cattattgat cggttcatgc agaataattg tgtgcccaag    900
aagatgctgc agctggttgg tgtcactgcc atgtttattg caagcaaata tgaagaaatg    960
taccctccag aaattggtga ctttgctttt gtgactgaca cacttatac taagcaccaa   1020 atcagacaga tggaaatgaa gattctaaga gctttaaact ttggtctggg tcggcctcta   1080
cctttgcact tccttcggag agcatctaag attggagagg ttgatgtcga gcaacatact   1140
ttggccaaat acctgatgga actaactatg ttggactatg acatggtgca ctttcctcct   1200
tctcaaattg cagcaggagc ttttttgctta gcactgaaaa ttctggataa tggtgaatgg   1260
acaccaactc tacaacatta cctgtcatat actgaagaat ctcttcttcc agttatgcag   1320
cacctggcta gaatgtgagt catggtaaat caaggactta caaagcacat gactgtcaag   1380
aacaagtatg ccacatcgaa gcatgctaag atcagcactc taccacagct gaattctgca   1440
ctagttcaag atttagccaa ggctgtggca aggtgtaac ttgtaaactt gagttggagt   1500
actatattta caaataaaat tggcaccatg tgccatctgt aaaaaaaaa aaaaaaaaa   1560 aaaaaaaaaa aaaaaaaa                                                 1578

<210> SEQ ID NO 293
<211> LENGTH: 3195
<212> TYPE: DNA
<213> ORGANISM: Homo sapiens

<400> SEQUENCE: 293
agaggcttcc ctggctggtg cctgagcccg gcgtccctcg cccccgccc tccccgcatc      60 cctctcctcc ctcgcgcctg gccctgtggc tcttcctccc tccctccttc ccccccccc     120 caccctcgc ccgctgcctc cctcggccca gccagctgtg ccggcgtttg ttggctgccc    180
tgcgcccggc cctccagcca gcttctgcc ggccccgccg cgatggaggt gccccagccg    240
gagcccgcgc caggctcggc tctcagtcca gcaggcgtgt gcggtggcgc ccagcgtccg    300
ggccacctcc cgggcctcct gctgggatct catggcctcc tggggtcccc ggtgcgggcg    360
gccgcttcct cgccggtcac cacctcacc cagaccatgc acgacctcgc cgggctcggc    420
agccgcagcc gcctgacgca cctatccctg tctcgacggg catccgaatc ctccctgtcg    480
tctgaatcct ccgaatcttc tgatgcaggt ctctgcatgg attcccccag ccctatggac    540
```

```
ccccacatgg cggagcagac gtttgaacag gccatccagg cagccagccg gatcattcga    600
aacgagcagt ttgccatcag acgcttccag tctatgccgg tgaggctgct gggccacagc    660
cccgtgcttc ggaacatcac caactcccag gcgcccgacg gccggaggaa gagcgaggcg    720
ggcagtggag ctgccagcag ctctggggaa gacaaggaga atgtgcgctt ctggaaggcc    780
ggggtgggag ctctccggga agaggagggg gcatgctggg gtggttccct ggcatgtgag    840
gaccctcctc tcccatcttg gctgcaggat ggatttgtct tcaagatgcc atggaagccc    900
acacatccca gctccaccca tgctctggca gagtgggcca gccgcaggga agcctttgcc    960
cagagaccca gctcggcccc cgacctgatg tgtctcagtc ctgaccggaa gatggaagtg   1020
gaggagctca gcccctggc cctaggtcgc ttctctctga cccctgcaga gggggatact   1080
gaggaagatg atggatttgt ggacatccta gagagtgact taaaggatga tgatgcagtt   1140
ccccaggca tggagagtct cattagtgcc ccactggtca agaccttgga aaaggaagag   1200
gaaaaggacc tcgtcatgta cagcaagtgc cagcggctct tccgctctcc gtccatgccc   1260
tgcagcgtga tccggcccat cctcaagagg ctggagcggc cccaggacag ggacacgccc   1320
gtgcagaata gcggaggcg gagcgtgacc cctcctgagg agcagcagga ggctgaggaa   1380
cctaaagccc gcgtcctccg ctcaaaatca ctgtgtcacg atgagatcga gaacctcctg   1440
gacagtgacc accgagagct gattggagat tactctaagg ccttcctcct acagacagta   1500
gacggaaagc accaagacct caagtacatc tcaccagaaa cgatggtggc cctattgacg   1560
ggcaagttca gcaacatcgt ggataagttt gtgattgtag actgcagata cccctatgaa   1620
tatgaaggcg ggcacatcaa gactgcggtg aacttgcccc tggaacgcga cgccgagagc   1680
ttcctactga gagcccat cgcgccctgt agcctggaca agagagtcat cctcattttc   1740
cactgtgaat tctcatctga gcgtgggccc cgcatgtgcc gtttcatcag ggaacgagac   1800
cgtgctgtca acgactaccc cagcctctac taccctgaga tgtatatcct gaaaggcggc   1860
tacaaggagt tcttccctca gcacccgaac ttctgtgaac cccaggacta ccggcccatg   1920
aaccacgagg ccttcaagga tgagctaaag accttccgcc tcaagactcg cagctgggct   1980
ggggagcgga gccggcggga gctctgtagc cggctgcagg accagtgagg ggcctgcgcc   2040
agtcctgcta cctcccttgc ctttcgaggc ctgaagccag ctgccctatg gcctgccgg   2100
gctgagggcc tgctggaggc ctcaggtgct gtccatggga aagatggtgt ggtgtcctgc   2160
ctgtctgccc cagcccagat tcccctgtgt catcccatca ttttccatat cctggtgccc   2220
cccaccctg gaagagccca gtctgttgag ttagttaagt tgggttaata ccagcttaaa   2280
ggcagtattt tgtgtcctcc aggagcttct tgtttccttg ttagggttaa cccttcatct   2340
tcctgtgtcc tgaaacgctc ctttgtgtgt gtgtcagctg aggctgggga gagccgtggt   2400
ccctgaggat gggtcagagc taaactcctt cctggcctga gagtcagctc tctgccctgt   2460
gtacttcccg ggccagggct gcccctaatc tctgtaggaa ccgtggtatg tctgccatgt   2520
tgcccctttc tcttttcccc tttcctgtcc caccatacga gcacctccag cctgaacaga   2580
agctcttact ctttcctatt tcagtgttac ctgtgtgctt ggtctgtttg actttacgcc   2640
catctcagga cacttccgta gactgtttag gttcccctgt caaatatcag ttacccactc   2700
ggtcccagtt ttgttgcccc agaaagggat gttattatcc ttgggggctc ccagggcaag   2760
ggttaaggcc tgaatcatga gcctgctgga agcccagccc ctactgctgt gaaccctggg   2820
gcctgactgc tcagaacttg ctgctgtctt gttgcggatg gatggaaggt tggatgatg   2880
ggtggatggc cgtggatggc cgtggatgcg cagtgccttg catacccaaa ccaggtggga   2940
```

```
gcgttttgtt gagcatgaca cctgcagcag gaatatatgt gtgcctattt gtgtggacaa    3000
aaatatttac acttagggtt tggagctatt caagaggaaa tgtcacagaa gcagctaaac    3060
caaggactga gcaccctctg gattctgaat ctcaagatgg gggcagggct gtgcttgaag    3120
gccctgctga gtcatctgtt agggccttgg ttcaataaag cactgagcaa gttgagaaaa    3180
aaaaaaaaaa aaaaa                                                     3195

<210> SEQ ID NO 294
<211> LENGTH: 3737
<212> TYPE: DNA
<213> ORGANISM: Homo sapiens

<400> SEQUENCE: 294
ggcgtccgcg cacacctccc cgcgccgccg ccgccaccgc ccgcactccg ccgcctctgc      60
ccgcaaccgc tgagccatcc atgggggtcg cgggccgcaa ccgtcccggg gcggcctggg     120
cggtgctgct gctgctgctg ctgctgccgc cactgctgct gctggcgggg gccgtcccgc     180
cgggtcgggg ccgtgccgcg gggccgcagg aggatgtaga tgagtgtgcc caagggctag     240
atgactgcca tgccgacgcc ctgtgtcaga acacacccac ctcctacaag tgctcctgca     300
agcctggcta ccaaggggaa ggcaggcagt gtgaggacat cgatgaatgt ggaaatgagc     360
tcaatggagg ctgtgtccat gactgtttga atattccagg caattatcgt tgcacttgtt     420
ttgatggctt catgttggct catgacggtc ataattgtct tgatgtggac gagtgcctgg     480
agaacaatgg cggctgccag cataccctgt caacgtcat ggggagctat gagtgctgct     540
```
(Note: line at 540 — best reading)
```
gcaaggaggg gttttcctg agtgacaatc agcacacctg cattcaccgc tcggaagagg     600
gcctgagctg catgaataag gatcacggct gtagtcacat ctgcaaggag gccccaaggg     660
gcagcgtcgc ctgtgagtgc aggcctggtt ttgagctggc caagaaccag agagactgca     720
tcttgacctg taaccatggg aacgtgggt gccagcactc ctgtgacgat acagccgatg     780
gcccagagtg cagctgccat ccacagtaca gatgcacac agatgggagg agctgccttg     840
agcgagagga cactgtcctg gaggtgacag agagcaacac cacatcagtg gtggatgggg     900
ataaacgggt gaaacggcgg ctgctcatgg aaacgtgtgc tgtcaacaat ggaggctgtg     960
accgcacctg taaggatact tcgacaggtg tccactgcag ttgtcctgtt ggattcactc    1020
tccagttgga tgggaagaca tgtaaagata ttgatgagtg ccagacccgc aatggaggtt    1080
gtgatcattt ctgcaaaaac atcgtgggca gttttgactg cggctgcaag aaaggattta    1140
aattattaac agatgagaag tcttgccaag atgtggatga gtgctctttg gataggacct    1200
gtgaccacag ctgcatcaac caccctggca catttgcttg tgcttgcaac cgagggtaca    1260
ccctgtatgg cttcacccac tgtggagaca ccaatgagtg cagcatcaac aacggaggct    1320
gtcagcaggt ctgtgtgaac acagtgggca gctatgaatg ccagtgccac cctgggtaca    1380
agctccactg gaataaaaaa gactgtgtgg aagtgaaggg gctcctgccc acaagtgtgt    1440
caccccgtgt gtccctgcac tgcggtaaga gtggtggagg agacgggtgc ttcctcagat    1500
gtcactctgg cattcacctc tcttcagatg tcaccaccat caggacaagt gtaacctta    1560 agctaaatga aggcaagtgt agtttgaaaa atgctgagct gtttcccgag ggtctgcgac    1620
cagcactacc agagaagcac agctcagtaa aagagagctt ccgctacgta aaccttacat    1680
gcagctctgg caagcaagtc ccaggagccc ctgccgacc aagcacccct aaggaaatgt    1740
ttatcactgt tgagtttgag cttgaaacta accaaaagga ggtgacagct tcttgtgacc    1800
```

```
tgagctgcat cgtaaagcga accgagaagc ggctccgtaa agccatccgc acgctcagaa   1860
aggccgtcca cagggagcag tttcacctcc agctctcagg catgaacctc gacgtggcta   1920
aaaagcctcc cagaacatct gaacgccagg cagagtcctg tggagtgggc cagggtcatg   1980
cagaaaacca atgtgtcagt tgcagggctg ggacctatta tgatggagca cgagaacgct   2040
gcattttatg tccaaatgga accttccaaa atgaggaagg acaaatgact tgtgaaccat   2100
gcccaagacc aggaaattct ggggccctga agaccccaga agcttggaat atgtctgaat   2160
gtggaggtct gtgtcaacct ggtgaatatt ctgcagatgg ctttgcacct tgccagctct   2220
gtgccctggg cacgttccag cctgaagctg gtcgaacttc ctgcttcccc tgtggaggag   2280
gccttgccac caaacatcag ggagctactt cctttcagga ctgtgaaacc agagttcaat   2340
gttcacctgg acatttctac aacaccacca ctcaccgatg tattcgttgc ccagtgggaa   2400
cataccagcc tgaatttgga aaaaataatt gtgtttcttg cccaggaaat actacgactg   2460
actttgatgg ctccacaaac ataacccagt gtaaaaacag aagatgtgga ggggagctgg   2520
gagatttcac tgggtacatt gaatccccaa actacccagg caattaccca gccaacaccg   2580
agtgtacgtg gaccatcaac ccacccccca agcgccgcat cctgatcgtg gtccctgaga   2640
tcttcctgcc catagaggac gactgtgggg actatctggt gatgcggaaa acctcttcat   2700
ccaattctgt gacaacatat gaaacctgcc agacctacga acgccccatc gccttcacct   2760
ccaggtcaaa gaagctgtgg attcagttca gtccaatga agggaacagc gctagagggt   2820
tccaggtccc atacgtgaca tatgatgagg actaccagga actcattgaa gacatagttc   2880
gagatggcag gctctatgca tctgagaacc atcaggaaat acttaaggat aagaaactta   2940
tcaaggctct gtttgatgtc ctggcccatc cccagaacta tttcaagtac acagcccagg   3000
agtcccgaga gatgtttcca agatcgttca tccgattgct acgttccaaa gtgtccaggt   3060
ttttgagacc ttacaaatga ctcagcccac gtgccactca atacaaatgt tctgctatag   3120
ggttggtggg acagagctgt cttccttctg catgtcagca cagtcgggta ttgctgcctc   3180
ccgtatcagt gactcattag agttcaattt ttatagataa tacagatatt ttggtaaatt   3240
gaacttggtt tttctttccc agcatcgtgg atgtagactg agaatggctt tgagtggcat   3300
cagcttctca ctgctgtggg cggatgtctt ggatagatca cgggctggct gagctggact   3360
ttggtcagcc taggtgagac tcacctgtcc ttctggggtc ttactcctcc tcaaggagtc   3420
tgtagtggaa aggaggccac agaataagct gcttattctg aaacttcagc ttcctctagc   3480
ccggccctct ctaagggagc cctctgcact cgtgtgcagg ctctgaccag gcagaacagg   3540
caagagggga gggaaggaga cccctgcagg ctccctccac ccaccttgag acctgggagg   3600
actcagtttc tccacagcct tctccagcct gtgtgataca agtttgatcc caggaacttg   3660
agttctaagc agtgctcgtg aaaaaaaaaa gcagaaagaa ttagaaataa ataaaaacta   3720
agcacttctg gagacat                                                  3737

<210> SEQ ID NO 295
<211> LENGTH: 2042
<212> TYPE: DNA
<213> ORGANISM: Homo sapiens

<400> SEQUENCE: 295
ggggccagtc gttcgccgga aagcatttgt ctcccacctc atcataacaa caattaattt     60
cctctggggc ctgaggaggg cagaatttca accttcggtg tgcttgggag tggcgattgt    120
gatttacacg acaaaatgcc gaggtgctcg gtggagtcat ggcagtgccc tttgtggaag    180
```

```
actgggactt ggtgcaaacc ctgggagaag gtgcctatgg agaagttcaa cttgctgtga    240
atagagtaac tgaagaagca gtcgcagtga agattgtaga tatgaagcgt gccgtagact    300
gtccagaaaa tattaagaaa gagatctgta tcaataaaat gctaaatcat gaaaatgtag    360
taaaattcta tggtcacagg agagaaggca atatccaata tttatttctg gagtactgta    420
gtggaggaga gcttttgac agaatagagc cagacatagg catgcctgaa ccagatgctc     480
agagattctt ccatcaactc atggcagggg tggtttatct gcatggtatt ggaataactc    540
acagggatat taaaccagaa aatcttctgt tggatgaaag ggataacctc aaaatctcag    600
actttggctt ggcaacagta tttcggtata ataatcgtga gcgtttgttg aacaagatgt    660
gtggtacttt accatatgtt gctccagaac ttctgaagag aagagaattt catgcagaac    720
cagttgatgt ttggtcctgt ggaatagtac ttactgcaat gctcgctgga gaattgccat    780
gggaccaacc cagtgacagc tgtcaggagt attctgactg gaagaaaaa aaaacatacc     840 tcaacccttg gaaaaaaatc gattctgctc ctctagctct gctgcataaa atcttagttg    900
agaatccatc agcaagaatt accattccag acatcaaaaa agatagatgg tacaacaaac    960
ccctcaagaa aggggcaaaa aggccccgag tcacttcagg tggtgtgtca gagtctccca    1020
gtggattttc taagcacatt caatccaatt tggacttctc tccagtaaac agtgcttcta    1080
gtgaagaaaa tgtgaagtac tccagttctc agccagaacc ccgcacaggt ctttccttat    1140
gggataccag cccctcatac attgataaat tggtacaagg gatcagcttt tcccagccca    1200
catgtcctga tcatatgctt ttgaatagtc agttacttgg cacccagga tcctcacaga     1260 accctggca gcggttggtc aaaagaatga cacgattctt taccaaattg gatgcagaca     1320
aatcttatca atgcctgaaa gagacttgtg agaagttggg ctatcaatgg aagaaaagtt    1380
gtatgaatca ggttactata tcaacaactg ataggagaaa caataaactc attttcaaag    1440
tgaatttgtt agaaatggat gataaaatat tggttgactt ccggctttct aagggtgatg    1500
gattggagtt caagagacac ttcctgaaga ttaaagggaa gctgattgat attgtgagca    1560
gccagaaggt ttggcttcct gccacatgat cggaccatcg gctctgggga atcctggtga    1620
atatagtgct gctatgttga cattattctt cctagagaag attatcctgt cctgcaaact    1680
gcaaatagta gttcctgaag tgttcacttc cctgtttatc caaacatctt ccaatttatt    1740
ttgtttgttc ggcatacaaa taatacctat atcttaattg taagcaaaac tttggggaaa    1800
ggatgaatag aattcatttg attatttctt catgtgtgtt tagtatctga atttgaaact    1860
catctggtgg aaaccaagtt tcaggggaca tgagttttcc agctttata cacacgtatc     1920 tcattttat caaacatttt tgtttaattc aaaaagtaca tatttcttcc atgttgattt     1980
aattctaaga tgaaccaata aagacataat tcttgcaaaa aaaaaaaaaa aaaaaaaaa     2040 aa                                                                   2042

<210> SEQ ID NO 296
<211> LENGTH: 2547
<212> TYPE: DNA
<213> ORGANISM: Homo sapiens

<400> SEQUENCE: 296
cttacaaggt acagtcctct gctcagggg gccaggaggg tcttataggc atcattcacc      60
agggtcgaat gcttctctga gaagtccttt tcagtctgag acctctggct gaagaaatct    120
gggtggacaa gacgctgcag ttgctggtac ctgtgctgga gcttcgctgt atcaactctg    180
```

```
aaggaacggt tgcagtccat aaggctgaag tagtctcgag tggggtcagg tgcctgcagc    240
gctcggcact gtgggcagaa gaacctgtcc tcccgcccgg ggcccatgg gccgccgcag    300 ttccaacagc ggggataatt gcttcccgcc tgcgacgcag catcgcagct tagcggtctc    360
cttctgggaa ccctgtcgg ccaaaacccc cacacccgga gcaaagcccc ggctctcccc    420
cgccacatct ggccggcggc ctatctagcc gtggtcactc gtggggaaaa gcaaagagag    480
cgtctaacca gactaatgtt gctgattggc tggggagtcg aggggcggg atcacccgag    540 gggaacccgg gttctaagtt ccgctctccc ttctaaacta caactcccag gaggcattga    600
ggcggcgcct gacggccaca tctgctgctc ctcattggtc cggcggcagg ggaggggtt    660 ttgattggct gagggtggag tttgtatctg caggtttagc gccactctgc tggctgaggc    720
tgcggagagt gtgcggctcc aggtgggctc acgcggtcgt gatgtctcgg gagtcggatg    780
ttgaggctca gcagtctcat ggcagcagtg cctgttcaca gccccatggc agcgttaccc    840
agtcccaagg ctcctcctca cagtcccagg gcatatccag ctcctctacc agcacgatgc    900
caaactccag ccagtcctct cactccagct ctgggacact gagctcctta gagacagtgt    960
ccactcagga actctattct attcctgagg accaagaacc tgaggaccaa gaacctgagg   1020
agcctacccc tgcccctgg gctcgattat gggcccttca ggatggattt gccaatcttg   1080
aatgtgtgaa tgacaactac tggtttggga gggacaaaag ctgtgaatat tgctttgatg   1140
aaccactgct gaaagaaaca gataaatacc gaacatacag caagaaacac tttcggattt   1200
tcagggaagt gggtcctaaa aactcttaca ttgcatacat agaagatcac agtggcaatg   1260
gaacctttgt aaatacagag cttgtaggga aggaaaacg ccgtcctttg aataacaatt   1320
ctgaaattgc actgtcacta agcagaaata agtttttgt ctttttgat ctgactgtag   1380 atgatcagtc agtttatcct aaggcattaa gagatgaata catcatgtca aaaactcttg   1440
gaagtggtgc ctgtgagag gtaaagctgg ctttcgagag gaaaacatgt aagaaagtag   1500
ccataaagat catcagcaaa aggaagtttg ctattggttc agcaagagag gcagacccag   1560
ctctcaatgt tgaaacagaa atagaaattt tgaaaaagct aaatcatcct tgcatcatca   1620
agattaaaaa ctttttgat gcagaagatt attatattgt tttggaattg atggaagggg   1680
gagagctgtt tgacaaagtg gtggggaata acgcctgaa agaagctacc tgcaagctct   1740 attttttacca gatgctcttg gctgtgcagt accttcatga aaacggtatt atacaccgtg   1800
acttaaagcc agagaatgtt ttactgtcat ctcaagaaga ggactgtctt ataaagatta   1860
ctgattttgg gcactccaag attttgggag agacctctct catgagaacc ttatgtggaa   1920 ccccaccta cttggcgcct gaagttcttg tttctgttgg gactgctggg tataaccgtg   1980
ctgtggactg ctggagttta ggagttattc tttttatctg ccttagtggg tatccacctt   2040
tctctgagca taggactcaa gtgtcactga aggatcagat caccagtgga aaatacaact   2100
tcattcctga agtctgggca gaagtctcag agaaagctct ggaccttgtc aagaagttgt   2160
tggtagtgga tccaaaggca cgttttacga cagaagaagc cttaagacac ccgtggcttc   2220
aggatgaaga catgaagaga aagtttcaag atcttctgtc tgaggaaaat gaatccacag   2280
ctctacccca ggttctagcc cagccttcta ctagtcgaaa gcggcccgt gaaggggaag   2340 ccgagggtgc cgagaccaca aagcgcccag ctgtgtgtgc tgctgtgttg tgaactccgt   2400
ggtttgaaca cgaaagaaat gtaccttctt tcactctgtc atctttcttt tctttgagtc   2460 tgtttttta tagtttgtat tttaattatg ggaataattg cttttcaca gtcactgatg   2520 tacaattaaa aacctgatgg aacctgg                                      2547
```

<210> SEQ ID NO 297
<211> LENGTH: 2768
<212> TYPE: DNA
<213> ORGANISM: Homo sapiens

<400> SEQUENCE: 297

| | | | | | |
|---|---|---|---|---|---|
| cactgctgtg | cagggcagga | aagctccatg | cacatagccc | agcaaagagc | aacacagagc | 60 |
| tgaaaggaag | actcagagga | gagagataag | taaggaaagt | agtgatggct | ctcatcccag | 120 |
| acttggccat | ggaaacctgg | cttctcctgg | ctgtcagcct | ggtgctcctc | tatctatatg | 180 |
| gaacccattc | acatggactt | tttaagaagc | ttggaattcc | agggcccaca | cctctgcctt | 240 |
| ttttgggaaa | tattttgtcc | taccataagg | gcttttgtat | gtttgacatg | gaatgtcata | 300 |
| aaaagtatgg | aaaagtgtgg | ggcttttatg | atggtcaaca | gcctgtgctg | gctatacag | 360 |
| atcctgacat | gatcaaaaca | gtgctagtga | agaatgtta | ttctgtcttc | acaaaccgga | 420 |
| ggccttttgg | tccagtggga | tttatgaaaa | gtgccatctc | tatagctgag | gatgaagaat | 480 |
| ggaagagatt | acgatcattg | ctgtctccaa | ccttcaccag | tggaaaactc | aaggagatgg | 540 |
| tccctatcat | tgcccagtat | ggagatgtgt | tggtgagaaa | tctgaggcgg | aagcagaga | 600 |
| caggcaagcc | tgtcaccttg | aaagacgtct | tggggccta | cagcatggat | gtgatcacta | 660 |
| gcacatcatt | tggagtgaac | atcgactctc | tcaacaatcc | acaagacccc | tttgtggaaa | 720 |
| acaccaagaa | gcttttaaga | tttgattttt | tggatccatt | ctttctctca | ataacagtct | 780 |
| ttccattcct | catcccaatt | cttgaagtat | taaatatctg | tgtgtttcca | agagaagtta | 840 |
| caaatttttt | aagaaaatct | gtaaaaagga | tgaaagaaag | tcgcctcgaa | gatacacaaa | 900 |
| agcaccgagt | ggatttcctt | cagctgatga | ttgactctca | gaattcaaaa | gaaactgagt | 960 |
| cccacaaagc | tctgtccgat | ctggagctcg | tgcccaatc | aattatcttt | attttgctg | 1020 |
| gctatgaaac | cacgagcagt | gttctctcct | tcattatgta | tgaactggcc | actcaccctg | 1080 |
| atgtccagca | gaaactgcag | gaggaaattg | atgcagtttt | acccaataag | gcaccaccca | 1140 |
| cctatgatac | tgtgctacag | atggagtatc | ttgacatggt | ggtgaatgaa | acgctcagat | 1200 |
| tattcccaat | tgctatgaga | cttgagaggg | tctgcaaaaa | agatgttgag | atcaatggga | 1260 |
| tgttcattcc | caaaggggtg | gtggtgatga | ttccaagcta | tgctcttcac | cgtgacccaa | 1320 |
| agtactggac | agagcctgag | aagttcctcc | ctgaaagatt | cagcaagaag | aacaaggaca | 1380 |
| acatagatcc | ttacatatac | acaccctttg | gaagtggacc | cagaaactgc | attggcatga | 1440 |
| ggtttgctct | catgaacatg | aaacttgctc | taatcagagt | ccttcagaac | ttctccttca | 1500 |
| aaccttgtaa | agaaacacag | atcccccctga | aattaagctt | aggaggactt | cttcaaccag | 1560 |
| aaaaacccgt | tgttctaaag | gttgagtcaa | gggatggcac | cgtaagtgga | gcctgaattt | 1620 |
| tcctaaggac | ttctgctttg | ctcttcaaga | aatctgtgcc | tgagaacacc | agagacctca | 1680 |
| aattactttg | tgaatagaac | tctgaaatga | agatgggctt | catccaatgg | actgcataaa | 1740 |
| taaccgggga | ttctgtacat | gcattgagct | ctctcattgt | ctgtgtagag | tgttatactt | 1800 |
| gggaatataa | aggaggtgac | caaatcagtg | tgaggaggta | gatttggctc | ctctgcttct | 1860 |
| cacgggacta | tttccaccac | ccccagttag | caccattaac | tcctcctgag | ctctgataag | 1920 |
| agaatcaaca | tttctcaata | atttcctcca | caaattatta | atgaaaataa | gaattatttt | 1980 |
| gatggctcta | acaatgacat | ttatatcaca | tgttttctct | ggagtattct | ataagttta | 2040 |
| tgttaaatca | ataaagacca | ctttacaaaa | gtattatcag | atgctttcct | gcacattaag | 2100 |

-continued

```
gagaaatcta tagaactgaa tgagaaccaa caagtaaata tttttggtca ttgtaatcac    2160
tgttggcgtg gggcctttgt cagaactaga atttgattat taacataggt gaaagttaat    2220
ccactgtgac tttgcccatt gtttagaaag aatattcata gtttaattat gcctttttg     2280 atcaggcaca gtggctcacg cctgtaatcc tagcagtttg ggaggctgag ccgggtggat    2340
cgcctgaggt caggagttca agacaagcct ggcctacatg gttgaaaccc catctctact    2400
aaaaatacac aaattagcta ggcatggtgg actcgcctgt aatctcacta cacaggaggc    2460
tgaggcagga gaatcacttg aacctgggag gcggatgttg aagtgagctg agattgcacc    2520
actgcactcc agtctgggtg agagtgagac tcagtcttaa aaaaatatgc cttttgaag    2580 cacgtacatt ttgtaacaaa gaactgaagc tcttattata ttattagttt tgatttaatg    2640
ttttcagccc atctcctttc atatttctgg gagacagaaa acatgtttcc ctacacctct    2700
tgcattccat cctcaacacc caactgtctc gatgcaatga acacttaata aaaaacagtc    2760
gattggtc                                                             2768

<210> SEQ ID NO 298
<211> LENGTH: 1358
<212> TYPE: DNA
<213> ORGANISM: Homo sapiens

<400> SEQUENCE: 298
ggcgtccgcg cgctgcacaa tggcggctct gaagagttgg ctgtcgcgca gcgtaacttc      60
attcttcagg tacagacagt gtttgtgtgt tcctgttgtg gctaacttta agaagcggtg     120
tttctcagaa ttgataagac catggcacaa aactgtgacg attggctttg gagtaaccct     180
gtgtgcggtt cctattgcac agaaatcaga gcctcattcc cttagtagtg aagcattgat     240
gaggagagca gtgtctttgg taacagatag cacctctacc tttctctctc agaccacata     300
tgcgttgatt gaagctatta ctgaatatac taaggctgtt tataccttaa cttctcttta     360
ccgacaatat acaagtttac ttgggaaaat gaattcagag gaggaagatg aagtgtggca     420
ggtgatcata ggagccagag ctgagatgac ttcaaaacac caagagtact gaagctgga     480 aaccacttgg atgactgcag ttggtctttc agagatggca gcagaagctg catatcaaac     540
tggcgcagat caggcctcta taaccgccag gaatcacatt cagctggtga aactgcaggt     600
ggaagaggtg caccagctct cccggaaagc agaaaccaag ctggcagaag cacagataga     660
agagctccgt cagaaaacac aggaggaagg ggaggagcgg gctgagtcgg agcaggaggc     720
ctacctgcgt gaggattgag ggcctgagca cactgccctg tctccccact cagtggggaa     780
agcaggggca gatgccaccc tgcccagggt tggcatgact gtctgtgcac cgagaagagg     840
cggcaggtcc tgccctggcc aatcaggcga gacgcctttg tgagctgtga gtgcctcctg     900
tggtctcagg cttgcgctgg acctggttct tagcccttgg gcactgcacc ctgtttaaca     960
tttcacccca ctctgtacag ctgctcttac ccattttttt tacctcacac ccaaagcatt    1020
ttgcctacct gggtcagaga gaggagtcct ttttgtcatg cccttaagtt cagcaactgt    1080
ttaacctgtt ttcagtctta tttacgtcgt caaaaatgat ttagtacttg ttccctctgt    1140
tgggatgcca gttgtggcag ggggaggga acctgtccag tttgtacgat ttctttgtat     1200
gtatttctga tgtgttctct gatctgcccc cactgtcctg tgaggacagc tgaggccaag    1260
gagtgaaaaa cctattacta ctaagagaag gggtgcagag tgtttacctg gtgctctcaa    1320
caggacttaa catcaacagg acttaacaca gaaaaaaa                            1358
```

-continued

<210> SEQ ID NO 299
<211> LENGTH: 4407
<212> TYPE: DNA
<213> ORGANISM: Homo sapiens

<400> SEQUENCE: 299

| | | | | | |
|---|---|---|---|---|---|
| tttcgactcg | cgctccggct | gctgtcactt | ggctctctgg | ctggagcttg | aggacgcaag | 60 |
| gagggtttgt | cactggcaga | ctcgagactg | taggcactgc | catggcccct | gtgctcagta | 120 |
| aggactcggc | ggacatcgag | agtatcctgg | ctttaaatcc | tcgaacacaa | actcatgcaa | 180 |
| ctctgtgttc | cacttcggcc | aagaaattag | acaagaaaca | ttggaaaaga | aatcctgata | 240 |
| agaactgctt | taattgtgag | aagctggaga | ataattttga | tgacatcaag | cacacgactc | 300 |
| ttggtgagcg | aggagctctc | cgagaagcaa | tgagatgcct | gaaatgtgca | gatgccccgt | 360 |
| gtcagaagag | ctgtccaact | aatcttgata | ttaaatcatt | catcacaagt | attgcaaaca | 420 |
| agaactatta | tggagctgct | aagatgatat | tttctgacaa | cccacttggt | ctgacttgtg | 480 |
| gaatggtatg | tccaacctct | gatctatgtg | taggtggatg | caatttatat | gccactgaag | 540 |
| agggacccat | taatattggt | ggattgcagc | aatttgctac | tgaggtattc | aaagcaatga | 600 |
| gtatcccaca | gatcagaaat | ccttcgctgc | ctcccccaga | aaaaatgtct | gaagcctatt | 660 |
| ctgcaaagat | tgctctttt | ggtgctgggc | ctgcaagtat | aagttgtgct | tccttttttgg | 720 |
| ctcgattggg | gtactctgac | atcactatat | ttgaaaaaca | agaatatgtt | ggtggtttaa | 780 |
| gtacttctga | aattcctcag | ttccggctgc | cgtatgatgt | agtgaatttt | gagattgagc | 840 |
| taatgaagga | ccttggtgta | aagataattt | gcggtaaaag | cctttcagtg | aatgaaatga | 900 |
| ctcttagcac | tttgaaagaa | aaaggctaca | agctgctttt | cattggaata | ggtttgccag | 960 |
| aacccaataa | agatgccatc | ttccaaggcc | tgacgcagga | ccaggggttt | tatacatcca | 1020 |
| aagactttt | gccacttgta | gccaaaggca | gtaaagcagg | aatgtgcgcc | tgtcactctc | 1080 |
| cattgccatc | gatacgggga | gtcgtgattg | tacttgagc | tggagacact | gccttcgact | 1140 |
| gtgcaacatc | tgctctacgt | tgtggagctc | gccgagtgtt | catcgtcttc | agaaaaggct | 1200 |
| tgttaatat | aagagctgtc | cctgaggaga | tggagcttgc | taaggaagaa | aagtgtgaat | 1260 |
| ttctgccatt | cctgtcccca | cggaaggtta | tagtaaaagg | tgggagaatt | gttgctatgc | 1320 |
| agtttgttcg | gacagagcaa | gatgaaactg | gaaaatggaa | tgaagatgaa | gatcagatgg | 1380 |
| tccatctgaa | agccgatgtg | gtcatcagtg | cctttggttc | agttctgagt | gatcctaaag | 1440 |
| taaaagaagc | cttgagccct | ataaaattta | acagatgggg | tctcccagaa | gtagatccag | 1500 |
| aaactatgca | aactagtgaa | gcatgggtat | ttgcaggtgg | tgatgtcgtt | ggtttggcta | 1560 |
| acactacagt | ggaatcggtg | aatgatgaa | agcaagcttc | ttggtacatt | cacaaatacg | 1620 |
| tacagtcaca | atatggagct | tccgtttctg | ccaagcctga | actacccctc | ttttacactc | 1680 |
| ctattgatct | ggtggacatt | agtgtagaaa | tggccggatt | gaagtttata | aatccttttg | 1740 |
| gtcttgctag | cgcaactcca | gccaccagca | catcaatgat | tcgaagagct | tttgaagctg | 1800 |
| gatgggttt | tgccctcacc | aaaactttct | ctcttgataa | ggacattgtg | acaaatgttt | 1860 |
| cccccagaat | catccgggga | accacctctg | gccccatgta | tggccctgga | caaagctcct | 1920 |
| ttctgaatat | tgagctcatc | agtgagaaaa | cggctgcata | ttggtgtcaa | agtgtcactg | 1980 |
| aactaaaggc | tgacttccca | gacaacattg | tgattgctag | cattatgtgc | agttacaata | 2040 |
| aaaatgactg | gacggaactt | gccaagaagt | ctgaggattc | tggagcagat | gccctggagt | 2100 |
| taaatttatc | atgtccacat | ggcatgggag | aaagaggaat | gggcctggcc | tgtgggcagg | 2160 |

```
atccagagct ggtgcggaac atctgccgct gggttaggca agctgttcag attccttttt    2220
ttgccaagct gaccccaaat gtcactgata ttgtgagcat cgcaagagct gcaaaggaag    2280
gtggtgccaa tggcgttaca gccaccaaca ctgtctcagg tctgatggga ttaaaatctg    2340
atggcacacc ttggccagca gtggggattg caaagcgaac tacatatgga ggagtgtctg    2400
ggacagcaat cagacctatt gctttgagag ctgtgacctc cattgctcgt gctctgcctg    2460
gatttcccat tttggctact ggtggaattg actctgctga aagtggtctt cagtttctcc    2520
atagtggtgc ttccgtcctc caggtatgca gtgccattca gaatcaggat ttcactgtga    2580
tcgaagacta ctgcactggc ctcaaagccc tgctttatct gaaaagcatt gaagaactac    2640
aagactggga tggacagagt ccagctactg tgagtcacca gaaagggaaa ccagttccac    2700
gtatagctga actcatggac aagaaactgc caagttttgg accttatctg gaacagcgca    2760
agaaaatcat agcagaaaac aagattagac tgaaagaaca aaatgtagct ttttcaccac    2820
ttaagagaag ctgtttttatc cccaaaaggc ctattcctac catcaaggat gtaataggaa    2880
aagcactgca gtaccttgga acatttggtg aattgagcaa cgtagagcaa gttgtggcta    2940
tgattgatga agaaatgtgt atcaactgtg gtaaatgcta catgacctgt aatgattctg    3000
gctaccaggc tatacagttt gatccagaaa cccacctgcc caccataacc gacacttgta    3060
caggctgtac tctgtgtctc agtgtttgcc ctattgtcga ctgcatcaaa atggtttcca    3120
ggacaacacc ttatgaacca agagaggcg taccttatc tgtgaatccg gtgtgttaag    3180
gtgatttgtg aaacagttgc tgtgaacttt catgtcacct acatatgctg atctcttaaa    3240
atcatgatcc ttgtgttcag ctctttccaa attaaaacaa atatacattt tctaaataaa    3300
aatatgtaat ttcaaaatac atttgtaagt gtaaaaaatg tctcatgtca atgaccattc    3360
aattagtggc ataaaataga ataattcttt tctgaggata gtagttaaat aactgtgtgg    3420
cagttaattg gatgttcact gccagttgtc ttatgtgaaa aattaacttt ttgtgtggca    3480
attagtgtga cagtttccaa attgccctat gctgtgctcc atatttgatt tctaattgta    3540
agtgaaatta agcattttga aacaaagtac tctttaacat acaagaaaat gtatccaagg    3600
aaacatttta tcaataaaaa ttacctttaa ttttaatgct gtttctaaga aaatgtagtt    3660
agctccataa agtacaaatg aagaaagtca aaaattattt gctatggcag ataagaaag    3720 cctaaaattg agtttgtgga ctttattaag taaaatcccc ttcgctgaaa ttgcttattt    3780
ttggtgttgg atagaggata gggagaatat ttactaacta aataccattc actactcatg    3840
cgtgagatgg gtgtacaaac tcatcctctt ttaatggcat ttctctttaa actatgttcc    3900
taaccaaatg agatgatagg atagatcctg gttaccactc ttttactgtg cacatatggg    3960
ccccggaatt ctttaatagt caccttcatg attatagcaa ctaatgtttg aacaaagctc    4020
aaagtatgca atgcttcatt attcaagaat gaaaaatata atgttgataa tatatattaa    4080
gtgtgccaaa tcagtttgac tactctctgt tttagtgttt atgtttaaaa gaaatatatt    4140
ttttgttatt attagataat attttttgtat ttctctatttt tcataatcag taaatagtgt    4200
catataaact catttatctc ctcttcatgg catcttcaat atgaatctat aagtagtaaa    4260
tcagaaagta acaatctatg gcttatttct atgacaaatt caagagctag aaaaataaaa    4320
tgtttcatta tgcacttttta gaatgcata tttgccacaa aacctgtatt actgaataat    4380
atcaaataaa atatcataaa gcatttt                                        4407
```

<210> SEQ ID NO 300
<211> LENGTH: 5532

<212> TYPE: DNA
<213> ORGANISM: Homo sapiens

<400> SEQUENCE: 300

```
gccgcgctgc gccggagtcc cgagctagcc ccggcgccgc cgccgcccag accggacgac      60
aggccacctc gtcggcgtcc gcccgagtcc ccgcctcgcc gccaacgcca caaccaccgc     120
gcacggcccc ctgactccgt ccagtattga tcgggagagc cggagcgagc tcttcgggga     180
gcagcgatgc gaccctccgg gacggccggg gcagcgctcc tggcgctgct ggctgcgctc     240
tgcccggcga gtcgggctct ggaggaaaag aaagtttgcc aaggcacgag taacaagctc     300
acgcagttgg gcacttttga agatcatttt ctcagcctcc agaggatgtt caataactgt     360
gaggtggtcc ttgggaattt ggaaattacc tatgtgcaga ggaattatga tctttccttc     420
ttaaagacca tccaggaggt ggctggttat gtcctcattg ccctcaacac agtggagcga     480
attcctttgg aaaacctgca gatcatcaga ggaaatatgt actacgaaaa ttcctatgcc     540
ttagcagtct tatctaacta tgatgcaaat aaaaccggac tgaaggagct gcccatgaga     600
aatttacagg aaatcctgca tggcgccgtg cggttcagca caaccctgcc ctgtgcaac      660
gtggagagca tccagtggcg ggacatagtc agcagtgact ttctcagcaa catgtcgatg     720
gacttccaga accacctggg cagctgccaa agtgtgatcc aagctgtcc caatgggagc      780
tgctggggtg caggagagga gaactgccag aaactgacca aaatcatctg tgcccagcag     840
tgctccgggc gctgccgtgg caagtccccc agtgactgct gccacaacca gtgtgctgca     900
ggctgcacag gccccggga gagcgactgc ctggtctgcc gcaaattccg agacgaagcc     960
acgtgcaagg acacctgccc cccactcatg ctctacaacc ccaccacgta ccagatggat    1020
gtgaaccccg agggcaaata cagctttggt gccacctgcg tgaagaagtg tccccgtaat    1080
tatgtggtga cagatcacgg ctcgtgcgtc cgagcctgtg gggccgacag ctatgagatg    1140
gaggaagacg gcgtccgcaa gtgtaagaag tgcgaagggc cttgccgcaa agtgtgtaac    1200
ggaataggta ttggtgaatt taaagactca ctctccataa atgctacgaa tattaaacac    1260
ttcaaaaact gcacctccat cagtggcgat ctccacatcc tgccggtggc atttagggt     1320
gactccttca cacatactcc tcctctggat ccacaggaac tggatattct gaaaaccgta    1380
aaggaaatca cagggttttt gctgattcag gcttggcctg aaaacaggac ggacctccat    1440
gcctttgaga acctagaaat catacgcggc aggaccaagc aacatggtca gttttctctt    1500
gcagtcgtca gcctgaacat aacatccttg ggattacgct ccctcaagga gataagtgat    1560
ggagatgtga taaatttcagg aaacaaaaat ttgtgctatg caaatacaat aaactggaaa    1620
aaactgtttg ggaccctccgg tcagaaaacc aaaattataa gcaacagagg tgaaaacagc    1680
tgcaaggcca caggccaggt ctgccatgcc ttgtgctccc ccgagggctg ctggggcccg    1740
gagcccaggg actgcgtctc ttgccggaat gtcagccgag gcaggaatg cgtggacaag    1800
tgcaagcttc tggaggtga gccaagggag tttgtggaga actctgagtg catacagtgc    1860
cacccagagt gcctgcctca ggccatgaac atcacctgca caggacgggg accagacaac    1920
tgtatccagt gtgcccacta cattgacggc ccccactgcg tcaagacctg cccggcagga    1980
gtcatgggag aaaacaacac cctggtctgg aagtacgcag acgccggcca tgtgtgccac    2040
ctgtgccatc caaactgcac ctacggatgc actgggccag tcttgaagg ctgtccaacg    2100
aatgggccta agatcccgtc catcgccact gggatggtgg gggcctcct cttgctgctg    2160
gtggtggccc tggggatcgg cctcttcatg cgaaggcgcc acatcgttcg gaagcgcacg    2220
```

```
ctgcggaggc tgctgcagga gagggagctt gtggagcctc ttacacccag tggagaagct    2280
cccaaccaag ctctcttgag gatcttgaag gaaactgaat tcaaaaagat caaagtgctg    2340
ggctccggtg cgttcggcac ggtgtataag ggactctgga tcccagaagg tgagaaagtt    2400
aaaattcccg tcgctatcaa ggaattaaga gaagcaacat ctccgaaagc caacaaggaa    2460
atcctcgatg aagcctacgt gatggccagc gtggacaacc cccacgtgtg ccgcctgctg    2520
ggcatctgcc tcacctccac cgtgcaactc atcacgcagc tcatgccctt cggctgcctc    2580
ctggactatg tccgggaaca caaagacaat attggctccc agtacctgct caactggtgt    2640
gtgcagatcg caaagggcat gaactacttg gaggaccgtc gcttggtgca ccgcgacctg    2700
gcagccagga acgtactggt gaaaacaccg cagcatgtca agatcacaga ttttgggctg    2760
gccaaactgc tgggtgcgga agagaaagaa taccatgcag aaggaggcaa agtgcctatc    2820
aagtggatgg cattggaatc aattttacac agaatctata cccaccagag tgatgtctgg    2880
agctacgggg tgaccgtttg ggagttgatg acctttggat ccaagccata tgacggaatc    2940
cctgccagcg agatctcctc catcctggag aaaggagaac gcctccctca gccacccata    3000
tgtaccatcg atgtctacat gatcatggtc aagtgctgga tgatagacgc agatagtcgc    3060
ccaaagttcc gtgagttgat catcgaattc tccaaaatgg cccgagaccc ccagcgctac    3120
cttgtcattc aggggatga agaatgcat ttgccaagtc ctacagactc caacttctac    3180
cgtgccctga tggatgaaga agacatggac gacgtggtgg atgccgacga gtacctcatc    3240
ccacagcagg gcttcttcag cagcccctcc acgtcacgga ctcccctcct gagctctctg    3300
agtgcaacca gcaacaattc caccgtggct tgcattgata gaaatgggct gcaaagctgt    3360
cccatcaagg aagacagctt cttgcagcga tacagctcag accccacagg cgccttgact    3420
gaggacagca tagacgacac cttcctccca gtgcctgaat acataaacca gtccgttccc    3480
aaaaggcccg ctggctctgt gcagaatcct gtctatcaca atcagcctct gaaccccgcg    3540
cccagcagag acccacacta ccaggacccc cacagcactg cagtgggcaa ccccgagtat    3600
ctcaacactg tccagcccac ctgtgtcaac agcacattcg acagccctgc ccactgggcc    3660
cagaaaggca gccaccaaat tagcctggac aaccctgact accagcagga cttctttccc    3720
aaggaagcca gccaaatgg catctttaag ggctccacag ctgaaaatgc agaatacca    3780
agggtcgcgc cacaaaagcag tgaatttatt ggagcatgac cacggaggat agtatgagcc    3840
ctaaaaatcc agactctttc gatacccagg accaagccac agcaggtcct ccatcccaac    3900
agccatgccc gcattagctc ttagacccac agactggttt tgcaacgttt acaccgacta    3960
gccaggaagt acttccacct cgggcacatt ttgggaagtt gcattccttt gtcttcaaac    4020
tgtgaagcat ttacagaaac gcatccagca agaatattgt ccctttgagc agaaatttat    4080
ctttcaaaga ggtatatttg aaaaaaaaaa aaaagtata tgtgaggatt tttattgatt    4140
ggggatcttg gagttttttca ttgtcgctat tgattttttac ttcaatgggc tcttccaaca    4200
aggaagaagc ttgctggtag cacttgctac cctgagttca tccaggccca actgtgagca    4260
aggagcacaa gccacaagtc ttccagagga tgcttgattc cagtggttct gcttcaaggc    4320
ttccactgca aaacactaaa gatccaagaa ggccttcatg gccccagcag gccggatcgg    4380
tactgtatca agtcatggca ggtacagtag gataagccac tctgtccctt cctgggcaaa    4440
gaagaaacgg aggggatgaa ttcttcctta gacttacttt tgtaaaaatg tccccacggt    4500
acttactccc cactgatgga ccagtggttt ccagtcatga gcgttagact gacttgtttg    4560
tcttccattc cattgttttg aaactcagta tgccgcccct gtcttgctgt catgaaatca    4620
```

```
gcaagagagg atgacacatc aaataataac tcggattcca gcccacattg gattcatcag    4680
catttggacc aatagcccac agctgagaat gtggaatacc taaggataac accgcttttg    4740
ttctcgcaaa aacgtatctc ctaatttgag gctcagatga aatgcatcag gtcctttggg    4800
gcatagatca gaagactaca aaaatgaagc tgctctgaaa tctcctttag ccatcacccc    4860
aaccccccaa aattagtttg tgttacttat ggaagatagt tttctccttt tacttcactt    4920
caaaagcttt ttactcaaag agtatatgtt ccctccaggt cagctgcccc caaacccccct   4980 ccttacgctt tgtcacacaa aaagtgtctc tgccttgagt catctattca agcacttaca    5040
gctctggcca caacagggca ttttacaggt gcgaatgaca gtagcattat gagtagtgtg    5100
aattcaggta gtaaatatga aactagggtt tgaaattgat aatgctttca caacatttgc    5160
agatgtttta gaaggaaaaa agttccttcc taaaataatt tctctacaat tggaagattg    5220
gaagattcag ctagttagga gcccattttt tcctaatctg tgtgtgccct gtaacctgac    5280
tggttaacag cagtcctttg taaacagtgt tttaaactct cctagtcaat atccacccca    5340
tccaatttat caaggaagaa atggttcaga aaatattttc agcctacagt tatgttcagt    5400
cacacacaca tacaaaatgt tccttttgct tttaaagtaa tttttgactc ccagatcagt    5460
cagagcccct acagcattgt taagaaagta tttgattttt gtctcaatga aaataaaact    5520
atattcattt cc                                                       5532

<210> SEQ ID NO 301
<211> LENGTH: 1528
<212> TYPE: DNA
<213> ORGANISM: Homo sapiens

<400> SEQUENCE: 301
cggcgagcga gcaccttcga cgcggtccgg ggacccctc gtcgctgtcc tcccgacgcg       60
gacccgcgtg ccccaggcct cgcgctgccc ggccggctcc tcgtgtccca ctccggcgc     120 acgccctccc gcgagtcccg ggcccctccc gcgcccctct tctcggcgcg cgcgcagcat    180 ggcgccccg caggtcctcg cgttcgggct tctgcttgcc gcggcgacgg cgactttgc     240 cgcagctcag gaagaatgtg tctgtgaaaa ctacaagctg gccgtaaact gctttgtgaa    300
taataatcgt caatgccagt gtacttcagt tggtgcacaa aatactgtca tttgctcaaa    360
gctggctgcc aaatgtttgg tgatgaaggc agaaatgaat ggctcaaaac ttgggagaag    420
agcaaaacct gaaggggccc tccagaacaa tgatgggctt tatgatcctg actgcgatga    480
gagcgggctc tttaaggcca agcagtgcaa cggcacctcc acgtgctggg tgtgtgaacac    540 tgctggggtc agaagaacag acaaggacac tgaaataacc tgctctgagc gagtgagaac    600
ctactggatc atcattgaac taaaacacaa agcaagagaa aaaccttatg atagtaaaag    660
tttgcggact gcacttcaga aggagatcac aacgcgttat caactggatc caaaatttat    720
cacgagtatt ttgtatgaga ataatgttat cactattgat ctggttcaaa attcttctca    780
aaaaactcag aatgatgtgg acatagctga tgtggcttat tattttgaaa agatgtttaa    840
aggtgaatcc ttgtttcatt ctaagaaaat ggacctgaca gtaaatgggg aacaactgga    900
tctggatcct ggtcaaactt taatttatta tgttgatgaa aaagcacctg aattctcaat    960
gcagggtcta aaagctggtg ttattgctgt tattgtggtt gtggtgatag cagttgttgc    1020
tggaattgtt gtgctggtta tttccagaaa aagagaatg gcaaagtatg agaaggctga   1080
gataaaggag atgggtgaga tgcatagaga actcaatgca taactatata atttgaagat   1140
```

```
tatagaagaa gggaaatagc aaatggacac aaattacaaa tgtgtgtgcg tgggacgaag    1200
acatctttga aggtcatgag tttgttagtt taacatcata tatttgtaat agtgaaacct    1260
gtactcaaaa tataagcagc ttgaaactgg ctttaccaat cttgaaattt gaccacaagt    1320
gtcttatata tgcagatcta atgtaaaatc cagaacttgg actccatcgt taaaattatt    1380
tatgtgtaac attcaaatgt gtgcattaaa tatgcttcca cagtaaaatc tgaaaaactg    1440
atttgtgatt gaaagctgcc tttctattta cttgagtctt gtacatacat acttttttat    1500
gagctatgaa ataaaacatt ttaaactg                                       1528

<210> SEQ ID NO 302
<211> LENGTH: 1856
<212> TYPE: DNA
<213> ORGANISM: Homo sapiens

<400> SEQUENCE: 302
ctgacttggc aggactgtgc aattgtcaga aggccgtggg gagtgggggc cagtgcctgc      60
agcctgccct gcctctctca caggccctta gagcatcgcc aggtgcagag ctccacagct     120
ctctttccca aggagtaatc agagggtgag aacgtggagc tggtggaca ggtgaaagca      180 ctgggatctt tctgcccaga aaggggaaag ttgcacattt atatcctaga gggaagcgac     240
agcagtgctt ctccctgtgc tgaggtacag gagccatgtg gctagaaatc ctcctcactt     300
cagtgctggg cttttgccatc tactggttca tctcccggga caaagaggaa actttgccac     360
ttgaagatgg gtggtggggg ccaggcacga ggtccgcagc cagggaggac dacagcatcc     420 gcccttcaa ggtggaaacg tcagatgagg agatccacga cttacaccag aggatcgata     480
agttccgttt caccccacct ttggaggaca gctgcttcca ctatggcttc aactccaact     540
acctgaagaa agtcatctcc tactggcgga tgaatttga ctggaagaag caggtggaga     600
ttctcaacag ataccctcac ttcaagacta agattgaagg gctggacatc cacttcatcc     660
acgtgaagcc ccccccagctg cccgcaggcc ataccccgaa gcccttgctg atggtgcacg     720
gctggcccgg ctcttttctac gagttttata agatcatccc actcctgact gaccccaaga     780
accatggcct gagcgatgag cacgtttttg aagtcatctg cccttccatc cctggctatg     840
gcttctcaga ggcatcctcc aagaagggt tcaactcggt ggccaccgcc aggatctttt     900
acaagctgat gctgcggctg ggcttccagg aattctacat tcaaggaggg gactggggg     960 ccctgatctg cactaatatg gcccagctgg tgcccagcca cgtgaaaggc ctgcacttga    1020
acatggcttt ggttttaagc aacttctcta ccctgaccct cctcctggga cagcgtttcg    1080
ggaggtttct tggcctcact gagagggatg tggagctgct gtaccccgtc aaggagaagg    1140
tattctacag cctgatgagg gagagcggct acatgcacat ccagtgcacc aagcctgaca    1200
ccgtaggctc tgctctgaat gactctcctg tgggtctggc tgcctatatt ctagagaagt    1260
tttccacctg gaccaatacg gaattccgat acctggagga tggaggcctg gaaaggaagt    1320
tctccctgga cgacctgctg accaacgtca tgctctactg gacaacaggc accatcatct    1380
cctcccagcg cttctacaag gagaacctgg acagggctg gatgacccag aagcatgagc    1440
ggatgaaggt ctatgtgccc actggcttct ctgccttccc ttttgagcta ttgcacacgc    1500
ctgaaaagtg ggtgaggttc aagtacccaa agctcatctc ctattcctac atggttcgtg    1560
ggggccactt tgcggccttt gaggagccgg agctgctcgc ccaggacatc cgcaagttcc    1620
tgtcggtgct ggagcggcaa tgacccaccc ctctccccc gcctgccacc tcccccaca     1680 agtgccctcc aggcttttct tggggaagat accccttttc tgaggaatga gtttgcctcc    1740
```

| | |
|---|---|
| gtcccctgcc catgctggga gcccacgctc acccctcac ccctccaagc tcactcccca | 1800 |
| accccaact ccgtgtggta agcaacatgg ctttgatgat aaacgactt actcta | 1856 |

<210> SEQ ID NO 303
<211> LENGTH: 6450
<212> TYPE: DNA
<213> ORGANISM: Homo sapiens

<400> SEQUENCE: 303

| | |
|---|---|
| gagttgtgcc tggagtgatg tttaagccaa tgtcagggca aggcaacagt ccctggccgt | 60 |
| cctccagcac ctttgtaatg catatgagct cgggagacca gtacttaaag ttggaggccc | 120 |
| gggagcccag gagctggcgg agggcgttcg tcctgggagc tgcacttgct ccgtcgggtc | 180 |
| gccggcttca ccggaccgca ggctcccggg gcagggccgg gccagagct cgcgtgtcgg | 240 |
| cgggacatgc gctgcgtcgc ctctaacctc gggctgtgct cttttccag gtggcccgcc | 300 |
| ggtttctgag ccttctgccc tgcggggaca cggtctgcac cctgcccgcg ccacggacc | 360 |
| atgaccatga ccctccacac caaagcatct gggatggccc tactgcatca gatccaaggg | 420 |
| aacgagctgg agcccctgaa ccgtccgcag ctcaagatcc cctggagcg gcccctgggc | 480 |
| gaggtgtacc tggacagcag caagcccgcc gtgtacaact accccgaggg cgccgcctac | 540 |
| gagttcaacg ccgcggccgc cgccaacgcg caggtctacg tcagaccgg cctcccctac | 600 |
| ggccccgggt ctgaggctgc ggcgttcggc tccaacggcc tgggggttt ccccccactc | 660 |
| aacagcgtgt ctccgagccc gctgatgcta ctgcacccgc cgccgcagct gtcgcctttc | 720 |
| ctgcagcccc acggccagca ggtgccctac tacctggaga cgagcccag cggctacacg | 780 |
| gtgcgcgagg ccggcccgcc ggcattctac aggccaaatt cagataatcg acgcagggt | 840 |
| ggcagagaaa gattggccag taccaatgac aagggaagta tggctatgga atctgccaag | 900 |
| gagactcgct actgtgcagt gtgcaatgac tatgcttcag ctaccatta tggagtctgg | 960 |
| tcctgtgagg gctgcaaggc cttcttcaag agaagtattc aaggacataa cgactatatg | 1020 |
| tgtccagcca ccaaccagtg caccattgat aaaaacagga ggaagagctg ccaggcctgc | 1080 |
| cggctccgca aatgctacga agtgggaatg atgaaaggtg ggatacgaaa agaccgaaga | 1140 |
| ggagggagaa tgttgaaaca caagcgccag agagatgatg ggagggcag gggtgaagtg | 1200 |
| gggtctgctg gagacatgag agctgccaac ctttggccaa gcccgctcat gatcaaacgc | 1260 |
| tctaagaaga acagcctggc cttgtccctg acggccgacc agatggtcag tgccttgttg | 1320 |
| gatgctgagc ccccatact ctattccgag tatgatccta ccagaccctt cagtgaagct | 1380 |
| tcgatgatgg gcttactgac caacctggca gacagggagc tggttcacat gatcaactgg | 1440 |
| gcgaagaggg tgccaggctt tgtggatttg accctccatg atcaggtcca ccttctagaa | 1500 |
| tgtgcctggc tagagatcct gatgattggt ctcgtctggc gctccatgga gcacccagtg | 1560 |
| aagctactgt ttgctcctaa cttgctcttg gacaggaacc agggaaaatg tgtagagggc | 1620 |
| atggtgggaga tcttcgacat gctgctggct acatcatctc ggttccgcat gatgaatctg | 1680 |
| cagggagagg agttttgtgtg cctcaaatct attattttgc ttaattctgg agtgtacaca | 1740 |
| tttctgtcca gcaccctgaa gtctctggaa gagaaggacc atatccaccg agtcctggac | 1800 |
| aagatcacag acactttgat ccacctgatg gccaaggcag gctgaccct gcagcagcag | 1860 |
| caccagcggc tggcccagct cctcctcatc ctctcccaca tcaggcacat gagtaacaaa | 1920 |
| ggcatggagc atctgtacag catgaagtgc aagaacgtgg tgcccctcta tgacctgctg | 1980 |

```
ctggagatgc tggacgccca ccgcctacat gcgcccacta gccgtggagg ggcatccgtg   2040
gaggagacgg accaaagcca cttggccact gcgggctcta cttcatcgca ttccttgcaa   2100
aagtattaca tcacgggga ggcagagggt ttccctgcca cagtctgaga gctccctggc   2160
tcccacacgg ttcagataat ccctgctgca ttttaccctc atcatgcacc actttagcca   2220
aattctgtct cctgcataca ctccggcatg catccaacac caatggcttt ctagatgagt   2280
ggccattcat ttgcttgctc agttcttagt ggcacatctt ctgtcttctg ttgggaacag   2340
ccaaagggat ccaaggcta aatctttgta acagctctct ttccccttg ctatgttact   2400 aagcgtgagg attcccgtag ctcttcacag ctgaactcag tctatgggtt ggggctcaga   2460
taactctgtg catttaagct acttgtagag acccaggcct ggagagtaga cattttgcct   2520
ctgataagca cttttaaat ggctctaaga ataagccaca gcaaagaatt taaagtggct   2580
cctttaattg gtgacttgga gaaagctagg tcaagggttt attatagcac cctcttgtat   2640
tcctatggca atgcatcctt ttatgaaagt ggtacacctt aaagctttta tatgactgta   2700
gcagagtatc tggtgattgt caattcactt cccctatag gaatacaagg ggccacacag   2760
ggaaggcaga tccctagtt ggccaagact tatttaact tgatacactg cagattcaga   2820
gtgtcctgaa gctctgcctc tggctttccg gtcatgggtt ccagttaatt catgcctccc   2880
atggacctat ggagagcaac aagttgatct tagttaagtc tccctatatg agggataagt   2940
tcctgatttt tgtttttatt tttgtgttac aaaagaaagc cctccctccc tgaacttgca   3000
gtaaggtcag cttcaggacc tgttccagtg ggcactgtac ttggatcttc ccggcgtgtg   3060
tgtgccttac acagggtga actgttcact gtggtgatgc atgatgaggg taaatggtag   3120
ttgaaaggag caggggccct ggtgttgcat ttagccctgg ggcatggagc tgaacagtac   3180
ttgtgcagga ttgttgtggc tactagagaa caagagggaa agtagggcag aaactggata   3240
cagttctgag cacagccaga cttgctcagg tggccctgca caggctgcag ctacctagga   3300
acattccttg cagaccccgc attgcctttg ggggtgccct gggatccctg gggtagtcca   3360
gctcttattc atttcccagc gtggcctcgg ttggaagaag cagctgtcaa gttgtagaca   3420
gctgtgttcc tacaattggc ccagcaccct ggggcacggg agaagggtgg ggaccgttgc   3480
tgtcactact caggctgact ggggcctggt cagattacgt atgcccttgg tggtttagag   3540
ataatccaaa atcagggttt ggtttgggga agaaaatcct cccccttcct cccccgcccc   3600
gttccctacc gcctccactc ctgccagctc atttccttca atttcctttg acctataggc   3660
taaaaaagaa aggctcattc cagccacagg gcagccttcc ctgggccttt gcttctctag   3720
cacaattatg ggttacttcc ttttcttaa caaaaaagaa tgtttgattt cctctgggtg   3780
accttattgt ctgtaattga acccctattg agaggtgatg tctgtgttag ccaatgaccc   3840
aggtagctgc tcgggcttct cttggtatgt cttgtttgga aaagtggatt tcattcattt   3900
ctgattgtcc agtaagtga tcaccaaagg actgagaatc tgggagggca aaaaaaaaaa   3960 aaaaagttt tatgtgcact taaatttggg gacaatttta tgtatctgtg ttaaggatat   4020
gcttaagaac ataattcttt tgttgctgtt tgtttaagaa gcaccttagt ttgtttaaga   4080
agcaccttat atagtataat atatattttt ttgaaattac attgcttgtt tatcagacaa   4140
ttgaatgtag taattctgtt ctggatttaa tttgactggg ttaacatgca aaaaccaagg   4200
aaaaatattt agttttttt tttttttttg tatactttc aagctacctt gtcatgtata   4260
cagtcattta tgcctaaagc ctggtgatta ttcatttaaa tgaagatcac atttcatatc   4320
aacttttgta tccacagtag acaaaatagc actaatccag atgcctattg ttggatattg   4380
```

```
aatgacagac aatcttatgt agcaaagatt atgcctgaaa aggaaaatta ttcagggcag    4440
ctaattttgc ttttaccaaa atatcagtag taatatttt ggacagtagc taatgggtca    4500
gtgggttctt tttaatgttt atacttagat tttcttttaa aaaaattaaa ataaaacaaa    4560
aaaaatttct aggactagac gatgtaatac cagctaaagc caaacaatta tacagtggaa    4620
ggttttacat tattcatcca atgtgtttct attcatgtta agatactact acatttgaag    4680
tgggcagaga acatcagatg attgaaatgt tcgcccaggg gtctccagca actttggaaa    4740 tctcttttgta tttttacttg aagtgccact aatggacagc agatattttc tggctgatgt    4800
tggtattggg tgtaggaaca tgatttaaaa aaaaaactct tgcctctgct ttcccccact    4860
ctgaggcaag ttaaaatgta aaagatgtga tttatctggg gggctcaggt atggtgggga    4920
agtggattca ggaatctggg gaatggcaaa tatattaaga agagtattga aagtatttgg    4980
aggaaaatgg ttaattctgg gtgtgcacca aggttcagta gagtccactt ctgccctgga    5040
gaccacaaat caactagctc catttacagc catttctaaa atggcagctt cagttctaga    5100
gaagaaagaa caacatcagc agtaaagtcc atggaatagc tagtggtctg tgtttctttt    5160
cgccattgcc tagcttgccg taatgattct ataatgccat catgcagcaa ttatgagagg    5220
ctaggtcatc caaagagaag accctatcaa tgtaggttgc aaaatctaac ccctaaggaa    5280
gtgcagtctt tgatttgatt tccctagtaa ccttgcagat atgtttaacc aagccatagc    5340
ccatgccttt tgagggctga acaaataagg gacttactga taatttactt ttgatcacat    5400
taaggtgttc tcaccttgaa atcttataca ctgaaatggc cattgattta ggccactggc    5460
ttagagtact ccttcccctg catgacactg attacaaata ctttcctatt catactttcc    5520
aattatgaga tggactgtgg gtactgggag tgatcactaa caccatagta atgtctaata    5580
ttcacaggca gatctgcttg gggaagctag ttatgtgaaa ggcaaataaa gtcatacagt    5640
agctcaaaag gcaaccataa ttctctttgg tgcaagtctt gggagcgtga tctagattac    5700
actgcaccat tcccaagtta atcccctgaa aacttactct caactggagc aaatgaactt    5760
tggtcccaaa tatccatctt ttcagtagcg ttaattatgc tctgtttcca actgcatttc    5820
ctttccaatt gaattaaagt gtggcctcgt ttttagtcat ttaaaattgt tttctaagta    5880
attgctgcct ctattatggc acttcaattt tgcactgtct tttgagattc aagaaaaatt    5940
tctattcatt tttttgcatc caattgtgcc tgaactttta aaatatgtaa atgctgccat    6000
gttccaaacc catcgtcagt gtgtgtgttt agagctgtgc accctagaaa caacatactt    6060
gtcccatgag caggtgcctg agacacagac ccctttgcat tcacagagag gtcattggtt    6120
atagagactt gaattaataa gtgacattat gccagtttct gttctctcac aggtgataaa    6180
caatgctttt tgtgcactac atactcttca gtgtagagct cttgttttat gggaaaaggc    6240
tcaaatgcca aattgtgttt gatggattaa tatgccattt tgccgatgca tactattact    6300
gatgtgactc ggttttgtcg cagctttgct tgtttaatg aaacacactt gtaaacctct    6360
tttgcacttt gaaaaagaat ccagcgggat gctcgagcac ctgtaaacaa ttttctcaac    6420
ctatttgatg ttcaaataaa gaattaaact                                     6450
```

<210> SEQ ID NO 304
<211> LENGTH: 3336
<212> TYPE: DNA
<213> ORGANISM: Homo sapiens
<220> FEATURE:
<221> NAME/KEY: unsure
<222> LOCATION: (0)...(0)

-continued

<223> OTHER INFORMATION: n = A, T, C or G

<400> SEQUENCE: 304

| | | | | | |
|---|---|---|---|---|---|
| cggcggcgac | tgcagtctgg | agggtccaca | cttgtgattc | tcaatggaga gtgaaaacgc | 60 |
| agattcataa | tgaaagctag | ccccgtcgg | ccactgattc | tcaaagacg gaggctgccc | 120 |
| cttcctgttc | aaaatgcccc | aagtgaaaca | tcagaggagg | aacctaagag atcccctgcc | 180 |
| caacaggagt | ctaatcaagc | agaggcctcc | aaggaagtgg | cggagtccaa ctcttgcaag | 240 |
| tttccagctg | ggatcaagat | tattaaccac | cccaccatgc | caacacgca agtagtggcc | 300 |
| atccccaaca | atgctaatat | tcacagcatc | atcacagcac | tgactgccaa gggaaaagag | 360 |
| agtggcagta | gtgggcccaa | caaattcatc | ctcatcagct | gtggggagc cccaactcag | 420 |
| cctccaggac | tccggcctca | aacccaaacc | agctatgatg | ccaaaaggac agaagtgacc | 480 |
| ctggagacct | tgggaccaaa | acctgcagct | agggatgtga | atcttcctag accacctgga | 540 |
| gcccttgcg | agcagaaacg | ggagacctgt | gcagatggtg | aggcagcagg ctgcactatc | 600 |
| aacaatagcc | tatccaacat | ccagtggctt | cgaaagatga | gttctgatgg actgggctcc | 660 |
| cgcagcatca | agcaagagat | ggaggaaaag | gagaattgtc | acctggagca gcgacaggtt | 720 |
| aaggttgagg | agccttcgag | accatcagcg | tcctggcaga | actctgtgtc tgagcggcca | 780 |
| ccctactctt | acatggccat | gatacaattc | gccatcaaca | gcactgagag aagcgcatg | 840 |
| actttgaaag | acatctatac | gtggattgag | gaccactttc | cctactttaa gcacattgcc | 900 |
| aagccaggct | ggaagaactc | catccgccac | aacctttccc | tgcacgacat gtttgtccgg | 960 |
| gagacgtctg | ccaatggcaa | ggtctccttc | tggaccattc | accccagtgc caaccgctac | 1020 |
| ttgacattgg | accaggtgtt | taagccactg | acccagggt | ctccacaatt gcccgagcac | 1080 |
| ttggaatcac | agcagaaacg | accgaatcca | gagctccgcc | ggaacatgac catcaaaacc | 1140 |
| gaactccccc | tgggcgcacg | gcggaagatg | aagccactgc | taccacgggt cagctcatac | 1200 |
| ctggtaccta | tccagttccc | ggtgaaccag | tcactggtgt | tgcagccctc ggtgaaggtg | 1260 |
| ccattgcccc | tggcggcttc | cctcatgagc | tcagagcttg | cccgccatag caagcgagtc | 1320 |
| cgcattgccc | ccaaggtgct | gctagctgag | gaggggatag | ctcctctttc ttctgcagga | 1380 |
| ccagggaaag | aggagaaact | cctgtttgga | gaagggtttt | ctcctttgct tccagttcag | 1440 |
| actatcaagg | aggaagaaat | ccagcctggg | gaggaaatgc | cacacttagc gagacccatc | 1500 |
| aaagtggaga | gccctcctt | ggaagagtgg | ccctccccgg | ccccatcttt caaagaggaa | 1560 |
| tcatctcact | cctgggagga | ttcgtcccaa | tctcccaccc | caagacccaa gaagtcctac | 1620 |
| agtgggctta | ggtccccaac | ccggtgtgtc | tcggaaatgc | ttgtgattca acacagggag | 1680 |
| aggagggaga | ggagccggtc | tcggaggaaa | cagcatctac | tgcctccctg tgtggatgag | 1740 |
| ccggagctgc | tcttctcaga | ggggcccagt | acttcccgct | gggccgcaga gctcccgttc | 1800 |
| ccagcagact | cctctgaccc | tgcctcccag | ctcagctact | cccaggaagt gggaggacct | 1860 |
| tttaagacac | ccattaagga | aacgctgccc | atctcctcca | ccccgagcaa atctgtcctc | 1920 |
| cccagaaccc | ctgaatcctg | gaggctcacg | ccccagcca | aagtaggggg actggatttc | 1980 |
| agcccagtac | aaacctccca | gggtgcctct | gaccccttgc | ctgacccct ggggctgatg | 2040 |
| gatctcagca | ccactccctt | gcaaagtgct | ccccccttg | aatcaccgca aaggctcctc | 2100 |
| agttcagaac | ccttagacct | catctccgtc | cccttggca | actcttctcc ctcagatata | 2160 |
| gacgtcccca | agccaggctc | cccggagcca | caggttctg | gccttgcagc caatcgttct | 2220 |
| ctgacagaag | gcctggtcct | ggacacaatg | aatgacagcc | tcagcaagat cctgctggac | 2280 |

```
atcagctttc ctggcctgga cgaggaccca ctgggccctg acaacatcaa ctggtcccag      2340
tttattcctg agctacagta gagccctgcc cttgcccctg tgctcaagct gtccaccatc      2400
ccgggcactc caaggctcag tgcaccccaa gcctctgagt gaggacagca ggcagggact      2460
gttctgctcc tcatagctcc ctgctgcctg attatgcaaa agtagcagtc acaccctagc      2520
cactgctggg accttgtgtt ccccaagagt atctgattcc tctgctgtcc ctgccaggag      2580
ctgaagggtg ggaacaacaa aggcaatggt gaaaagagat taggaacccc ccagcctgtt      2640
tccattctct gcccagcagt ctcttacctt ccctgatctt tgcagggtgg tccgtgtaaa      2700
tagtataaat tctccaaatt atcctctaat tataaatgta agcttatttc cttagatcat      2760
tatccagaga ctgccagaag gtgggtagga tgacctgggg tttcaattga cttctgttcc      2820
ttgcttttag ttttgataga agggaagacc tgcagtgcac ggtttcttcc aggctgaggt      2880
acctggatct tgggttcttc actgcaggga cccagacaag tggatctgct tgccagagtc      2940 cttttttgccc ctccctgcca cctccccgtg tttccaagtc agctttcctg caagaagaaa      3000
tcctggttaa aaaagtcttt tgtattgggt caggagttga atttgggtg ggaggatgga      3060 tgcaactgaa gcagagtgtg ggtgcccaga tgtgcgctat tagatgtttc tctgataatg      3120
tccccaatca taccagggag actggcattg acgagaactc aggtggaggc ttgagaaggc      3180
cgaaagggcc cctgacctgc ctggcttcct tagcttgccc ctcagctttg caaagagcca      3240
ccctaggccc cagctgaccg catgggtgtg agccagcttg agaacactaa ctactcaata      3300
aaagcgaagg tggaccnaaa aaaaaaaaaa aaaaaa      3336
```

<210> SEQ ID NO 305
<211> LENGTH: 2365
<212> TYPE: DNA
<213> ORGANISM: Homo sapiens

<400> SEQUENCE: 305

```
tcccagcctt ccatccccc caccgaaagc aaatcattca acgaccccg accctccgac        60 ggcaggagcc cccgacctc ccaggcggac cgcccttccc tccccgcgcg ggttccgggc       120
ccggcgagag ggcgcgacga cagccgaggc catggaggtg acggcggacc agccgcgctg       180
ggtgagccac caccacccg ccgtgctcaa cgggcagcac ccggacacgc accacccggg       240
cctcagccac tcctacatgg acgcggcgca gtacccgctg ccggaggagg tggatgtgct       300
ttttaacatc gacggtcaag gcaaccacgt ccgccctac tacggaaact cggtcagggc       360
cacggtgcag aggtaccctc cgacccacca cgggagccag gtgtgccgcc cgcctctgct       420
tcatggatcc ctaccctggc tggacggcgg caaagccctg gcagccacc acaccgcctc       480 cccctggaat ctcagcccct tctccaagac gtccatccac cacggctccc cggggcccct       540
ctccgtctac ccccggcct cgtcctcctc ctttgtcgggg gccacgcca gcccgcacct       600 cttcaccttc ccgcccaccc cgccgaagga cgtctccccg acccatcgc tgtccacccc       660 aggctcggcc ggctcggccc ggcaggacga gaaagagtgc ctcaagtacc aggtgccctt       720
gcccgacagc atgaagctgg agtcgtccca ctcccgtggc agcatgaccg ccctgggtgg       780
agcctcctcg tcgacccacc accccatcac cacctacccg ccctacgtgc ccgagtacag       840
ctccggactc ttcccccca gcagcctgct gggcggctcc cccaccggct cggatgcaa       900 gtccaggccc aaggccggt ccagcacagg caggagtgt gtgaactgtg ggcaacctc       960 gaccccactg tggcggcgag atggcacggg acactacctg tgcaacgcct gcgggctcta      1020
```

```
tcacaaaatg aacggacaga accggcccct cattaagccc aagcgaaggc tgtctgcagc    1080
caggagagca gggacgtcct gtgcgaactg tcagaccacc acaaccacac tctggaggag    1140
gaatgccaat ggggaccctg tctgcaatgc ctgtgggctc tactacaagc ttcacaatat    1200
taacagaccc ctgactatga agaaggaagg catccagacc agaaaccgaa aaatgtctag    1260
caaatccaaa aagtgcaaaa aagtgcatga ctcactggag gacttcccca agaacagctc    1320
gtttaacccg gccgccctct ccagacacat gtcctccctg agccacatct cgcccttcag    1380
ccactccagc cacatgctga ccacgcccac gccgatgcac ccgccatcca gcctgtcctt    1440
tggaccacac cacccctcca gcatggtcac cgccatgggt tagagccctg ctcgatgctc    1500
acagggcccc cagcgagagt ccctgcagtc cctttcgact tgcatttttg caggagcagt    1560
atcatgaagc ctaaacgcga tggatatatg tttttgaagg cagaaagcaa aattatgttt    1620
gccactttgc aaaggagctc actgtggtgt ctgtgttcca accactgaat ctggacccca    1680
tctgtgaata agccattctg actcatatcc cctatttaac agggtctcta gtgctgtgaa    1740
aaaaaaaaat cctgaacatt gcatataact tatattgtaa gaaatactgt acaatgactt    1800
tattgcatct gggtagctgt aaggcatgaa ggatgccaag aagtttaagg aatatgggag    1860
aaatagtgtg gaaattaaga agaaactagg tctgatattc aaatggacaa actgccagtt    1920
ttgtttcctt tcactggcca cagttgtttg atgcattaaa agaaaataaa aaaagaaaa    1980 aagagaaaag aaaaaaaaag aaaaagttg taggcgaatc atttgttcaa agctgttggc    2040
cctctgcaaa ggaaatacca gttctgggca atcagtgtta ccgttcacca gttgccattg    2100 aggggtttcag agagccttttt tctaggccta catgctttgt gaacaagtcc ctgtaattgt    2160
tgtttgtatg tataattcaa agcaccaaaa taagaaaaga tgtagattta tttcatcata    2220
ttatacagac cgaactgttg tataaattta tttactgcta gtcttaagaa ctgctttctt    2280
tcgtttgttt gtttcaatat tttccttctc tctcaatttt cggttgaata aactagatta    2340
cattcagttg gcaaaaaaaa aaaaa                                          2365

<210> SEQ ID NO 306
<211> LENGTH: 1117
<212> TYPE: DNA
<213> ORGANISM: Homo sapiens

<400> SEQUENCE: 306
gcaccaacca gcaccatgcc catgatactg gggtactggg acatccgcgg gctggcccac      60
gccatccgcc tgctcctgga atacacagac tcaagctatg aggaaaagaa gtacacgatg     120
ggggacgctc ctgattatga cagaagccag tggctgaatg aaaaattcaa gctgggcctg     180
gactttccca atctgcccta cttgattgat ggggctcaca gatcacccca gagcaacgcc     240
atcttgtgct acattgcccg caagcacaac ctgtgtgggg agacagaaga ggagaagatt     300
cgtgtggaca ttttggagaa ccagaccatg gacaaccata tgcagctggg catgatctgc     360
tacaatccag aatttgagaa actgaagcca agtacttgg aggaactccc tgaaaagcta     420
aagctctact cagagtttct ggggaagcgg ccatggtttg caggaaacaa gatcactttt     480
gtagattttc tcgtctatga tgtccttgac ctccaccgta tatttgagcc caactgcttg     540
gacgccttcc caaatctgaa ggacttcatc tcccgctttg agggcttgga agatctct       600 gcctacatga agtccagccg cttcctccca agacctgtgt tctcaaagat ggctgtctgg     660
ggcaacaagt agggccttga aggcaggagg tgggagtgag gagcccatac tcagcctgct     720
gcccaggctg tgcagcgcag ctggactctg catcccagca cctgcctcct cgttcctttc     780
```

| | |
|---|---|
| tcctgtttat tcccatcttt actcccaaga cttcattgtc cctcttcact cccctaaac | 840 |
| ccctgtccca tgcaggccct ttgaagcctc agctacccac tatccttcgt gaacatcccc | 900 |
| tcccatcatt acccttccct gcactaaagc cagcctgacc ttccttcctg ttagtggttg | 960 |
| tgtctgcttt aaagcctgcc tggcccctcg cctgtggagc tcagcccga gctgtccccg | 1020 |
| tgttgcatga aggagcagca ttgactggtt tacaggccct gctcctgcag catggtccct | 1080 |
| gcctaggcct acctgatgga agtaaagcct caaccac | 1117 |

<210> SEQ ID NO 307
<211> LENGTH: 1266
<212> TYPE: DNA
<213> ORGANISM: Homo sapiens

<400> SEQUENCE: 307

| | |
|---|---|
| ctcggaagcc cgtcaccatg tcgtgcgagt cgtctatggt tctcgggtac tgggatattc | 60 |
| gtgggctggc gcacgccatc cgcctgctcc tggagttcac ggatacctct tatgaggaga | 120 |
| aacggtacac gtgcggggaa gctcctgact atgatcgaag ccaatggctg gatgtgaaat | 180 |
| tcaagctaga cctggacttt cctaatctgc cctacctcct ggatgggaag aacaagatca | 240 |
| cccagagcaa tgccatcttg cgctacatcg ctcgcaagca caacatgtgt ggtgagactg | 300 |
| aagaagaaaa gattcgagtg gacatcatag agaaccaagt aatggatttc gcacacaac | 360 |
| tgataaggct ctgttacagc tctgaccacg aaaaactgaa gcctcagtac ttggaagagc | 420 |
| tacctggaca actgaaacaa ttctccatgt ttctgtggaa attctcatgg tttgccgggg | 480 |
| aaaagctcac ctttgtggat tttctcacct atgatatctt ggatcagaac cgtatatttg | 540 |
| accccaagtg cctggatgag ttcccaaacc tgaaggcttt catgtgccgt tttgaggctt | 600 |
| tggagaaaat cgctgcctac ttacagtctg atcagttctg caagatgccc atcaacaaca | 660 |
| agatggccca gtggggcaac aagcctgtat gctgagcagg aggcagactt gcagagcttg | 720 |
| ttttgtttca tcctgtccgt aaggggtcag cgctcttgct ttgctctttt caatgaatag | 780 |
| cacttatgtt actggtgtcc agctgagttt ctcttgggta taaaggctaa aagggaaaaa | 840 |
| ggatatgtgg agaatcatca agatatgaat tgaatcgctg cgatactgtg gcatttccct | 900 |
| actcccaac tgagttcaag ggctgtaggt tcatgcccaa gccctgagag tgggtactag | 960 |
| aaaaaacgag attgcacagt tggagagagc aggtgtgtta aatggactgg agtccctgtg | 1020 |
| aagactgggt gaggataaca caagtaaaac tgtggtactg atggacttaa ccggagttcg | 1080 |
| gaaaccgtcc tgtgtacaca tgggagttta gtgtgataaa ggcagtattt cagactggtg | 1140 |
| ggctagccaa tagagttggc aattgcttat tgaaactcat taaaataat agagccccac | 1200 |
| ttgacactat tcactaaaat taatctggaa tttaaggccc aacattaaac acaaagctgt | 1260 |
| attgat | 1266 |

<210> SEQ ID NO 308
<211> LENGTH: 2162
<212> TYPE: DNA
<213> ORGANISM: Homo sapiens

<400> SEQUENCE: 308

| | |
|---|---|
| gggctgcgct gtccagctgt ggctatggcc ccagccccga gatgaggagg gagagaacta | 60 |
| ggggcccgca ggcctgggaa tttccgtccc ccaccaagtc cggatgctca ctccaaagtc | 120 |
| tcagcaggcc cctgagggag ggagctgtca gccagggaaa accgagaaca ccatcaccat | 180 |

-continued

```
gacaaccagt caccagcctc aggacagata caaagctgtc tggcttatct tcttcatgct      240
gggtctggga acgctgctcc cgtggaattt tttcatgacg ccactcagt atttcacaaa       300 ccgcctggac atgtcccaga atgtgtcctt ggtcactgct gaactgagca aggacgccca      360
ggcgtcagcc gcccctgcag cacccttgcc tgagcggaac tctctcagtg ccatcttcaa      420
caatgtcatg accctatgtg ccatgctgcc cctgctgtta ttcacctacc tcaactcctt      480
cctgcatcag aggatccccc agtccgtacg gatcctgggc agcctggtgg ccatcctgct      540
ggtgtttctg atcactgcca tcctggtgaa ggtgcagctg gatgctctgc ccttctttgt      600
catcaccatg atcaagatcg tgctcattaa ttcatttggt gccatcctgc agggcagcct      660
gtttggtctg gctggccttc tgcctgccag ctacacggcc cccatcatga gtggccaggg      720
cctagcaggc ttctttgcct ccgtggccat gatctgcgct attgccagtg gctcggaact      780
atcagaaagt gccttcggct actttatcac agcctgtgct gttatcattt tgaccatcat      840
ctgttacctg ggcctgcccc gcctggaatt ctaccgctac taccagcagc tcaagcttga      900
aggacccggg gagcaggaga ccaagttgga cctcattagc aaaggagagg agccaagagc      960
aggcaaagag gaatctggag tttcagtctc caactctcag cccaccaatg aaagccactc     1020
tatcaaagcc atcctgaaaa atatctcagt cctggctttc tctgtctgct tcatcttcac     1080
tatcaccatt gggatgtttc agccgtgac tgttgaggtc aagtccagca tcgcaggcag     1140
cagcacctgg aacgttact tcattcctgt gtcctgtttc ttgactttca atatctttga     1200
ctggttgggc cggagcctca cagctgtatt catgtggcct gggaaggaca gccgctggct     1260
gccaagcctg gtgctggccc ggctggtgtt tgtgccactg ctgctgctgt gcaacattaa     1320
gccccgccgc tacctgactg tggtcttcga gcacgatgcc tggttcatct tcttcatggc     1380 tgccttttgcc ttctccaacg gctacctcgc cagcctctgc atgtgcttcg ggcccaagaa     1440
agtgaagcca gctgaggcag agaccgcagg agccatcatg gccttcttcc tgtgtctggg     1500
tctggcactg ggggctgttt tctccttcct gttccgggca attgtgtgac aaaggatgga     1560
cagaaggact gcctgcctcc ctccctgtct gcctcctgcc ccttccttct gccaggggtg     1620
atcctgagtg gtctggcggt tttttcttct aactgacttc tgctttccac ggcgtgtgct     1680
gggcccggat ctccaggccc tggggaggga gcctctggac ggacagtggg gacattgtgg     1740
gtttggggct cagagtcgag ggacggggtg tagcctcggc atttgcttga gtttctccac     1800
tcttggctct gactgatccc tgcttgtgca ggccagtgga ggctcttggg cttggagaac     1860
acgtgtgtct ctgtgtatgt gtctgtgtgt ctgcgtccgt gtctgtcaga ctgtctgcct     1920
gtcctggggt ggctaggagc tgggtctgac cgttgtatgg tttgacctga tatactccat     1980
tctcccctgc gcctcctcct ctgtgttttt tccatgtccc cctcccaact ccccatgccc     2040 agttttttacc catcatgcac cctgtacagt tgccacgtta ctgccttttt taaaaatata     2100
tttgacagaa accaggtgcc ttcagaggct ctctgattta aataaacctt tcttgttttt     2160
tt                                                                    2162
```

<210> SEQ ID NO 309
<211> LENGTH: 3933
<212> TYPE: DNA
<213> ORGANISM: Homo sapiens

<400> SEQUENCE: 309

```
cacgaggcag cactctcttc gtcgcttcgg ccagtgtgtc gggctgggcc ctgacaagcc       60
acctgaggag aggctcggag ccgggcccgg accccggcga ttgccgcccg cttctctcta      120
```

-continued

```
gtctcacgag gggtttcccg cctcgcaccc ccacctctgg acttgccttt ccttctcttc    180
tccgcgtgtg gagggagcca gcgcttaggc cggagcgagc ctgggggccg cccgccgtga    240
agacatcgcg gggaccgatt caccatggag ggcgccggcg gcgcgaacga caagaaaaag    300
ataagttctg aacgtcgaaa agaaaagtct cgagatgcag ccagatctcg gcgaagtaaa    360
gaatctgaag ttttttatga gcttgctcat cagttgccac ttccacataa tgtgagttcg    420
catcttgata aggcctctgt gatgaggctt accatcagct atttgcgtgt gaggaaactt    480
ctggatgctg gtgatttgga tattgaagat gacatgaaag cacagatgaa ttgcttttat    540
ttgaaagcct tggatggttt tgttatggtt ctcacagatg atggtgacat gatttacatt    600
tctgataatg tgaacaaata catgggatta actcagtttg aactaactgg acacagtgtg    660
tttgatttta ctcatccatg tgaccatgag gaaatgagag aaatgcttac acacagaaat    720
ggccttgtga aaagggtaa agaacaaaac acacagcgaa gcttttttct cagaatgaag    780
tgtaccctaa ctagccgagg aagaactatg aacataaagt ctgcaacatg gaaggtattg    840
cactgcacag gccacattca cgtatatgat accaacagta accaacctca gtgtgggtat    900
aagaaaccac ctatgacctg cttggtgctg atttgtgaac ccattcctca cccatcaaat    960
attgaaattc ctttagatag caagactttc ctcagtcgac acagcctgga tatgaaattt    1020
tcttattgtg atgaaagaat taccgaattg atgggatatg agccagaaga acttttaggc    1080
cgctcaattt atgaatatta tcatgctttg actctgatc atctgaccaa aactcatcat    1140
gatatgttta ctaaaggaca agtcaccaca ggacagtaca ggatgcttgc caaaagaggt    1200
ggatatgtct gggttgaaac tcaagcaact gtcatatata acaccaagaa ttctcaacca    1260
cagtgcattg tatgtgtgaa ttcgttgtg agtggtatta ttcagcacga cttgattttc    1320
tcccttcaac aaacagaatg tgtccttaaa ccggttgaat cttcagatat gaaaatgact    1380
cagctattca ccaaagttga atcagaagat acaagtagcc tctttgacaa acttaagaag    1440
gaacctgatg ctttaacttt gctggcccca gccgctggag acacaatcat atctttagat    1500
tttggcagca acgacacaga aactgatgac cagcaacttg aggaagtacc attatataat    1560
gatgtaatgc tcccctcacc caacgaaaaa ttacagaata taaatttggc aatgtctcca    1620
ttacccaccg ctgaaacgcc aaagccactt cgaagtagtc ctgaccctgc actcaatcaa    1680
gaagttgcat taaaattaga accaaatcca gagtcactgg aactttcttt taccatgccc    1740
cagattcagg atcagacacc tagtccttcc gatggaagca ctagacaaag ttcacctgag    1800
cctaatagtc ccagtgaata ttgttttttat gtggatagtg atatggtcaa tgaattcaag    1860
ttggaattgg tagaaaaact ttttgctgaa gacacagaag caaagaaccc attttctact    1920
caggacacag atttagactt ggagatgtta gctccctata tcccaatgga tgatgacttc    1980
cagttacgtt ccttcgatca gttgtcacca ttagaaagca gttccgcaag ccctgaaagc    2040
gcaagtcctc aaagcacagt tacagtattc cagcagactc aaatacaaga acctactgct    2100
aatgccacca ctaccactgc caccactgat gaattaaaaa cagtgacaaa agaccgtatg    2160
gaagacatta aatattgat tgcatctcca tctcctaccc acatacataa agaaactact    2220
agtgccacat catcaccata tagagatact caaagtcgga cagcctcacc aaacagagca    2280
ggaaaaggag tcatagaaca gacagaaaaa tctcatccaa gaagccctaa cgtgttatct    2340
gtcgctttga gtcaaagaac tacagttcct gaggaagaac taaatccaaa gatactagct    2400
ttgcagaatg ctcagagaaa gcgaaaaatg gaacatgatg gttcactttt tcaagcagta    2460
```

```
ggaattggaa cattattaca gcagccagac gatcatgcag ctactacatc actttcttgg    2520
aaacgtgtaa aaggatgcaa atctagtgaa cagaatggaa tggagcaaaa gacaattatt    2580
ttaataccct ctgatttagc atgtagactg ctggggcaat caatggatga agtggatta    2640 ccacagctga ccagttatga ttgtgaagtt aatgctccta tacaaggcag cagaaaccta    2700
ctgcagggtg aagaattact cagagctttg gatcaagtta actgagcttt ttcttaattt    2760 cattccttt tttggacact ggtggctcac tacctaaagc agtctattta tattttctac    2820
atctaatttt agaagcctgg ctacaatact gcacaaactt ggttagttca attttgatc    2880 cccttctac ttaatttaca ttaatgctct tttttagtat gttctttaat gctggatcac    2940
agacagctca ttttctcagt tttttggtat ttaaccatt gcattgcagt agcatcattt    3000 taaaaatgc acctttttat ttatttatt ttggctaggg agtttatccc tttttcgaat    3060 tattttaag aagatgccaa tataatttt gtaagaaggc agtaacctt catcatgatc    3120 ataggcagtt gaaaaatttt tacaccttt ttttcacatt ttacataaat aataatgctt    3180
tgccagcagt acgtggtagc cacaattgca caatatattt tcttaaaaaa taccagcagt    3240
tactcatgga atatattctg cgtttataaa actagttttt aagaagaaat ttttttttggc    3300 ctatgaaatt gttaaacctg aacatgaca ttgttaatca tataataatg attcttaaat    3360
gctgtatggt ttattattta aatgggtaaa gccatttaca taatatagaa agatatgcat    3420
atatctagaa ggtatgtggc atttatttgg ataaaattct caattcagag aaatcatctg    3480
atgtttctat agtcactttg ccagctcaaa agaaaacaat accctatgta gttgtggaag    3540
tttatgctaa tattgtgtaa ctgatattaa acctaaatgt tctgcctacc ctgttggtat    3600
aaagatattt tgagcagact gtaaacaaga aaaaaaaaat catgcattct tagcaaaatt    3660
gcctagtatg ttaatttgct caaaatacaa tgtttgattt tatgcacttt gtcgctatta    3720
acatcctttt tttcatgtag atttcaataa ttgagtaatt ttagaagcat tattttagga    3780
atatatagtt gtcacagtaa atatcttgtt ttttctatgt acattgtaca aattttcat    3840 tcctttgct ctttgtggtt ggatctaaca ctaactgtat tgttttgtta catcaaataa    3900
acatcttctg tggaaaaaaa aaaaaaaaaa aaa                                3933

<210> SEQ ID NO 310
<211> LENGTH: 2872
<212> TYPE: DNA
<213> ORGANISM: Homo sapiens

<400> SEQUENCE: 310
tccaggaatc gatagtgcat tcgtgcgcgc ggccgcccgt cgcttcgcac agggctggat      60
ggttgtattg ggcagggtgg ctccaggatg ttaggaactg tgaagatgga agggcatgaa     120
accagcgact ggaacagcta ctacgcagac acgcaggagg cctactcctc ggtcccggtc     180
agcaacatga actcaggcct gggctccatg aactccatga acacctacat gaccatgaac     240
accatgacta cgagcggcaa catgaccccg cgtccttca acatgtccta tgccaacccg     300
gccttagggg ccggcctgag tcccggcgca gtagccggca tgccgggggg ctcggcgggc     360
gccatgaaca gcatgactgc ggccggcgtg acggccatgg gtacggcgct gagcccgagc     420
ggcatgggcg ccatgggtgc gcagcaggcg gcctccatga tgaatggcct gggcccctac     480
gcggccgcca tgaacccgtg catgagcccc atggcgtacg cgccgtccaa cctgggccgc     540
agccgcgcgg gcggcggcgg cgacgccaag acgttcaagc gcagttaccc gcacgccaag     600
ccgccctact cgtacatctc gctcatcacc atggccatcc agcgggcgcc cagcaagatg     660
```

```
ctcacgctga gcgagatcta ccagtggatc atggacctct tccctatta ccggcagaac    720
cagcagcgct ggcagaactc catccgccac tcgctgtcct tcaatgactg cttcgtcaag    780
gtggcacgct ccccggacaa gccgggcaag ggctcctact ggacgctgca cccggactcc    840
ggcaacatgt tcgagaacgg ctgctacttg cgccgccaga agcgcttcaa gtgcgagaag    900
cagccggggg ccggcggcgg gggcgggagc ggaagcgggg gcagcggcgc caagggcggc    960
cctgagagcc gcaaggaccc ctctggcgcc tctaaccca gcgccgactc gcccctccat   1020
cggggtgtgc acgggaagac cggccagcta gagggcgcgc cggccccggg cccggccgcc   1080
agcccccaga ctctggacca cagtggggcg acggcgacag ggggcgcctc ggagttgaag   1140
actccagcct cctcaactgc gcccccata agctccgggc ccggggcgct ggcctctgtg   1200
cccgcctctc acccggcaca cggcttggca ccccacgagt cccagctgca cctgaaaggg   1260
gaccccact actccttcaa ccaccccgttc tccatcaaca acctcatgtc ctcctcggag   1320
cagcagcata agctggactt caaggcatac gaacaggcac tgcaatactc gccttacggc   1380
tctacgttgc ccgccagcct gcctctaggc agcgcctcgg tgaccaccag gagccccatc   1440
gagccctcag ccctggagcc ggcgtactac caaggtgtgt attccagacc cgtcctaaac   1500
acttcctagc tcccgggact gggggtttg tctggcatag ccatgctggt agcaagagag   1560
aaaaaatcaa cagcaaacaa aaccacacaa accaaaccgt caacagcata ataaaatcca   1620
acaactattt ttatttcatt tttcatgcac aaccttgccc ccagtgcaaa agactgttac   1680
tttattattg tattcaaaat tcattgtgta tattactaca aagacggccc caaaccaatt   1740
tttttcctgc gaagtttaat gatccacaag tgtatatatg aaattctcct ccttccttgc   1800
cccctctct ttcttccctc ttggccctcc agacattcta gtttgtggag ggttattaa   1860
aaaacaaaaa ggaagatggt caagtttgta aaatatttgt ttgtgctttt ccccctcct   1920
tacctgaccc cctacgagtt tacaggcttg tggcaatact cttaaccata agaattgaaa   1980
tggtgaagaa acaagtatac actagaggct cttaaaagta ttgaaaagac aatactgctg   2040
ttatatagca agacataaac agattataaa catcagagcc atttgcttct cagtttacat   2100
ttctgataca tgcagatagc agatgtcttt aaatgaaata catgtatatt gtgtatggac   2160
ttaattatgc acatgctcag atgtgtagac atcctccgta tatttacata acatatagag   2220
gtaatagata ggtgatatac gtgatacgtt ctcaagagtt gcttgaccga aagttacaag   2280
gaccccaacc cctttgctct ctacccacag atggccctgg aacaatcct caggaattgc   2340
cctcaagaac tcgcttcttt gctttgagag tgccatggtc atgtcattct gaggtacata   2400
acacataaat tagtttctat gagtgtatac catttaaaga ttttttcagt aaagggaata   2460
ttacatgttg ggaggaggag ataagttata gggagctgga tttcaaacgg tggtccaaga   2520
ttcaaaaatc ctattgatag tggccatttt aatcattgcc atcgtgtgct tgtttcatcc   2580
agtgttatgc actttccaca gttggtgtta gtatagccag agggtttcat tattatttct   2640
ctttgctttc tcaatgttaa tttattgcat ggtttattct ttttctttac agctgaaatt   2700
gctttaaatg atggttaaaa ttacaaatta aattgggaat tttatcaat gtgattgtaa   2760
ttaaaaatat tttgatttaa ataacaaaaa taataccaga ttttaagccg cggaaaatgt   2820
tcttgatcat ttgcagttaa ggactttaaa taaatcaaat gttaacaaaa aa           2872
```

<210> SEQ ID NO 311
<211> LENGTH: 926
<212> TYPE: DNA

<213> ORGANISM: Homo sapiens

<400> SEQUENCE: 311

```
ggggcccatt ctgtttcagc cagtcgccaa gaatcatgaa agtcgccagt ggcagcaccg      60
ccaccgccgc cgcgggcccc agctgcgcgc tgaaggccgg caagacagcg agcggtgcgg     120
gcgaggtggt gcgctgtctg tctgagcaga gcgtggccat ctcgcgctgc cggggcgccg     180
gggcgcgcct gcctgcccty ctggacgagc agcaggtaaa cgtgctgctc tacgacatga     240
acggctgtta ctcacgcctc aaggagctgg tgcccaccct gccccagaac cgcaaggtga     300
gcaaggtgga gattctccag cacgtcatcg actacatcgg gaccttcag ttggagctga      360
actcggaatc cgaagttggg accccgggg gccgagggct gccggtccgg gctccgctca      420
gcaccctcaa cggcgagatc agcgccctga cggccgaggc ggcatgcgtt cctgcggacg     480
atcgcatctt gtgtcgctga agcgcctccc ccagggaccg gcggaccca gccatccagg      540
gggcaagagg aattacgtgc tctgtgggtc tccccaacg cgcctcgccg gatctgaggg      600
agaacaagac cgatcggcgg ccactgcgcc cttaactgca tccagcctgg ggctgaggct     660
gaggcactgg cgaggagagg gcgctcctct ctgcacacct actagtcacc agagacttta     720
gggggtggga ttccactcgt gtgtttctat tttttgaaaa gcagacattt taaaaaatgg     780
tcacgtttgg tgcttctcag atttctgagg aaattgcttt gtattgtata ttacaatgat     840
caccgactga gaatattgtt ttacaatagt tctgtggggc tgttttttg ttattaaaca      900
aataatttag atggtgaaaa aaaaaa                                           926
```

<210> SEQ ID NO 312
<211> LENGTH: 4989
<212> TYPE: DNA
<213> ORGANISM: Homo sapiens

<400> SEQUENCE: 312

```
tttttttttt ttttgagaaa gggaatttca tcccaaataa aaggaatgaa gtctggctcc      60
ggaggagggt ccccgacctc gctgtggggg ctcctgtttc tctccgccgc gctctcgctc     120
tggccgacga gtggagaaat ctgcgggcca ggcatcgaca tccgcaacga ctatcagcag     180
ctgaagcgcc tggagaactg cacggtgatc gagggctacc tccacatcct gctcatctcc     240
aaggccgagg actaccgcag ctaccgcttc cccaagctca cggtcattac cgagtacttg     300
ctgctgttcc gagtggctgg cctcgagagc ctcggagacc tcttcccaa cctcacggtc      360
atccgcggct ggaaactctt ctacaactac gccctggtca tcttcgagat gaccaatctc     420
aaggatattg ggctttacaa cctgaggaac attactcggg gggccatcag gattgagaaa     480
aatgctgacc tctgttacct ctccactgtg gactggtccc tgatcctgga tgcggtgtcc     540
ataactacta ttgtggggaa taagccccca aaggaatgtg gggacctgtg tccagggacc     600
atggaggaga agccgatgtg tgagaagacc accatcaaca tgagtacaa ctaccgctgc      660
tggaccacaa accgctgcca gaaaatgtgc ccaagcacgt gtgggaagcg ggcgtgcacc     720
gagaacaatg agtgctgcca ccccgagtgc ctgggcagct gcagcgcgcc tgacaacgac     780
acggcctgtg tagcttgccg ccactactac tatgccggtg tctgtgtgcc tgcctgcccg     840
cccaacacct acaggtttga gggctggcgc tgtgtggacc gtgacttctg cgccaacatc     900
ctcagcgccg agagcagcga ctcgaggggg tttgtgatcc acgacggcga gtgcatgcag     960
gagtgcccct cgggcttcat ccgcaacggc agccagagca tgtactgcat cccttgtgaa    1020
ggtccttgcc cgaaggtctg tgaggaagaa aagaaaacaa agaccattga ttctgttact    1080
```

```
tctgctcaga tgctccaagg atgcaccatc ttcaagggca atttgctcat taacatccga    1140
cgggggaata acattgcttc agagctggag aacttcatgg ggctcatcga ggtggtgacg    1200
ggctacgtga agatccgcca ttctcatgcc ttggtctcct tgtccttcct aaaaaacctt    1260
cgcctcatcc taggagagga gcagctagaa gggaattact ccttctacgt cctcgacaac    1320
cagaacttgc agcaactgtg ggactgggac caccgcaacc tgaccatcaa agcagggaaa    1380
atgtactttg ctttcaatcc caaattatgt gtttccgaaa tttaccgcat ggaggaagtg    1440
acggggacta aagggcgcca aagcaaaggg gacataaaca ccaggaacaa cggggagaga    1500
gcctcctgtg aaagtgacgt cctgcatttc acctccacca ccacgtcgaa gaatcgcatc    1560
atcataacct ggcaccggta ccggcccccct gactacaggg atctcatcag cttcaccgtt    1620
tactacaagg aagcacccctt taagaatgtc acagagtatg atgggcagga tgcctgcggc    1680
tccaacagct ggaacatggt ggacgtggac ctcccgccca caaggacgt ggagcccggc    1740
atcttactac atgggctgaa gccctggact cagtacgccg tttacgtcaa ggctgtgacc    1800
ctcaccatgg tggagaacga ccatatccgt ggggccaaga gtgagatctt gtacattcgc    1860
accaatgctt cagttccttc cattcccttg gacgttcttt cagcatcgaa ctcctcttct    1920
cagttaatcg tgaagtggaa ccctcccctct ctgcccaacg gcaacctgag ttactacatt    1980
gtgcgctggc agcggcagcc tcaggacggc tacctttacc ggcacaatta ctgctccaaa    2040
gacaaaatcc ccatcaggaa gtatgccgac ggcaccatcg acattgagga ggtcacagag    2100
aaccccaaga ctgaggtgtg tggtggggag aaagggcctt gctgcgcctg ccccaaaact    2160
gaagccgaga agcaggccga aaggaggag gctgaatacc gcaaagtctt tgagaatttc    2220
ctgcacaact ccatcttcgt gcccagacct gaaaggaagc ggagagatgt catgcaagtg    2280
gccaacacca ccatgtccag ccgaagcagg aacaccacgg ccgcagacac ctacaacatc    2340
accgacccgg aagagctgga cacagagtac cctttctttg agagcagagt ggataacaag    2400
gagagaactg tcatttctaa ccttcggcct ttcacattgt accgcatcga tatccacagc    2460
tgcaaccacg aggctgagaa gctgggctgc agcgcctcca acttcgtctt tgcaaggact    2520
atgcccgcag aaggagcaga tgacattcct gggccagtga cctgggagcc aaggcctgaa    2580
aactccatct ttttaaagtg gccggaacct gagaatccca atggattgat tctaatgtat    2640
gaaataaaat acggatcaca agttgaggat cagcgagaat gtgtgtccag acaggaatac    2700
aggaagtatg gaggggccaa gctaaaccgg ctaaacccgg ggaactacac agcccggatt    2760
caggccacat ctctctctgg gaatgggtcg tggacagatc ctgtgttctt ctatgtccag    2820
gccaaaacag gatatgaaaa cttcatccat ctgatcatcg ctctgcccgt cgctgtcctg    2880
ttgatcgtgg agggttggt gattatgctg tacgtcttcc atagaaagag aaataacagc    2940
aggctgggga tggagtgct gtatgcctct gtgaacccgg agtacttcag cgctgctgat    3000
gtgtacgttc ctgatgagtg ggaggtggct cgggagaaga tcaccatgag ccgggaactt    3060
gggcaggggt cgtttggat ggtctatgaa ggagttgcca agggtgtggt gaaagatgaa    3120
cctgaaacca gagtggccat taaaacagtg aacgaggccg caagcatgcg tgagaggatt    3180
gagtttctca cgaagcttc tgtgatgaag gagttcaatt gtcaccatgt ggtgcgattg    3240
ctgggtgtgg tgtcccaagg ccagccaaca ctggtcatca tggaactgat gacacggggc    3300
gatctcaaaa gttatctccg gtctctgagg ccagaaatgg agaataatcc agtcctagca    3360
cctccaagcc tgagcaagat gattcagatg gccggagaga ttgcagacgg catggcatac    3420
```

```
ctcaacgcca ataagttcgt ccacagagac cttgctgccc ggaattgcat ggtagccgaa    3480
gatttcacag tcaaaatcgg agattttggt atgacgcgag atatctatga gacagactat    3540
taccggaaag gaggcaaagg gctgctgccc gtgcgctgga tgtctcctga gtccctcaag    3600
gatggagtct tcaccactta ctcggacgtc tggtccttcg gggtcgtcct ctgggagatc    3660
gccacactgg ccgagcagcc ctaccagggc ttgtccaacg agcaagtcct tcgcttcgtc    3720
atggagggcg gccttctgga caagccagac aactgtcctg acatgctgtt tgaactgatg    3780
cgcatgtgct ggcagtataa ccccaagatg aggccttcct tcctggagat catcagcagc    3840
atcaaagagg agatggagcc tggcttccgg gaggtctcct tctactacag cgaggagaac    3900
aagctgcccg agccgagga gctggacctg agccagaga acatggagag cgtcccctg     3960
gacccctcgg cctcctcgtc ctccctgcca ctgcccgaca cactcagg acacaaggcc     4020
gagaacggcc ccggccctgg ggtgctggtc ctccgcgcca gcttcgacga gagacagcct    4080
tacgcccaca tgaacggggg ccgcaagaac gagcgggcct gccgctgccc ccagtcttcg    4140
acctgctgat ccttggatcc tgaatctgtg caaacagtaa cgtgtgcgca cgcgcagcgg    4200
ggtgggggg agagagagt tttaacaatc cattcacaag cctcctgtac ctcagtggat     4260
cttcagttct gcccttgctg cccgcgggag acagcttctc tgcagtaaaa cacatttggg    4320
atgttccttt tttcaatatg caagcagctt tttattccct gcccaaaccc ttaactgaca    4380
tgggcccttta agaaccttaa tgacaacact taatagcaac agagcacttg agaaccagtc    4440
tcctcactct gtccctgtcc ttccctgttc tccctttctc tctcctctct gcttcataac    4500
ggaaaaataa ttgccacaag tccagctggg aagccctttt tatcagtttg aggaagtggc    4560
tgtccctgtg gcccccatcca accactgtac acacccgcct gacaccgtgg gtcattacaa    4620
aaaaacacgt ggagatggaa atttttacct ttatctttca cctttctagg gacatgaaat    4680
ttacaaaggg ccatcgttca tccaaggctg ttaccatttt aacgctgcct aattttgcca    4740
aaatcctgaa ctttctccct catcggcccg gcgctgattc ctcgtgtccg gaggcatggg    4800
tgagcatggc agctggttgc tccatttgag agacacgctg gcgacacact ccgtccatcc    4860
gactgcccct gctgtgctgc tcaaggccac aggcacacag gtctcattgc ttctgactag    4920
attattattt ggggggaactg gacacaatag gtctttctct cagtgaaggt ggggagaagc    4980
tgaaccggc                                                           4989

<210> SEQ ID NO 313
<211> LENGTH: 12515
<212> TYPE: DNA
<213> ORGANISM: Homo sapiens

<400> SEQUENCE: 313
ctaccgggcg gaggtgagcg cggcgccggc tcctcctgcg gcggactttg ggtgcgactt      60
gacgagcggt ggttcgacaa gtggccttgc gggccggatc gtcccagtgg aagagttgta    120
aatttgcttc tggccttccc ctacggatta tacctggcct tccctacgg attatactca    180
acttactgtt tagaaaatgt ggcccacgag acgcctggtt actatcaaaa ggagcggggt    240
cgacggtccc cactttcccc tgagcctcag cacctgcttg tttggaaggg gtattgaatg    300
tgacatccgt atccagcttc ctgttgtgtc aaaacaacat tgcaaaattg aaatccatga    360
gcaggaggca atattacata atttcagttc cacaaatcca acacaagtaa atgggtctgt    420
tattgatgag cctgtacggc taaaacatgg agatgtaata actattattg atcgttcctt    480
caggtatgaa aatgaaagtc ttcagaatgg aaggaagtca actgaatttc caagaaaaat    540
```

-continued

```
acgtgaacag gagccagcac gtcgtgtctc aagatctagc ttctcttctg accctgatga    600
gaaagctcaa gattccaagg cctattcaaa aatcactgaa ggaaaagttt caggaaatcc    660
tcaggtacat atcaagaatg tcaaagaaga cagtaccgca gatgactcaa aagacagtgt    720
tgctcaggga acaactaatg ttcattcctc agaacatgct ggacgtaatg cagaaatgc    780
agctgatccc atttctgggg attttaaaga aatttccagc gttaaattag tgagccgtta    840
tggagaattg aagtctgttc ccactacaca atgtcttgac aatagcaaaa aaaatgaatc    900
tcccttttgg aagctttatg agtcagtgaa gaaagagttg gatgtaaaat cacaaaaaga    960
aaatgtccta cagtattgta gaaaatctgg attacaaact gattacgcaa cagagaaaga   1020
aagtgctgat ggtttacagg gggagaccca actgttggtc tcgcgtaagt caagaccaaa   1080
atctggtggg agcggccacg ctgtggcaga gcctgcttca cctgaacaag agcttgacca   1140
gaacaagggg aagggaagag acgtggagtc tgttcagact cccagcaagg ctgtgggcgc   1200
cagctttcct ctctatgagc cggctaaaat gaagaccect gtacaatatt cacagcaaca   1260
aaattctcca caaaaacata gaacaaaga cctgtatact actggtagaa gagaatctgt   1320
gaatctgggt aaaagtgaag gcttcaaggc tggtgataaa actcttactc ccaggaagct   1380
ttcaactaga aatcgaacac cagctaaagt tgaagatgca gctgactctg ccactaagcc   1440
agaaaatctc tcttccaaaa ccagaggaag tattcctaca gatgtggaag ttctgcctac   1500
ggaaactgaa attcacaatg agccattttt aactctgtgg ctcactcaag ttgagaggaa   1560
gatccaaaag gattccctca gcaagcctga gaaattgggc actacagctg acagatgtg   1620
ctctgggtta cctggtctta gttcagttga tatcaacaac tttggtgatt ccattaatga   1680
gagtgaggga ataccttga aaagaaggcg tgtgtccttt ggtgggcacc taagacctga   1740
actatttgat gaaacttgc ctcctaatac gcctctcaaa aggggagaag ccccaaccaa   1800
aagaaagtct ctggtaatgc acactccacc tgtcctgaag aaaatcatca aggaacagcc   1860
tcaaccatca ggaaaacaag agtcaggttc agaaatccat gtggaagtga aggcacaaag   1920
cttggttata agccctccag ctcctagtcc taggaaaact ccagttgcca gtgatcaacg   1980
ccgtaggtcc tgcaaaacag cccctgcttc cagcagcaaa tctcagacag aggttcctaa   2040
gagaggagga gaaagagtgg caacctgcct tcaaaagaga gtgtctatca gccgaagtca   2100
acatgatatt ttacagatga tatgttccaa aagaagaagt ggtgcttcgg aagcaaatct   2160
gattgttgca aaatcatggg cagatgtagt aaaaacttggt gcaaaacaaa cacaaactaa   2220
agtcataaaa catggtcctc aaaggtcaat gaacaaaagg caaagaagac ctgctactcc   2280
aaagaagcct gtgggcgaag ttcacagtca atttagtaca ggccacgcaa actctccttg   2340
taccataata ataggaaag ctcatactga aaaagtacat gtgcctgctc gacectacag   2400
agtgctcaac aacttcattt ccaaccaaaa aatggacttt aaggaagatc tttcaggaat   2460
agctgaaatg ttcaagaccc cagtgaagga gcaaccgcag ttgacaagca catgtcacat   2520
cgctatttca aattcagaga atttgcttgg aaaacagttt caaggaactg attcaggaga   2580
agaacctctg ctccccacct cagagagttt tggaggaaat gtgttcttca gtgcacagaa   2640
tgcagcaaaa cagccatctg ataaatgctc tgcaagccct cccttaagac ggcagtgtat   2700
tagagaaaat ggaaacgtag caaaaacgcc caggaacacc tacaaaatga cttctctgga   2760
gacaaaaact tcagatactg agacagagcc ttcaaaaaca gtatccactg taaacaggtc   2820
aggaaggtct acagagttca ggaatataca gaagctacct gtgaaagta agagtgaaga   2880
```

```
aacaaataca gaaattgttg agtgcatcct aaaaagaggt cagaaggcaa cactactaca    2940
acaaaggaga gaaggagaga tgaaggaaat agaaagacct tttgagacat ataaggaaaa    3000
tattgaatta aaagaaaacg atgaaaagat gaaagcaatg aagagatcaa gaacttgggg    3060
gcagaaatgt gcaccaatgt ctgacctgac agacctcaag agcttgcctg atacagaact    3120
catgaaagac acggcacgtg ccagaatctc cctccaaacc caagatcatg ccaaggcacc    3180
aaagagtgag aaaggcaaaa tcactaaaat gccctgccag tcattacaac cagaaccaat    3240
aaacacccca acacacacaa aacaacagtt gaaggcatcc ctggggaaag taggtgtgaa    3300
agaagagctc ctagcagtcg gcaagttcac acggacgtca ggggagacca cgcacacgca    3360
cagagagcca gcaggagatg gcaagagcat cagaacgttt aaggagtctc caaagcagat    3420
cctggaccca gcagcccgtg taactggaat gaagaagtgg ccaagaacgc taaggaaga    3480
ggcccagtca ctagaagacc tggctggctt caaagagctc ttccagacac caggtccctc    3540
tgaggaatca atgactgatg agaaaactac caaaatagcc tgcaaatctc caccaccaga    3600
atcagtggac actccaacaa gcacaaagca atggcctaag agaagtctca ggaaagcaga    3660
tgtagaggaa gaattcttag cactcaggaa actaacacca tcagcaggga aagccatgct    3720
tacgcccaaa ccagcaggag gtgatgagaa agacattaaa gcatttatgg aactccagt    3780
gcagaaactg gacctggcag gaactttacc tggcagcaaa agacagctac agactcctaa    3840
ggaaaaggcc caggctctag aagacctggc tggctttaaa gagctcttcc agactcctgg    3900
tcacaccgag gaattagtgg ctgctggtaa aaccactaaa ataccctgcg actctccaca    3960
gtcagaccca gtggacaccc caacaagcac aaagcaacga cccaagagaa gtatcaggaa    4020
agcagatgta gagggagaac tcttagcgtg caggaatcta atgccatcag caggcaaagc    4080
catgcacacg cctaaaccat cagtaggtga agagaaagac atcatcatat tgtgtgggaac    4140
tccagtgcag aaactggacc tgacagagaa cttaaccggc agcaagagac ggccacaaac    4200
tcctaaggaa gaggcccagg ctctggaaga cctgactggc tttaaagagc tcttccagac    4260
ccctggtcat actgaagaag cagtggctgc tggcaaaact actaaaatgc cctgcgaatc    4320
ttctccacca gaatcagcag acaccccaac aagcacaaga aggcagccca agacaccttt    4380
ggagaaaagg gacgtacaga aggagctctc agccctgaag aagctcacac agacatcagg    4440
ggaaaccaca cacacagata agtaccagg aggtgaggat aaaagcatca acgcgtttag    4500
ggaaactgca aaacagaaac tggacccagc agcaagtgta actggtagca agaggcaccc    4560
aaaaactaag gaaaaggccc aaccctaga gacctggct ggctggaaag agctcttcca    4620
gacaccagta tgcactgaca gcccacgac tcacgagaaa actaccaaaa tagcctgcag    4680
atcacaacca gacccagtgg acacaccaac aagctccaag ccacagtcca agagaagtct    4740
caggaaagtg gacgtagaag aagaattctt cgcactcagg aaacgaacac catcagcagg    4800
caaagccatg cacacaccca accagcagt aagtggtgag aaaaacatct acgcatttat    4860
gggaactcca gtgcagaaac tggacctgac agagaactta actggcagca agagacggct    4920
acaaactcct aaggaaaagg cccaggctct agaagacctg gctggcttta aagagctctt    4980
ccagacacga ggtcacactg aggaatcaat gactaacgat aaaactgcca agtagcctg    5040
caaatcttca caaccagacc tagacaaaaa cccagcaagc tccaagcgac ggctcaagac    5100
atccctgggg aaagtgggcg tgaaagaaga gctcctagca gttggcaagc tcacacagac    5160
atcaggagag actacacaca cacacacaga gccaacagga gatggtaaga gcatgaaagc    5220
atttatggag tctccaaagc agatcttaga ctcagcagca agtctaactg gcagcaagag    5280
```

```
gcagctgaga actcctaagg gaaagtctga agtccctgaa gacctggccg gcttcatcga    5340
gctcttccag acaccaagtc acactaagga atcaatgact aatgaaaaaa ctaccaaagt    5400
atcctacaga gcttcacagc cagacctagt ggacacccca acaagctcca agccacagcc    5460
caagagaagt ctcaggaaag cagacactga agaagaattt ttagcattta ggaaacaaac    5520
gccatcagca ggcaaagcca tgcacacacc caaaccagca gtaggtgaag agaaagacat    5580
caacacgttt ttgggaactc cagtgcagaa actggaccag ccaggaaatt tacctggcag    5640
caatagacgg ctacaaactc gtaaggaaaa ggcccaggct ctagaagaac tgactggctt    5700
cagagagctt ttccagacac catgcactga taaccccaca gctgatgaga aaactaccaa    5760
aaaaatactc tgcaaatctc cgcaatcaga cccagcggac accccaacaa acacaaagca    5820
acggcccaag agaagcctca agaaagcaga cgtagaggaa gaattttag cattcaggaa    5880 actaacacca tcagcaggca aagccatgca cacgcctaaa gcagcagtag gtgaagagaa    5940
agacatcaac acatttgtgg ggactccagt ggagaaactg gacctgctag gaaatttacc    6000
tggcagcaag agacggccac aaaactcctaa agaaaaggcc aaggctctag aagatctggc    6060
tggcttcaaa gagctcttcc agacaccagg tcacactgag gaatcaatga ccgatgacaa    6120
aatcacagaa gtatcctgca aatctccaca accagcccca gtcaaaaccc caacaagctc    6180
caagcaacga ctcaagatat ccttggggaa agtaggtgtg aaagaagagg tcctaccagt    6240
cggcaagctc acacagacgt cagggaagac cacacagaca cacagagaga cagcaggaga    6300
tggaaagagc atcaaagcgt ttaaggaatc tgcaaagcag atgctggacc cagcaaacta    6360
tggaactggg atggagaggt ggccaagaac acctaaggaa gaggcccaat cactagaaga    6420
cctggccggc ttcaaagagc tcttccagac accagaccac actgaggaat caacaactga    6480
tgacaaaact accaaaatag cctgcaaatc tccaccacca gaatcaatgg acactccaac    6540
aagcacaagg aggcggccca aaacaccttt ggggaaaagg gatatagtgg aagagctctc    6600
agccctgaag cagctcacac agaccacaca cacagacaaa gtaccaggag atgaggataa    6660
aggcatcaac gtgttcaggg aaactgcaaa acagaaactg acccagcag caagtgtaac    6720 tggtagcaag aggcagccaa gaactcctaa gggaaaagcc caaccctag aagacttggc    6780 tggcttgaaa gagctcttcc agacaccagt atgcactgac aagcccacga ctcacgagaa    6840
aactaccaaa atagcctgca gatctccaca accagaccca gtgggtaccc caacaatctt    6900
caagccacag tccaagagaa gtctcaggaa agcagacgta gaggaagaat ccttagcact    6960
caggaaacga acaccatcag tagggaaagc tatggacaca cccaaaccag caggaggtga    7020
tgagaaagac atgaaagcat ttatgggaac tccagtgcag aaattggacc tgccaggaaa    7080
tttacctggc agcaaaagat ggccacaaac tcctaaggaa aaggcccagg ctctagaaga    7140
cctggctggc ttcaaagagc tcttccagac accaggcact gacaagccca cgactgatga    7200
gaaaactacc aaaatagcct gcaaatctcc acaaccagac ccagtggaca ccccagcaag    7260
cacaaagcaa cggcccaaga gaaacctcag gaaagcagac gtagaggaag aattttag    7320 actcaggaaa cgaacaccat cagcaggcaa agccatggac accccaaaac cagcagtaag    7380
tgatgagaaa aatatcaaca catttgtgga aactccagtg cagaaactgg acctgctagg    7440
aaatttacct ggcagcaaga gacagccaca gactcctaag gaaaaggctg aggctctaga    7500
ggacctggtt ggcttcaaag aactcttcca gacaccaggt cacactgagg aatcaatgac    7560
tgatgacaaa atcacagaag tatcctgtaa atctccacag ccagagtcat tcaaaaacctc    7620
```

```
aagaagctcc aagcaaaggc tcaagatacc cctggtgaaa gtggacatga aagaagagcc    7680
cctagcagtc agcaagctca cacggacatc aggggagact acgcaaacac acacagagcc    7740
aacaggagat agtaagagca tcaaagcgtt taaggagtct ccaaagcaga tcctggaccc    7800
agcagcaagt gtaactggta gcaggaggca gctgagaact cgtaaggaaa aggcccgtgc    7860
tctagaagac ctggttgact tcaaagagct cttctcagca ccaggtcaca ctgaagagtc    7920
aatgactatt gacaaaaaca caaaaattcc ctgcaaatct cccccaccag aactaacaga    7980
cactgccacg agcacaaaga gatgccccaa gacacgtccc aggaaagaag taaaagagga    8040
gctctcagca gttgagaggc tcacgcaaac atcaggcaa agcacacaca cacacaaaga    8100
accagcaagc ggtgatgagg gcatcaaagt attgaagcaa cgtgcaaaga agaaaccaaa    8160
cccagtagaa gaggaaccca gcaggagaag gccaagagca cctaaggaaa aggcccaacc    8220
cctggaagac ctggccggct tcacagagct ctctgaaaca tcaggtcaca ctcaggaatc    8280
actgactgct ggcaaagcca ctaaaatacc ctgcgaatct cccccactag aagtggtaga    8340
caccacagca agcacaaaga ggcatctcag gacacgtgtg cagaaggtac aagtaaaaga    8400
agagccttca gcagtcaagt tcacacaaac atcaggggaa accacggatg cagacaaaga    8460
accagcaggt gaagataaag gcatcaaagc attgaaggaa tctgcaaaac agacaccggc    8520
tccagcagca agtgtaactg gcagcaggag acggccaaga gcacccaggg aaagtgccca    8580
agccatagaa gacctagctg gcttcaaaga cccagcagca ggtcacactg aagaatcaat    8640
gactgatgac aaaaccacta aaatacctg caaatcatca ccagaactag aagacaccgc    8700
aacaagctca aagagacggc ccaggacacg tgcccagaaa gtagaagtga aggaggagct    8760
gttagcagtt ggcaagctca cacaaacctc aggggagacc acgcacaccg acaaagagcc    8820
ggtaggtgag ggcaaaggca cgaaagcatt taagcaacct gcaaagcgga acgtggacgc    8880
agaagatgta attggcagca ggagacagcc aagagcacct aaggaaaagg cccaacccct    8940
ggaagacctg gccagcttcc aagagctctc tcaaacacca ggccacactg aggaactggc    9000
aaatggtgct gctgatagct ttacaagcgc tccaaagcaa acacctgaca gtggaaaacc    9060
tctaaaaata tccagaagag ttcttcgggc ccctaaagta gaacccgtgg gagacgtggt    9120
aagcaccaga gaccctgtaa aatcacaaag caaaagcaac acttccctgc ccccactgcc    9180
cttcaagagg ggaggtggca agatggaag cgtcacggga accaagaggc tgcgctgcat    9240
gccagcacca gaggaaattg tggaggagct gccagccagc aagaagcaga gggttgctcc    9300
cagggcaaga ggcaaatcat ccgaacccgt ggtcatcatg aagagaagtt tgaggacttc    9360
tgcaaaaaga attgaacctg cggaagagct gaacagcaac gacatgaaaa ccaacaaaga    9420
ggaacacaaa ttacaagact cggtccctga aaataaggga atatccctgc gctccagacg    9480
ccaagataag actgaggcag aacagcaaat aactgaggtc tttgtattag cagaaagaat    9540
agaaataaac agaaatgaaa agaagcccat gaagacctcc ccagagatgg acattcagaa    9600
tccagatgat ggagcccgga aacccatacc tagagacaaa gtcactgaga acaaaaggtg    9660
cttgaggtct gctagacaga atgagagctc ccagcctaag gtggcagagg agagcggagg    9720
gcagaagagt gcgaaggttc tcatgcagaa tcagaaaggg aaaggagaag caggaaattc    9780
agactccatg tgcctgagat caagaaagac aaaaagccag cctgcagcaa gcactttgga    9840
gagcaaatct gtgcagagag taacgcggag tgtcaagagg tgtgcagaaa atccaaagaa    9900
ggctgaggac aatgtgtgtg tcaagaaaat aacaaccaga agtcataggg acagtgaaga    9960
tatttgacag aaaaatcgaa ctgggaaaaa tataataaag ttagttttgt gataagttct   10020
```

```
agtgcagttt tgtcataaa ttacaagtga attctgtaag taaggctgtc agtctgctta  10080
agggaagaaa actttggatt tgctgggtct gaatcggctt cataaactcc actgggagca  10140
ctgctgggct cctggactga aatagttga acaccggggg cttttgtgaag gagtctgggc  10200
caaggtttgc cctcagcttt gcagaatgaa gccttgaggt ctgtcaccac ccacagccac  10260
cctacagcag ccttaactgt gacacttgcc acactgtgtc gtcgtttgtt tgcctatgtt  10320
ctccagggca cggtggcagg aacaactatc ctcgtctgtc ccaacactga gcaggcactc  10380
ggtaaacacg aatgaatgga taagcgcacg gatgaatgga gcttacaaga tctgtctttc  10440
caatggccgg gggcatttgg tccccaaatt aaggctattg acatctgca caggacagtc  10500
ctatttttga tgtcctttcc tttctgaaaa taaagttttg tgctttggag aatgactcgt  10560
gagcacatct ttagggacca agagtgactt tctgtaagga gtgactcgtg gcttgccttg  10620
gtctcttggg aatacttttc taactagggt tgctctcacc tgagacattc tccacccgcg  10680
gaatctcagg gtcccaggct gtgggccatc acgacctcaa actggctcct aatctccagc  10740
tttcctgtca ttgaaagctt cggaagttta ctggctctgc tcccgcctgt tttctttctg  10800
actctatctg gcagcccgat gccacccagt acaggaagtg acaccagtac tctgtaaagc  10860
atcatcatcc ttggagagac tgagcactca gcaccttcag ccacgatttc aggatcgctt  10920
ccttgtgagc cgctgcctcc gaaatctcct ttgaagccca gacatctttc tccagcttca  10980
gacttgtaga tataactcgt tcatcttcat ttactttcca cttttgcccc tgtcctctct  11040
gtgttcccca aatcagagaa tagcccgcca tcccccagat cacctgtctg gattcctccc  11100
cattcaccca ccttgccagg tgcaggtgag gatggtgcac cagacagggt agctgtcccc  11160
caaaatgtgc cctgtgcggg cagtgccctg tctccacgtt tgtttcccca gtgtctggcg  11220
gggagccagg tgacatcata aatacttgct gaatgaatgc agaaatcagc ggtactgact  11280
tgtactatat tggctgccat gatagggttc tcacagcgtc atccatgatc gtaagggaga  11340
atgacattct gcttgaggga gggaatagaa aggggcaggg aggggacatc tgagggcttc  11400
acagggctgc aaagggtaca gggattgcac caggcagaa caggggaggg tgttcaagga  11460
agagtggctc ttagcagagg cactttggaa ggtgtgaggc ataaatgctt ccttctacgt  11520
aggccaacct caaaactttc agtaggaatg ttgctatgat caagttgttc taacacttta  11580
gacttagtag taattatgaa cctcacatag aaaaatttca tccagccata tgcctgtgga  11640
gtggaatatt ctgtttagta gaaaaatcct ttagagttca gctctaacca gaaatcttgc  11700
tgaagtatgt cagcaccttt tctcaccctg gtaagtacag tatttcaaga gcacgctaag  11760
ggtggttttc attttacagg gctgttgatg atgggtaaa aatgttcatt taagggctac  11820
ccccgtgttt aatagatgaa caccacttct acacaaccct ccttggtact gggggaggga  11880
gagatctgac aaatactgcc cattccccta ggctgactgg atttgagaac aaatacccac  11940
ccatttccac catggtatgg taacttctct gagcttcagt ttccaagtga atttccatgt  12000
aataggacat tcccattaaa tacaagctgt ttttactttt tcgcctccca gggcctgtgc  12060
gatctggtcc cccagcctct cttgggcttt cttacactaa ctctgtacct accatctcct  12120
gcctccctta ggcaggcacc tccaaccacc acacactccc tgctgttttc cctgcctgga  12180
actttcccac cagcccacc aagatcattt catccagtcc tgagctcagc ttaagggagg  12240
cttcttgcct gtgggttccc tcaccccat gcctgtcctc caggctgggg caggttctta  12300
gtttgcctgg aattgttctg tacctctttg tagcacgtag tgttgtgaaa ctaagccact  12360
```

<210> SEQ ID NO 314
<211> LENGTH: 2444
<212> TYPE: DNA
<213> ORGANISM: Homo sapiens

<400> SEQUENCE: 314

| | | | | | |
|---|---|---|---|---|---|
| ggcacgaggc | ggggccgggt | cgcagctggg | cccgcggcat | ggacgaactg | ttccccctca | 60 |
| tcttcccggc | agagcagccc | aagcagcggg | gcatgcgctt | ccgctacaag | tgcgagggggc | 120 |
| gctccgcggg | cagcatccca | ggcgagagga | gcacagatac | caccaagacc | caccccacca | 180 |
| tcaagatcaa | tggctacaca | ggaccaggga | cagtgcgcat | ctccctggtc | accaaggacc | 240 |
| ctcctcaccg | gcctcacccc | cacgagcttg | taggaaagga | ctgccgggat | ggcttctatg | 300 |
| aggctgagct | ctgcccggac | cgctgcatcc | acagtttcca | gaacctggga | atccagtgtg | 360 |
| tgaagaagcg | ggacctggag | caggctatca | gtcagcgcat | ccagaccaac | aacaacccct | 420 |
| tccaagttcc | tatagaagag | cagcgtgggg | actacgacct | gaatgctgtg | cggctctgct | 480 |
| tccaggtgac | agtgcgggac | ccatcaggca | ggccccctccg | cctgccgcct | gtcctttctc | 540 |
| atcccatctt | tgacaatcgt | gccccccaaca | ctgccgagct | caagatctgc | cgagtgaacc | 600 |
| gaaactctgg | cagctgcctc | ggtggggatg | agatcttcct | actgtgtgac | aaggtgcaga | 660 |
| agaggacat | tgaggtgtat | ttcacgggac | caggctggga | ggcccgaggc | tccttttcgc | 720 |
| aagctgatgt | gcaccgacaa | gtggccattg | tgttccggac | ccctccctac | gcagacccca | 780 |
| gcctgcaggc | tcctgtgcgt | gtctccatgc | agctgcggcg | gccttccgac | cgggagctca | 840 |
| gtgagcccat | ggaattccag | tacctgccag | atacagacga | tcgtcaccgg | attgaggaga | 900 |
| aacgtaaaag | gacatatgag | accttcaaga | gcatcatgaa | gaagagtcct | ttcagcggac | 960 |
| ccaccgaccc | ccggcctcca | cctcgacgca | ttgctgtgcc | ttcccgcagc | tcagcttctg | 1020 |
| tccccaagcc | agcaccccag | ccctatccct | ttacgtcatc | cctgagcacc | atcaactatg | 1080 |
| atgagtttcc | caccatggtg | tttccttctg | ggcagatcag | ccaggcctcg | gccttggccc | 1140 |
| cggcccctcc | ccaagtcctg | cccaggctc | cagcccctgc | cctgctcca | gccatggtat | 1200 |
| cagctctggc | ccaggcccca | gccctgtcc | cagtcctagc | cccaggccct | cctcaggctg | 1260 |
| tggccccacc | tgcccccaag | cccacccagg | ctggggaagg | aacgctgtca | gaggccctgc | 1320 |
| tgcagctgca | gtttgatgat | gaagacctgg | gggccttgct | tggcaacagc | acagacccag | 1380 |
| ctgtgttcac | agacctggca | tccgtcgaca | actccgagtt | tcagcagctg | ctgaaccagg | 1440 |
| gcatacctgt | ggccccccac | acaactgagc | ccatgctgat | ggagtaccct | gaggctataa | 1500 |
| ctcgcctagt | gacagcccag | aggcccccg | acccagctcc | tgctccactg | ggggcccgg | 1560 |
| ggctccccaa | tggcctcctt | tcaggagatg | aagacttctc | ctccattgcg | gacatggact | 1620 |
| tctcagccct | gctgagtcag | atcagctcct | aaggggggtga | cgcctgccct | ccccagagca | 1680 |
| ctggttgcag | gggattgaag | ccctccaaaa | gcacttacgg | attctggtgg | ggtgtgttcc | 1740 |
| aactgccccc | aactttgtgg | atgtcttcct | tggagggggg | agccatattt | tattcttta | 1800 |
| ttgtcagtat | ctgtatctct | ctctcttttt | ggaggtgctt | aagcagaagc | attaacttct | 1860 |
| ctggaaaggg | gggagctggg | gaaactcaaa | cttttcccct | gtcctgatgg | tcagctccc | 1920 |
| tctctgtagg | gaactgtggg | gtccccccatc | cccatcctcc | agcttctggt | actctcctag | 1980 |

```
agacagaagc aggctggagg taaggccttt gagcccacaa agccttatca agtgtcttcc    2040
atcatggatt cattacagct taatcaaaat aacgccccag ataccagccc ctgtatggca    2100
ctggcattgt ccctgtgcct aacaccagcg tttgaggggc tgccttcctg ccctacagag    2160
gtctctgccg gctctttcct tgctcaacca tggctgaagg aaacagtgca acagcactgg    2220
ctctctccag gatccagaag gggtttggtc tggacttcct tgctctcccc tcttctcaag    2280
tgccttaata gtagggtaag ttgttaagag tgggggagag caggctggca gctctccagt    2340
caggaggcat agtttttagt gaacaatcaa agcacttgga ctcttgctct ttctactctg    2400
aactaataaa gctgttgcca agctggacgg cacgagctcg tgcc                    2444

<210> SEQ ID NO 315
<211> LENGTH: 732
<212> TYPE: DNA
<213> ORGANISM: Homo sapiens

<400> SEQUENCE: 315
tgctgcgaac cacgtgggtc ccgggcgcgt ttcgggtgct ggcggctgca gccggagttc      60
aaacctaagc agctggaagg aaccatggcc aactgtgagc gtaccttcat tgcgatcaaa     120
ccagatgggg tccagcgggg tcttgtggga gagattatca agcgttttga gcagaaagga     180
ttccgccttg ttggtctgaa attcatgcaa gcttccgaag atcttctcaa ggaacactac     240
gttgacctga aggaccgtcc attctttgcc ggcctggtga atacatgca ctcagggccg      300 gtagttgcca tggtctggga ggggctgaat gtggtgaaga cgggccgagt catgctcggg     360
gagaccaacc ctgcagactc caagcctggg accatccgtg gagacttctg catacaagtt     420
ggcaggaaca ttatacatgg cagtgattct gtggagagtg cagagaagga gatcggcttg     480
tggtttcacc ctgaggaact ggtagattac acgagctgtg ctcagaactg gatctatgaa     540
tgacaggagg gcagaccaca ttgcttttca catccatttc ccctccttcc catgggcaga     600
ggaccaggct gtaggaaatc tagttattta caggaacttc atcataattt ggagggaagc     660
tcttggagct gtgagttctc cctgtacagt gttaccatcc ccgaccatct gattaaaatg     720
cttcctccca gc                                                        732

<210> SEQ ID NO 316
<211> LENGTH: 2422
<212> TYPE: DNA
<213> ORGANISM: Homo sapiens

<400> SEQUENCE: 316
gtcagcctcc cttccaccgc catattgggc cactaaaaaa aggggggctcg tcttttcggg     60 gtgttttttct cccctcccc tgtccccgct tgctcacggc tctgcgactc cgacgccggc    120
aaggtttgga gagcggctgg gttcgcggga cccgcgggct tgcacccgcc cagactcgga    180
cgggctttgc caccctctcc gcttgcctgg tcccctctcc tctccgccct ccgctcgcc    240 agtccatttg atcagcggag actcggcggc cgggccgggg cttccccgca gcccctgcgc    300
gctcctagag ctcgggccgt ggctcgtcgg ggtctgtgtc ttttggctcc gagggcagtc    360
gctgggcttc cgagagggt tcgggccgcg tagggggcgct ttgttttgtt cggttttgtt    420
tttttgagag tgcgagagag gcggtcgtgc agacccggga gaaagatgtc aaacgtgcga    480
gtgtctaacg ggagccctag cctgagcgg atgacgccca ggcaggcgga gcaccccaag     540 cccctcggcct gcaggaacct cttcggcccg gtggaccacg aagagttaac ccgggacttg    600
```

| | |
|---|---:|
| gagaagcact gcagagacat ggaagaggcg agccagcgca agtggaattt cgattttcag | 660 |
| aatcacaaac ccctagaggg caagtacgag tggcaagagg tggagaaggg cagcttgccc | 720 |
| gagttctact acagaccccc gcggcccccc aaaggtgcct gcaaggtgcc ggcgcaggag | 780 |
| agccaggatg tcagcgggag ccgcccggcg gcgcctttaa ttggggctcc ggctaactct | 840 |
| gaggacacgc atttggtgga cccaaagact gatccgtcgg acagccagac ggggttagcg | 900 |
| gagcaatgcg caggaataag gaagcgacct gcaaccgacg attcttctac tcaaaacaaa | 960 |
| agagccaaca gaacagaaga aaatgtttca gacggttccc caaatgccgg ttctgtggag | 1020 |
| cagacgccca gaagcctggg cctcagaaga cgtcaaacgt aaacagctcg aattaagaat | 1080 |
| atgtttcctt gtttatcaga tacatcactg cttgatgaag caaggaagat atacatgaaa | 1140 |
| attttaaaaa tacatatcgc tgacttcatg gaatggacat cctgtataag cactgaaaaa | 1200 |
| caacaacaca ataacactaa aattttaggc actcttaaat gatctgcctc taaaagcgtt | 1260 |
| ggatgtagca ttatgcaatt aggttttttcc ttatttgctt cattgtacta cctgtgtata | 1320 |
| tagtttttac ctttttatgta gcacataaac tttggggaag ggagggcagg gtggggctga | 1380 |
| ggaactgacg tggagcgggg tatgaagagc ttgctttgat ttacagcaag tagataaata | 1440 |
| tttgacttgc atgaagagaa gcaattttgg ggaagggttt gaattgtttt ctttaaagat | 1500 |
| gtaatgtccc tttcagagac agctgatact tcatttaaaa aaatcacaaa aatttgaaca | 1560 |
| ctggctaaag ataattgcta tttatttta caagaagttt attctcattt gggagatctg | 1620 |
| gtgatctccc aagctatcta agttttgtta gatagctgca tgtggctttt ttaaaaaagc | 1680 |
| aacagaaacc tatcctcact gccctcccca gtctctctta aagttggaat ttaccagtta | 1740 |
| attactcagc agaatggtga tcactccagg tagtttgggg caaaaatccg aggtgcttgg | 1800 |
| gagttttgaa tgttaagaat tgaccatctg cttttattaa atttgttgac aaaattttct | 1860 |
| cattttcttt tcacttcggg ctgtgtaaac acagtcaaaa taattctaaa tccctcgata | 1920 |
| tttttaaaga tctgtaagta acttcacatt aaaaaatgaa atatttttta atttaaagct | 1980 |
| tactctgtcc atttatccac aggaaagtgt tattttaaa ggaaggttca tgtagagaaa | 2040 |
| agcacacttg taggataagt gaaatggata ctacatcttt aaacagtatt tcattgcctg | 2100 |
| tgtatggaaa aaccatttga agtgtacctg tgtacataac tctgtaaaaa cactgaaaaa | 2160 |
| ttatactaac ttatttatgt taaaagattt tttttaatct agacaatata caagccaaag | 2220 |
| tggcatgttt tgtgcatttg taatgctgt gttgggtaga ataggttttc ccctcttttg | 2280 |
| ttaaataata tggctatgct taaaaggttg catactgagc caagtataat tttttgtaat | 2340 |
| gtgtgaaaaa gatgccaatt attgttacac attaagtaat caataaagaa aacttccata | 2400 |
| gctaaaaaaa aaaaaaaaa aa | 2422 |

```
<210> SEQ ID NO 317
<211> LENGTH: 5061
<212> TYPE: DNA
<213> ORGANISM: Homo sapiens

<400> SEQUENCE: 317
```

| | |
|---|---:|
| atggctcaga tatttagcaa cagcggattt aaagaatgtc cattttcaca tccggaacca | 60 |
| acaagagcaa aagatgtgga caagaagaa gcattacaga tggaagcaga ggctttagca | 120 |
| aaactgcaaa aggatagaca agtgactgac aatcagagag gctttgagtt gtcaagcagc | 180 |
| accagaaaaa aagcacaggt ttataacaag caggattatg atctcatggt gtttcctgaa | 240 |
| tcagattccc aaaaaagagc attagatatt gatgtagaaa agctcaccca agctgaactt | 300 |

```
gagaaactat tgctggatga cagtttcgag actaaaaaaa cacctgtatt accagttact    360
cctattctga gcccttcctt ttcagcacag ctctatttta gacctactat tcagagagga    420
cagtggccac ctggattacc tgggccttcc acttatgctt taccttctat ttatccttct    480
acttacagta aacaggctgc attccaaaat ggcttcaatc caagaatgcc cacttttcca    540
tctacagaac ctatatattt aagtcttccg gacaatctc catatttctc atatcctttg     600
acacctgcca caccctttca tccacaagga agcttaccta tctatcgtcc agtagtcagt    660
actgacatgg caaaactatt tgacaaaata gctagtacat cagaattttt aaaaaatggg    720
aaagcaagga ctgatttgga gataacagat tcaaaagtca gcaatctaca ggtatctcca    780
aagtctgagg atatcagtaa atttgactgg ttagacttgg atcctctaag taagcctaag    840
gtggataatg tggaggtatt agaccatgag gaagagaaaa atgtttcaag tttgctagca    900
aaggatcctt gggatgctgt tcttcttgaa gagagatcga cagcaaattg tcatcttgaa    960
agaaaggtga atggaaaatc cctttctgtg gcaactgtta caagaagcca gtctttaaat   1020
attcgaacaa ctcagcttgc aaaagcccag ggccatatat ctcagaaaga cccaaatggg   1080
accagtagtt tgccaactgg aagttctctt cttcaagaag ttgaagtaca gaatgaggag   1140
atggcagctt tttgtcgatc cattacaaaa ttgaagacca aatttccata taccaatcac   1200
cgcacaaacc caggctattt gttaagtcca gtcacagcgc aaagaaacat atgcggagaa   1260
aatgctagtg tgaaggtctc cattgacatt gaaggatttc agctaccagt tacttttacg   1320
tgtgatgtga gttctactgt agaaatcatt ataatgcaag ccctttgctg ggtacatgat   1380
gacttgaatc aagtagatgt tggcagctat gttctaaaag tttgtggtca agaggaagtg   1440
ctgcagaata atcattgcct tggaagtcat gagcatattc aaaactgtcg aaaatgggac   1500
acagaaatta gactacaact cttgaccttc agtgcaatgt gtcaaaatct ggcccgaaca   1560
gcagaagatg atgaaacacc cgtggattta acaaacacc tgtatcaaat agaaaaaacct   1620
tgcaaagaag ccatgacgag acaccctgtt gaagaactct agattcttta tcacaaccaa   1680
gtagaactgg ctcttcaaat tgaaaaccaa caccgagcag tagatcaagt aattaaagct   1740
gtaagaaaaa tctgtagtgc tttagatggt gtcgagactc ttgccattac agaatcagta   1800
aagaagctaa agagagcagt taatcttcca aggagtaaaa ctgctgatgt gacttctttg   1860
tttggaggag aagacactag caggagttca actaggggct cacttaatcc tgaaaatcct   1920
gttcaagtaa gcataaacca attaactgca gcaatttatg atcttctcag actccatgca   1980
aattctggta ggagtcctac agactgtgcc caaagtagca agagtgtcaa ggaagcatgg   2040
actacaacag agcagctcca gtttactatt tttgctgctc atggaatttc aagtaattgg   2100
gtatcaaatt atgaaaaata ctacttgata tgttcactgt ctcacaatgg aaaggatctt   2160
tttaaaccta ttcaatcaaa gaaggttggc acttacaaga atttcttcta tcttattaaa   2220
tgggatgaac taatcatttt tcctatccag atatcacaat tgccattaga atcagttctt   2280
caccttactc tttttggaat tttaaatcag agcagtggaa gttcccctga ttctaataag   2340
cagagaaagg gaccagaagc tttgggcaaa gtttctttac ctctttgtga ctttagacgg   2400
tttttaacat gtggaactaa acttctatat ctttggactt catcacatac aaattctgtt   2460
cctggaacag ttaccaaaaa aggatatgtc atggaagaa tagtgctaca ggttgatttt   2520
ccttctcctg catttgatat tatttataca actcctcaag ttgacagaag cattatacag   2580
caacataact tagaaacact agagaatgat ataaaaggga aacttcttga tattcttcat   2640
```

```
aaagactcat cacttggact ttctaaagaa gataaagctt ttttatggga gaaacgttat     2700
tattgcttca aacacccaaa ttgtcttcct aaaatattag caagcgcccc aaactggaaa     2760
tggggtaatc ttgccaaaac ttactcattg cttcaccagt ggcctgcatt gtacccacta     2820
attgcattgg aacttcttga ttcaaaattt gctgatcagg aagtaagatc cctagctgtg     2880
acctggattg aggccattag tgatgatgag ctaacagatc ttcttccaca gtttgtacaa     2940
gctttgaaat atgaaattta cttgaatagt tcattagtgc aattccrtttt gtccagggca     3000 ttgggaaata tccagatagc acacaattta tattggcttc tcaaagatgc cctgcatgat     3060
gtacagttta gtacccgata cgaacatgtt ttgggtgctc tcctgtcagt aggaggaaaa     3120
cgacttagag aagaacttct aaaacagacg aaacttgtac agcttttagg aggagtagca     3180
gaaaaagtaa ggcaggctag tggatcagcc agacaggttg ttctccaaag aagtatggaa     3240
cgagtacagt cctttttca gaaaaataaa tgccgtctcc ctctcaagcc aagtctagtg     3300 gcaaagaat taaatattaa gtcgtgttcc ttcttcagtt ctaatgctgt cccctaaaa     3360 gtcacaatgg tgaatgctga ccctctggga aagaaatta atgtcatgtt taaggttggt     3420
gaagatcttc ggcaagatat gttagcttta cagatgataa agattatgga taagatctgg     3480
cttaaagaag gactagatct gaggatggta atttttcaaat gtctctcaac tggcagagat     3540
cgaggcatgt tggagctggt tcctgcttcc gataccctca ggaaaatcca agtgaatat     3600 ggtgtgacag atcctttaa agataaacca cttgcagagt ggctaaggaa atacaatccc     3660
tctgaagaag aatatgaaaa ggcttcagag aactttatct attcctgtgc tggatgctgt     3720
gtagccacct atgttttagg catctgtgat cgacacaatg acaatataat gcttcgaagc     3780 acggacaca tgtttcacat tgactttgga agttttttgg gacatgcaca gatgtttggc     3840
agcttcaaaa gggatcgggc tccttttgtg ctgacctctg atatggcata tgtcattaat     3900
gggggtgaaa agcccaccat tcgttttcag ttgtttgtgg acctctgctg tcaggcctac     3960
aacttgataa gaaagcagac aaacctttttt cttaacctcc tttcactgat gattccttca     4020
gggttaccag aacttacaag tattcaagat ttgaaatacg ttagagatgc acttcaaccc     4080
caaactacag acgcagaagc tacaatttttc tttactaggc ttattgaatc aagtttggga     4140
agcattgcca caaagtttaa cttcttcatt cacaaccttg ctcagcttcg tttttctggt     4200
cttccttcta atgatgagcc catcctttca ttttcaccta aaacatactc ctttagacaa     4260
gatggtcgaa tcaaggaagt ctctgttttt acatatcata agaaatacaa cccagataaa     4320
cattatattt atgtagtccg aattttgtgg gaaggacaga ttgaaccatc atttgtcttc     4380
cgaacatttg tcgaatttca ggaacttcac aataagctca gtattatttt tccactttgg     4440
aagttaccag gctttcctaa taggatggtt ctaggaagaa cacacataaa agatgtagca     4500
gccaaaagga aaattgagtt aaacagttac ttacagagtt tgatgaatgc ttcaacggat     4560
gtagcagagt gtgatcttgt ttgtacttttc ttccaccctt tacttcgtga tgagaaagct     4620
gaagggatag ctaggtctgc agatgcaggt tccttcagtc ctactccagg ccaaatagga     4680
ggagctgtga aattatccat ctcttaccga aatggtactc ttttcatcat ggtgatgcat     4740
atcaaagatc ttgttactga agatggagct gacccaaatc catatgtcaa aacatcccta     4800
cttccagata accacaaaac atccaaacgt aaaaccaaaa tttcacgaaa aacgaggaat     4860
ccgacattca atgaaatgct tgtatacagt ggatatagca agaaaccct aagacagcga     4920 gaacttcaac taagtgtact cagtgcagaa tctctgcggg agaattttttt cttgggtgga     4980 gtaaccctgc ctttgaaaga tttcaacttg agcaaagaga cggttaaatg gtatcagctg     5040
```
actgcggcaa catacttgta a    5061

<210> SEQ ID NO 318
<211> LENGTH: 3014
<212> TYPE: DNA
<213> ORGANISM: Homo sapiens

<400> SEQUENCE: 318

| | | | | | |
|---|---|---|---|---|---|
| ctgaccagcg | ccgccctccc | ccgccccga | cccaggaggt | ggagatccct | ccggtccagc | 60 |
| cacattcaac | acccactttc | tcctccctct | gccctatat | tcccgaaacc | ccctcctcct | 120 |
| tccctttcc | ctcctccctg | gagacggggg | aggagaaaag | gggagtccag | tcgtcatgac | 180 |
| tgagctgaag | gcaaagggtc | cccggggctcc | ccacgtggcg | ggcggcccgc | cctccccga | 240 |
| ggtcggatcc | ccactgctgt | gtcgcccagc | cgcaggtccg | ttcccgggga | gccagacctc | 300 |
| ggacaccttg | cctgaagttt | cggccatacc | tatctccctg | gacgggctac | tcttccctcg | 360 |
| gccctgccag | ggacaggacc | cctccgacga | aaagacgcag | gaccagcagt | cgctgtcgga | 420 |
| cgtggagggc | gcatattcca | gagctgaagc | tacaaggggt | gctggaggca | gcagttctag | 480 |
| tccccccagaa | aaggacagcg | gactgctgga | cagtgtcttg | gacactctgt | ggcgccctc | 540 |
| aggtcccggg | cagagccaac | ccagccctcc | cgcctgcgag | gtcaccagct | cttggtgcct | 600 |
| gtttggcccc | gaacttcccg | aagatccacc | ggctgccccc | gccacccagc | gggtgttgtc | 660 |
| cccgctcatg | agccggtccg | ggtgcaaggt | tggagacagc | tccgggacgg | cagctgccca | 720 |
| taaagtgctg | ccccggggcc | tgtcaccagc | ccggcagctg | ctgctcccgg | cctctgagag | 780 |
| ccctcactgg | tccggggccc | cagtgaagcc | gtctccgcag | gccgctgcgg | tggaggttga | 840 |
| ggaggaggat | ggctctgagt | ccgaggagtc | tgcgggtccg | cttctgaagg | gcaaacctcg | 900 |
| ggctctgggt | ggcgcggcgg | ctggaggagg | agccgcggct | gtcccgccgg | ggcggcagc | 960 |
| aggaggcgtc | gccctggtcc | ccaaggaaga | ttccgcttc | tcagcgccca | gggtcgccct | 1020 |
| ggtggagcag | gacgcgccga | tggcgcccgg | gcgctcccg | ctggccacca | cggtgatgga | 1080 |
| tttcatccac | gtgcctatcc | tgcctctcaa | tcacgcctta | ttggcagccc | gcactcggca | 1140 |
| gctgctggaa | gacgaaagtt | acgacggcgg | ggccggggct | gccagcgcct | ttgccccgcc | 1200 |
| gcggagttca | ccctgtgcct | cgtccacccc | ggtcgctgta | ggcgacttcc | ccgactcgc | 1260 |
| gtacccgccc | gacgccgagc | ccaaggacga | cgcgtaccct | ctctatagcg | acttccagcc | 1320 |
| gcccgctcta | aagataaagg | aggaggagga | aggcgcggag | gcctccgcgc | gctcccgcg | 1380 |
| ttcctacctt | gtggccggtg | ccaaccccgc | agccttcccg | gatttcccgt | tggggccacc | 1440 |
| gcccccgctg | ccgccgcgag | cgaccccatc | cagacccggg | gaagcggcgg | tgacggccgc | 1500 |
| acccgccagt | gcctcagtct | cgtctgcgtc | ctcctcgggg | tcgaccctgg | agtgcatcct | 1560 |
| gtacaaagcg | gagggcgcgc | cgccccagca | gggcccgttc | gcgccgccgc | cctgcaaggc | 1620 |
| gccgggcgcg | agcggctgcc | tgctcccgcg | ggacggcctg | ccctccacct | ccgcctctgc | 1680 |
| cgccgccgcc | ggggcgggcc | ccgcgctcta | ccctgcactc | ggcctcaacg | ggctcccgca | 1740 |
| gctcggctac | caggccgccg | tgctcaagga | gggcctgccg | caggtctacc | cgccctatct | 1800 |
| caactacctg | aggccggatt | cagaagccag | ccagagccca | caatacagct | tcgagtcatt | 1860 |
| acctcagaag | atttgtttaa | tctgtgggga | tgaagcatca | ggctgtcatt | atggtgtcct | 1920 |
| tacctgtggg | agctgtaagg | tcttctttaa | gagggcaatg | gaagggcagc | acaactactt | 1980 |
| atgtgctgga | agaaatgact | gcatcgttga | taaaatccgc | agaaaaaact | gcccagcatg | 2040 |

-continued

| | |
|---|---|
| tcgccttaga aagtgctgtc aggctggcat ggtccttgga ggtcgaaaat ttaaaaagtt | 2100 |
| caataaagtc agagttgtga gagcactgga tgctgttgct ctcccacagc cagtgggcgt | 2160 |
| tccaaatgaa agccaagccc taagccagag attcactttt tcaccaggtc aagacataca | 2220 |
| gttgattcca ccactgatca acctgttaat gagcattgaa ccagatgtga tctatgcagg | 2280 |
| acatgacaac acaaaacctg acacctccag ttctttgctg acaagtctta atcaactagg | 2340 |
| cgagaggcaa cttctttcag tagtcaagtg gtctaaatca ttgccaggtt ttcgaaactt | 2400 |
| acatattgat gaccagataa ctctcattca gtattcttgg atgagcttaa tggtgtttgg | 2460 |
| tctaggatgg agatcctaca aacacgtcag tgggcagatg ctgtattttg cacctgatct | 2520 |
| aatactaaat gaacagcgga tgaaagaatc atcattctat tcattatgcc ttaccatgtg | 2580 |
| gcagatccca caggagtttg tcaagcttca agttagccaa gaagagttcc tctgtatgaa | 2640 |
| agtattgtta cttcttaata caattccttt ggaagggcta cgaagtcaaa cccagtttga | 2700 |
| ggagatgagg tcaagctaca ttagagagct catcaaggca attggtttga ggcaaaaagg | 2760 |
| agttgtgtcg agctcacagc gtttctatca acttacaaaa cttcttgata acttgcatga | 2820 |
| tcttgtcaaa caacttcatc tgtactgctt gaatacattt atccagtccc gggcactgag | 2880 |
| tgttgaattt ccagaaatga tgtctgaagt tattgctgca caattaccca agatattggc | 2940 |
| agggatggtg aaacccttc tctttcataa aaagtgaatg tcatcttttt cttttaaaga | 3000 |
| attaaatttt gtgg | 3014 |

<210> SEQ ID NO 319
<211> LENGTH: 2148
<212> TYPE: DNA
<213> ORGANISM: Homo sapiens

<400> SEQUENCE: 319

| | |
|---|---|
| gcttcagggt acagctcccc cgcagccaga agccgggcct gcagcgcctc agcaccgctc | 60 |
| cgggacaccc cacccgcttc ccaggcgtga cctgtcaaca gcaacttcgc ggtgtggtga | 120 |
| actctctgag gaaaaaccat tttgattatt actctcagac gtgcgtggca acaagtgact | 180 |
| gagacctaga atccaagcg ttggaggtcc tgaggccagc ctaagtcgct tcaaaatgga | 240 |
| acgaaggcgt ttgtggggtt ccattcagag ccgatacatc agcatgagtg tgtgacaag | 300 |
| cccacggaga cttgtggagc tggcagggca gagcctgctg aaggatgagg ccctggccat | 360 |
| tgccgccctg gagttgctgc ccagggagct cttcccgcca ctcttcatgg cagcctttga | 420 |
| cgggagacac agccagaccc tgaaggcaat ggtgcaggc tggcccttca cctgcctccc | 480 |
| tctgggagtg ctgatgaagg acaacatct tcacctggag accttcaaag ctgtgcttga | 540 |
| tggacttgat gtgctccttg cccaggaggt tcgcccagg aggtggaaac ttcaagtgct | 600 |
| ggatttacgg aagaactctc atcaggactt ctggactgta tggtctggaa acagggccag | 660 |
| tctgtactca tttccagagc cagaagcagc tcagcccatg acaaagaagc gaaaagtaga | 720 |
| tggtttgagc acagaggcag agcagcccctt cattccagta gaggtgctcg tagacctgtt | 780 |
| cctcaaggaa ggtgcctgtg atgaattgtt ctcctacctc attgagaaag tgaagcgaaa | 840 |
| gaaaaatgta ctacgcctgt gctgtaagaa gctgaagatt tttgcaatgc ccatgcagga | 900 |
| tatcaagatg atcctgaaaa tggtgcagct ggactctatt gaagatttgg aagtgacttg | 960 |
| tacctggaag ctacccacct tggcgaaatt ttctccttac ctgggccaga tgattaatct | 1020 |
| gcgtagactc ctcctctccc acatccatgc atcttcctac atttcccgg agaaggaaga | 1080 |
| gcagtatatc gcccagttca cctctcagtt cctcagtctg cagtgcctgc aggctctcta | 1140 |

```
tgtggactct ttattttcc ttagaggccg cctggatcag ttgctcaggc acgtgatgaa      1200
ccccttggaa accctctcaa taactaactg ccggctttcg aaggggatg tgatgcatct      1260 gtcccagagt cccagcgtca gtcagctaag tgtcctgagt ctaagtgggg tcatgctgac     1320
cgatgtaagt cccgagcccc tccaagctct gctggagaga gcctctgcca ccctccagga    1380
cctggtcttt gatgagtgtg ggatcacgga tgatcagctc cttgccctcc tgccttccct    1440
gagccactgc tcccagctta aaccttaag cttctacggg aattccatct ccatatctgc     1500
cttgcagagt ctcctgcagc acctcatcgg gctgagcaat ctgacccacg tgctgtatcc    1560 tgtcccctg gagagttatg aggacatcca tggtaccctc cacctggaga ggcttgccta    1620
tctgcatgcc aggctcaggg agttgctgtg tgagttgggg cggccagca tggtctggct     1680 tagtgccaac ccctgtcctc actgtgggga cagaaccttc tatgacccgg agccatcct    1740 gtgcccctgt tcatgccta actagctggg tgcacatatc aaatgcttca ttctgcatac    1800
ttggacacta aagccaggat gtgcatgcat cttgaagcaa caaagcagcc acagtttcag   1860
acaaatgttc agtgtgagtg aggaaaacat gttcagtgag gaaaaacat tcagacaaat    1920 gttcagtgag gaaaaaaagg ggaagttggg gataggcaga tgttgacttg aggagttaat   1980
gtgatctttg gggagataca tcttatagag ttagaaatag aatctgaatt tctaaaggga    2040
gattctggct tgggaagtac atgtaggagt taatccctgt gtagactgtt gtaaagaaac   2100
tgttgaaaat aaagagaagc aatgtgaagc aaaaaaaaaa aaaaaaaa                 2148
```

<210> SEQ ID NO 320
<211> LENGTH: 540
<212> TYPE: DNA
<213> ORGANISM: Homo sapiens

<400> SEQUENCE: 320

```
atccctgact cggggtcgcc tttggagcag agaggaggca atggccacca tggagaacaa     60
ggtgatctgc gccctggtcc tggtgtccat gctggccctc ggcaccctgg ccgaggccca    120
gacagagacg tgtacagtgg ccccccgtga aagcagaat tgtggttttc ctggtgtcac    180
gccctcccag tgtgcaaata agggctgctg ttttcgacga accgttcgtg gggtcccctg    240
gtgcttctat cctaatacca tcgacgtccc tccagaagag gagtgtgaat tttagacact    300
tctgcaggga tctgcctgca tcctgacggg gtgccgtccc cagcacggtg attagtccca    360
gagctcggct gccacctcca ccggacacct cagacacgct tctgcagctg tgcctcggct    420
cacaacacag attgactgct ctgactttga ctactcaaaa ttggcctaaa aattaaaaga    480
gatcgatatt aaaaaaaaaa aaaaaaaaa aaaaaaaaa aaaaaaaaa aaaaaaaaa        540
```

<210> SEQ ID NO 321
<211> LENGTH: 2346
<212> TYPE: DNA
<213> ORGANISM: Homo sapiens

<400> SEQUENCE: 321

```
gcacgaggct gcggcgggtc cgggcccatg aggcgacgaa ggaggcggga cggcttttac      60
ccagccccgg acttccgaga cagggaagct gaggacatgg caggagtgtt tgacatagac    120
ctggaccagc cagaggacgc gggctctgag gatgagctgg aggaggggg tcagttaaat    180 gaaagcatgg accatggggg agttggacca tatgaacttg gcatggaaca ttgtgagaaa   240
tttgaaatct cagaaactag tgtgaacaga gggccagaaa aaatcagacc agaatgtttt   300
```

```
gagctacttc gggtacttgg taaagggggc tatggaaagg ttttcaagt acgaaaagta      360 acaggagcaa atactgggaa aatatttgcc atgaaggtgc ttaaaaaggc aatgatagta      420
agaaatgcta aagatacagc tcatacaaaa gcagaacgga atattctgga ggaagtaaag      480
catcccttca tcgtggattt aatttatgcc tttcagactg gtggaaaact ctacctcatc      540
cttgagtatc tcagtggagg agaactattt atgcagttag aaagagaggg aatatttatg      600
gaagacactg cctgctttta cttggcagaa atctccatgg ctttgggca tttacatcaa       660 aaggggatca tctacagaga cctgaagccg gagaatatca tgcttaatca ccaaggtcat      720
gtgaaactaa cagactttgg actatgcaaa gaatctattc atgatggaac agtcacacac      780
acattttgtg gaacaataga atacatggcc cctgaaatct tgatgagaag tggccacaat      840
cgtgctgtgg attggtggag tttgggagca ttaatgtatg acatgctgac tggagcaccc      900
ccattcactg gggagaatag aaagaaaaca attgacaaaa tcctcaaatg taaactcaat      960
ttgcctccct acctcacaca agaagccaga gatctgctta aaaagctgct gaaaagaaat     1020
gctgcttctc gtctgggagc tggtcctggg gacgctggag aagttcaagc tcatccattc     1080
tttagacaca ttaactggga agaacttctg gctcgaaagg tggagccccc ctttaaacct     1140
ctgttgcaat ctgaagagga tgtaagtcag tttgattcca agtttacacg tcagacacct     1200
gtcgacagcc cagatgactc aactctcagt gaaagtgcca atcaggtctt tctgggtttt     1260
acatatgtgg ctccatctgt acttgaaagt gtgaaagaaa gttttccctt tgaaccaaaa     1320
atccgatcac ctcgaagatt tattggcagc ccacgaacac ctgtcagccc agtcaaattt     1380
tctcctgggg atttctgggg aagaggtgct tcggccagca cagcaaatcc tcagacacct     1440
gtggaatacc caatggaaac aagtggcata gagcagatgg atgtgacaat gagtgggga      1500 gcatcggcac cacttccaat acgacagccg aactctgggc catacaaaaa acaagctttt     1560
cccatgatct ccaaacggcc agagcacctg cgtatgaatc tatgacagag caatgctttt     1620
aatgaattta aggcaaaaag gtggagaggg agatgtgtga gcatcctgca aggtgaaaca     1680
agactcaaaa tgacagtttc agagagtcaa tgtcattaca tagaacactt cggacacagg     1740
aaaaataaac gtggatttta aaaatcaat caatggtgca aaaaaaact taaagcaaaa       1800 tagtattgct gaactcttag gcacatcaat taattgattc ctcgcgacat ctttctcaac     1860
cttatcaagg atttcatgt tgatgactcg aaactgacag tattaagggt aggatgttgc      1920
tctgaatcac tgtgagtctg atgtgtgaag aagggtatcc ttcattagg caagtacaaa      1980 ttgcctataa tacttgcaac taaggacaaa ttagcatgca agcttggtca aacttttccc     2040
aggcaaaatg ggaaggcaaa gacaaaagaa acttaccaat tgatgtttta cgtgcaaaca     2100
acctgaatct tttttttata taaatatata tttttcaaat agattttttga ttcagctcat    2160 tatgaaaaac atcccaaact ttaaaatgcg aaattattgg ttggtgtgaa gaaagccaga     2220
caacttctgt ttcttctctt ggtgaaataa taaaatgcaa atgaatcatt gttaacacag     2280
ctgtggctcg tttgagggat tggggtggac ctggggttta ttttcagtaa cccagctgcg     2340
gagcct                                                                2346

<210> SEQ ID NO 322
<211> LENGTH: 2420
<212> TYPE: DNA
<213> ORGANISM: Homo sapiens

<400> SEQUENCE: 322
tccggggcgg cccccggcag ccagcgcgac gttccaaaat cgaacctcag tggcggcgct       60
```

-continued

```
cggaagcgga actctgccgg ggccgcgccg gctacattgt ttcctccccc cgactccctc    120
ccgccccctt cccccgcctt tcttccctcc gcgacccggg ccgtgcgtcc gtcccsctgc    180
ctctgcctgg cggtccctcc tcccctctcc ttgcacccat acctctttgt accgcacccc    240
ctggggaccc ctgcgcccct cccctccccc ctgaccgcat ggaccgtccc gcaggccgct    300
gatgccgccc gcggcgaggt ggccggaccg cagtgccccc aagagagctc taatggtacc    360
aagtgacagg ttggctttac tgtgactcgg ggacgccaga gctcctgaga agatgtcagc    420
aatacaggcc gcctggccat ccggtacaga atgtattgcc aagtacaact tccacggcac    480
tgccgagcag gacctgccct tctgcaaagg agacgtgctc accattgtgg ccgtcaccaa    540
ggaccccaac tggtacaaag ccaaaaacaa ggtgggccgt gagggcatca tcccagccaa    600
ctacgtccag aagcgggagg gcgtgaaggc gggtaccaaa ctcagcctca tgccttggtt    660
ccacggcaag atcacacggg agcaggctga gcggcttctg tacccgccgg agacaggcct    720
gttcctggtg cgggagagca ccaactaccc cggagactac acgctgtgcg tgagctgcga    780
cggcaaggtg gagcactacc gcatcatgta ccatgccagc aagctcagca tcgacgagga    840
ggtgtacttt gagaacctca tgcagctggt ggagcactac acctcagacg cagatggact    900
ctgtacgcgc tcattaaac caaaggtcat ggagggcaca gtggcggccc aggatgagtt    960
ctaccgcagc ggctgggccc tgaacatgaa ggagctgaag ctgctgcaga ccatcgggaa    1020
gggggagttc ggagacgtga tgctgggcga ttaccgaggg aacaaagtcg ccgtcaagtg    1080
cattaagaac gacgccactg cccaggcctt cctggctgaa gcctcagtca tgacgcaact    1140
gcggcatagc aacctggtgc agctcctggg cgtgatcgtg gaggagaagg gcgggctcta    1200
catcgtcact gagtacatgg ccaaggggag ccttgtggac tacctgcggt ctaggggtcg    1260
gtcagtgctg ggcggagact gtctcctcaa gttctcgcta gatgtctgcg aggccatgga    1320
ataccctggag ggcaacaatt tcgtgcatcg agacctggct gcccgcaatg tgctggtgtc    1380
tgaggacaac gtggccaagg tcagcgactt tggtctcacc aaggaggcgt ccagcaccca    1440
ggacacgggc aagctgccag tcaagtggac agccctgag gccctgagag agaagaaatt    1500
ctccactaag tctgacgtgt ggagtttcgg aatccttctc tgggaaatct actccttggg    1560
gcgagtgcct tatccaagaa ttcccctgaa ggacgtcgtc cctcgggtgg agaagggcta    1620
caagatggat gcccccgacg gctgcccgcc cgcagtctat gaagtcatga gaactgctg    1680
gcacctggac gccgccatgc ggccctcctt cctacagctc cgagagcagc ttgagcacat    1740
caaaacccac gagctgcacc tgtgacggct ggcctccgcc tgggtcatgg gcctgtgggg    1800
actgaacctg gaagatcatg gacctggtgc cctgctcac tgggcccgag cctgaactga    1860
gccccagcgg gctggcgggc cttttcctg cgtcccagcc tgcaccctc cggccccgtc    1920
tctcttggac ccacctgtgg ggcctgggga gcccactgag gggccaggga ggaaggaggc    1980
cacggagcgg gcggcagcgc cccaccacgt cgggcttccc tggcctcccg ccactcgcct    2040
tcttagagtt ttattccttt cctttttga gattttttt ccgtgtgttt atttttatt    2100
atttttcaag ataaggagaa agaaagtacc cagcaaatgg gcattttaca agaagtacga    2160
atcttatttt tcctgtcctg cccgtgaggt ggggggggacc gggcccctct ctagggaccc    2220
ctcgcccag cctcattccc cattctgtgt cccatgtccc gtgtctcctc ggtcgccccg    2280
tgtttgcgct tgaccatgtt gcactgtttg catgcgcccg aggcagacgt ctgtcagggg    2340
cttggattcc gtgtgccgct gccacccgcc cacccgcctt gtgagatgga atcgtaataa    2400
```

-continued

| | |
|---|---|
| accacgccat gaggaaaaaa | 2420 |

<210> SEQ ID NO 323
<211> LENGTH: 2253
<212> TYPE: DNA
<213> ORGANISM: Homo sapiens

<400> SEQUENCE: 323

| | |
|---|---|
| ggaagacttg ggtccttggg tcgcaggtgg gagccgacgg gtgggtagac cgtgggggat | 60 |
| atctcagtgg cggacgagga cggcggggac aaggggcggc tggtcggagt ggcggagcgt | 120 |
| caagtcccct gtcggttcct ccgtccctga gtgtccttgg cgctgccttg tgcccgccca | 180 |
| gcgcctttgc atccgctcct gggcaccgag gcgccctgta ggatactgct tgttacttat | 240 |
| tacagctaga ggcatcatgg accgatctaa agaaaactgc atttcaggac tgttaaggc | 300 |
| tacagctcca gttggaggtc caaaacgtgt tctcgtgact cagcaaattc cttgtcagaa | 360 |
| tccattacct gtaaatagtg gccaggctca gcggtcttg tgtccttcaa attcttccca | 420 |
| gcgcgttcct ttgcaagcac aaaagcttgt ctccagtcac aagccggttc agaatcagaa | 480 |
| gcagaagcaa ttgcaggcaa ccagtgtacc tcatcctgtc tccaggccac tgaataacac | 540 |
| ccaaaagagc aagcagcccc tgccatcggc acctgaaaat aatcctgagg aggaactggc | 600 |
| atcaaaacag aaaaatgaag aatcaaaaaa gaggcagtgg gctttggaag actttgaaat | 660 |
| tggtcgccct ctgggtaaag gaaagtttgg taatgtttat ttggcaagag aaaagcaaag | 720 |
| caagtttatt ctggctctta agtgttatt taaagctcag ctggagaaag ccggagtgga | 780 |
| gcatcagctc agaagagaag tagaaataca gtcccacctt cggcatccta atattcttag | 840 |
| actgtatggt tatttccatg atgctaccag agtctaccta attctggaat atgcaccact | 900 |
| tggaacagtt tatagagaac ttcagaaact ttcaaagttt gatgagcaga gaactgctac | 960 |
| ttatataaca gaattggcaa atgccctgtc ttactgtcat tcgaagagag ttattcatag | 1020 |
| agacattaag ccagagaact tacttcttgg atcagctgga gagcttaaaa ttgcagattt | 1080 |
| tgggtggtca gtacatgctc catcttccag gaggaccact ctctgtggca ccctggacta | 1140 |
| cctgcccccct gaaatgattg aaggtcggat gcatgatgag aaggtggatc tctggagcct | 1200 |
| tggagttctt tgctatgaat ttttagttgg gaagcctcct tttgaggcaa acacatacca | 1260 |
| agagacctac aaaagaatat cacgggttga attcacattc cctgactttg taacagaggg | 1320 |
| agccagggac ctcatttcaa gactgttgaa gcataatccc agccagaggc aatgctcag | 1380 |
| agaagtactt gaacacccct ggatcacagc aaattcatca aaaccatcaa attgccaaaa | 1440 |
| caaagaatca gctagcaaac agtcttagga atcgtgcagg gggagaaatc cttgagccag | 1500 |
| ggctgccata taacctgaca ggaacatgct actgaagttt attttaccat tgactgctgc | 1560 |
| cctcaatcta gaacgctaca caagaaatat ttgtttact cagcaggtgt gccttaacct | 1620 |
| ccctattcag aaagctccac atcaataaac atgacactct gaagtgaaag tagccacgag | 1680 |
| aattgtgcta cttatactgg ttcataatct ggaggcaagg ttcgactgca gccgccccgt | 1740 |
| cagcctgtgc taggcatggt gtcttcacag gaggcaaatc cagagcctgg ctgtggggaa | 1800 |
| agtgaccact ctgccctgac cccgatcagt taaggagctg tgcaataacc ttcctagtac | 1860 |
| ctgagtgagt gtgtaactta ttgggttggc gaagcctggt aaagctgttg gaatgagtat | 1920 |
| gtgattcttt ttaagtatga aaataaagat atatgtacag acttgtattt tttctctggt | 1980 |
| ggcattcctt taggaatgct gtgtgtctgt ccggcacccc ggtaggcctg attgggtttc | 2040 |
| tagtcctcct taaccactta tctcccatat gagagtgtga aaaataggaa cacgtgctct | 2100 |

-continued

| | |
|---|---|
| acctccattt agggatttgc ttgggataca gaagaggcca tgtgtctcag agctgttaag | 2160 |
| ggcttatttt tttaaaacat tggagtcata gcatgtgtgt aaactttaaa tatgcaaata | 2220 |
| aataagtatc tatgtctaaa aaaaaaaaaa aaa | 2253 |

<210> SEQ ID NO 324
<211> LENGTH: 1619
<212> TYPE: DNA
<213> ORGANISM: Homo sapiens

<400> SEQUENCE: 324

| | |
|---|---|
| ccgccagatt tgaatcgcgg gacccgttgg cagaggtggc ggcggcggca tgggtgcccc | 60 |
| gacgttgccc cctgcctggc agccctttct caaggaccac cgcatctcta cattcaagaa | 120 |
| ctggcccttc ttggagggct gcgcctgcac cccggagcgg atggccgagg ctggcttcat | 180 |
| ccactgcccc actgagaacg agccagactt ggcccagtgt ttcttctgct tcaaggagct | 240 |
| ggaaggctgg gagccagatg acgaccccat agaggaacat aaaaagcatt cgtccggttg | 300 |
| cgctttcctt tctgtcaaga agcagtttga agaattaacc cttggtgaat ttttgaaact | 360 |
| ggacagagaa agagccaaga acaaaattgc aaaggaaacc aacaataaga agaaagaatt | 420 |
| tgaggaaact gcgaagaaag tgcgccgtgc catcgagcag ctggctgcca tggattgagg | 480 |
| cctctggccg gagctgcctg gtcccagagt ggctgcacca cttccagggt ttattccctg | 540 |
| gtgccaccag ccttcctgtg ggccccttag caatgtctta ggaaaggaga tcaacatttt | 600 |
| caaattagat gtttcaactg tgctcctgtt ttgtcttgaa agtggcacca gaggtgcttc | 660 |
| tgcctgtgca gcgggtgctg ctggtaacag tggctgcttc tctctctctc tctcttttt | 720 |
| gggggctcat ttttgctgtt ttgattcccg ggcttaccag gtgagaagtg agggaggaag | 780 |
| aaggcagtgt cccttttgct agagctgaca gctttgttcg cgtgggcaga gccttccaca | 840 |
| gtgaatgtgt ctggacctca tgttgttgag gctgtcacag tcctgagtgt ggacttggca | 900 |
| ggtgcctgtt gaatctgagc tgcaggttcc ttatctgtca cacctgtgcc tcctcagagg | 960 |
| acagtttttt tgttgttgtg ttttttttgtt tttttttttt ggtagatgca tgacttgtgt | 1020 |
| gtgatgagag aatggagaca gagtccctgg ctcctctact gtttaacaac atggctttct | 1080 |
| tatttttgttt gaattgttaa ttcacagaat agcacaaact acaattaaaa ctaagcacaa | 1140 |
| agccattcta agtcattggg gaaacggggt gaacttcagg tggatgagga gacagaatag | 1200 |
| agtgatagga agcgtctggc agatactcct tttgccactg ctgtgtgatt agacaggccc | 1260 |
| agtgagccgc ggggcacatg ctggccgctc ctccctcaga aaaaggcagt ggcctaaatc | 1320 |
| cttttttaaat gacttggctc gatgctgtgg gggactggct gggctgctgc aggccgtgtg | 1380 |
| tctgtcagcc caaccttcac atctgtcacg ttctccacac gggggagaga cgcagtccgc | 1440 |
| ccaggtcccc gctttctttg gaggcagcag ctcccgcagg gctgaagtct ggcgtaagat | 1500 |
| gatggatttg attcgccctc ctccctgtca tagagctgca gggtggattg ttacagcttc | 1560 |
| gctggaaacc tctggaggtc atctcggctg ttcctgagaa ataaaaagcc tgtcatttc | 1619 |

<210> SEQ ID NO 325
<211> LENGTH: 5010
<212> TYPE: DNA
<213> ORGANISM: Homo sapiens

<400> SEQUENCE: 325

| | |
|---|---|
| ggcggctcgg gacggaggac gcgctagtgt gagtgcgggc ttctagaact acaccgaccc | 60 |

-continued

```
tcgtgtcctc ccttcatcct gcggggctgg ctggagcggc cgctccggtg ctgtccagca      120
gccataggga gccgcacggg gagcgggaaa gcggtcgcgg ccccaggcgg ggcggccggg      180
atggagcggg gccgcgagcc tgtggggaag gggctgtggc ggcgcctcga gcggctgcag      240
gttcttctgt gtggcagttc agaatgatgg atcaagctag atcagcattc tctaacttgt      300
ttggtgggaga accattgtca tatcccggt tcagcctggc tcggcaagta gatggcgata      360
acagtcatgt ggagatgaaa cttgctgtag atgaagaaga aaatgctgac aataacacaa      420
aggccaatgt cacaaaacca aaaggtgta gtggaagtat ctgctatggg actattgctg      480
tgatcgtctt tttcttgatt ggatttatga ttggctactt gggctattgt aaaggggtag      540
aaccaaaaac tgagtgtgag agactggcag gaaccgagtc tccagtgagg gaggagccag      600
gagaggactt ccctgcagca cgtcgcttat attgggatga cctgaagaga aagttgtcgg      660
agaaactgga cagcacagac ttcaccagca ccatcaagct gctgaatgaa aattcatatg      720
tccctcgtga ggctggatct caaaaagatg aaaatcttgc gttgtatgtt gaaaatcaat      780
ttcgtgaatt taaactcagc aaagtctggc gtgatcaaca ttttgttaag attcaggtca      840
aagacagcgc tcaaaactcg gtgatcatag ttgataagaa cggtagactt gtttacctgg      900
tggagaatcc tgggggttat gtggcgtata gtaaggctgc aacagttact ggtaaactgg      960
tccatgctaa ttttggtact aaaaaagatt ttgaggattt atacactcct gtgaatggat     1020
ctatagtgat tgtcagagca gggaaaatca cctttgcaga aaaggttgca aatgctgaaa     1080
gcttaaatgc aattggtgtg ttgatataca tggaccagac taaatttccc attgttaacg     1140
cagaactttc attctttgga catgctcatc tggggacagg tgacccttac acacctggat     1200
tcccttcctt caatcacact cagtttccac catctcggtc atcaggattg cctaatatac     1260
ctgtccagac aatctccaga gctgctgcag aaaagctgtt tgggaatatg aaggagact      1320
gtccctctga ctggaaaaca gactctacat gtaggatggt aacctcagaa agcaagaatg     1380
tgaagctcac tgtgagcaat gtgctgaaag agataaaaat tcttaacatc tttggagtta     1440
ttaaaggctt tgtagaacca gatcactatg ttgtagttgg ggcccagaga gatgcatggg     1500
gccctggagc tgcaaaatcc ggtgtaggca cagctctcct attgaaactt gcccagatgt     1560
tctcagatat ggtcttaaaa gatgggtttc agcccagcag aagcattatc tttgccagtt     1620
ggagtgctgg agactttgga tcggttggtg ccactgaatg gctagaggga tacctttcgt     1680
ccctgcattt aaaggctttc acttatatta atctggataa agcggttctt ggtaccagca     1740
acttcaaggt ttctgccagc ccactgttgt atacgcttat tgagaaaaca atgcaaaatg     1800
tgaagcatcc ggttactggg caatttctat atcaggacag caactgggcc agcaaagttg     1860
agaaactcac tttagacaat gctgctttcc ctttccttgc atattctgga atcccagcag     1920
tttcttctg ttttttgcgag gacacagatt atccttattt gggtaccacc atggacacct     1980
ataaggaact gattgagagg attcctgagt tgaacaaagt ggcacgagca gctgcagagg     2040
tcgctggtca gttcgtgatt aaactaaccc atgatgttga attgaacctg gactatgaga     2100
ggtacaacag ccaactgctt tcatttgtga gggatctgaa ccaatacaga gcagacataa     2160
aggaaatggg cctgagttta cagtggctgt attctgctcg tgagacttc ttccgtgcta     2220
cttccagact aacaacagat ttcgggaatg ctgagaaaac agacagattt gtcatgaaga     2280
aactcaatga tcgtgtcatg agagtggagt atcacttcct ctctccctac gtatctccaa     2340
aagagtctcc tttccgacat gtcttctggg gctccggctc tcacacgctg ccagctttac     2400
tggagaactt gaaactgcgt aaacaaaata acggtgcttt taatgaaacg ctgttcagaa     2460
```

```
accagttggc tctagctact tggactattc agggagctgc aaatgccctc tctggtgacg  2520
tttgggacat tgacaatgag ttttaaatgt gatacccata gcttccatga gaacagcagg  2580
gtagtctggt ttctagactt gtgctgatcg tgctaaattt tcagtagggc tacaaaacct  2640
gatgttaaaa ttccatccca tcatcttggt actactagat gtctttaggc agcagctttt  2700
aatacagggt agataacctg tacttcaagt taaagtgaat aaccacttaa aaaatgtcca  2760
tgatggaata ttcccctatc tctagaattt taagtgcttt gtaatgggaa ctgcctcttt  2820
cctgttgttg ttaatgaaaa tgtcagaaac cagttatgtg aatgatctct ctgaatccta  2880
agggctggtc tctgctgaag gttgtaagtg gttcgcttac tttgagtgat cctccaactt  2940
catttgatgc taaataggag ataccaggtt gaaagacctc tccaaatgag atctaagcct  3000
ttccataagg aatgtagcag gtttcctcat tcctgaaaga aacagttaac tttcagaaga  3060
gatgggcttg ttttcttgcc aatgaggtct gaaatggagg tccttctgct ggataaaatg  3120
aggttcaact gttgattgca ggaataaggc cttaatatgt taacctcagt gtcatttatg  3180
aaaagagggg accagaagcc aaagacttag tatattttct tttcctctgt cccttccccc  3240
ataagcctcc atttagttct ttgttatttt tgtttcttcc aaagcacatt gaaagagaac  3300
cagtttcagg tgtttagttg cagactcagt ttgtcagact ttaaagaata atatgctgcc  3360
aaattttggc caaagtgtta atcttagggg agagcttcct gtccttttgg cactgagata  3420
tttattgttt atttatcagt gacagagttc actataaatg gtgttttttt aatagaatat  3480
aattatcgga agcagtgcct tccataatta tgacagttat actgtcggtt tttttaaat  3540 aaaagcagca tctgctaata aaacccaaca gatactggaa gttttgcatt tatggtcaac  3600
acttaagggt tttagaaaac agccgtcagc caaatgtaat tgaataaagt tgaagctaag  3660
atttagagat gaattaaatt taattagggg ttgctaagaa gcgagcactg accagataag  3720
aatgctggtt ttcctaaatg cagtgaattg tgaccaagtt ataaatcaat gtcacttaaa  3780
ggctgtggta gtactcctgc aaaattttat agctcagttt atccaaggtg taactctaat  3840
tcccatttgc aaaattttcca gtaccttgt cacaatccta acacattatc gggagcagtg  3900
tcttccataa tgtataaaga acaaggtagt ttttacctac cacagtgtct gtatcggaga  3960
cagtgatctc catatgttac actaagggtg taagtaatta tcgggaacag tgtttcccat  4020
aattttcttc atgcaatgac atcttcaaag cttgaagatc gttagtatct aacatgtatc  4080
ccaactccta taattcccta tcttttagtt ttagttgcag aaacattttg tggtcattaa  4140
gcattgggtg ggtaaattca accactgtaa aatgaaatta ctacaaaatt tgaaatttag  4200
cttgggtttt tgttaccttt atggtttctc caggtcctct acttaatgag atagcagcat  4260
acatttataa tgtttgctat tgacaagtca ttttaattta tcacattatt tgcatgttac  4320
ctcctataaa cttagtgcgg acaagtttta atccagaatt gaccttttga cttaaagcag  4380
agggactttg tatagaaggt ttgggggctg tggggaagga gagtcccctg aaggtctgac  4440
acgtctgcct acccattcgt ggtgatcaat taaatgtagg tatgaataag ttcgaagctc  4500
cgtgagtgaa ccatcatata aacgtgtagt acagctgttt gtcatagggc agttggaaac  4560
ggcctcctag ggaaaagttc atagggtctc ttcaggttct tagtgtcact tacctagatt  4620
tacagcctca cttgaatgtg tcactactca cagtctcttt aatcttcagt tttatcttta  4680
atctcctctt ttatcttgga ctgacattta gcgtagctaa gtgaaaaggt catagctgag  4740
attcctggtt cgggtgttac gcacacgtac ttaaatgaaa gcatgtggca tgttcatcgt  4800
```

```
ataacacaat atgaatacag ggcatgcatt ttgcagcagt gagtctcttc agaaaacccT    4860
tttctacagt tagggttgag ttacttccta tcaagccagt acgtgctaac aggctcaata    4920
ttcctgaatg aaatatcaga ctagtgacaa gctcctggtc ttgagatgtc ttctcgttaa    4980
ggagtagggc cttttggagg taaaggtata                                     5010
```

<210> SEQ ID NO 326
<211> LENGTH: 2574
<212> TYPE: DNA
<213> ORGANISM: Homo sapiens

<400> SEQUENCE: 326

```
cctgtttaga cacatggaca acaatcccag cgctacaagg cacacagtcc gcttcttcgt      60
cctcagggtt gccagcgctt cctggaagtc ctgaagctct cgcagtgcag tgagttcatg     120
caccttcttg ccaagcctca gtctttggga tctggggagg ccgcctggtt ttcctccctc     180
cttctgcacg tctgctgggg tctcttcctc tccaggcctt gccgtccccc tggcctctct     240
tcccagctca cacatgaaga tgcacttgca aagggctctg gtggtcctgg ccctgctgaa     300
cttTgccacg gtcagcctct ctctgtccac ttgcaccacc ttggacttcg ccacatcaa      360
gaagaagagg gtggaagcca ttaggggaca gatcttgagc aagctcaggc tcaccagccc     420
ccctgagcca acgtgatga cccacgtccc ctatcaggtc ctggcccttt acaacagcac      480
ccgggagctg ctggaggaga tgcatgggga gagggaggaa ggctgcaccc aggaaaacac     540
cgagtcggaa tactatgcca aagaaatcca taaattcgac atgatccagg ggctggcgga     600
gcacaacgaa ctggctgtct gccctaaagg aattacctcc aaggttttcc gcttcaatgt     660
gtcctcagtg gagaaaaata gaaccaacct attccgagca gaattccggg tcttgcgggt     720
gcccaacccc agctctaagc ggaatgagca gaggatcgag ctcttccaga tccttcggcc     780
agatgagcac attgccaaac agcgctatat cggtgggcaag aatctgccca cacggggcac     840
tgccgagtgg ctgtccttTg atgtcactga cactgtgcgt gagtggctgt tgagaagaga     900
gtccaactta ggtctagaaa tcagcattca ctgtccatgt cacaccTttc agcccaatgg     960
agatatcctg gaaaacattc acgaggtgat ggaaatcaaa ttcaaaggcg tggacaatga    1020
ggatgaccat ggccgtggag atctggggcg cctcaagaag cagaaggatc accacaaccc    1080
tcatctaatc ctcatgatga ttccccccaca ccggctcgac aacccgggcc agggggtca     1140
gaggaagaag cgggctttgg acaccaatta ctgcttccgc aacttggagg agaactgctg    1200
tgtgcgcccc ctctacattg acttccgaca ggatctgggc tggaagtggg tccatgaacc    1260
taagggctac tatgccaact tctgctcagg cccttgccca tacctccgca gtgcagacac    1320
aacccacagc acggtgctgg gactgtacaa cactctgaac cctgaagcat ctgcctcgcc    1380
ttgctgcgtg ccccaggacc tggagcccct gaccatcctg tactatgttg gaggaccccc    1440
caaagtggag cagctctcca acatggtggt gaagtcttgt aaatgtagct gagaccccac    1500
gtgcgacaga gagagggggag agaaccac cactgcctga ctgcccgctc ctcgggaaac     1560
acacaagcaa caaacctcac tgagaggcct ggagcccaca accttcggct ccgggcaaat    1620
ggctgagatg gaggtttcct ttTggaacat ttctttcttg ctggctctga gaatcacggt     1680
ggtaaagaaa gtgtgggttt ggttagagga aggctgaact cttcagaaca cacagacttt    1740
ctgtgacgca gacagagggg atgggggatag aggaaaggga tggtaagttg agatgttgtg    1800
tggcaatggg atttgggcta ccctaaaggg agaaggaagg gcagagaatg gctgggtcag    1860
ggccagactg gaagacactt cagatctgag gttggatttg ctcattgctg taccacatct    1920
```

-continued

```
gctctaggga atctggatta tgttatacaa ggcaagcatt ttttttttta aagacaggtt    1980
acgaagacaa agtcccagaa ttgtatctca tactgtctgg gattaagggc aaatctatta    2040
cttttgcaaa ctgtcctcta catcaattaa catcgtgggt cactacaggg agaaaatcca    2100
ggtcatgcag ttcctggccc atcaactgta ttgggccttt tggatatgct gaacgcagaa    2160
gaaagggtgg aaatcaaccc tctcctgtct gccctctggg tccctcctct cacctctccc    2220
tcgatcatat ttcccccttgg acacttggtt agacgccttc caggtcagga tgcacatttc    2280
tggattgtgg ttccatgcag ccttggggca ttatgggtct tcccccactt ccctccaag    2340 accctgtgtt catttggtgt tcctggaagc aggtgctaca acatgtgagg cattcgggga    2400
agctgcacat gtgccacaca gtgacttggc cccagacgca tagactgagg tataaagaca    2460
agtatgaata ttactctcaa aatctttgta taaataaata ttttggggc atcctggatg    2520 atttcatctt ctggaatatt gtttctagaa cagtaaaagc cttattctaa ggtg          2574
```

<210> SEQ ID NO 327
<211> LENGTH: 1421
<212> TYPE: DNA
<213> ORGANISM: Homo sapiens

<400> SEQUENCE: 327

```
acttactgcg ggacggcctt ggagagtact cgggttcgtg aacttcccgg aggcgcaatg      60
agctgcatta acctgcccac tgtgctgccc ggctccccca gcaagacccg ggggcagatc     120
caggtgattc tcgggccgat gttctcagga aaaagcacag agttgatgag acgcgtccgt     180
cgcttccaga ttgctcagta caagtgcctg gtgatcaagt atgccaaaga cactcgctac     240
agcagcagct tctgcacaca tgaccggaac accatggagg cgctgcccgc ctgcctgctc     300
cgagacgtgg cccaggaggc cctgggcgtg gctgtcatag catcgacga ggggcagttt     360 ttcccctgaca tcatggagtt ctgcgaggcc atggccaacg ccgggaagac cgtaattgtg    420
gctgcactgg atgggacctt ccagaggaag ccatttgggg ccatcctgaa cctggtgccg    480
ctggccgaga gcgtggtgaa gctgacggcg gtgtgcatgg agtgcttccg ggaagccgcc    540
tataccaaga ggctcggcac agagaaggag gtcgaggtga ttgggggagc agacaagtac    600
cactccgtgt gtcggctctg ctacttcaag aaggcctcag gccagcctgc cgggccggac    660
aacaaagaga actgcccagt gccaggaaag ccaggggaag ccgtggctgc aggaagctc    720 tttgccccac agcagattct gcaatgcagc cctgccaact gagggacctg caagggccgc    780
ccgctccctt cctgccactg ccgcctactg gacgctgccc tgcatgctgc ccagccactc    840
caggaggaag tcgggaggcg tggagggtga ccacaccttg gccttctggg aactctcctt    900
tgtgtggctg ccccacctgc cgcatgctcc ctcctctcct acccactggt ctgcttaaag    960
cttccctctc agctgctggg acgatcgccc aggctggagc tggccccgct tggtggcctg   1020
ggatctggca cactccctct ccttggggtg agggacagag ccccacgctg ttgacatcag   1080
cctgcttctt cccctctgcg gctttcactg ctgagtttct gttctccctg ggaagcctgt   1140
gccagcacct ttgagccttg gcccacactg aggcttaggc ctctctgcct gggatgggct   1200
cccaccctcc cctgaggatg gcctggattc acgccctctt gtttccttttt gggctcaaag   1260 cccttcctac ctctggtgat ggtttccaca ggaacaacag catctttcac caagatgggt   1320
ggcaccaacc ttgctgggac ttggatccca gggcttatc tcttcaagtg tggagagggc   1380
agggtccacg cctctgctgt agcttatgaa attaactaat t                         1421
```

```
<210> SEQ ID NO 328
<211> LENGTH: 4604
<212> TYPE: DNA
<213> ORGANISM: Homo sapiens

<400> SEQUENCE: 328
ggaacagctt gtccacccgc cggccggacc agaagccttt gggtctgaag tgtctgtgag      60
acctcacaga agagcacccc tgggctccac ttacctgccc cctgctcctt cagggatgga     120
ggcaatggcg gccagcactt ccctgcctga ccctggagac tttgaccgga acgtgccccg     180
gatctgtggg gtgtgtggag accgagccac tggctttcac ttcaatgcta tgacctgtga     240
aggctgcaaa ggcttcttca ggcgaagcat gaagcggaag cactattca cctgcccctt     300 caacggggac tgccgcatca ccaaggacaa ccgacgccac tgccaggcct gccggctcaa     360
acgctgtgtg gacatcggca tgatgaagga gttcattctg acagatgagg aagtgcagag     420
gaagcgggag atgatcctga gcggaaggag gaggaggcc ttgaaggaca gtctgcggcc     480
caagctgtct gaggagcagc agcgcatcat tgccatactg ctggacgccc accataagac     540
ctacgacccc acctactccg acttctgcca gttccggcct ccagttcgtg tgaatgatgg     600
tggagggagc catccttcca ggcccaactc cagacacact cccagcttct ctggggactc     660
ctcctcctcc tgctcagatc actgtatcac ctcttcagac atgatggact cgtccagctt     720
ctccaatctg gatctgagtg aagaagattc agatgaccct tctgtgaccc tagagctgtc     780
ccagctctcc atgctgcccc acctggctga cctggtcagt tacagcatcc aaaaggtcat     840
tggctttgct aagatgatac caggattcag agacctcacc tctgaggacc agatcgtact     900
gctgaagtca gtgccattg aggtcatcat gttgcgctcc aatgagtcct tcaccatgga     960
cgacatgtcc tggacctgtg gcaaccaaga ctacaagtac cgcgtcagtg acgtgaccaa    1020
agccggacac agcctggagc tgattgagcc cctcatcaag ttccaggtgg gactgaagaa    1080
gctgaacttg catgaggagg agcatgtcct gctcatggcc atctgcatcg tctccccaga    1140
tcgtcctggg gtgcaggacg ccgcgctgat tgaggccatc caggaccgcc tgtccaacac    1200
actgcagacg tacatccgct gccgccaccc gccccgggc agccacctgc tctatgccaa    1260
gatgatccag aagctagccg acctgcgcag cctcaatgag gagcactcca agcagtaccg    1320
ctgcctctcc ttccagcctg agtgcagcat gaagctaacg ccccttgtgc tcgaagtgtt    1380
tggcaatgag atctcctgac taggacagcc tgtgcggtgc ctgggtgggg ctgctcctcc    1440
agggccacgt gccaggcccg ggctggcgg ctactcagca gccctcctca cccgtctggg    1500
gttcagcccc tcctctgcca cctcccctat ccacccagcc cattctctct cctgtccaac    1560
ctaacccctt tcctgcgggc ttttcccgg tcccttgaga cctcagccat gaggagttgc    1620
tgtttgtttg acaaagaaac ccaagtgggg gcagagggca gaggctggag gcaggccttg    1680
cccagagatg cctccaccgc tgcctaagtg ctgctgact gatgttgagg aacagacag    1740 gagaaatgca tccattcctc agggacagag acacctgcac ctccccccac tgcaggcccc    1800
gcttgtccag cgcctagtgg ggtctccctc tcctgcctta ctcacgataa ataatcggcc    1860
cacagctccc accccacccc cttcagtgcc caccaacatc ccattgccct ggttatattc    1920
tcacgggcag tagctgtggt gaggtgggtt ttcttcccat cactggagca ccaggcacga    1980
acccacctgc tgagagaccc aaggaggaaa acagacaaa acagcctca cagaagaata    2040 tgacagctgt ccctgtcacc aagctcacag ttcctcgccc tgggtctaag gggttggttg    2100
aggtggaagc cctccttcca cggatccatg tagcaggact gaattgtccc cagtttgcag    2160
```

```
aaaagcacct gccgacctcg tcctcccct gccagtgcct tacctcctgc ccaggagagc    2220
cagccctccc tgtcctcctc ggatcaccga gagtagccga gagcctgctc ccccacccc     2280 tccccagggg agagggtctg gagaagcagt gagccgcatc ttctccatct ggcagggtgg    2340
gatggaggag aagaattttc agaccccagc ggctgagtca tgatctccct gccgcctcaa    2400
tgtggttgca aggccgctgt tcaccacagg gctaagagct aggctgccgc accccagagt    2460
gtgggaaggg agagcggggc agtctcgggt ggctagtcag agagagtgtt tgggggttcc    2520
gtgatgtagg gtaaggtgcc ttcttattct cactccacca cccaaaagtc aaaaggtgcc    2580
tgtgaggcag gggcggagtg atacaacttc aagtgcatgc tctctgcagg tcgagcccag    2640
cccagctggt gggaagcgtc tgtccgttta ctccaaggtg ggtctttgtg agagtgagct    2700
gtaggtgtgc gggaccggta cagaaaggcg ttcttcgagg tggatcacag aggcttcttc    2760
agatcaatgc ttgagtttgg aatcggccgc attccctgag tcaccaggaa tgttaaagtc    2820
agtgggaacg tgactgcccc aactcctgga agctgtgtcc ttgcacctgc atccgtagtt    2880
ccctgaaaac ccagagagga atcagacttc acactgcaag agccttggtg tccacctggc    2940
cccatgtctc tcagaattct tcaggtggaa aaacatctga agccacgtt ccttactgca      3000 gaatagcata tatatcgctt aatcttaaat ttattagata tgagttgttt tcagactcag    3060
actccatttg tattatagtc taatatacag ggtagcaggt accactgatt tggagatatt    3120
tatgggggga gaacttacat tgtgaaactt ctgtacatta attattattg ctgttgttat    3180
tttacaaggg tctagggaga gacccttgtt tgattttagc tgcagaactg tattggtcca    3240
gcttgctctt cagtgggaga aaacacttg taagttgcta aacgagtcaa tcccctcatt      3300
caggaaaact gacagaggag ggcgtgactc acccaagcca tatataacta gctagaagtg    3360
ggccaggaca ggccgggcgc ggtggctcac gcctgtaatc ccagcagttt gggaggtcga    3420
ggtaggtgga tcacctgagg tcgggagttc gagaccaacc tgaccaacat ggagaaaccc    3480
tgtctctatt aaaaatacaa aaaaaaaaa aaaaaaaat agccgggcat ggtggcgcaa       3540
gcctgtaatc ccagctactc aggaggctga ggcagaagaa ttgaacccag gaggtggagg    3600
ttgcagtgag ctgagatcgt gccgttactc tccaacctgg acaacaagag cgaaactccg    3660
tcttagaagt ggaccaggac aggaccagat tttggagtca tggtccggtg tccttttcac    3720
tacaccatgt ttgagctcag acccccactc tcattcccca ggtggctgac ccagtccctg    3780
ggggaagccc tggatttcag aaagagccaa gtctggatct gggaccctt ccttccttcc     3840 ctggcttgta actccaccaa gcccatcaga aggagaagga aggagactca cctctgcctc    3900
aatgtgaatc agaccctacc ccaccacgat gtgccctggc tgctgggctc tccacctcag    3960
gccttggata atgctgttgc ctcatctata acatgcattt gtctttgtaa tgtcaccacc    4020
ttcccagctc tccctctggc cctgcttctt cggggaactc ctgaaatatc agttactcag    4080
ccctgggccc caccacctag gccactcctc caaaggaagt ctaggagctg ggaggaaaag    4140
aaaagagggg aaaatgagtt tttatggggc tgaacgggga gaaaggtca tcatcgattc       4200 tactttagaa tgagagtgtg aaatagacat ttgtaaatgt aaaacttta aggtatatca      4260 ttataactga aggagaaggt gccccaaaat gcaagatttt ccacaagatt cccagagaca    4320
ggaaaatcct ctggctggct aactggaagc atgtaggaga atccaagcga ggtcaacaga    4380
gaaggcagga atgtgtggca gatttagtga aagctagaga tatggcagcg aaaggatgta    4440
aacagtgcct gctgaatgat ttccaaagag aaaaaaagtt tgccagaagt ttgtcaagtc    4500
```

```
aaccaatgta gaaagctttg cttatggtaa taaaaatggc tcatacttat atagcactta    4560
ctttgtttgc aagtactgct gtaaataaat gctttatgca aacc                     4604

<210> SEQ ID NO 329
<211> LENGTH: 2076
<212> TYPE: DNA
<213> ORGANISM: Homo sapiens

<400> SEQUENCE: 329
cggggaaggg gagggaggag ggggacgagg gctctggcgg gtttggaggg gctgaacatc      60
gcggggtgtt ctggtgtccc ccgccccgcc tctccaaaaa gctacaccga cgcggaccgc     120
ggcggcgtcc tccctcgccc tcgcttcacc tcgcgggctc cgaatgcggg gagctcggat     180
gtccggtttc ctgtgaggct tttacctgac acccgccgcc tttccccggc actggctggg     240
agggcgccct gcaaagttgg gaacgcggag ccccggaccc gctcccgccg cctccggctc     300 gcccagggg ggtcgccggg aggagcccgg gggagaggga ccaggagggg cccgcggcct      360 cgcagggcg cccgcgcccc caccccctgcc cccgccagcg gaccggtccc ccaccccccgg   420 tccttccacc atgcacttgc tgggcttctt ctctgtggcg tgttctctgc tcgccgctgc     480
gctgctcccg ggtcctcgcg aggcgcccgc cgccgccgcc gccttcgagt ccggactcga     540
cctctcggac gcggagcccg acgcgggcga ggccacggct tatgcaagca agatctggga     600
ggagcagtta cggtctgtgt ccagtgtaga tgaactcatg actgtactct acccagaata     660
ttggaaaatg tacaagtgtc agctaaggaa aggaggctgg caacataaca gagaacaggc     720
caacctcaac tcaaggacag aagagactat aaaatttgct gcagcacatt ataatacaga     780
gatcttgaaa agtattgata tgagtgtgag aaagactcaa tgcatgccac gggaggtgtg     840
tatagatgtg gggaaggagt ttggagtcgc gacaaacacc ttctttaaac ctccatgtgt     900
gtccgtctac agatgtgggg gttgctgcaa tagtgagggg ctgcagtgca tgaacaccag     960
cacgagctac ctcagcaaga cgttatttga aattacagtg cctctctctc aaggccccaa    1020
accagtaaca atcagttttg ccaatcacac ttcctgccga tgcatgtcta aactggatgt    1080
ttacagacaa gttcattcca ttattagacg ttccctgcca gcaacactac cacagtgtca    1140
ggcagcgaac aagacctgcc ccaccaatta catgtggaat aatcacatct gcagatgcct    1200
ggctcaggaa gattttatgt tttcctcgga tgctggagat gactcaacag atggattcca    1260
tgacatctgt ggaccaaaca aggagctgga tgaagagacc tgtcagtgtg tctgcagagc    1320
ggggcttcgg cctgccagct gtggaccca caaagaacta gacagaaact catgccagtg     1380
tgtctgtaaa aacaaactct cccagcca atgtggggcc aaccgagaat tgatgaaaa       1440 cacatgccag tgtgtatgta aagaacctg ccccagaaat caaccctaa atcctggaaa      1500 atgtgcctgt gaatgtacag aaagtccaca gaaatgcttg ttaaaggaa agaagttcca     1560 ccaccaaaca tgcagctgtt acagacggcc atgtacgaac cgcagaagg cttgtgagcc     1620 aggattttca tatagtgaag aagtgtgtcg ttgtgtccct tcatattgga aagaccaca     1680 aatgagctaa gattgtactg ttttccagtt catcgatttt ctattatgga aaactgtgtt    1740
gccacagtag aactgtctgt gaacagagag acccttgtgg gtccatgcta acaaagacaa    1800
aagtctgtct ttcctgaacc atgtggataa ctttacagaa atggactgga gctcatctgc    1860
aaaaggcctc ttgtaaagac tggttttctg ccaatgacca aacagccaag attttcctct    1920
tgtgatttct ttaaaagaat gactatataa tttatttcca ctaaaaatat tgtttctgca    1980 ttcatttta tagcaacaac aattggtaaa actcactgtg atcaatattt ttatatcatg     2040
```

```
caaaatatgt ttaaaataaa atgaaaattg tattat                              2076

<210> SEQ ID NO 330
<211> LENGTH: 2819
<212> TYPE: DNA
<213> ORGANISM: Homo sapiens

<400> SEQUENCE: 330
ctgggcccag ctcccccgag aggtggtcgg atcctctggg ctgctcggtc gatgcctgtg      60
ccactgacgt ccaggcatga ggtggttcct gccctggacg ctggcagcag tgacagcagc     120
agccgccagc accgtcctgg ccacggccct ctctccagcc cctacgacca tggactttac     180
cccagctcca ctggaggaca cctcctcacg ccccccaattc tgcaagtggc catgtgagtg     240
cccgccatcc ccacccccgct gcccgctggg ggtcagcctc atcacagatg ctgtgagtg     300 ctgtaagatg tgcgctcagc agcttgggga caactcacg gaggctgcca tctgtgaccc     360
ccaccggggc ctctactgtg actacagcgg ggaccgcccg aggtacgcaa taggagtgtg     420
tgcacaggtg gtcggtgtgg gctgcgtcct ggatggggtg cgctacaaca acggccagtc     480
cttccagcct aactgcaagt acaactgcac gtgcatcgac ggcgcggtgg gctgcacacc     540
actgtgcctc cgagtgcgcc cccgcgtctc tggtgccccc acccgcggc gcgtgagcat     600 acctggccac tgctgtgagc agtgggtatg tgaggacgac gccaagaggc cacgcaagac     660
cgcaccccgt gacacaggag ccttcgatgc tgtgggtgag gtggaggcat ggcacaggaa     720
ctgcatagcc tacacaagcc cctggagccc ttgctccacc agctgcggcc tggggggtctc     780 cactcggatc tccaatgtta acgcccagtg ctggcctgag caagagagcc gcctctgcaa     840
cttgcggcca tgcgatgtgg acatccatac actcattaag gcagggaaga agtgtctggc     900
tgtgtaccag ccagaggcat ccatgaactt cacacttgcg ggctgcatca gcacacgctc     960
ctatcaaccc aagtactgtg agttttgcat ggacaatagg tgctgcatcc cctacaagtc    1020
taagactatc gacgtgtcct tccagtgtcc tgatgggctt ggcttctccc gccaggtcct    1080
atggattaat gcctgcttct gtaacctgag ctgtaggaat cccaatgaca tctttgctga    1140
cttggaatcc taccctgact ctcagaaaat tgccaactag gcaggcacaa atcttgggtc    1200
ttggggacta acccaatgcc tgtgaagcag tcagccctta tggccaataa cttttcacca    1260
atgagcctta gttaccctga tctggaccct tggcctccat ttctgtctct aaccattcaa    1320
atgacgccta atggtgctgc tcaggcccat gctatgagtt ttctccttga tatcattcag    1380
catctactct aaagaaaaat gcctgtctct agctgttctg gactacaccc aagcctgatc    1440
cagcctttcc aagtcactag aagtcctgct ggatcttgcc taaatcccaa gaaatggaat    1500
caggtagact tttaatatca ctaatttctt ctttagatgc caaaccacaa gactctttgg    1560
gtccattcag atgaatagat ggaattagga acaatagaat aatctattat ttggagcctg    1620
ccaagaggta ctgtaatggg taattctgac gtcagcgcac caaaactatc ctgattccaa    1680
atatgtatgc acctcaaggt catcaaacat ttgccaagtg agttgaatag ttgcttaatt    1740
ttgattttta atggaaagtt gtatccatta acctgggcat tgttgaggtt aagtttctct    1800 tcaccccctac actgtgaagg gtacagatta ggtttgtccc agtcagaaat aaaatttgat    1860
aaacattcct gttgatggga aaagccccca gttaatactc cagagacagg gaaaggtcag    1920
cccgtttcag aaggaccaat tgactctcac actgaatcag ctgctgactg gcagggcttt    1980
gggcagttgg ccaggctctt ccttgaatct tctcccttgt cctgcttggg gttcatagga    2040
```

| | | | | |
|---|---|---|---|---|
| attggtaagg | cctctggact | ggcctgtctg | gcccctgaga | gtggtgccct | ggaacactcc | 2100 |
| tctactctta | cagagccttg | agagaccag | ctgcagacca | tgccagaccc | actgaaatga | 2160 |
| ccaagacagg | ttcaggtagg | ggtgtgggtc | aaaccaagaa | gtgggtgccc | ttggtagcag | 2220 |
| cctggggtga | cctctagagc | tggaggctgt | gggactccag | gggcccccgt | gttcaggaca | 2280 |
| catctattgc | agagactcat | ttcacagcct | ttcgttctgc | tgaccaaatg | gccagttttc | 2340 |
| tggtaggaag | atggaggttt | accggttgtt | tagaaacaga | aatagactta | ataaaggttt | 2400 |
| aaagctgaag | aggttgaagc | taaaaggaaa | aggttgttgt | taatgaatat | caggctatta | 2460 |
| tttattgtat | taggaaaata | taatatttac | tgttagaatt | cttttattta | gggccttttc | 2520 |
| tgtgccagac | attgctctca | gtgctttgca | tgtattagct | cactgaatct | tcacgacaat | 2580 |
| gttgagaagt | tcccattatt | atttctgttc | ttacaaatgt | gaaacggaag | ctcatagagg | 2640 |
| tgagaaaact | caaccagagt | cacccagttg | gtgactggga | agttaggat | tcagatcgaa | 2700 |
| attggactgt | ctttataacc | catatttcc | ccctgttttt | agagcttcca | aatgtgtcag | 2760 |
| aataggaaaa | cattgcaata | aatggcttga | tttttaaaa | aaaaaaaaa | aaaaaaaa | 2819 |

<210> SEQ ID NO 331
<211> LENGTH: 2540
<212> TYPE: DNA
<213> ORGANISM: Homo sapiens

<400> SEQUENCE: 331

| | | | | | |
|---|---|---|---|---|---|
| gaaaaggtgg | acaagtccta | ttttcaagag | aagatgactt | ttaacagttt | tgaaggatct | 60 |
| aaaacttgtg | tacctgcaga | catcaataag | gaagaagaat | ttgtagaaga | gtttaataga | 120 |
| ttaaaaactt | ttgctaattt | tccaagtggt | agtcctgttt | cagcatcaac | actggcacga | 180 |
| gcagggtttc | tttatactgg | tgaaggagat | accgtgcggt | gctttagttg | tcatgcagct | 240 |
| gtagatagat | ggcaatatgg | agactcagca | gttggaagac | acaggaaagt | atccccaaat | 300 |
| tgcagattta | tcaacggctt | ttatcttgaa | aatagtgcca | cgcagtctac | aaattctggt | 360 |
| atccagaatg | gtcagtacaa | agttgaaaac | tatctgggaa | gcagagatca | ttttgcctta | 420 |
| gacaggccat | ctgagacaca | tgcagactat | cttttgagaa | ctgggcaggt | tgtagatata | 480 |
| tcagacacca | tatcccgag | gaaccctgcc | atgtattgtg | aagaagctag | attaaagtcc | 540 |
| tttcagaact | ggccagacta | tgctcaccta | accccaagag | agttagcaag | tgctggactc | 600 |
| tactacacag | gtattggtga | ccaagtgcag | tgcttttgtt | gtggtggaaa | actgaaaaat | 660 |
| tgggaacctt | gtgatcgtgc | ctggtcagaa | cacaggcgac | actttcctaa | ttgcttcttt | 720 |
| gttttgggcc | ggaatcttaa | tattcgaagt | gaatctgatg | ctgtgagttc | tgataggaat | 780 |
| ttcccaaatt | caacaaatct | tccaagaaat | ccatccatgg | cagattatga | agcacggatc | 840 |
| tttactttg | ggacatggat | atactcagtt | aacaaggagc | agcttgcaag | agctggattt | 900 |
| tatgctttag | gtgaaggtga | taaagtaaag | tgctttcact | gtggaggagg | ctaactgat | 960 |
| tggaagccca | gtgaagaccc | ttgggaacaa | catgctaaat | ggtatccagg | gtgcaaatat | 1020 |
| ctgttagaac | agaagggaca | agaatatata | aacaatattc | atttaactca | ttcacttgag | 1080 |
| gagtgtctgg | taagaactac | tgagaaaaca | ccatcactaa | ctagaagaat | tgatgatacc | 1140 |
| atcttccaaa | atcctatggt | acaagaagct | atacgaatgg | ggttcagttt | caaggacatt | 1200 |
| aagaaaataa | tggaggaaaa | aattcagata | tctgggagca | actataaatc | acttgaggtt | 1260 |
| ctggttgcag | atctagtgaa | tgctcagaaa | gacagtatgc | aagatgagtc | aagtcagact | 1320 |
| tcattacaga | aagagattag | tactgaagag | cagctaaggc | gcctgcaaga | ggagaagctt | 1380 |

```
tgcaaaatct gtatggatag aaatattgct atcgttttg ttccttgtgg acatctagtc   1440
acttgtaaac aatgtgctga agcagttgac aagtgtccca tgtgctacac agtcattact   1500
ttcaagcaaa aaattttat gtcttaatct aactctatag taggcatgtt atgttgttct    1560
tattaccctg attgaatgtg tgatgtgaac tgactttaag taatcaggat tgaattccat   1620
tagcatttgc taccaagtag gaaaaaaaat gtacatggca gtgttttagt tggcaatata   1680
atctttgaat tcttgatttt ttcagggtat tagctgtatt atccattttt tttactgtta    1740
tttaattgaa accatagact aagaataaga agcatcatac tataactgaa cacaatgtgt   1800
attcatagta tactgattta atttctaagt gtaagtgaat taatcatctg gattttttat   1860
tcttttcaga taggcttaac aaatggagct ttctgtatat aaatgtggag attagagtta   1920
atctccccaa tcacataatt tgttttgtgt gaaaaggaa taaattgttc catgctggtg    1980
gaaagataga gattgttttt agaggttggt tgttgtgttt taggattctg tccattttct   2040
tgtaaaggga taaacacgga cgtgtgcgaa atatgtttgt aaagtgattt gccattgttg   2100
aaagcgtatt taatgataga atactatcga gccaacatgt actgacatgg aaagatgtca   2160
gagatatgtt aagtgtaaaa tgcaagtggc gggacactat gtatagtctg agccagatca   2220
aagtatgtat gttgttaata tgcatagaac gagagatttg gaaagatata caccaaactg   2280
ttaaatgtgg tttctcttcg ggaggggggg gattgggga ggggcccag agggttta     2340 gaggggcctt ttcactttcg acttttttca ttttgttctg ttcggatttt ttataagtat   2400
gtagaccccg aagggtttta tgggaactaa catcagtaac ctaaccccg tgactatcct    2460 gtgctcttcc tagggagctg tgttgttcc cacccaccac ccttccctct gaacaaatgc    2520
ctgagtgctg gggcactttg                                              2540

<210> SEQ ID NO 332
<211> LENGTH: 1474
<212> TYPE: DNA
<213> ORGANISM: Homo sapiens

<400> SEQUENCE: 332
aaaaagaaat caagaatgca atttatttta caatagtcac gccggaaata cctagaaata     60
aatttaactg aggatgtaaa agacctctac aaggagagtt caatgcgtag cgggagcgga   120
gagctgaccc cagagagccc tgggcagccc cacctccgcc gccggcctag ttaccatcac   180
accccggaga gccgcagct gccgcagccg gccccagtca ccatcaccgc aaccatgagc   240
agcgaggccg agacccagca gccgcccgcc gccccccccg ccgccccgc cctcagcgcc   300 gccgacacca gcccggcac taccggagcg gcgcagggag cggtggcccg ggcggctcac   360
atcggcggcg ctggcgcggg cgacaagaag gtcatcgcaa cgaaggtttt gggaacagta   420
aaatggttca atgtaaggaa cggatatggt ttcatcaaca ggaatgacac caaggaagat   480
gtatttgtac accagactgc cataaagaag aataacccca ggaagtacct tcgcagtgta   540
ggagatggag agactgtgga gtttgatgtt gttgaaggag aaaagggtgc ggaggcagca   600
aatgttacag gtcctggtgg tgttccagtt caaggcagta aatatgcagc agaccgtaac   660
cattatagac gctatccacg tcgtaggggt cctccacgca attaccagca aaattaccag   720
aatagtgaga gtgggggaaaa gaacgaggga tcggagagtg ctcccgaagc caggcccaac   780
aacgccggcc ctacgcaggc gaaggttccc accttactac atgcggagac ctatgggcgt   840
cgaccacagt attccaaccc tcctgtgcag ggagaagtga tggagggtgc tgacaaccag   900
```

```
ggtgcaggag aacaaggtag accagtgagg cagatatgta tcggggatat agaccacgat    960
tccgcagggg ccctcctcgc caaaagacag cctagagagg acggcaatga agaagataaa   1020
gaaaatcaag gagatgagac ccaaggtcag cagccacctc aagctcggta ccgccgcaac   1080
ttcaattacc gacgcagacg cccagaaaac cctaaaccac aagatggcaa agagacaaaa   1140
gcagccgatc caccagctga gaattcgtcc gctcccgagg ctgagcaggg cggggctgag   1200
taaatgccgg cttaccatct ctaccatcat ccggtttagt catccaacaa gaagaaatat   1260
gaaattccag caataagaaa tgaacaaaag attggagctg aagacctaaa gtgcttgctt   1320
tttgcccgtt gaccagataa atagaactat ctgcattatc tatgcagcat ggggttttta   1380
ttatgtttta cctaaagacg tctcttttg gtaataacaa accgtgtttt ttaaaaaagc    1440
ctggtttttc tcaatacgcc tttaaaggaa ttcc                              1474

<210> SEQ ID NO 333
<211> LENGTH: 4079
<212> TYPE: DNA
<213> ORGANISM: Homo sapiens

<400> SEQUENCE: 333
ggagcggcgg gcgggcggga gggctggcgg ggcgaacgtc tgggagacgt ctgaaagacc     60
aacgagactt tggagaccag agacgcgcct gggggggacct ggggcttggg gcgtgcgaga   120
tttcccttgc attcgctggg agctcgcgca gggatcgtcc catggccggg gctcggagcc   180
gcgacccttg gggggcctcc gggatttgct accttttttgg ctccctgctc gtcgaactgc   240
tcttctcacg ggctgtcgcc ttcaatctgg acgtgatggg tgccttgcgc aaggagggcg   300
agccaggcag cctcttcggc ttctctgtgg ccctgcaccg gcagttgcag ccccgacccc   360
agagctggct gctggtgggt gctccccagg ccctggctct tcctgggcag caggcgaatc   420
gcactggagg cctcttcgct tgcccgttga gcctggagga gactgactgc tacagagtgg   480
acatcgacca gggagctgat atgcaaaagg aaagcaagga gaaccagtgg ttgggagtca   540
gtgttcggag ccaggggcct gggggcaaga ttgttacctg tgcacaccga tatgaggcaa   600
ggcagcgagt ggaccagatc ctggagacgc gggatatgat tggtcgctgc tttgtgctca   660
gccaggacct ggccatccgg gatgagttgg atggtgggga atggaagttc tgtgagggac   720
gcccccaagg ccatgaacaa tttgggttct gccagcaggg cacagctgcc gccttctccc   780
ctgatagcca ctacctcctc tttgggggcc caggaaccta taattggaag gggttgcttt   840
ttgtgaccaa cattgatagc tcagaccccg accagctggt gtataaaact ttggaccctg   900
ctgaccggct cccaggacca gccggagact tggccctcaa tagctactta ggcttctcta   960
ttgactcggg gaaaggtctg gtgcgtgcag aagagctgag ctttgtggct ggagcccccc   1020
gcgccaacca caagggtgct gtggttatcc tgcgcaagga cagcgccagt cgcctggtgc   1080
ccgaggttat gctgtctggg gagcgcctga cctccggctt tggctactca ctggctgtgg   1140
ctgacctcaa cagtgatggc tggccagacc tgatagtggg tgcccccetac ttctttgagc   1200
gccaagaaga gctgggggt gctgtgtatg tgtacttgaa ccaggggggt cactgggctg   1260
ggatctcccc tctccggctc tgcggctccc ctgactccat gttcgggatc agcctggctg   1320
tcctggggga cctcaaccaa gatggctttc cagatattgc agtgggtgcc ccctttgatg   1380
gtgatgggaa agtcttcatc taccatggga gcagcctggg ggttgtcgcc aaaccttcac   1440
aggtgctgga gggcgaggct gtgggcatca gagcttcgg ctactccctg tcaggcagct   1500
tggatatgga tgggaaccaa taccctgacc tgctggtggg ctccctggct gacaccgcag   1560
```

```
tgctcttcag ggccagaccc atcctccatg tctcccatga ggtctctatt gctccacgaa   1620
gcatcgacct ggagcagccc aactgtgctg gcggccactc ggtctgtgtg gacctaaggg   1680
tctgtttcag ctacattgca gtccccagca gctatagccc tactgtggcc ctggactatg   1740
tgttagatgc ggacacagac cggaggctcc ggggccaggt tccccgtgtg acgttcctga   1800
gccgtaacct ggaagaaccc aagcaccagg cctcgggcac cgtgtggctg aagcaccagc   1860
atgaccgagt ctgtggagac gccatgttcc agctccagga aaatgtcaaa gacaagcttc   1920
gggccattgt agtgaccttg tcctacagtc tccagacccc tcggctccgg cgacaggctc   1980
ctggccaggg gctgcctcca gtggccccca tcctcaatgc ccaccagccc agcacccagc   2040
gggcagagat ccacttcctg aagcaaggct gtggtgaaga caagatctgc cagagcaatc   2100
tgcagctggt ccacgcccgc ttctgtaccc gggtcagcga cacggaattc caacctctgc   2160
ccatggatgt ggatggaaca acagcccgtg ttgcactgag tgggcagcca gtcattggcc   2220
tggagctgat ggtcaccaac ctgccatcgg acccagccca gccccaggct gatggggatg   2280
atgcccatga agcccagctc ctggtcatgc ttcctgactc actgcactac tcaggggtcc   2340
gggccctgga ccctgcggag aagccactct gcctgtccaa tgagaatgcc tcccatgttg   2400
agtgtgagct ggggaacccc atgaagagag gtgcccaggt caccttctac ctcatcctta   2460
gcacctccgg gatcagcatt gagaccacgg aactggaggt agagctgctg ttggccacga   2520
tcagtgagca ggagctgcat ccagtctctg cacgagcccg tgtcttcatt gagctgccac   2580
tgtccattgc aggaatggcc attccccagc aactcttctt ctctggtgtg gtgagggggcg   2640 agagagccat gcagtctgag cgggatgtgg gcagcaaggt caagtatgag gtcacggttt   2700
ccaaccaagg ccagtcgctc agaaccctgg gctctgcctt cctcaacatc atgtggcctc   2760
atgagattgc caatgggaag tggttgctgt acccaatgca ggttgagctg agggcgggc   2820 aggggcctgg gcagaaaggg ctttgctctc ccaggcccaa catcctccac ctggatgtgg   2880
acagtaggga taggaggcgg cgggagctgg agccacctga gcagcaggag cctggtgagc   2940
ggcaggagcc cagcatgtcc tggtggccag tgtcctctgc tgagaagaag aaaaacatca   3000
ccctggactg cgcccggggc acggccaact gtgtggtgtt cagctgccca ctctacagct   3060
ttgaccgcgc ggctgtgctg catgtctggg gccgtctctg gaacagcacc tttctggagg   3120
agtactcagc tgtgaagtcc ctggaagtga ttgtccgggc caacatcaca gtgaagtcct   3180
ccataaagaa cttgatgctc cgagatgcct ccacagtgat cccagtgatg gtatacttgg   3240
accccatggc tgtggtggca aaggagtgcc ctggtgggt catcctcctg gctgtactgg   3300
ctgggctgct ggtgctagca ctgctggtgc tgctcctgtg aagatggga ttcttcaaac   3360 gggcgaagca ccccgaggcc accgtgcccc agtaccatgc ggtgaagatt cctcgggaag   3420
accgacagca gttcaaggag gagaagacgg gcaccatcct gaggaacaac tggggcagcc   3480
cccggcggga gggcccggat gcacaccccca tcctggctgc tgacgggcat cccgagctgg   3540
gccccgatgg gcatccaggg ccaggcaccg cctaggttcc catgtcccag cctggcctgt   3600
ggctgccctc catcccttcc ccagagatgg ctccttggga tgaagagggt agagtgggct   3660
gctggtgtcg catcaagatt tggcaggatc ggcttcctca ggggcacaga cctctcccac   3720
ccacaagaac tcctcccacc caacttcccc ttagagtgct gtgagatgag agtgggtaaa   3780
tcagggacag ggccatgggg tagggtgaga agggcagggg tgtcctgatg caaaggtggg   3840
gagaagggat cctaatccct tcctctccca ttcaccctgt gtaacaggac cccaaggacc   3900
```

```
tgcctcccg gaagtgcctt aacctagagg gtcggggagg aggttgtgtc actgactcag    3960
gctgctcctt ctctagtttc ccctctcatc tgaccttagt ttgctgccat cagtctagtg    4020
gtttcgtggt ttcgtctatt tattaaaaaa tatttgagaa caaaaaaaaa aaaaaaaa     4079
```

<210> SEQ ID NO 334
<211> LENGTH: 3373
<212> TYPE: DNA
<213> ORGANISM: Homo sapiens

<400> SEQUENCE: 334

```
ggtggcaact tctcctcctg cggccgggag cggcctgcct gcctccctgc gcacccgcag      60
cctcccccgc tgcctcccta gggctcccct ccggccgcca gcgcccattt ttcattccct     120
agatagagat actttgcgcg cacacacata catacgcgcg caaaaaggaa aaaaaaaaa     180 aaaagcccac cctccagcct cgctgcaaag agaaaccgg agcagccgca gctcgcagct     240
cgcagctcgc agcccgcagc ccgcagagga cgcccgagagc ggcgagcagg cgggcagacg     300
gaccgacgga ctcgcgccgc gtccacctgt cggccgggcc cagccgagcg cgcagcgggc     360
acgccgcgcg cgcggagcag ccgtgcccgc gccccgggcc cgccgccagg cgcacacgc      420 tcccgccccc ctacccggcc cgggcgggag tttgcacctc tccctgcccg ggtgctcgag     480
ctgccgttgc aaagccaact ttggaaaaag tttttttgggg gagacttggg ccttgaggtg     540
cccagctccg cgctttccga ttttgggggc ctttccagaa aatgttgcaa aaaagctaag     600
ccggcgggca gaggaaaacg cctgtagccg gcgagtgaag acgaaccatc gactgccgtg     660
ttccttttcc tcttggaggt tggagtcccc tgggcgcccc cacacggcta gacgcctcgg     720
ctggttcgcg acgcagcccc ccggccgtgg atgctgcact cgggctcggg atccgcccag     780
gtagccggcc tcggacccag gtcctgcgcc caggtcctcc cctgccccccc agcgacggag     840 ccggggccgg gggcggcggc gccggggca tgcgggtgag ccgcggctgc agaggcctga     900
gcgcctgatc gccgcggacc tgagccgagc ccaccccccct ccccagcccc ccacccctggc     960 cgcgggggcg gcgcgctcga tctacgcgtc cggggcccccg cggggccggg cccggagtcg    1020
gcatgaatcg ctgctgggcg ctcttcctgt ctctctgctg ctacctgcgt ctggtcagcg    1080 ccgagggggga ccccattccc gaggagcttt atgagatgct gagtgaccac tcgatccgct    1140
cctttgatga tctccaacgc ctgctgcacg gagacccgg agaggaagat ggggccgagt     1200
tggacctgaa catgaccgc tcccactctg gaggcgagct ggagagcttg gctcgtggaa     1260
gaaggagcct gggttccctg accattgctg agccggccat gatcgccgag tgcaagacgc     1320
gcaccgaggt gttcgagatc tcccggcgcc tcatagaccg caccaacgcc aacttcctgg    1380
tgtggccgcc ctgtgtggag gtgcagcgct gctccggctg ctgcaacaac gcaacgtgc     1440 agtgccgccc cacccaggtg cagctgcgac ctgtccaggt gagaaagatc gagattgtgc    1500
ggaagaagcc aatctttaag aaggccacgg tgacgctgga agaccacctg gcatgcaagt    1560
gtgagacagt ggcagctgca cggcctgtga cccgaagccc ggggggttcc caggagcagc    1620
gagccaaaac gccccaaact cgggtgacca ttcgacggt gcgagtccgc cggccccca     1680 agggcaagca ccggaaattc aagcacacgc atgacaagac ggcactgaag gagaccttg    1740 gagcctaggg gcatcggcag gagagtgtgt gggcagggtt atttaatatg gtatttgctg    1800 tattgcccc atgggtcct tggagtgata atattgtttc cctcgtccgt ctgtctcgat     1860
gcctgattcg gacggccaat ggtgcttccc ccacccctcc acgtgtccgt ccacccttcc    1920
atcagcgggt ctcctcccag cggcctccgg tcttgcccag cagctcaaag aagaaaaga    1980
```

| | | |
|---|---|---|
| aggactgaac tccatcgcca tcttcttccc ttaactccaa gaacttggga taagagtgtg | 2040 |
| agagagactg atggggtcgc tctttggggg aaacgggttc cttcccctgc acctggcctg | 2100 |
| ggccacacct gagcgctgtg gactgtcctg aggagccctg aggacctctc agcatagcct | 2160 |
| gcctgatccc tgaacccctg gccagctctg aggggaggca cctccaggca ggccaggctg | 2220 |
| cctcggactc catggctaag accacagacg ggcacacaga ctggagaaaa ccctcccac | 2280 |
| ggtgcccaaa caccagtcac ctcgtctccc tggtgcctct gtgcacagtg gcttctttc | 2340 |
| gttttcgttt tgaagacgtg gactcctctt ggtgggtgtg gccagcacac caagtggctg | 2400 |
| ggtgccctct caggtgggtt agagatggag tttgctgttg aggtggtgta gatggtgacc | 2460 |
| tgggtatccc ctgcctcctg ccacccctc ctccccatac tccactctga ttcacctctt | 2520 |
| cctctggttc ctttcatctc tctacctcca ccctgcattt tcctcttgtc ctggcccttc | 2580 |
| agtctgctcc accaaggggc tcttgaaccc cttattaagg ccccagatga ccccagtcac | 2640 |
| tcctctctag ggcagaagac tagaggccag ggcagcaagg gacctgctca tcatattcca | 2700 |
| acccagccac gactgccatg taaggttgtg cagggtgtgt actgcacaag gacattgtat | 2760 |
| gcagggagca ctgttcacat catagataaa gctgatttgt atatttatta tgacaatttc | 2820 |
| tggcagatgt aggtaaagag gaaaaggatc cttttcctaa ttcacacaaa gactccttgt | 2880 |
| ggactggctg tgcccctgat gcagcctgtg gctggagtgg ccaaatagga gggagactgt | 2940 |
| ggtaggggca gggaggcaac actgctgtcc acatgacctc catttcccaa agtcctctgc | 3000 |
| tccagcaact gcccttccag gtgggtgtgg gacacctggg agaaggtctc caagggaggg | 3060 |
| tgcagccctc ttgcccgcac ccctccctgc ttgcacactt ccccatcttt gatccttctg | 3120 |
| agctccacct ctggtggctc ctcctaggaa accagctcgt gggctgggaa tgggggagag | 3180 |
| aagggaaaag atccccaaga ccccctgggg tgggatctga gctcccacct cccttcccac | 3240 |
| ctactgcact ttccccttc ccgccttcca aaacctgctt ccttcagttt gtaaagtcgg | 3300 |
| tgattatatt tttgggggct ttccttttat tttttaaatg taaaatttat ttatattccg | 3360 |
| tatttaaagt tgt | 3373 |

<210> SEQ ID NO 335
<211> LENGTH: 2304
<212> TYPE: DNA
<213> ORGANISM: Homo sapiens

<400> SEQUENCE: 335

| | | |
|---|---|---|
| gtccccgcag cgccgtcgcg ccctcctgcc gcaggccacc gaggccgccg ccgtctagcg | 60 |
| ccccgacctc gccaccatga gagccctgct ggcgcgcctg cttctctgcg tcctggtcgt | 120 |
| gagcgactcc aaaggcagca atgaacttca tcaagttcca tcgaactgtg actgtctaaa | 180 |
| tggaggaaca tgtgtgtcca acaagtactt ctccaacatt cactggtgca actgcccaaa | 240 |
| gaaattcgga gggcagcact gtgaaataga taagtcaaaa acctgctatg aggggaatgg | 300 |
| tcactttac cgaggaaagg ccagcactga caccatgggc cggccctgcc tgccctggaa | 360 |
| ctctgccact gtccttcagc aaacgtacca tgcccacaga tctgatgctc ttcagctggg | 420 |
| cctggggaaa cataattact gcaggaaccc agacaaccgg aggcgaccct ggtgctatgt | 480 |
| gcaggtgggc ctaaagccgc ttgtccaaga gtgcatggtg catgactgcg cagatggaaa | 540 |
| aaagcccctcc tctcctccag aagaattaaa atttcagtgt ggccaaaaga ctctgaggcc | 600 |
| ccgctttaag attattgggg gagaattcac caccatcgag aaccagccct ggtttgcggc | 660 |

-continued

| | |
|---|---|
| catctacagg aggcaccggg ggggctctgt cacctacgtg tgtggaggca gcctcatcag | 720 |
| cccttgctgg gtgatcagcg ccacacactg cttcattgat tacccaaaga aggaggacta | 780 |
| catcgtctac ctgggtcgct caaggcttaa ctccaacacg caaggggaga tgaagtttga | 840 |
| ggtggaaaac ctcatcctac acaaggacta cagcgctgac acgcttgctc accacaacga | 900 |
| cattgccttg ctgaagatcc gttccaagga gggcaggtgt gcgcagccat cccggactat | 960 |
| acagaccatc tgcctgccct cgatgtataa cgatccccag tttggcacaa gctgtgagat | 1020 |
| cactggcttt ggaaaagaga attctaccga ctatctctat ccggagcagc tgaaaatgac | 1080 |
| tgttgtgaag ctgatttccc accgggagtg tcagcagccc cactactacg ctctgaagt | 1140 |
| caccaccaaa atgctatgtg ctgctgaccc ccaatggaaa acagattcct gccagggaga | 1200 |
| ctcaggggga cccctcgtct gttccctcca aggccgcatg actttgactg gaattgtgag | 1260 |
| ctggggccgt ggatgtgccc tgaaggacaa gccaggcgtc tacacgagag tctcacactt | 1320 |
| cttaccctgg atccgcagtc acaccaagga agagaatggc ctggccctct gagggtcccc | 1380 |
| agggaggaaa cggcaccac ccgctttctt gctggttgtc atttttgcag tagagtcatc | 1440 |
| tccatcagct gtaagaagag actgggaaga taggctctgc acagatggat ttgcctgtgg | 1500 |
| caccaccagg gtgaacgaca atagctttac cctcacggat aggcctgggt gctggctgcc | 1560 |
| cagaccctct ggccaggatg gaggggtggt cctgactcaa catgttactg accagcaact | 1620 |
| tgtcttttc tggactgaag cctgcaggag ttaaaaaggg cagggcatct cctgtgcatg | 1680 |
| ggctcgaagg gagagccagc tcccccgacc ggtgggcatt tgtgaggccc atggttgaga | 1740 |
| aatgaataat ttcccaatta ggaagtgtaa gcagctgagg tctcttgagg gagcttagcc | 1800 |
| aatgtgggag cagcggtttg gggagcagag acactaacga cttcagggca gggctctgat | 1860 |
| attccatgaa tgtatcagga aatatatatg tgtgtgtatg tttgcacact tgttgtgtgg | 1920 |
| gctgtgagtg taagtgtgag taagagctgg tgtctgattg ttaagtctaa atatttcctt | 1980 |
| aaactgtgtg gactgtgatg ccacacagag tggtctttct ggagaggtta taggtcactc | 2040 |
| ctggggcctc ttgggtcccc cacgtgacag tgcctgggaa tgtacttatt ctgcagcatg | 2100 |
| acctgtgacc agcactgtct cagtttcact ttcacataga tgtcccttc ttggccagtt | 2160 |
| atcccttcct tttagcctag ttcatccaat cctcactggg tggggtgagg accactcctt | 2220 |
| acactgaata tttatatttc actatttta tttatattt tgtaattta aataaaagtg | 2280 |
| atcaataaaa tgtgattttt ctga | 2304 |

<210> SEQ ID NO 336
<211> LENGTH: 1876
<212> TYPE: DNA
<213> ORGANISM: Homo sapiens

<400> SEQUENCE: 336

| | |
|---|---|
| cgcggccgcg gttcgctgtg gcgggcgcct gggccgccgg ctgtttaact tcgcttccgc | 60 |
| tggcccatag tgatctttgc agtgacccag cagcatcact gtttcttggc gtgtgaagat | 120 |
| aacccaagga attgaggaag ttgctgagaa gagtgtgctg gagatgctct aggaaaaaat | 180 |
| tgaatagtga gacgagttcc agcgcaaggg tttctggttt gccaagaaga aagtgaacat | 240 |
| catggatcag aacaacagcc tgccaccttc gctcagggc ttggcctccc ctcagggtgc | 300 |
| catgactccc ggaatcccta tctttagtcc aatgatgcct tatggcactg gactgacccc | 360 |
| acagcctatt cagaacacca atagtctgtc tattttggaa gagcaacaaa ggcagcagca | 420 |
| gcaacaacaa cagcagcagc agcagcagca gcagcagcaa cagcaacagc agcagcagca | 480 |

```
gcagcagcag cagcagcagc agcagcagca gcagcagcag caacaggcag tggcagctgc        540
agccgttcag cagtcaacgt cccagcaggc aacacaggga acctcaggcc aggcaccaca        600
gctcttccac tcacagactc tcacaactgc acccttgccg ggcaccactc cactgtatcc        660
ctcccccatg actcccatga cccccatcac tcctgccacg ccagcttcgg agagttctgg        720
gattgtaccg cagctgcaaa atattgtatc cacagtgaat cttggttgta aacttgacct        780
aaagaccatt gcacttcgtg cccgaaacgc cgaatataat cccaagcggt ttgctgcggt        840
aatcatgagg ataagagagc cacgaaccac ggcactgatt ttcagttctg ggaaaatggt        900
gtgcacagga gccaagagtg aagaacagtc cagactggca gcaagaaaat atgctagagt        960
tgtacagaag ttgggttttc cagctaagtt cttggacttc aagattcaga acatggtggg       1020
gagctgtgat gtgaagtttc ctataaggtt agaaggcctt gtgctcaccc accaacaatt       1080
tagtagttat gagccagagt tatttcctgg tttaatctac agaatgatca acccagaat        1140 tgttctcctt atttttgttt ctggaaaagt tgtattaaca ggtgctaaag tcagagcaga       1200
aatttatgaa gcatttgaaa acatctaccc tattctaaag ggattcagga agacgacgta       1260
atggctctca tgtacccttg cctcccccac ccccttcttt tttttttttt aaacaaatca       1320
gtttgttttg gtacctttaa atggtggtgt tgtgagaaga tggatgttga gttgcagggt       1380
gtggcaccag gtgatgccct tctgtaagtg cccaccgcgg gatgccggga agggcatta        1440 tttgtgcact gagaacaccg cgcagcgtga ctgtgagttg ctcataccgt gctgctatct       1500
gggcagcgct gcccatttat ttatatgtag attttaaaca ctgctgttga caagttggtt       1560
tgagggagaa aactttaagt gttaaagcca cctctataat tgattggact ttttaatttt       1620
aatgtttttc cccatgaacc acagttttta tatttctacc agaaagtaa aaatcttttt        1680 taaaagtgtt gttttcctaa tttataactc ctaggggtta tttctgtgcc agacacattc       1740
cacctctcca gtattgcagg acggaatata tgtgttaatg aaaatgaatg gctgtacata       1800
ttttttctct tcttcagagt actctgtaca ataaatgcag tttataaaag tgttaaaaaa       1860
aaaaaaaaaa aaaaaa                                                       1876

<210> SEQ ID NO 337
<211> LENGTH: 6633
<212> TYPE: DNA
<213> ORGANISM: Homo sapiens

<400> SEQUENCE: 337
ttctccccgc cccccagttg ttgtcgaagt ctggggggttg ggactggacc ccctgattgc        60
gtaagagcaa aaagcgaagg cgcaatctgg acactgggag attcggagcg cagggagttt       120
gagagaaact tttattttga agagaccaag gttgaggggg ggcttatttc ctgacagcta       180
tttacttaga gcaaatgatt agttttagaa ggatggacta taacattgaa tcaattacaa       240
aacgcggttt ttgagcccat tactgttgga gctacaggga gagaaacagg aggagactgc       300
aagagatcat ttgggaaggc cgtgggcacg ctctttactc catgtgtggg acattcattg       360
cggaataaca tcggaggaga agtttcccag agctatgggg acttcccatc cggcgttcct       420
ggtcttaggc tgtcttctca cagggctgag cctaatcctc tgccagcttt cattaccctc       480
tatccttcca aatgaaaatg aaaaggttgt gcagctgaat tcatccttttt ctctgagatg       540 ctttggggag agtgaagtga gctggcagta ccccatgtct gaagaagaga gctccgatgt       600
ggaaatcaga aatgaagaaa acaacagcgg ccttttttgtg acggtcttgg aagtgagcag       660
```

```
tgcctcggcg gcccacacag ggttgtacac ttgctattac aaccacactc agacagaaga    720
gaatgagctt gaaggcaggc acatttacat ctatgtgcca gacccagatg tagcctttgt    780
acctctagga atgacggatt atttagtcat cgtggaggat gatgattctg ccattatacc    840
ttgtcgcaca actgatcccg agactcctgt aaccttacac aacagtgagg gggtggtacc    900
tgcctcctac gacagcagac agggcttaa tgggaccttc actgtagggc cctatatctg     960
tgaggccacc gtcaaaggaa agaagttcca gaccatccca tttaatgttt atgcttttaaa   1020
agcaacatca gagctggatc tagaaatgga agctcttaaa accgtgtata agtcagggga    1080
aacgattgtg gtcacctgtg ctgttttttaa caatgaggtg gttgaccttc aatggactta   1140
ccctggagaa gtgaaaggca aaggcatcac aatgctggaa gaaatcaaag tcccatccat    1200
caaattggtg tacactttga cggtccccga ggccacggtg aaagacagtg agattacga    1260
atgtgctgcc cgccaggcta ccagggaggt caaagaaatg aagaaagtca ctatttctgt   1320
ccatgagaaa ggtttcattg aaatcaaacc caccttcagc cagttggaag ctgtcaacct   1380
gcatgaagtc aaacattttg ttgtagaggt gcgggcctac ccacctccca ggatatcctg    1440
gctgaaaaac aatctgactc tgattgaaaa tctcactgag atcaccactg atgtggaaaa   1500
gattcaggaa ataaggtatc gaagcaaatt aaagctgatc cgtgctaagg aagaagacag    1560
tggccattat actattgtag ctcaaaatga agatgctgtg aagagctata cttttgaact    1620
gttaactcaa gttccttcat ccattctgga cttggtcgat gatcaccatg gctcaactgg    1680
gggacagacg gtgaggtgca cagctgaagg cacgccgctt cctgatattg agtggatgat    1740
atgcaaagat attaagaaat gtaataatga aacttcctgg actatttttgg ccaacaatgt    1800
ctcaaacatc atcacggaga tccactcccg agacaggagt accgtggagg gccgtgtgac    1860
tttcgccaaa gtggaggaga ccatcgccgt gcgatgcctg gctaagaatc tccttggagc    1920
tgagaaccga gagctgaagc tggtggctcc caccctgcgt tctgaactca cggtggctgc   1980
tgcagtcctg gtgctgttgg tgattgtgat catctcactt attgtcctgg ttgtcatttg    2040
gaaacagaaa ccgaggtatg aaattcgctg gagggtcatt gaatcaatca gcccggatgg   2100
acatgaatat atttatgtgg acccgatgca gctgccttat gactcaagat gggagtttcc    2160
aagagatgga ctagtgcttg gtcgggtctt ggggtctgga gcgtttggga aggtggttga    2220
aggaacagcc tatggattaa gccggtccca acctgtcatg aaagttgcag tgaagatgct    2280
aaaacccacg gccagatcca gtgaaaaaca agctctcatg tctgaactga gataatgac    2340
tcacctgggg ccacatttga acattgtaaa cttgctggga gcctgcacca agtcaggccc    2400
catttacatc atcacagagt attgcttcta tggagatttg gtcaactatt tgcataagaa    2460
tagggatagc ttcctgagcc accccccaga gaagccaaag aaagagctgg atatctttgg   2520
attgaaccct gctgatgaaa gcacacggag ctatgttatt ttatctttttg aaaacaatgg    2580
tgactacatg gacatgaagc aggctgatac tacacagtat gtccccatgc tagaaaggaa    2640
agaggtttct aaatattccg acatccagag atcactctat gatcgtccag cctcatataa   2700
gaagaaatct atgttagact cagaagtcaa aaacctcctt tcagatgata actcagaagg    2760
ccttactta ttggatttgt tgagcttcac ctatcaagtt gcccgaggaa tggagttttt    2820
ggcttcaaaa aattgtgtcc accgtgatct ggctgctcgc aacgtcctcc tggcacaagg    2880
aaaaattgtg aagatctgtg actttggcct ggccagagac atcatgcatg attcgaacta   2940
tgtgtcgaaa ggcagtacct ttctgcccgt gaagtggatg gctcctgaga gcatctttga   3000
caacctctac accacactga gtgatgtctg gtcttatggc attctgctct gggagatctt    3060
```

```
ttcccttggt ggcaccccett acccecggcat gatggtggat tctactttct acaataagat    3120
caagagtggg taccggatgg ccaagcctga ccacgctacc agtgaagtct acgagatcat    3180
ggtgaaatgc tggaacagtg agccggagaa gagaccctcc ttttaccacc tgagtgagat    3240
tgtggagaat ctgctgcctg acaatataa aaagagttat gaaaaaattc acctggactt    3300
cctgaagagt gaccatcctg ctgtggcacg catgcgtgtg gactcagaca atgcatacat    3360
tggtgtcacc tacaaaaacg aggaagacaa gctgaaggac tgggagggtg gtctggatga    3420
gcagagactg agcgctgaca gtggctacat cattcctctg cctgacattg accctgtccc    3480
tgaggaggag gacctgggca agaggaacag acacagctcg cagacctctg aagagagtgc    3540
cattgagacg ggttccagca gttccacctt catcaagaga gaggacgaga ccattgaaga    3600
catcgacatg atggacgaca tcggcataga ctcttcagac ctggtggaag acagcttcct    3660
gtaactggcg gattcgaggg gttccttcca cttctggggc cacctctgga tcccgttcag    3720
aaaaccactt tattgcaatg cggaggttga gaggaggact tggttgatgt ttaaagagaa    3780
gttcccagcc aagggcctcg gggagcgttc taaatatgaa tgaatgggat attttgaaat    3840
gaactttgtc agtgttgcct ctcgcaatgc ctcagtagca tctcagtggt gtgtgaagtt    3900
tggagataga tggataaggg aataataggc cacagaaggt gaactttgtg cttcaaggac    3960
attggtgaga gtccaacaga cacaatttat actgcgacag aacttcagca ttgtaattat    4020
gtaaataact ctaaccaagg ctgtgtttag attgtattaa ctatcttctt tggacttctg    4080
aagagaccac tcaatccatc catgtacttc cctcttgaaa cctgatgtca gctgctgttg    4140
aactttttaa agaagtgcat gaaaaaccat ttttgaacct taaaaggtac tggtactata    4200
gcattttgct atcttttta gtgttaagag ataaagaata ataattaacc aaccttgttt    4260
aatagatttg ggtcatttag aagcctgaca actcattttc atattgtaat ctatgtttat    4320
aatactacta ctgttatcag taatgctaaa tgtgtaataa tgtaacatga tttccctcca    4380
gagaaagcac aatttaaaac aatccttact aagtaggtga tgagtttgac agttttgac    4440
atttatatta ataacatgt ttctctataa agtatggtaa tagctttagt gaattaaatt    4500
tagttgagca tagagaacaa agtaaaagta gtgttgtcca ggaagtcaga attttaact    4560
gtactgaata ggttccccaa tccatcgtat taaaaaacaa ttaactgccc tctgaaataa    4620
tgggattaga aacaaacaaa actcttaagt cctaaaagtt ctcaatgtag aggcataaac    4680
ctgtgctgaa cataacttct catgtatatt acccaatgga aaatataatg atcagcaaaa    4740
agactggatt tgcagaagtt ttttttttt ttcttcatgc ctgatgaaag ctttggcaac    4800
cccaatatat gtatttttg aatctatgaa cctgaaaagg gtcagaagga tgcccagaca    4860
tcagcctcct tctttcaccc cttaccccaa agagaaagag tttgaaactc gagaccataa    4920
agatattctt tagtggaggc tggatgtgca ttagcctgga tcctcagttc tcaaatgtgt    4980
gtggcagcca ggatgactag atcctgggtt tccatccttg agattctgaa gtatgaagtc    5040
tgagggaaac cagagtctgt atttttctaa actcccctggc tgttctgatc ggccagtttt    5100
cggaaacact gacttaggtt tcaggaagtt gccatgggaa acaaataatt tgaactttgg    5160
aacagggttg gaattcaacc acgcaggaag cctactattt aaatccttgg cttcaggtta    5220
gtgacattta atgccatcta gctagcaatt gcgaccttaa tttaactttc cagtcttagc    5280
tgaggctgag aaagctaaag tttgttttttg acaggttttc caaaagtaaa gatgctactt    5340
cccactgtat gggggagatt gaactttccc cgtctcccgt cttctgcctc ccactccata    5400
```

```
cccgccaag gaaaggcatg tacaaaaatt atgcaattca gtgttccaag tctctgtgta    5460
accagctcag tgttttggtg gaaaaaacat tttaagtttt actgataatt tgaggttaga    5520
tgggaggatg aattgtcaca tctatccaca ctgtcaaaca ggttggtgtg ggttcattgg    5580
cattctttgc aatactgctt aattgctgat accatatgaa tgaaacatgg gctgtgatta    5640
ctgcaatcac tgtgctatcg gcagatgatg ctttggaaga tgcagaagca ataataaagt    5700
acttgactac ctactggtgt aatctcaatg caagccccaa ctttcttatc caacttttc    5760 atagtaagtg cgaagactga gccagattgg ccaattaaaa acgaaaacct gactaggttc    5820
tgtagagcca attagacttg aaatacgttt gtgtttctag aatcacagct caagcattct    5880
gtttatcgct cactctccct tgtacagcct tattttgttg gtgctttgca ttttgatatt    5940
gctgtgagcc ttgcatgaca tcatgaggcc ggatgaaact tctcagtcca gcagtttcca    6000
gtcctaacaa atgctcccac ctgaatttgt atatgactgc atttgtgggt gtgtgtgtgt    6060
tttcagcaaa ttccagattt gtttcctttt ggcctcctgc aaagtctcca gaagaaaatt    6120
tgccaatctt tcctactttc tattttatg atgacaatca aagccggcct gagaaacact    6180
atttgtgact tttaaacga ttagtgatgt ccttaaaatg tggtctgcca atctgtacaa    6240
aatggtccta tttttgtgaa gagggacata agataaaatg atgttataca tcaatatgta    6300
tatatgtatt tctatataga cttggagaat actgccaaaa catttatgac aagctgtatc    6360
actgccttcg tttatatttt tttaactgtg ataatcccca caggcacatt aactgttgca    6420
cttttgaatg tccaaaattt atattttaga aataataaaa agaaagatac ttacatgttc    6480
ccaaaacaat ggtgtggtga atgtgtgaga aaaactaact tgatagggtc taccaataca    6540
aaatgtatta cgaatgcccc tgttcatgtt tttgttttaa aacgtgtaaa tgaagatctt    6600
tatatttcaa taaatgatat ataatttaaa gtt    6633
```

<210> SEQ ID NO 338
<211> LENGTH: 994
<212> TYPE: DNA
<213> ORGANISM: Homo sapiens

<400> SEQUENCE: 338

```
tgctggccag cacctcgagg gaagatggcg gacgaggaga agctgccgcc cggctgggag      60
aagcgcatga gccgcagctc aggccgagtg tactacttca accacatcac taacgccagc     120
cagtgggagc ggcccagcgg caacagcagc agtggtggca aaaacgggca ggggagcct     180 gccagggtcc gctgctcgca cctgctggtg aagcacagca gtcacggcg ccctcgtcc     240 tggcggcagg agaagatcac ccggaccaag gaggaggccc tggagctgat caacggctac     300
atccagaaga tcagtcgggg agaggaggac tttgagtctc tggcctcaca gttcagcgac     360
tgcagctcag ccaaggccag gggagacctg ggtgccttca gcagaggtca gatgcagaag     420
ccatttgaag acgcctcgtt tgcgctgcgg acggggaga tgagcgggcc cgtgttcacg     480
gattccggca tccacatcat cctccgcact gagtgagggt ggggagccca ggcctggcct     540
cggggcaggg cagggcggct aggccggcca gctccccctt gccgccagc cagtggccga     600 accccccact ccctgccacc gtcacacagt atttattgtt cccacaatgg ctgggagggg     660
gcccttccag attgggggcc ctgggtccc cactccctgt ccatcccag ttggggctgc     720 gaccgccaga ttctcccttca aggaattgac ttcagcaggg gtgggaggct cccagaccca     780
gggcagtgtg gtgggagggg tgttccaaag agaaggcctg gtcagcagag ccgcccgtg     840 tccccccagg tgctggaggc agactcgagg gccgaattgt ttctagttag gccacgctcc     900
```

| | |
|---|---|
| tctgttcagt cgcaaaggtg aacactcatg cggcagccat gggccctctg agcaactgtg | 960 |
| cagacccttt caccccaat taaacccaga acca | 994 |

<210> SEQ ID NO 339
<211> LENGTH: 772
<212> TYPE: DNA
<213> ORGANISM: Homo sapiens

<400> SEQUENCE: 339

| | |
|---|---|
| agctcgtgcc gaattcggca cgagccgggt cggagccatg gcggtggcaa attcaagtcc | 60 |
| tgttaacccc gtggtgttct ttgatgtcag tattggcggt caggaagttg gccgcatgaa | 120 |
| gatcgagctc tttgcagacg ttgtgcctaa gacggccgag aactttaggc agttctgcac | 180 |
| cggagaattc aggaaagatg gggttccaat aggatacaaa ggaagcacct tccacagggt | 240 |
| cataaaggat ttcatgattc agggtggaga ttttgttaat ggagatggta ctggagtcgc | 300 |
| cagtatttac cgggggccat tgcagatga aaattttaaa cttagacact cagctccagg | 360 |
| cctgctttcc atggcgaaca gtggtccaag tacaaatggc tgtcagttct ttatcacctg | 420 |
| ctctaagtgc gattggctgg atgggaagca tgtggtgttt ggaaaaatca tcgatggact | 480 |
| tctagtgatg agaaagattg agaatgttcc cacaggcccc aacaataagc ccaagctacc | 540 |
| tgtggtgatc tcgcagtgtg gggagatgta gtccagacaa agactgaatc aggccttccc | 600 |
| ttcttcttgg tggtgttctt gagtaagata atctggactg ccccgtct ttgcttccct | 660 |
| gcctgctgct gccccatttg atcaagagac catggaagtg tcagagattc agaatccaag | 720 |
| attgtctta gttttcaac tgtaaataaa gttttttgt atgcgtaaaa aa | 772 |

<210> SEQ ID NO 340
<211> LENGTH: 919
<212> TYPE: DNA
<213> ORGANISM: Homo sapiens

<400> SEQUENCE: 340

| | |
|---|---|
| cgctcgcctc cctcgctcca cgcgcgcccg gacgcggcgg ccaggcttgc gcgtggttcc | 60 |
| cctcccggtg ggcggattcc tgggcaagat gaagtgggtg tgggcgctct tgctgttggc | 120 |
| ggcgtgggca gcgccgagc gcgactgccg agtgagcagc ttccgagtca aggagaactt | 180 |
| cgacaaggct cgcttctctg ggacctggta cgccatggcc aagaaggacc ccgagggcct | 240 |
| ctttctgcag gacaacatcg tcgcggagtt ctcggtggac gagaccggcc agatgagcgc | 300 |
| cacagccaag ggccgagtcc gtcttttgaa taactgggac gtgtgcgcag acatggtggg | 360 |
| caccttcaca gacaccgagg accctgccaa gttcaagatg aagtactggg gcgtagcctc | 420 |
| ctttctgcag aaaggaaatg atgaccactg gatcgtcgac acagactacg acacgtatgc | 480 |
| cgtacagtac tcctgccgcc tcctgaacct cgatggcacc tgtgctgaca gctactcctt | 540 |
| cgtgttttcc cggaccccca acggcctgcc cccagaagcg cagaagattg taaggcagcg | 600 |
| gcaggaggag ctgtgcctgg ccaggcagta caggctgatc gtccacaacg gttactgcga | 660 |
| tggcagatca gaaagaaacc ttttgtagca atatcaagaa tctagtttca tctgagaact | 720 |
| tctgattagc tctcagtctt cagctctatt tatcttagga gtttaatttg cccttctctc | 780 |
| cccatcttcc ctcagttccc ataaaacctt cattacacat aaagatacac gtggggtca | 840 |
| gtgaatctgc ttgcctttcc tgaaagtttc tggggcttaa gattccagac tctgattcat | 900 |
| taaactatag tcacccgtg | 919 |

<210> SEQ ID NO 341
<211> LENGTH: 7365
<212> TYPE: DNA
<213> ORGANISM: Homo sapiens

<400> SEQUENCE: 341

| | | | | | |
|---|---|---|---|---|---|
| ggcagtttgt | aggtcgcgag | ggaagcgctg | aggatcagga | aggggcact | gagtgtccgt | 60 |
| gggggaatcc | tcgtgatagg | aactggaata | tgccttgagg | gggacactat | gtctttaaaa | 120 |
| acgtcggctg | gtcatgaggt | caggagttcc | agaccagcct | gaccaacgtg | gtgaaactcc | 180 |
| gtctctacta | aaaatacaaa | aattagccgg | gcgtggtgcc | gctccagcta | ctcaggaggc | 240 |
| tgaggcagga | gaatcgctag | aacccgggag | gcggaggttg | cagtgagccg | agatcgcgcc | 300 |
| attgcactcc | agcctgggcg | acagagcgag | actgtctcaa | aacaaaacaa | aacaaaacaa | 360 |
| aacaaaaaac | accggctgtt | cattggaaca | gaaagaaatg | gatttatctg | ctcttcgcgt | 420 |
| tgaagaagta | caaaatgtca | ttaatgctat | gcagaaaatc | ttagagtgtc | ccatctgtct | 480 |
| ggagttgatc | aaggaacctg | tctccacaaa | gtgtgaccac | atattttgca | aattttgcat | 540 |
| gctgaaactt | ctcaaccaga | gaaagggcc | ttcacagtgt | cctttatgta | agaatgatat | 600 |
| aaccaaaagg | agcctacaag | aaagtacgag | atttagtcaa | cttgttgaag | agctattgaa | 660 |
| aatcatttgt | gcttttcagc | ttgacacagg | tttggagtat | gcaaacagct | ataattttgc | 720 |
| aaaaaaggaa | ataactctc | ctgaacatct | aaaagatgaa | gtttctatca | tccaaagtat | 780 |
| gggctacaga | aaccgtgcca | aaagacttct | acagagtgaa | cccgaaaatc | cttccttgca | 840 |
| ggaaaccagt | ctcagtgtcc | aactctctaa | ccttggaact | gtgagaactc | tgaggacaaa | 900 |
| gcagcggata | caacctcaaa | agacgtctgt | ctacattgaa | ttgggatctg | attcttctga | 960 |
| agataccgtt | aataaggcaa | cttattgcag | tgtgggagat | caagaattgt | tacaaatcac | 1020 |
| ccctcaagga | accagggatg | aaatcagttt | ggattctgca | aaaaaggctg | cttgtgaatt | 1080 |
| ttctgagacg | gatgtaacaa | atactgaaca | tcatcaaccc | agtaataatg | atttgaacac | 1140 |
| cactgagaag | cgtgcagctg | agaggcatcc | agaaaagtat | cagggtagtt | ctgtttcaaa | 1200 |
| cttgcatgtg | gagccatgtg | gcacaaatac | tcatgccagc | tcattacagc | atgagaacag | 1260 |
| cagtttatta | ctcactaaag | acagaatgaa | tgtagaaaag | gctgaattct | gtaataaaag | 1320 |
| caaacagcct | ggcttagcaa | ggagccaaca | taacagatgg | gctggaagta | aggaaacatg | 1380 |
| taatgatagg | cggactccca | gcacagaaaa | aaaggtagat | ctgaatgctg | atccctgtgt | 1440 |
| tgagagaaaa | gaatggaata | agcagaaact | gccatgctca | gagaatccta | gagatactga | 1500 |
| agatgttcct | tggataacac | taaatagcag | cattcagaaa | gttaatgagt | ggttttccag | 1560 |
| aagtgatgaa | ctgttaggtt | ctgatgactc | acatgatggg | gagtctgaat | caaatgccaa | 1620 |
| agtagctgat | gtattggacg | ttctaaatga | ggtagatgaa | tattctggtt | cttcagagaa | 1680 |
| aatagactta | ctggccagtg | atcctcatga | ggctttaata | tgtaaaagtg | aaagagttca | 1740 |
| ctccaaatca | gtagagagta | atattgaaga | caaatatttt | gggaaaacct | atcggaagaa | 1800 |
| ggcaagcctc | cccaacttaa | gccatgtaac | tgaaaatcta | attataggag | catttgttac | 1860 |
| tgagccacag | ataatacaag | agcgtcccct | cacaaataaa | ttaaagcgta | aaaggagacc | 1920 |
| tacatcaggc | cttcatcctg | aggatttat | caagaaagca | gatttggcag | ttcaaaagac | 1980 |
| tcctgaaatg | ataaatcagg | gaactaacca | aacggagcag | aatggtcaag | tgatgaatat | 2040 |
| tactaatagt | ggtcatgaga | ataaaacaaa | aggtgattct | attcagaatg | agaaaaatcc | 2100 |
| taacccaata | gaatcactcg | aaaaagaatc | tgctttcaaa | acgaaagctg | aacctataag | 2160 |

```
cagcagtata agcaatatgg aactcgaatt aaatatccac aattcaaaag cacctaaaaa    2220
gaataggctg aggaggaagt cttctaccag gcatattcat gcgcttgaac tagtagtcag    2280
tagaaatcta agcccaccta attgtactga attgcaaatt gatagttgtt ctagcagtga    2340
agagataaag aaaaaaaagt acaaccaaat gccagtcagg cacagcagaa acctacaact    2400
catggaaggt aaagaacctg caactggagc caagaagagt aacaagccaa atgaacagac    2460
aagtaaaaga catgacagcg atactttccc agagctgaag ttaacaaatg cacctggttc    2520
ttttactaag tgttcaaata ccagtgaact aaagaatttt gtcaatccta gccttccaag    2580
agaagaaaaa gaagagaaac tagaaacagt taaagtgtct aataatgctg aagaccccaa    2640
agatctcatg ttaagtggag aaagggtttt gcaaactgaa agatctgtag agagtagcag    2700
tatttcattg gtacctggta ctgattatgg cactcaggaa agtatctcgt tactggaagt    2760
tagcactcta gggaaggcaa aaacagaacc aaataaatgt gtgagtcagt gtgcagcatt    2820
tgaaaacccc aagggactaa ttcatggttg ttccaaagat aatagaaatg cacagaaggg    2880
ctttaagtat ccattgggac atgaagttaa ccacagtcgg gaaacaagca tagaaatgga    2940
agaaagtgaa cttgatgctc agtatttgca gaatacattc aaggtttcaa agcgccagtc    3000
atttgctccg ttttcaaatc caggaaatgc agaagaggaa tgtgcaacat tctctgccca    3060
ctctgggtcc ttaaagaaac aaagtccaaa agtcactttt gaatgtgaac aaaaggaaga    3120
aaatcaagga aagaatgagt ctaatatcaa gcctgtacag acagttaata tcactgcagg    3180 cttttcctgtg gttggtcaga agataagcc agttgataat gccaaatgta gtatcaaagg    3240
aggctctagg ttttgtctat catctcagtt cagaggcaac gaaactggac tcattactcc    3300
aaataaacat ggactttac aaaacccata tcgtatacca ccactttttc ccatcaagtc    3360
atttgttaaa actaaatgta agaaaaatct gctagaggaa actttgagg aacattcaat    3420 gtcacctgaa agagaaatgg gaaatgagaa cattccaagt acagtgagca caattagccg    3480
taataacatt agagaaaatg ttttttaaga gccagctca agcaatatta atgaagtagg    3540
ttccagtact aatgaagtgg gctccagtat taatgaaata ggttccagtg atgaaaacat    3600
tcaagcagaa ctaggtagaa acagagggcc aaaattgaat gctatgctta gattaggggt    3660
tttgcaacct gaggtctata acaaagtct tcctggaagt aattgtaagc atcctgaaat    3720
aaaaaagcaa gaatatgaag aagtagttca gactgttaat acagatttct ctccatatct    3780
gatttcagat aacttagaac agccatgggg aagtagtcat gcatctcagg tttgttctga    3840
gacacctgat gacctgttag atgatggtga aataaaggaa gatactagtt ttgctgaaaa    3900
tgacattaag gaaagttctg ctgtttttag caaaagcgtc cagaaaggag agcttagcag    3960
gagtcctagc ccttttcaccc atacacattt ggctcagggt taccgaagag gggccaagaa    4020
attagagtcc tcagaagaga acttatctag tgaggatgaa gagcttccct gcttccaaca    4080 cttgttatt ggtaaagtaa acaatatacc ttctcagtct actaggcata gcaccgttgc    4140
taccgagtgt ctgtctaaga acacagagga gaatttatta tcattgaaga atagcttaaa    4200
tgactgcagt aaccaggtaa tattggcaaa ggcatctcag gaacatcacc ttagtgagga    4260
aacaaaatgt tctgctagct tgttttcttc acagtgcagt gaattggaag acttgactgc    4320
aaatacaaac acccaggatc ctttcttgat tggttcttcc aaacaaatga ggcatcagtc    4380
tgaaagccag ggagttggtc tgagtgacaa ggaattggtt tcagatgatg aagaaagagg    4440
aacgggcttg gaagaaaata atcaagaaga gcaaagcatg gattcaaact aggtgaagc    4500
```

```
agcatctggg tgtgagagtg aaacaagcgt ctctgaagac tgctcagggc tatcctctca    4560
gagtgacatt ttaaccactc agcagaggga taccatgcaa cataacctga taaagctcca    4620
gcaggaaatg gctgaactag aagctgtgtt agaacagcat gggagccagc cttctaacag    4680
ctacccttcc atcataagtg actcttctgc ccttgaggac ctgcgaaatc cagaacaaag    4740
cacatcagaa aaagcagtat taacttcaca gaaaagtagt gaatacccta taagccagaa    4800
tccagaaggc ctttctgctg acaagtttga ggtgtctgca gatagttcta ccagtaaaaa    4860
taaagaacca ggagtggaaa ggtcatcccc ttctaaatgc ccatcattag atgataggtg    4920
gtacatgcac agttgctctg ggagtcttca aatagaaac tacccatctc aagaggagct    4980
cattaaggtt gttgatgtgg aggagcaaca gctggaagag tctgggccac acgatttgac    5040
ggaaacatct tacttgccaa ggcaagatct agagggaacc ccttacctgg aatctggaat    5100
cagcctcttc tctgatgacc ctgaatctga tccttctgaa gacagagccc cagagtcagc    5160
tcgtgttggc aacataccat cttcaacctc tgcattgaaa gttccccaat tgaaagttgc    5220
agaatctgcc cagagtccag ctgctgctca tactactgat actgctgggt ataatgcaat    5280
ggaagaaagt gtgagcaggg agaagccaga attgacagct caacagaaa gggtcaacaa    5340 aagaatgtcc atggtggtgt ctggcctgac cccagaagaa tttatgctcg tgtacaagtt    5400
tgccagaaaa caccacatca ctttaactaa tctaattact gaagagacta ctcatgttgt    5460
tatgaaaaca gatgctgagt tgtgtgtga acggacactg aaatattttc taggaattgc    5520
gggaggaaaa tgggtagtta gctatttctg ggtgacccag tctattaaag aaagaaaaat    5580
gctgaatgag catgattttg aagtcagagg agatgtggtc aatggaagaa accaccaagg    5640
tccaaagcga gcaagagaat cccaggacag aaagatcttc aggggctag aaatctgttg    5700 ctatgggccc ttcaccaaca tgcccacaga tcaactggaa tggatggtac agctgtgtgg    5760
tgcttctgtg gtgaaggagc tttcatcatt caccttggc acaggtgtcc acccaattgt    5820
ggttgtgcag ccagatgcct ggacagagga caatggcttc catgcaattg gcagatgtg    5880 tgaggcacct gtggtgaccc gagtgggt gttggacagt gtagcactct accagtgcca    5940
ggagctggac acctacctga taccccagat cccccacagc cactactgac tgcagccagc    6000
cacaggtaca gagccacagg accccaagaa tgagcttaca aagtggcctt tccaggccct    6060
gggagctcct ctcactcttc agtccttcta ctgtcctggc tactaaatat tttatgtaca    6120
tcagcctgaa aaggacttct ggctatgcaa gggtccctta aagatttct gcttgaagtc    6180 tcccttggaa atctgccatg agcacaaaat tatggtaatt tttcacctga aagatttta    6240 aaaccattta aacgccacca attgagcaag atgctgattc attatttatc agccctattc    6300
tttctattca ggctgttgtt ggcttaggc tggaagcaca gagtggcttg gcctcaagag    6360
aatagctggt ttccctaagt ttacttctct aaaaccctgt gttcacaaag gcagagagtc    6420
agaccctcca atgaaggag agtgcttggg atcgattatg tgacttaaag tcagaatagt    6480
ccttgggcag ttctcaaatg ttggagtgga acattgggga ggaaattctg aggcaggtat    6540
tagaaatgaa aaggaaactt gaaacctggg catggtggct cacgcctgta atcccagcac    6600
tttgggaggc caaggtgggc agatcactgg aggtcaggag ttcgaaacca gcctggccaa    6660
catggtgaaa ccccatctct actaaaaata cagaaattag ccggtcatgg tggtggacac    6720
ctgtaatccc agctactcag gtggctaagg caggagaatc acttcagccc gggaggtgga    6780
ggttgcagtg agccaagatc ataccacggc actccagcct gggtgacagt gagactgtgg    6840
ctcaaaaaaa aaaaaaaaaa aggaaaatga aactaggaaa ggtttcttaa agtctgagat    6900
```

| | |
|---|---|
| atatttgcta gatttctaaa gaatgtgttc taaaacagca gaagattttc aagaaccggt | 6960 |
| ttccaaagac agtcttctaa ttcctcatta gtaataagta aaatgtttat tgttgtagct | 7020 |
| ctggtatata atccattcct cttaaaatat aagacctctg gcatgaatat tcatatctca | 7080 |
| taaaatgaca gatcccacca ggaaggaagc tgttgctttc tttgaggtga tttttttcct | 7140 |
| ttgctccctg ttgctgaaac catacagctt cataaataat tttgcttgct gaaggaagaa | 7200 |
| aaagtgtttt tcataaaccc attatccagg actgtttata gctgttggaa ggactaggtc | 7260 |
| ttccctagcc cccccagtgt gcaagggcag tgaagacttg attgtacaaa atacgttttg | 7320 |
| taaatgttgt gctgttaaca ctgcaaataa acttggtagc aaaca | 7365 |

<210> SEQ ID NO 342
<211> LENGTH: 10386
<212> TYPE: DNA
<213> ORGANISM: Homo sapiens
<220> FEATURE:
<221> NAME/KEY: unsure
<222> LOCATION: (0)...(0)
<223> OTHER INFORMATION: n = a, t, c or g

<400> SEQUENCE: 342

| | |
|---|---|
| attgaggact cggaaatgag gtccaagggt agccaaggat ggctgcagct tcatatgatc | 60 |
| agttgttaaa gcaagttgag gcactgaaga tggagaactc aaatcttcga caagagctag | 120 |
| aagataattc caatcatctt acaaaactgg aaactgaggc atctaatatg aaggaagtac | 180 |
| ttaaacaact acaaggaagt attgaagatg aagctatggc ttcttctgga cagattgatt | 240 |
| tattagagcg tcttaaagag cttaacttag atagcagtaa tttccctgga gtaaaactgc | 300 |
| ggtcaaaaat gtccctccgt tcttatggaa gccgggaagg atctgtatca agccgttctg | 360 |
| gagagtgcag tcctgttcct atgggttcat ttccaagaag agggtttgta aatggaagca | 420 |
| gagaaagtac tggatattta gaagaacttg agaaagagag gtcattgctt cttgctgatc | 480 |
| ttgacaaaga agaaaaggaa aaagactggt attacgctca acttcagaat ctcactaaaa | 540 |
| gaatagatag tcttccttta actgaaaatt tttccttaca aacagatatg accagaaggc | 600 |
| aattggaata tgaagcaagg caaatcagag ttgcgatgga agaacaacta ggtacctgcc | 660 |
| aggatatgga aaaacgagca cagcgaagaa tagccagaat tcagcaaatc gaaaaggaca | 720 |
| tacttcgtat acgacagctt ttacagtccc aagcaacaga agcagagagg tcatctcaga | 780 |
| acaagcatga aaccggctca catgatgctg agcggcagaa tgaaggtcaa ggagtgggag | 840 |
| aaatcaacat ggcaacttct ggtaatggtc agggttcaac tacacgaatg gaccatgaaa | 900 |
| cagccagtgt tttgagttct agtagcacac actctgcacc tcgaaggctg acaagtcatc | 960 |
| tgggaaccaa ggtggaaatg gtgtattcat tgttgtcaat gcttggtact catgataagg | 1020 |
| atgatatgtc gcgaactttg ctagctatgt ctagctccca agacagctgt atatccatgc | 1080 |
| gacagtctgg atgtcttcct ctcctcatcc agcttttaca tggcaatgac aaagactctg | 1140 |
| tattgttggg aaattcccgg ggcagtaaag aggctcgggc cagggccagt gcagcactcc | 1200 |
| acaacatcat tcactcacag cctgatgaca agagaggcag gcgtgaaatc cgagtccttc | 1260 |
| atcttttgga acagatacgc gcttactgtg aaacctgttg ggagtggcag gaagctcatg | 1320 |
| aaccaggcat ggaccaggac aaaaatccaa tgccagctcc tgttgaacat cagatctgtc | 1380 |
| ctgctgtgtg tgttctaatg aaactttcat ttgatgaaga gcatagacat gcaatgaatg | 1440 |
| aactaggggg actacaggcc attgcagaat tattgcaagt ggactgtgaa atgtacgggc | 1500 |

```
ttactaatga ccactacagt attacactaa gacgatatgc tggaatggct ttgacaaact    1560
tgacttttgg agatgtagcc aacaaggcta cgctatgctc tatgaaaggc tgcatgagag    1620
cacttgtggc ccaactaaaa tctgaaagtg aagacttaca gcaggttatt gcaagtgttt    1680
tgaggaattt gtcttggcga gcagatgtaa atagtaaaaa gacgttgcga gaagttggaa    1740
gtgtgaaagc attgatggaa tgtgctttag aagttaaaaa ggaatcaacc ctcaaaagcg    1800
tattgagtgc cttatggaat ttgtcagcac attgcactga gaataaagct gatatatgtg    1860
ctgtagatgg tgcacttgca ttttggttg gcactcttac ttaccggagc cagacaaaca    1920 cttagccat tattgaaagt ggaggtggga tattacggaa tgtgtccagc ttgatagcta    1980
caaatgagga ccacaggcaa atcctaagag agaacaactg tctacaaact ttattacaac    2040
acttaaaatc tcatagtttg acaatagtca gtaatgcatg tggaactttg tggaatctct    2100
cagcaagaaa tcctaaagac caggaagcat tatgggacat gggggcagtt agcatgctca    2160
agaacctcat tcattcaaag cacaaaatga ttgctatggg aagtgctgca gctttaagga    2220
atctcatggc aaataggcct gcgaagtaca aggatgccaa tattatgtct cctggctcaa    2280
gcttgccatc tcttcatgtt aggaaacaaa aagccctaga agcagaatta gatgctcagc    2340
acttatcaga aacttttgac aatatagaca atttaagtcc caaggcatct catcgtagta    2400
agcagagaca caagcaaagt ctctatggtg attatgtttt tgacaccaat cgacatgatg    2460
ataataggtc agacaatttt aatactggca acatgactgt cctttcacca tatttgaata    2520
ctacagtgtt acccagctcc tcttcatcaa gaggaagctt agatagttct cgttctgaaa    2580
aagatagaag tttggagaga gaacgcggaa ttggtctagg caactaccat ccagcaacag    2640
aaaatccagg aacttcttca aagcgaggtt gcagatctc caccactgca gcccagattg    2700
ccaaagtcat ggaagaagtg tcagccattc atacctctca ggaagacaga agttctgggt    2760
ctaccactga attacattgt gtgacagatg agagaaatgc acttagaaga agctctgctg    2820
cccatacaca ttcaaacact tacaatttca ctaagtcgga aaattcaaat aggacatgtt    2880
ctatgcctta tgccaaatta gaatacaaga gatcttcaaa tgatagttta aatagtgtca    2940
gtagtagtga tggttatggt aaaagaggtc aaatgaaacc ctcgattgaa tcctattctg    3000
aagatgatga agtaagtttt tgcagttatg gtcaataccc agccgaccta gcccataaaa    3060
tacatagtgc aaatcatatg gatgataatg atggagaact agatacacca ataaattata    3120
gtcttaaata ttcagatgag cagttgaact ctggaaggca aagtccttca cagaatgaaa    3180
gatgggcaag acccaaacac ataatagaag atgaaataaa acaaagtgag caaagacaat    3240
caaggaatca agtacaact tatcctgttt tatactgagag cactgatgat aaacacctca    3300
agttccaacc acattttgga cagcaggaat gtgtttctcc atacaggtca cggggagcca    3360
atggttcaga acaaatcga gtgggttcta atcatggaat taatcaaaat gtaagccagt    3420
ctttgtgtca agaagatgac tatgaagatg ataagcctac caattatagt gaacgttact    3480
ctgaagaaga acagcatgaa gaagaagaga gaccaacaaa ttatagcata aaatataatg    3540
aagagaaacg tcatgtggat cagcctattg attatagttt aaaatatgcc acagatattc    3600
cttcatcaca gaaacagtca ttttcattct caaagagttc atctggacaa gcagtaaaa    3660 ccgaacatat gtcttcaagc agtgagaata cgtccacacc ttcatctaat gccaagaggc    3720
agaatcagct ccatccaagt tctgcacaga gtagaagtgg tcagcctcaa aaggctgcca    3780
cttgcaaagt ttcttctatt aaccaagaaa caatacagac ttattgtgta gaagatactc    3840
caatatgttt ttcaagatgt agttcattat catctttgtc atcagctgaa gatgaaatag    3900
```

-continued

```
gatgtaatca gacgacacag gaagcagatt ctgctaatac cctgcaaata gcagaaataa      3960
aagaaaagat tggaactagg tcagctgaag atcctgtgag cgaagttcca gcagtgtcac      4020
agcaccctag aaccaaatcc agcagactgc agggttctag tttatcttca gaatcagcca      4080
ggcacaaagc tgttgaattt tcttcaggag cgaaatctcc ctccaaaagt ggtgctcaga      4140
cacccaaaag tccacctgaa cactatgttc aggagacccc actcatgttt agcagatgta      4200
cttctgtcag ttcacttgat agttttgaga gtcgttcgat tgccagctcc gttcagagtg      4260
aaccatgcag tggaatggta agtggcatta aagccccag tgatcttcca gatagccctg       4320
gacaaaccat gccaccaagc agaagtaaaa cacctccacc acctcctcaa acagctcaaa      4380
ccaagcgaga agtacctaaa aataaagcac ctactgctga aaagagagag agtggaccta      4440
agcaagctgc agtaaatgct gcagttcaga gggtccaggt tcttccagat gctgatactt      4500 tattcattt tgccacggaa agtactccag atggattttc ttgttcatcc agcctgagtg       4560
ctctgagcct cgatgagcca tttatacaga aagatgtgga attaagaata atgcctccag      4620
ttcaggaaaa tgacaatggg aatgaaacag aatcagagca gcctaaagaa tcaaatgaaa      4680
accaagagaa agaggcagaa aaaactattg attctgaaaa ggacctatta gatgattcag      4740
atgatgatga tattgaaata ctagaagaat gtattatttc tgccatgcca acaaagtcat      4800
cacgtaaagc aaaaaagcca gcccagactg cttcaaaatt acctccacct gtggcaagga      4860
aaccaagtca gctgcctgtg tacaaacttc taccatcaca aaacaggttg caaccccaaa      4920
agcatgttag ttttacaccg ggggatgata tgccacgggt gtattgtgtt gaagggacac      4980
ctataaactt ttccacagct acatctctaa gtgatctaac aatcgaatcc cctccaaatg      5040
agttagctgc tggagaagga gttagaggag agcacagtc aggtgaattt gaaaaacgag       5100
ataccattcc tacagaaggc agaagtacag atgaggctca aggaggaaaa acctcatctg      5160
taaccatacc tgaattggat gacaataaag cagaggaagg tgatattctt gcagaatgca      5220
ttaattctgc tatgcccaaa gggaaaagtc acaagccttt ccgtgtgaaa aagataatgg      5280
accaggtcca gcaagcatct gcgtcgtctt ctgcacccaa caaaaatcag ttagatggta      5340
agaaaaagaa accaacttca ccagtaaaac ctataccaca aaatactgaa tataggacac      5400
gtgtaagaaa aaatgcagac tcaaaaaata atttaaatgc tgagagagtt ttctcagaca      5460
acaaagattc aaagaaacag aatttgaaaa ataattccaa ggacttcaat gataagctcc      5520
caaataatga agatagagtc agaggaagtt ttgcttttga ttcacctcat cattacacgc      5580
ctattgaagg aactccttac tgttttttcac gaaatgattc tttgagttct ctagattttg      5640
atgatgatga tgttgacctt tccagggaaa aggctgaatt aagaaaggca aaagaaaata      5700
aggaatcaga ggctaaagtt accagccaca cagaactaac ctccaaccaa caatcagcta      5760
ataagacaca agctattgca aagcagccaa taaatcgagg tcagcctaaa cccatacttc      5820
agaaacaatc cacttttccc cagtcatcca agacatacc agacagaggg gcagcaactg       5880
atgaaaagtt acagaatttt gctattgaaa atactccagt ttgctttttct cataattcct      5940 ctctgagttc tctcagtgac attgaccaag aaaacaacaa taaagaaaat gaacctatca      6000
aagagactga gcccctgac tcacagggag aaccaagtaa acctcaagca tcaggctatg       6060
ctcctaaatc atttcatgtt gaagatacc cagtttgttt ctcaagaaac agttctctca       6120
gttctcttag tattgactct gaagatgacc tgttgcagga atgtataagc tccgcaatgc      6180
caaaaaagaa aaagccttca agactcaagg gtgataatga aaaacatagt cccagaaata      6240
```

```
tgggtggcat attaggtgaa gatctgacac ttgatttgaa agatatacag agaccagatt    6300
cagaacatgg tctatcccct gattcagaaa attttgattg gaaagctatt caggaaggtg    6360
caaattccat agtaagtagt ttacatcaag ctgctgctgc tgcatgttta tctagacaag    6420
cttcgtctga ttcagattcc atcctttccc tgaaatcagg aatctctctg ggatcaccat    6480
ttcatcttac acctgatcaa gaagaaaaac cctttacaag taataaaggc ccacgaattc    6540
taaaaccagg ggagaaaagt acattggaaa ctaaaaagat agaatctgaa agtaaaggaa    6600
tcaaaggagg aaaaaaagtt tataaaagtt tgattactgg aaaagttcga tctaattcag    6660
aaatttcagg ccaaatgaaa cagccccttc aagcaaacat gccttcaatc tctcgaggca    6720
ggacaatgat tcatattcca ggagttcgaa atagctcctc aagtacaagt cctgtttcta    6780
aaaaaggccc acccccttaag actccagcct ccaaaagccc tagtgaaggt caaacagcca    6840
ccacttctcc tagaggagcc aagccatctg tgaaatcaga attaagccct gttgccaggc    6900
agacatccca aataggtggg tcaagtaaag caccttctag atcaggatct agagattcga    6960
ccccttcaag acctgcccag caaccattaa gtagacctat acagtctcct ggccgaaact    7020
caatttcccc tggtagaaat ggaataagtc ctcctaacaa attatctcaa cttccaagga    7080
catcatcccc tagtactgct tcaactaagt cctcaggttc tggaaaaatg tcatatacat    7140
ctccaggtag acagatgagc caacagaacc ttaccaaaca aacaggttta tccaagaatg    7200
ccagtagtat tccaagaagt gagtctgcct ccaaaggact aaatcagatg aataatggta    7260
atggagccaa taaaaaggta gaactttcta gaatgtcttc aactaaatca agtggaagtg    7320
aatctgatag atcagaaaga cctgtattag tacgccagtc aactttcatc aaagaagctc    7380
caagcccaac cttaagaaga aaattggagg aatctgcttc atttgaatct ctttctccat    7440
catctagacc agcttctccc actaggtccc aggcacaaac tccagtttta agtccttccc    7500
ttcctgatat gtctctatcc acacattcgt ctgttcaggc tggtggatgg cgaaaactcc    7560
cacctaatct cagtcccact atagagtata atgatggaag accagcaaag cgccatgata    7620
ttgcacggtc tcattctgaa agtccttcta gacttccaat caataggtca ggaacctgga    7680
aacgtgagca cagcaaacat tcatcatccc ttcctcgagt aagcacttgg agaagaactg    7740
gaagttcatc ttcaattctt tctgcttcat cagaatccag tgaaaaagca aaagtgagg    7800 atgaaaaaca tgtgaactct atttcaggaa ccaaacaaag taaagaaaac caagtatccg    7860
caaaaggaac atggagaaaa ataaagaaa atgaattttc tcccacaaat agtacttctc    7920
agaccgtttc ctcaggtgct acaaatggtg ctgaatcaaa gactctaatt tatcaaatgg    7980
cacctgctgt ttctaaaaca gaggatgttt gggtgagaat tgaggactgt cccattaaca    8040
atcctagatc tggaagatct cccacaggta atactccccc ggtgattgac agtgtttcag    8100
aaaaggcaaa tccaaacatt aaagattcaa aagataatca ggcaaaacaa aatgtgggta    8160
atggcagtgt tcccatgcgt accgtgggtt tggaaaatcg cctgaactcc tttattcagg    8220
tggatgcccc tgaccaaaaa ggaactgaga taaaaccagg acaaaataat cctgtccctg    8280
tatcagagac taatgaaagt tctatagtgg aacgtacccc attcagttct agcagctcaa    8340
gcaaacacag ttcacctagt gggactgttg ctgccagagt gactccttt aattacaacc    8400 caagccctag gaaaagcagc gcagatagca cttcagctcg gccatctcag atcccaactc    8460
cagtgaataa caacacaaag aagcgagatt ccaaaactga cagcacagaa tccagtggaa    8520
cccaaagtcc taagcgccat tctgggtctt accttgtgac atctgtttaa aagagaggaa    8580
gaatgaaact aagaaaattc tatgttaatt acaactgcta tatagacatt ttgtttcaaa    8640
```

```
tgaaacttta aaagactgaa aaattttgta aataggtttg attcttgtta gagggttttt      8700
gttctggaag ccatatttga tagtatactt tgtcttcact ggtcttattt tgggaggcac      8760
tcttgatggt taggaaaaaa atagtaaagc caagtatgtt tgtacagtat gttttacatg      8820
tatttaaagt agcatcccat cccaacttcc tttaattatt gcttgtctta aaataatgaa      8880
cactacagat agaaaatatg atatattgct gttatcaatc atttctagat tataaactga      8940
ctaaacttac atcagggaaa aattggtatt tatgcaaaaa aaatgtttt tgtccttgtg       9000 agtccatcta acatcataat taatcatgtg gctgtgaaat tcacagtaat atggttcccg      9060
atgaacaagc tttacccagc ctgtttgctt tactgcatga atgaaactga tggttcaatt      9120
tcagaagtaa tgattaacag ttatgtggtc acatgatgtg catagagata gctacagtgt      9180
aataatttac actattttgt gctccaaaca aaacaaaaat ctgtgtaact gtaaaacatt      9240
gaatgaaact attttacctg aactagattt tatctgaaag taggtagaat ttttgctatg      9300
ctgtaatttg ttgtatattc tggtatttga ggtgagatgg ctgctctttt attaatgaga      9360
catgaattgt gtctcaacag aaactaaatg aacatttcag aataaattat tgctgtatgt      9420
aaactgttac tgaaattggt atttgtttga agggtcttgt ttcacatttg tattaataat      9480
tgtttaaaat gcctctttta aaagcttata taaattttt ncttcagctt ctatgcatta      9540
agagtaaaat tcctcttact gtaataaaaa caattgaaga agactgttgc cacttaacca      9600
ttccatgcgt tggcacttat ctattcctga aattcttta tgtgattagc tcatcttgat       9660
ttttaacatt tttccactta aacttttttt tcttactcca ctggagctca gtaaaagtaa      9720
attcatgtaa tagcaatgca agcagcctag cacagactaa gcattgagca taataggccc      9780
acataatttc ctctttctta atattataga aattctgtac ttgaaattga ttcttagaca      9840
ttgcagtctc ttcgaggctt tacagtgtaa actgtcttgc cccttcatct tcttgttgca      9900
actgggtctg acatgaacac tttttatcac cctgtatgtt agggcaagat ctcagcagtg      9960
aagtataatc agcactttgc catgctcaga aaattcaaat cacatggaac tttagaggta     10020
gatttaatac gattaagata ttcagaagta tattttagaa tccctgcctg ttaaggaaac     10080
tttatttgtg gtaggtacag ttctggggta catgttaagt gtccccttat acagtggagg     10140
gaagtcttcc ttcctgaagg aaaataaact gacacttatt aactaagata atttacttaa     10200
tatatcttcc ctgatttgtt ttaaaagatc agagggtgac tgatgataca tgcatacata     10260
tttgttgaat aaatgaaaat ttattttag tgataagatt catacactct gtatttgggg      10320
agagaaaacc tttttaagca tggtgggggca ctcagatagg agtgaataca cctacctggt    10380
ggtcat                                                                10386
```

<210> SEQ ID NO 343
<211> LENGTH: 2191
<212> TYPE: DNA
<213> ORGANISM: Homo sapiens

<400> SEQUENCE: 343

```
ggtggccgag cggggaccg ggaagcatgg cccggggtc ggcggttgcc tgggcggcgc          60
tcgggccgtt gttgtgggc tgcgcgctgg ggctgcaggg cggatgctg taccccagg          120 agagcccgtc gcgggagtgc aaggagctgg acggcctctg gagcttccgc gccgacttct        180
ctgacaaccg acgccgggc ttcgaggagc agtggtaccg gcggccgctg tgggagtcag         240
gccccaccgt ggacatgcca gttccctcca gcttcaatga catcagccag gactggcgtc        300
```

| | |
|---|---|
| tgcggcattt tgtcggctgg gtgtggtacg aacgggaggt gatcctgccg gagcgatgga | 360 |
| cccaggacct gcgcacaaga gtggtgctga ggattggcag tgcccattcc tatgccatcg | 420 |
| tgtgggtgaa tggggtcgac acgctagagc atgagggggg ctacctcccc ttcgaggccg | 480 |
| acatcagcaa cctggtccag gtggggcccc tgccctcccg gctccgaatc actatcgcca | 540 |
| tcaacaacac actcaccccc accaccctgc caccagggac catccaatac ctgactgaca | 600 |
| cctccaagta tcccaagggt tactttgtcc agaacacata ttttgacttt ttcaactacg | 660 |
| ctggactgca gcggtctgta cttctgtaca cgacacccac cacctacatc gatgacatca | 720 |
| ccgtcaccac cagcgtggag caagacagtg ggctggtgaa ttaccagatc tctgtcaagg | 780 |
| gcagtaacct gttcaagttg gaagtgcgtc ttttggatgc agaaaacaaa gtcgtggcga | 840 |
| atgggactgg gacccagggc caacttaagg tgccaggtgt cagcctctgg tggccgtacc | 900 |
| tgatgcacga acgccctgcc tatctgtatt cattggaggt gcagctgact gcacagacgt | 960 |
| cactggggcc tgtgtctgac ttctacacac tccctgtggg gatccgcact gtggctgtca | 1020 |
| ccaagagcca gttcctcatc aatgggaaac ctttctattt ccacggtgtc aacaagcatg | 1080 |
| aggatgcgga catccgaggg aagggcttcg actggccgct gctggtgaag gacttcaacc | 1140 |
| tgcttcgctg gcttggtgcc aacgctttcc gtaccagcca ctaccctat gcagaggaag | 1200 |
| tgatgcagat gtgtgaccgc tatgggattg tggtcatcga tgagtgtccc ggcgtgggcc | 1260 |
| tggcgctgcc gcagttcttc aacaacgttt ctctgcatca ccacatgcag gtgatggaag | 1320 |
| aagtggtgcg tagggacaag aaccacccccg cggtcgtgat gtggtctgtg ccaacgagc | 1380 |
| ctgcgtccca cctagaatct gctggctact acttgaagat ggtgatcgct cacaccaaat | 1440 |
| ccttggaccc ctcccggcct gtgacctttg tgagcaactc taactatgca gcagacaagg | 1500 |
| gggctccgta tgtggatgtg atctgtttga acagctacta ctcttggtat cacgactacg | 1560 |
| ggcacctgga gttgattcag ctgcagctgg ccacccagtt tgagaactgg tataagaagt | 1620 |
| atcagaagcc cattattcag agcgagtatg agcagaaaac gattgcaggg tttcaccagg | 1680 |
| atccacctct gatgttcact gaagagtacc agaaaagtct gctagagcag taccatctgg | 1740 |
| gtctggatca aaaacgcaga aaatatgtgg ttggagagct catttggaat tttgccgatt | 1800 |
| tcatgactga acagtcaccg acgagagtgc tggggaataa aaaggggatc ttcactcggc | 1860 |
| agagacaacc aaaaagtgca gcgttccttt tgcgagagag atactggaag attgccaatg | 1920 |
| aaaccaggta tccccactca gtagccaagt cacaatgttt ggaaaacagc ccgtttactt | 1980 |
| gagcaagact gataccacct gcgtgtccct tcctccccga gtcagggcga cttccacagc | 2040 |
| agcagaacaa gtgcctcctg gactgttcac ggcagaccag aacgtttctg gcctgggttt | 2100 |
| tgtggtcatc tattctagca gggaacacta aggtgaaa taaagatttt tctattatgg | 2160 |
| aaataaagag ttggcatgaa agtcgctact g | 2191 |

<210> SEQ ID NO 344
<211> LENGTH: 2776
<212> TYPE: DNA
<213> ORGANISM: Homo sapiens

<400> SEQUENCE: 344

| | |
|---|---|
| cagggcagac tggtagcaaa gccccacgc ccagccagga gcaccgccgc ggactccagc | 60 |
| acaccgaggg acatgctggg cctgcgcccc ccactgctcg ccctggtggg gctgctctcc | 120 |
| ctcgggtgcg tcctctctca ggagtgcacg aagttcaagg tcagcagctg ccgggaatgc | 180 |
| atcgagtcgg ggcccggctg cacctggtgc cagaagctga acttcacagg gccgggggat | 240 |

-continued

```
cctgactcca ttcgctgcga cacccggcca cagctgctca tgaggggctg tgcggctgac    300
gacatcatgg accccacaag cctcgctgaa acccaggaag accacaatgg gggccagaag    360
cagctgtccc cacaaaaagt gacgctttac ctgcgaccag gccaggcagc agcgttcaac    420
gtgaccttcc ggcgggccaa gggctacccc atcgacctgt actatctgat ggacctctcc    480
tactccatgc ttgatgacct caggaatgtc aagaagctag gtggcgacct gctccgggcc    540
ctcaacgaga tcaccgagtc cggccgcatt ggcttcgggt ccttcgtgga caagaccgtg    600
ctgccgttcg tgaacacgca ccctgataag ctgcgaaacc catgccccaa caaggagaaa    660
gagtgccagc ccccgtttgc cttcaggcac gtgctgaagc tgaccaacaa ctccaaccag    720
tttcagaccg aggtcgggaa gcagctgatt tccggaaacc tggatgcacc cgagggtggg    780
ctggacgcca tgatgcaggt cgccgcctgc ccggaggaaa tcggctggcg caacgtcacg    840
cggctgctgg tgtttgccac tgatgacggc ttccatttcg cgggcgacgg aaagctgggc    900
gccatcctga cccccaacga cggccgctgt cacctggagg acaacttgta caagaggagc    960
aacgaattcg actacccatc ggtgggccag ctggcgcaca agctggctga aaacaacatc   1020
cagcccatct tcgcggtgac cagtaggatg gtgaagacct acgagaaact caccgagatc   1080
atccccaagt cagccgtggg ggagctgtct gaggactcca gcaatgtggt ccatctcatt   1140
aagaatgctt acaataaact ctcctccagg gtcttcctgg atcacaacgc cctccccgac   1200
accctgaaag tcacctacga ctccttctgc agcaatggag tgacgcacag gaaccagccc   1260
agaggtgact gtgatggcgt gcagatcaat gtcccgatca ccttccaggt gaaggtcacg   1320
gccacagagt gcatccagga gcagtcgttt gtcatccggg cgctgggctt cacggacata   1380
gtgaccgtgc aggttcttcc ccagtgtgag tgccggtgcc gggaccagag cagagaccgc   1440
agcctctgcc atggcaaggg cttcttggag tgcggcatct gcaggtgtga cactggctac   1500
attgggaaaa actgtgagtg ccagacacag ggccggagca gccaggagct ggaaggaagc   1560
tgccggaagg acaacaactc catcatctgc tcagggctgg gggactgtgt ctgcgggcag   1620
tgcctgtgcc acaccagcga cgtccccggc aagctgatat acgggcagta ctgcgagtgt   1680
gacaccatca actgtgagcg ctacaacggc caggtctgcg gcggcccggg aggggggctc   1740
tgcttctgcg ggaagtgccg ctgccacccg ggctttgagg gctcagcgtg ccagtgcgag   1800
aggaccactg agggctgcct gaacccgcgg cgtgttgagt gtagtggtcg tggccggtgc   1860
cgctgcaacg tatgcgagtg ccattcaggc taccagctgc ctctgtgcca ggagtgcccc   1920
ggctgcccct caccctgtgg caagtacatc tcctgcgccg agtgcctgaa gttcgaaaag   1980
ggccccttttg ggaagaactg cagcgcggcg tgtccgggcc tgcagctgtc gaacaacccc   2040
gtgaagggca ggacctgcaa ggagagggac tcagagggct gctgggtggc ctacacgctg   2100
gagcagcagg acgggatgga ccgctacctc atctatgtgg atgagagccg agagtgtgtg   2160
gcaggcccca acatcgccgc catcgtcggg ggcaccgtgg caggcatcgt gctgatcggc   2220
attctcctgc tggtcatctg gaaggctctg atccacctga gcgacctccg ggagtacagg   2280
cgctttgaga aggagaagct caagtcccag tggaacaatg ataatccccc tttcaagagc   2340
gccaccacga cggtcatgaa ccccaagttt gctgagagtt aggagcactt ggtgaagaca   2400
aggccgtcag gacccaccat gtctgcccca tcacgcggcc gagacatggc ttggccacag   2460
ctcttgagga tgtcaccaat taaccagaaa tccagttatt ttccgccctc aaaatgacag   2520
ccatggccgg ccggtgcttc tgggggctcg tcgggggggac agctccactc tgactggcac   2580
```

-continued

| | |
|---|---|
| agtctttgca tggagacttg aggagggctt gaggttggtg aggttaggtg cgtgtttcct | 2640 |
| gtgcaagtca ggacatcagt ctgattaaag gtggtgccaa tttatttaca tttaaacttg | 2700 |
| tcagggtata aaatgacatc ccattaatta tattgttaat caatcacgtg tatagaaaaa | 2760 |
| aaaataaaac ttcaat | 2776 |

<210> SEQ ID NO 345
<211> LENGTH: 3160
<212> TYPE: DNA
<213> ORGANISM: Homo sapiens

<400> SEQUENCE: 345

| | |
|---|---|
| cctcccctcg cccggcgcgg tcccgtccgc ctctcgctcg cctcccgcct ccccctcggtc | 60 |
| ttccgaggcg cccgggctcc cggcgcggcg gcggaggggg cgggcaggcc ggcgggcggt | 120 |
| gatgtggcag gactctttat gcgctgcggc aggatacgcg ctcggcgctg ggacgcgact | 180 |
| gcgctcagtt ctctcctctc ggaagctgca gccatgatgg aagtttgaga gttgagccgc | 240 |
| tgtgaggcga ggccgggctc aggcgaggga gatgagagac ggcggcggcc gcggcccgga | 300 |
| gcccctctca gcgcctgtga gcagccgcgg gggcagcgcc ctcggggagc cggccggcct | 360 |
| gcggcggcgg cagcggcggc gtttctcgcc tcctcttcgt ctttttctaac cgtgcagcct | 420 |
| cttcctcggc ttctcctgaa agggaaggtg aagccgtgg gctcgggcgg gagccggctg | 480 |
| aggcgcggcg gcggcggcgg cggcacctcc cgctcctgga gcgggggga gaagcggcgg | 540 |
| cggcggcggc cgcggcggct gcagctccag ggaggggtc tgagtcgcct gtcaccattt | 600 |
| ccagggctgg gaacgccgga gagttggtct ctcccttct actgcctcca acacggcggc | 660 |
| ggcggcggcg gcacatccag ggacccgggc cggttttaaa cctcccgtcc gccgccgccg | 720 |
| caccccccgt ggcccgggct ccggaggccg ccggcggagg cagccgttcg gaggattatt | 780 |
| cgtcttctcc ccattccgct gccgccgctg ccaggcctct ggctgctgag gagaagcagg | 840 |
| cccagtcgct gcaaccatcc agcagccgcc gcagcagcca ttacccggct gcggtccaga | 900 |
| gccaagcggc ggcagagcga ggggcatcag ctaccgccaa gtccagagcc atttccatcc | 960 |
| tgcagaagaa gccccgccac cagcagcttc tgccatctct ctcctccttt tcttcagcc | 1020 |
| acaggctccc agacatgaca gccatcatca aagagatcgt tagcagaaac aaaaggagat | 1080 |
| atcaagagga tggattcgac ttagacttga cctatattta tccaaacatt attgctatgg | 1140 |
| gatttcctgc agaaagactt gaaggcgtat acaggaacaa tattgatgat gtagtaaggt | 1200 |
| ttttggattc aaagcataaa aaccattaca agatatacaa tctttgtgct gaaagacatt | 1260 |
| atgacaccgc caaatttaat tgcagagttg cacaatatcc ttttgaagac cataacccac | 1320 |
| cacagctaga acttatcaaa ccccttttgtg aagatcttga ccaatggcta agtgaagatg | 1380 |
| acaatcatgt tgcagcaatt cactgtaaag ctggaaaggg acgaactggt gtaatgatat | 1440 |
| gtgcatattt attacatcgg ggcaaatttt taaaggcaca agaggcccta gatttctatg | 1500 |
| gggaagtaag gaccagagac aaaaagggag taactattcc cagtcagagg cgctatgtgt | 1560 |
| attattatag ctacctgtta aagaatcatc tggattatag accagtggca ctgttgtttc | 1620 |
| acaagatgat gtttgaaact attccaatgt tcagtggcgg aacttgcaat cctcagtttg | 1680 |
| tggtctgcca gctaaaggtg aagatatatt cctccaattc aggacccaca cgacgggaag | 1740 |
| acaagttcat gtactttgag ttccctcagc cgttacctgt gtgtggtgat atcaaagtag | 1800 |
| agttcttcca caaacagaac aagatgctaa aaaaggacaa aatgtttcac ttttgggtaa | 1860 |
| atacattctt cataccagga ccagaggaaa cctcagaaaa agtagaaaat ggaagtctat | 1920 |

```
gtgatcaaga aatcgatagc atttgcagta tagagcgtgc agataatgac aaggaatatc    1980
tagtacttac tttaacaaaa aatgatcttg acaaagcaaa taaagacaaa gccaaccgat    2040
acttttctcc aaattttaag gtgaagctgt acttcacaaa aacagtagag gagccgtcaa    2100
atccagaggc tagcagttca acttctgtaa caccagatgt tagtgacaat gaacctgatc    2160
attatagata ttctgacacc actgactctg atccagagaa tgaacctttt gatgaagatc    2220
agcatacaca aattacaaaa gtctgaattt ttttttatca agagggataa acaccatga     2280 aaataaactt gaataaactg aaaatggacc tttttttttt taatggcaat aggacattgt    2340
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460
tatataccct tttgtgtcaa aaggacattt aaaattcaat taggattaat aaagatggca    2520
cttccccgtt ttattccagt tttataaaaa gtggagacag actgatgtgt atacgtagga    2580
attttttcct tttgtgttct gtcaccaact gaagtggcta aagagctttg tgatatactg    2640
gttcacatcc taccccttt g cacttgtggc aacagataag tttgcagttg gctaagagag    2700
gtttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                          3160
```

<210> SEQ ID NO 346
<211> LENGTH: 2629
<212> TYPE: DNA
<213> ORGANISM: Homo sapiens

<400> SEQUENCE: 346

```
acttgtcatg gcgactgtcc agctttgtgc caggagcctc gcaggggttg atgggattgg      60
ggttttcccc tcccatgtgc tcaagactgg cgctaaaagt tttgagcttc tcaaaagtct     120
agagccaccg tccagggagc aggtagctgc tgggctccgg ggacactttg cgttcgggct     180
gggagcgtgc tttccacgac ggtgacacgc ttccctggat tggcagccag actgccttcc     240
gggtcactgc catggaggag ccgcagtcag atcctagcgt cgagccccct ctgagtcagg     300
aaacattttc agacctatgg aaactacttc ctgaaaacaa cgttctgtcc cccttgccgt     360
cccaagcaat ggatgatttg atgctgtccc ggacgatat tgaacaatgg ttcactgaag     420
acccaggtcc agatgaagct cccagaatgc cagaggctgc tccccgcgtg gcccctgcac    480
cagcagctcc tacaccggcg gcccctgcac cagccccctc ctggcccctg tcatcttctg    540
tcccttccca gaaaacctac cagggcagct acggtttccg tctgggcttc ttgcattctg    600
ggacagccaa gtctgtgact tgcacgtact cccctgccct caacaagatg ttttgccaac    660
tggccaagac ctgccctgtg cagctgtggg ttgattccac accccgcccc ggcacccgcg    720
tccgcgccat ggccatctac aagcagtcac agcacatgac ggaggttgtg aggcgctgcc    780
cccaccatga gcgctgctca gatagcgatg gtctggccc tcctcagcat cttatccgag    840
```

| | | | |
|---|---|---|---|
| tggaaggaaa | tttgcgtgtg | gagtatttgg | atgacagaaa | cacttttcga catagtgtgg | 900 |
| tggtgcccta | tgagccgcct | gaggttggct | ctgactgtac | caccatccac tacaactaca | 960 |
| tgtgtaacag | ttcctgcatg | gcggcatga | accggaggcc | catcctcacc atcatcacac | 1020 |
| tggaagactc | cagtggtaat | ctactgggac | ggaacagctt | tgaggtgcgt gtttgtgcct | 1080 |
| gtcctgggag | agaccggcgc | acagaggaag | agaatctccg | caagaaaggg gagcctcacc | 1140 |
| acgagctgcc | cccagggagc | actaagcgag | cactgcccaa | caacaccagc tcctctcccc | 1200 |
| agccaaagaa | gaaaccactg | gatggagaat | atttcaccct | tcagatccgt gggcgtgagc | 1260 |
| gcttcgagat | gttccgagag | ctgaatgagg | ccttggaact | caaggatgcc caggctggga | 1320 |
| aggagccagg | ggggagcagg | gctcactcca | gccacctgaa | gtccaaaaag ggtcagtcta | 1380 |
| cctcccgcca | taaaaaactc | atgttcaaga | cagaagggcc | tgactcagac tgacattctc | 1440 |
| cacttcttgt | tccccactga | cagcctccca | ccccatctc | tcctcccct gccattttgg | 1500 |
| gttttgggtc | tttgaaccct | tgcttgcaat | aggtgtgcgt | cagaagcacc caggacttcc | 1560 |
| atttgctttg | tcccggggct | ccactgaaca | agttggcctg | cactggtgtt ttgttgtggg | 1620 |
| gaggaggatg | gggagtagga | cataccagct | tagattttaa | ggttttact gtgagggatg | 1680 |
| tttgggagat | gtaagaaatg | ttcttgcagt | taagggttag | tttacaatca gccacattct | 1740 |
| aggtaggtag | gggcccactt | caccgtacta | accaggaag | ctgtccctca tgttgaattt | 1800 |
| tctctaactt | caaggcccat | atctgtgaaa | tgctggcatt | tgcacctacc tcacagagtg | 1860 |
| cattgtgagg | gttaatgaaa | taatgtacat | ctggccttga | aaccacccttt tattacatgg | 1920 |
| ggtctaaaac | ttgacccct | tgagggtgcc | tgttccctct | ccctctccct gttggctggt | 1980 |
| gggttggtag | tttctacagt | tgggcagctg | gttaggtaga | gggagttgtc aagtcttgct | 2040 |
| ggcccagcca | aaccctgtct | gacaacctct | tggtcgacct | tagtacctaa aaggaaatct | 2100 |
| caccccatcc | cacaccctgg | aggatttcat | ctcttgtata | tgatgatctg gatccaccaa | 2160 |
| gacttgtttt | atgctcaggg | tcaatttctt | ttttctttt | tttttttt tttcttttc | 2220 |
| tttgagactg | gtctcgctt | tgttgcccag | gctggagtgg | agtggcgtga tcttggctta | 2280 |
| ctgcagcctt | tgcctccccg | gctcgagcag | tcctgcctca | gcctccggag tagctgggac | 2340 |
| cacaggttca | tgccaccatg | gccagccaac | ttttgcatgt | tttgtagaga tggggtctca | 2400 |
| cagtgttgcc | caggctggtc | tcaaactcct | gggctcaggc | gatccacctg tctcagcctc | 2460 |
| ccagagtgct | gggattacaa | ttgtgagcca | ccacgtggag | ctggaagggt caacatcttt | 2520 |
| tacattctgc | aagcacatct | gcattttcac | cccacccttc | cctccttct cccttttat | 2580 |
| atcccatttt | tatatcgatc | tcttatttta | caataaaact | ttgctgcca | 2629 |

<210> SEQ ID NO 347
<211> LENGTH: 3442
<212> TYPE: DNA
<213> ORGANISM: Homo sapiens

<400> SEQUENCE: 347

| | | | | |
|---|---|---|---|---|
| agccggtgcg | ccgcagacta | gggcgcctcg | ggccagggag | cgcggaggag ccatggccac | 60 |
| cgctaacggg | gccgtggaaa | acgggcagcc | ggacgggaag | ccgccggccc tgccgcgccc | 120 |
| catccgcaac | ctggaggtca | agttcaccaa | gatatttatc | aacaatgaat ggcacgaatc | 180 |
| caagagtggg | aaaaagtttg | ctacatgtaa | cccttcaact | cgggagcaaa tatgtgaagt | 240 |
| ggaagaagga | gataagcccg | acgtggacaa | ggctgtggag | gctgcacagg ttgccttcca | 300 |
| gaggggctcg | ccatggcgcc | ggctggatgc | cctgagtcgt | gggcggctgc tgcaccagct | 360 |

```
ggctgacctg gtggagaggg accgcgccac cttggccgcc ctggagacga tggatacagg    420
gaagccattt cttcatgctt ttttcatcga cctggagggc tgtattagaa ccctcagata    480
ctttgcaggg tgggcagaca aaatccaggg caagaccatc cccacagatg acaacgtcgt    540
atgcttcacc aggcatgagc ccattggtgt ctgtgggcc  atcactccat ggaacttccc    600
cctgctgatg ctggtgtgga agctggcacc cgccctctgc tgtgggaaca ccatggtcct    660
gaagcctgcg gagcagacac ctctcaccgc cctttatctc ggctctctga tcaaagaggc    720
cgggttccct ccaggagtgg tgaacattgt gccaggattc gggcccacag tgggagcagc    780
aatttcttct caccctcaga tcaacaagat cgccttcacc ggctccacag aggttggaaa    840
actggttaaa gaagctgcgt cccggagcaa tctgaagcgg gtgacgctgg agctgggggg    900
gaagaacccc tgcatcgtgt gtgcggacgc tgacttggac ttggcagtgg agtgtgccca    960
tcagggagtg ttcttcaacc aaggccagtg ttgcacggca gcctccaggg tgttcgtgga    1020
ggagcaggtc tactctgagt tgtcaggcg  gagcgtggag tatgccaaga acggcccgt    1080 gggagacccc ttcgatgtca aaacagaaca ggggcctcag attgatcaaa agcagttcga    1140
caaaatctta gagctgatcg agagtgggaa gaaggaaggg gccaagctgg aatgcggggg    1200
ctcagccatg gaagacaagg ggctcttcat caaacccact gtcttctcag aagtcacaga    1260
caacatgcgg attgccaaag aggagatttt cgggccagtg caaccaatac tgaagttcaa    1320
aagtatcgaa gaagtgataa aaagagcgaa tagcaccgac tatggactca cagcagccgt    1380
gttcacaaaa aatctcgaca aagccctgaa gttggcttct gccttagagt ctggaacggt    1440
ctggatcaac tgctacaacg ccctctatgc acaggctcca tttggtggct ttaaaatgtc    1500
aggaaatggc agagaactag tgaatacgc  tttggccgaa tacacagaag tgaaaactgt    1560
caccatcaaa cttggcgaca agaacccctg aaggaaaggc ggggctcctt cctcaaacat    1620
cggacggcgg aatgtggcag atgaaatgtg ctggaggaaa aaaatgacat ttctgacctt    1680
cccgggacac attcttctgg aggctttaca tctactggag ttgaatgatt gctgttttcc    1740
tctcactctc ctgtttattc accagactgg ggatgcctat aggttgtctg tgaaatcgca    1800
gtcctgcctg gggagggagc tgttggccat ttctgtgttt ccctttaaac cagatcctgg    1860
agacagtgag atactcaggg cgttgttaac agggagtggt atttgaagtg tccagcagtt    1920
gcttgaaatg ctttgccgaa tctgactcca gtaagaatgt gggaaaaccc cctgtgtgtt    1980
ctgcaagcag ggctcttgca ccagcggtct cctcagggtg gacctgctta cagagcaagc    2040
cacgcctctt tccgaggtga aggtgggacc attccttggg aaaggattca gtaaggtt     2100 ttttggtttt tgttttttgt ttcttgtttt taaaaaaag gatttcacag tgagaaagtt    2160
ttggttagtg cataccgtgg aagggcgcca gggtctttgt ggattgcatg ttgacattga    2220
ccgtgagatt cggcttcaaa ccaatactgc ctttggaata tgacagaatc aatagcccag    2280
agagcttagt caaagacgat atcacggtct accttaacca aggcactttc ttaagcagaa    2340
aatattgttg aggttacctt tgctgctaaa gatccaatct tctaacgcca caacagcata    2400
gcaaatccta ggataattca cctcctcatt tgacaaatca gagctgtaat tcactttaac    2460
aaattacgca tttctatcac gttcactaac agcttatgat aagtctgtgt agtcttcctt    2520
ttctccagtt ctgttaccca atttagatta gtaaagcgta cacaactgga aagactgctg    2580
taataacaca gccttgttat ttttaagtcc tattttgata ttaatttctg attagttagt    2640
aaataacacc tggattctat ggaggacctc ggtcttcatc caagtggcct gagtatttca    2700
```

-continued

```
ctggcaggtt gtgaattttt cttttcctct ttgggaatcc aaatgatgat gtgcaatttc    2760
atgttttaac ttgggaaact gaaagtgttc ccatatagct tcaaaaacaa aaacaaatgt    2820
gttatccgac ggatactttt atggttacta actagtactt tcctaattgg gaaagtagtg    2880
cttaagtttg caaattaagt tggggagggc aataataaaa tgagggcccg taacagaacc    2940
agtgtgtgta taacgaaaac catgtataaa atgggcctat caccctttgtc agagatataa   3000 attaccacat ttggcttccc ttcatcagct aacacttatc acttatacta ccaataactt    3060
gttaaatcag gatttggctt catacactga attttcagta ttttatctca gtagatata     3120 gacactaacc ttgatagtga tacgttagag ggttcctatt cttccattgt acgataatgt    3180
ctttaatatg aaatgctaca ttatttataa ttggtagagt tattgtatct ttttatagtt    3240
gtaagtacac agaggtggta tatttaaact tctgtaatat actgtattta gaaatggaaa    3300
tatatatagt gttaggtttc acttctttta aggtttaccc ctgtggtgtg gtttaaaaat    3360
ctataggcct gggaattccg atcctagctg cagatcgcat cccacaatgc gagaatgata    3420
aaataaaatt ggatatttga ga                                             3442

<210> SEQ ID NO 348
<211> LENGTH: 737
<212> TYPE: DNA
<213> ORGANISM: Homo sapiens

<400> SEQUENCE: 348
ggagtttcgc cgccgcagtc ttcgccacca tgccgcccta caccgtggtc tatttcccag    60
ttcgaggccg ctgcgcggcc ctgcgcatgc tgctggcaga tcagggccag agctggaagg    120
aggaggtggt gaccgtggag acgtggcagg agggctcact caaagcctcc tgcctatacg    180
ggcagctccc caagttccag gacggagacc tcaccctgta ccagtccaat accatcctgc    240
gtcacctggg ccgcacccct gggctctatg ggaaggacca gcaggaggca gccctggtgg    300
acatggtgaa tgacggcgtg gaggacctcc gctgcaaata catctccctc atctacacca    360
actatgaggc gggcaaggat gactatgtga aggcactgcc cggcaactga agccttttg    420 agaccctgct gtcccagaac cagggaggca agaccttcat tgtgggagac cagatctcct    480
tcgctgacta caacctgctg gacttgctgc tgatccatga ggtcctagcc cctggctgcc    540
tggatgcgtt ccccctgctc tcagcatatg tggggcgcct cagcgcccgg cccaagctca    600
aggccttcct ggcctcccct gagtacgtga acctccccat caatggcaac gggaaacagt    660
gagggttggg gggactctga gcgggaggca gagtttgcct tccttctcc aggaccaata    720 aaatttctaa gagagct                                                   737

<210> SEQ ID NO 349
<211> LENGTH: 5189
<212> TYPE: DNA
<213> ORGANISM: Homo sapiens

<400> SEQUENCE: 349
atggccaagt cgggtggctg cggcgcggga gccggcgtgg cggcggcaa cggggcactg    60 acctgggtga caatgctgc aaaaaaagaa gagtcagaaa ctgccaacaa aaatgattct    120
tcaaagaagt tgtctgttga gagagtgtat cagaagaaga cacaacttga acacattctt    180
cttcgtcctg atacatatat tgggtcagtg gagccattga cgcagttcat gtgggtgtat    240
gatgaagatg taggaatgaa ttgcaggag gttacctttg tgccaggttt atacaagatc    300
tttgatgaaa ttttggttaa tgctgctgac aataaacaga gggataagaa catgactgt     360
```

```
attaaagttt ctattgatcc tgaatctaac attataagca tttggaataa tgggaaaggc    420
attccagtag tagaacacaa ggtagagaaa gtttatgttc ctgctttaat ttttggacag    480
cttttaacat ccagtaacta tgatgatgat gagaaaaaag ttacaggtgg tcgtaatggt    540
tatggtgcaa aactttgtaa tattttcagt acaaagttta cagtagaaac agcttgcaaa    600
gaatacaaac acagttttaa gcagacatgg atgaataata tgatgaagac ttctgaagcc    660
aaaattaaac attttgatgg tgaagattac acatgcataa cattccaacc agatctgtcc    720
aaatttaaga tggaaaaact tgacaaggat attgtgggcc tcatgactag aagggcatat    780
gatttggctg gttcgtgtag aggggtcaag gtcatgttta tggaaagaa attgcctgta    840
aatggatttc gcagttatgt agatctttat gtgaaagaca aattggatga aactggggtg    900
gccctgaaag ttattcatga gcttgcaaat gaaagatggg atgtttgtct cacattgagt    960
gaaaaaggat ccagcaaat cagctttgta aatagtattg caactacaaa aggtggacgg   1020
cacgtggatt atgtggtaga tcaagttgtt ggtaaactga ttgaagtagt taagaaaaag   1080
aacaaagctg gtgtatcagt gaaccattt caagtaaaaa accatatatg gttttattt    1140
aattgcctta ttgaaaatcc aactttttgat tctcagacta aggaaaacat gactctgcag   1200
cccaaaagtt ttgggtctaa atgccagctg tcagaaaaat tttttaaagc agcctctaat   1260
tgtggcattg tagaaagtat cctgaactgg gtgaaattta aggctcagac tcagctgaat   1320
aagaagtgtt catcagtaaa atacagtaaa atcaaaggta ttcccaaact ggatgatgct   1380
aatgatgctg gtggtaaaca ttcctgggag tgtacactga tattaacaga gggagactct   1440
gccaaatcac tggctgtgtc tggattaggt gtgattggac gagacagata cggagttttt   1500
ccactcaggg gcaaaattct taatgtacgg gaagcttctc ataaacagat catggaaaat   1560
gctgaaataa ataatattat taaaatagtt ggtctacaat ataagaaaag ttacgatgat   1620
gcagaatctc tgaaaacctt acgctatgga aagattatga ttatgaccga tcaggatcaa   1680
gatggttctc acataaaagg cctgcttatt aatttcatcc atcacaattg gccatcactt   1740
ttgaagcatg gttttcttga agagttcatt actcctattg taaaggcaag caaaaataag   1800
caggaacttt ccttctacag tattcctgaa tttgacgaat ggaaaaaaca tatagaaaac   1860
cagaaagcct ggaaaataaa gtactataaa ggattgggta ctagtacagc taagaagca   1920
aaggaatatt ttgctgatat ggaaaggcat cgcatcttgt ttagatatgc tggtcctgaa   1980
gatgatgctg ccattacctt ggcatttagt aagaagaaga ttgatgacag aaaagaatgg   2040
ttaacaaatt ttatggaaga ccggagacag cgtaggctac atggcttacc agagcaattt   2100
ttatatggta ctgcaacaaa gcatttgact tataatgatt tcatcaacaa ggaattgatt   2160
ctcttctcaa actcagacaa tgaaagatct ataccatctc ttgttgatgg ctttaaacct   2220
ggccagcgga aagttttatt tacctgtttc aagaggaatg ataaacgtga agtaaaagtt   2280
gcccagttgg ctggctctgt tgctgagatg tcggcttatc atcatggaga acaagcattg   2340
atgatgacta ttgtgaattt ggctcagaac tttgtgggaa gtaacaacat taacttgctt   2400
cagcctattg gtcagtttgg aactcggctt catggtggca aagatgctgc aagccctcgt   2460
tatattttca caatgttaag cactttagca aggctacttt ttcctgctgt ggatgacaac   2520
ctccttaagt tcctttatga tgataatcaa cgtgtagagc ctgagtggta tattcctata   2580
attcccatgg ttttaataaa tggtgctgag ggcattggta ctggatgggc ttgtaaacta   2640
cccaactatg atgctaggga aattgtgaac aatgtcagac gaatgctaga tggcctggat   2700
```

```
cctcatccca tgcttccaaa ctacaaaaac tttaaaggca cgattcaaga acttggtcaa    2760
aaccagtatg cagtcagtgg tgaaatattt gtagtggaca gaaacacagt agaaattaca    2820
gagcttccag ttagaacttg dacacaggta tataaagaac aggttttaga acctatgcta    2880
aatggaacag ataaaacacc agcattaatt tctgattata aagaatatca tactgacaca    2940
actgtgaaat ttgtggtgaa aatgactgaa gagaaactag cacaagcaga agctgctgga    3000
ctgcataaag ttttttaaact tcaaactact cttacttgta attccatggt acttttttgat   3060 catatgggat gtctgaagaa atatgaaact gtgcaagaca ttctgaaaga attctttgat    3120
ttacgattaa gttattacgg tttacgtaag gagtggcttg tgggaatgtt gggagcagaa    3180
tctacaaagc ttaacaatca agcccgtttc attttagaga agatacaagg gaaaattact    3240
atagagaata ggtcaaagaa agatttgatt caaatgttag tccagagagg ttatgaatct    3300
gacccagtga aagcctggaa agaagcacaa gaaaaggcag cagaagagga tgaaacacaa    3360
aaccagcatg atgatagttc ctccgattca ggaactcctt caggcccaga ttttaattat    3420 atttttaaata tgtctctgtg gtctcttact aaagaaaaag ttgaagaact gattaaacag    3480
agagatgcaa aagggcgaga ggtcaatgat cttaaaagaa aatctccttc agatctttgg    3540
aaagaggatt tagcggcatt tgttgaagaa ctggataaag tggaatctca agaacgagaa    3600
gatgttctgg ctggaatgtc tggaaaagca attaaaggta aagttggcaa acctaaggtg    3660
aagaaactcc agttggaaga gacaatgccc tcaccttatg gcagaagaat aattcctgaa    3720
attacagcta tgaaggcaga tgccagcaaa aagttgctga agaagaagaa gggtgatctt    3780
gatactgcag cagtaaaagt ggaatttgat gaagaattca gtggagcacc agtagaaggt    3840
gcaggagaag aggcattgac tccatcagtt cctataaata aaggtcccaa acctaagagg    3900
gagaagaagg agcctggtac cagagtgaga aaaacaccta catcatctgg taaacctagt    3960
gcaaagaaag tgaagaaacg gaatccttgg tcagatgatg aatccaagtc agaaagtgat    4020
ttggaagaaa cagaacctgt ggttattcca agagattctt tgcttaggag agcagcagcc    4080
gaaagaccta aatacacatt tgatttctca gaagaagagg atgatgatgc tgatgatgat    4140
gatgatgaca ataatgattt agaggaattg aaagttaaag catctcccat aacaaatgat    4200
ggggaagatg aatttgttcc ttcagatggg ttagataaag atgaatatac attttcacca    4260
ggcaaatcaa aagccactcc agaaaaatct ttgcatgaca aaaaaagtca ggattttgga    4320
aatctcttct catttccttc atattctcag aagtcagaag atgattcagc taaatttgac    4380
agtaatgaag aagattctgc ttctgttttt tcaccatcat ttggtctgaa acagacagat    4440
aaagttccaa gtaaaacggt agctgctaaa aagggaaaac cgtcttcaga tacagtccct    4500
aagcccaaga gagcccccaaa acagaagaaa gtagtagagg ctgtaaactc tgactcggat    4560
tcagaatttg gcattccaaa gaagactaca acaccaaaag gtaaaggccg aggggcaaag    4620
aaaaggaaag catctggctc tgaaaatgaa ggcgattata accctggcag gaaaacatcc    4680
aaaacaacaa gcaagaaacc gaagaagaca tcttttgatc aggattcaga tgtggacatc    4740
ttcccctcag acttccctac tgagccacct tctctgccac gaaccggtcg ggctaggaaa    4800
gaagtaaaat attttgcaga gtctgatgaa gaagaagatg atgttgattt tgcaatgttt    4860
aattaagtgc ccaaagagca caaacatttt tcaacaaata tcttgtgttg tccttttgtc    4920
ttctctgtct cagacttttg tacatctggc ttatttttaat gtgatgatgt aattgacggt    4980 ttttattat tgtggtaggc cttttaacat tttgttctta cacatacagt ttatgctct    5040 tttttactca ttgaaatgtc acgtactgtc tgattggctt gtagaattgt tatagactgc    5100
```

| | |
|---|---|
| cgtgcattag cacagatttt aattgtcatg gttacaaact acagacctgc tttttgaaat | 5160 |
| gaaatttaaa cattaaaaat ggaactgtg | 5189 |

<210> SEQ ID NO 350
<211> LENGTH: 1536
<212> TYPE: DNA
<213> ORGANISM: Homo sapiens

<400> SEQUENCE: 350

| | |
|---|---|
| ggggggggggg ggaccacttg gcctgcctcc gtcccgccgc gccacttggc ctgcctccgt | 60 |
| cccgccgcgc cacttcgcct gcctccgtcc cccgcccgcc gcgccatgcc tgtggccggc | 120 |
| tcggagctgc cgcgccggcc cttgcccccc gccgcacagg agcgggacgc cgagccgcgt | 180 |
| ccgccgcacg gggagctgca gtacctgggg cagatccaac acatcctccg ctgcggcgtc | 240 |
| aggaaggacg accgcacggg caccggcacc ctgtcggtat tcggcatgca ggcgcgctac | 300 |
| agcctgagag atgaattccc tctgctgaca accaaacgtg tgttctggaa gggtgttttg | 360 |
| gaggagttgc tgtggtttat caagggatcc acaaatgcta aagagctgtc ttccaaggga | 420 |
| gtgaaaatct gggatgccaa tggatcccga gacttttttgg acagcctggg attctccacc | 480 |
| agagaagaag gggacttggg cccagtttat ggcttccagt ggaggcattt tggggcagaa | 540 |
| tacagagata tggaatcaga ttattcagga cagggagttg accaactgca aagagtgatt | 600 |
| gacaccatca aaccaaccc tgacgacaga agaatcatca tgtgcgcttg aatccaaga | 660 |
| gatcttcctc tgatggcgct gcctccatgc catgccctct gccagttcta tgtggtgaac | 720 |
| agtgagctgt cctgccagct gtaccagaga tcgggagaca tgggcctcgg tgtgcctttc | 780 |
| aacatcgcca gctacgccct gctcacgtac atgattgcgc acatcacggg cctgaagcca | 840 |
| ggtgacttta tacacacttt gggagatgca catatttacc tgaatcacat cgagccactg | 900 |
| aaaattcagc ttcagcgaga acccagacct ttcccaaagc tcaggattct tcgaaaagtt | 960 |
| gagaaaattg atgacttcaa agctgaagac tttcagattg aagggtacaa tccgcatcca | 1020 |
| actattaaaa tggaaatggc tgtttagggt gctttcaaag gagcttgaag gatattgtca | 1080 |
| gtctttaggg gttgggctgg atgccgaggt aaaagttctt tttgctctaa aagaaaaagg | 1140 |
| aactaggtca aaaatctgtc cgtgacctat cagttattaa ttttttaagga tgttgccact | 1200 |
| ggcaaatgta actgtgccag ttcttttccat aataaaaggc tttgagttaa ctcactgagg | 1260 |
| gtatctgaca atgctgaggt tatgaacaaa gtgaggagaa tgaaatgtat gtgctcttag | 1320 |
| caaaaacatg tatgtgcatt tcaatcccac gtacttataa agaaggttgg tgaatttcac | 1380 |
| aagctattt tggaatattt ttagaatatt ttaagaattt cacaagctat tccctcaaat | 1440 |
| ctgagggagc tgagtaacac catcgatcat gatgtagagt gtggttatga actttatagt | 1500 |
| tgttttatat gttgctataa taaagaagtg ttctgc | 1536 |

<210> SEQ ID NO 351
<211> LENGTH: 2386
<212> TYPE: DNA
<213> ORGANISM: Homo sapiens

<400> SEQUENCE: 351

| | |
|---|---|
| ggaggaggaa gcaagcgagg gggctggttc ctgagcttcg caattcctgt gtcgccttct | 60 |
| gggctcccag cctgccgggt cgcatgatcc ctccggccgg agctggtttt tttgccagcc | 120 |
| accgcgaggc cggctgagtt accggcatcc ccgcagccac ctcctctccc gacctgtgat | 180 |

```
acaaaagatc ttccgggggc tgcacctgcc tgcctttgcc taaggcggat ttgaatctct      240
ttctctccct tcagaatctt atcttggctt tggatcttag aagagaatca ctaaccagag      300
acgagactca gtgagtgagc aggtgttttg acaatggac tggttgagcc catccctatt       360
ataaaaatgt ctcagagcaa ccgggagctg gtggttgact ttctctccta caagctttcc      420
cagaaaggat acagctggag tcagtttagt gatgtggaag agaacaggac tgaggcccca      480
gaagggactg aatcggagat ggagacccc agtgccatca atggcaaccc atcctggcac       540
ctggcagaca gccccgcggt gaatggagcc actggccaca gcagcagttt ggatgcccgg      600
gaggtgatcc ccatgcagc agtaaagcaa gcgctgaggg aggcaggcga cgagtttgaa       660
ctgcggtacc ggcgggcatt cagtgacctg acatcccagc tccacatcac cccagggaca      720
gcatatcaga gctttgaaca ggatactttt gtggaactct atgggaacaa tgcagcagcc      780
gagagccgaa agggccagga acgcttcaac cgctggttcc tgacgggcat gactgtggcc      840
ggcgtggttc tgctgggctc actcttcagt cggaaatgac agacactga ccatccactc       900 taccctccca cccccttctc tgctccacca catcctccgt ccagccgcca ttgccaccag      960
gagaaccact acatgcagcc catgcccacc tgcccatcac agggttgggc ccagatctgg     1020
tcccttgcag ctagttttct agaatttatc acacttctgt gagaccccca cacctcagtt     1080
cccttggcct cagaattcac aaaatttcca caaaatctgt ccaaggagg ctggcaggta     1140 tggaagggtt tgtggctggg gcaggaggg ccctacctga ttggtgcaac ccttacccct     1200
tagcctccct gaaaatgttt ttctgccagg gagcttgaaa gttttcagaa cctcttcccc     1260
agaaaggaga ctagattgcc tttgttttga tgtttgtggc ctcagaattg atcattttcc     1320
ccccactctc cccacactaa cctgggttcc ctttccttcc atccctaccc cctaagagcc     1380
atttaggggc cacttttgac tagggattca ggctgcttgg gataaagatg caaggaccag     1440
gactccctcc tcacctctgg actggctaga gtcctcactc ccagtccaaa tgtcctccag     1500
aagcctctgg ctagaggcca gccccaccca ggagggaggg ggctatagct acaggaagca     1560
ccccatgcca aagctagggt ggcccttgca gttcagcacc accctagtcc cttcccctcc     1620
ctggctccca tgaccatact gagggaccaa ctgggcccaa gacagatgcc ccagagctgt     1680
ttatggcctc agctgcctca cttcctacaa gagcagcctg tggcatcttt gccttgggct     1740
gctcctcatg gtgggttcag gggactcagc cctgaggtga agggagcta tcaggaacag     1800 ctatgggagc cccagggtct tccctacctc aggcaggaag ggcaggaagg agagcctgct     1860
gcatggggtg gggtagggct gactagaagg gccagtcctg cctggccagg cagatctgtg     1920
ccccatgcct gtccagcctg ggcagccagg ctgccaaggc cagagtggcc tggccaggag     1980
ctcttcaggc ctccctctct cttctgctcc acccttggcc tgtctcatcc caggggtcc      2040 cagccacccc gggctctctg ctgtacatat ttgagactag ttttattcc ttgtgaagat      2100 gatatactat ttttgttaag cgtgtctgta tttatgtgtg aggagctgct ggcttgcagt     2160
gcgcgtgcac gtggagagct ggtgcccgga gattggacgg cctgatgctc cctcccctgc     2220
cctggtccag ggaagctggc cgagggtcct ggctcctgag gggcatctgc ccctccccca     2280
acccccaccc cacacttgtt ccagctcttt gaaatagtct gtgtgaaggt gaaagtgcag     2340
ttcagtaata aactgtgttt actcagtgaa aaaaaaaaa aaaaaa                     2386

<210> SEQ ID NO 352
<211> LENGTH: 1270
<212> TYPE: DNA
<213> ORGANISM: Homo sapiens
```

<400> SEQUENCE: 352

```
agacgttcgc acacctgggt gccagcgccc cagaggtccc gggacagccc gaggcgccgc        60
gcccgccgcc ccgagctccc caagccttcg agagcggcgc acactcccgg tctccactcg       120
ctcttccaac acccgctcgt tttggcggca gctcgtgtcc cagagaccga gttgccccag       180
agaccgagac gccgccgctg cgaaggacca atgagagccc cgctgctacc gccggcgccg       240
gtggtgctgt cgctcttgat actcggctca ggccattatg ctgctggatt ggacctcaat       300
gacacctact ctgggaagcg tgaaccattt tctggggacc acagtgctga tggatttgag       360
gttacctcaa gaagtgagat gtcttcaggg agtgagattt ccctgtgag tgaaatgcct        420
tctagtagtg aaccgtcctc gggagccgac tatgactact cagaagagta tgataacgaa       480
ccacaaatac ctggctatat tgtcgatgat tcagtcagag ttgaacaggt agttaagccc       540
ccccaaaaca gacggaaag tgaaaatact tcagataaac ccaaaagaaa gaaaagggaa        600
ggcaaaaatg gaaaaaatag aagaaacaga aagaagaaaa atccatgtaa tgcagaattt       660
caaaatttct gcattcacgg agaatgcaaa tatatagagc acctggaagc agtaacatgc       720
aaatgtcagc aagaatattt cggtgaacgg tgtgggaaaa agtccatgaa aactcacagc       780
atgattgaca gtagtttatc aaaaattgca ttagcagcca tagctgcctt tatgtctgct       840
gtgatcctca cagctgttgc tgttattaca gtccagctta aagacaata cgtcaggaaa        900
tatgaaggag aagctgagga acgaaagaaa cttcgacaag agaatggaaa tgtacatgct       960
atagcataac tgaagataaa attacaggat atcacattgg agtcactgcc aagtcatagc      1020
cataaatgat gagtcggtcc tctttccagt ggatcataag acaatggacc cttttttgtta     1080
tgatggtttt aaactttcaa ttgtcacttt ttatgctatt tctgtatata aaggtgcacg      1140
aaggtaaaaa gtatttttc aagttgtaaa taatttattt aatatttaat ggaagtgtat       1200
ttattttaca gctcattaaa cttttttaac caaacagaaa aaaaaaaaa aaaaaaaaa        1260
aaaaaaaaaa                                                             1270
```

<210> SEQ ID NO 353
<211> LENGTH: 1600
<212> TYPE: DNA
<213> ORGANISM: Homo sapiens

<400> SEQUENCE: 353

```
gccccgccgc cggcagtgga ccgctgtgcg cgaaccctga accctacggt cccgacccgc        60
gggcgaggcc gggtacctgg gctgggatcc ggagcaagcg ggcgagggca gcgccctaag       120
caggcccgga gcgatggcag ccttgatgac cccgggaacc ggggcccac ccgcgcctgg        180
tgacttctcc ggggaaggga gccagggact tcccgaccct tcgccagagc ccaagcagct       240
cccggagctg atccgcatga agcgagacg aggccgcctg agcgaagcgg acatcagggg       300
cttcgtggcc gctgtggtga tgggagcgc gcagggcgca cagatcgggg ccatgctgat       360
ggccatccga cttcggggca tggatctgga ggagacctcg gtgctgaccc aggccctggc       420
tcagtcggga cagcagctgg agtggccaga ggcctggcgc cagcagcttg tggacaagca       480
ttccacaggg ggtgtgggtg acaaggtcag cctggtcctc gcacctgccc tggcggcatg       540
tggctgcaag gtgccaatga tcagcggacg tggtctgggg cacacaggag gcaccttgga       600
taagctggag tctattcctg gattcaatgt catccagagc ccagagcaga tgcaagtgct       660
gctggaccag gcgggctgct gtatcgtggg tcagagtgag cagctggttc ctgcggacgg       720
```

-continued

| | | | | |
|---|---|---|---|---|
| aatcctatat | gcagccagag | atgtgacagc | caccgtggac | agcctgccac tcatcacagc | 780 |
| ctccattctc | agtaagaaac | tcgtggaggg | gctgtccgct | ctggtggtgg acgttaagtt | 840 |
| cggaggggcc | gccgtcttcc | ccaaccagga | gcaggcccgg | gagctggcaa agacgctggt | 900 |
| tggcgtggga | gccagcctag | ggcttcgggt | cgcggcagcg | ctgaccgcca tggacaagcc | 960 |
| cctgggtcgc | tgcgtgggcc | acgccctgga | ggtggaggag | gcgctgctct gcatggacgg | 1020 |
| cgcaggcccg | ccagacttaa | gggacctggt | caccacgctc | ggggggcgccc tgctctggct | 1080 |
| cagcggacac | gcggggactc | aggctcaggg | cgctgcccgg | gtggccgcgg cgctggacga | 1140 |
| cggctcggcc | cttggccgct | tcgagcggat | gctggcggcg | cagggcgtgg atcccggtct | 1200 |
| ggccccgagcc | ctgtgctcgg | gaagtcccgc | agaacgccgg | cagctgctgc ctcgcgcccg | 1260 |
| ggagcaggag | gagctgctgg | cgcccgcaga | tggcaccgtg | gagctggtcc gggcgctgcc | 1320 |
| gctggcgctg | gtgctgcacg | agctcggggc | cgggcgcagc | cgcgctgggg agccgctccg | 1380 |
| cctggggtg | ggcgcagagc | tgctggtcga | cgtgggtcag | aggctgcgcc gtgggacccc | 1440 |
| ctggctccgc | gtgcaccggg | acggccccgc | gctcagcggc | ccgcagagcc gcgccctgca | 1500 |
| ggaggcgctc | gtactctccg | accgcgcgcc | attcgccgcc | ccctcgccct tcgcagagct | 1560 |
| cgttctgccg | ccgcagcaat | aaagctcctt | tgccgcgaaa | | 1600 |

<210> SEQ ID NO 354
<211> LENGTH: 1842
<212> TYPE: DNA
<213> ORGANISM: Homo sapiens

<400> SEQUENCE: 354

| | | | | |
|---|---|---|---|---|
| cgatcagatc | gatctaagat | ggcgactgtc | gaaccggaaa | ccaccccctac tcctaatccc | 60 |
| ccgactacag | aagaggagaa | aacggaatct | aatcaggagg | ttgctaaccc agaacactat | 120 |
| attaaacatc | ccctacagaa | cagatgggca | ctctggtttt | ttaaaaatga taaaagcaaa | 180 |
| acttggcaag | caaacctgcg | gctgatctcc | aagtttgata | ctgttgaaga cttttgggct | 240 |
| ctgtacaacc | atatccagtt | gtctagtaat | ttaatgcctg | gctgtgacta ctcacttttt | 300 |
| aaggatggta | ttgagcctat | gtgggaagat | gagaaaaaca | aacggggagg acgatggcta | 360 |
| attacattga | acaaacagca | gagacgaagt | gacctcgatc | gcttttggct agagacactt | 420 |
| ctgtgcctta | ttggagaatc | ttttgatgac | tacagtgatg | atgtatgtgg cgctgttgtt | 480 |
| aatgttagag | ctaaaggtga | taagatagca | atatggacta | ctgaatgtga aaacagagaa | 540 |
| gctgttacac | atataggag | ggtatacaag | gaaaggttag | gacttcctcc aaagatagtg | 600 |
| attggttatc | agtcccacgc | agacacagct | actaagagcg | gctccaccac taaaaatagg | 660 |
| tttgttgttt | aagaagacac | cttctgagta | ttctcatagg | agactgcgtc aagcaatcga | 720 |
| gatttgggag | ctgaaccaaa | gcctcttcaa | aaagcagagt | ggactgcatt taaatttgat | 780 |
| ttccatctta | atgttactca | gatataagag | aagtctcatt | cgcctttgtc ttgtacttct | 840 |
| gtgttcattt | ttttttttttt | ttttggcta | gagtttccac | tatcccaatc aaagaattac | 900 |
| agtacacatc | cccagaatcc | ataaatgtgt | tcctggccca | ctctgtaata gttcagtaga | 960 |
| attaccatta | attacataca | gattttacct | atccacaata | gtcagaaaac aacttggcat | 1020 |
| ttctatactt | tacaggaaaa | aaaattctgt | tgttccattt | tatgcagaag catatttgc | 1080 |
| tggtttgaaa | gattatgatg | catacagttt | tctagcaatt | ttcttttgttt cttttttacag | 1140 |
| cattgtcttt | gctgtactct | tgctgatggc | tgctagattt | taatttattt gtttccctac | 1200 |
| ttgataatat | tagtgattct | gatttcagtt | tttcatttgt | tttgcttaaa ttttttttttt | 1260 |

```
tttttttcctc atgtaacatt ggtgaaggat ccaggaatat gacacaaagg tggaataaac    1320
attaattttg tgcattcttt ggtaattttt tttgttttt  gtaactacaa agctttgcta    1380
caaatttatg catttcattc aaatcagtga tctatgtttg tgtgatttcc taaacataat    1440
tgtggattat aaaaaatgta acatcataat tacattccta actagaatta gtatgtctgt    1500
ttttgtatct ttatgctgta ttttaacact ttgtattact taggttattt tgctttggtt    1560
aaaaatggct caagtagaaa agcagtccca ttcatattaa gacagtgtac aaaactgtaa    1620
ataaaatgtg tacagtgaat tgtcttttag acaactagat ttgtcctttt atttctccat    1680
ctttatagaa ggaatttgta cttcttattg caggcaagtc tctatattat gtcctctttt    1740
gtggtgtctt ccatgtgaac agcataagtt tggagcacta gtttgattat tatgtttatt    1800
acaattttta ataaattgaa taggtagtat catatatatg ga                      1842

<210> SEQ ID NO 355
<211> LENGTH: 4975
<212> TYPE: DNA
<213> ORGANISM: Homo sapiens

<400> SEQUENCE: 355
ctctcacaca cacacacccc tccctgcca  tccctcccg  gactccggct ccggctccga      60
ttgcaatttg caacctccgc tgccgtcgcc gcagcagcca ccaattcgcc agcggttcag     120
gtggctcttg cctcgatgtc ctagcctagg ggccccgggg ccggacttgg ctgggctccc     180
ttcaccctct gcggagtcat gagggcgaac gacgctctgc aggtgctggg cttgcttttc     240
agcctggccc ggggctccga ggtgggcaac tctcaggcag tgtgtcctgg gactctgaat     300
ggcctgagtg tgaccggcga tgctgagaac caataccaga cactgtacaa gctctacgag     360
aggtgtgagg tggtgatggg gaaccttgag attgtgctca cgggacacaa tgccgacctc     420
tccttcctgc agtggattcg agaagtgaca ggctatgtcc tcgtggccat gaatgaattc     480
tctactctac cattgcccaa cctccgcgtg gtgcgaggga cccaggtcta cgatgggaag     540
tttgccatct tcgtcatgtt gaactataac accaactcca gccacgctct cgccagctc      600 cgcttgactc agctcaccga gattctgtca gggggtgttt atattgagaa gaacgataag     660
ctttgtcaca tggacacaat tgactggagg gacatcgtga gggaccgaga tgctgagata     720
gtggtgaagg acaatggcag aagctgtccc ccctgtcatg aggtttgcaa ggggcgatgc     780
tggggtcctg gatcagaaga ctgccagaca ttgaccaaga ccatctgtgc tcctcagtgt     840
aatggtcact gctttgggcc aaccccaac  cagtgctgcc atgatgagtg tgccgggggc     900
tgctcaggcc ctcaggacac agactgcttt gcctgccggc acttcaatga cagtggagcc     960
tgtgtacctc gctgtccaca gcctcttgtc tacaacaagc taactttcca gctggaaccc    1020
aatccccaca ccaagtatca gtatggagga gtttgtgtag ccagctgtcc ccataacttt    1080
gtggtggatc aaacatcctg tgtcagggcc tgtcctcctg acaagatgga agtagataaa    1140
aatgggctca gatgtgtga  gccttgtggg ggactatgtc ccaaagcctg tgagggaaca    1200
ggctctggga gccgcttcca gactgtggac tcgagcaaca ttgatggatt tgtgaactgc    1260
accaagatcc tgggcaacct ggactttctg atcaccggcc tcaatggaga ccctggcac     1320 aagatccctg ccctggaccc agagaagctc aatgtcttcc ggacagtacg ggagatcaca    1380
ggttacctga acatccagtc ctggccgccc cacatgcaca acttcagtgt tttttccaat    1440
ttgacaacca ttggaggcag aagcctctac aaccgggggct tctcattgtt gatcatgaag    1500
```

```
aacttgaatg tcacatctct gggcttccga tccctgaagg aaattagtgc tgggcgtatc   1560
tatataagtg ccaataggca gctctgctac caccactctt tgaactggac caaggtgctt   1620
cgggggccta cggaagagcg actagacatc aagcataatc ggccgcgcag agactgcgtg   1680
gcagagggca aagtgtgtga cccactgtgc tcctctgggg gatgctgggg cccaggccct   1740
ggtcagtgct tgtcctgtcg aaattatagc cgaggaggtg tctgtgtgac ccactgcaac   1800
tttctgaatg gggagcctcg agaatttgcc catgaggccg aatgcttctc ctgccacccg   1860
gaatgccaac ccatgggggg cactgccaca tgcaatggct cgggctctga tacttgtgct   1920
caatgtgccc attttcgaga tgggcccccac tgtgtgagca gctgccccca tggagtccta   1980
ggtgccaagg gcccaatcta caagtaccca gatgttcaga atgaatgtcg gccctgccat   2040
gagaactgca cccaggggtg taaaggacca gagcttcaag actgtttagg acaaacactg   2100
gtgctgatcg gcaaaaccca tctgacaatg gctttgacag tgatagcagg attggtagtg   2160
attttcatga tgctgggcgg cacttttctc tactggcgtg ggcgccggat tcagaataaa   2220
agggctatga ggcgatactt ggaacggggt gagagcatag agcctctgga ccccagtgag   2280
aaggctaaca aagtcttggc cagaatcttc aaagagacag agctaaggaa gcttaaagtg   2340
cttggctcgg gtgtctttgg aactgtgcac aaaggagtgt ggatccctga gggtgaatca   2400
atcaagattc cagtctgcat taaagtcatt gaggacaaga gtggacggca gagtttttcaa   2460
gctgtgacag atcatatgct ggccattggc agcctggacc atgcccacat tgtaaggctg   2520
ctgggactat gcccagggtc atctctgcag cttgtcactc aatatttgcc tctgggttct   2580
ctgctggatc atgtgagaca acaccggggg gcactggggc cacagctgct gctcaactgg   2640
ggagtacaaa ttgccaaggg aatgtactac cttgaggaac atggtatggt gcatagaaac   2700
ctggctgccc gaaacgtgct actcaagtca cccagtcagg ttcaggtggc agattttggt   2760
gtggctgacc tgctgcctcc tgatgataag cagctgctat acagtgaggc caagactcca   2820
attaagtgga tggcccttga gagtatccac tttgggaaat acacacacca gagtgatgtc   2880
tggagctatg tgtgtgacagt ttgggagttg atgaccttcg gggcagagcc ctatgcaggg   2940
ctacgattgg ctgaagtacc agacctgcta gagaaggggg agcggttggc acagccccag   3000
atctgcacaa ttgatgtcta catggtgatg gtcaagtgtt ggatgattga tgagaacatt   3060
cgcccaacct ttaaagaact agccaatgag ttcaccagga tggcccgaga cccaccacgg   3120
tatctggtca taaagagaga gagtgggcct ggaatagccc ctgggccaga gccccatggt   3180
ctgacaaaca agaagctaga ggaagtagag ctggagccag aactagacct agacctagac   3240
ttggaagcag aggaggacaa cctggcaacc accacactgg gctccgccct cagcctacca   3300
gttgaacac ttaatcggcc acgtgggagc cagagccttt taagtccatc atctggatac   3360
atgcccatga accagggtaa tcttgggggg tcttgccagg agtctgcagt ttctgggagc   3420
agtgaacggt gccccgtcc agtctctcta cacccaatgc cacggggatg cctggcatca   3480
gagtcatcag aggggcatgt aacaggctct gaggctgagc tccaggagaa agtgtcaatg   3540
tgtagaagcc ggagcaggag ccggagccca cggccacgcg gagatagcgc ctaccattcc   3600
cagcgccaca gtctgctgac tcctgttacc ccactctccc cacccgggtt agaggaagag   3660
gatgtcaacg gttatgtcat gccagataca cacctcaaag gtactccctc ctcccggaaa   3720
ggcaccctttt cttcagtggg tctcagttct gtcctgggta ctgaagaaga agatgaagat   3780
gaggagtatg aatacatgaa ccggaggaga aggcacagtc cacctcatcc ccctaggcca   3840
agttcccttg aggagctggg ttatgagtac atggatgtgg ggtcagacct cagtgcctct   3900
```

```
ctgggcagca cacagagttg cccactccac cctgtaccca tcatgcccac tgcaggcaca    3960
actccagatg aagactatga atatatgaat cggcaacgag atggaggtgg tcctgggggt    4020
gattatgcag ccatggggc ctgcccagca tctgagcaag ggtatgaaga gatgagagct    4080
tttcaggggc ctggacatca ggcccccat gtccattatg cccgcctaaa aactctacgt    4140
agcttagagg ctacagactc tgcctttgat aaccctgatt actggcatag caggcttttc    4200
cccaaggcta atgcccagag aacgtaactc ctgctccctg tggcactcag ggagcattta    4260
atggcagcta gtgcctttag agggtaccgt cttctcccta ttccctctct ctcccaggtc    4320 ccagccctt ttccccagtc ccagacaatt ccattcaatc tttggaggct tttaaacatt    4380
ttgacacaaa attcttatgg tatgtagcca gctgtgcact ttcttctctt tcccaacccc    4440
aggaaaggtt ttccttattt tgtgtgcttt cccagtccca ttcctcagct tcttcacagg    4500
cactcctgga gatatgaagg attactctcc atatcccttc ctctcaggct cttgactact    4560
tggaactagg ctcttatgtg tgcctttgtt tcccatcaga ctgtcaagaa gaggaaaggg    4620
aggaaaccta gcagaggaaa gtgtaatttt ggtttatgac tcttaacccc ctagaaagac    4680
agaagcttaa aatctgtgaa gaaagaggtt aggagtagat attgattact atcataattc    4740
agcacttaac tatgagccag gcatcatact aaacttcacc tacattatct cacttagtcc    4800
tttatcatcc ttaaaacaat tctgtgacat acatattatc tcattttaca caaagggaag    4860
tcgggcatgg tggctcatgc ctgtaatctc agcactttgg gaggctgagg cagaaggatt    4920
acctgaggca aggagtttga gaccagctta gccaacatag taagaccccc atctc        4975

<210> SEQ ID NO 356
<211> LENGTH: 4627
<212> TYPE: DNA
<213> ORGANISM: Homo sapiens

<400> SEQUENCE: 356
tcacttgcct gatatttcca gtgtcagagg gacacagcca acgtggggtc ccttctaggc      60
tgacagccgc tctccagcca ctgccgcgag cccgtctgct cccgccctgc ccgtgcactc     120
tccgcagccg ccctccgcca agccccagcg cccgctccca tcgccgatga ccgcggggag     180
gaggatggag atgctctgtg ccggcagggt ccctgcgctg ctgctctgcc tgggtttcca     240
tcttctacag gcagtcctca gtacaactgt gattccatca tgtatcccag agagtccag     300 tgataactgc acagctttag ttcagacaga agacaatcca cgtgtggctc aagtgtcaat     360
aacaaagtgt agctctgaca tgaatggcta ttgtttgcat ggacagtgca tctatctggt     420
ggacatgagt caaaactact gcaggtgtga agtgggttat actggtgtcc gatgtgaaca     480
cttcttttta accgtccacc aacctttaag caaagagtat gtggctttga ccgtgattct     540 tattatttg tttcttatca cagtcgtcgg ttccacatat tatttctgca gatggtacag     600
aaatcgaaaa agtaaagaac caagaagga atatgagaga gttacctcag gggatccaga     660
gttgccgcaa gtctgaatgg cgccatcaaa cttatgggca gggataacag tgtgcctggt     720
taatattaat attccatttt attaataata tttatgttgg gtcaagtgtt aggtcaataa     780
cactgtattt taatgtactt gaaaaatgtt tttattttg ttttattttt gacagactat     840
ttgctaatgt ataatgtgca gaaaatattt aatatcaaaa gaaaattgat atttttatac     900
aagtaatttc ctgagctaaa tgcttcattg aaagcttcaa agtttatatg cctggtgcac     960
agtgcttaga agtaagcaat tcccaggtca tagctcaaga attgttagca aatgacagat    1020
```

```
ttctgtaagc ctatatatat agtcaaatcg atttagtaag tatgtttttt atgttcctca    1080
aatcagtgat aattggtttg actgtaccat ggtttgatat gtagttggca ccatggtatc    1140
atatattaaa acaataatgc aattagaatt tgggagaagc aaatataggt cctgtgttaa    1200
acactacaca tttgaaacaa gctaaccctg gggagtctat ggtctcttca ctcaggtctc    1260
agctataatt ctgttatatg aggggcagtg gacagttccc tatgccaact cacgactcct    1320
acaggtacta gtcactcatc taccagattc tgcctatgta aaatgaattg aaaaacaatt    1380
ttctgtaatc tttatttaa gtagtgggca tttcatagct tcacaatgtt ccttttttgt    1440
atattacaac atttatgtga ggtaattatt gctcaacaga caattagaaa aaagtccaca    1500
cttgaagcct aaatttgtgc tttttaagaa tattttttaga ctatttcttt ttatagggggc    1560 tttgctgaat tctaacatta aatcacagcc caaaatttga tggactaatt attattttaa    1620
aatatatgaa gacaataatt ctacatgttg tcttaagatg gaaatacagt tatttcatct    1680
tttattcaag gaagttttaa ctttaataca gctcagtaaa tggcttcttc tagaatgtaa    1740
agttatgtat ttaaagttgt atcttgacac aggaaatggg aaaaaactta aaaattaata    1800
tggtgtattt ttccaaatga aaaatctcaa ttgaaagctt ttaaaatgta gaaacttaaa    1860
cacaccttcc tgtggaggct gagatgaaaa ctagggctca ttttcctgac atttgtttat    1920
tttttggaag agacaaagat ttcttctgca ctctgagccc ataggtctca gagagttaat    1980 aggagtatttt ttgggctatt gcataaggag ccactgctgc caccactttt ggattttatg    2040
ggaggctcct tcatcgaatg ctaaaccttt gagtagagtc tccctggatc acataccagg    2100
tcagggagga tctgttcttc ctctacgttt atcctggcat gtgctagggt aaacgaaggc    2160
ataataagcc atggctgacc tctggagcac caggtgccag gacttgtctc catgtgtatc    2220
catgcattat ataccctggt gcaatcacac gactgtcatc taaagtcctg gccctggccc    2280
ttactattag gaaaataaac agacaaaaac aagtaaatat atatggtcct atacatattg    2340
tatatatatt catatacaaa catgtatgta tacatgacct taatggatca tagaattgca    2400
gtcatttggt gctctgctaa ccatttatat aaaacttaaa aacaagagaa aagaaaaatc    2460
aattagatct aaacagttat ttctgtttcc tatttaatat agctgaagtc aaaatatgta    2520
agaacacatt ttaaatactc tacttacagt tggccctctg tggttagttc cacatctgtg    2580
gattcaacca accaaggacg gaaaatgctt aaaaaataat acaacaacaa caaaaaatac    2640
attataacaa ctatttactt ttttttttttt cttttttgaga tggagtctcg ctctgttgcc    2700
caggttggag tgcagtggca cgatctcggc tcactgcaac ctcacctccc gggttcaaga    2760
gatcctcctg cctcagcctc ctgagcagct gggactacag gcgcatgcca ccatgcccag    2820 ctaattttttg tattttttagt agaggcgggg tttcaccatg ttggccagga tggtctcaat    2880
ctcctaacct tgagatccac cctccacagc ctcccaaact gctgggatta caggcgtgag    2940
ccaccgcacg tagcatttac attaggtatt acaagtaatg taaagatgat ttaagtatac    3000
aggaggatgt gaataggtta tatgcaagca ctatgcccct ttatataagt gacttgaaca    3060
tctgtgcccg attttagtat gtgcaggggg gcgatctggg aatcagtccc ctgtggatac    3120
caaggtacaa ctgtatttat taacgcttac tagatgtgag gagagtctga atattttcag    3180
tgatcttggc tgtttcaaaa aaatctattg acttttcaat aaatcagctg caatccattt    3240
atttcattta caaagagattt attgtaagcc tctcaatctt ggttttttcag ttgatcttaa    3300 gcatgtcaat tcataaaaac aagtcatttt tgtatttttc atctttaaga atgcttaaaa    3360
aagctaatcc ctaaaatagt tagatctttg taaatgcata ttaaataata aagtatgacc    3420
```

```
cacattactt tttatgggtg aaaataagac aaaaataata gttttagtga ggatggtgct    3480
gagtaaacat aaaaactgat ttgctctcag ctgatgtgtc ctgtacacag tgggaagatt    3540
ttagttcaca cttagtctaa ctcccccatt ttacagattt ctcactatat atatttctag    3600
aaggggctat gcatattcaa tgtattgaga accaaagcaa ccacaaatgc ataaatgcat    3660
aatttatggt cttcaaccaa ggccacataa taacccagtt aacttactct ttaaccagga    3720
atattaagtt ctataactag tactcaaggt ttaaccttaa aattaagatt tccttaacct    3780
taaccttaaa attgatatta tattaaacat acataataca atgtaactcc actgttctcc    3840
tgaatatttt ttgctctaat ctctctgccg aaagtcaaag tgatgggaga attggtatac    3900
tggtatgact acgtcttaag tcagatttt atttatgagt ctttgagact aaattcaatc    3960
accaccaggt atcaaatcaa cttttatgca gcaaatatat gattctagtg tctgactttt    4020
gttaaattca gtaatgcagt ttttaaaaac ctgtatctga cccactttgt aattttttgct    4080 ccaatatcca ttctgtagac ttttgaaaaa aaagttttta atttgatgcc caatatattc    4140
tgaccgttaa aaaattcttg ttcatatggg agaagggggaa gtaatgactt gtacaaacag    4200
tatttctggt gtatatttta atgttttttaa aaagagtaat ttcatttaaa tatctgttat    4260
tcaaatttga tgatgttaaa tgtaataataa tgtatttttct ttttattttg cactctgtaa    4320
ttgcactttt taagtttgaa gagccatttt ggtaaacggt ttttattaaa gatgctatgg    4380
aacataaagt tgtattgcat gcaatttaaa gtaacttatt tgactatgaa tattatcgga    4440
ttactgaatt gtatcaattt gtttgtgttc aatatcagct ttgataattg tgtaccttaa    4500
gatattgaag gagaaaatag ataatttaca agatattatt aattttttatt tattttttctt    4560 gggaattgaa aaaaattgaa ataaataaaa atgcattgaa catcttgcat tcaaaatctt    4620
cactgac                                                              4627
```

<210> SEQ ID NO 357
<211> LENGTH: 2634
<212> TYPE: DNA
<213> ORGANISM: Homo sapiens

<400> SEQUENCE: 357

```
ggcacgaggc tgagtgtccg tctcgcgccc ggaagcgggc gaccgccgtc agcccggagg      60
aggaggagga ggaggaggag gaggggggcgg ccatggggct gctgtcccag ggctcgccgc    120
tgagctggga ggaaaccaag cgccatgccg accacgtgcg gcggcacggg atcctccagt    180
tcctgcacat ctaccacgcc gtcaaggacc ggcacaagga cgttctcaag tggggcgatg    240
aggtggaata catgttggta tcttttgatc atgaaaataa aaaagtccgg ttggtcctgt    300
ctggggagaa agttcttgaa actctgcaag agaaggggga aaggacaaac ccaaaccatc    360 ctacccttttg gagaccagag tatgggagtt acatgattga agggacacca ggacagccct    420
acggaggaac aatgtccgag ttcaatacag ttgaggccaa catgcgaaaa cgccggaagg    480
aggctacttc tatattagaa gaaaatcagg ctctttgcac aataacttca tttcccagat    540
taggctgtcc tgggttcaca ctgcccgagg tcaaacccaa cccagtggaa ggaggagctt    600
ccaagtccct cttctttcca gatgaagcaa taaacaagca ccctcgcttc agtaccttaa    660
caagaaatat ccgacatagg agaggagaaa aggttgtcat caatgtacca atatttaagg    720
acaagaatac accatctcca tttatagaaa catttactga ggatgatgaa gcttcaaggg    780
cttctaagcc ggatcatatt tacatggatg ccatgggatt tggaatgggc aattgctgtc    840
```

| | | |
|---|---|---|
| tccaggtgac attccaagcc tgcagtatat ctgaggccag atacctttat gatcagttgg | 900 | |
| ctactatctg tccaattgtt atggctttga gtgctgcatc tcccttttac cgaggctatg | 960 | |
| tgtcagacat tgattgtcgc tggggagtga tttctgcatc tgtagatgat agaactcggg | 1020 | |
| aggagcgagg actggagcca ttgaagaaca ataactatag gatcagtaaa tcccgatatg | 1080 | |
| actcaataga cagctattta tctaagtgtg gtgagaaata taatgacatc gacttgacga | 1140 | |
| tagataaaga gatctacgaa cagctgttgc aggaaggcat tgatcatctc ctggcccagc | 1200 | |
| atgttgctca tctctttatt agagacccac tgacactgtt tgaagagaaa atacacctgg | 1260 | |
| atgatgctaa tgagtctgac cattttgaga atattcagtc cacaaattgg cagacaatga | 1320 | |
| gatttaagcc ccctcctcca aactcagaca ttggatggag agtagaattt cgacccatgg | 1380 | |
| aggtgcaatt aacagacttt gagaactctg cctatgtggt gtttgtggta ctgctcacca | 1440 | |
| gagtgatcct ttcctacaaa ttggattttc tcattccact gtcaaaggtt gatgagaaca | 1500 | |
| tgaaggtagc acagaaaaga gatgctgtct tgcagggaat gttttatttc aggaaagata | 1560 | |
| tttgcaaagg tggcaatgca gtggtggatg gttgtggcaa ggcccagaac agcacggagc | 1620 | |
| tcgctgcaga ggagtacacc ctcatgagca tagacaccat catcaatggg aaggaaggtg | 1680 | |
| tgtttcctgg actgatccca attctgaact cttaccttga aaacatggaa gtggatgtgg | 1740 | |
| acaccagatg tagtattctg aactacctaa agctaattaa gaagagagca tctggagaac | 1800 | |
| taatgacagt tgccagatgg atgagggagt ttatcgcaaa ccatcctgac tacaagcaag | 1860 | |
| acagtgtcat aactgatgaa atgaattata gccttatttt gaagtgtaac caaattgcaa | 1920 | |
| atgaattatg tgaatgccca gagttacttg gatcagcatt taggaaagta aaatatagtg | 1980 | |
| gaagtaaaac tgactcatcc aactagacat tctacagaaa gaaaaatgca ttattgacga | 2040 | |
| actggctaca gtaccatgcc tctcagcccg tgtgtataat atgaagacca aatgatagaa | 2100 | |
| ctgtactgtt ttctgggcca gtgagccaga aattgattaa ggctttcttt ggtaggtaaa | 2160 | |
| tctagagttt atacagtgta catgtacata gtaaagtatt tttgattaac aatgtatttt | 2220 | |
| aataacatat ctaaagtcat catgaactgg cttgtacatt tttaaattct tactctggag | 2280 | |
| caacctactg tctaagcagt tttgtaaatg tactggtaat tgtacaatac ttgcattcca | 2340 | |
| gagttaaaat gttactgta aattttgtt cttttaaaga ctacctggga cctgatttat | 2400 | |
| tgaaattttt ctctttaaaa acattttctc tcgttaattt tcctttgtca tttcctttgt | 2460 | |
| tgtctacatt aaatcacttg aatccattga aagtgcttca agggtaatct tgggtttcta | 2520 | |
| gcaccttatc tatgatgttt cttttgcaat tggaataatc acttggtcac cttgccccaa | 2580 | |
| gctttcccct ctgaataaat acccattgaa ctctgaaaaa aaaaaaaaa aaaa | 2634 | |

<210> SEQ ID NO 358
<211> LENGTH: 1246
<212> TYPE: DNA
<213> ORGANISM: Homo sapiens

<400> SEQUENCE: 358

| | | |
|---|---|---|
| gaccagccta cagccgcctg catctgtatc cagcgccagg tcccgccagt cccagctgcg | 60 | |
| cgcgcccccc agtcccgcac ccgttcggcc caggctaagt tagccctcac catgccggtc | 120 | |
| aaaggaggca ccaagtgcat caaataccotg ctgttcggat ttaacttcat cttctggctt | 180 | |
| gccgggattg ctgtccttgc cattggacta tggctccgat tcgactctca gaccaagagc | 240 | |
| atcttcgagc aagaaactaa taataataat tccagcttct acacaggagt ctatattctg | 300 | |
| atcggagccg gcgccctcat gatgctggtg ggcttcctgg gctgctgcgg ggctgtgcag | 360 | |

```
gagtcccagt gcatgctggg actgttcttc ggcttcctct tggtgatatt cgccattgaa    420
atagctgcgg ccatctgggg atattcccac aaggatgagg tgattaagga agtccaggag    480
ttttacaagg acacctacaa caagctgaaa accaaggatg agccccagcg ggaaacgctg    540
aaagccatcc actatgcgtt gaactgctgt ggtttggctg ggggcgtgga acagtttatc    600
tcagacatct gccccaagaa ggacgtactc gaaaccttca ccgtgaagtc ctgtcctgat    660
gccatcaaag aggtcttcga caataaattc cacatcatcg gcgcagtggg catcggcatt    720
gccgtggtca tgatatttgg catgatcttc agtatgatct tgtgctgtgc tatccgcagg    780
aaccgcgaga tggtctagag tcagcttaca tccctgagca ggaaagttta cccatgaaga    840
ttggtgggat tttttgtttg tttgttttgt tttgttgtt gtttgttgtt tgttttttg     900 ccactaattt tagtattcat tctgcattgc tagataaaag ctgaagttac tttatgtttg    960
tcttttaatg cttcattcaa tattgacatt tgtagttgag cgggggttt ggtttgcttt    1020 ggtttatatt ttttcagttg tttgtttttg cttgttatat taagcagaaa tcctgcaatg    1080
aaaggtacta tatttgctag actctagaca agatattgta cataaaagaa tttttttgtc    1140
tttaaataga tacaaatgtc tatcaacttt aatcaagttg taacttatat tgaagacaat    1200
ttgatacata ataaaaaatt atgacaatgt caaaaaaaaa aaaaaa                   1246

<210> SEQ ID NO 359
<211> LENGTH: 2360
<212> TYPE: DNA
<213> ORGANISM: Homo sapiens

<400> SEQUENCE: 359
gctacgcggg ccacgctgct ggctggcctg acctaggcgc gcggggtcgg gcggccgcgc     60
gggcgggctg agtgagcaag acaagacact caagaagagc gagctgcgcc tgggtcccgg    120
ccaggcttgc acgcagaggc gggcggcaga cggtgcccgg cggaatctcc tgagctccgc    180
cgcccagctc tggtgccagc gcccagtggc cgccgcttcg aaagtgactg gtgcctcgcc    240
gcctcctctc ggtgcgggac catgaagctg ctgccgtcgg tggtgctgaa gctctttctg    300
gctgcagttc tctcggcact ggtgactggc gagagcctgg agcggcttcg gagagggcta    360
gctgctggaa ccagcaaccc ggaccctccc actgtatcca cggaccagct gctaccccta    420
ggaggcggcc gggaccggaa agtccgtgac ttgcaagagg cagatctgga ccttttgaga    480
gtcactttat cctccaagcc acaagcactg gccacaccaa acaaggagga gcacgggaaa    540
agaaagaaga aaggcaaggg gctagggaag aagagggacc catgtcttcg gaaatacaag    600
gacttctgca tccatggaga atgcaaatat gtgaaggagc tccgggctcc ctcctgcatc    660
tgccacccgg gttaccatgg agagaggtgt catgggctga gcctcccagt ggaaaatcgc    720
ttatatacct atgaccacac aaccatcctg gccgtggtgg ctgtggtgct gtcatctgtc    780
tgtctgctgg tcatcgtggg gcttctcatg tttaggtacc ataggagagg aggttatgat    840
gtggaaaatg aagagaaagt gaagttgggc atgactaatt cccactgaga gagacttgtg    900
ctcaaggaat cggctgggga ctgctacctc tgagaagaca caaggtgatt tcagactgca    960
gaggggaaag acttccatct agtcacaaag actccttcgt ccccagttgc cgtctaggat    1020
tgggcctccc ataattgctt tgccaaaata ccagagcctt caagtgccaa acagagtatg    1080
tccgatggta tctgggtaag aagaaagcaa aagcaaggga ccttcatgcc cttctgattc    1140
ccctccacca aaccccactt ccctcataa gtttgtttaa acacttatct tctggattag    1200
```

| | |
|---|---|
| aatgccggtt aaattccata tgctccagga tctttgactg aaaaaaaaaa agaagaagaa | 1260 |
| gaaggagagc aagaaggaaa gatttgtgaa ctggaagaaa gcaacaaaga ttgagaagcc | 1320 |
| atgtactcaa gtaccaccaa gggatctgcc attgggaccc tccagtgctg gatttgatga | 1380 |
| gttaactgtg aaataccaca agcctgagaa ctgaattttg ggacttctac ccagatggaa | 1440 |
| aaataacaac tatttttgtt gttgttgttt gtaaatgcct cttaaattat atatttattt | 1500 |
| tattctatgt atgttaattt atttagtttt taacaatcta acaataatat ttcaagtgcc | 1560 |
| tagactgtta ctttggcaat ttcctggccc tccactcctc atccccacaa tctggcttag | 1620 |
| tgccacccac ctttgccaca aagctaggat ggttctgtga cccatctgta gtaatttatt | 1680 |
| gtctgtctac atttctgcag atcttccgtg gtcagagtgc cactgcggga gctctgtatg | 1740 |
| gtcaggatgt aggggttaac ttggtcagag ccactctatg agttggactt cagtcttgcc | 1800 |
| taggcgattt tgtctaccat ttgtgttttg aaagcccaag gtgctgatgt caaagtgtaa | 1860 |
| cagatatcag tgtctccccg tgtcctctcc ctgccaagtc tcagaagagg ttgggcttcc | 1920 |
| atgcctgtag cttcctggt ccctcacccc catggcccca ggccacagcg tgggaactca | 1980 |
| cttcccttg tgtcaagaca tttctctaac tcctgccatt cttctggtgc tactccatgc | 2040 |
| aggggtcagt gcagcagagg acagtctgga gaaggtatta gcaaagcaaa aggctgagaa | 2100 |
| ggaacaggga acattggagc tgactgttct tggtaactga ttacctgcca attgctaccg | 2160 |
| agaaggttgg aggtggggaa ggctttgtat aatcccaccc acctcaccaa aacgatgaag | 2220 |
| gtatgctgtc atggtccttt ctggaagttt ctggtgccat ttctgaactg ttacaacttg | 2280 |
| tatttccaaa cctggttcat atttatactt tgcaatccaa ataaagataa cccttattcc | 2340 |
| ataaaaaaaa aaaaaaaaaa | 2360 |

<210> SEQ ID NO 360
<211> LENGTH: 1433
<212> TYPE: DNA
<213> ORGANISM: Homo sapiens

<400> SEQUENCE: 360

| | |
|---|---|
| attcggggcg agggaggagg aagaagcgga ggaggcggct cccgctcgca gggccgtgca | 60 |
| cctgcccgcc cgcccgctcg ctcgctcgcc cgccgcgccg cgctgccgac cgccagcatg | 120 |
| ctgccgagag tgggctgccc cgcgctgccg ctgccgccgc cgccgctgct gccgctgctg | 180 |
| ccgctgctgc tgctgctact gggcgcgagt ggcggcggcg gcggggcgcg cgcggaggtg | 240 |
| ctgttccgct gcccgccctg cacacccgag cgcctggccg cctgcgggcc ccgccggtt | 300 |
| gcgccgcccg ccgcggtggc cgcagtggcc ggaggcgccc gcatgccatg cgcggagctc | 360 |
| gtccgggagc cgggctgcgg ctgctgctcg gtgtgcgccc ggctggaggg cgaggcgtgc | 420 |
| ggcgtctaca ccccgcgctg cggccagggg ctgcgctgct atccccaccc gggctccgag | 480 |
| ctgccccctgc aggcgctggt catgggcgag ggcacttgtg agaagcgccg ggacgccgag | 540 |
| tatggcgcca gccggagca ggttgcagac aatggcgatg accactcaga aggaggcctg | 600 |
| gtggagaacc acgtggacag caccatgaac atgttgggcg gggaggcag tgctggccgg | 660 |
| aagcccctca gtcgggtat gaaggagctg gccgtgttcc gggagaaggt cactgagcag | 720 |
| caccggcaga tgggcaaggg tggcaagcat caccttggcc tggaggagcc caagaagctg | 780 |
| cgaccacccc ctgccaggac tccctgccaa caggaactgg accaggtcct ggagcggatc | 840 |
| tccaccatgc gccttccgga tgagcggggc cctctggagc acctctactc cctgcacatc | 900 |
| cccaactgtg acaagcatgg cctgtacaac ctcaaacagt gcaagatgtc tctgaacggg | 960 |

```
cagcgtgggg agtgctggtg tgtgaacccc aacaccggga agctgatcca gggagccccc    1020
accatccggg gggaccccga gtgtcatctc ttctacaatg agcagcagga ggcttgcggg    1080
gtgcacaccc agcggatgca gtagaccgca gccagccggt gcctggcgcc cctgcccccc    1140 gccctctcc aaacaccggc agaaaacgga gagtgcttgg gtggtgggtg ctggaggatt     1200
ttccagttct gacacacgta tttatatttg gaaagagacc agcaccgagc tcggcacctc    1260
cccggcctct ctcttcccag ctgcagatgc cacacctgct ccttcttgct ttccccgggg    1320
gaggaagggg gttgtggtcg gggagctggg gtacaggttt ggggagggg aagagaaatt    1380 tttattttg aaccctgtg tccctttgc ataagattaa aggaaggaaa agt              1433

<210> SEQ ID NO 361
<211> LENGTH: 1632
<212> TYPE: DNA
<213> ORGANISM: Homo sapiens

<400> SEQUENCE: 361
gccggccgaa cccagacccg aggttttaga agcagagtca ggcgaagctg ggccagaacc      60
gcgacctccg caaccttgag cggcatccgt ggagtgcgcc tgcgcagcta cgaccgcagc     120
aggaaagcgc cgccggccag gcccagctgt ggccggacag ggactggaag agaggacgcg     180
gtcgagtagg tgtgcaccag ccctggcaac gagagcgtct accccgaact ctgctggcct     240
tgaggtgggg aagccgggga gggcagttga ggaccccgcg gaggcgcgtg actggttgag     300
cgggcaggcc agcctccgag ccgggtggac acaggtttta aaacatgaat cctacactca     360
tccttgctgc cttttgcctg ggaattgcct cagctactct aacatttgat cacagtttag     420
aggcacagtg gaccaagtgg aaggcgatgc acaacagatt atacggcatg aatgaagaag     480
gatggaggag agcagtgtgg gagaagaaca tgaagatgat tgaactgcac aatcaggaat     540
acagggaagg gaaacacagc ttcacaatgg ccatgaacgc ctttggagac atgaccagtg     600
aagaattcag gcaggtgatg aatggctttc aaaaccgtaa gcccaggaag gggaaagtgt     660
tccaggaacc tctgttttat gaggcccca gatctgtgga ttggagagag aaaggctacg      720
tgactcctgt gaagaatcag ggtcagtgtg gttcttgttg ggcttttagt gctactggtg     780
ctcttgaagg acagatgttc cggaaaactg gggagcttat ctcactgagt gagcagaatc     840
tggtagactg ctctgggcct caaggcaatg aaggctgcaa tggtggccta atggattatg     900 cttttccagta tgttcaggat aatggaggcc tggactctga ggaatcctat ccatatgagg     960
caacagaaga atcctgtaag tacaatccca gtattctgt tgctaatgac accggctttg     1020
tggacatccc taagcaggag aaggccctga tgaaggcagt tgcaactgtg gggcccattt    1080
ctgttgctat tgatgcaggt catgagtcct tcctgttcta taagaaggc atttatttg     1140 agccagactg tagcagtgaa gacatggatc atggtgtgct ggtggttggc tacgatttg     1200 aaagcacaga atcagataac aataaatatt ggctggtgaa gaacagctgg ggtgaagaat    1260
ggggcatgtg tggctacgta aagatggcca aagccggag aaaccattgt ggaattgcct    1320
cagcagccag ctaccccact gtgtgagctg gtggacggtg atgaggaagg acttgactgg    1380
ggatggcgca tgcatgggag gaattcatct tcagtctacc agccccgct gtgtcggata    1440 cacactcgaa tcattgaaga tccgagtgtg atttgaattc tgtgatattt tcacactggt    1500
aaatgttacc tctattttaa ttactgctat aaataggttt atattattga ttcacttact    1560
gactttgcat tttcgtttt aaaaggatgt ataaattttc acctgtttaa ataaaattta    1620
```

-continued

| | |
|---|---|
| atttcaaatg ta | 1632 |

<210> SEQ ID NO 362
<211> LENGTH: 2756
<212> TYPE: DNA
<213> ORGANISM: Homo sapiens

<400> SEQUENCE: 362

| | |
|---|---|
| atgctgtcct tccagtaccc cgacgtgtac cgcgacgaga ccgccgtaca ggattatcat | 60 |
| ggtcataaaa tttgtgaccc ttacgcctgg cttgaagacc ccgacagtga acagactaag | 120 |
| gcctttgtgg aggcccagaa taagattact gtgccatttc ttgagcagtg tcccatcaga | 180 |
| ggtttataca agagagaat gactgaacta tatgattatc ccagtatag ttgccacttc | 240 |
| aagaaaggaa acggtattt ttatttttac aatacaggtt tgcagaacca gcgagtatta | 300 |
| tatgtacagg attccttaga gggtgaggcc agagtgttcc tggaccccaa catactgtct | 360 |
| gacgatggca cagtggcact ccgaggttat gcgttcagcg aagatggtga atattttgcc | 420 |
| tatggtctga gtgccagtgg ctcagactgg gtgacaatca agttcatgaa agttgatggt | 480 |
| gccaaagagc ttccagatgt gcttgaaaga gtcaagttca gctgtatggc ctggacccat | 540 |
| gatgggaagg gaatgttcta caactcatac cctcaacagg atggaaaaag tgatggcaca | 600 |
| gagacatcta ccaatctcca ccaaaagctc tactaccatg tcttgggaac cgatcagtca | 660 |
| gaagatattt tgtgtgctga gtttcctgat gaacctaaat ggatgggtgg agctgagtta | 720 |
| tctgatgatg gccgctatgt cttgttatca ataagggaag gatgtgatcc agtaaaccga | 780 |
| ctctggtact gtgacctaca gcaggaatcc agtggcatcg cgggaatcct gaagtgggta | 840 |
| aaactgattg acaactttga aggggaatat gactacgtga ccaatgaggg ggcggtgttc | 900 |
| acattcaaga cgaatcgcca gtctcccaac tatcgcgtga tcaacattga cttcagggat | 960 |
| cctgaagagt ctaagtggaa agtacttgtt cctgagcatg agaaagatgt cttagaatgg | 1020 |
| atagcttgtg tcaggtccaa cttcttggtc ttatgctacc tccatgacgt caagaacatt | 1080 |
| ctgcagctcc atgacctgac tactggtgct ctccttaaga ccttcccgct cgatgtcggc | 1140 |
| agcattgtag ggtacagcgg tcagaagaag gacactgaaa tcttctatca gtttacttcc | 1200 |
| tttttatctc caggtatcat ttatcactgt gatcttacca agaggagct ggagccaaga | 1260 |
| gttttccgag aggtgaccgt aaaaggaatt gatgcttctg attaccagac agtccagatt | 1320 |
| ttctacccta gcaaggatgg tacgaagatt ccaatgttca ttgtgcataa aaaaagcata | 1380 |
| aaattggatg gctctcatcc agctttctta tatggctatg gcggcttcaa catatccatc | 1440 |
| acacccaact acagtgtttc caggcttatt tttgtgagac acatgggtgg tatcctggca | 1500 |
| gtggccaaca tcagaggagg tggcgaatat ggagagacgt ggcataaagg tggtatcttg | 1560 |
| gccaacaaac aaaactgctt tgatgacttt cagtgtgctg ctgagtatct gatcaaggaa | 1620 |
| ggttacacat ctcccaagag gctgactatt aatggaggtt caaatggagg cctcttagtg | 1680 |
| gctgcttgtg caaatcagag acctgacctc tttggttgtg ttattgccca agttggagta | 1740 |
| atggacatgc tgaagtttca taaatatacc atcggccatg cttggaccac tgattatggg | 1800 |
| tgctcggaca gcaaacaaca ctttgaatgg cttgtcaaat actctccatt gcataatgtg | 1860 |
| aagttaccag aagcagatga catccagtac ccgtccatgc tgctcctcac tgctgaccat | 1920 |
| gatgaccgcg tggtcccgct tcactccctg aagttcattg ccaccccttca gtacatcgtg | 1980 |
| ggccgcagca ggaagcaaag caaccccctg cttatccacg tggacaccaa ggcgggccac | 2040 |
| ggggcgggga agcccacagc caaagtgata gaggaagtct cagacatgtt tgcgttcatc | 2100 |

```
gcgcggtgcc tgaacgtcga ctggattcca taaacagttt tcgtgcttcc tcctgacagc    2160
gacagaaaac ctcaagggct ttcccacgtt gacaccaaga aaccactggg cataatgctt    2220
ccccacggga acattattcc tggactgaca ggctacagtt gaacagaact gccgtgggaa    2280
ttttatcttt tttaggcttc tccttttag caaggccttg gtgtttcttt ttccaccctg    2340
tctaggcaca tgtggttttt tggtgttttt tttaagggca tgttgggata aatagctaaa    2400
tggcaacaaa cacattgtga atattagatt gctgaattaa ggatcatagt cgggcatact    2460
tatctatatc cataacctct atatctttaa ataaatgtga gaactgttct catggagaag    2520
acttctttgc aacaataata aatgttattt aagaatgaca gggatttact tccggtttct    2580
tcatattgag gggcaactcc agaagtggag ttttctgtga gaataaagca tttcacctttt   2640 ctgcaacaag ttagttttca agcagttaag tcatagaatg tttgttagct gtgaaaataa    2700
gttgttcatc caaaaaaaaa aaaaaaaaaa aaaaaaaaaa aaaaaaaaag gaattc        2756
```

<210> SEQ ID NO 363
<211> LENGTH: 2768
<212> TYPE: DNA
<213> ORGANISM: Homo sapiens

<400> SEQUENCE: 363

```
cactgctgtg cagggcagga aagctccatg cacatagccc agcaaagagc aacacagagc      60
tgaaaggaag actcagagga gagagataag taaggaaagt agtgatggct ctcatcccag     120
acttggccat ggaaacctgg cttctcctgg ctgtcagcct ggtgctcctc tatctatatg     180
gaacccattc acatggactt tttaagaagc ttggaattcc agggcccaca cctctgcctt     240
ttttgggaaa tattttgtcc taccataagg gcttttgtat gtttgacatg gaatgtcata     300
aaaagtatgg aaaagtgtgg ggcttttatg atggtcaaca gcctgtgctg gctatcacag     360
atcctgacat gatcaaaaca gtgctagtga aagaatgtta ttctgtcttc acaaaccgga     420
ggccttttgg tccagtggga tttatgaaaa gtgccatctc tatagctgag gatgaagaat     480
ggaagagatt acgatcattg ctgtctccaa ccttcaccag tggaaaactc aaggagatgg     540
tccctatcat tgcccagtat ggagatgtgt tggtgagaaa tctgaggcgg gaagcagaga     600
caggcaagcc tgtcaccttg aaagacgtct ttggggccta cagcatggat gtgatcacta     660
gcacatcatt tggagtgaac atcgactctc tcaacaatcc acaagacccc tttgtggaaa     720
acaccaagaa gcttttaaga tttgattttt tggatccatt ctttctctca ataacagtct     780
ttccattcct catcccaatt cttgaagtat aaatatctg tgtgtttcca agagaagtta     840
caaatttttt aagaaaatct gtaaaaagga tgaaagaaag tcgcctcgaa gatacacaaa     900
agcaccgagt ggatttcctt cagctgatga ttgactctca gaattcaaaa gaaactgagt     960
cccacaaagc tctgtccgat ctggagctcg tgcccaatc aattatcttt attttttgctg    1020 gctatgaaac cacgagcagt gttctctcct tcattatgta tgaactggcc actcaccctg    1080
atgtccagca gaaactgcag gaggaaattg atgcagtttt acccaataag gcaccaccca    1140
cctatgatac tgtgctacag atggagtatc ttgacatggt ggtgaatgaa acgctcagat    1200
tattcccaat tgctatgaga cttgagaggg tctgcaaaaa agatgttgag atcaatggga    1260
tgttcattcc caaagggtg gtggtgatga ttccaagcta tgctcttcac cgtgacccaa     1320
agtactggac agagcctgag aagttcctcc ctgaaagatt cagcaagaag aacaaggaca    1380
acatagatcc ttacatatac acaccccttt gaagtggacc cagaaactgc attggcatga    1440
```

| | | | | |
|---|---|---|---|---|
| ggtttgctct | catgaacatg | aaacttgctc | taatcagagt | ccttcagaac | ttctccttca | 1500 |
| aaccttgtaa | agaaacacag | atcccctga | aattaagctt | aggaggactt | cttcaaccag | 1560 |
| aaaaacccgt | tgttctaaag | gttgagtcaa | gggatggcac | cgtaagtgga | gcctgaattt | 1620 |
| tcctaaggac | ttctgctttg | ctcttcaaga | aatctgtgcc | tgagaacacc | agagacctca | 1680 |
| aattactttg | tgaatagaac | tctgaaatga | agatgggctt | catccaatgg | actgcataaa | 1740 |
| taaccgggga | ttctgtacat | gcattgagct | ctctcattgt | ctgtgtagag | tgttatactt | 1800 |
| gggaatataa | aggaggtgac | caaatcagtg | tgaggaggta | gatttggctc | ctctgcttct | 1860 |
| cacgggacta | tttccaccac | ccccagttag | caccattaac | tcctcctgag | ctctgataag | 1920 |
| agaatcaaca | tttctcaata | atttcctcca | caaattatta | atgaaaataa | gaattatttt | 1980 |
| gatggctcta | acaatgacat | ttatatcaca | tgttttctct | ggagtattct | ataagtttta | 2040 |
| tgttaaatca | ataaagacca | ctttacaaaa | gtattatcag | atgctttcct | gcacattaag | 2100 |
| gagaaatcta | tagaactgaa | tgagaaccaa | caagtaaata | ttttggtca | ttgtaatcac | 2160 |
| tgttggcgtg | gggcctttgt | cagaactaga | atttgattat | taacataggt | gaaagttaat | 2220 |
| ccactgtgac | tttgcccatt | gtttagaaag | aatattcata | gtttaattat | gccttttttg | 2280 |
| atcaggcaca | gtggctcacg | cctgtaatcc | tagcagtttg | ggaggctgag | ccgggtggat | 2340 |
| cgcctgaggt | caggagttca | agacaagcct | ggcctacatg | gttgaaaccc | catctctact | 2400 |
| aaaaatacac | aaattagcta | ggcatggtgg | actcgcctgt | aatctcacta | cacaggaggc | 2460 |
| tgaggcagga | gaatcacttg | aacctgggag | gcggatgttg | aagtgagctg | agattgcacc | 2520 |
| actgcactcc | agtctgggtg | agagtgagac | tcagtcttaa | aaaaatatgc | cttttttgaag | 2580 |
| cacgtacatt | ttgtaacaaa | gaactgaagc | tcttattata | ttattagttt | tgatttaatg | 2640 |
| ttttcagccc | atctcctttc | atatttctgg | gagacagaaa | acatgtttcc | ctacacctct | 2700 |
| tgcattccat | cctcaacacc | caactgtctc | gatgcaatga | acacttaata | aaaaacagtc | 2760 |
| gattggtc | | | | | 2768 |

<210> SEQ ID NO 364
<211> LENGTH: 2984
<212> TYPE: DNA
<213> ORGANISM: Homo sapiens

<400> SEQUENCE: 364

| | | | | | |
|---|---|---|---|---|---|
| gaggaggaac | agaaaagaaa | agaaaagaaa | aagtgggaaa | caaataatct | aagaatgagg | 60 |
| agaaagcaag | aagagtgacc | cccttgtggg | cactccattg | gttttatggc | gcctctactt | 120 |
| tctggagttt | gtgtaaaaca | aaatatattat | ggtctttgtg | cacatttaca | tcaagctcag | 180 |
| cctgggcggc | acagccagat | gcgagatgcg | tctctgctga | tctgagtctg | cctgcagcat | 240 |
| ggacctgggt | cttccctgaa | gcatctccag | ggctggaggg | acgactgcca | tgcaccgagg | 300 |
| gctcatccat | ccacagagca | gggcagtggg | aggagacgcc | atgaccccca | tcctcacggt | 360 |
| cctgatctgt | tcgggctga | gtctgggccc | ccggacccac | gtgcaggcag | ggcacctccc | 420 |
| caagcccacc | ctctgggctg | aaccaggctc | tgtgatcacc | caggggagtc | ctgtgaccct | 480 |
| caggtgtcag | gggggccagg | agacccagga | gtaccgtcta | tatagagaaa | agaaaacagc | 540 |
| accctggatt | acacggatcc | cacaggagct | tgtgaagaag | ggccagttcc | ccatcccatc | 600 |
| catcacctgg | gaacatgcag | ggcggtatcg | ctgttactat | ggtagcgaca | ctgcaggccg | 660 |
| ctcagagagc | agtgacccccc | tggagctggt | ggtgacagga | gcctacatca | aacccaccct | 720 |
| ctcagcccag | cccagccccg | tggtgaactc | aggagggaat | gtaaccctcc | agtgtgactc | 780 |

```
acaggtggca tttgatggct tcattctgtg taaggaagga gaagatgaac acccacaatg      840
cctgaactcc cagccccatg cccgtgggtc gtcccgcgcc atcttctccg tgggccccgt      900
gagcccgagt cgcaggtggt ggtacaggtg ctatgcttat gactcgaact ctccctatga      960
gtggtctcta cccagtgatc tcctggagct cctggtccta ggtgtttcta agaagccatc     1020
actctcagtg cagccaggtc ctatcgtggc ccctgaggag accctgactc tgcagtgtgg     1080
ctctgatgct ggctacaaca gatttgttct gtataaggac ggggaacgtg acttccttca     1140
gctcgctggc gcacagcccc aggctgggct ctcccaggcc aacttcaccc tgggccctgt     1200
gagccgctcc tacgggggcc agtacagatg ctacggtgca cacaacctct cctccgagtg     1260
gtcggccccc agcgaccccc tggacatcct gatcgcagga cagttctatg acagagtctc     1320
cctctcggtg cagccgggcc ccacggtggc ctcaggagag aacgtgaccc tgctgtgtca     1380
gtcacaggga tggatgcaaa ctttccttct gaccaaggag ggggcagctg atgacccatg     1440
gcgtctaaga tcaacgtacc aatctcaaaa ataccaggct gaattcccca tgggtcctgt     1500
gacctcagcc catgcgggga cctacaggtg ctacggctca cagagctcca aaccctacct     1560
gctgactcac cccagtgacc ccctggagct cgtggtctca ggaccgtctg ggggcccag      1620 ctccccgaca acaggcccca cctccacatc tggccctgag gaccagcccc tcaccccac      1680 cgggtcggat ccccagagtg gtctgggaag gcacctgggg gttgtgatcg gcatcttggt     1740
ggccgtcatc ctactgctcc tcctcctcct cctcctcttc ctcatcctcc gacatcgacg     1800
tcagggcaaa cactggacat cgacccagag aaaggctgat ttccaacatc ctgcaggggc     1860
tgtggggcca gagcccacag acagaggcct gcagtggagg tccagcccag ctgccgatgc     1920
ccaggaagaa aacctctatg ctgccgtgaa gcacacacag cctgaggatg gggtggagat     1980
ggacactcgg agcccacacg atgaagaccc ccaggcagtg acgtatgccg aggtgaaaca     2040
ctccagacct aggagagaaa tggcctctcc tccttcccca ctgtctgggg aattcctgga     2100
cacaaaggac agacaggcgg aagaggacag gcagatggac actgaggctg ctgcatctga     2160 agcccccag gatgtgacct acgcccagct gcacagcttg acccttagac ggaaggcaac     2220
tgagcctcct ccatcccagg aagggccctc tccagctgtg cccagcatct acgccactct     2280
ggccatccac tagcccaggg ggggacgcag accccacact ccatggagtc tggaatgcat     2340
gggagctgcc cccccagtgg acaccattgg accccaccca gcctggatct accccaggag     2400
actctgggaa cttttagggg tcactcaatt ctgcagtata ataactaat gtctctacaa      2460 ttttgaaata aagcaacaga cttctcaata atcaatgaag tagctgagaa aactaagtca     2520
gaaagtgcat taaactgaat cacaatgtaa atattacaca tcaagcgatg aaactggaaa     2580
actacaagcc acgaatgaat gaattaggaa agaaaaaaag taggaaatga atgatcttgg     2640
ctttcctata agaaatttag ggcagggcac ggtggctcac gcctgtaatt ccagcacttt     2700
gggaggccga ggcgggcaga tcacgagttc aggagatcga gaccatcttg gccaacatgg     2760
tgaaaccctg tctctcctaa aaatacaaaa attagctgga tgtggtggca gtgcctgtaa     2820
tcccagctat ttgggaggct gaggcaggag aatcgcttga accagggagt cagaggtttc     2880
agtgagccaa gatcgcacca ctgctctcca gcctggcgac agaggagac tccatctcaa      2940 attaaaaaaa aaaaaaaaa agaaagaaaa aaaaaaaaaa aaaa                       2984
```

<210> SEQ ID NO 365
<211> LENGTH: 3061
<212> TYPE: DNA

<213> ORGANISM: Homo sapiens

<400> SEQUENCE: 365

```
cggcacgagg cgactttggt ggaggtagtt ctttggcagc gggcatggcg ggtaccgtgg      60
tgctggacga tgtggagctg cgggaggctc agagagatta cctggacttc ctggacgacg     120
aggaagacca gggaatttat cagagcaaag ttcgggagct gatcagtgac aaccaatacc     180
ggctgattgt caatgtgaat gacctgcgca ggaaaaacga agagggct aaccggcttc       240
tgaacaatgc ctttgaggag ctggttgcct ccagcgggc cttaaaggat tttgtggcct      300
ccattgatgc tacctatgcc aagcagtatg aggagttcta cgtaggactg gaaggcagct     360
ttggctccaa gcacgtctcc ccgcggactc ttacctcctg cttcctcagc tgtgtggtct     420
gtgtggaggg cattgtcact aaatgttctc tagttcgtcc caaagtcgtc cgcagtgtcc     480
actactgtcc tgctactaag aagaccatag agcgacgtta ttctgatctc accaccctgg     540
tggcctttcc ctccagctct gtctatccta ccaaggatga ggagaacaat ccccttgaga     600
cagaatatgg cctttctgtc tacaaggatc accagaccat caccatccag gagatgccgg     660
agaaggcccc agccggccag ctccccccgct ctgtggacgt cattctggat gatgacttgg    720
tggataaagc gaagcctggt gaccgggttc aggtggtggg aacctaccgt gccttcctg      780
gaaagaaggg aggctacacc tctgggacct tcaggactgt cctgattgcc tgtaatgtta     840
agcagatgag caaggatgct cagccctctt tctctgctga ggatatagcc aagatcaaga     900
agttcagtaa aacccgatcc aaggatatct ttgaccagct ggccaagtca ttggccccaa     960
gtatccatgg gcatgactat gtcaagaaag caatcctctg cttgctcttg ggaggggtgg    1020
aacgagacct agaaaatggc agccacatcc gtggggacat caatattctt ctaataggag    1080
acccatccgt tgccaagtct cagcttctgc ggtatgtgct ttgcactgca ccccgagcta    1140
tccccaccac tggccggggc tcctctggag tgggtctgac ggctgctgtc accacagacc    1200
aggaaacagg agagcgccgt ctggaagcag gggccatggt cctggctgac cgaggcgtgg    1260
tttgcattga tgaatttgac aaaatgtctg acatggatcg cacagccatc catgaagtga    1320
tggagcaggg tcgagtgacc attgccaagg ctggcatcca tgctcggctg aatgcccgct    1380
gcagtgtttt ggcagctgcc aaccctgtct acggcaggta tgaccagtat aagactccaa    1440
tggagaacat tgggctacag gactcactgc tgtcacgatt tgacttgctc ttcatcatgc    1500
tggatcagat ggatcctgag caggatcggg agatctcaga ccatgtcctt cggatgcacc    1560
gttacagagc acctggggag caggatggcg atgctatgcc cttgggtagt gctgtggata    1620
tcctggccac agatgatccc aactttagcc aggaagatca gcaggacacc cagatttatg    1680
agaagcatga caaccttcta catgggacca agaagaaaaa ggagaagatg gtgagtgcag    1740
cattcatgaa gaagtacatc catgtggcca aaatcatcaa gcctgtcctg acacaggagt    1800
cggccaccta cattgcagaa gagtattcac gcctgcgcag ccaggatagc atgagctcag    1860
acaccgccag gacatctcca gttacagccc gaacactgga aactctgatt cgactggcca    1920
cagcccatgc gaaggcccgc atgagcaaga ctgtggacct gcaggatgca gaggaagctg    1980
tggagttggt ccagtatgct tactttaaga ggttctggaa gaaggagaag aaacgtaaga    2040
agcgaagtga ggatgaatca gagacagaag atgaagagga gaaagccaa gaggaccagg     2100
agcagaagag gaagagaagg aagactcgcc agccagatgc caagatggg gattcatacg     2160
accccctatga cttcagtgac acagaggagg aaatgcctca gtacacact ccaaagacgg     2220
cagactcaca ggagaccaag gaatcccaga aagtggagtt gagtgaatcc aggttgaagg    2280
```

```
cattcaaggt ggccctcttg gatgtgttcc gggaagctca tgcgcagtca atcggcatga    2340
atcgcctcac agaatccatc aaccgggaca gcgaagagcc cttctcttca gttgagatcc    2400
aggctgctct gagcaagatg caggatgaca atcaggtcat ggtgtctgag gcatcatct    2460 tcctcatctg aggaggcctc gtctctgaac ttgggttgtg ccgagagagt ttgttctgtg    2520
tttcccaccc tctccctgac ccaagtcttt gcctctactc ccttaacagt gttgaattca    2580
actgaaggcg aggaatgttg gtgatgaagc tgagttcagg actcggtgga ccctttggga    2640
atgggtcatg aaagctgcca tggggtgagg aaagaggaga cagtgggaga ggacaatgac    2700
tattgcatct tcattgcaaa agcactggct catccgccct acttcccatc ccacacaaac    2760
ccaattgtaa ataacatatg acttctgagt acttttgggg gcacaactgt tttctgtttg    2820
ctgttttttt gttttgtttt ttttctccag agcactttgg tctagactag gctttgggtg    2880
gttccaattg gtggagagaa gctctgaggc acgtcatgca ggtcaagaaa gctttctttg    2940
cagtagcacc agttaaggtg aatatgtatt gtatcacaaa acaaacccaa tatccagatg    3000
aatatccgag atgttgaata aacttagcca tttcgtacaa aaaaggggg gcccggtaaa    3060 c                                                                    3061

<210> SEQ ID NO 366
<211> LENGTH: 1360
<212> TYPE: DNA
<213> ORGANISM: Homo sapiens

<400> SEQUENCE: 366
cgggggttgc tccgtccgtg ctccgcctcg ccatgacttc ctacagctat cgccagtcgt      60
cggccacgtc gtccttcgga ggcctgggcg gcggctccgt gcgttttggg ccggggtcg     120 cttttcgcgc gcccagcatt cacggggggct ccggcggccg cggcgtatcc gtgtcctccg     180
cccgctttgt gtcctcgtcc tcctcggggg gctacggcgg cggctacggc ggcgtcctga     240
ccgcgtccga cgggctgctg gcgggcaacg agaagctaac catgcagaac ctcaacgacc     300
gcctggcctc ctacctggac aaggtgcgcg ccctggaggc ggccaacggc gagctagagg     360
tgaagatccg cgactggtac cagaagcagg ggcctgggcc ctcccgcgac tacagccact     420
actacacgac catccaggac ctgcgggaca agattcttgg tgccaccatt gagaactcca     480
ggattgtcct gcagatcgac aacgcccgtc tggctgcaga tgacttccga accaagtttg     540
agacggaaca ggctctgcgc atgagcgtgg aggccgacat caacggcctg cgcagggtgc     600
tggatgagct gacccctggcc aggaccgacc tggagatgca gatcgaaggc ctgaaggaag     660
agctggccta cctgaagaag aaccatgagg aggaaatcag tacgctgagg gccaagtgg     720 gaggccaggt cagtgtggag gtggattccg ctccgggcac cgatctcgcc aagatcctga     780
gtgacatgcg aagccaatat gaggtcatgg ccgagcagaa ccggaaggat gctgaagcct     840
ggttcaccag ccggactgaa gaattgaacc gggaggtcgc tggccacacg gagcagctcc     900
agatgagcag gtccgaggtt actgacctgc ggcgcaccct tcagggtctt gagattgagc     960
tgcagtcaca gctgagcatg aaagctgcct tggaagacac actggcagaa acggaggcgc    1020 gctttgagc ccagctggcg catatccagg cgctgatcag cggtattgaa gcccagctgg    1080
cggatgtgcg agctgatagt gagcggcaga atcaggagta ccagcggctc atggacatca    1140
agtcgcggct ggagcaggag attgccacct accgcagcct gctcgaggga caggaagatc    1200
actacaacaa tttgtctgcc tccaaggtcc tctgaggcag caggctctgg ggcttctgct    1260
```

```
gtcctttgga gggtgtcttc tgggtagagg gatgggaagg aagggaccct taccccggc    1320 tcttctcctg acctgccaat aaaaatttat ggtccaaggg                         1360
```

<210> SEQ ID NO 367
<211> LENGTH: 1412
<212> TYPE: DNA
<213> ORGANISM: Homo sapiens

<400> SEQUENCE: 367

```
cggggtcgtc cgcaaagcct gagtcctgtc ctttctctct ccccggacag catgagcttc     60
accactcgct ccaccttctc caccaactac cggtccctgg gctctgtcca ggcgccagc    120 tacggcgccc ggccggtcag cagcgcggcc agcgtctatg caggcgctgg gggctctggt    180
tcccggatct ccgtgtcccg ctccaccagc ttcaggggcg gcatgggagtc cggggggcctg   240 gccaccggga tagccggggg tctggcagga atgggaggca tccagaacga aaggagacc    300 atgcaaagcc tgaacgaccg cctggcctct tacctggaca gagtgaggag cctggagacc    360
gagaaccgga ggctggagag caaaatccgg gagcacttgg agaagaaggg accccaggtc    420
agagactgga gccattactt caagatcatc gaggacctga gggctcagat cttcgcaaat    480
actgtggaca atgcccgcat cgttctgcag attgacaatg cccgtcttgc tgctgatgac    540
tttagagtca agtatgagac agagctggcc atgcgccagt ctgtggagaa cgacatccat    600
gggctccgca aggtcattga tgacaccaat atcacacgac tgcagctgga gacagagatc    660
gaggctctca aggaggagct gctcttcatg aagaagaacc acgaagagga agtaaaaggc    720
ctacaagccc agattgccag ctctgggttg accgtggagg tagatgcccc caaatctcag    780
gacctcgcca agatcatggc agacatccgg gcccaatatg acgagctggc tcggaagaac    840
cgagaggagc tagacaagta ctggtctcag cagattgagg agagcaccac agtggtcacc    900
acacagtctg ctgaggttgg agctgctgag acgacgctca cagagctgag acgtacagtc    960
cagtccttgg agatcgacct ggactccatg agaaatctga aggccagctt ggagaacagc   1020
ctgagggagg tggaggcccg ctacgcccta cagatggagc agctcaacgg gatcctgctg   1080
caccttgagt cagagctggc acagacccgg gcagagggac agcgccaggc ccaggagtat   1140
gaggccctgc tgaacatcaa ggtcaagctg gaggctgaga tcgccaccta ccgccgcctg   1200
ctggaagatg gcgaggactt taatcttggt gatgccttgg acagcagcaa ctccatgcaa   1260
accatccaaa agaccaccac ccgccggata gtggatggca agtggtgtc tgagaccaat   1320 gacaccaaag ttctgaggca ttaagccagc agaagcaggg taccctttgg ggagcaggag   1380
gccaataaaa agttcagagt tcattggatg tc                                1412
```

<210> SEQ ID NO 368
<211> LENGTH: 1075
<212> TYPE: DNA
<213> ORGANISM: Homo sapiens

<400> SEQUENCE: 368

```
cgcagcaaac acatccgtag aaggcagcgc ggccgccgag agccgcagcg ccgctcgccc     60 gccgccccc accccgccgc cccgcccggc gaattgcgcc ccgcgcccct cccctcgcgc    120
ccccgagaca aagaggagag aaagtttgcg cggccgagcg gggcaggtga ggagggtgag    180
ccgcgcggga ggggcccgcc tcggccccgg ctcagccccc gccgcgcgcc cagcccgcc    240 gccgcgagca gcgcccggac ccccagcggc ggcccccgc ccgccagcc cccggcccg     300 ccatgggcgc cgcggccgc accctgcggc tggcgctcgg cctcctgctg ctggcgacgc    360
```

-continued

| | |
|---|---|
| tgcttcgccc ggccgacgcc tgcagctgct ccccggtgca cccgcaacag gcgttttgca | 420 |
| atgcagatgt agtgatcagg gccaaagcgg tcagtgagaa ggaagtggac tctggaaacg | 480 |
| acatttatgg caaccctatc aagaggatcc agtatgagat caagcagata agatgttca | 540 |
| aagggcctga aaggatata gagtttatct acacggcccc ctcctcggca gtgtgtgggg | 600 |
| tctcgctgga cgttggagga aagaaggaat atctcattgc aggaaaggcc gaggggacg | 660 |
| gcaagatgca catcaccctc tgtgacttca tcgtgccctg ggacaccctg agcaccaccc | 720 |
| agaagaagag cctgaaccac aggtaccaga tgggctgcga gtgcaagatc acgcgctgcc | 780 |
| ccatgatccc gtgctacatc tcctcccgg acgagtgcct ctggatggac tgggtcacag | 840 |
| agaagaacat caacgggcac caggccaagt tcttcgcctg catcaagaga agtgacggct | 900 |
| cctgtgcgtg gtaccgcggc gcggcgcccc ccaagcagga gtttctcgac atcgaggacc | 960 |
| cataagcagg cctccaacgc ccctgtggcc aactgcaaaa aaagcctcca agggtttcga | 1020 |
| ctggtccagc tctgacatcc cttcctggaa acagcatgaa taaaacactc atccc | 1075 |

<210> SEQ ID NO 369
<211> LENGTH: 1127
<212> TYPE: DNA
<213> ORGANISM: Homo sapiens

<400> SEQUENCE: 369

| | |
|---|---|
| cacgggcggg gcggggcctg ggtccaccgg ggttctgagg ggagactgag gtcctgagcc | 60 |
| gacagcctca gctccctgcc aggccagacc cggcagacag atgagggccc aggaggcctg | 120 |
| gcgggcctgg gggcgctacg gtgggagagg aagccagggg tacctgcctc tgccttccag | 180 |
| ggccaccgtt ggccccagct gtgccttgac tacgtaacat cttgtcctca cagcccagag | 240 |
| catgttccag atcccagagt ttgagccgag tgagcaggaa gactccagct ctgcagagag | 300 |
| gggcctgggc cccagccccg caggggacgg gccctcaggc tccggcaagc atcatcgcca | 360 |
| ggccccaggc ctcctgtggg acgccagtca ccagcaggag cagccaacca gcagcagcca | 420 |
| tcatggaggc gctggggctg tggagatccg gagtcgccac agctcctacc ccgcggggac | 480 |
| ggaggacgac gaagggatgg gggaggagcc cagccccttt cggggccgct cgcgctcggc | 540 |
| gcccccaac ctctgggcag cacagcgcta tggccgcgag ctccggagga tgagtgacga | 600 |
| gtttgtggac tcctttaaga agggacttcc tcgcccgaag agcgcgggca cagcaacgca | 660 |
| gatgcggcaa agctccagct ggacgcgagt cttccagtcc tggtgggatc ggaacttggg | 720 |
| caggggaagc tccgcccct cccagtgacc ttcgctccac atcccgaaac tccacccgtt | 780 |
| cccactgccc tgggcagcca tcttgaatat gggcggaagt acttccctca ggcctatgca | 840 |
| aaaagaggat ccgtgctgtc tcctttggag ggagggctga cccagattcc cttccggtgc | 900 |
| gtgtgaagcc acgaaggct tggtcccatc ggaagttttg ggttttccgc ccacagccgc | 960 |
| cggaagtggc tccgtggccc cgccctcagg ctccgggctt tccccaggc gcctgcgcta | 1020 |
| agtcgcgagc caggtttaac cgttgcgtca ccgggacccg agccccgcg atgccctggg | 1080 |
| ggccgtgctc actaccaaat gttaataaag cccgcgtctg tgccgcc | 1127 |

<210> SEQ ID NO 370
<211> LENGTH: 1890
<212> TYPE: DNA
<213> ORGANISM: Homo sapiens

<400> SEQUENCE: 370

```
cttaataaga agagaaggct tcaatggaac cttttgtggt cctggtgctg tgtctctctt        60
ttatgcttct cttttcactc tggagacaga gctgtaggag aaggaagctc cctcctggcc       120
ccactcctct tcctattatt ggaaatatgc tacagataga tgttaaggac atctgcaaat       180
ctttcaccaa tttctcaaaa gtctatggtc ctgtgttcac cgtgtatttt ggcatgaatc       240
ccatagtggt gtttcatgga tatgaggcag tgaaggaagc cctgattgat aatggagagg       300
agttttctgg aagaggcaat tccccaatat ctcaaagaat tactaaagga cttggaatca       360
tttccagcaa tggaaagaga tggaaggaga tccggcgttt ctccctcaca aacttgcgga       420
attttgggat ggggaagagg agcattgagg accgtgttca agaggaagct cactgccttg       480
tggaggagtt gagaaaaacc aaggcttcac cctgtgatcc cactttcatc ctgggctgtg       540
ctccctgcaa tgtgatctgc tccgttgttt tccagaaacg atttgattat aaagatcaga       600
attttctcac cctgatgaaa agattcaatg aaaacttcag gattctgaac tccccatgga       660
tccaggtctg caataatttc cctctactca ttgattgttt cccaggaact cacaacaaag       720
tgcttaaaaa tgttgctctt acacgaagtt acattaggga gaaagtaaaa gaacaccaag       780
catcactgga tgttaacaat cctcgggact ttatggattg cttcctgatc aaaatggagc       840
aggaaaagga caaccaaaag tcagaattca atattgaaaa cttggttggc actgtagctg       900
atctatttgt tgctggaaca gagacaacaa gcaccactct gagatatgga ctcctgctcc       960
tgctgaagca cccagaggtc acagctaaag tccaggaaga gattgatcat gtaattggca      1020
gacacaggag ccctgcatg caggatagga gccacatgcc ttacactgat gctgtagtgc       1080
acgagatcca gagatacagt gaccttgtcc ccaccggtgt gccccatgca gtgaccactg      1140
atactaagtt cagaaactac ctcatcccca gagctttga taacaagata atgctggctg      1200
cataaaacta gggcacaacc ataatggcat tactgacttc cgtgctacat gatgacaaag      1260
aatttcctaa tccaaatatc tttgaccctg gccacttct agataagaat ggcaactttta     1320 agaaaagtga ctacttcatg cctttctcag caggaaaacg aatttgtgca ggagaaggac      1380
ttgcccgcat ggagctattt ttatttctaa ccacaatttt acagaacttt aacctgaaat      1440
ctgttgatga tttaaagaac ctcaatacta ctgcagttac caaagggatt gtttctctgc      1500
caccctcata ccagatctgc ttcatccctg tctgaagaat gctagcccat ctggctgctg      1560
atctgctatc acctgcaact ctttttttat caaggacatt cccactatta tgtcttctct      1620
gacctctcat caaatcttcc cattcactca atatcccata agcatccaaa ctccattaag      1680
gagagttgtt caggtcactg cacaaatata tctgcaatta ttcatactct gtaacacttg      1740
tattaattgc tgcatatgct aatacttttc taatgctgac ttttaatat gttatcactg       1800 taaaacacag aaaagtgatt aatgaatgat aatttagtcc atttcttttg tgaatgtgct      1860
aaataaaaag tgttattaat tgctggttca                                       1890
```

<210> SEQ ID NO 371
<211> LENGTH: 4946
<212> TYPE: DNA
<213> ORGANISM: Homo sapiens

<400> SEQUENCE: 371

```
agtcagccct gctgccagcc agtgccgggt gctggggact cagggaggcc cgccgggacc        60
actgcgggac agtgagccga gcagaagctg gaacgcagga gaggaaggag aggggggcggt     120 cagggctctc aggagccggg tcctgggcaa ggcgcagccg ttttcaaatt ttcaggaaag      180
cggtcggctc acactcgagc agtaaaaaga tgcctctggg gaggaggccc gtgcagctct      240
```

-continued

```
ccgggcaatg gtggtggctc ggcctagaga ggcggtagtg gaacgcagac cctggtgggg    300
gaatgacatc aagggaggag acgggcggga ccccagattt ctgcctgtgg gcgatggaag    360
tgaggttcac tggccagcgg agccggacac agaacgcgca aaacgccgtg taggcctgga    420
ggagccgaag agcaggcgga ccccctccgc gggggaacag tttccgccgg gagcacaaag    480
caacggaccg gaagtggggg gcggaagtgc agtgggctca gcgccgactg cgcgcctctg    540
cccgcgaaaa ctctgagctg gctgacagct ggggacgggt ggcggccctc gactggagtc    600
ggttgagttc ctgagggacc ccggttctgg aaggttcgcc gcggagacaa gtgagcagtc    660
tgtgccatag ggattctcga agagaacagc gttgtgtccc agtgcacatg ctcgcatcgc    720
ttaccaggag tgcccgagac cctaagatgt tcggagtggt tttttcgcac agacccgaat    780
agcctgcccc tcagccacgc tctgtgccct tctgagaaca ggctgatatg cccaagatag    840
tcctgaatgg tgtgaccgta gacttcccct tccagcccta caaatgccaa caggagtaca    900
tgaccaaggt cctggaatgt ctgcagcaga aggtgaatgg catcctggag agccctacgg    960
gtacagggaa gacgctgtgc ctgctgtgca ccacgctggc ctggcgagaa cacctccgag   1020
acggcatctc tgcccgcaag attgccgaga gggcgcaagg agagcttttc ccggatcggg   1080
ccttgtcatc ctggggcaac gctgctgctg ctgctggaga ccccatagct tgctacacgg   1140
acatcccaaa gattatttac gcctccagga cccactcgca actcacacag gtcatcaacg   1200
agcttcggaa cacctcctac cggcctaagg tgtgtgtgct gggctcccgg gagcagctgt   1260
gcatccatcc tgaggtgaag aaacaagaga gtaaccatct acagatccac ttgtgccgta   1320
agaaggtggc aagtcgctcc tgtcatttct acaacaacgt agaagaaaaa agcctggagc   1380
aggagctggc cagccccatc ctggacattg aggacttggt caagagcgga agcaagcaca   1440
gggtgtgccc ttactacctg tcccggaacc tgaagcagca agccgacatc atattcatgc   1500
cgtacaatta cttgttggat gccaagagcc gcagagcaca caacattgac ctgaagggga   1560
cagtcgtgat ctttgacgaa gctcacaacg tggagaagat gtgtgaagaa tcggcatcct   1620
ttgacctgac tccccatgac ctggcttcag gactggacgt catagaccag gtgctggagg   1680
agcagaccaa ggcagcgcag cagggtgagc ccacccggga gttcagcgcg gactccccca   1740
gcccagggct gaacatggag ctggaagaca ttgcaaagct gaagatgatc ctgctgcgcc   1800
tggagggggc catcgatgct gttgagctgc ctggagacga cagcggtgtc accaagccag   1860
ggagctacat ctttgagctg tttgctgaag cccagatcac gtttcagacc aagggctgca   1920
tcctggactc gctggaccag atcatccagc acctggcagg acgtgctgga gtgttcacca   1980
acacggccgg actgcagaag ctggcggaca ttatccagat tgtgttcagt gtggacccct   2040
ccgagggcag ccctggttcc ccagcagggc tgggggcctt acagtcctat aaggtgcaca   2100
tccatcctga tgctggtcac cggaggacga ctcagcggtc tgatgcctgg agcaccactg   2160
cagccagaaa gcgagggaag gtgctgagct actggtgctt cagtcccggc cacagcatgc   2220
acgagctggt ccgccagggc gtccgctccc tcatccttac cagcggcacg ctggccccgg   2280
tgtcctcctt tgctctggag atgcagatcc ctttcccagt ctgcctggag aacccacaca   2340
tcatcgacaa gcaccagatc tgggtggggg tcgtccccag aggccccgat ggagcccagt   2400
tgagctccgc gtttgacaga cggttttccg aggagtgctt atcctccctg gggaaggctc   2460
tgggcaacat cgcccgcgtg gtgcccatat ggctcctgat cttcttccct tcctatcctg   2520
tcatggagaa gagcctggag ttctggcggg cccgcgactt ggccaggaag atggaggcgc   2580
```

-continued

```
tgaagccgct gtttgtggag cccaggagca aaggcagctt ctccgagacc atcagtgctt    2640
actatgcaag ggttgccgcc cctgggtcca ccggcgccac cttcctggcg gtctgccggg    2700
gcaaggccag cgaggggctg gacttctcag acacgaatgg ccgtggtgtg attgtcacgg    2760
gcctcccgta ccccccacgc atggacccc gggttgtcct caagatgcag ttcctggatg    2820
agatgaaggg ccaggtgggg ctgggggcc agttcctctc tgggcaggag tggtaccggc     2880
agcaggcgtc cagggctgtg aaccaggcca tcgggcgagt gatccggcac cgccaggact    2940
acggagctgt cttcctctgt gaccacaggt tcgcctttgc cgacgcaaga gcccaactgc    3000
cctcctgggt gcgtccccac gtcagggtgt atgacaactt tggccatgtc atccgagacg    3060
tggcccagtt cttccgtgtt gccgagcgaa ctatgccagc gccggccccc cgggctacag    3120
cacccagtgt gcgtggagaa gatgctgtca gcgaggccaa gtcgcctggc cccttcttct    3180
ccaccaggaa agctaagagt ctggacctgc atgtccccag cctgaagcag aggtcctcag    3240
ggtcaccagc tgccggggac cccgagagta gcctgtgtgt ggagtatgag caggagccag    3300
ttcctgcccg gcagaggccc aggggctgc tggccgccct ggagcacagc gaacagcggg     3360
cggggagccc tggcgaggag caggcccaca gctgctccac cctgtccctc ctgtctgaga    3420
agaggccggc agaagaaccg cgaggaggga ggaagaagat ccggctggtc agccacccgg    3480
aggagcccgt ggctggtgca cagacggaca gggccaagct cttcatggtg gccgtgaagc    3540
aggagttgag ccaagccaac tttgccacct tcacccaggc cctgcaggac tacaagggtt    3600
ccgatgactt cgccgccctg gccgcctgtc tcggccccct cttgctgag gacccccaaga    3660 agcacaacct gctccaaggc ttctaccagt tgtgcggcc caccataag cagcagtttg      3720 aggaggtctg tatccagctg acaggacgag gctgtggcta tcggcctgag cacagcattc    3780
cccgaaggca gcgggcacag ccggtcctgg accccactgg aagaacggcg ccggatccca    3840
agctgaccgt gtccacggct gcagcccagc agctggaccc caagagcac ctgaaccagg     3900 gcaggcccca cctgtcgccc aggccacccc caacaggaga ccctggcagc caaccacagt    3960
gggggtctgg agtgcccaga gcagggaagc agggccagca cgccgtgagc gcctacctgg    4020
ctgatgcccg cagggccctg gggtccgcgg gctgtagcca actcttggca gcgctgacag    4080
cctataagca agacgacgac ctcgacaagg tgctggctgt gttggccgcc ctgaccactg    4140
caaagccaga ggacttcccc ctgctgcaca ggttcagcat gtttgtgcgt ccacaccaca    4200
agcagcgctt ctcacagacg tgcacagacc tgaccggccg gccctacccg ggcatggagc    4260
caccgggacc ccaggaggag aggcttgccg tgcctcctgt gcttacccac agggctcccc    4320
aaccaggccc ctcacggtcc gagaagaccg ggaagaccca gagcaagatc tcgtccttcc    4380
ttagacagag gccagcaggg actgtgggg cgggcggtga ggatgcaggt cccagccagt     4440
cctcaggacc tccccacggg cctgcagcat ctgagtgggg cctctaggat gtgcccagcc    4500
tgccacaccg cctccaggaa gcagagcgtc atgcaggtct tctggccaga gcccagtga     4560 gtgcccacgg aggcccccag cacacccaac gtggcttgat cacctgcctg tccagctctg    4620
gtgggccaag aacccacccca acagaatagg ccagcccatg ccagccggct ggcccgctg    4680 caggcctcag gcaggcgggg cccatggttg gtccctgcgg tgggaccgga tctgggcctg    4740
cctctgagaa gccctgagct accttgggt ctggggtggg tttctgggaa agtgcttccc     4800
cagaacttcc ctggctcctg gcctgtgagt ggtgccacag gggcacccca gctgagcccc    4860
tcaccgggaa ggaggagacc cccgtgggca cgtgtccact tttaatcagg ggacagggct    4920
ctctaataaa gctgctggca gtgccc                                         4946
```

<210> SEQ ID NO 372
<211> LENGTH: 1743
<212> TYPE: DNA
<213> ORGANISM: Homo sapiens

<400> SEQUENCE: 372

| | | | | | |
|---|---|---|---|---|---|
| cagtatccct | cctgacaaaa | ctaacaaaaa | tcctgttagc | caaataatca | gccacattca | 60 |
| tatttaccgt | caaagttttt | atcctcattt | tacagcagtg | gagagcgatt | gccccgggtc | 120 |
| ccacgttagg | aagagagaga | actgggattt | gcacccaggc | aatctgggga | cagagctgtg | 180 |
| atcacaactc | catgagtcag | ggccgagcca | gccccttcac | caccagccgg | ccgcgccccg | 240 |
| ggaaggaagt | ttgtggcgga | ggaggttcgt | acgggaggag | ggggaggcgc | ccacgcatct | 300 |
| ggggctgact | cgctctttcg | caaaacgtct | gggaggagtc | cctggggcca | caaaactgcc | 360 |
| tccttcctga | ggccagaagg | agagaagacg | tgcaggacc | ccgcgcacag | gagctgccct | 420 |
| cgcgacatgg | gtcacccgcc | gctgctgccg | ctgctgctgc | tgctccacac | ctgcgtccca | 480 |
| gcctcttggg | gcctgcgtg | catgcagtgt | aagaccaacg | gggattgccg | tgtggaagag | 540 |
| tgcgccctgg | acaggacct | ctgcaggacc | acgatcgtgc | gcttgtggga | agaaggagaa | 600 |
| gagctggagc | tggtggagaa | aagctgtacc | cactcagaga | agaccaacag | gaccctgagc | 660 |
| tatcggactg | gcttgaagat | caccagcctt | accgaggttg | tgtgtgggtt | agacttgtgc | 720 |
| aaccagggca | actctggccg | ggctgtcacc | tattcccgaa | gccgttacct | cgaatgcatt | 780 |
| tcctgtggct | catcagacat | gagctgtgag | aggggccggc | accagagcct | gcagtgccgc | 840 |
| agccctgaag | aacagtgcct | ggatgtggtg | acccactgga | tccaggaagg | tgaagaaggg | 900 |
| cgtccaaagg | atgaccgcca | cctccgtggc | tgtggctacc | ttcccggctg | cccgggctcc | 960 |
| aatggtttcc | acaacaacga | caccttccac | ttcctgaaat | gctgcaacac | caccaaatgc | 1020 |
| aacgagggcc | caatcctgga | gcttgaaaat | ctgccgcaga | atggccgcca | gtgttacagc | 1080 |
| tgcaagggga | acagcacca | tggatgctcc | tctgaagaga | ctttcctcat | tgactgccga | 1140 |
| ggccccatga | atcaatgtct | ggtagccacc | ggcactcacg | aaccgaaaaa | ccaaagctat | 1200 |
| atggtaagag | gctgtgcaac | cgcctcaatg | tgccaacatg | cccacctggg | tgacgccttc | 1260 |
| agcatgaacc | acattgatgt | ctcctgctgt | actaaaagtg | gctgtaacca | cccagacctg | 1320 |
| gatgtccagt | accgcagtgg | ggctgctcct | cagcctggcc | ctgcccatct | cagcctcacc | 1380 |
| atcaccctgc | taatgactgc | cagactgtgg | ggaggcactc | tcctctggac | ctaaacctga | 1440 |
| aatcccctc | tctgccctgg | ctggatccgg | gggacccctt | tgcccttccc | tcggctccca | 1500 |
| gccctacaga | cttgctgtgt | gacctcaggc | cagtgtgccg | acctctctgg | gcctcagttt | 1560 |
| tcccagctat | gaaaacagct | atctcacaaa | gttgtgtgaa | gcagaagaga | aaagctggag | 1620 |
| gaaggccgtg | ggcaatggga | gagctcttgt | tattattaat | attgttgccg | ctgttgtgtt | 1680 |
| gttgttatta | attaatattc | atattattta | ttttatactt | acataaagat | tttgtaccag | 1740 |
| tgg | | | | | | 1743 |

<210> SEQ ID NO 373
<211> LENGTH: 5061
<212> TYPE: DNA
<213> ORGANISM: Homo sapiens

<400> SEQUENCE: 373

| | | | | | |
|---|---|---|---|---|---|
| atggctcaga | tatttagcaa | cagcggattt | aaagaatgtc | catttttcaca | tccggaacca | 60 |

-continued

```
acaagagcaa aagatgtgga caaagaagaa gcattacaga tggaagcaga ggctttagca    120
aaactgcaaa aggatagaca agtgactgac aatcagagag gctttgagtt gtcaagcagc    180
accagaaaaa aagcacaggt ttataacaag caggattatg atctcatggt gtttcctgaa    240
tcagattccc aaaaaagagc attagatatt gatgtagaaa agctcaccca agctgaactt    300
gagaaactat tgctggatga cagtttcgag actaaaaaaa cacctgtatt accagttact    360
cctattctga gcccttcctt ttcagcacag ctctatttta gacctactat tcagagagga    420
cagtggccac ctggattacc tgggccttcc acttatgctt taccttctat ttatccttct    480
acttacagta aacaggctgc attccaaaat ggcttcaatc aagaatgcc cacttttcca    540 tctacagaac ctatatattt aagtcttccg ggacaatctc catatttctc atatcctttg    600
acacctgcca caccctttca tccacaagga agcttaccta tctatcgtcc agtagtcagt    660
actgacatgg caaaactatt tgacaaaata gctagtacat cagaattttt aaaaaatggg    720
aaagcaagga ctgatttgga gataacagat tcaaaagtca gcaatctaca ggtatctcca    780
aagtctgagg atatcagtaa atttgactgg ttagacttgg atcctctaag taagcctaag    840
gtggataatg tggaggtatt agaccatgag gaagagaaaa atgtttcaag tttgctagca    900
aaggatcctt gggatgctgt tcttcttgaa gagagatcga cagcaaattg tcatcttgaa    960
agaaaggtga atgaaaatc cctttctgtg gcaactgtta caagaagcca gtctttaaat   1020
attcgaacaa ctcagcttgc aaaagcccag ggccatatat ctcagaaaga cccaaatggg   1080
accagtagtt tgccaactgg aagttctctt cttcaagaag ttgaagtaca gaatgaggag   1140
atggcagctt tttgtcgatc cattacaaaa ttgaagacca aatttccata taccaatcac   1200
cgcacaaacc caggctattt gttaagtcca gtcacagcgc aaagaaacat atgcggagaa   1260
aatgctagtg tgaaggtctc cattgacatt gaaggatttc agctaccagt tacttttacg   1320
tgtgatgtga gttctactgt agaaatcatt ataatgcaag ccctttgctg ggtacatgat   1380
gacttgaatc aagtagatgt tggcagctat gttctaaaag tttgtggtca agaggaagtg   1440
ctgcagaata atcattgcct tggaagtcat gagcatattc aaaactgtcg aaaatgggac   1500
acagaaatta gactacaact cttgaccttc agtgcaatgt gtcaaaatct ggcccgaaca   1560
gcagaagatg atgaaacacc cgtggattta aacaaacacc tgtatcaaat agaaaaacct   1620
tgcaaagaag ccatgacgag acaccctgtt gaagaactct tagattctta tcacaaccaa   1680
gtagaactgg ctcttcaaat tgaaaaccaa caccgagcag tagatcaagt aattaaagct   1740
gtaagaaaaa tctgtagtgc tttagatggt gtcgagactc ttgccattac agaatcagta   1800
aagaagctaa agagagcagt taatcttcca aggagtaaaa ctgctgatgt gacttctttg   1860
tttggaggag aagacactag caggagttca actaggggct cacttaatcc tgaaaatcct   1920
gttcaagtaa gcataaacca attaactgca gcaatttatg atcttctcag actccatgca   1980
aattctggta ggagtcctac agactgtgcc caaagtagca agagtgtcaa ggaagcatgg   2040
actacaacag agcagctcca gtttactatt tttgctgctc atggaatttc aagtaattgg   2100
gtatcaaatt atgaaaaata ctacttgata tgttcactgt ctcacaatgg aaaggatctt   2160
tttaaaccta ttcaatcaaa gaaggttggc acttacaaga atttcttcta tcttattaaa   2220
tgggatgaac taatcatttt tcctatccag atatcacaat tgccattaga atcagttctt   2280
caccttactc tttttggaat tttaaatcag agcagtggaa gttcccctga ttctaataag   2340
cagagaaagg gaccagaagc tttgggcaaa gtttctttac ctctttgtga ctttagacgg   2400
tttttaacat gtggaactaa acttctatat ctttggactt catcacatac aaattctgtt   2460
```

```
cctggaacag ttaccaaaaa aggatatgtc atggaaagaa tagtgctaca ggttgatttt    2520
ccttctcctg catttgatat tatttataca actcctcaag ttgacagaag cattatacag    2580
caacataact tagaaacact agagaatgat ataaaaggga aacttcttga tattcttcat    2640
aaagactcat cacttggact ttctaaagaa gataaagctt ttttatggga gaaacgttat    2700
tattgcttca acacccaaa ttgtcttcct aaaatattag caagcgcccc aaactggaaa    2760
tggggtaatc ttgccaaaac ttactcattg cttcaccagt ggcctgcatt gtacccacta    2820
attgcattgg aacttcttga ttcaaaattt gctgatcagg aagtaagatc cctagctgtg    2880
acctggattg aggccattag tgatgatgag ctaacagatc ttcttccaca gtttgtacaa    2940
gctttgaaat atgaaattta cttgaatagt tcattagtgc aattccttt gtccagggca    3000 ttgggaaata tccagatagc acacaattta tattggcttc tcaaagatgc cctgcatgat    3060
gtacagttta gtacccgata cgaacatgtt tgggtgctc tcctgtcagt aggaggaaaa    3120
cgacttagag aagaacttct aaaacagacg aaacttgtac agcttttagg aggagtagca    3180
gaaaaagtaa ggcaggctag tggatcagcc agacaggttg ttctccaaag aagtatggaa    3240
cgagtacagt cctttttca gaaaaataaa tgccgtctcc ctctcaagcc aagtctagtg    3300 gcaaagaat taaatattaa gtcgtgttcc ttcttcagtt ctaatgctgt cccctaaaa    3360 gtcacaatgg tgaatgctga ccctctggga gaagaaatta atgtcatgtt taaggttggt    3420
gaagatcttc ggcaagatat gttagcttta cagatgataa agattatgga taagatctgg    3480
cttaaagaag gactagatct gaggatggta attttcaaat gtctctcaac tggcagagat    3540
cgaggcatgg tggagctggt tcctgcttcc gataccctca ggaaaatcca agtggaatat    3600
ggtgtgacag gatcctttaa agataaacca cttgcagagt ggctaaggaa atacaatccc    3660
tctgaagaag aatatgaaaa ggcttcagag aactttatct attcctgtgc tggatgctgt    3720
gtagccacct atgttttagg catctgtgat cgacacaatg acaatataat gcttcgaagc    3780
acgggacaca tgtttcacat tgactttgga aagttttgg acatgcaca gatgtttggc    3840 agcttcaaaa gggatcgggc tccttttgtg ctgacctctg atatggcata tgtcattaat    3900
gggggtgaaa agcccaccat tcgttttcag ttgtttgtgg acctctgctg tcaggcctac    3960
aacttgataa gaaagcagac aaacctttt cttaacctcc tttcactgat gattccttca    4020
gggttaccag aacttacaag tattcaagat ttgaaatacg ttagagatgc acttcaaccc    4080 caaactcag acgcagaagc tacaattttc tttactaggc ttattgaatc aagtttggga    4140
agcattgcca caaagtttaa cttcttcatt cacaaccttg ctcagcttcg ttttctggt    4200 cttccttcta atgatgagcc catcctttca ttttcaccta aaacatactc ctttagacaa    4260
gatggtcgaa tcaaggaagt ctctgttttt acatatcata agaaatacaa cccagataaa    4320
cattatattt atgtagtccg aattttgtgg gaaggacaga ttgaaccatc atttgtcttc    4380
cgaacatttg tcgaatttca ggaacttcac aataagctca gtattatttt tccactttgg    4440
aagttaccag gctttcctaa taggatggtt ctaggaagaa cacacataaa agatgtagca    4500
gccaaaagga aaattgagtt aaacagttac ttacagagtt tgatgaatgc ttcaacggat    4560
gtagcagagt gtgatcttgt tgtactttc ttccacccctt tacttcgtga tgagaaagct    4620
gaagggatag ctaggtctgc agatgcaggt tccttcagtc ctactccagg ccaaatagga    4680
ggagctgtga aattatccat ctcttaccga aatggtactc ttttcatcat ggtgatgcat    4740
atcaaagatc ttgttactga agatggagct gacccaaatc catatgtcaa aacataccta    4800
```

| | |
|---|---|
| cttccagata accacaaaac atccaaacgt aaaaccaaaa tttcacgaaa acgaggaat | 4860 |
| ccgacattca atgaaatgct tgtatacagt ggatatagca aagaaaccct aagacagcga | 4920 |
| gaacttcaac taagtgtact cagtgcagaa tctctgcggg agaattttt cttgggtgga | 4980 |
| gtaaccctgc ctttgaaaga tttcaacttg agcaaagaga cggttaaatg gtatcagctg | 5040 |
| actgcggcaa catacttgta a | 5061 |

<210> SEQ ID NO 374
<211> LENGTH: 6802
<212> TYPE: DNA
<213> ORGANISM: Homo sapiens

<400> SEQUENCE: 374

| | |
|---|---|
| cggccccaga aacccgagc gagtagggg cggcgcgcag gagggaggag aactgggggc | 60 |
| gcgggaggct ggtgggtgtc gggggtggag atgtagaaga tgtgacgccg cggcccggcg | 120 |
| ggtgccagat tagcggacgg ctgcccgcgg ttgcaacggg atcccgggcg ctgcagcttg | 180 |
| ggaggcggct ctccccaggc ggcgtccgcg gagacaccca tccgtgaacc ccaggtcccg | 240 |
| ggccgccggc tcgccgcgca ccaggggccg gcggacagaa gagcggccga gcggctcgag | 300 |
| gctgggggac cgcgggcgcg gccgcgcgct gccgggcggg aggctggggg gccggggccg | 360 |
| gggccgtgcc ccggagcggg tcggaggccg gggccggggc cggggacgg cggctccccg | 420 |
| cgcggctcca gcggctcggg gatcccggcc gggccccgca gggaccatgg cagccgggag | 480 |
| catcaccacg ctgcccgcct tgcccgagga tggcggcagc ggcgccttcc cgcccggcca | 540 |
| cttcaaggac cccaagcggc tgtactgcaa aaacgggggc ttcttcctgc gcatccaccc | 600 |
| cgacggccga gttgacgggg tccgggagaa gagcgaccct cacatcaagc tacaacttca | 660 |
| agcagaagag agaggagttg tgtctatcaa aggagtgtgt gctaaccgtt acctggctat | 720 |
| gaaggaagat ggaagattac tggcttctaa atgtgttacg gatgagtgtt tcttttttga | 780 |
| acgattggaa tctaataact acaatactta ccggtcaagg aaatacacca gttggtatgt | 840 |
| ggcactgaaa cgaactgggc agtataaact tggatccaaa acaggacctg gcagaaagc | 900 |
| tatactttt cttccaatgt ctgctaagag ctgattttaa tggccacatc taatctcatt | 960 |
| tcacatgaaa aagaagtat attttagaaa tttgttaatg agagtaaaag aaaataaatg | 1020 |
| tgtatagctc agtttggata ttggtcaaa caatttttta tccagtagta aaatatgtaa | 1080 |
| ccattgtccc agtaaagaaa aataacaaaa gttgtaaaat gtatattctc cctttatat | 1140 |
| tgcatctgct gttacccagt gaagcttacc tagagcaatg atctttttca cgcatttgct | 1200 |
| ttattcgaaa agaggctttt aaaatgtgca tgtttagaaa caaaatttct tcatggaaat | 1260 |
| catatacatt agaaaatcac agtcagatgt ttaatcaatc caaaatgtcc actatttctt | 1320 |
| atgtcattcg ttagtctaca tgtttctaaa catataaatg tgaatttaat caattccttt | 1380 |
| catagtttta taattctctg gcagttcctt atgatagagt ttataaaca gtcctgtgta | 1440 |
| aactgctgga agttcttcca cagtcaggtc aatttttgtca aacccttctc tgtacccata | 1500 |
| cagcagcagc ctagcaactc tgctggtgat gggagttgta ttttcagtct cgccaggtc | 1560 |
| attgagatcc atccactcac atcttaagca ttcttcctgg caaaaattta tggtgaatga | 1620 |
| atatggcttt aggcggcaga tgatatacat atctgacttc ccaaaagctc caggatttgt | 1680 |
| gtgctgttgc cgaatactca ggacggacct gaattctgat tttataccag tctcttcaaa | 1740 |
| aacttctcga accgctgtgt ctcctacgta aaaaagaga tgtacaaatc aataataatt | 1800 |
| acactttag aaactgtatc atcaaagatt ttcagttaaa gtagcattat gtaaaggctc | 1860 |

```
aaaacattac cctaacaaag taaagttttc aatacaaatt ctttgccttg tggatatcaa    1920
gaaatcccaa aatattttct taccactgta aattcaagaa gcttttgaaa tgctgaatat    1980
ttctttggct gctacttgga ggcttatcta cctgtacatt tttggggtca gctcttttta    2040
acttcttgct gctctttttc ccaaaaggta aaaatataga ttgaaaagtt aaaacatttt    2100
gcatggctgc agttcctttg tttcttgaga taagattcca aagaacttag attcatttct    2160
tcaacaccga aatgctggag gtgtttgatc agttttcaag aaacttggaa tataaataat    2220
tttataattc aacaaaggtt ttcacatttt ataaggttga tttttcaatt aaatgcaaat    2280
ttgtgtggca ggattttat tgccattaac atattttgt ggctgctttt tctacacatc      2340
cagatggtcc ctctaactgg gctttctcta attttgtgat gttctgtcat tgtctcccaa    2400
agtatttagg agaagcccttt taaaaagctg ccttcctcta ccactttgct ggaaagcttc   2460
acaattgtca cagacaaaga ttttttgttcc aatactcgtt ttgcctctat ttttcttgtt    2520
tgtcaaatag taaatgatat ttgcccttgc agtaattcta ctggtgaaaa acatgcaaag    2580
aagaggaagt cacagaaaca tgtctcaatt cccatgtgct gtgactgtag actgtcttac    2640
catagactgt cttacccatc ccctggatat gctcttgttt tttccctcta atagctatgg    2700
aaagatgcat agaaagagta taatgtttta aaacataagg cattcatctg ccattttca     2760 attacatgct gacttcccctt acaattgaga tttgcccata ggttaaacat ggttagaaac   2820
aactgaaagc ataaagaaa aatctaggcc gggtgcagtg gctcatgcct atattccctg     2880
cactttggga ggccaaagca ggaggatcgc ttgagcccag gagttcaaga ccaacctggt    2940 gaaacccccgt ctctacaaaa aaacacaaaa aatagccagg catggtggcg tgtacatgtg   3000
gtctcagata cttgggaggc tgaggtggga gggttgatca cttgaggctg agaggtcaag    3060
gttgcagtga gccataatcg tgccactgca gtccagccta ggcaacagag tgagactttg    3120
tctcaaaaaa agagaaattt tcctaataa gaaagtaat tttttactctg atgtgcaata    3180 catttgttat taaatttatt atttaagatg gtagcactag tcttaaattg tataaaatat    3240 ccctaacat gtttaaatgt ccattttat tcattatgct ttgaaaaata attatgggga     3300
aatacatgtt tgttattaaa tttattatta aagatagtag cactagtctt aaatttgata    3360
taacatctcc taacttgttt aaatgtccat ttttattctt tatgcttgaa ataaattat    3420 ggggatccta tttagctctt agtaccacta atcaaaagtt cggcatgtag ctcatgatct    3480
atgctgtttc tatgtcgtgg aagcaccgga tgggggtagt gagcaaatct gccctgctca    3540
gcagtcacca tagcagctga ctgaaaatca gcactgcctg agtagttttg atcagtttaa    3600
cttgaatcac taactgactg aaaattgaat gggcaaataa gtgcttttgt ctccagagta    3660
tgcgggagac ccttccacct caagatggat atttcttccc caaggatttc aagatgaatt    3720
gaaattttta atcaagatag tgtgcttat tctgttgtat ttttattat ttaatatac     3780 tgtaagccaa actgaaataa catttgctgt tttataggtt tgaagaacat aggaaaaact    3840
aagaggtttt gtttttattt ttgctgatga agagatatgt ttaaatatgt tgtattgttt    3900
tgtttagtta caggacaata atgaaatgga gtttatattt gttatttcta ttttgttata    3960
tttaataata gaattagatt gaaataaaat ataatgggaa ataatctgca gaatgtgggt    4020
ttcctggtgt ttcctctgac tctagtgcac tgatgatctc tgataaggct cagctgcttt    4080
atagttctct ggctaatgca gcagatactc ttcctgccag tggtaatacg attttttaag    4140
aaggcagttt gtcaatttta atcttgtgga tacctttata ctcttagggt attattttat    4200
```

```
acaaaagcct tgaggattgc attctatttt ctatatgacc ctcttgatat ttaaaaaaca    4260
ctatggataa caattcttca tttacctagt attatgaaag aatgaaggag ttcaaacaaa    4320
tgtgtttccc agttaactag ggtttactgt ttgagccaat ataaatgttt aactgtttgt    4380
gatggcagta ttcctaaagt acattgcatg ttttcctaaa tacagagttt aaataatttc    4440
agtaattctt agatgattca gcttcatcat taagaatatc ttttgtttta tgttgagtta    4500
gaaatgcctt catatagaca tagtctttca gacctctact gtcagttttc atttctagct    4560
gctttcaggg ttttatgaat tttcaggcaa agctttaatt tatactaagc ttaggaagta    4620
tggctaatgc caacggcagt ttttttcttc ttaattccac atgactgagg catatatgat    4680
ctctgggtag gtgagttgtt gtgacaacca caagcacttt tttttttttt aaagaaaaaa    4740
aggtagtgaa tttttaatca tctggacttt aagaaggatt ctggagtata cttaggcctg    4800
aaattatata tatttggctt ggaaatgtgt ttttcttcaa ttacatctac aagtaagtac    4860
agctgaaatt cagaggaccc ataagagttc acatgaaaaa aatcaattca tttgaaaagg    4920
caagatgcag gagagaggaa gccttgcaaa cctgcagact gcttttttgcc caatatagat    4980
tgggtaaggc tgcaaaacat aagcttaatt agctcacatg ctctgctctc acgtggcacc    5040
agtggatagt gtgagagaat taggctgtag aacaaatggc cttctctttc agcattcaca    5100
ccactacaaa atcatctttt atatcaacag aagaataagc ataaactaag caaaaggtca    5160
ataagtacct gaaaccaaga ttggctagag atatatctta atgcaatcca ttttctgatg    5220
gattgttacg agttggctat ataatgtatg tatggtattt tgatttgtgt aaaagtttta    5280
aaaatcaagc tttaagtaca tggacatttt taaataaaat atttaaagac aatttagaaa    5340
attgccttaa tatcattgtt ggctaaatag aatagggggac atgcatatta aggaaaaggt    5400
catggagaaa taatattggt atcaaacaaa tacattgatt tgtcatgata cacattgaat    5460
ttgatccaat agtttaagga ataggtagga aaatttggtt tctattttc gatttcctgt    5520
aaatcagtga cataaataat tcttagctta ttttatattt ccttgtctta aatactgagc    5580
tcagtaagtt gtgttagggg attatttctc agttgagact ttcttatatg acattttact    5640
atgtttgac ttcctgacta ttaaaaataa atagtagaaa caattttcat aaagtgaaga    5700
attatataat cactgcttta taactgactt tattatattt atttcaaagt tcatttaaag    5760
gctactattc atcctctgtg atggaatggt caggaatttg ttttctcata gtttaattcc    5820
aacaacaata ttagtcgtat ccaaaataac ctttaatgct aaactttact gatgtatatc    5880
caaagcttct cctttcaga cagattaatc cagaagcagt cataaacaga agaataggtg    5940
gtatgttcct aatgatatta tttctactaa tggaataaac tgtaatatta gaaattatgc    6000
tgctaattat atcagctctg aggtaatttc tgaaatgttc agactcagtc ggaacaaatt    6060
ggaaattta aattttatt cttagctata aagcaagaaa gtaaacacat taatttcctc    6120
aacatttta agccaattaa aaatataaaa gatacacacc aatatcttct tcaggctctg    6180
acaggcctcc tggaaacttc cacatatttt tcaactgcag tataaagtca gaaaataaag    6240
ttaacataac tttcactaac acacacatat gtagatttca caaatccac ctataattgg    6300
tcaaagtggt tgagaatata ttttttagta attgcatgca aattttttct agcttccatc    6360
ctttctccct cgtttcttct tttttgggg gagctggtaa ctgatgaaat cttttcccac    6420
cttttctctt caggaaatat aagtggtttt gtttggttaa cgtgatacat tctgtatgaa    6480
tgaaacattg gagggaaaca tctactgaat ttctgtaatt taaaatatttt tgctgctagt    6540
taactatgaa cagatagaag aatcttacag atgctgctat aaataagtag aaaatataaa    6600
```

-continued

| | |
|---|---|
| tttcatcact aaaatatgct attttaaaat ctatttccta tattgtattt ctaatcagat | 6660 |
| gtattactct tattatttct attgtatgtg ttaatgattt tatgtaaaaa tgtaattgct | 6720 |
| tttcatgagt agtatgaata aaattgatta gtttgtgttt tcttgtctcc cgaaaaaaaa | 6780 |
| aaaaaaaaaa aaaaaaaaaa aa | 6802 |

<210> SEQ ID NO 375
<211> LENGTH: 1840
<212> TYPE: DNA
<213> ORGANISM: Homo sapiens

<400> SEQUENCE: 375

| | |
|---|---|
| cccattaggt gacaggtttt tagagaagcc aatcacgtcg ccgcggtcct ggttctaaag | 60 |
| tcctcgctca cccacccgga ctcattctcc ccagacgcca aggatggtgg tcatggcgcc | 120 |
| ccgaaccctc ttcctgctgc tctcgggggc cctgaccctg accgagacct gggcgggctc | 180 |
| ccactccatg aggtatttca gcgccgccgt gtcccggccc ggccgcgggg agccccgctt | 240 |
| catcgccatg ggctacgtgg acgacacgca gttcgtgcgg ttcgacagcg actcggcgtg | 300 |
| tccgaggatg gagccgcggg cgccgtgggt ggagcaggag gggccggagt attgggaaga | 360 |
| ggagacacgg aacaccaagg cccacgcaca gactgacaga atgaacctgc agaccctgcg | 420 |
| cggctactac aaccagagcg aggccagttc tcacaccctc cagtggatga ttggctgcga | 480 |
| cctggggtcc gacggacgcc tcctccgcgg gtatgaacag tatgcctacg atggcaagga | 540 |
| ttacctcgcc ctgaacgagg acctgcgctc ctggaccgca gcggacactg cggctcagat | 600 |
| ctccaagcgc aagtgtgagg cggccaatgt ggctgaacaa aggagagcct acctggaggg | 660 |
| cacgtgcgtg gagtggctcc acagatacct ggagaacggg aaggagatgc tgcagcgcgc | 720 |
| ggaccccccc aagacacacg tgacccacca ccctgtcttt gactatgagg ccaccctgag | 780 |
| gtgctgggcc ctgggcttct accctgcgga gatcatactg acctggcagc gggatgggga | 840 |
| ggaccagacc caggacgtgg agctcgtgga gaccaggcct gcagggatg aaccttcca | 900 |
| gaagtgggca gctgtggtgg tgccttctgg agaggagcag agatacacgt gccatgtgca | 960 |
| gcatgagggg ctgccggagc ccctcatgct gagatggaag cagtcttccc tgcccaccat | 1020 |
| ccccatcatg ggtatcgttg ctggcctggt tgtccttgca gctgtagtca ctggagctgc | 1080 |
| ggtcgctgct gtgctgtgga gaaagaagag ctcagattga aaaggaggga gctactctca | 1140 |
| ggctgcaagt aagtatgaag gaggctgatc cctgagatcc ttgggatctt gtgtttggga | 1200 |
| gccatggggg agctcaccca ccccacaatt cctcctctgg ccacatctcc tgtggtctct | 1260 |
| gaccaggtgc tgttttttgtt ctactctagg cagtgacagt gcccagggct ctaatgtgtc | 1320 |
| tctcacggct tgtaaatgtg acaccccggg gggcctgatg tgtgtgggtt gttgagggga | 1380 |
| acagggggaca tagctgtgct atgaggtttc tttgacttca atgtattgag catgtgatgg | 1440 |
| gctgtttaaa gtgtcacccc tcactgtgac tgatatgaat ttgttcatga atattttct | 1500 |
| gtagtgtgaa acagctgccc tgtgtgggac tgagtggcaa gtcccttgt gacttcaaga | 1560 |
| accctgactt ctctttgtgc agagaccagc ccacccctgt gcccaccatg accctcttcc | 1620 |
| tcatgctgaa ctgcattcct tccccaatca cctttcctgt tccagaaaag gggctgggat | 1680 |
| gtctccgtct ctgtctcaaa tttgtggtcc actgagctat aacttacttc tgtattaaaa | 1740 |
| ttagaatctg agtgtaaatt tacttttca aattatttcc aagagagatt gatgggttaa | 1800 |
| ttaaaggaga agattcctga aatttgagag acaaaataaa | 1840 |

<210> SEQ ID NO 376
<211> LENGTH: 6754
<212> TYPE: DNA
<213> ORGANISM: Homo sapiens

<400> SEQUENCE: 376

| | | | | | | |
|---|---|---|---|---|---|---|
| gtcgacgtgg | cggccggcgg | cggctgcggg | ctgagcggcg | agtttccgat | ttaaagctga | 60 |
| gctgcgagga | aaatggcggc | gggaggatca | aaatacttgc | tggatggtgg | actcagagac | 120 |
| caataaaaat | aaactgcttg | aacatccttt | gactggttag | ccagttgctg | atgtatattc | 180 |
| aagatgagtg | gattaggaga | aaacttggat | ccactggcca | gtgattcacg | aaaacgcaaa | 240 |
| ttgccatgtg | atactccagg | acaaggtctt | acctgcagtg | gtgaaaaacg | gagacgggag | 300 |
| caggaaagta | aatatattga | agaattggct | gagctgatat | ctgccaatct | tagtgatatt | 360 |
| gacaatttca | atgtcaaacc | agataaatgt | gcgattttaa | aggaaacagt | aagacagata | 420 |
| cgtcaaataa | aagagcaagg | aaaaactatt | tccaatgatg | atgatgttca | aaaagccgat | 480 |
| gtatcttcta | cagggcaggg | agttattgat | aaagactcct | taggaccgct | tttacttcag | 540 |
| gcattggatg | gtttcctatt | tgtggtgaat | cgagacggaa | acattgtatt | tgtatcagaa | 600 |
| aatgtcacac | aatacctgca | atataagcaa | gaggacctgg | ttaacacaag | tgtttacaat | 660 |
| atcttacatg | aagaagacag | aaaggatttt | cttaagaatt | taccaaaatc | tacagttaat | 720 |
| ggagttttcct | ggacaaatga | gacccaaaga | caaaaaagcc | atacatttaa | ttgccgtatg | 780 |
| ttgatgaaaa | caccacatga | tattctggaa | gacataaacg | ccagtcctga | aatgcgccag | 840 |
| agatatgaaa | caatgcagtg | cttttgccctg | tctcagccac | gagctatgat | ggaggaaggg | 900 |
| gaagatttgc | aatcttgtat | gatctgtgtg | gcacgccgca | ttactacagg | agaaagaaca | 960 |
| tttccatcaa | accctgagag | ctttattacc | agacatgatc | tttcaggaaa | ggttgtcaat | 1020 |
| atagatacaa | attcactgag | atcctccatg | aggcctggct | ttgaagatat | aatccgaagg | 1080 |
| tgtattcaga | attttttag | tctaaatgat | gggcagtcat | ggtcccagaa | acgtcactat | 1140 |
| caagaagtta | ccagtgatgg | gatattttcc | ccaacagctt | atcttaatgg | ccatgcagaa | 1200 |
| accccagtat | atcgattctc | gttggctgat | ggaactatag | tgactgcaca | gacaaaaagc | 1260 |
| aaactcttcc | gaaatcctgt | aacaaatgat | cgacatggct | tgtctcaac | ccacttcctt | 1320 |
| cagagagaac | agaatggata | tagaccaaac | ccaaatcctg | ttggacaagg | gattagacca | 1380 |
| cctatggctg | atgcaacag | ttcggtaggc | ggcatgagta | tgtcgccaaa | ccaaggctta | 1440 |
| cagatgccga | gcagcagggc | ctatggcttg | cagaccccta | gcaccacagg | gcagatgagt | 1500 |
| ggagctaggt | atgggggttc | cagtaacata | gcttcattga | ccctgggcc | aggcatgcaa | 1560 |
| tcaccatctt | cctaccagaa | caacaactat | aggctcaaca | tgagtagccc | cccacatggg | 1620 |
| agtcctggtc | ttgccccaaa | ccagcagaat | atcatgattt | ctcctcgtaa | tcgtgggagt | 1680 |
| ccaaagatag | cctcacatca | gttttctcct | gttgcaggt | tgcactctcc | catggcatct | 1740 |
| tctggcaata | ctgggaacca | cagcttttcc | agcagctctc | tcagtgccct | gcaagccatc | 1800 |
| agtgaaggtg | tgggggacttc | ccttttatct | actctgtcat | caccaggccc | caaattggat | 1860 |
| aactctccca | atatgaatat | tacccaacca | agtaaagtaa | gcaatcagga | ttccaagagt | 1920 |
| cctctgggct | ttattgcga | ccaaaatcca | gtggagagtt | caatgtgtca | gtcaaatagc | 1980 |
| agagatcacc | tcagtgacaa | agaaagtaag | gagagcagtg | ttgaggggc | agagaatcaa | 2040 |
| aggggtcctt | tggaaagcaa | aggtcataaa | aaattactgc | agttacttac | ctgttcttct | 2100 |
| gatgaccggg | gtcattcctc | cttgaccaac | tccccccctag | attcaagttg | taaagaatct | 2160 |

```
tctgttagtg tcaccagccc ctctggagtc tcctcctcta catctggagg agtatcctct  2220
acatccaata tgcatgggtc actgttacaa gagaagcacc ggattttgca caagttgctg  2280
cagaatggga attcaccagc tgaggtagcc aagattactg cagaagccac tgggaaagac  2340
accagcagta taacttcttg tggggacgga atgttgtca agcaggagca gctaagtcct  2400
aagaagaagg agaataatgc acttcttaga tacctgctgg acaggatga tcctagtgat  2460
gcactctcta aagaactaca gccccaagtg aaggagtgg ataataaaat gagtcagtgc  2520
accagctcca ccattcctag ctcaagtcaa gagaaagacc ctaaaattaa dacagagaca  2580
agtgaagagg gatctggaga cttggataat ctagatgcta ttcttggtga tctgactagt  2640
tctgactttt acaataattc catatcctca aatggtagtc atctggggac taagcaacag  2700
gtgtttcaag gaactaattc tctgggtttg aaaagttcac agtctgtgca gtctattcgt  2760
cctccatata accgagcagt gtctctggat agccctgttt ctgttggctc aagtcctcca  2820
gtaaaaaata tcagtgcttt ccccatgtta ccaaagcaac ccatgttggg tgggaatcca  2880
agaatgatgg atagtcagga aaattatggc tcaagtatgg gagactgggg cttaccaaac  2940
tcaaaggccg gcagaatgga acctatgaat tcaaactcca tgggaagacc aggaggagat  3000
tataatactt cttacccag acctgcactg ggtggctcta ttcccacatt gcctcttcgg  3060
tctaatagca taccaggtgc gagaccagta ttgcaacagc agcagcagat gcttcaaatg  3120
aggcctggtg aaatccccat gggaatgggg gctaatccct atggccaagc agcagcatct  3180
aaccaactgg gttcctggcc cgatggcatg ttgtccatgg aacaagtttc tcatggcact  3240
caaaataggc ctcttcttag gaattccctg gatgatcttg ttgggccacc ttccaacctg  3300
gaaggccaga gtgacgaaag agcattattg gaccagctgc acactcttct cagcaacaca  3360
gatgccacag gctggaaga aattgacaga gctttgggca ttcctgaact tgtcaatcag  3420
ggacaggcat tagagcccaa acaggatgct ttccaaggcc aagaagcagc agtaatgatg  3480
gatcagaagg caggattata tggacagaca tacccagcac aggggcctcc aatgcaagga  3540
ggctttcatc ttcagggaca atcaccatct tttaactcta tgatgaatca gatgaaccag  3600
caaggcaatt ttcctctcca aggaatgcac ccacgagcca acatcatgag accccggaca  3660
aacacccca gcaacttag aatgcagctt cagcagaggc tgcagggcca gcagttttg  3720
aatcagagcc gacaggcact tgaattgaaa atggaaaacc ctactgctgg tggtgctgcg  3780
gtgatgaggc ctatgatgca gccccagcag ggttttctta atgctcaaat ggtcgcccaa  3840
cgcagcagag agctgctaag tcatcacttc cgacaacaga gggtggctat gatgatgcag  3900
cagcagcaac agcagcagca gcagcagcag cagcagcaac agcaacagca acagcaacag  3960
cagcaacagc agcaaaccca ggccttcagc ccacctccta atgtgactgc ttcccccagc  4020
atggatgggt ttttggcagg acccacaatg ccacaagctc ctccgcaaca gtttccatat  4080
caaccaaatt atggaatggg acaacaacca gatccagcct ttggtcgagt gtctagtcct  4140
cccaatgcaa tgatgtcgtc aagaatgggt ccctcccaga atcccatgat gcaacacccg  4200
caggctgcat ccatctatca gtcctcagaa atgaagggct ggccatcagg aaatttggcc  4260
aggaacagct ccttttccca gcagcagttt gcccaccagg ggaatcctgc agtgtatagt  4320
atggtgcaca tgaatggcag cagtggtcac atgggacaga tgaacatgaa ccccatgccc  4380
atgtctggca tgcctatggg tcctgatcag aaatactgct gacatctctg caccaggacc  4440
tcttaaggaa accactgtac aaatgacact gcactaggat tattgggaag gaatcattgt  4500
```

```
tccaggcatc catcttggaa gaaaggacca gctttgagct ccatcaaggg tattttaagt   4560
gatgtcattt gagcaggact ggattttaag ccgaagggca atatctacgt gttttttccc   4620
cctccttctg ctgtgtatca tggtgttcaa aacagaaatg ttttttggca ttccacctcc   4680
tagggatata attctggaga catggagtgt tactgatcat aaaacttttg tgtcactttt   4740
ttctgccttg ctagccaaaa tctcttaaat acacgtaggt gggccagaga acattggaag   4800
aatcaagaga gattagaata tctggtttct ctagttgcag tattggacaa agagcatagt   4860
cccagccttc aggtgtagta gttctgtgtt gaccctttgt ccagtggaat tggtgattct   4920
gaattgtcct ttactaatgg tgttgagttg ctctgtccct attatttgcc ctaggctttc   4980
tcctaatgaa ggttttcatt tgccattcat gtcctgtaat acttcacctc caggaactgt   5040
catgatgtc caaatggctt tgcagaaagg aaatgagatg acagtattta atcgcagcag   5100
tagcaaactt ttcacatgct aatgtgcagc tgagtgcact ttatttaaaa agaatggata   5160
aatgcaatat tcttgaggtc ttgagggaat agtgaaacac attcctggtt tttgcctaca   5220
cttacgtgtt agacaagaac tatgattttt tttttttaaag tactggtgtc acccttgcc   5280
tatatggtag agcaataatg cttttttaaaa ataaacttct gaaaacccaa ggccaggtac   5340
tgcattctga atcagaatct cgcagtgttt ctgtgaatag atttttttgt aaatatgacc   5400
tttaagatat tgtattatgt aaaatatgta tatacctttt tttgtaggtc acaacaactc   5460
attttttacag agtttgtgaa gctaaatatt taacattgtt gatttcagta agctgtgtgg   5520
tgaggctacc agtggaagag acatccttg acttttgtgg cctggggag gggtagtgca   5580
ccacagcttt tccttcccca ccccccagcc ttagatgcct cgctcttttc aatctcttaa   5640
tctaaatgct ttttaaagag attatttgtt tagatgtagg cattttaatt ttttaaaaat   5700
tcctctacca gaactaagca ctttgttaat ttgggggaa agaatagata tggggaaata   5760
aacttaaaaa aaaatcagga atttaaaaaa aacgagcaat ttgaagagaa tcttttggat   5820
tttaagcagt ccgaaataat agcaattcat gggctgtgtg tgtgtgtgta tgtgtgtgtg   5880
tgtgtgtgta tgtttaatta tgttacctttt tcatcccctt taggagcgtt ttcagatttt   5940
ggttcgtaag acctgaatcc catattgaga tctcgagtag aatccttggt gtggtttctg   6000
gtgtctgctc agctgtcccc tcattctact aatgtgatgc tttcattatg tccctgtgga   6060
ttagaatagt gtcagttatt tcttaagtaa ctcagtaccc agaacagcca gttttactgt   6120
gattcagagc cacagtctaa ctgagcacct tttaaacccc tccctcttct gcccctacc   6180
acttttctgc tgttgcctct ctttgacacc tgttttagtc agttgggagg aagggaaaaa   6240
tcaagtttaa ttcccttat ctgggttaat tcatttggtt caaatagttg acggaattgg   6300
gtttctgaat gtctgtgaat ttcagaggtc tctgctagcc ttggtatcat tttctagcaa   6360
taactgagag ccagttaatt ttaagaattt cacacattta gccaatcttt ctagatgtct   6420
ctgaaggtaa gatcatttaa tatctttgat atgcttacga gtaagtgaat cctgattatt   6480
tccagaccca ccaccagagt ggatcttatt tcaaagcag tatagacaat tatgagtttg   6540
ccctctttcc cctaccaagt tcaaaatata tctaagaaag attgtaaatc cgaaaacttc   6600
cattgtagtg gcctgtgctt ttcagatagt atactctcct gtttggagac agaggaagaa   6660
ccaggtcagt ctgtctcttt ttcagctcaa ttgtatctga ccccttcttta agttatgtgt   6720
gtggggagaa atagaatggt gctcttatgt cgac                              6754
```

<210> SEQ ID NO 377
<211> LENGTH: 757

```
<212> TYPE: DNA
<213> ORGANISM: Homo sapiens

<400> SEQUENCE: 377
ggaaccgaga ggctgagact aacccagaaa catccaattc tcaaactgaa gctcgcactc      60
tcgcctccag catgaaagtc tctgccgccc ttctgtgcct gctgctcata gcagccacct     120
tcattcccca agggctcgct cagccagatg caatcaatgc cccagtcacc tgctgttata     180
acttcaccaa taggaagatc tcagtgcaga ggctcgcgag ctatagaaga atcaccagca     240
gcaagtgtcc caagaagct gtgatcttca agaccattgt ggccaaggag atctgtgctg     300
accccaagca gaagtgggtt caggattcca tggaccacct ggacaagcaa acccaaactc     360
cgaagacttg aacactcact ccacaaccca agaatctgca gctaacttat tttcccctag     420
cttttcccag acaccctgtt ttattttatt ataatgaatt ttgtttgttg atgtgaaaca     480
ttatgcctta agtaatgtta attcttattt aagttattga tgttttaagt ttatctttca     540
tggtactagt gttttttaga tacagagact tggggaaatt gcttttcctc ttgaaccaca     600
gttctacccc tgggatgttt tgagggtctt tgcaagaatc attaatacaa agaattttt       660
ttaacattcc aatgcattgc taaaatatta ttgtggaaat gaatattttg taactattac     720
accaaataaa tatattttg tacaaaaaaa aaaaaaa                               757

<210> SEQ ID NO 378
<211> LENGTH: 476
<212> TYPE: DNA
<213> ORGANISM: Homo sapiens

<400> SEQUENCE: 378
taaaggcaaa gaaggttttt atttaagtga caacatttga gagctaaaaa ccagctcaca      60
tcaaaatcaa gacccagttg taaaaatctt ttaactccat aatgctgttt ttgtcttgtt     120
agaaatctga tatcttacat tagcgtttct aacggatttt gtacaaggca gccataagga     180
atataataaa ccttttttcac cacagaacca tctgtcacag ataatactga aagttacaca     240
cttaggaaca gtcagaccac agacaaggtc agactggctg ccaccaccaa gtaaacaact     300
agaaaaggac agcggggtcc aagggtgggg gtccctgtgc acgagtcgcc ctcctctggc     360
ctgccccccc tcgggtcacc tgtttctcct ttgcccaaa gagggtggag tcaaatgcag     420
attttcctcc caactgcctg ttagtgtctc aacaaggaga gcagagccca ggtcag         476

<210> SEQ ID NO 379
<211> LENGTH: 2518
<212> TYPE: DNA
<213> ORGANISM: Homo sapiens

<400> SEQUENCE: 379
gggtgcgctc ggccgtggcg cacctggtga gctccggggg cgctccgcct ccgcgcccca      60
aatccccgga cctgcccaac gccgcctcgg cgccgcccgc cgccgctcca gaagcgccca     120
ggagccctcc cgcgaaggct gggagcggga gcgcgacgcc cgcgaaggct gttgaggctc     180
gagcgagctt ctccagaccg acctttctgc agctgagccc cgggggctg cgacgcgccg       240
atgaccacgc gggccgggct gtgcaaagcc cccggacac gggccgccgc ctgccctgga      300
gcacaggcta cgccgagtga gcgcccctg gggcacccaa accaggatgg ggctcccacc     360
cctctcccca gctccgcatc cccggcgcta ggacgcgttc cccacgccgc gtccgggcca     420
ggagctccct tttccgtgga ccttttgctat cctctggtct tcgggccgca ccccctccca     480
```

```
acccatttc cagtgggggg cagcctgtgt caccttcttc cgctccttcc cgctcattga    540
ctgccctcgc ccacgccgcc tcaggaccct gttctgcccc agagcccgga gggcggagag    600
cccggcgaag gatgagttgg ccagttcccc gtcgcggccc ggcagcttaa aggctaaggg    660
aaaaggggtt tcacgaagga gcggggttct ttttaatagg ggacatagcg gttgggaaga    720
ctcgctcacc cgcttccggg ctccagcgcc ccagttccct gtccctctta ccgtagttcc    780
cctccccctc cacacccaga aatagcccgc gacaccagga ggccgccagc ttccccagga    840
gcggggaggg ggacgcccgg ggtagaggag ggtcccattt agatgcccct cagcctgcca    900
actcgtgctg gcctggcaaa gaagcggacc ccctgcccgg agcggccggc tggccccgg     960
gctgtgtgta ttttaaatgc atctgccggg aacgcagagc accgagggag atgggggcgc   1020
tcagttcgct gaggaaggtg gctggtggcc catggaccca ccaccacctc ccttagcctc   1080
ctgtgtggga ggagtttatg ggtatgtggc tcctgcccag tccaggtggg cttcacttc    1140
tactctattt cagttcctct ttcccgatct gggctggaga gcttcctcat tgttaaggca   1200
gcagaaactt tcgctggatg gttttaggat aagggggtcat caatgctggc aagagtcggc  1260
acaatgagga ccaggcttgc tgtgaagtgg tgtatgtgga aggtcggagg agtgttacag   1320
gagtacctag ggagcctagc cgaggccagg gactctgctt ctactactgg ggcctatttg   1380
atgggcatgc agggggcgga gctgctgaaa tggcctcacg gctcctgcat cgccatatcc   1440
gagagcagct aaaggacctg aaggaagtga gccacgagag cctggtagtg ggggccattg   1500
agaatgcctt ccagctcatg gatgagcaga tggcccggga gcggcgtggc caccaagtgg   1560
agggggggctg ctgtgcactg gttgtgatct acctgctagg caaggtgtac gtggccaatg   1620
caggcgatag cagggccatc attgtccgga atggtgaaat cattccaatg tcccgggagt   1680
ttaccccgga gactgagcgc cagcgtcttc agctgcttgg cttcctgaaa ccagagctgc   1740
taggcagtga attcacccac cttgagttcc cccgcagagt tctgcccaag gagctggggc   1800
agaggatgtt gtaccgggac cagaacatga ccggctgggc ctacaaaaag atcgagctgg   1860
aggatctcag gtttcctctg gtctgtgggg agggcaaaaa ggctcgggtg atggccacca   1920
ttgggggtgac ccgaggcttg ggagaccaca gccttaaggt ctgcagttcc accctgccca   1980
tcaagccctt tctctcctgc ttccctgagg tacgagtgta tgacctgaca caatatgagc   2040
actgcccaga tgatgtgcta gtcctgggaa cagatggcct gtgggatgtc actactgact   2100
gtgaggtagc tgccactgtg gacagggtgc tgtcggccta tgagcctaat gaccacagca   2160
ggtatacagc tctgcccaa gctctggtcc tggggggccccg gggtaccccc cgagaccgtg    2220
gctggcgtct ccccaacaac aagctgggtt ccggggatga catctctgtc ttcgtcatcc   2280
ccctgggagg gccaggcagt tactcctgag gggctgaaca ccatccctcc cactagcctc   2340
tccatactta ctcctctcac agcccaaatt ctgaagttgt ctccctgacc cttctttagt   2400
ggcaacttaa ctgaagaagg gatgtccgct atatccaaaa ttacagctat ggcaaataa    2460
acgagatgga taaaaaaaaa aaaaaaaaa aaaaaaaaaa aaaaaaaaaa aaaaaaa       2518
```

<210> SEQ ID NO 380
<211> LENGTH: 4160
<212> TYPE: DNA
<213> ORGANISM: Homo sapiens
<400> SEQUENCE: 380

```
gcgcttgcgg aggattgcgt tgacgagact cttatttatt gtcaccaacc tgtggtggaa      60
tttgcagttg cacattggat ctgattcgcc ccgccccgaa tgacgcctgc ccggaggcag     120
```

```
tgaaagtaca gccgcgccgc cccaagtcag cctggacaca taaatcagca cgcggccgga      180
gaaccccgca atctctgcgc ccacaaaata caccgacgat gcccgatcta ctttaagggc      240
tgaaacccac gggcctgaga gactataaga gcgttcccta ccgccatgga acaacgggga      300
cagaacgccc cggccgcttc gggggcccgg aaaaggcacg gcccaggacc cagggaggcg      360
cggggagcca ggcctgggct ccgggtcccc aagacccttg tgctcgttgt cgccgcggtc      420
ctgctgttgg tctcagctga gtctgctctg atcacccaac aagacctagc tccccagcag      480
agagcggccc cacaacaaaa gaggtccagc ccctcagagg gattgtgtcc acctggacac      540
catatctcag aagacggtag agattgcatc tcctgcaaat atggacagga ctatagcact      600
cactggaatg acctcctttt ctgcttgcgc tgcaccaggt gtgattcagg tgaagtggag      660
ctaagtccct gcaccacgac cagaaacaca gtgtgtcagt gcgaagaagg caccttccgg      720
gaagaagatt ctcctgagat gtgccggaag tgccgcacag ggtgtcccag agggatggtc      780
aaggtcggtg attgtacacc ctggagtgac atcgaatgtg tccacaaaga atcaggtaca      840
aagcacagtg gggaagcccc agctgtggag gagacggtga cctccagccc agggactcct      900
gcctctccct gttctctctc aggcatcatc ataggagtca cagttgcagc cgtagtcttg      960
attgtggctg tgtttgtttg caagtcttta ctgtggaaga aagtccttcc ttacctgaaa     1020
ggcatctgct caggtggtgg tgggggaccct gagcgtgtgg acagaagctc acaacgacct     1080
ggggctgagg acaatgtcct caatgagatc gtgagtatct gcagcccac ccaggtccct     1140 gagcaggaaa tggaagtcca ggagccagca gagccaacag tgtcaacat gttgtccccc     1200 ggggagtcag agcatctgct ggaaccggca gaagctgaaa ggtctcagag gaggaggctg     1260
ctggttccag caaatgaagg tgatcccact gagactctga cagtgcttt cgatgacttt     1320 gcagacttgg tgccctttga ctcctgggag ccgctcatga ggaagttggg cctcatggac     1380
aatgagataa aggtggctaa agctgaggca gcggccacca gggacacctt gtacacgatg     1440
ctgataaagt gggtcaacaa aaccgggcga gatgcctctg tccacaccct gctggatgcc     1500
ttggagacgc tgggagagag acttgccaag cagaagattg aggaccactt gttgagctct     1560
ggaaagttca tgtatctaga aggtaatgca gactctgcca tgtcctaagt gtgattctct     1620
tcaggaagtc agaccttccc tggtttacct tttttctgga aaaagcccaa ctggactcca     1680
gtcagtagga aagtgccaca attgtcacat gaccggtact ggaagaaact ctcccatcca     1740
acatcaccca gtggatggaa catcctgtaa cttttcactg cacttggcat tatttttata     1800
agctgaatgt gataataagg acactatgga aatgtctgga tcattccgtt tgtgcgtact     1860
ttgagatttg gtttgggatg tcattgtttt cacagcactt ttttatccta atgtaaatgc     1920
tttatttatt tatttgggct acattgtaag atccatctac acagtcgttg tccgacttca     1980
cttgatacta tatgatatga acctttttg ggtgggggt gcggggcagt tcactctgtc     2040
tcccaggctg gagtgcaatg gtgcaatctt ggctcactat agccttgacc tctcaggctc     2100
aagcgattct cccacctcag ccatccaaat agctgggacc acaggtgtgc accaccacgc     2160
ccggctaatt ttttgtattt tgtctagata taggggctct ctatgttgct cagggtggtc     2220
tcgaattcct ggactcaagc agtctgccca cctcagactc ccaaagcggt ggaattagag     2280
gcgtgagccc ccatgcttgg ccttaccttt ctacttttat aattctgtat gttattattt     2340
tatgaacatg aagaaacttt agtaaatgta cttgtttaca tagttatgtg aatagattag     2400
ataaacataa aaggaggaga catacaatgg gggaagaaga agaagtcccc tgtaagatgt     2460
```

-continued

```
cactgtctgg gttccagccc tccctcagat gtactttggc ttcaatgatt ggcaacttct    2520
acagggccca gtcttttgaa ctggacaacc ttacaagtat atgagtatta tttataggta    2580
gttgtttaca tatgagtcgg gaccaaagag aactggatcc acgtgaagtc ctgtgtgtgg    2640
ctggtcccta cctgggcagt ctcatttgca cccatagccc ccatctatgg acaggctggg    2700
acagaggcag atgggttaga tcacacataa caatagggtc tatgtcatat cccaagtgaa    2760
cttgagccct gtttgggctc aggagataga agacaaaatc tgtctcccac gtctgccatg    2820
gcatcaaggg ggaagagtag atggtgcttg agaatggtgt gaaatggttg ccatctcagg    2880
agtagatggc ccggctcact tctggttatc tgtcaccctg agcccatgag ctgcctttta    2940
gggtacagat tgcctacttg aggaccttgg ccgctctgta agcatctgac tcatctcaga    3000
aatgtcaatt cttaaacact gtggcaacag gacctagaat ggctgacgca ttaaggtttt    3060
cttcttgtgt cctgttctat tattgtttta agacctcagt aaccatttca gcctctttcc    3120
agcaaaccct tctccatagt atttcagtca tggaaggatc atttatgcag gtagtcattc    3180
caggagtttt tggtcttttc tgtctcaagg cattgtgtgt tttgttccgg gactggtttg    3240
ggtgggacaa agttagaatt gcctgaagat cacacattca gactgttgtg tctgtgggagt    3300 tttaggagtg gggggtgacc tttctggtct ttgcacttcc atcctctccc acttccatct    3360
ggcatcccac gcgttgtccc ctgcacttct ggaaggcaca gggtgctgct gcctcctggt    3420
cttrgccttt gctgggcctt ctgtgcagga cgctcagcct cagggctcag aaggtgccag    3480
tccggtccca ggtcccttgt cccttccaca gaggccttcc tagaagatgc atctagagtg    3540
tcagccttat cagtgtttaa gatttgtctt ttatttttaa ttttttttgag acagaatctc    3600 actctctcgc ccaggctgga gtgcaacggt acgatcttgg ctcagtgcaa cctccgcctc    3660
ctgggttcaa gcgattctcg tgcctcagcc tccggagtag ctgggattgc aggcacccgc    3720
caccacgcct ggctaatttt tgtattttta gtagagacgg ggtttcacca tgttggtcag    3780
gctggtctcg aactcctgac ctcaggtgat ccaccttggc ctccgaaagt gctgggatta    3840
caggcgtgag ccaccagcca ggccaagcta ttcttttaaa gtaagcttcc tgacgacatg    3900
aaataattgg gggttttgtt gtttagttac attaggcttt gctatatccc caggccaaat    3960
agcatgtgac acaggacagc catagtatag tgtgtcactc gtggttggtg tcctttcatg    4020
cttctgccct gtcaaaggtc cctatttgaa atgtgttata atacaaacaa ggaagcacat    4080
tgtgtacaaa atacttatgt atttatgaat ccatgaccaa attaaatatg aaaccttata    4140
taaaaaaaaa aaaaaaaaaa                                               4160
```

<210> SEQ ID NO 381
<211> LENGTH: 1295
<212> TYPE: DNA
<213> ORGANISM: Homo sapiens

<400> SEQUENCE: 381

```
gtgcggagtt tggctgctcc ggggttagca ggtgagcctg cgatgcgcgg aagacgttc      60 cgctttgaaa tgcagcggga tttggtgagt ttcccgctgt ctccagcggt gcgggtgaag    120
ctggtgtctg cggggttcca gactgctgag gaactcctag aggtgaaacc ctccgagctt    180
agcaaagaag ttgggatatc taaagcagaa gccttagaaa ctctgcaaat tatcagaaga    240
gaatgtctca caaataaacc aagatatgct ggtacatctg agtcacacaa gaagtgtaca    300
gcactggaac ttcttgagca ggagcatacc cagggcttca taatcacctt ctgttcagca    360
ctagatgata ttcttggggg tggagtgccc ttaatgaaaa caacagaaat ttgtggtgca    420
```

```
ccaggtgttg gaaaaacaca attatgtatg cagttggcag tagatgtgca gataccagaa    480
tgttttggag gagtggcagg tgaagcagtt tttattgata cagagggaag ttttatggtt    540
gatagagtgg tagaccttgc tactgcctgc attcagcacc ttcagcttat agcagaaaaa    600
cacaagggag aggaacaccg aaaagctttg gaggatttca ctcttgataa tattctttct    660
catatttatt attttcgctg tcgtgactac acagagttac tggcacaagt ttatcttctt    720
ccagatttcc tttcagaaca ctcaaaggtt cgactagtga tagtggatgg tattgctttt    780
ccatttcgtc atgacctaga tgacctgtct cttcgtactc ggttattaaa tggcctagcc    840
cagcaaatga tcagccttgc aaataatcac agattagctg taattttaac caatcagatg    900
acaacaaaga ttgatagaaa tcaggccttg cttgttcctg cattagggga agttggggga    960
catgctgcta caatacggct aatctttcat tgggaccgaa agcaaaggtt ggcaacattg   1020
tacaagtcac ccagccagaa ggaatgcaca gtactgtttc aaatcaaacc tcagggattt   1080
agagatactg ttgttacttc tgcatgttca ttgcaaacag aaggttcctt gagcacccgg   1140
aaacggtcac gagacccaga ggaagaatta aacccagaa acaaatctca aagtgtacaa    1200
atttattgat gttgtgaaat caatgtgtac aagtggactt gttaccttaa agtataaata   1260
aacacactat ggcatgaatg aaaaaaaaaa aaaaa                              1295
```

<210> SEQ ID NO 382
<211> LENGTH: 2210
<212> TYPE: DNA
<213> ORGANISM: Homo sapiens

<400> SEQUENCE: 382

```
cgcgcccctc cctcctcgcg gacctggcgg tgccggcgcc cggagtggcc ctttaaaagg     60
cagcttattg tccggagggg gcgggcgggg ggcgccgacc gcggcctgag gcccggcccc    120 tccctctcc ctccctctgt ccccgcgtcg ctcgctggct agctcgctgg ctcgctcgcc    180
cgtccggcgc acgctccgcc tccgtcagtt ggctccgctg tcgggtgcgc ggcgtggagc    240
ggcagccggt ctggacgcgc ggccggggct ggggctgggg agcgcggcgc gcaagatctc    300
cccgcgcgag agcggccccct gccaccgggc gaggcctgcg ccgcgatggc agagatgggc    360
agtaaagggg tgacggcggg aaagatcgcc agcaacgtgc agaagaagct cacccgcgcg    420
caggagaagg ttctccagaa gctggggaag gcagatgaga ccaaggatga gcagtttgag    480
cagtgcgtcc agaatttcaa caagcagctg acggagggca cccggctgca gaaggatctc    540
cggacctacc tggcctccgt caaagccatg cacgaggctt ccaagaagct gaatgagtgt    600
ctgcaggagt gtatgagcc cgattggccc ggcaggatg aggcaaacaa gatcgcagag    660
aacaacgacc tgctgtggat ggattaccac cagaagctgg tggaccaggc gctgctgacc    720
atggacacgt acctgggcca gttccccgac atcaagtcac gcattgccaa gcgggggcgc    780
aagctggtgg actacgacag tgcccggcac cactacgagt cccttcaaac tgccaaaaag    840
aaggatgaag ccaaaattgc caaggccgag gaggagctca tcaaagccca gaaggtgttt    900
gaggagatga atgtggatct gcaggaggag ctgccgtccc tgtggaacag ccgcgtaggt    960
ttctacgtca acacgttcca gagcatcgcg ggcctggagg aaaacttcca aggagatg   1020 agcaagctca ccagaacct caatgatgtg ctggtcggcc tggagaagca cacgggagc   1080 aacaccttca cggtcaaggc ccagcccaga aagaaaagta aactgttttc gcggctgcgc   1140
agaaagaaga acagtgacaa cgcgcctgca aagggaacaa agagcccttc gcctccagat   1200
```

```
ggctcccctg ccgccacccc cgagatcaga gtcaaccacg agccagagcc ggccggcggg   1260
gccacgcccg gggccaccct ccccaagtcc ccatctcagc cagcagaggc ctcggaggtg   1320
gcgggtggga cccaacctgc ggctggagcc caggagccag gggagacggc ggcaagtgaa   1380
gcagcctcca gctctcttcc tgctgtcgtg gtggagacct cccagcaac tgtgaatggc    1440 accgtggagg gcggcagtgg ggccgggcgc ttggacctgc cccaggtttt catgttcaag   1500
gtacaggccc agcacgacta cacgccacct gacacagacg agctgcagct caaggctggt   1560
gatgtggtgc tggtgatccc cttccagaac cctgaagagc aggatgaagg ctggctcatg   1620
ggcgtgaagg agagcgactg gaaccagcac aaggagctgg agaagtgccg tggcgtcttc   1680
cccgagaact tcactgagag ggtcccatga cggcggggcc caggcagcct ccgggcgtgt   1740
gaagaacacc tcctcccgaa aaatgtgtgg ttctttttt tgttttgttt tcgttttca     1800 tcttttgaag agcaaaggga aatcaagagg acccccag gcagaggggc gttctcccaa     1860
agattaggtc gttttccaaa gagccgcgtc ccggcaagtc cggcggaatt caccagtgtt   1920
cctgaagctg ctgtgtcctc tagttgagtt tctggcgccc ctgcctgtgc ccgcatgtgt   1980
gcctggccgc agggcgggc tggggctgc cgagccacca tgcttgcctg aagcttcggc     2040
cgcgccaccc gggcaagggt cctcttttcc tggcagctgc tgtgggtggg gcccagacac   2100
cagcctagcc tggctctgcc ccgcagacgg tctgtgtgct gtttgaaaat aaatcttagt   2160
gttcaaaaca aaatgaaaca aaaaaaaaat gataaaaact ctcaaaaaaa              2210

<210> SEQ ID NO 383
<211> LENGTH: 4604
<212> TYPE: DNA
<213> ORGANISM: Homo sapiens

<400> SEQUENCE: 383
ggaacagctt gtccacccgc cggccggacc agaagccttt gggtctgaag tgtctgtgag     60
acctcacaga agagcacccc tgggctccac ttacctgccc cctgctcctt cagggatgga   120
ggcaatggcg ccagcactt ccctgcctga ccctggagac tttgaccgga acgtgccccg    180
gatctgtggg gtgtgtggag accgagccac tggctttcac ttcaatgcta tgacctgtga   240
aggctgcaaa ggcttcttca ggcgaagcat gaagcggaag gcactattca cctgcccctt   300
caacggggac tgccgcatca ccaaggacaa ccgacgccac tgccaggcct gccggctcaa   360
acgctgtgtg gacatcggca tgatgaagga gttcattctg acagatgagg aagtgcagag   420
gaagcgggag atgatcctga gcggaagga ggaggaggcc ttgaaggaca gtctgcggcc   480
caagctgtct gaggagcagc agcgcatcat tgccatactg ctggacgccc accataagac   540
ctacgacccc acctactccg acttctgcca gttccgccct ccagttcgtg tgaatgatgg   600 tgggggagc catccttcca ggcccaactc cagacacact cccagcttct ctggggactc   660
ctcctcctcc tgctcagatc actgtatcac ctcttcagac atgatggact cgtccagctt   720
ctccaatctg gatctgagtg aagaagattc agatgaccct tctgtgaccc tagagctgtc   780
ccagctctcc atgctgcccc acctggctga cctggtcagt tacagcatcc aaaaggtcat   840
tggctttgct aagatgatac caggattcag agacctcacc tctgaggacc agatcgtact   900
gctgaagtca gtgccattg aggtcatcat gttgcgctcc aatgagtcct tcaccatgga    960
cgacatgtcc tggacctgtg gcaaccaaga ctacaagtac cgcgtcagtg acgtgaccaa   1020
agccggacac agcctggagc tgattgagcc cctcatcaag ttccaggtgg gactgaagaa   1080
gctgaacttg catgaggagg agcatgtcct gctcatggcc atctgcatcg tctccccaga   1140
```

-continued

```
tcgtcctggg gtgcaggacg ccgcgctgat tgaggccatc caggaccgcc tgtccaacac    1200
actgcagacg tacatccgct gccgccaccc gccccgggc agccacctgc tctatgccaa     1260
gatgatccag aagctagccg acctgcgcag cctcaatgag gagcactcca agcagtaccg    1320
ctgcctctcc ttccagcctg agtgcagcat gaagctaacg ccccttgtgc tcgaagtgtt    1380
tggcaatgag atctcctgac taggacagcc tgtgcggtgc ctgggtgggg ctgctcctcc    1440
agggccacgt gccaggcccg ggctggcgg ctactcagca gccctcctca cccgtctggg     1500
gttcagcccc tcctctgcca cctcccctat ccacccagcc cattctctct cctgtccaac    1560 ctaaccccctt tcctgcgggc ttttccccgg tcccttgaga cctcagccat gaggagttgc   1620
tgtttgtttg acaaagaaac ccaagtgggg gcagagggca gaggctggag gcaggccttg    1680
cccagagatg cctccaccgc tgcctaagtg gctgctgact gatgttgagg gaacagacag    1740
gagaaatgca tccattcctc agggacagag acacctgcac ctccccccac tgcaggcccc    1800
gcttgtccag cgcctagtgg ggtctccctc tcctgcctta ctcacgataa ataatcggcc    1860
cacagctccc accccacccc cttcagtgcc caccaacatc ccattgccct ggttatattc    1920
tcacgggcag tagctgtggt gaggtgggtt ttcttcccat cactggagca ccaggcacga    1980
acccacctgc tgagagaccc aaggaggaaa aacagacaaa aacagcctca cagaagaata    2040
tgacagctgt ccctgtcacc aagctcacag ttcctcgccc tgggtctaag gggttggttg    2100
aggtggaagc cctccttcca cggatccatg tagcaggact gaattgtccc cagtttgcag    2160
aaaagcacct gccgacctcg tcctcccccct gccagtgcct tacctcctgc ccaggagagc   2220
cagccctccc tgtcctcctc ggatcaccga gagtagccga gagcctgctc ccccaccccc    2280
tccccagggg agagggtctg gagaagcagt gagccgcatc ttctccatct ggcagggtgg    2340
gatggaggag aagaattttc agaccccagc ggctgagtca tgatctccct gccgcctcaa    2400
tgtggttgca aggccgctgt tcaccacagg gctaagagct aggctgccgc accccagagt    2460
gtgggaaggg agagcggggc agtctcgggt ggctagtcag agagagtgtt tgggggttcc    2520
gtgatgtagg gtaaggtgcc ttcttattct cactccacca cccaaaagtc aaaaggtgcc    2580
tgtgaggcag gggcggagtg atacaacttc aagtgcatgc tctctgcagg tcgagcccag    2640
cccagctggt gggaagcgtc tgtccgttta ctccaaggtg ggtctttgtg agagtgagct    2700
gtaggtgtgc gggaccggta cagaaaggcg ttcttcgagg tggatcacag aggcttcttc    2760
agatcaatgc ttgagtttgg aatcggccgc attccctgag tcaccaggaa tgttaaagtc    2820
agtgggaacg tgactgcccc aactcctgga agctgtgtcc ttgcacctgc atccgtagtt    2880
ccctgaaaac ccagagagga atcagacttc acactgcaag agccttggtg tccacctggc    2940
cccatgtctc tcagaattct tcaggtggaa aaacatctga agccacgtt ccttactgca     3000 gaatagcata tatatcgctt aatcttaaat ttattagata tgagttgttt tcagactcag    3060
actccatttg tattatagtc taatatacag ggtagcaggt accactgatt tggagatatt    3120
tatgggggga gaacttacat tgtgaaactt ctgtacatta attattattg ctgttgttat    3180
tttacaaggg tctagggaga gacccttgtt tgattttagc tgcagaactg tattggtcca    3240
gcttgctctt cagtgggaga aaacacttg taagttgcta aacgagtcaa tcccctcatt     3300
caggaaaact gacagaggag ggcgtgactc acccaagcca tatataacta gctagaagtg    3360
ggccaggaca ggccgggcgc ggtggctcac gcctgtaatc ccagcagttt gggaggtcga    3420
ggtaggtgga tcacctgagg tcgggagttc gagaccaacc tgaccaacat ggagaaaccc    3480
```

```
                                        -continued
tgtctctatt aaaaatacaa aaaaaaaaaa aaaaaaaaat agccgggcat ggtggcgcaa      3540
gcctgtaatc ccagctactc aggaggctga ggcagaagaa ttgaacccag gaggtggagg      3600
ttgcagtgag ctgagatcgt gccgttactc tccaacctgg acaacaagag cgaaactccg      3660
tcttagaagt ggaccaggac aggaccagat tttggagtca tggtccggtg tccttttcac      3720
tacaccatgt ttgagctcag accccactc tcattcccca ggtggctgac ccagtccctg       3780
ggggaagccc tggatttcag aaagagccaa gtctggatct gggacccttt ccttccttcc      3840
ctggcttgta actccaccaa gcccatcaga aggagaagga aggagactca cctctgcctc      3900
aatgtgaatc agaccctacc ccaccacgat gtgccctggc tgctgggctc tccacctcag      3960
gccttggata atgctgttgc ctcatctata acatgcattt gtctttgtaa tgtcaccacc      4020
ttcccagctc tccctctggc cctgcttctt cggggaactc ctgaaatatc agttactcag      4080
ccctgggccc caccacctag gccactcctc caaaggaagt ctaggagctg ggaggaaaag      4140
aaaagagggg aaaatgagtt tttatggggc tgaacgggga gaaaaggtca tcatcgattc      4200
tactttagaa tgagagtgtg aaatagacat ttgtaaatgt aaaactttta aggtatatca      4260
ttataactga aggagaaggt gccccaaaat gcaagatttt ccacaagatt cccagagaca      4320
ggaaaatcct ctggctggct aactggaagc atgtaggaga atccaagcga ggtcaacaga      4380
gaaggcagga atgtgtggca gatttagtga aagctagaa tatggcagcg aaaggatgta      4440
aacagtgcct gctgaatgat ttccaaagag aaaaaagtt tgccagaagt ttgtcaagtc       4500
aaccaatgta gaaagctttg cttatggtaa taaaaatggc tcatacttat atagcactta      4560
ctttgtttgc aagtactgct gtaaataaat gctttatgca aacc                      4604

<210> SEQ ID NO 384
<211> LENGTH: 545
<212> TYPE: DNA
<213> ORGANISM: Homo sapiens

<400> SEQUENCE: 384
gagtgactct cacgagagcc gcgagagtca gcttggccaa tccgtgcggt cggcggccgc        60 tcccttata  agccgactcg cccggcagcg caccggggttg cggagggtgg gcctgggagg      120
ggtggtggcc atttttgtc  taaccctaac tgagaagggc gtaggcgccg tgcttttgct      180
ccccgcgcgc tgtttttctc gctgactttc agcgggcgga aaagcctcgg cctgccgcct      240
tccaccgttc attctagagc aaacaaaaa  tgtcagctgc tggcccgttc gcccctcccg      300
gggacctgcg gcgggtcgcc tgcccagccc ccgaaccccg cctggaggcc gcggtcggcc      360
cggggcttct ccggaggcac ccactgccac cgcgaagagt tgggctctgt cagccgcggg      420
tctctcgggg gcgagggcga ggttcaggcc tttcaggccg caggaagagg aacggagcga      480
gtccccgcgc gcggcgcgat tccctgagct gtgggacgtg cacccaggac tcggctcaca      540
catgc                                                                 545
```

GENE EXPRESSION PROFILING IN BIOPSIED TUMOR TISSUES

CROSS-REFERENCE

This application is a continuation of, and claims priority under 35 USC§120 to, U.S. application Ser. No. 10/388,360 filed Mar. 12, 2003, now U.S. Pat. No. 7,081,340, which claims the benefit under 35 U.S.C. 119(e) of provisional application Ser. No. 60/412,049, filed Sep. 18, 2002 the entire disclosure of which is hereby incorporated by reference.

BACKGROUND OF THE INVENTION

Field of the Invention

The present invention relates to gene expression profiling in biopsied tumor tissues. In particular, the present invention concerns sensitive methods to measure mRNA levels in biopsied tumor tissues, including archived paraffin-embedded biopsy material. In addition, the invention provides a set of genes the expression of which is important in the diagnosis and treatment of breast cancer.

Oncologists have a number of treatment options available to them, including different combinations of chemotherapeutic drugs that are characterized as "standard of care," and a number of drugs that do not carry a label claim for a particular cancer, but for which there is evidence of efficacy in that cancer. Best likelihood of good treatment outcome requires that patients be assigned to optimal available cancer treatment, and that this assignment be made as quickly as possible following diagnosis.

Currently, diagnostic tests used in clinical practice are single analyte, and therefore do not capture the potential value of knowing relationships between dozens of different markers. Moreover, diagnostic tests are frequently not quantitative, relying on immunohistochemistry. This method often yields different results in different laboratories, in part because the reagents are not standardized, and in part because the interpretations are subjective and cannot be easily quantified. RNA-based tests have not often been used because of the problem of RNA degradation over time and the fact that it is difficult to obtain fresh tissue samples from patients for analysis. Fixed paraffin-embedded tissue is more readily available and methods have been established to detect RNA in fixed tissue. However, these methods typically do not allow for the study of large numbers of genes (DNA or RNA) from small amounts of material. Thus, traditionally fixed tissue has been rarely used other than for immunohistochemistry detection of proteins.

Recently, several groups have published studies concerning the classification of various cancer types by microarray gene expression analysis (see, e.g. Golub et al., *Science* 286: 531-537 (1999); Bhattacharjae et al., *Proc. Natl. Acad. Sci. USA* 98:13790-13795 (2001); Chen-Hsiang et al., *Bioinformatics* 17 (Suppl. 1):S316-S322 (2001); Ramaswamy et al., *Proc. Natl. Acad. Sci. USA* 98:15149-15154 (2001)). Certain classifications of human breast cancers based on gene expression patterns have also been reported (Martin et al., *Cancer Res.* 60:2232-2238 (2000); West et al., *Proc. Natl. Acad. Sci. USA* 98:11462-11467 (2001); Sorlie et al., *Proc. Natl. Acad. Sci. USA* 98:10869-10874 (2001); Yan et al., *Cancer Res.* 61:8375-8380 (2001)). However, these studies mostly focus on improving and refining the already established classification of various types of cancer, including breast cancer, and generally do not provide new insights into the relationships of the differentially expressed genes, and do not link the findings to treatment strategies in order to improve the clinical outcome of cancer therapy.

Although modern molecular biology and biochemistry have revealed more than 100 genes whose activities influence the behavior of tumor cells, state of their differentiation, and their sensitivity or resistance to certain therapeutic drugs, with a few exceptions, the status of these genes has not been exploited for the purpose of routinely making clinical decisions about drug treatments. One notable exception is the use of estrogen receptor (ER) protein expression in breast carcinomas to select patients to treatment with anti-estrogen drugs, such as tamdxifen. Another exceptional example is the use of ErbB2 (Her2) protein expression in breast carcinomas to select patients with the Her2 antagonist drug Herceptin® (Genentech, Inc., South San Francisco, Calif.).

Despite recent advances, the challenge of cancer treatment remains to target specific treatment regimens to pathogenically distinct tumor types, and ultimately personalize tumor treatment in order to maximize outcome. Hence, a need exists for tests that simultaneously provide predictive information about patient responses to the variety of treatment options. This is particularly true for breast cancer, the biology of which is poorly understood. It is clear that the classification of breast cancer into a few subgroups, such as ErbB2$^+$ subgroup, and subgroups characterized by low to absent gene expression of the estrogen receptor (ER) and a few additional transcriptional factors (Perou et al., *Nature* 406:747-752 (2000)) does not reflect the cellular and molecular heterogeneity of breast cancer, and does not allow the design of treatment strategies maximizing patient response.

SUMMARY OF THE INVENTION

The present invention provides (1) sensitive methods to measure mRNA levels in biopsied tumor tissue, (2) a set of approximately 190 genes, the expression of which is important in the diagnosis of breast cancer, and (3) the significance of abnormally low or high expression for the genes identified and included in the gene set, through activation or disruption of biochemical regulatory pathways that influence patient response to particular drugs used or potentially useful in the treatment of breast cancer. These results permit assessment of genomic evidence of the efficacy of more than a dozen relevant drugs.

The present invention accommodates the use of archived paraffin-embedded biopsy material for assay of all markers in the set, and therefore is compatible with the most widely available type of biopsy material. The invention presents an efficient method for extraction of RNA from wax-embedded, fixed tissues, which reduces cost of mass production process for acquisition of this information without sacrificing quality of the analysis. In addition, the invention describes a novel highly effective method for amplifying mRNA copy number, which permits increased assay sensitivity and the ability to monitor expression of large numbers of different genes given the limited amounts of biopsy material. The invention also captures the predictive significance of relationships between expressions of certain markers in the breast cancer marker set. Finally, for each member of the gene set, the invention specifies the oligonucleotide sequences to be used in the test.

In one aspect, the invention concerns a method for predicting clinical outcome for a patient diagnosed with cancer, comprising determining the expression level of one or more genes, or their expression products, selected from the group consisting of p53BP2, cathepsin B, cathepsin L, Ki67/MiB1, and thymidine kinase in a cancer tissue obtained from the patient, normalized against a control gene or genes, and compared to the amount found in a reference cancer tissue set, wherein a poor outcome is predicted if:

(a) the expression level of p53BP2 is in the lower $10^{th}$ percentile; or (b) the expression level of either cathepsin B or cathepsin L is in the upper $10^{th}$ percentile; or (c) the expression level of any either Ki67/MiB1 or thymidine kinase is in the upper $10^{th}$ percentile.

Poor clinical outcome can be measured, for example, in terms of shortened survival or increased risk of cancer recurrence, e.g. following surgical removal of the cancer.

In another embodiment, the inventor concerns a method of predicting the likelihood of the recurrence of cancer, following treatment, in a cancer patient, comprising determining the expression level of p27, or its expression product, in a cancer tissue obtained from the patient, normalized against a control gene or genes, and compared to the amount found in a reference cancer tissue set, wherein an expression level in the upper 10th percentile indicates decreased risk of recurrence following treatment.

In another aspect, the invention concerns a method for classifying cancer comprising, determining the expression level of two or more genes selected from the group consisting of Bcl2, hepatocyte nuclear factor 3, ER, ErbB2, and Grb7, or their expression products, in a cancer tissue, normalized against a control gene or genes, and compared to the amount found in a reference cancer tissue set, wherein (i) tumors expressing at least one of Bcl2, hepatocyte nuclear factor 3, and ER, or their expression products, above the mean expression level in the reference tissue set are classified as having a good prognosis for disease free and overall patient survival following treatment; and (ii) tumors expressing elevated levels of ErbB2 and Grb7, or their expression products, at levels ten-fold or more above the mean expression level in the reference tissue set are classified as having poor prognosis of disease free and overall patient survival following treatment.

All types of cancer are included, such as, for example, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer. The foregoing methods are particularly suitable for prognosis/classification of breast cancer.

In all previous aspects, in a specific embodiment, the expression level is determined using RNA obtained from a formalin-fixed, paraffin-embedded tissue sample. While all techniques of gene expression profiling, as well as proteomics techniques, are suitable for use in performing the foregoing aspects of the invention, the gene expression levels are often determined by reverse transcription polymerase chain reaction (RT-PCR).

If the source of the tissue is a formalin-fixed, paraffin embedded tissue sample, the RNA is often fragmented.

The expression data can be further subjected to multivariate analysis, for example using the Cox Proportional Hazards model.

In a further aspect, the invention concerns a method for the preparation of nucleic acid from a fixed, wax-embedded tissue specimen, comprising:

(a) incubating a section of the fixed, wax-embedded tissue specimen at a temperature of about 56° C. to 70° C. in a lysis buffer, in the presence of a protease, without prior dewaxing, to form a lysis solution;

(b) cooling the lysis solution to a temperature where the wax solidifies; and (c) isolating the nucleic acid from the lysis solution.

The lysis buffer may comprise urea, such as 4M urea. In a particular embodiment, incubation in step (a) of the foregoing method is performed at about 65° C.

In another particular embodiment, the protease used in the foregoing method is proteinase K.

In another embodiment, the cooling in step (b) is performed at room temperature.

In a further embodiment, the nucleic acid is isolated after protein removal with 2.5 M NH$_4$OAc.

The nucleic acid can, for example, be total nucleic acid present in the fixed, wax-embedded tissue specimen.

In yet another embodiment, the total nucleic acid is isolated by precipitation from the lysis solution, following protein removal, with 2.5 M NH$_4$OAc. The precipitation may, for example, be performed with isopropanol.

The method described above may further comprise the step of removing DNA from the total nucleic acid, for example by DNAse treatment.

The tissue specimen may, for example, be obtained from a tumor, and the RNA may be obtained from a microdissected portion of the tissue specimen enriched for tumor cells.

All types of tumor are included, such as, without limitation, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer, in particular breast cancer.

The method described above may further comprise the step of subjecting the RNA to gene expression profiling. Thus, the gene expression profile may be completed for a set of genes comprising at least two of the genes listed in Table 1.

Although all methods of gene expression profiling are contemplated, in a particular embodiment, gene expression profiling is performed by RT-PCR which may be preceded by an amplification step.

In another aspect, the invention concerns a method for preparing fragmented RNA for gene expression analysis, comprising the steps of:

(a) mixing the RNA with at least one gene-specific, single-stranded DNA scaffold under conditions such that fragments of the RNA complementary to the DNA scaffold hybridize with the DNA scaffold;

(b) extending the hybridized RNA fragments with a DNA polymerase to form a DNA-DNA duplex; and (c) removing the DNA scaffold from the duplex.

In a specific embodiment, in step (b) of this method, the RNA may be mixed with a mixture of single-stranded DNA templates specific for each gene of interest.

The method can further comprise the step of heat-denaturing and reannealing the duplexed DNA to the DNA scaffold, with or without additional overlapping scaffolds, and further extending the duplexed sense strand with DNA polymerase prior to removal of the scaffold in step (c).

The DNA templates may be, but do not need to be, fully complementary to the gene of interest.

In a particular embodiment, at least one of the DNA templates is complementary to a specific segment of the gene of interest.

In another embodiment, the DNA templates include sequences complementary to polymorphic variants of the same gene.

The DNA template may include one or more dUTP or rNTP sites. In this case. In step (c) the DNA template may be removed by fragmenting the DNA template present in the DNA-DNA duplex formed in step (b) at the dUTP or rNTP sites.

In an important embodiment, the RNA is extracted from fixed, wax-embedded tissue specimens, and purified sufficiently to act as a substrate in an enzyme assay. The RNA purification may, but does not need to, include an oligo-dT based step.

In a further aspect, the invention concerns a method for amplifying RNA fragments in a sample comprising fragmented RNA representing at least one gene of interest, comprising the steps of:

(a) contacting the sample with a pool of single-stranded DNA scaffolds comprising an RNA polymerase promoter at the 5' end under conditions such that the RNA fragments complementary to the DNA scaffolds hybridize with the DNA scaffolds;

(b) extending the hybridized RNA fragments with a DNA polymerase along the DNA scaffolds to form DNA-DNA duplexes;

(c) amplifying the gene or genes of interest by in vitro transcription; and (d) removing the DNA scaffolds from the duplexes.

An exemplary promoter is the T7 RNA polymerase promoter, while an exemplary DNA polymerase is DNA polymerase I.

In step (d) the DNA scaffolds may be removed, for example, by treatment with DNase I.

In a further embodiment, the pool of single-stranded DNA scaffolds comprises partial or complete gene sequences of interest, such as a library of cDNA clones.

In a specific embodiment, the sample represents a whole genome or a fraction thereof. In a preferred embodiment, the genome is the human genome.

In another aspect, the invention concerns a method of preparing a personalized genomics profile for a patient, comprising the steps of:

(a) subjecting RNA extracted from a tissue obtained from the patient to gene expression analysis;

(b) determining the expression level in such tissue of at least two genes selected from the gene set listed in Table 1, wherein the expression level is normalized against a control gene or genes, and is compared to the amount found in a cancer tissue reference set;

(c) and creating a report summarizing the data obtained by the gene expression analysis.

The tissue obtained from the patient may, but does not have to, comprise cancer cells. Just as before, the cancer can, for example, be breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, or brain cancer, breast cancer being particularly preferred.

In a particular embodiment, the RNA is obtained from a microdissected portion of breast cancer tissue enriched for cancer cells. The control gene set may, for example, comprise S-actin, and ribosomal protein LPO.

The report prepared for the use of the patient or the patient's physician, may include the identification of at least one drug potentially beneficial in the treatment of the patient.

Step (b) of the foregoing method may comprise the step of determining the expression level of a gene specifically influencing cellular sensitivity to a drug, where the gene can, for example, be selected from the group consisting of aldehyde dehydrogenase 1A1, aldehyde dehydrogenase 1A3, amphiregulin, ARG, BRK, BCRP, CD9, CD31, CD82/KAI-1, COX2, c-abl, c-kit, c-kit L, CYP1B1, CYP2C9, DHFR, dihydropyrimidine dehydrogenase, EGF, epiregulin, ER-alpha, ErbB-1, ErbB-2, ErbB-3, ErbB-4, ER-beta, farnesyl pyrophosphate synthetase, gamma-GCS (glutamyl cysteine synthetase), GATA3, geranyl pyrophosphate synthetase, Grb7, GST-alpha, GST-pi, HB-EGF, hsp 27, human chorionic gonadotropin/CGA, IGF-1, IGF-2, IGF1R, KDR, LIV1, Lung Resistance Protein/MVP, Lot1, MDR-1, microsoinal epoxide hydrolase, MMP9, MRP1, MRP2, MRP3, MRP4, PAI1, PDGF-A, PDGF-B, PDGF-C, PDGF-D, PGDFR-alpha, PDGFR-beta, PLAGa (pleiomorphic adenoma 1), PREP prolyl endopeptidase, progesterone receptor, pS2/trefoil factor 1, PTEN, PTB1b, RAR-alpha, RAR-beta2, Reduced Folate Carrier, SXR, TGF-alpha, thymidine phosphorylase, thymidine synthase, topoisomerase II-alpha, topoisomerase II-beta, VEGF, XIST, and YB-1.

In another embodiment, step (b) of the foregoing process includes determining the expression level of multidrug resistance factors, such as, for example, gamma-glutamyl-cysteine synthetase (GCS), GST-α, GST-π, MDR-1, MRP1-4, breast cancer resistance protein (BCRP), lung cancer resistance protein (MVP), SXR, or YB-1.

In another embodiment, step (b) of the foregoing process comprises determination of the expression level of eukaryotic translation initiation factor 4E (EIF4E).

In yet another embodiment, step (b) of the foregoing process comprises determination of the expression level of a DNA repair enzyme.

In a further embodiment, step (b) of the foregoing process comprises determination of the expression level of a cell cycle regulator, such as, for example, c-MYC, c-Src, Cyclin D1, Ha-Ras, mdm2. p14ARF, p21WAF1/CI, p16INK4a/p14, p23, p27, p53, PI3K, PKC-epsilon, or PKC-delta.

In a still further embodiment, step (b) of the foregoing process comprises determination of the expression level of a tumor suppressor or a related protein, such as, for example, APC or E-cadherin.

In another embodiment, step (b) of the foregoing method comprises determination of the expression level of a gene regulating apoptosis, such as, for example, p53, BCl2, Bcl-x1, Bak, Bax, and related factors, NFκ-B, CIAP1, CIAP2, survivin, and related factors, p53BP1/ASPP1, or p53BP2/ASPP2.

In yet another embodiment, step (b) of the foregoing process comprises determination of the expression level of a factor that controls cell invasion or angiogenesis, such as, for example, uPA, PAI1, cathepsin B, C, and L, scatter factor (HGF), c-met, KDR, VEGF, or CD31.

In a different embodiment, step (b) of the foregoing method comprises determination of the expression level of a marker for immune or inflammatory cells or processes, such as, for example, Ig light chain λ, CD18, CD3, CD68. Fas(CD95), or Fas. Ligand.

In a further embodiment, step (b) of the foregoing process comprises determination of the expression level of a cell proliferation marker, such as, for example, Ki67/MiB1, PCNA, Pin1, or thymidine kinase.

In a still further embodiment, step (b) of the foregoing process comprises determination of the expression level of a growth factor or growth factor receptor., such as, for example, IGF1, IGF2, IGFBP3, IGF1R, FGF2, CSF-1, CSF-1R/fins, SCF-1, IL6 or IL8.

In another embodiment, step (b) of the foregoing process comprises determination of the expression level of a gene marker that defines a subclass of breast cancer, where the gene marker can, for example, be GRO1 oncogene alpha, Grb7, cytokeratins 5 and 17, retinol binding protein 4, hepatocyte nuclear factor 3, integrin subunit alpha 7, or lipoprotein lipase.

In a still further aspect, the invention concerns a method for predicting the response of a patient diagnosed with breast cancer to 5-fluorouracil (5-FU) or an analog thereof, comprising the steps of:

(a) subjecting RNA extracted from a breast cancer tissue obtained from the patient to gene expression analysis;

(b) determining the expression level in the tissue of thymidylate synthase mRNA, wherein the expression level is normalized against a control gene or genes, and is compared to the amount found in a reference breast cancer tissue set; and (c) predicting patient response based on the normalized thymidylate synthase mRNA level.

Step (d) of the foregoing method can further comprise determining the expression level of dihydropyrimidine phosphorylase.

In another embodiment, step (b) of the method can further comprise determining the expression level of thymidine phosphorylase.

In yet another embodiment, a positive response to 5-FU or an analog thereof is predicted if: (i) normalized thymidylate synthase mRNA level determined in step (b) is at or below the $15^{th}$ percentile; or (ii) the sum of normalized expression levels of thymidylate synthase and dihydropyrimidine phosphorylase determined in step (b) is at or below the $25^{th}$ percentile; or (iii) the sum of normalized expression levels of thymidylate synthase, dihydropyrimidine phosphorylase, plus thymidine phosphorylase determined in step (b) is at or below the $20^{th}$ percentile.

In a further embodiment, in step (b) of the foregoing method the expression level of c-myc and wild-type p53 is determined. In this case, a positive response to 5-FU or an analog thereof is predicted, if the normalized expression level of c-myc relative to the normalized expression level of wild-type p53 is in the upper $15^{th}$ percentile.

In a still further embodiment, in step (b) of the foregoing method, expression level of NFκB and cIAP2 is determined. In this particular embodiment, resistance to 5-FU or an analog thereof is typically predicted if the normalized expression level of NFκB and cIAP2 is at or above the $10^{th}$ percentile.

In another aspect, the invention concerns a method for predicting the response of a patient diagnosed with breast cancer to methotrexate or an analog thereof, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting decreased patient sensitivity to methotrexate or analog if (i) DHFR levels are more than tenfold higher than the average expression level of DHFR in the control gene set, or (ii) the normalized expression levels of members of the reduced folate carrier (RFC) family are below the $10^{th}$ percentile.

In yet another aspect, the invention concerns a method for predicting the response of a patient diagnosed with breast cancer to an anthracycline or an analog thereof, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting patient resistance or decreased sensitivity to the anthracycline or analog if (i) the normalized expression level of topoisomerase IIα is below the $10^{th}$ percentile, or (ii) the normalized expression level of topoisomerase IIβ is below the $10^{th}$ percentile, or (iii) the combined normalized topoisomerase IIα or IIβ, expression levels are below the $10^{th}$ percentile.

In a different aspect, the invention concerns a method for predicting the response of a patient diagnosed with breast cancer to a docetaxol, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting reduced sensitivity to docetaxol if the normalized expression level of CYP1B1 is in the upper $10^{th}$ percentile.

The invention further concerns a method for predicting the response of a patient diagnosed with breast cancer to cyclophosphamide or an analog thereof, comprising (a) subjecting RNA extracted from a breast cancer tissue obtained from the patient to gene expression analysis, wherein gene expression levels are normalized against a control gene or genes, and compared to the amount found in a reference breast cancer tissue set; and (b) predicting reduced sensitivity to the cyclophosphamide or analog if the sum of the expression levels of aldehyde dehydrogenase 1A1 and 1A3 is more than tenfold higher than the average of their combined expression levels in the reference tissue set.

In a further aspect, the invention concerns a method for predicting the response of a patient diagnosed with breast cancer to anti-estrogen therapy, comprising (a) subjecting RNA extracted from a breast cancer tissue obtained from the patient to gene expression analysis, wherein gene expression levels are normalized against a control gene or genes, and compared to the amount found in a reference breast cancer tissue set that contains both specimens negative for and positive for estrogen receptor-α (ERα) and progesterone receptor-α (PRα); and (b) predicting patient response based upon the normalized expression levels of ERα or PRα, and at least one of microsomal epoxide hydrolase, pS2/trefoil factor 1, GATA3 and human chorionic gonadotropin.

In a specific embodiment, lack of response or decreased responsiveness is predicted if (i) the normalized expression level of microsomal epoxide hydrolase is in the upper $10^{th}$ percentile; or (ii) the normalized expression level of pS2/trefoil factor 1, or GATA3 or human chorionic gonaostropin is at or below the corresponding average expression level in said breast cancer tissue set, regardless of the expression level of ERα or PRα in the breast cancer tissue obtained from the patient.

In another aspect, the invention concerns a method for predicting the response of a patient diagnosed with breast cancer to a taxane, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting reduced sensitivity to taxane if (i) no or minimal XIST expression is detected; or (ii) the normalized expression level of GST-π or propyl endopeptidase (PREP) is in the upper $10^{th}$ percentile; or (iii) the normalized expression level of PLAG1 is in the upper $10^{th}$ percentile.

The invention also concerns a method for predicting the response of a patient diagnosed with breast cancer to cisplatin or an analog thereof, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting resistance or reduced sensitivity if the normalized expression level of ERCC1 is in the upper $10^{th}$ percentile.

The invention further concerns a method for predicting the response of a patient diagnosed with breast cancer to an ErbB2 or EGFR antagonist, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting patient response based on the normalized expression levels of at least one of Grb7, IGF1R, IGF1 and IGF2.

In particular embodiment, a positive response is predicted if the normalized expression level of Grb7 is in the upper $10^{th}$ percentile, and the expression of IGF1R, IGF1 and IGF2 is not elevated above the $90^{th}$ percentile.

In a further particular embodiment, a decreased responsiveness is predicted if the expression level of at least one of IGF1R, IGF1 and IGF2 is elevated.

In another aspect, the invention concerns a method for predicting the response of a patient diagnosed with breast cancer to a bis-phosphonate drug, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting a positive response if the breast cancer tissue obtained from the patient expresses mutant Ha-Ras and additionally expresses farnesyl pyrophosphate synthetase or geranyl pyrophosphone synthetase at a normalized expression level at or above the $90^{th}$ percentile.

In yet another aspect, the invention concerns a method for predicting the response of a patient diagnosed with breast cancer to treatment with a cyclooxygenase 2 inhibitor, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting a positive response if the normalized expression level of COX2 in the breast cancer tissue obtained from the patient is at or above the $90^{th}$ percentile.

The invention further concerns a method for predicting the response of a patient diagnosed with breast cancer to an EGF receptor (EGFR) antagonist, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting a positive response to an EGFR antagonist, if (i) the normalized expression level of EGFR is at or above the $10^{th}$ percentile, and (ii) the normalized expression level of at least one of epiregulin, TGF-α, amphiregulin, ErbB3, BRK, CD9, MMP9, CD82, and Lot1 is above the $90^{th}$ percentile.

In another aspect, the invention concerns a method for monitoring the response of a patient diagnosed with breast cancer to treatment with an EGFR antagonist, comprising monitoring the expression level of a gene selected from the group consisting of epiregulin, TGF-α, amphiregulin, ErbB3, BRK, CD9, MMP9, CD82, and Lot1 in the patient during treatment, wherein reduction in the expression level is indicative of positive response to such treatment.

In yet another aspect, the invention concerns a method for predicting the response of a patient diagnosed with breast cancer to a drug targeting a tyrosine kinase selected from the group consisting of abl, c-kit, PDGFR-α, PDGFR-β and ARG, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set;

(b) determining the normalized expression level of a tyrosine kinase selected from the group consisting of abl, c-kit, PDGFR-α, PDGFR-β and ARG, and the cognate ligand of the tyrosine kinase, and if the normalized expression level of the tyrosine kinase is in the upper $10^{th}$ percentile, (c) determining whether the sequence of the tyrosine kinase contains any mutation, wherein a positive response is predicted if (i) the normalized expression level of the tyrosine kinase is in the upper $10^{th}$ percentile, (ii) the sequence of the tyrosine kinase contains an activating mutation, or (iii) the normalized expression level of the tyrosine kinase is normal and the expression level of the ligand is in the upper $10^{th}$ percentile.

Another aspect of the invention is a method for predicting the response of a patient diagnosed with breast cancer to treatment with an anti-angiogenic drug, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting a positive response if (i) the normalized expression level of VEGF is in the upper $10^{th}$ percentile and (ii) the normalized expression level of KDR or CD31 is in the upper $20^{th}$ percentile.

A further aspect of the invention is a method for predicting the likelihood that a patient diagnosed with breast cancer develops resistance to a drug interacting with the MRP-1 gene coding for the multidrug resistance protein P-glycoprotein, comprising the steps of:

(a) subjecting RNA extracted from a breast cancer tissue obtained from the patient to gene expression analysis to determine the expression level of PTP1b, wherein the expression level is normalized against a control gene or genes, and compared to the amount found in a reference breast cancer tissue set; and (b) concluding that the patient is likely to develop resistance to said drug if the normalized expression level of the MRP-1 gene is above the $90^{th}$ percentile.

The invention further relates to a method for predicting the likelihood that a patient diagnosed with breast cancer develops resistance to a chemotherapeutic drug or toxin used in cancer treatment, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) determining the normalized expression levels of at least one of the following genes: MDR1, SGTα, GSTπ, SXR, BCRP YB-1, and LRP/MVP, wherein the finding of a normalized expression level in the upper $4^{th}$ percentile is an indication that the patient is likely to develop resistance to the drug.

Also included herein is a method for measuring the translational efficiency of VEGF mRNA in a breast cancer tissue sample, comprising determining the expression levels of the VEGF and EIF4E mRNA in the sample, normalized against a control gene or genes, and compared to the amount found in a reference breast cancer tissue set, wherein a higher normalized EIF4E expression level for the same. VEGF expression level is indicative of relatively higher translational efficiency for VEGF.

In another aspect, the invention provides a method for predicting the response of a patient diagnosed with breast cancer to a VEGF antagonist, comprising determining the expression level of VEGF and EIF4E mRNA normalized against a control gene or genes, and compared to the amount found in a reference breast cancer tissue set, wherein a VEGF expression level above the $90^{th}$ percentile and an EIF4E expression level above the $50^{th}$ percentile is a predictor of good patient response.

The invention further provides a method for predicting the likelihood of the recurrence of breast cancer in a patient diagnosed with breast cancer, comprising determining the ratio of p53:p21 mRNA expression or p53:mdm2 mRNA expression in a breast cancer tissue obtained from the patient, normalized against a control gene or genes, and compared to the amount found in a reference breast cancer tissue set, wherein an above normal ratio is indicative of a higher risk of recurrence. Typically, a higher risk of recurrence is indicated if the ratio is in the upper $10^{th}$ percentile.

In yet another aspect, the invention concerns a method for predicting the likelihood of the recurrence of breast cancer in a breast cancer patient following surgery, comprising determining the expression level of cyclin D1 in a breast cancer tissue obtained from the patient, normalized against a control gene or genes, and compared to the amount found in a reference breast cancer tissue set, wherein an expression level in the upper $10^{th}$ percentile indicates increased risk of recurrence following surgery. In a particular embodiment of this method, the patient is subjected to adjuvant chemotherapy, if the expression level is in the upper $10^{th}$ percentile.

Another aspect of the invention is a method for predicting the likelihood of the recurrence of breast cancer in a breast cancer patient following surgery, comprising determining the expression level of APC or E-cadherin in a breast cancer tissue obtained from the patient, normalized against a control gene or genes, and compared to the amount found in a reference breast cancer tissue set, wherein an expression level in the upper $5^{th}$ percentile, indicates high risk of recurrence following surgery, and heightened risk of shortened survival.

A further aspect of the invention is a method for predicting the response of a patient diagnosed with breast cancer to treatment with a proapoptotic drug comprising determining the expression levels of BCl2 and c-MYC in a breast cancer tissue obtained from the patient, normalized against a control gene or genes, and compared to the amount found in a reference breast cancer tissue set, wherein (i) a BCl2 expression level in the upper $10^{th}$ percentile in the absence of elevated expression of c-MYC indicates good response, and (ii) a good response is not indicated if the expression level c-MYC is elevated, regardless of the expression level of BCl2.

A still further aspect of the invention is a method for predicting treatment outcome for a patient diagnosed with breast cancer, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) determining the normalized expression levels of NFκB and at least one gene selected from the group consisting of cIAP1, cIAP2, XIAP, and Survivin, wherein a poor prognosis is indicated if the expression levels for NFκB and at least one of the genes selected from the group consisting of cIAP1, cIAP2, XIAP, and Survivin is in the upper $5^{th}$ percentile.

The invention further concerns a method for predicting treatment outcome for a patient diagnosed with breast cancer, comprising determining the expression levels of p53BP1 and p53BP2 in a breast cancer tissue obtained from the patient, normalized against a control gene or genes, and compared to the amount found in a reference breast cancer tissue set, wherein a poor outcome is predicted if the expression level of either p53BP1 or p53BP2 is in the lower $10^{th}$ percentile.

The invention additionally concerns a method for predicting treatment outcome for a patient diagnosed with breast cancer, comprising determining the expression levels of uPA and PAI1 in a breast cancer tissue obtained from the patient, normalized against a control gene or genes, and compared to the amount found in a reference breast cancer tissue set, wherein (i) a poor outcome is predicted if the expression levels of uPA and PAI1 are in the upper $20^{th}$ percentile, and (ii) a decreased risk of recurrence is predicted if the expression levels of uPA and PAI1 are not elevated above the mean observed in the breast cancer reference set. In a particular embodiment, poor outcome is measured in terms of shortened survival or increased risk of cancer recurrence following surgery. In another particular embodiment, uPA and PAI1 are expressed at normal levels, and the patient is subjected to adjuvant chemotherapy following surgery.

Another aspect of the invention is a method for predicting treatment outcome in a patient diagnosed with breast cancer, comprising determining the expression levels of cathepsin B and cathepsin L in a breast cancer tissue obtained from the patient, normalized against a control gene or genes, and compared to the amount found in a reference breast cancer tissue set, wherein a poor outcome is predicted if the expression level of either cathepsin B or cathepsin L is in the upper $10^{th}$ percentile. Just as before, poor treatment outcome may be measured, for example, in terms of shortened survival or increased risk of cancer recurrence.

A further aspect of the invention is a method for devising the treatment of a patient diagnosed with breast cancer, comprising the steps of (a) determining the expression levels of scatter factor and c-met in a breast cancer tissue obtained from the patient, normalized against a control gene or genes, and compared to the amount found in a reference breast cancer tissue set, and (b) suggesting prompt aggressive chemotherapeutic treatment if the expression levels of scatter factor and c-met or the combination of both, are above the $90^{th}$ percentile.

A still further aspect of the invention is a method for predicting treatment outcome for a patient diagnosed with breast cancer, comprising determining the expression levels of VEGF, CD31, and KDR in a breast cancer tissue obtained from the patient, normalized against a control gene or genes, and compared to the amount found in a reference breast cancer tissue set, wherein a poor treatment outcome is predicted if the expression level of any of VEGF, CD31, and KDR is in the upper 10$^{th}$ percentile.

Yet another aspect of the invention is a method for predicting treatment outcome for a patient diagnosed with breast cancer, comprising determining the expression levels of Ki67/MiB1, PCNA, Pin1, and thymidine kinase in a breast cancer tissue obtained from the patient, normalized against a control gene or genes, and compared to the amount found in a reference breast cancer tissue set, wherein a poor treatment outcome is predicted if the expression level of any of Ki67/MiB1, PCNA, Pin1, and thymidine kinase is in the upper 10$^{th}$ percentile.

The invention further concerns a method for predicting treatment outcome for a patient diagnosed with breast cancer, comprising determining the expression level of soluble and full length CD95 in a breast cancer tissue obtained from the patient, normalized against a control gene or genes, and compared to the amount found in a reference breast cancer tissue set, wherein the presence of soluble CD95 correlates with poor patient survival.

The invention also concerns a method for predicting treatment outcome for a patient diagnosed with breast cancer, comprising determining the expression levels of IGF1, IGF1R and IGFBP3 in a breast cancer tissue obtained from the patient, normalized against a control gene or genes, and compared to the amount found in a reference breast cancer tissue set, wherein a poor treatment outcome is predicted if the sum of the expression levels of IGF1, IGF1R and IGFBP3 is in the upper 10$^{th}$ percentile.

The invention additionally concerns a method for classifying breast cancer comprising, determining the expression level of two or more genes selected from the group consisting of Bcl12, hepatocyte nuclear factor 3, LIV1, ER, lipoprotein lipase, retinol binding protein 4, integrin α7, cytokeratin 5, cytokeratin 17, GRO oncogen, ErbB2 and Grb7, in a breast cancer tissue, normalized against a control gene or genes, and compared to the amount found in a reference breast cancer tissue set, wherein (i) tumors expressing at least one of Bcl1, hepatocyte nuclear factor 3, LIV1, and ER above the mean expression level in the reference tissue set are classified as having a good prognosis for disease free and overall patient survival following surgical removal; (ii) tumors characterized by elevated expression of at least one of lipoprotein lipase, retinol binding protein 4, integrin α7 compared to the reference tissue set are classified as having intermediate prognosis of disease free and overall patient survival following surgical removal; and (iii) tumors expressing either elevated levels of cytokeratins 5 and 17, and GRO oncogen at levels four-fold or greater above the mean expression level in the reference tissue set, or ErbB2 and Grb7 at levels ten-fold or more above the mean expression level in the reference tissue set are classified as having poor prognosis of disease free and overall patient survival following surgical removal.

Another aspect of the invention is a panel of two or more gene specific primers selected from the group consisting of the forward and reverse primers listed in Table 2.

Yet another aspect of the invention is a method for reverse transcription of a fragmented RNA population in RT-PCR amplification, comprising using a multiplicity of gene specific primers as the reverse primers in the amplification reaction. In a particular embodiment, the method uses between two and about 40,000 gene specific primers in the same amplification reaction. In another embodiment, the gene specific primers are about 18 to 24 bases, such as about 20 bases in length. In another embodiment, the Tm of the primers is about 58-60° C. The primers can, for example, be selected from the group consisting of the forward and reverse primers listed in Table 2.

The invention also concerns a method of reverse transcriptase driven first strand cDNA synthesis, comprising using a gene specific primer of about 18 to 24 bases in length and having a Tm optimum between about 58° C. and about 60° C. In a particular embodiment, the first strand cDNA synthesis is followed by PCR DNA amplification, and the primer serves as the reverse primer that drives the PCR amplification. In another embodiment, the method uses a plurality of gene specific primers in the same first strand cDNA synthesis reaction mixture. The number of the gene specific primers can, for example, be between 2 and about 40,000.

In a different aspect, the invention concerns a method of predicting the likelihood of long-term survival of a breast cancer patient without the recurrence of breast cancer, following surgical removal of the primary tumor, comprising determining the expression level of one or more prognostic RNA transcripts or their product in a breast cancer tissue sample obtained from said patient, normalized against the expression level of all RNA transcripts or their products in said breast cancer tissue sample, or of a reference set of RNA transcripts or their products, wherein the prognostic transcript is the transcript of one or more genes selected from the group consisting of: FOXM1, PRAME, Bcl2, STK15, CEGP1, Ki-67, GSTM1, CA9, PR, BBC3, NME1, BIRC5, GATA3, TFRC, YB-1, DPYD, GSTM3, RPS6 KB1, Src, Chk1, ID1, ESR1, p27, CCNB1, XIAP, Chk2, CDC25B, IGF1R, AK055699, P13KC2A, TGFB3, BAGI1, CYP3A4, EpCAM, VEGFC, pS2, hENT1, WISP1, HNF3A, NFKBp65, BRCA2, EGFR, TK1, VDR, Contig51037, pENT1, EPHX1, IF1A, DIABLO, CDH1, HIF1α, IGFBP3, CTSB, and Her2, wherein overexpression of one or more of FOXM1, PRAME, STK15, Ki-67, CA9, NME1, BIRC5, TFRC, YB-1, RPS6 KB1, Src, Chk1, CCNB1, Chk2, CDC25B, CYP3A4, EpCAM, VEGFC, hENT1, BRCA2, EGFR, TK1, VDR, EPHX1, IF1A, Contig51037, CDH1, HIF1α, IGFBP3, CTSB, Her2, and pENT1 indicates a decreased likelihood of long-term survival without breast cancer recurrence, and the overexpression of one or more of Bcl2, CEGP1, GSTM1, PR, BBC3, GATA3, DPYD, GSTM3, ID1, ESR1, p27, XIAP, IGF1R, AK055699, P13KC2A, TGFB3, BAGI1, pS2, WISP1, HNF3A, NFKBp65, and DIABLO indicates an increased likelihood of long-term survival without breast cancer recurrence.

In a particular embodiment of this method, the expression level of at least 2, preferably at least 5, more preferably at least 10, most preferably at least 15 prognostic transcripts or their expression products is determined.

When the breast cancer is invasive breast carcinoma, including both estrogen receptor (ER) overexpressing (ER positive) and ER negative tumors, the analysis includes determination of the expression levels of the transcripts of at least two of the following genes, or their expression products: FOXM1, PRAME, Bcl2, STK15, CEGP1, Ki-67, GSTM1, PR, BBC3, NME1, SURV, GATA3, TFRC, YB-1, DPYD, Src, CA9, Contig51037, RPS6K1 and Her2.

When the breast cancer is ER positive invasive breast carcinoma, the analysis includes determination of the expression levels of the transcripts of at least two of the following genes, or their expression products: PRAME, Bcl2, FOXM1, DIABLO, EPHX1, HIF1A, VEGFC, Ki-67, IGF1R, VDR, NME1, GSTM3, Contig51037, CDC25B, CTSB, p27, CDH1, and IGFBP3.

Just as before, it is preferred to determine the expression levels of at least 5, more preferably at least 10, most preferably at least 15 genes, or their respective expression products.

In a particular embodiment, the expression level of one or more prognostic RNA transcripts is determined, where RNA may, for example, be obtained from a fixed, wax-embedded breast cancer tissue specimen of the patient. The isolation of RNA can, for example, be carried out following any of the procedures described above or throughout the application, or by any other method known in the art.

In yet another aspect, the invention concerns an array comprising polynucleotides hybridizing to the following genes: FOXM1, PRAME, Bcl2, STK15, CEGP1, Ki-67, GSTM1, PR, BBC3, NME1, SURV, GATA3, TFRC, YB-1, DPYD, CA9, Contig51037, RPS6K1 and Her2, immobilized on a solid surface.

In a particular embodiment, the array comprises polynucleotides hybridizing to the following genes: FOXM1, PRAME, Bcl2, STK15, CEGP1, Ki-67, GSTM1, CA9, PR, BBC3, NME1, BIRC5, GATA3, TFRC, YB-1, DPYD, GSTM3, RPS6 KB1, Src, Chk1, ID1, ESR1, p27, CCNB1, XIAP, Chk2, CDC25B, IGF1R, AK055699, P13KC2A, TGFB3, BAGI1, CYP3A4, EpCAM, VEGFC, pS2, hENT1, WISP1, HNF3A, NFKBp65, BRCA2, EGFR, TK1, VDR, Contig51037, pENT1, EPHX1, IF1A, CDH1, HIF1α, IGFBP3, CTSB, Her2 and DIABLO.

In a further aspect, the invention concerns a method of predicting the likelihood of long-term survival of a patient diagnosed with invasive breast cancer, without the recurrence of breast cancer, following surgical removal of the primary tumor, comprising the steps of:

(1) determining the expression levels of the RNA transcripts or the expression products of genes of a gene set selected from the group consisting of
 (a) Bcl2, cyclinG1, NFKBp65, NME1, EPHX1, TOP2B, DR5, TERC, Src, DLABLO;
 (b) Ki67, XIAP, hENT1, TS, CD9, p27, cyclinG1, pS2, NFKBp65, CYP3A4;
 (c) GSTM1, XIAP, Ki67, TS, cyclinG1, p27, CYP3A4, pS2, NFKBp65, ErbB3;
 (d) PR, NME1, XIAP, upa, cyclinG1, Contig51037, TERC, EPHX1, ALDH1A3, CTSL;
 (e) CA9, NME1, TERC, cyclinG1, EPHX1, DPYD, Src, TOP2B, NFKBp65, VEGFC;
 (f) TFRC, XIAP, Ki67, TS, cyclinG1, p27, CYP3A4, pS2, ErbB3, NFKBp65;
 (g) Bcl2, PRAME, cyclinG1, FOXM1, NFKBp65, TS, XIAP, Ki67, CYP3A4, p27;
 (h) FOXM1, cyclinG1, XIAP, Contig51037, PRAME, TS, Ki67, PDGFRa, p27, NFKBp65;
 (i) PRAME, FOXM1, cyclinG1, XIAP, Contig51037, TS, Ki6, PDGFRa, p27, NFKBp65;
 (j) Ki67, XIAP, PRAME, hENT1, contig51037, TS, CD9, p27, ErbB3, cyclinG1;
 (k) STK15, XIAP, PRAME, PLAUR, p27, CTSL, CD18, PREP, p53, RPS6KB1;
 (l) GSTM1, XIAP, PRAME, p27, Contig51037, ErbB3, GSTp, EREG, ID1, PLAUR;
 (m) PR, PRAME, NME1, XIAP, PLAUR, cyclinG1, Contig51037, TERC, EPHX1, DR5;
 (n) CA9, FOXM1, cyclinG1, XIAP, TS, Ki67, NFKBp65, CYP3A4, GSTM3, p27;
 (o) TFRC, XIAP, PRAME, p27, Contig51037, ErbB3, DPYD, TERC, NME1, VEGFC; and
 (p) CEGP1, PRAME, hENT1, XLKP, Contig51037, ErbB3, DPYD, NFKBp65, ID1, TS in a breast cancer tissue sample obtained from said patient, normalized against the expression levels of all RNA transcripts or their products in said breast cancer tissue sample, or of a reference set of RNA transcripts or their products;

(2) subjecting the data obtained in step (a) to statistical analysis; and (3) determining whether the likelihood of said long-term survival has increased or decreased.

In a still further aspect, the invention concerns a method of predicting the likelihood of long-term survival of a patient diagnosed with estrogen receptor (ER)-positive invasive breast cancer, without the recurrence of breast cancer, following surgical removal of the primary tumor, comprising the steps of:

(1) determining the expression levels of the RNA transcripts or the expression products of genes of a gene set selected from the group consisting of
 (a) PRAME, p27, IGFBP2, HIF1A, T1MP2, ILT2, CYP3A4, ID1, ESR1, DIABLO;
 (b) Contig51037, EPHX1, Ki67, TIMP2, cyclinG1, DPYD, CYP3A4, TP, AIB1, CYP2C8;
 (c) Bcl2, hENT1, FOXM1, Contig51037, cyclinG1, Contig46653, PTEN, CYP3A4, TIMP2, AREG;
 (d) HIF1A, PRAME, p27, IGFBP2, T1MP2, ILT2, CYP3A4, ID1, ESR1, DIABLO;
 (e) IGF1R, PRAME, EPHX1, Contig51037, cyclinG1, Bcl2, NME1, PTEN, TBP, TIMP2;
 (f) FOXM1, Contig51037, VEGFC, TBP, HIF1A, DPYD, RAD51C, DCR3, cyclinG1, BAG1;
 (g) EPHX1, Contig51037, Ki67, TIMP2, cyclinG1, DPYD, CYP3A4, TP, AIB1, CYP2C8;
 (h) Ki67, VEGFC, VDR, GSTM3, p27, upa, ITGA7, rhoC, TERC, Pin1;
 (i) CDC25B, Contig51037, hENT1, Bcl2, HLAG, TERC, NME1, upa, ID1, CYP;
 (j) VEGFC, Ki67, VDR, GSTM3, p27, upa, ITGA7, rhoC, TERC, Pint;
 (k) CTSB, PRAME, p27, IGFBP2, EPHX1, CTSL, BAD, DRS, DCR3, XIAP;
 (l) DIABLO, Ki67, hENT1, TIMP2, ID1, p27, KRT19, IGFBP2, TS, PDGFB;
 (m) p27, PRAME, IGFBP2, HIF1A, T1MP2, ILT2, CYP3A4, ID1, ESR1, DIABLO;
 (n) CDH1; PRAME, VEGFC; HIF1A; DPYD, TIMP2, CYP3A4, ESR1, RBP4, p27;
 (o) IGFBP3, PRAME, p27, Bcl2, XIAP, ESR1, Ki67, TS, Src, VEGF;
 (p) GSTM3, PRAME, p27, IGFBP3, XIAP, FGF2, hENT1, PTEN, ESR1, APC;
 (q) hENT1, Bcl2, FOXM1, Contig51037, CyclinG1, Contig46653, PTEN, CYP3A4, TIMP2, AREG;
 (r) STK15, VEGFC, PRAME, p27, GCLC, hENT1, ID1, TIMP2, ESR1, MCP1;
 (s) NME1, PRAM, p27, IGFBP3, XIAP, PTEN, hENT1, Bcl2, CYP3A4, HLAG;
 (t) VDR, Bcl2, p27, hENT1, p53, PI3KC2A, EIF4E, TFRC, MCM3, ID1;
 (u) EIF4E, Contig51037, EPHX1, cyclinG1, Bcl2, DRS, TBP, PTEN, NME1, HER2;
 (v) CCNB1, PRAME, VEGFC, HIF1A, hENT1, GCLC, TIMP2, ID1, p27, upa;
 (w) ID1, PRAME, DIABLO, hENT1, p27, PDGFRa, NME1, BIN1, BRCA1, TP;
 (x). FBXO5, PRAME, IGFBP3, p27, GSTM3, hENT1, XIAP, FGF2, TS, PTEN;
 (y) GUS, HIA1A, VEGFC, GSTM3, DPYD, hENT1, EBXO5, CA9, CYP, KRT18; and (z) Bclx, Bcl2, hENT1, Contig51037, HLAG, CD9, ID1, BRCA1, BIN1, HBEGF;
(2) subjecting the data obtained in step (1) to statistical analysis; and
(3) determining whether the likelihood of said long-term survival has increased or decreased.

In a different aspect, the invention concerns an array comprising polynucleotides hybridizing to a gene set selected from the group consisting of:
(a) Bcl2, cyclinG1, NFKBp65, NME1, EPHX1, TOP2B, DR5, TERC, Src, DIABLO;
(b) Ki67, XIAP, hENT1, TS, CD9, p27, cyclinG1, pS2, NFKBp65, CYP3A4;
(c) GSTM1, XIAP, Ki67, TS, cyclinG1, p27, CYP3A4, pS2, NFKBp65, ErbB3;
(d) PR, NME1, XIAP, upa, cyclinG1, Contig51037, TERC, EPHX1, ALDH1A3, CTSL;
(e) CA9, NME1, TERC, cyclinG1, EPHX1, DPYD, Src, TOP2B, NFKBp65, VEGFC;
(f) TFRC, XIAP, Ki67, TS, cyclinG1, p27, CYP3A4, pS2, ErbB3, NFKBp65;
(g) Bcl2, PRAME, cyclinG1, FOXM1, NFKBp65, TS, XIAP, Ki67, CYP3A4, p27;
(h) FOXM1, cyclinG1, XIAP, Contig51037, PRAME, TS, Ki67, PDGFRa, p27, NFKBp65;
(i) PRAME, FOXM1, cyclinG1, XIAP, Contig51037, TS, Ki6, PDGFRa, p27, NFKBp65;
(j) Ki67, XIAP, PRAME, hENT1, contig51037, TS, CD9, p27, ErbB3, cyclinG1;
(k) STK15, XIAP, PRAME, PLAUR, p27, CTSL, CD18, PREP, p53, RPS6KB1;
(l) GSTM1, XIAP, PRAME, p27, Contig51037, ErbB3, GSTp, EREG, ID1, PLAUR;
(m) PR, PRAME, NME1, XLAP, PLAUR, cyclinG1, Contig51037, TERC, EPHX1, DR5;
(n) CA9, FOXM1, cyclinG1, XIAP, TS, Ki67, NFKBp65, CYP3A4, GSTM3, p27;
(o) TFRC, XIAP, PRAME, p27, Contig51037, ErbB3, DPYD, TERC, NME1, VEGFC; and
(p) CEGP1, PRAME, hENT1, XIAP, Contig51037, ErbB3, DPYD, NFKBp65, ID1, TS, immobilized on a solid surface.

In an additional aspect, the invention concerns an array comprising polynucleotides hybridizing to a gene set selected from the group consisting of:
(a) PRAME, p27, IGFBP2, HIF1A, T1MP2, ILT2, CYP3A4, ID1, ESR1, DIABLO;
(b) Contig51037, EPHX1, Ki67, TIMP2, cyclinG1, DPYD, CYP3A4, TP, AIB1, CYP2C8;
(c) Bcl2, hENT1, FOXM1, Contig51037, cyclinG1, Contig46653, PTEN, CYP3A4, TIMP2, AREG;
(d) HIF1A, PRAME, p27, IGFBP2, T1MP2, ILT2, CYP3A4, ID1, ESR1, DIABLO;
(e) IGF1R, PRAME, EPHX1, Contig51037, cyclinG1, Bcl2, NME1, PTEN, TBP, TIMP2;
(f) FOXM1, Contig51037, VEGFC, TBP, HIF1A, DPYD, RAD51C, DCR3, cyclinG1, BAG1;
(g) EPHX1, Contig51037, Ki67, TIMP2, cyclinG1, DPYD, CYP3A4, TP, AIB1, CYP2C8;
(h) Ki67, VEGFC, VDR, GSTM3, p27, upa, ITGA7, rhoC, TERC, Pin1;
(i) CDC25B, Contig51037, hENT1, Bcl2, HLAG, TERC, NME1, upa, ID1, CYP;
(j) VEGFC, Ki67, VDR, GSTM3, p27, upa, ITGA7, rhoC, TERC, Pin1;
(k) CTSB, PRAME, p27, IGFBP2, EPHX1, CTSL, BAD, DR5, DCR3, XIAP;
(l) DIABLO, Ki67, hENT1, TIMP2, ID1, p27, KRT19, IGFBP2, TS, PDGFB;
(m) p27, PRAME, IGFBP2, HIF1A, T1MP2, ILT2, CYP3A4, ID1, ESR1, DIABLO;
(n) CDH1; PRAME, VEGFC; HIF1A; DPYD, TIMP2, CYP3A4, ESR1, RBP4, p27;
(o) IGFBP3, PRAME, p27, Bcl2, XIAP, ESR1, Ki67, TS, Src, VEGF;
(p) GSTM3, PRAME, p27, IGFBP3, XIAP, FGF2, hENT1, PTEN, ESR1, APC;
(q) hENT1, Bcl2, FOXM1, Contig51037, CyclinG1, Contig46653, PTEN, CYP3A4, TIMP2, AREG;
(r) STK15, VEGFC, PRAME, p27, GCLC, hENT1, ID1, TIMP2, ESR1, MCP1;
(s) NME1, PRAM, p27, IGFBP3, XIAP, PTEN, hENT1, Bcl2, CYP3A4, HLAG;
(t) VDR, Bcl2, p27, hENT1, p53, PI3KC2A, EIF4E, TFRC, MCM3, ID1;
(u) EIF4E, Contig51037, EPHX1, cyclinG1, Bcl2, DR5, TBP, PTEN, NME1, HER2;
(v) CCNB1, PRAME, VEGFC, HIF1A, hENT1, GCLC, TIMP2, ID1, p27, upa;
(w) ID1, PRAME, DIABLO, hENT1, p27, PDGFRa, NME1, BIN1, BRCA1, TP;
(x) FBXO5, PRAME, IGFBP3, p27, GSTM3, hENT1, XIAP, FGF2, TS, PTEN;
(y) GUS, HIA1A, VEGFC, GSTM3, DPYD, hENT1, FBXO5, CA9, CYP, KRT18; and
(z) Bclx, Bcl2, hENT1, Contig51037, HLAG, CD9, ID1, BRCA1, BIN1, HBEGF, immobilized on a solid surface.

In all aspects, the polynucleotides can be cDNAs ("cDNA arrays") that are typically about 500 to 5000 bases long, although shorter or longer cDNAs can also be used and are within the scope of this invention. Alternatively, the polynucleotides can be oligonucleotides (DNA microarrays), which are typically about 20 to 80 bases long, although shorter and longer oligonucleotides are also suitable and are within the scope of the invention. The solid surface can, for example, be glass or nylon, or any other solid surface typically used in preparing arrays, such as microarrays, and is typically glass.

Figure 1:
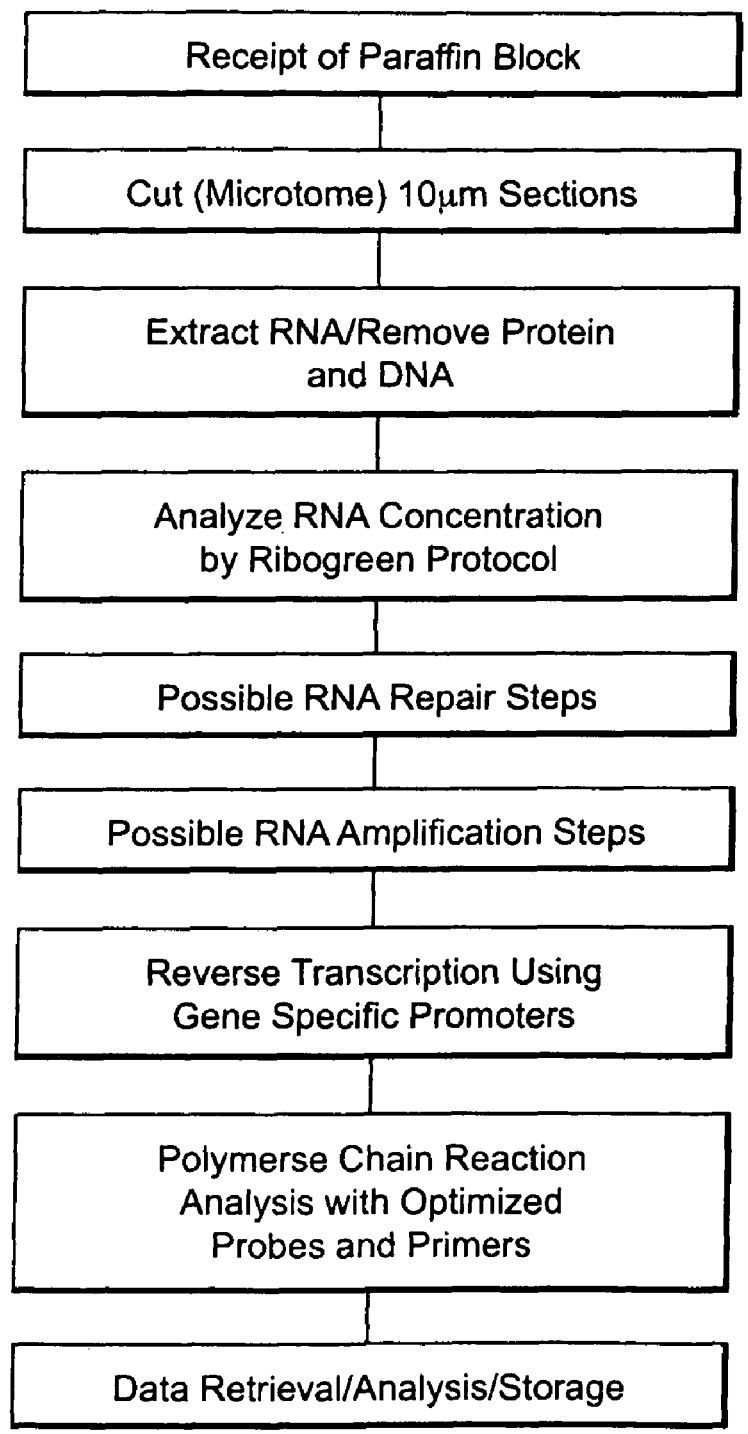
FIG. 1 is a chart illustrating the overall workflow of the process of the invention for measurement of gene expression. In the Figure, FPET stands for "fixed paraffin-embedded tissue," and "RT-PCR" stands for "reverse transcriptase PCR." RNA concentration is determined by using the commercial RiboGreen T RNA Quantitation Reagent and Protocol.

Table 1 shows a breast cancer gene list.

Table 2 sets forth amplicon and primer sequences used for amplification of fragmented mRNA.

Table 3 shows the Accession Nos. and SEQ ID NOS of the breast cancer genes examined.

DETAILED DESCRIPTION OF THE PREFERRED EMBODIMENT

A. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "microarray" refers to an ordered arrangement of hybridizable array elements, preferably polynucleotide probes, on a substrate.

The term "polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNAs and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is activated to a higher or lower level in a subject suffering from a disease, specifically cancer, such as breast cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for, example. Differential gene expression may include a comparison of expression between two or more genes, or a comparison of the ratios of the expression between two or more genes, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about two-fold, preferably at least about four-fold, more preferably at least about six-fold, most preferably at least about ten-fold difference between the expression of a given gene in normal and diseased subjects, or in various stages of disease development in a diseased subject.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

The term "prognosis" is used herein to refer to the prediction of the likelihood of cancer-attributable death or progression, including recurrence, metastatic spread, and drug resistance, of a neoplastic disease, such as breast cancer. The term "prediction" is used herein to refer to the likelihood that a patient will respond either favorably or unfavorably to a drug or set of drugs, and also the extent of those responses. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention, chemotherapy with a given drug or drug combination, and/or radiation therapy.

The term "increased resistance" to a particular drug or treatment option, when used in accordance with the present invention, means decreased response to a standard dose of the drug or to a standard treatment protocol.

The term "decreased sensitivity" to a particular drug or treatment option, when used in accordance with the present invention, means decreased response to a standard dose of the drug or to a standard treatment protocol, where decreased response can be compensated for (at least partially) by increasing the dose of drug, or the intensity of treatment.

"Patient response" can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition (i.e. reduction, slowing down or complete stopping) of metastasis; (6) enhancement of anti-tumor immune response, which may, but does not have to, result in the regression or rejection of the tumor; (7) relief, to some extent, of one or more symptoms associated with the tumor; (8) increase in the length of survival following treatment; and/or (9) decreased mortality at a given point of time following treatment.

The term "treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6-5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic, strength and % SDS) less stringent that those described above. An example of moderately stringent conditions is overnight incubation at. 37° C. in a solution comprising:. 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In the context of the present invention, reference to "at least one," "at least two," "at least five," etc. of the genes listed in any particular gene set means any one or any and all combinations of the genes listed.

The terms "splicing" and "RNA splicing" are used interchangeably and refer to RNA processing that removes introns and joins exons to produce mature mRNA with continuous coding sequence that moves into the cytoplasm of an eukaryotic cell.

In theory, the term "exon" refers to any segment of an interrupted gene that is represented in the mature RNA product (B. Lewin. *Genes IV* Cell Press, Cambridge Mass. 1990). In theory the term "intron" refers to any segment of DNA that is transcribed but removed from within the transcript by splicing together the exons on either side of it. Operationally, exon sequences occur in the mRNA sequence of a gene as defined by Ref. Seq ID numbers. Operationally, intron sequences are the intervening sequences within the genomic DNA of a gene, bracketed by exon sequences and having GT and AG splice consensus sequences at their 5' and 3' boundaries.

B. Detailed Description

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

1. Gene Expression Profiling

In general, methods of gene expression profiling can be divided into two large groups: methods based on hybridization analysis of polynucleotides, and methods based on sequencing of polynucleotides. The most commonly used methods known in the art for the quantification of mRNA expression in a sample include northern blotting and in situ hybridization (Parker & Barnes, *Methods in Molecular Biology* 106:247-283 (1999)); RNAse protection assays (Hod, *Biotechniques* 13:852-854 (1992)); and reverse transcription polymerase chain reaction (RT-PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

2. Reverse Transcriptase PCR (RT-PCR)

Of the techniques listed above, the most sensitive and most flexible quantitative method is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, etc., tumor, or tumor cell lines, with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A67 (1987), and De Andrés et al., *BioTechniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include Master-Pure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., *Genome Research* 6:986-994 (1996).

3. Microarrays

Differential gene expression can also be identified, or confirmed using the microarray technique. Thus, the expression profile of breast cancer-associated genes can be measured in either fresh or paraffin-embedded tumor tissue, using microarray technology. In this method, polynucleotide sequences of interest are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types.

4. Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated-by determining the abundance of individual tags, and identifying the gene corresponding to each tag. For more details see, e.g. Velculescu et al., *Science* 270:484-487 (1995); and Velculescu et al., *Cell* 88:243-51 (1997).

5. Gene Expression Analysis by Massively Parallel Signature Sequencing (MPSS)

This method, described by Brenner et al., *Nature Biotechnology* 18:630-634 (2000), is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

6. General Description of the mRNA Isolation, Purification and Amplification Methods of the Invention The steps of a representative protocol of the invention, including mRNA isolation, purification, primer extension and amplification are illustrated in FIG. 1. As shown in FIG. 1, this representative process starts with cutting about 10 μm thick sections of paraffin-embedded tumor tissue samples. The RNA is then extracted, and protein and DNA are removed, following the method of the invention described below. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumor sample examined. The individual steps of this protocol will be discussed in greater detail below.

7. Improved Method for Isolation of Nucleic Acid from Archived Tissue Specimens

As discussed above, in the first step of the method of the invention, total RNA is extracted from the source material of interest, including fixed, paraffin-embedded tissue specimens, and purified sufficiently to act as a substrate in an enzyme assay. Despite the availability of commercial products, and the extensive knowledge available concerning the isolation of nucleic acid, such as RNA, from tissues, isolation of nucleic acid (RNA) from fixed, paraffin-embedded tissue specimens (FPET) is not without difficulty.

In one aspect, the present invention concerns an improved method for the isolation of nucleic acid from archived, e.g. FPET tissue specimens. Measured levels of mRNA species are useful for defining the physiological or pathological status of cells and tissues. RT-PCR (which is discussed above) is one of the most sensitive, reproducible and quantitative methods for this "gene expression profiling". Paraffin-embedded, formalin-fixed tissue is the most widely available material for such studies. Several laboratories have demonstrated that it is possible to successfully use fixed-paraffin-embedded tissue (FPET) as a source of RNA for RT-PCR (Stanta et al., *Biotechniques* 11:304-308 (1991); Stanta et al., *Methods Mol. Biol.* 86:23-26 (1998); Jackson et al., *Lancet* 1:1391 (1989); Jackson et al., *J. Clin. Pathol.* 43:499-504 (1999); Finke et al., *Biotechniques* 14:448-453 (1993); Goldsworthy et al., *Mol. Carcinog.* 25:86-91 (1999); Stanta and Bonin, *Biotechniques* 24:271-276 (1998); Godfrey et al., *J. Mol. Diagnostics* 2:84 (2000); Specht et al., *J. Mol. Med.* 78:B27 (2000); Specht et al., *Am. J. Pathol.* 158:419-429 (2001)). This allows gene expression profiling to be carried out on the most commonly available source of human biopsy specimens, and therefore potentially to create new valuable diagnostic and therapeutic information.

The most widely used protocols utilize hazardous organic solvents, such as xylene, or octane (Finke et al., supra) to dewax the tissue in the paraffin blocks before nucleic acid (RNA and/or DNA) extraction. Obligatory organic solvent removal (e.g. with ethanol) and rehydration steps follow, which necessitate multiple manipulations, and addition of substantial total time to the protocol, which can take up to several days. Commercial kits and protocols for RNA extraction from FPET [MasterPure™ Complete DNA and RNA Purification Kit (EPICENTRE®, Madison, Wis.); Paraffin Block RNA Isolation Kit (Ambion, Inc.) and RNeasy™ Mini kit (Qiagen, Chatsworth, Calif.)] use xylene for deparaffinization, in procedures which typically require multiple centrifugations and ethanol buffer changes, and incubations following incubation with xylene.

The present invention provides an improved nucleic acid extraction protocol that produces nucleic acid, in particular RNA, sufficiently intact for gene expression measurements. The key step in the nucleic acid extraction protocol herein is the performance of dewaxing without the use of any organic solvent, thereby eliminating the need for multiple manipulations associated with the removal of the organic solvent, and substantially reducing the total time to the protocol. According to the invention, wax, e.g. paraffin is removed from wax-embedded tissue samples by incubation at 65-75° C. in a lysis buffer that solubilizes the tissue and hydrolyzes the protein, following by cooling to solidify the wax.

Figure 2:
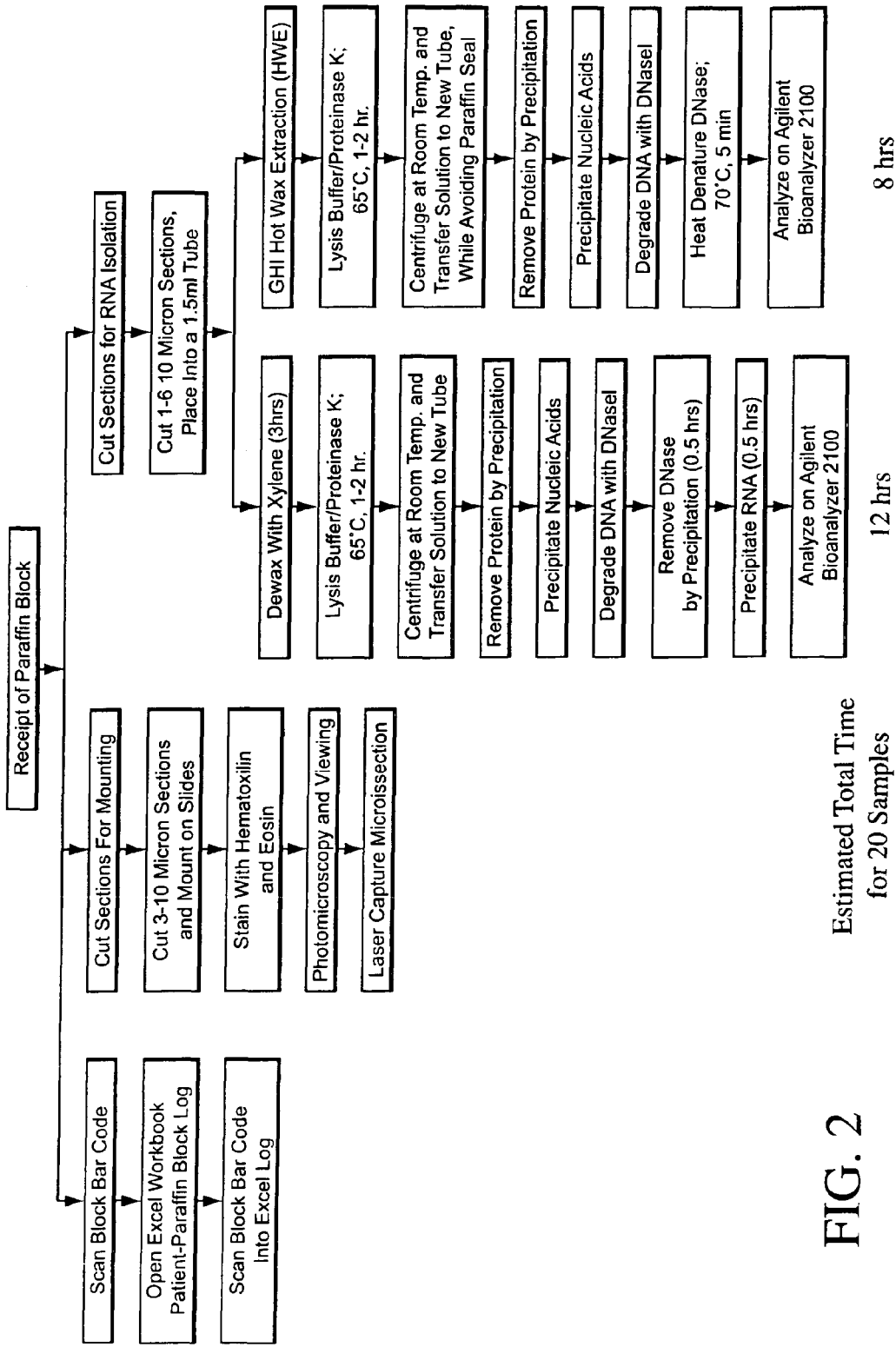
FIG. 2 is a flow chart showing the steps of an RNA extraction method according to the invention alongside a flow chart of a representative commercial method.

FIG. 2 shows a flow chart of an RNA extraction protocol of the present invention in comparison with a representative commercial method, using xylene to remove wax. The times required for individual steps in the processes and for the overall processes are shown in the chart. As shown, the commercial process requires approximately 50% more time than the process of the invention.

The lysis buffer can be any buffer known for cell lysis. It is, however, preferred that oligo-dT-based methods of selectively purifying polyadenylated mRNA not be used to isolate RNA for the present invention, since the bulk of the mRNA molecules are expected to be fragmented and therefore will not have an intact polyadenylated tail, and will not be recovered or available for subsequent analytical assays. Otherwise, any number of standard nucleic acid purification schemes can be used. These include chaotrope and organic solvent extractions, extraction using glass beads or filters, salting out and precipitation based methods, or any of the purification methods known in the art to recover total RNA or total nucleic acids from a biological source.

Lysis buffers are commercially available, such as, for example, from Qiagen, Epicentre, or Ambion. A preferred group of lysis buffers typically contains urea, and Proteinase K or other protease. Proteinase K is very useful in the isolation of high quality, undamaged DNA or RNA, since most mammalian DNases and RNases are rapidly inactivated by this enzyme, especially in the presence of 0.5-1% sodium dodecyl sulfate (SDS). This is particularly important in the case of RNA, which is more susceptible to degradation than DNA. While DNases require metal ions for activity, and can therefore be easily inactivated by chelating agents, such as EDTA, there is no similar co-factor requirement for RNases.

Cooling and resultant solidification of the wax permits easy separation of the wax from the total nucleic acid, which can be conveniently precipitated, e.g. by isopropanol. Further processing depends on the intended purpose. If the proposed method of RNA analysis is subject to bias by contaminating DNA in an extract, the RNA extract can be further treated, e.g. by DNase, post purification to specifically remove DNA while preserving RNA. For example, if the goal is to isolate high quality RNA for subsequent RT-PCR amplification, nucleic acid precipitation is followed by the removal of DNA, usually by DNase treatment. However, DNA can be removed at various stages of nucleic acid isolation, by DNase or other techniques well known in the art.

While the advantages of the nucleic acid extraction protocol of the invention are most apparent for the isolation of RNA from archived, paraffin embedded tissue samples, the wax removal step of the present invention, which does not involve the use of an organic solvent, can also be included in any conventional protocol for the extraction of total nucleic acid (RNA and DNA) or DNA only. All of these aspects are specifically within the, scope of the invention.

By using heat followed by cooling to remove paraffin, the process of the present invention saves valuable processing time, and eliminates a series of manipulations, thereby potentially increasing the yield of nucleic acid. Indeed, experimental evidence presented in the examples below, demonstrates that the method of the present invention does not compromise RNA yield.

8. 5'-multiplexed Gene Specific Priming of Reverse Transcription

RT-PCR requires reverse transcription of the test RNA population as a first step. The most commonly used primer for reverse transcription is oligo-dT, which works well when RNA is intact. However, this primer will not be effective when RNA is highly fragmented as is the case in FPE tissues.

The present invention includes the use of gene specific primers, which are roughly 20 bases in length with a Tm optimum between about 58° C. and 60° C. These primers will also serve as the reverse primers that drive PCR DNA amplification.

Figure 9:
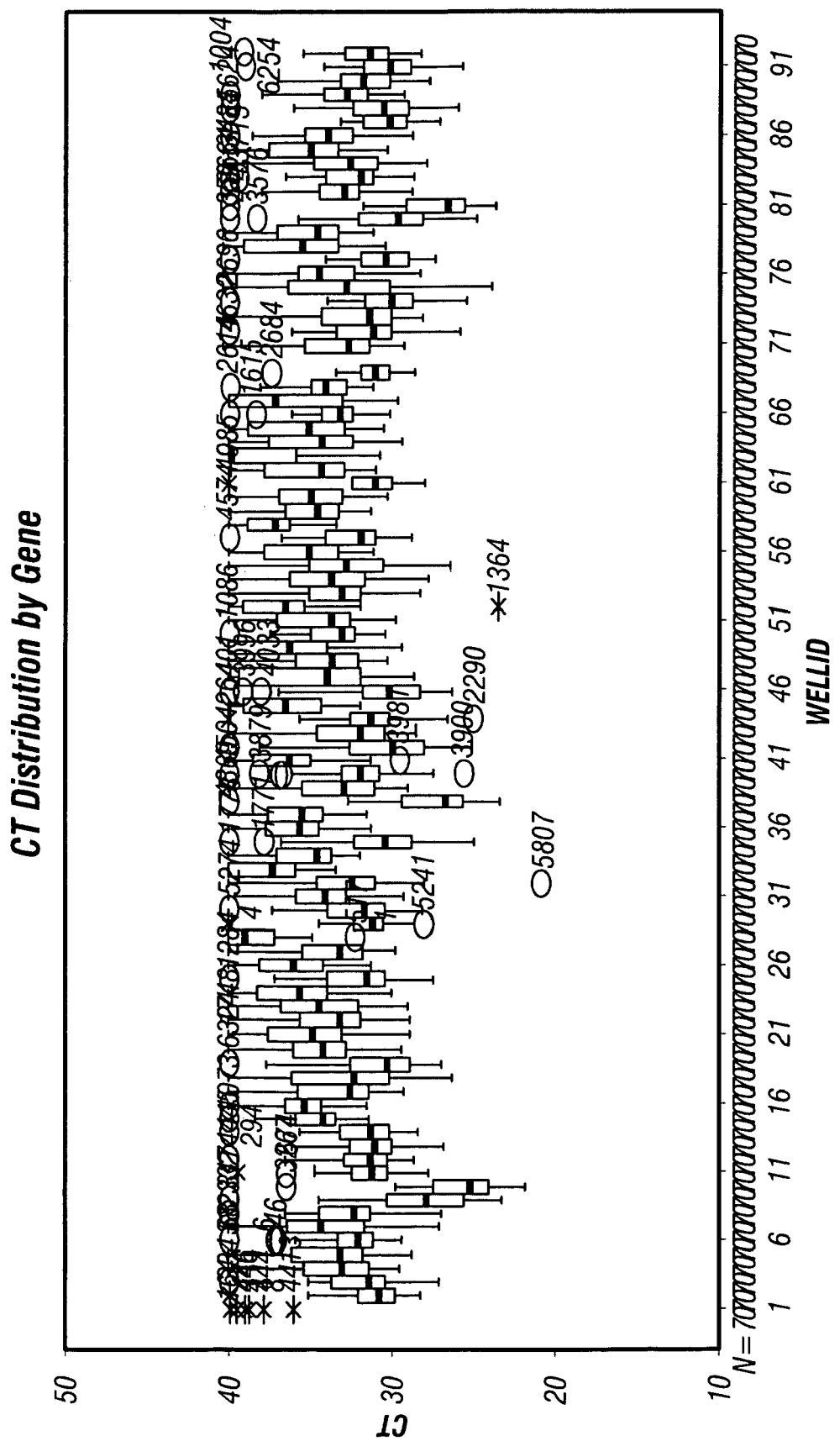
FIG. 9 is a representation of the expression of 92 genes across 70 FPE breast cancer specimens. The y-axis shows expression as cycle threshold times. These genes are a subset of the genes listed in Table 1.

Another aspect of the invention is the inclusion of multiple gene-specific primers in the same reaction mixture. The number of such different primers can vary greatly and can be as low as two and as high as 40,000 or more. Table 2 displays examples of reverse primers that can be successfully used in carrying out the methods of the invention. FIG. 9 shows expression data obtained using this multiplexed gene-specific priming strategy. Specifically, FIG. 9 is a representation of the expression of 92 genes (a subset of genes listed in Table 1) across 70 FPE breast cancer specimens. The y-axis shows expression as cycle threshold times.

An alternative approach is based on the use of random hexamers as primers for cDNA synthesis. However, we have experimentally demonstrated that the method of using a multiplicity of gene-specific primers is superior over the known approach using random hexamers.

9. Preparation of Fragmented mRNA for Expression Profiling Assays

It is of interest to analyze the abundance of specific mRNA species in biological samples, since this expression profile provides an index of the physiological state of that sample. mRNA is notoriously difficult to extract and maintain in its native state, consequently, mRNA recovered from biological sources is often fragmented or somewhat degraded. This is especially true of human tissue specimen which have been chemically fixed and stored for extended periods of time.

In one aspect, the present invention provides a means of preparing the mRNA extracted from various sources, including archived tissue specimens, for expression profiling in a way that its relative abundance is preserved and the mRNA's of interest can be successfully measured: This method is useful as a means of preparing mRNA for analysis by any of the known expression profiling methods, including RT-PCR coupled with 5' exonuclease of reporter probes (TaqMan® type assays), as discussed above, flap endonuclease assays (Cleavase® and Invader® type assays), oligonucleotide hybridization arrays, cDNA hybridization arrays, oligonucleotide ligation assays, 3' single nucleotide extension assays and other assays designed to assess the abundance of specific mRNA sequences in a biological sample.

According to the method of the invention, total RNA is extracted from the source material and sufficiently purified to act as a substrate in an enzyme assay. The extraction procedure, including a new and improved way of removing the wax (e.g. paraffin) used for embedding the tissue samples, has been discussed above. It has also been noted that it is preferred that oligo-dT based methods of selectively purifying polyadenylated mRNA not be used to isolate RNA for this invention since the bulk of the mRNA is expected to be fragmented, will not be polyadenylated and, therefore, will not be recovered and available for subsequent analytical assays if an oligo-dT based method is used.

Figure 3:
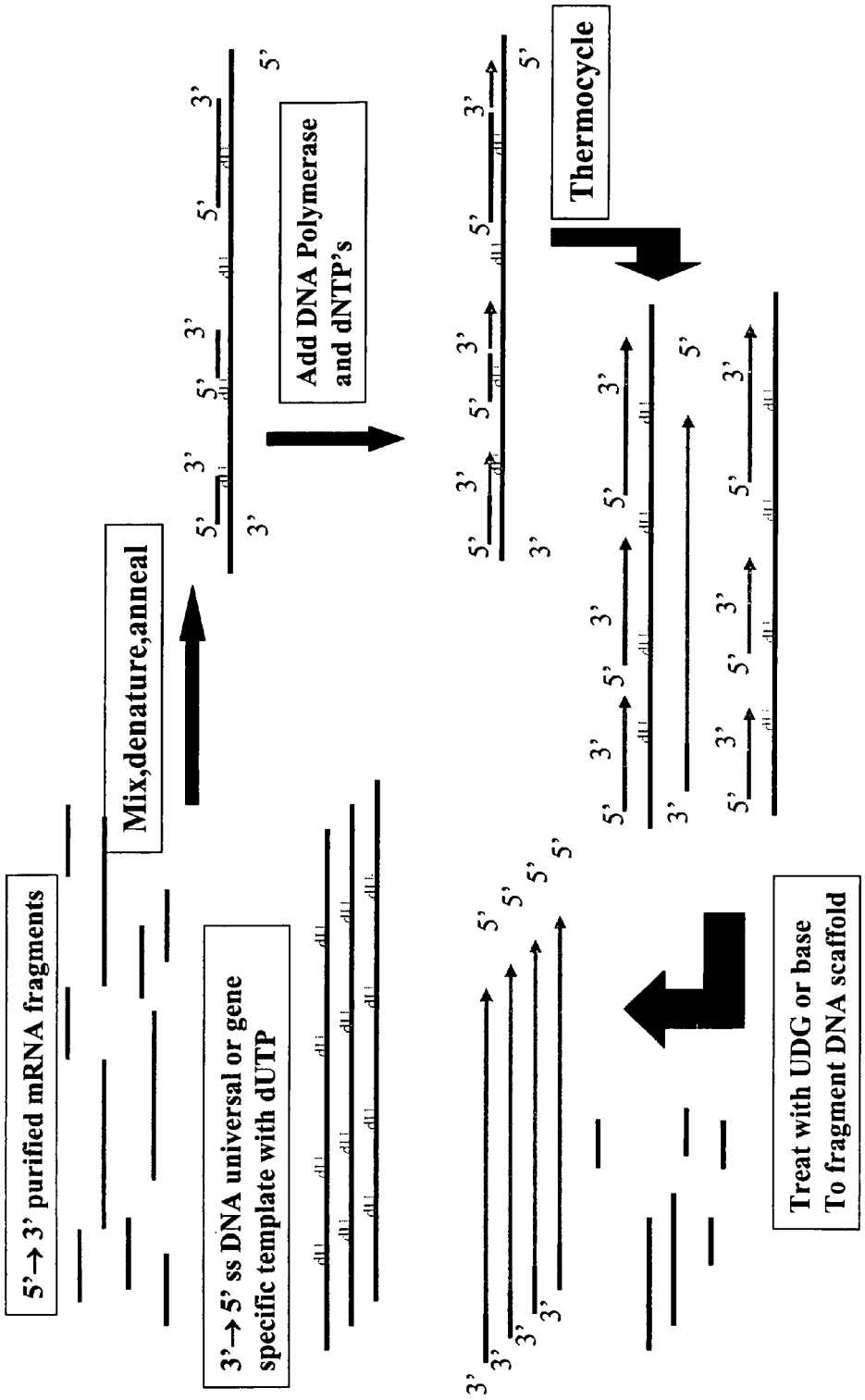
FIG. 3 is a scheme illustrating the steps of an improved method for preparing fragmented mRNA for expression profiling analysis.

A diagram of an improved method for repairing fragmented RNA is shown in FIG. 3. The fragmented RNA purified from the tissue sample is mixed with universal or gene-specific, single-stranded, DNA templates for each mRNA species of interest. These templates may be full length DNA copies of the mRNA derived from cloned gene sources, they may be fragments of the gene representing only the segment of the gene to be assayed, they may be a series of long oligonucleotides representing either the full length gene or the specific segment(s) of interest. The template can represent either a single consensus sequence or be a mixture of polymorphic variants of the gene. This DNA template, or scaffold, will preferably include one or more dUTP or rNTP sites in its length. This will provide a means of removing the template prior to carrying out subsequent analytical steps to avoid its acting as a substrate or target in later analysis assays. This removal is accomplished by treating the sample with uracil-DNA glycosylase (UDG) and heating it to cause strand breaks where UDG has generated abasic sites. In the case of rNTP's, the sample can be heated in the presence of a basic buffer (pH -10) to induce strand breaks where rNTP's are located in the template.

The single stranded DNA template is mixed with the purified RNA, the mixture is denatured and annealed so that the RNA fragments complementary to the DNA template effectively become primers that can be extended along the single stranded DNA templates. DNA polymerase I requires a primer for extension but will efficiently use either a DNA or an RNA primer. Therefore in the presence of DNA polymerase I and dNTP's, the fragmented RNA can be extended along the complementary DNA templates. In order to increase the efficiency of the extension, this reaction can be thermally cycled, allowing overlapping templates and extension products to hybridize and extend until the overall population of fragmented RNA becomes represented as double stranded DNA extended from RNA fragment primers.

Following the generation of this "repaired" RNA, the sample should be treated with UDG or heat-treated in a mildly based solution to fragment the DNA template (scaffold) and prevent it from participating in subsequent analytical reactions.

The product resulting from this enzyme extension can then be used as a template in a standard enzyme profiling assay that includes amplification and detectable signal generation such as fluorescent, chemiluminescent, colorimetric or other common read outs from enzyme based assays. For example, for TaqMan® type assays, this double stranded DNA product is added as the template in a standard assay; and, for array hybridization, this product acts as the cDNA template for the cRNA labeling reaction typically used to generate single-stranded, labeled RNA for array hybridization.

This method of preparing template has the advantage of recovering information from mRNA fragments too short to effectively act as templates in standard cDNA generation schemes. In addition, this method acts to preserve the specific locations in mRNA sequences targeted by specific analysis assays. For example, TaqMan® assays rely on a single contiguous sequence in a cDNA copy of mRNA to act as a PCR amplification template targeted by a labeled reporter probe. If mRNA strand breaks occur in this sequence, the assay will not detect that template and will underestimate the quantity of that mRNA in the original sample. This target preparation method minimizes that effect from RNA fragmentation.

The extension product formed in the RNA primer extension assay can be controlled by controlling the input quantity of the single stranded DNA template and by doing limited cycling of the extension reaction. This is important in preserving the relative abundance of the mRNA sequences targeted for analysis.

This method has the added advantage of not requiring parallel preparation for each target sequence since it is easily multiplexed. It is also possible to use large pools of random sequence long oligonucleotides or full libraries of cloned sequences to extend the entire population of mRNA sequences in the sample extract for whole expressed genome analysis rather than targeted gene specific analysis.

10. Amplification of mRNA Species Prior to RT-PCR

Due to the limited amount and poor quality of mRNA that can be isolated from FPET, a new procedure that could accurately amplify mRNAs of interest would be very useful, particularly for real time quantitation of gene expression (TaqMan®) and especially for quantitatively large number (>50) of genes >50 to 10,000.

Figure 4:
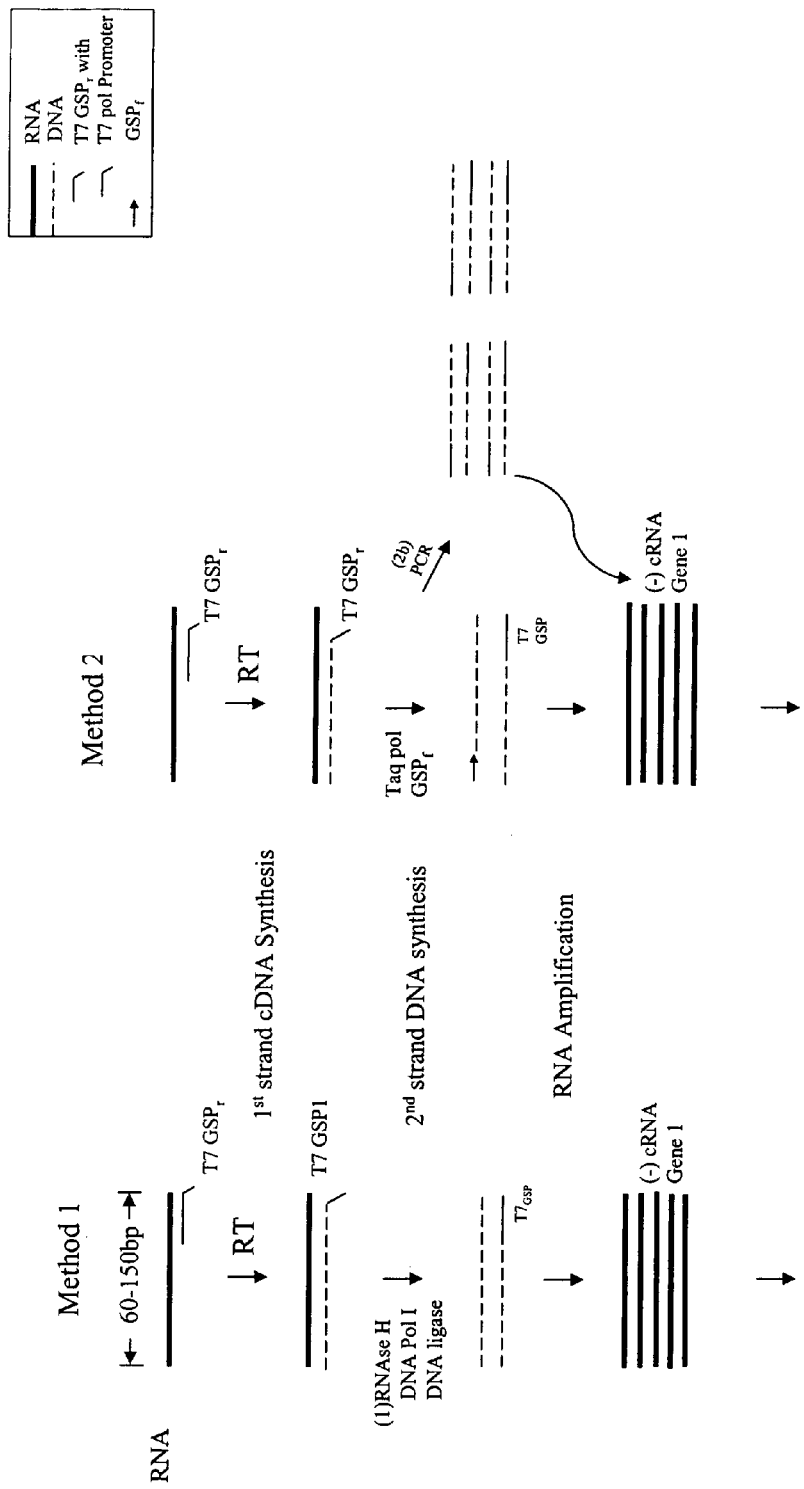
FIG. 4 illustrates methods for amplification of RNA prior to RT-PCR.

Current protocols (e.g. Eberwine, *Biotechniques* 20:584-91 (1996)) are optimized for mRNA amplification from small amount of total or poly $A^+$ RNA mainly for microarray analysis. The present invention provides a protocol optimized for amplification of small amounts of fragmented total RNA (average size about 60-150 bps), utilizing gene-specific sequences as primers, as illustrated in FIG. 4.

The amplification procedure of the invention uses a very large number, typically as many as 100-190,000 gene specific primers (GSP's) in one reverse transcription run. Each GSP contains an RNA polymerase promoter, e.g. a T7 DNA-dependent RNA polymerase promoter, at the 5' end for subsequent RNA amplification. GSP's are preferred as primers because of the small size of the RNA. Current protocols utilize dT primers, which would not adequately represent all reverse transcripts of mRNAs due to the small size of the FPET RNA. GSP's can be designed by optimizing usual parameters, such as length, Tm, etc. For example, GSP's can be designed using the Primer Express® (Applied Biosystems), or Primer 3 (MIT) software program. Typically at least 3 sets per gene are designed, and the ones giving the lowest Ct on FPET RNA (best performers) are selected.

Second strand cDNA synthesis is performed by standard procedures (see FIG. 4, Method 1), or by $GSP_f$ primers and Taq pol under PCR conditions (e.g., 95° C., 10 min (Taq activation) then 60° C., 45 sec). The advantages of the latter method are that the second gene specific primer, $SGF_f$ adds additional specificity (and potentially more efficient second strand synthesis) and the option of performing several cycles of PCR, if more starting DNA is necessary for RNA amplification by T7 RNA polymerase. RNA amplification is then performed under standard conditions to generate multiple copies of cRNA, which is then used in a standard TaqMan® reaction.

Although this process is illustrated by using T7-based RNA amplification, a person skilled in the art will understand that other RNA polymerase promoters that do not require a primer, such as T3 or Sp6 can also be used, and are within the scope of the invention.

11. A method of Elonzation of Fragmented RNA and Subsequent Amplification

Figure 5:
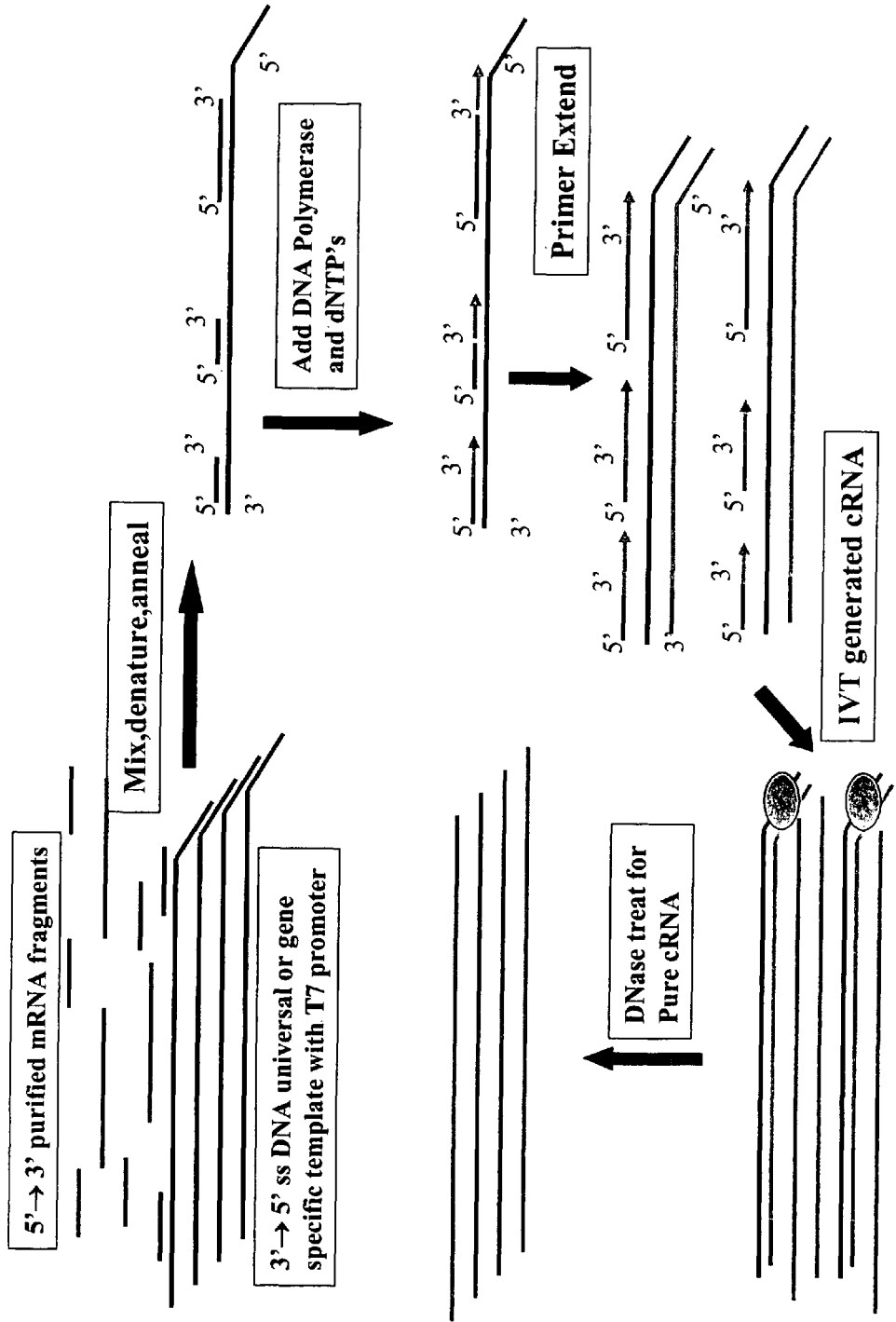
FIG. 5 illustrates an alternative scheme for repair and amplification of fragmented mRNA.

This method, which combines and modifies the inventions described in sections 9 and 10 above, is illustrated in FIG. 5. The procedure begins with elongation of fragmented mRNA. This occurs as described above except that the scaffold DNAs are tagged with the T7 RNA polymerase promoter sequence at their 5' ends, leading to double-stranded DNA extended from RNA fragments. The template sequences need-to be removed after in vitro transcription. These templates can include dUTP or rNTP nucleotides, enabling enzymatic removal of the templates as described in section 9, or the templates can be removed by DNaseI treatment.

The template DNA can be a population representing different mRNAs of any number. A high sequence complexity source of DNA templates (scaffolds) can be generated by pooling RNA from a variety of cells or tissues. In one embodiment, these RNAs are converted into double stranded DNA and cloned into phagemids. Single stranded DNA can then be rescued by phagemid growth and single stranded DNA isolation from purified phagemids.

This invention is useful because it increases gene expression profile signals two different ways: both by increasing test mRNA polynucleotide sequence length and by in vitro transcription amplification. An additional advantage is that it eliminates the need to carry out reverse transcription optimization with gene specific primers tagged with the T7 RNA polymerase promoter sequence, and thus, is comparatively fast and economical.

This invention can be used with a variety of different methods to profile gene expression, e.g., RT-PCR or a variety of DNA array methods. Just as in the previous protocol, this approach is illustrated by using a T7 promoter but the invention is not so limited. A person skilled in the art will appreciate, however, that other RNA polymerase promoters, such as T3 or Sp6 can also be used.

12. Breast Cancer Gene Set, Assayed Gene Subsequences, and Clinical Application of Gene Expression Data An important aspect of the present invention is to use the measured expression of certain genes by breast cancer tissue to match patients to best drugs or drug combinations, and to provide prognostic information. For this purpose it is necessary to correct for (normalize away) both differences in the amount of RNA assayed and variability in the quality of the RNA used. Therefore, the assay measures and incorporates the expression of certain normalizing genes, including well known housekeeping genes, such as GAPDH and Cyp1. Alternatively, normalization can be based on the mean or median signal (Ct) of all of the assayed genes or a large subset thereof (global normalization approach). On a gene-by-gene basis, measured normalized amount of a patient tumor mRNA is compared to the amount found in a breast cancer tissue reference set. The number (N) of breast cancer tissues in this reference set should be sufficiently high to ensure that different reference sets (as a whole) behave essentially the same way. If this condition is met, the identity of the individual breast cancer tissues present in a particular set will have no significant impact on the relative amounts of the genes assayed. Usually, the breast cancer tissue reference set consists of at least about 30, preferably at least about 40 different FPE breast cancer tissue specimens. Unless noted otherwise, normalized expression levels for each mRNA/tested tumor/patient will be expressed as a percentage of the expression level measured in the reference set. More specifically, the reference set of a sufficiently high number (e.g. 40) tumors yields a distribution of normalized levels of each mRNA species. The level measured in a particular tumor sample to be analyzed falls at some percentile within this range, which can be determined by methods well known in the art. Below, unless noted otherwise, reference to expression levels of a gene assume normalized expression relative to the reference set although this is not always explicitly stated.

The breast cancer gene set is shown in Table 1. The gene Accession Numbers, and the SEQ ID NOs for the forward primer, reverse primer and amplicon sequences that can be used for gene amplification, are listed in Table 2. The basis for inclusion of markers, as well as the clinical significance of mR-NA level variations with respect to the reference set, is indicated below. Genes are grouped into subsets based on the type of clinical significance indicated by their expression levels: A. Prediction of patient response to drugs used in breast cancer treatment, or to drugs that are approved for other indications and could be used off-label in the treatment of breast cancer. B. Prognostic for survival or recurrence of cancer.

C. Prediction of Patient Response to Therapeutic Drugs

1. Molecules that Specifically Influence Cellular Sensitivity to Drugs

Table 1 lists 74 genes. (shown in italics) that specifically influence cellular sensitivity to potent drugs, which are also listed. Most of the drugs shown are approved and already used to treat breast cancer (e.g., anthracyclines; cyclophosphamide; methotrexate; 5-FU and analogues). Several of the drugs are used to treat breast cancer off-label or are in clinical development phase (e.g., bisphosphonates and anti-VEGF mAb). Several of the drugs have not been widely used to treat breast cancer but are used in other cancers in which the indicated target is expressed (e.g., Celebrex is used to treat familial colon cancer; cisplatin is used to treat ovarian and other cancers.)

Patient response to 5FU is indicated if normalized thymidylate synthase mRNA amount is at or below the $15^{th}$ percentile, or the sum of expression of thymidylate synthase plus dihydropyrimidine phosphorylase is at or below the $25^{th}$ percentile, or the sum of expression of these mRNAs plus thymidine phosphorylase is at or below the $20^{th}$ percentile.

Patients with dihydropyrimidine dehydrogenase below $5^{th}$ percentile are at risk of adverse response to 5FU, or analogs such as Xeloda.

When levels of thymidylate synthase, and dihydropyrimidine dehydrogenase, are within the acceptable range as defined in the preceding paragraph, amplification of c-myc mRNA in the upper 15%, against a background of wild-type p5.3 [as defined below] predicts a beneficial response to 5FU (see D. Arango et al., *Cancer Res.* 61:4910-4915 (2001)). In the presence of normal levels of thymidylate synthase and dihydropyrimidine dehydrogenase, levels of NFκB and cIAP2 in the upper 10% indicate resistance of breast tumors to the chemotherapeutic drug 5FU.

Patient resistance to anthracyclines is indicated if the normalized mRNA level of topoisomerase IIα is below the $10^{th}$ percentile, or if the topoisomerase IIβ normalized mRNA level is below the $10^{th}$ percentile or if the combined normalized topoisomerase IIα and D signals are below the $10^{th}$ percentile.

Patient sensitivity to methotrexate is compromised if DHFR levels are more than tenfold higher than the average reference set level for this mRNA species, or if reduced folate carrier levels are below $10^{th}$ percentile.

Patients whose tumors express CYP1B1 in the upper 10%, have reduced likelihood of responding to docetaxol.

The sum of signals for aldehyde dehydrogenase 1A1 and 1A3, when more than tenfold higher than the reference set average, indicates reduced likelihood of response to cyclophosphamide.

Figure 6:
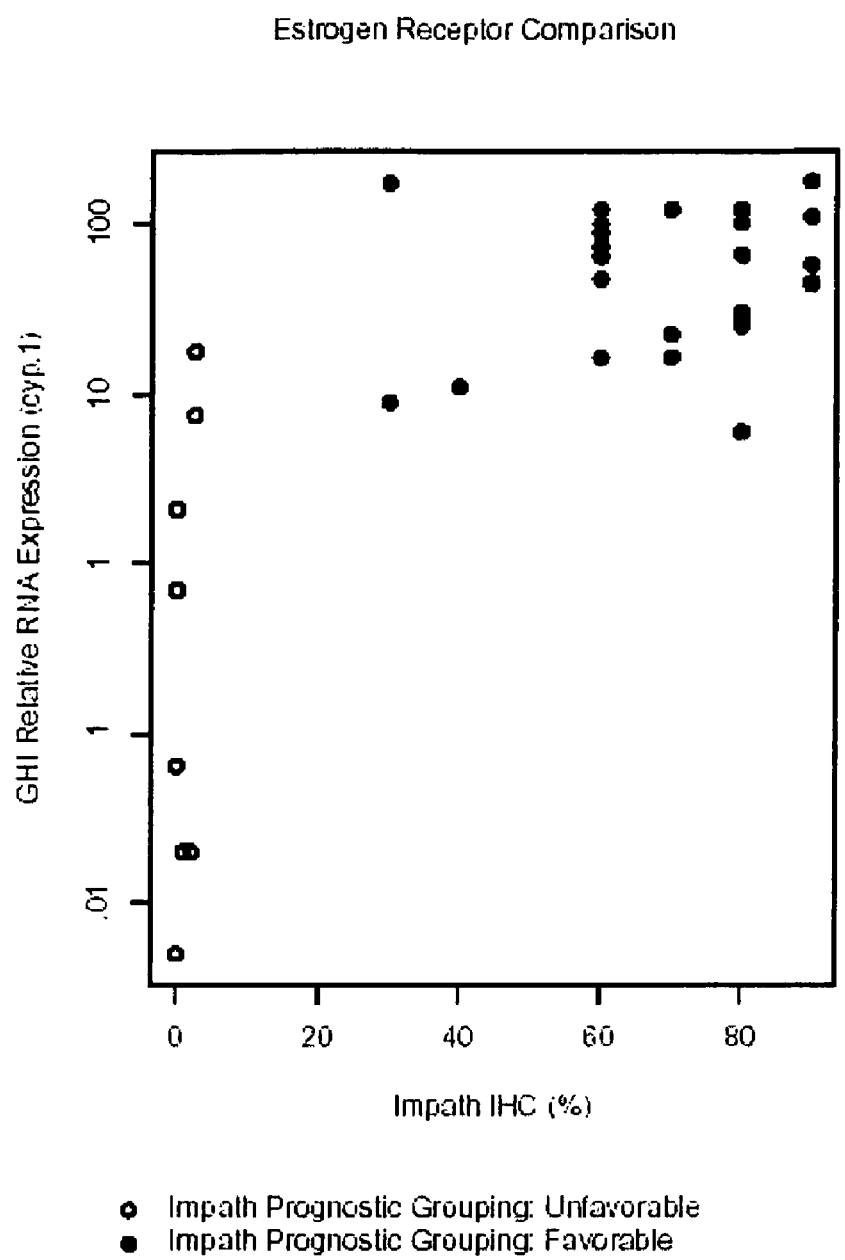
FIG. 6 shows the measurement of estrogen receptor mRNA levels in 40 FPE breast cancer specimens via RT-PCR. Three 10 micron sections were used for each measurement. Each data point represents the average of triplicate measurements.
Figure 7:
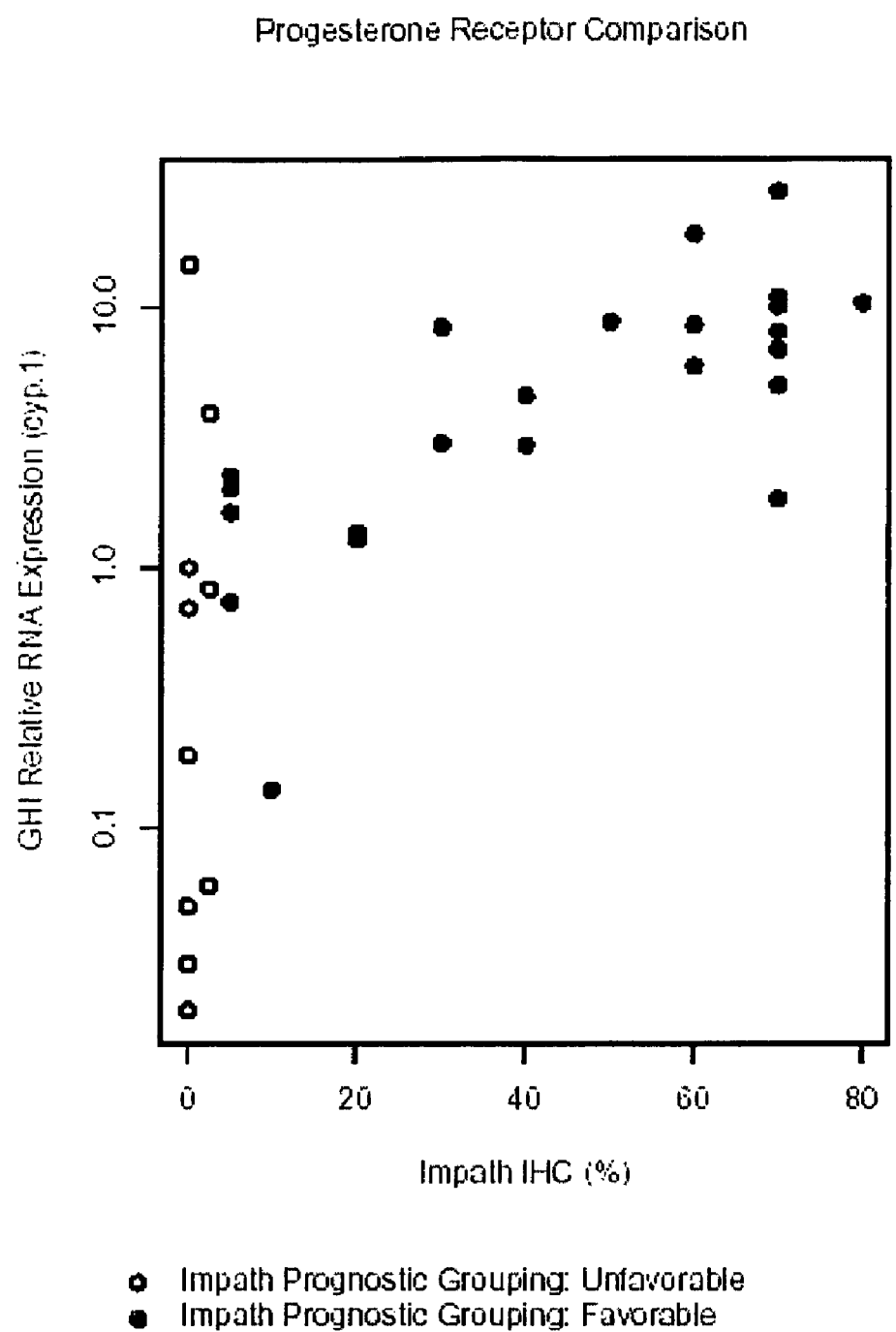
FIG. 7 shows the results of the measurement of progesterone receptor mRNA levels in 40 FPE breast cancer specimens via RT-PCR performed as described in the legend of FIG. 6 above.

Currently, estrogen and progesterone receptor expression as measured by immunohistochemistry is used to select patients for anti-estrogen therapy. We have demonstrated RT-PCR assays for estrogen and progesterone receptor mRNA levels that predict levels of these proteins as determined by a standard clinical diagnostic tests, with high degree of concordance (FIGS. 6 and 7).

Patients whose tumors express ERα or PR mRNA in the upper 70%, are likely to respond to tamoxifen or other anti-estrogens (thus, operationally, lower levels of ERα than this are to defined ERα-negative). However, when the signal for microsomal epoxide hydrolase is in the upper 10% or when mRNAs for pS2/trefoil factor, GATA3 or human chorionic gonadotropin are at or below average levels found in ERα-negative tumors, anti-estrogen therapy will not be beneficial.

Absence of XIST signal compromises the likelihood of response to taxanes, as does elevation of the GST-π or prolyl endopeptidase [PREP] signal in the upper 10%. Elevation of PLAG1 in the upper 10% decreases sensitivity to taxanes.

Expression of ERCC1 mRNA in the upper 10% indicate significant risk of resistance to cisplatin or analogs.

An RT-PCR assay of Her2 mRNA expression predicts Her2 overexpression as measured by a standard diagnostic test, with high degree of concordance (data not shown). Patients whose tumors express Her2 (normalized to cyp.1) in the upper 10% have increased likelihood of beneficial response to treatment with Herceptin or other ErbB2 antagonists. Measurement of expression of Grb7 mRNA serves as a test for HER2 gene amplification, because the Grb7 gene is closely linked to Her2. When Her2 is expression is high as defined above in this paragraph, similarly elevated Grb7 indicates Her2 gene amplification. Overexpression of IGF1R and or IGF1 or IGF2 decreases likelihood of beneficial response to Herceptin and also to EGFR antagonists.

Patients whose tumors express mutant Ha-Ras, and also express farnesyl pyrophosphate synthetase or geranyl pyrophosphonate synthetase mRNAs at levels above the tenth percentile comprise a group that is especially likely to exhibit a beneficial response to bis-phosphonate drugs.

Cox2 is a key control enzyme in the synthesis of prostaglandins. It is frequently expressed at elevated levels in subsets of various types of carcinomas including carcinoma of the breast. Expression of this gene is controlled at the transcriptional level, so RT-PCR serves a valid indicator of the cellular enzyme activity. Nonclinical research has shown that cox2 promotes tumor angiogenesis, suggesting that this enzyme is a promising drug target in solid tumors. Several Cox2 antagonists are marketed products for use in anti-inflammatory conditions. Treatment of familial adenomatous polyposis patients with the cox2 inhibitor Celebrex significantly decreased the number and size of neoplastic polyps. No cox2 inhibitor has yet been approved for treatment of breast cancer, but generally this class of drugs is safe and could be prescribed off-label in breast cancers in which cox2 is overexpressed. Tumors expressing COX2 at levels in the upper ten percentile have increased chance of beneficial response to Celebrex or other cyclooxygenase 2 inhibitors.

The tyrosine kinases ErbB1 [EGFR], ErbB3 [Her3] and ErbB4 [Her4]; also the ligands TGFalpha, amphiregulin, heparin-binding EGF-like growth factor, and epiregulin; also BRK, a non-receptor kinase. Several drugs in clinical development block the EGF receptor. ErbB2-4, the indicated ligands, and BRK also increase the activity of the EGFR pathway. Breast cancer patients whose tumors express high levels of EGFR or EGFR and abnormally high levels of the other indicated activators of the EGFR pathway are potential candidates for treatment with an EGFR antagonist.

Patients whose tumors express less than 10% of the average level of EGFR mRNA observed in the reference panel are relatively less likely to respond to EGFR antagonists [such as Iressa, or ImClone 225]. In cases in which the EGFR is above this low range, the additional presence of epiregulin, TGFα, amphiregulin, or ErbB3, or BRK, CD9, MMP9, or Lot1 at levels above the $90^{th}$ percentile predisposes to response to EGFR antagonists. Epiregulin gene expression, in particular, is a good surrogate marker for EGFR activation, and can be used to not only to predict response to EGFR antagonists, but also to monitor response to EGFR antagonists [taking fine needle biopsies to provide tumor tissue during treatment]. Levels of CD82 above the $90^{th}$ percentile suggest poorer efficacy from EGFR antagonists.

The tyrosine kinases abl, c-kit, PDGFRalpha, PDGFbeta, and ARG; also, the signal transmitting ligands c-kit ligand, PDGFA, B, C and D. The listed tyrosine kinases are all targets of the drug Gleevec™ (imatinib mesylate, Novartis), and the listed ligands stimulate one or more of the listed tyrosine kinases. In the two indications for which Gleevec™ is approved, tyrosine kinase targets (bcr-abl and ckit) are overexpressed and also contain activating mutations. A finding that one of the Gleevec™ target tyrosine kinase targets is expressed in breast cancer tissue will prompt a second stage of analysis wherein the gene will be sequenced to determine whether it is mutated. That a mutation found is an activating mutation can be proved by methods known in the art, such as, for example, by measuring kinase enzyme activity or by measuring phosphorylation status of the particular kinase, relative to the corresponding wild-type kinase. Breast cancer patients whose tumors express high levels of mRNAs encoding Gleevec™ target tyrsine kinases, specifically, in the upper ten percentile, or mRNAs for Gleevec™ target tyrosine kinases in the average range and mRNAs for their cognate growth stimulating ligands in the upper ten percentile, are particularly good candidates for treatment with Gleevec™.

VEGF is a potent and pathologically important angiogenic factor. (See below under Prognostic Indicators.) When VEGF mRNA levels are in the upper ten percentile, aggressive treatment is warranted. Such levels particularly suggest the value of treatment with anti-angiogenic drugs, including VEGF antagonists, such as anti-VEGF antibodies. Additionally, KDR or CD31 mRNA level in the upper 20 percentile further increases likelihood of benefit from VEGF antagonists.

Farnesyl pyrophosphatase synthetase and geranyl pyrophosphatase synthetase. These enzymes are targets of commercialized bisphosphonate drugs, which were developed originally for treatment of osteoporosis but recently have begun to prescribe them off-label in breast cancer. Elevated levels of mRNAs encoding these enzymes in breast cancer tissue, above the 90$^{th}$ percentile, suggest use of bisphosphonates as a treatment option.

2. Multidrug Resistance Factors

These factors include 10 Genes: gamma glutamyl cysteine synthetase [GCS]; GST-α; GST-N; MDR-1; MRP1-4; breast cancer resistance protein [BCRP]; lung resistance protein [MVP]; SXR; YB-1.

GCS and both GST-α and GST-π regulate glutathione levels, which decrease cellular sensitivity to chemotherapeutic drugs and other toxins by reductive derivatization. Glutathione is a necessary cofactor for multi-drug resistant pumps, MDR-1 and the MRPs. MDR1 and MRPs function to actively transport out of cells several important chemotherapeutic drugs used in breast cancer.

GSTs, MDR-1, and MRP-1 have all been studied extensively to determine possible have prognostic or predictive significance in human cancer. However, a great deal of disagreement exists in the literature with respect to these questions. Recently, new members of the MRP family have been identified: MRP-2, MRP-3, MRP-4, BCRP, and lung resistance protein [major vault protein]. These have substrate specificities that overlap with those of MDR-1 and MRP-1. The incorporation of all of these relevant ABC family members as well as glutathione synthetic enzymes into the present invention captures the contribution of this family to drug resistance, in a way that single or double analyte assays cannot.

MRP-1, the gene coding for the multidrug resistance protein.

P-glycoprotein, is not regulated primarily at the transcriptional level. However, p-glycoprotein stimulates the transcription of PTP1b. An embodiment of the present invention is the use of the level of the mRNA for the phosphatase PTP1b as a surrogate measure of MRP-1/p-glycoprotein activity.

The gene SXR is also an activator of multidrug resistance, as it stimulates transcription of certain multidrug resistance factors.

The impact of multidrug resistance factors with respect to chemotherapeutic agents used in breast cancer is as follows. Beneficial response to doxorubicin is compromised when the mRNA levels of either MDR1, GSTα, GSTπ, SXR, BCRP YB-1, or LRP/MVP are in the upper four percentile. Beneficial response to methotrexate is inhibited if mRNA levels of any of MRP1, MRP2, MRP3, or MRP4 or gamma-glutamyl cysteine synthetase are in the upper four percentile.

3. Eukaryotic Translation Initiation Factor 4E [EIF4E]

EIF4E mRNA levels provides evidence of protein expression and so expands the capability of RT-PCR to indicate variation in gene expression. Thus, one claim of the present invention is the use of EIF4E as an added indicator of gene expression of certain genes [e.g., cyclinD1, mdm2, VEGF, and others]. For example, in two tissue specimens containing the same amount of normalized VEGF mRNA, it is likely that the tissue containing the higher normalized level of EIF4E exhibits the greater level of VEGF gene expression.

The background is as follows. A key point in the regulation of mRNA translation is selection of mRNAs by the EIF4G complex to bind to the 43S ribosomal subunit. The protein EIF4E [the m7G CAP-binding protein] is often limiting because more mRNAs than EIF4E copies exist in cells. Highly structured 5'UTRs or highly GC-rich ones are inefficiently translated, and these often code for genes that carry out functions relevant to cancer [e.g., cyclinD1, mdm2, and VEGF]. EIF4E is itself regulated at the transcriptional/mRNA level. Thus, expression of EIF4E provides added indication of increased activity of a number of proteins.

It is also noteworthy that overexpression of EIF4E transforms cultured cells, and hence is an oncogene. Overexpression of EIF4E occurs in several different types of carcinomas but is particularly significant in breast cancer. EIF4E is typically expressed at very low levels in normal breast tissue.

D. Prognostic Indicators

1. DNA Repair Enzymes

Loss of BRCA1 or BRCA2 activity via mutation represents the critical oncogenic step in the most common type[s] of familial breast cancer. The levels of mRNAs of these important enzymes are abnormal in subsets of sporadic breast cancer as well. Loss of signals from either [to within the lower ten percentile] heightens risk of short survival.

2. Cell Cycle Regulators

Cell cycle regulators include 14 genes: c-MYC; c-Src; Cyclin D1; Ha-Ras; mdm2; p14ARF; p21WAF1/CIP; p16INK4a/p14; p23; p27; p53; PI3K; PKC-epsilon; PKC-delta.

The gene for p53 [TP53] is mutated in a large fraction of breast cancers. Frequently p53 levels are elevated when loss of function mutation occurs. When the mutation is dominant-negative, it creates survival value for the cancer cell because growth is promoted and apoptosis is inhibited. Thousands of different p53 mutations have been found in human cancer, and the functional consequences of many of them are not clear. A large body of academic literature addresses the prognostic and predictive significance of mutated p53 and the results are highly conflicting. The present invention provides a functional genomic measure of p53 activity, as follows. The activated wild type p53 molecule triggers transcription of the cell cycle inhibitor p21. Thus, the ratio of p53 to p21 should be low when p53 is wild-type and activated. When p53 is detectable and the ratio of p53 to p21 is elevated in tumors relative to normal breast, it signifies nonfunctional or dominant negative p53. The cancer literature provides evidence for this as born out by poor prognosis.

Mdm2 is an important p53 regulator. Activated wildtype p53 stimulates transcription of mdm2. The mdm2 protein binds p53 and promotes its proteolytic destruction. Thus, abnormally low levels of mdm2 in the presence of normal or higher levels of p53 indicate that p53 is mutated and inactivated.

One aspect of the present invention is the use of ratios of mRNAs levels p53:p21 and p53:mdm2 to provide a picture of p53 status. Evidence for dominant negative mutation of p53 (as indicated by high p53:p21 and/or high p53:mdm2 mRNA ratios-specifically in the upper ten percentile) presages higher risk of recurrence in breast cancer and therefore weights toward a decision to use chemotherapy in node negative post surgery breast cancer.

Another important cell cycle regulator is p27, which in the activated form blocks cell cycle progression at the level of cdk4. The protein is regulated primarily via phosphorylation/dephosphorylation, rather than at the transcriptional level. However, levels of p27 mRNAs do vary. Therefore a level of p27 mRNA in the upper ten percentile indicates reduced risk of recurrence of breast cancer post surgery.

Cyclin D1 is a principle positive regulator of entry into S phase of the cell cycle. The gene for cyclin D1 is amplified in about 20% of breast cancer patients, and therefore promotes tumor promotes tumor growth in those cases. One aspect of the present invention is use of cyclin D1 mRNA levels for diagnostic purposes in breast cancer. A level of cyclin D1 mRNA in the upper ten percentile suggests high risk of recurrence in breast cancer following surgery and suggests particular benefit of adjuvant chemotherapy.

3. Other Tumor Suppressors and Related Proteins

These include APC and E-cadherin. It has long been known that the tumor suppressor APC is lost in about 50% of colon cancers, with concomitant transcriptional upregulation of E-cadherin, an important cell adhesion molecule and growth suppressor. Recently, it has been found that the APC gene silenced in 15-40% of breast. cancers. Likewise, the E-cadherin gene is silenced [via CpG island methylation] in about 30% of breast cancers. An abnormally low level of APC and/or E-cadherin mRNA in the lower 5 percentile suggests high risk of recurrence in breast cancer following surgery and heightened risk of shortened survival.

4. Regulators of Apoptosis

These include BCl/BAX family members BCl2, Bcl-x1, Bak, Bax and related factors, NFκ-B and related factors, and also p53BP1/ASPP1 and p53BP2/ASPP2.

Bax and Bak are pro-apoptotic and BCl2 and Bcl-x1 are anti-apoptotic. Therefore, the ratios of these factors influence the resistance or sensitivity of a cell to toxic (pro-apoptotic) drugs. In breast cancer, unlike other cancers, elevated level of BCl2 (in the upper ten percentile) correlates with good outcome. This reflects the fact that BCl2 has growth inhibitory activity as well as anti-apoptotic activity, and in breast cancer the significance of the former activity outweighs the significance of the latter. The impact of BCl2 is in turn dependent on the status of the growth stimulating transcription factor c-MYC. The gene for c-MYC is amplified in about 20% of breast cancers. When c-MYC message levels are abnormally elevated relative to BCl2 (such that this ratio is in the upper ten percentile), then elevated level of BCl2 mRNA is no longer a positive indicator.

NFκ-B is another important anti-apoptotic factor. Originally, recognized as a pro-inflammatory transcription factor, it is now clear that it prevents programmed cell death in response to several extracellular toxic factors [such as tumor necrosis factor]. The activity of this transcription factor is regulated principally via phosphorylation/dephosphorylation events. However, levels of NFκ-B nevertheless do vary from cell to cell, and elevated levels should correlate with increased resistance to apoptosis. Importantly for present purposes, NFκ-B, exerts its anti-apoptotic activity largely through its stimulation of transcription of mRNAs encoding certain members of the IAP [inhibitor of apoptosis] family of proteins, specifically cIAP1, cIAP2, XIAP, and Survivin. Thus, abnormally elevated levels of mRNAs for these IAPs and for NFκ-B any in the upper 5 percentile] signify activation of the NFκ-B anti-apoptotic pathway. This suggests high risk of recurrence in breast cancer following chemotherapy and therefore poor prognosis. One embodiment of the present invention is the inclusion in the gene set of the above apoptotic regulators, and the above-outlined use of combinations and ratios of the levels of their mRNAs for prognosis in breast cancer.

The proteins p53BP1 and 2 bind to p53 and promote transcriptional activation of pro-apoptotic genes. The levels of p53BP1 and 2 are suppressed in a significant fraction of breast cancers, correlating with poor prognosis. When either is expressed in the lower tenth percentile poor prognosis is indicated.

5. Factors that Control Cell Invasion and Angiogenesis

These include uPA, PAI1, cathepsinsB, G and L, scatter factor [HGF], c-met, KDR, VEGF, and CD31. The plasminogen activator uPA and its serpin regulator PAI1 promote breakdown of extracellular matrices and tumor cell invasion. Abnormally elevated levels of both mRNAs in malignant breast tumors (in the upper twenty percentile) signify an increased risk of shortened survival, increased recurrence in breast cancer patients post surgery, and increased importance of receiving adjuvant chemotherapy. On the other hand, node negative patients whose tumors do not express elevated levels of these mRNA species are less likely to have recurrence of this cancer and could more seriously consider whether the benefits of standard chemotherapy justifies the associated toxicity.

Cathepsins B or L, when expressed in the upper ten percentile, predict poor disease-free and overall, survival. In particular, cathepsin L predicts short survival in node positive patients.

Scatter factor and its cognate receptor c-met promote cell motility and invasion, cell growth, and angiogenesis. In breast cancer elevated levels of mRNAs encoding these factors should prompt aggressive treatment with chemotherapeutic drugs, when expression of either, or the combination, is above the $90^{th}$ percentile.

VEGF is a central positive regulator of angiogenesis, and elevated levels in solid tumors predict short survival [note many references showing that elevated level of VEGF predicts short survival]. Inhibitors of VEGF therefore slow the growth of solid tumors in animals and humans. VEGF activity is controlled at the level of transcription. VEGF mRNA levels in the upper ten percentile indicate significantly worse than average prognosis. Other markers of vascularization, CD31 [PECAM], and KDR indicate high vessel density in tumors and that the tumor will be particularly malignant and aggressive, and hence that an aggressive therapeutic strategy is warranted.

6. Markers for Immune and Inflammatory Cells and Processes

These markers include the genes for Immunoglobulin light chain λ, CD18, CD3, CD68, Fas [CD95], and Fas Ligand.

Several lines of evidence suggest that the mechanisms of action of certain drugs used in breast cancer entail activation of the host immune/inflammatory response (For example, Herceptin®). One aspect of the present invention is the inclusion in the gene set of markers for inflammatory and immune cells, and markers that predict tumor resistance to immune surveillance. Immunoglobulin light chain lambda is a marker for immunoglobulin producing cells. CD18 is a marker for all white cells. CD3 is a marker for T-cells. CD68 is a marker for macrophages.

CD95 and Fas ligand are a receptor: ligand pair that mediate one of two major pathways by which cytotoxic T cells and NK cells kill targeted cells. Decreased expression of CD95 and increased expression of Fas Ligand indicates poor prognosis in breast cancer. Both CD95 and Fas Ligand are transmembrane proteins, and need to be membrane anchored to trigger cell death. Certain tumor cells produce a truncated soluble variant of CD95, created as a result of alternative splicing of the CD95 mRNA. This blocks NK cell and cytotoxic T cell Fas Ligand-mediated killing of the tumors cells.

Presence of soluble CD95 correlates with poor survival in breast cancer. The gene set includes both soluble and full-length variants of CD95.

7. Cell Proliferation Markers

The gene set includes the cell proliferation markers Ki67/MiB1, PCNA, Pin1, and thymidine kinase. High levels of expression of proliferation markers associate with high histologic grade, and short survival. High levels of thymidine kinase in the upper ten percentile suggest in creased risk of short survival. Pin1 is a prolyl isomerase that stimulates cell growth, in part through the transcriptional activation of the cyclin D1 gene, and levels in the upper ten percentile contribute to a negative prognostic profile.

8. Other Growth Factors and Receptors

This gene set includes IGF1, IGF2, IGFBP3, IGF1R, FGF2, FGFR1, CSF-1R/fms, CSF-1, IL6 and IL8. All of these proteins are expressed in breast cancer. Most stimulate tumor growth. However, expression of the growth factor FGF2 correlates with good outcome. Some have anti-apoptotic activity, prominently IGF1. Activation of the IGF1 axis via elevated IGF1, IGF1R, or IGFBP3 (as indicated by the sum of these signals in the upper ten percentile) inhibits tumor cell death and strongly contributes to a poor prognostic profile.

9. Gene Expression Markers that Define Subclasses of Breast Cancer

These include: GRO1 oncogene alpha, Grb7, cytokeratins 5 and 17, retinal binding protein 4, hepatocyte nuclear factor 3, integrin alpha 7, and lipoprotein lipase. These markers subset breast cancer into different cell types that are phenotypically different at the level of gene expression. Tumors expressing signals for Bcl2, hepatocyte nuclear factor 3, LIV1 and ER above the mean have the best prognosis for disease free and overall survival following surgical removal of the cancer. Another category of breast cancer tumor type, characterized by elevated expression of lipoprotein lipase, retinol binding protein 4, and integrin α7, carry intermediate prognosis. Tumors expressing either elevated levels of cytokeratins 5, and 17, GRO oncogene at levels four-fold or greater above the mean, or ErbB2 and Grb7 at levels ten-fold or more above the mean, have worst prognosis.

Although throughout the present description, including the Examples below, various aspects of the invention are explained with reference to gene expression studies, the invention can be performed in a similar manner, and similar results can be reached by applying proteomics techniques that are well known in the art. The proteome is the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry and/or N-terminal sequencing, and (3) analysis of the data using bioinformatics. Proteomics methods are valuable supplements to other methods of gene expression profiling, and can be used, alone or in combination with other methods of the present invention, to detect the products of the gene markers of the present invention.

Further details of the invention will be described in the following non-limiting Examples.

Example 1

Isolation of RNA from Formalin-Fixed, Paraffin-Embedded (FPET) Tissue Specimens

A. Protocols

I. EPICENTRE® Xylene Protocol

RNA Isolation (1) Cut 1-6 sections (each 10 μm thick) of paraffin-embedded tissue per sample using a clean microtome blade and place into a 1.5 ml eppendorf tube.

(2) To extract paraffin, add 1 ml of xylene and invert the tubes for 10 minutes by rocking on a nutator.

(3) Pellet the sections by centrifugation for 10 minutes at 14,000×g in an eppendorf microcentrifuge.

(4) Remove the xylene, leaving some in the bottom to avoid dislodging the pellet.

(5) Repeat steps 2-4.

(6) Add 1 ml of 100% ethanol and invert for 3 minutes by rocking on the nutator.

(7) Pellet the debris by centrifugation for 10 minutes at 14,000×g in an eppendorf microcentrifuge.

(8) Remove the ethanol, leaving some at the bottom to avoid the pellet.

(9) Repeat steps 6-8 twice.

(10) Remove all of the remaining ethanol.

(11) For each sample, add 2 μl of 50 label Proteinase K to 300 μl of Tissue and Cell Lysis Solution.

(12) Add 300 μl of Tissue and Cell Lysis Solution containing the Proteinase K to each sample and mix thoroughly.

(13) Incubate at 65° C. for 90 minutes (vortex mixing every 5 minutes). Visually monitor the remaining tissue fragment. If still visible after 30 minutes, add an additional 2 μl of 50 μg/μl Proteinase K and continue incubating at 65° C. until fragment dissolves.

(14) Place the samples on ice for 3-5 minutes and proceed with protein removal and total nucleic acid precipitation.

Protein Removal and Precipitation of Total Nucleic Acid (1) Add 150 μl of MPC Protein Precipitation Reagent to each lysed sample and vortex vigorously for 10 seconds.

(2) Pellet the debris by centrifugation for 10 minutes at 14,000×g in an eppendorf microcentrifuge.

(3) Transfer the supernatant into clean eppendorf tubes and discard the pellet.

(4) Add 500 μl of isopropanol to the recovered supernatant and thoroughly mix by rocking on the nutator for 3 minutes.

(5) Pellet the RNA/DNA by centrifugation at 4° C. for 10 minutes at 14,000×g in an eppendorf microcentrifuge.

(6). Remove all of the isopropanol with a pipet, being careful not to dislodge the pellet.

Removal of Contaminating DNA from RNA Preparations (1) Prepare 200 μl of DNase I solution for each sample by adding 5 μl of RNase-Free DNase I (1 U/μl) to 195 μl of 1× DNase Buffer.

(2) Completely resuspend the pelleted RNA in 200 μl of DNase I solution by vortexing.

(3) Incubate the samples at 37° C. for 60 minutes.

(4) Add 200 μl of 2× T and C Lysis Solution to each' sample and vortex for 5 seconds.

(5) Add 200 μl of MPC Protein Precipitation Reagent, mix by vortexing for 10 seconds and place on ice for 3-5 minutes.

(6) Pellet the debris by centrifugation for 10 minutes at 14,000×g in an eppendorf microcentrifuge.

(7) Transfer the supernatant containing the RNA to clean eppendorf tubes and discard the pellet. (Be careful to avoid transferring the pellet.)

(8) Add 500 µl of isopropanol to each supernatant and rock samples on the nutator for 3 minutes.

(9) Pellet the RNA by centrifugation at 4° C. for 10 minutes at 14,000×g in an eppendorf microcentrifuge.

(10) Remove the isopropanol, leaving some at the bottom to avoid dislodging the pellet.

(11) Rinse twice with 1 ml of 75% ethanol. Centrifuge briefly if the RNA pellet is dislodged.

(12) Remove ethanol carefully.

(13) Set under fume hood for about 3 minutes to remove residual ethanol.

(14) Resuspend the RNA in 30 µl of TE Buffer and store at −30° C.

II. Hot Wax/Urea Protocol of the Invention RNA Isolation (1) Cut 3 sections (each 10 µm thick) of paraffin-embedded tissue using a clean microtome blade and place into a 1.5 ml eppendorf tube.

(2) Add 300 µl of lysis buffer (10 mM Tris 7.5, 0.5% sodium lauroyl sarcosine, 0.1 mM EDTA pH 7.5, 4M Urea) containing 330 µg/ml Proteinase K (added freshly from a 50 µg/µl stock solution) and vortex briefly.

(3) Incubate at 65° C. for 90 minutes (vortex mixing every 5 minutes). Visually monitor the tissue fragment. If still visible after 30 minutes, add an additional 2 µl of 50 µg/µl Proteinase K and continue incubating at 65° C. until fragment dissolves.

(4) Centrifuge for 5 minutes at 14,000×g and transfer upper aqueous phase to new tube, being careful not to disrupt the paraffin seal.

(5) Place the samples on ice for 3-5 minutes and proceed with protein removal and total nucleic acid precipitation.

Protein Removal and Precipitation of Total Nucleic Acid (1) Add 150 µl of 7.5M $NH_4OAc$ to each lysed sample and vortex vigorously for 10 seconds.

(2) Pellet the debris by centrifugation for 10 minutes at 14,000×g in an eppendorf microcentrifuge.

(3) Transfer the supernatant into clean eppendorf tubes and discard the pellet.

(4) Add 500 µl of isopropanol to the recovered supernatant and thoroughly mix by rocking on the nutator for 3 minutes.

(5) Pellet the RNA/DNA by centrifugation at 4° C. for 10 minutes at 14,000×g in an eppendorf microcentrifuge.

(6) Remove all of the isopropanol with a pipet, being careful not to dislodge the pellet.

Removal of Contaminating DNA from RNA Preparations (1) Add 45 µl of 1× DNase I buffer (10 mM Tris-Cl, pH 7.5, 2.5 mM $MgCl_2$, 0.1 mM $CaCl_2$) and 5 µl of RNase-Free DNase I (2U/µl, Ambion) to each sample.

(2) Incubate the samples at 37° C. for 60 minutes. Inactivate the DNaseI by heating at 70° C. for 5 minutes.

B. Results

Experimental evidence demonstrates that the hot RNA extraction protocol of the invention does not compromise RNA yield. Using 19 FPE breast cancer specimens, extracting RNA from three adjacent sections in the same specimens, RNA yields were measured via capillary electrophoresis with fluorescence detection (Agilent Bioanalyzer). Average RNA yields in nanograms and standard deviations with the invented and commercial methods, respectively, were: 139±21 versus 141±34.

Also, it was found that the urea-containing lysis buffer of the present invention can be substituted for the EPICENTRE® T&C lysis buffer, and the 7.5 M $NH_4OAc$ reagent used for protein precipitation in accordance with the present invention can be substituted for the EPICENTRE® MPC protein precipitation solution with neither significant compromise of RNA yield nor TaqMan® efficiency.

Example 2

Amplification of mRNA Species Prior to RT-PCR

The method described in section 10 above was used with RNA isolated from fixed, paraffin-embedded breast cancer tissue. TaqMan® analyses were performed with first strand cDNA generated with the T7-GSP primer (unamplified (T7-GSPr)), T7 amplified RNA (amplified (T7-GSPr)). RNA was amplified according to step 2 of FIG. 4. As a control, Taq-Man® was also performed with cDNA generated with an unmodified GSPr (amplified (GSPr)). An equivalent amount of initial template (1 ng/well) was used in each TaqMan® reaction.

Figure 8:
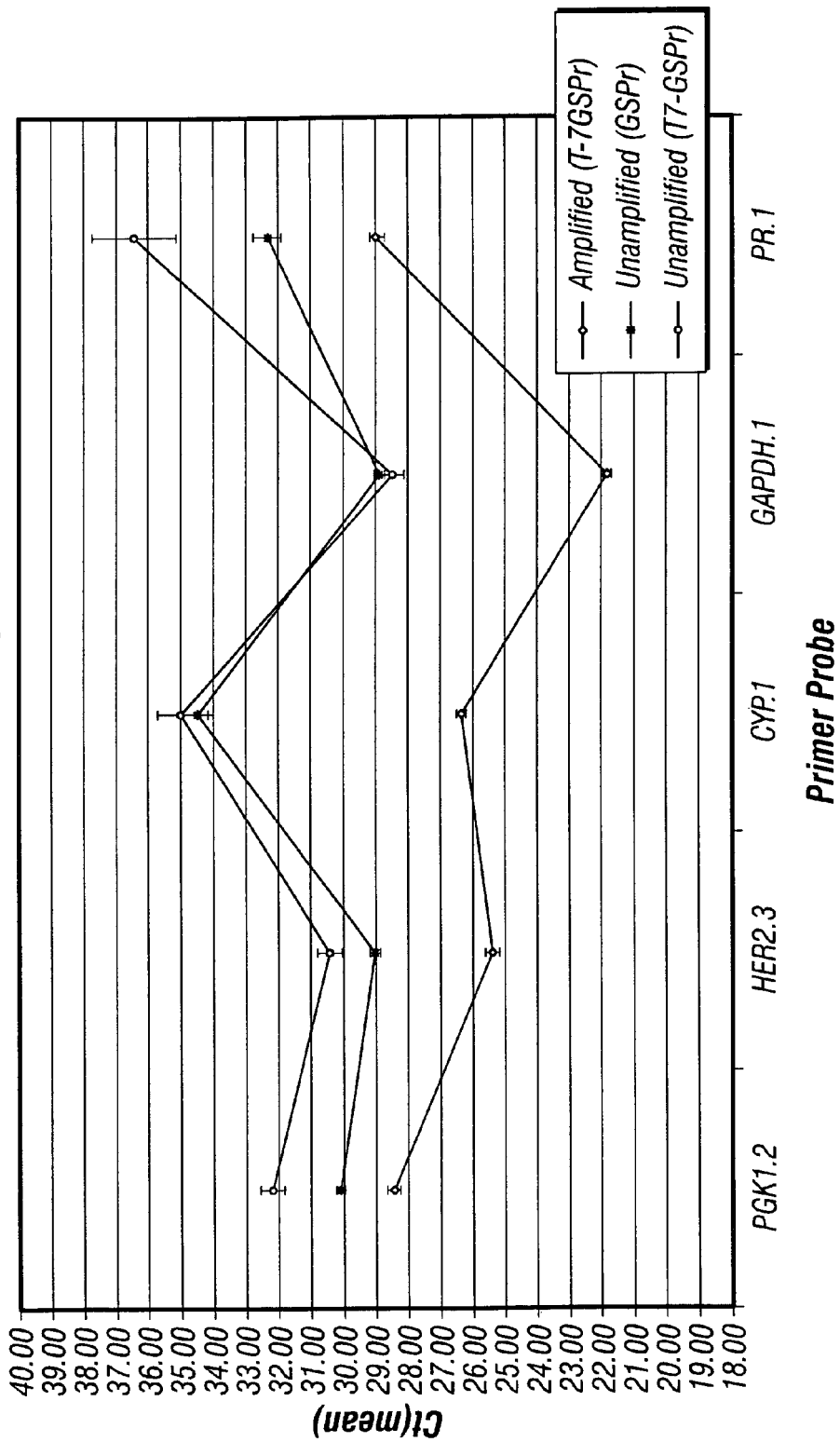
FIG. 8 shows results from an IVT/RT-PCR experiment.

The results are shown in FIG. 8. In vitro transcription increased RT-PCR signal intensity by more than 10 fold, and for certain genes by more than 100 fold relative to controls in which the RT-PCR primers were the same primers used in method 2 for the generation of double-stranded DNA for in vitro transcription ($GSP-T7_r$ and $GSP_f$). Also shown in FIG. 8 are RT-PCR data generated when standard optimized RT-PCR primers (i.e., lacking T7 tails) were used. As shown, compared to this control, the new method yielded substantial increases in RT-PCR signal (from 4 to 64 fold in this experiment).

The new method requires that each T7-GSP sequence be optimized so that the increase in the RT-PCR signal is the same for each gene, relative to the standard optimized RT-PCR (with non-T7 tailed primers).

Example 3

A Study of Gene Expression in Premalignant and Malignant Breast Tumors

A gene expression study was designed and conducted with the primary goal to molecularly characterize gene expression in paraffin-embedded, fixed tissue samples of invasive breast ductal carcinoma, and to explore the correlation between such molecular profiles and disease-free survival. A further objective of the study was to compare the molecular profiles in tissue samples of invasive breast cancer with the molecular profiles obtained in ductal carcinoma in situ. The study was further designed to obtain data on the molecular profiles in lobular carcinoma in situ and in paraffin-embedded, fixed tissue samples of invasive lobular carcinoma.

Molecular assays were performed on paraffin-embedded, formalin-fixed primary breast tumor tissues obtained from 202 individual patients diagnosed with breast cancer. All patients underwent surgery with diagnosis of invasive ductal carcinoma of the breast, pure ductal carcinoma in situ (DCIS), lobular carcinoma of the breast, or pure lobular carcinoma in situ (LCIS). Patients were included in the study only if histopathologic assessment, performed as described in the Materials and Methods section, indicated adequate amounts of tumor tissue and homogeneous pathology.

The individuals participating in the study were divided into the following groups:

Group 1: Pure ductal carcinoma in situ (DCIS); n=18
Group 2: Invasive ductal carcinoma n=130
Group 3: Pure lobular carcinoma in situ (LCIS); n=7
Group 4: Invasive lobular carcinoma n=16

Materials and Methods

Each representative tumor block was characterized by standard histopathology for diagnosis, semi-quantitative assessment of amount of tumor, and tumor grade. A total of 6 sections (10 microns in thickness each) were prepared and placed in two Costar Brand Microcentrifuge Tubes (Polypropylene, 1.7 mL tubes, clear; 3 sections in each tube). If the tumor constituted less than 30% of the total specimen area, the sample may have been crudely dissected by the pathologist, using gross microdissection, putting the tumor tissue directly into the Costar tube.

If more than one tumor block was obtained as part of the surgical procedure, all tumor blocks were subjected to the same characterization, as described above, and the block most representative of the pathology was used for analysis.

Gene Expression Analysis mRNA was extracted and purified from fixed, paraffin-embedded tissue samples, and prepared for gene expression analysis as described in chapters 7-11 above. Molecular assays of quantitative gene expression were performed by RT-PCR, using the ABI PRISM 7900™ Sequence Detection System™ (Perkin-Elmer-Applied Biosystems, Foster City, Calif., USA). ABI PRISM 7900™ consists of a thermocycler, laser, charge-coupled device (CCD), camera and computer. The system amplifies samples in a 384-well format on a thermocycler. During amplification, laser-induced fluorescent signal is collected in real-time through fiber optics cables for all 384 wells, and detected at the CCD. The system includes software for running the instrument and for analyzing the data.

Analysis and Results

Tumor tissue was analyzed for 185 cancer-related genes and 7 reference genes. The threshold cycle (CT) values for each patient were normalized based on the median of all genes for that particular patient. Clinical outcome data were available for all patients from a review of registry data and selected patient charts.

Outcomes were classified as:

0 died due to breast cancer or to unknown cause or alive with breast cancer recurrence;

1 alive without breast cancer recurrence or died due to a cause other than breast cancer Analysis was performed by:

1. Analysis of the relationship between normalized gene expression and the binary outcomes of 0 or 1.

2. Analysis of the relationship between normalized gene expression and the time to outcome (0 or 1 as defined above) where patients who were alive without breast cancer recurrence or who died due to a cause other than breast cancer were censored. This approach was used to evaluate the prognostic impact of individual genes and also sets of multiple genes.

Analysis of Patients with Invasive Breast Carcinoma by Binary Approach

In the first (binary) approach, analysis was performed on all 146 patients with invasive breast carcinoma. A t test was performed on the group of patients classified as 0 or 1 and the p-values for the differences between the groups for each gene were calculated.

The following Table 4 lists the 45 genes for which the p-value for the differences between the groups was <0.05.

TABLE 4

| Gene/ SEQ ID NO: | Mean CT Alive | Mean CT Deceased | t-value | Degrees of freedom | p |
|---|---|---|---|---|---|
| FOXM1 | 33.66 | 32.52 | 3.92 | 144 | 0.0001 |
| PRAME | 35.45 | 33.84 | 3.71 | 144 | 0.0003 |
| Bcl2 | 28.52 | 29.32 | -3.53 | 144 | 0.0006 |
| STK15 | 30.82 | 30.10 | 3.49 | 144 | 0.0006 |
| CEGP1 | 29.12 | 30.86 | -3.39 | 144 | 0.0009 |
| Ki-67 | 30.57 | 29.62 | 3.34 | 144 | 0.0011 |
| GSTM1 | 30.62 | 31.63 | -3.27 | 144 | 0.0014 |
| CA9 | 34.96 | 33.54 | 3.18 | 144 | 0.0018 |
| PR | 29.56 | 31.22 | -3.16 | 144 | 0.0019 |
| BBC3 | 31.54 | 32.10 | -3.10 | 144 | 0.0023 |
| NME1 | 27.31 | 26.68 | 3.04 | 144 | 0.0028 |
| BIRC5 | 31.64 | 30.68 | 2.92 | 144 | 0.0041 |
| GATA3 | 26.06 | 26.99 | -2.91 | 144 | 0.0042 |
| TFRC | 28.96 | 28.48 | 2.87 | 144 | 0.0047 |
| YB-1 | 26.72 | 26.41 | 2.79 | 144 | 0.0060 |
| DPYD | 28.51 | 28.84 | -2.67 | 144 | 0.0084 |
| GSTM3 | 28.21 | 29.03 | -2.63 | 144 | 0.0095 |
| RPS6KB1 | 31.18 | 30.61 | 2.61 | 144 | 0.0099 |
| Src | 27.97 | 27.69 | 2.59 | 144 | 0.0105 |
| Chk1 | 32.63 | 31.99 | 2.57 | 144 | 0.0113 |
| ID1 | 28.73 | 29.13 | -2.48 | 144 | 0.0141 |
| ESR1 | 24.22 | 25.40 | -2.44 | 144 | 0.0160 |
| p27 | 27.15 | 27.51 | -2.41 | 144 | 0.0174 |
| CCNB1 | 31.63 | 30.87 | 2.40 | 144 | 0.0176 |
| XIAP | 30.27 | 30.51 | -2.40 | 144 | 0.0178 |
| Chk2 | 31.48 | 31.11 | 2.39 | 144 | 0.0179 |
| CDC25B | 29.75 | 29.39 | 2.37 | 144 | 0.0193 |
| IGF1R | 28.85 | 29.44 | -2.34 | 144 | 0.0209 |
| AK055699 | 33.23 | 34.11 | -2.28 | 144 | 0.0242 |
| PI3KC2A | 31.07 | 31.42 | -2.25 | 144 | 0.0257 |
| TGFB3 | 28.42 | 28.85 | -2.25 | 144 | 0.0258 |
| BAGI1 | 28.40 | 28.75 | -2.24 | 144 | 0.0269 |
| CYP3A4 | 35.70 | 35.32 | 2.17 | 144 | 0.0317 |
| EpCAM | 28.73 | 28.34 | 2.16 | 144 | 0.0321 |
| VEGFC | 32.28 | 31.82 | 2.16 | 144 | 0.0326 |
| pS2 | 28.96 | 30.60 | -2.14 | 144 | 0.0341 |
| hENT1 | 27.19 | 26.91 | 2.12 | 144 | 0.0357 |
| WISP1 | 31.20 | 31.64 | -2.10 | 144 | 0.0377 |
| HNF3A | 27.89 | 28.64 | -2.09 | 144 | 0.0384 |
| NFKBp65 | 33.22 | 33.80 | -2.08 | 144 | 0.0396 |
| BRCA2 | 33.06 | 32.62 | 2.08 | 144 | 0.0397 |
| EGFR | 30.68 | 30.13 | 2.06 | 144 | 0.0414 |
| TK1 | 32.27 | 31.72 | 2.02 | 144 | 0.0453 |
| VDR | 30.08 | 29.73 | 1.99 | 144 | 0.0488 |

In the foregoing Table 4, lower (negative) t-values indicate higher expression (or lower CTs), associated with better outcomes, and, inversely, higher (positive) t-values indicate higher expression (lower CTs) associated with worse outcomes. Thus, for example, elevated expression of the FOXM1 gene (t-value=3.92, CT mean alive>CT mean deceased) indicates a reduced likelihood of disease free survival. Similarly, elevated expression of the CEGP1 gene (t-value=-3.39; CT mean alive<CT mean deceased) indicates an increased likelihood of disease free survival.

Based on the data set forth in Table 4, the overexpression of any of the following genes in breast cancer indicates a reduced likelihood of survival without cancer recurrence following surgery: FOXM1; PRAME; SKT15, Ki-67; CA9; NME1; SURV; TFRC; YB-1; RPS6KB1; Src; Chk1; CCNB1; Chk2; CDC25B; CYP3A4; EPCAM; VEGFC; hENT1; BRCA2; EGFR; TK1; VDR.

Based on the data set forth in Table 4, the overexpression of any of the following genes in breast cancer indicates a better prognosis for survival without cancer recurrence following surgery: Blc12; CEGP1; GSTM1; PR; BBC3; GATA3; DPYD; GSTM3; ID1; ESR1; p27; XIAP; IGF1R; AK055699; P13KC2A; TGFB3; BAGI1; pS2; WISP1; HNF3A; NFKBp65.

Analysis of 108 ER Positive Patient by Binary Approach 108 patients with normalized CT for estrogen receptor (ER)<25.2 (i.e., ER positive patients) were subjected to separate analysis. A t test was performed on the groups of patients classified as 0 or 1 and the p-values for the differences between the groups for each gene were calculated. The following Table 5 lists the 12 genes where the p-value for the differences between the groups was <0.05.

TABLE 5

| Gene/ SEQ ID NO: | Mean CT Alive | Mean CT Deceased | t-value | Degrees of freedom | p |
|---|---|---|---|---|---|
| PRAME | 35.54 | 33.88 | 3.03 | 106 | 0.0031 |
| Bcl2 | 28.24 | 28.87 | −2.70 | 106 | 0.0082 |
| FOXM1 | 33.82 | 32.85 | 2.66 | 106 | 0.089 |
| DIABLO | 30.33 | 30.71 | −2.47 | 106 | 0.0153 |
| EPHX1 | 28.62 | 28.03 | 2.44 | 106 | 0.0163 |
| HIF1A | 29.37 | 28.88 | 2.40 | 106 | 0.0180 |
| VEGFC | 32.39 | 31.69 | 2.39 | 106 | 0.0187 |
| Ki-67 | 30.73 | 29.82 | 2.38 | 106 | 0.0191 |
| IGF1R | 28.60 | 29.18 | −2.37 | 106 | 0.0194 |
| VDR | 30.14 | 29.60 | 2.17 | 106 | 0.0322 |
| NME1 | 27.34 | 26.80 | 2.03 | 106 | 0.0452 |
| GSTM3 | 28.08 | 28.92 | −2.00 | 106 | 0.0485 |

For each gene, a classification algorithm was utilized to identify the best threshold value (CT) for using each gene alone in predicting clinical outcome.

Based on the data set forth in Table 5, overexpression of the following genes in ER-positive cancer is indicative of a reduced likelihood of survival without cancer recurrence following surgery: PRAME; FOXM1; EPHX1; HIF1A; VEGFC; Ki-67; VDR; NME1. Some of these genes (PRAME; FOXM1; VEGFC; Ki-67; VDR; and NME1) were also identified as indicators of poor prognosis in the previous analysis, not limited to ER-positive breast cancer. The overexpression of the remaining genes (EPHX1 and HIF1A) appears to be negative indicator of disease free survival in ER-positive breast cancer only. Based on the data set forth in Table 5, overexpression of the following genes in ER-positive cancer is indicative of a better prognosis for survival without cancer recurrence following surgery: Bcl-2; DIABLO; IGF1R; GSTM3. Of the latter genes, Bcl-2; IGFR1; and GSTM3 have also been identified as indicators of good prognosis in the previous analysis, not limited to ER-positive breast cancer. The overexpression of DIABLO appears to be positive indicator of disease free survival in ER-positive breast cancer only.

Analysis of Multiple Genes and Indicators of Outcome

Two approaches were taken in order to determine whether using multiple genes would provide better discrimination between outcomes.

First, a discrimination analysis was performed using a forward stepwise approach. Models were generated that classified outcome with greater discrimination than was obtained with any single gene alone.

According to a second approach (time-to-event approach), for each gene a Cox Proportional Hazards model (see, e.g. Cox, D. R., and Oakes, D. (1984), *Analysis of Survival Data*, Chapman and Hall, London, N.Y.) was defined with time to recurrence or death as the dependent variable, and the expression level of the gene as the independent variable. The genes that have a p-value <0.05 in the Cox model were identified. For each gene, the Cox model provides the relative risk (RR) of recurrence or death for a unit change in the expression of the gene. One can choose to partition the patients into subgroups at any threshold value of the measured expression (on the CT scale), where all patients with expression values above the threshold have higher risk, and all patients with expression values below the threshold have lower risk, or vice versa, depending-on whether the gene is an indicator of good (RR>1.01) or poor (RR<1.01) prognosis. Thus, any threshold value will define subgroups of patients with respectively increased or decreased risk. The results are summarized in the following Tables 6 and 7.

TABLE 6

Cox Model Results for 146 Patients with Invasive Breast Cancer

| Gene | Relative Risk (RR) | SE Relative Risk | p value |
|---|---|---|---|
| FOXM1 | 0.58 | 0.15 | 0.0002 |
| STK15 | 0.51 | 0.20 | 0.0006 |
| PRAME | 0.78 | 0.07 | 0.0007 |
| Bcl2 | 1.66 | 0.15 | 0.0009 |
| CEGP1 | 1.25 | 0.07 | 0.0014 |
| GSTM1 | 1.40 | 0.11 | 0.0014 |
| Ki67 | 0.62 | 0.15 | 0.0016 |
| PR | 1.23 | 0.07 | 0.0017 |
| Contig51037 | 0.81 | 0.07 | 0.0022 |
| NME1 | 0.64 | 0.15 | 0.0023 |
| YB-1 | 0.39 | 0.32 | 0.0033 |
| TFRC | 0.53 | 0.21 | 0.0035 |
| BBC3 | 1.72 | 0.19 | 0.0036 |
| GATA3 | 1.32 | 0.10 | 0.0039 |
| CA9 | 0.81 | 0.07 | 0.0049 |
| BIRC5 | 0.69 | 0.13 | 0.0049 |
| DPYD | 2.58 | 0.34 | 0.0052 |
| RPS6KB1 | 0.60 | 0.18 | 0.0055 |
| GSTM3 | 1.36 | 0.12 | 0.0078 |
| Src.2 | 0.39 | 0.36 | 0.0094 |
| TGFB3 | 1.61 | 0.19 | 0.0109 |
| CDC25B | 0.54 | 0.25 | 0.0122 |
| XIAP | 3.20 | 0.47 | 0.0126 |
| CCNB1 | 0.68 | 0.16 | 0.0151 |
| IGF1R | 1.42 | 0.15 | 0.0153 |
| Chk1 | 0.68 | 0.16 | 0.0155 |
| ID1 | 1.80 | 0.25 | 0.0164 |
| p27 | 1.69 | 0.22 | 0.0168 |
| Chk2 | 0.52 | 0.27 | 0.0175 |
| ESR1 | 1.17 | 0.07 | 0.0196 |
| HNF3A | 1.21 | 0.08 | 0.206 |
| pS2 | 1.12 | 0.05 | 0.0230 |
| BAGI1 | 1.88 | 0.29 | 0.0266 |
| AK055699 | 1.24 | 0.10 | 0.0276 |
| pENT1 | 0.51 | 0.31 | 0.0293 |
| EpCAM | 0.62 | 0.22 | 0.0310 |
| WISP1 | 1.39 | 0.16 | 0.0338 |
| VEGFC | 0.62 | 0.23 | 0.0364 |
| TK1 | 0.73 | 0.15 | 0.0382 |
| NFKBp65 | 1.32 | 0.14 | 0.0384 |
| BRCA2 | 0.66 | 0.20 | 0.0404 |
| CYP3A4 | 0.60 | 0.25 | 0.0417 |
| EGFR | 0.72 | 0.16 | 0.0436 |

TABLE 7

Cox Model Results for 108 Patients wih ER+ Invasive Breast Cancer

| Gene | Relative Risk (RR) | SE Relative Risk | p-value |
|---|---|---|---|
| PRAME | 0.75 | 0.10 | 0.0045 |
| Contig51037 | 0.75 | 0.11 | 0.0060 |
| Blc2 | 2.11 | 0.28 | 0.0075 |
| HIF1A | 0.42 | 0.34 | 0.0117 |
| IGF1R | 1.92 | 0.26 | 0.0117 |
| FOXM1 | 0.54 | 0.24 | 0.0119 |
| EPHX1 | 0.43 | 0.33 | 0.0120 |
| Ki67 | 0.60 | 0.21 | 0.0160 |
| CDC25B | 0.41 | 0.38 | 0.0200 |
| VEGFC | 0.45 | 0.37 | 0.0288 |

TABLE 7-continued

Cox Model Results for 108 Patients wih ER+ Invasive Breast Cancer

| Gene | Relative Risk (RR) | SE Relative Risk | p-value |
|---|---|---|---|
| CTSB | 0.32 | 0.53 | 0.0328 |
| DIABLO | 2.91 | 0.50 | 0.0328 |
| p27 | 1.83 | 0.28 | 0.0341 |
| CDH1 | 0.57 | 0.27 | 0.0352 |
| IGFBP3 | 0.45 | 0.40 | 0.0499 |

The binary and time-to-event analyses, with few exceptions, identified the same genes as prognostic markers. For example, comparison of Tables 4 and 6 shows that, with the exception of a single gene, the two analyses generated the same list of top 15 markers (as defined by the smallest p values). Furthermore, when both analyses identified the same gene, they were concordant with respect to the direction (positive or negative sign) of the correlation with survival/recurrence. Overall, these results strengthen the conclusion that the identified markers have significant prognostic value.

For Cox models comprising more than two genes (multivariate models), stepwise entry of each individual gene into the model is performed, where the first gene entered is preselected from among those genes having significant univariate p-values, and the gene selected for entry into the model at each subsequent step is the gene that best improves the fit of the model to the data. This analysis can be performed with any total number of genes. In the analysis the results of which are shown below, stepwise entry was performed for up to 10 genes.

Multivariate analysis is performed using the following equation:

$$RR = \exp[\text{coef}(geneA) \times Ct(geneA) + \text{coef}(geneB) \times Ct(geneB) + \text{coef}(geneC) \times Ct(geneC) + \ldots].$$

In this equation, coefficients for genes that are predictors of beneficial outcome are positive numbers and coefficients for genes that are predictors of unfavorable outcome are negative numbers. The "Ct" values in the equation are ΔCts, i.e. reflect the difference between the average normalized Ct value for a population and the normalized Ct measured for the patient in question. The convention used in the present analysis has been that ΔCts below and above the population average have positive signs and negative signs, respectively (reflecting greater or lesser mRNA abundance). The relative risk (RR) calculated by solving this equation will indicate if the patient has an enhanced or reduced chance of long-term survival without cancer recurrence.

Multivariate Gene Analysis of Patients with Invasive Breast Carcinoma (a) A multivariate stepwise analysis, using the Cox Proportional Hazards Model, was performed on the gene expression data obtained for all 146 patients with invasive breast carcinoma. Genes CEGP1, FOXM1, STK15 and PRAME were excluded from this analysis. The following sets of ten genes have been identified by this analysis as having particularly strong predictive value of patient survival without cancer recurrence following surgical removal of primary tumor.

1. Bcl2, cyclinG1, NFKBp65, NME1, EPHX1, TOP2B, DRS, TERC, Src, DIABLO;
2. Ki67, XIAP, hENT1, TS, CD9, p27, cyclinG1, pS2, NFKBp65, CYP3A4;
3. GSTM1, XIAP, Ki67, TS, cyclinG1, p27, CYP3A4, pS2, NFKBp65, ErbB3;
4. PR, NME1, XIAP, upa, cyclinG1, Contig51037, TERC, EPHX1, ALDH1A3, CTSL;
5. CA9, NME1, TERC, cyclinG1, EPHX1, DPYD, Src, TOP2B, NFKBp65, VEGFC;
6. TFRC, XIAP, Ki67, TS, cyclinG1, p27, CYP3A4, pS2, ErbB3, NFKBp65.

(b) A multivariate stepwise analysis, using the Cox Proportional Hazards Model, was performed on the gene expression data obtained for all 146 patients with invasive breast carcinoma, using an interrogation set including a reduced number of genes. The following ten-gene sets have been identified by this analysis as having particularly strong predictive value of patient survival without cancer recurrence following surgical removal of primary tumor.

1. Bcl2, PRAME, cyclinG1, FOXM1, NFKBp65, TS, XIAP, Ki67, CYP3A4, p27;
2. FOXM1, cyclinG1, XIAP, Contig51037, PRAME, TS, Ki67, PDGFRa, p27, NFKBp65;
3. PRAME, FOXM1, cyclinG1, XIAP, Contig51037, TS, Ki6, PDGFRa, p27, NFKBp65;
4. Ki67, XIAP, PRAME, hENT1, contig51037, TS, CD9, p27, ErbB3, cyclinG1;
5. STK15, XLAP, PRAME, PLAUR, p27, CTSL, CD18, PREP, p53, RPS6KB1;
6. GSTM1, XIAP, PRAME, p27, Contig51037, ErbB3, GSTp, EREG, ID1, PLAUR;
7. PR, PRAME, NME1, XIAP, PLAUR, cyclinG1, Contig51037, TERC, EPHX1, DR5;
8. CA9, FOXM1, cyclinG1, XIAP, TS, Ki67, NFKBp65, CYP3A4, GSTM3, p27;
9. TFRC, XIAP, PRAME, p27, Contig51037, ErbB3, DPYD, TERC, NME1, VEGFC,
10. CEGP1, PRAME, hENT1, XIAP, Contig51037, ErbB3, DPYD, NFKBp65, ID1, TS.

Muiltivariate Analysis of Patients with ER Positive Invasive Breast Carcinoma

A multivariate stepwise analysis, using the Cox Proportional Hazards Model, was performed on the gene expression data obtained for patients with ER positive invasive breast carcinoma. The following sets of ten genes have been identified by this analysis as having particularly strong predictive value of patient survival without cancer recurrence following surgical removal of primary tumor.

1. PRAME, p27, IGFBP2, HIF1A, T1MP2, ILT2, CYP3A4, ID1, ESR1, DIABLO;
2. Contig51037, EPHX1, Ki67, TIMP2, cyclinG1, DPYD, CYP3A4, TP, AIB1, CYP2C8;
3. Bcl2, hENT1, FOXM1, Contig51037, cyclinG1, Contig46653, PTEN, CYP3A4, TIMP2, AREG;
4. HIF1A, PRAME, p27, IGFBP2, T1MP2, ILT2, CYP3A4, ID1, ESR1, DIABLO;
5. IGF1R, PRAME, EPHX1, Contig51037, cyclinG1, Bcl2, NME1, PTEN, TBP, TIMP2;
6. FOXM1, Contig51037, VEGFC, TBP, HIF1A, DPYD, RAD51C, DCR3, cyclinG1, BAG1;
7. EPHX1, Contig51037, Ki67, TIMP2, cyclinG1, DPYD, CYP3A4, TP, AIB1, CYP2C8;
8. Ki67, VEGFC, VDR, GSTM3, p27, upa, ITGA7, rhoC, TERC, Pint;
9. CDC25B, Contig51037, hENT1, Bcl2, HLAG, TERC, NME1, upa, ID1, CYP;
10. VEGFC, Ki67, VDR, GSTM3, p27, upa, ITGA7, rhoC, TERC, Pint;
11. CTSB, PRAME, p27, IGFBP2, EPHX1, CTSL, BAD, DRS, DCR3, XIAP;
12. DIABLO, Ki67, hENT1, TIMP2, ID1, p27, KRT19, IGFBP2, TS, PDGFB;

13. p27, PRAME, IGFBP2, HIF1A, T1MP2, ILT2, CYP3A4, ID1, ESR1, DIABLO;
14. CDH1; PRAME, VEGFC; HIF1A; DPYD, TIMP2, CYP3A4, ESR1, RBP4, p27;
15. IGFBP3, PRAME, p27, Bcl2, XIAP, ESR1, Ki67, TS, Src, VEGF;
16. GSTM3, PRAME, p27, IGFBP3, XIAP, FGF2, hENT1, PTEN, ESR1, APC;
17. hENT1, Bcl2, FOXM1, Contig51037, CyclinG1, Contig46653, PTEN, CYP3A4, TIMP2, AREG;
18. STK15, VEGFC, PRAME, p27, GCLC, hENT1, ID1, TIMP2, ESR1, MCP1;
19. NME1, PRAM, p27, IGFBP3, XIAP, PTEN, hENT1, Bcl2, CYP3A4, HLAG;
20. VDR, Bcl2, p27, hENT1, p53, PI3KC2A, EIF4E, TFRC, MCM3, ID1;
21. EIF4E, Contig51037, EPHX1, cyclinG1, Bcl2, DRS, TBP, PTEN, NME1, HER2;
22. CCNB1, PRAME, VEGFC, HIF1A, hENT1, GCLC, TIMP2, ID1, p27, upa;
23. ID1, PRAME, DIABLO, hENT1, p27, PDGFRa, NME1, BIN1, BRCA1, TP;
24. FBXO5, PRAME, IGFBP3, p27, GSTM3, hENT1, XIAP, FGF2, TS, PTEN;
25. GUS, HIA1A, VEGFC, GSTM3, DPYD, hENT1, FBXO5, CA9, CYP, KRT18;
26. Bclx, Bcl2, hENT1, Contig51037, HLAG, CD9, ID1, BRCA1, BIN1, HBEGF.

It is noteworthy that many of the foregoing gene sets include genes that alone did not have sufficient predictive value to qualify as prognostic markers under the standards discussed above, but in combination with other genes, their presence provides valuable information about the likelihood of long-term patient survival without cancer recurrence All references cited throughout the disclosure are hereby expressly incorporated by reference.

While the present invention has been described with reference to what are considered to be the specific embodiments, it is to be understood that the invention is not limited to such embodiments. To the contrary, the invention is intended to cover various modifications and equivalents included within the spirit and scope of the appended claims. For example, while the disclosure focuses on the identification of various breast cancer associated genes and gene sets, and on the diagnosis and treatment of breast cancer, similar genes, gene sets and methods concerning other types of cancer are specifically within the scope herein.

TABLE 1

| | |
|---|---|
| 1. | ADD3 (adducin 3 gamma)* |
| 2. | AKT1/Protein Kinase B |
| 3. | AKT 2 |
| 4. | AKT 3 |
| 5. | Aldehyde dehydrogenase 1A1 |
| 6. | Aldehyde dehydrogenase 1A3 |
| 7. | amphiregulin |
| 8. | APC |
| 9. | ARG |
| 10. | ATM |
| 11. | Bak |
| 12. | Bax |
| 13. | Bcl2 |
| 14. | Bcl-xl |
| 15. | BRK |
| 16. | BCRP |

TABLE 1-continued

| | |
|---|---|
| 17. | BRCA-1 |
| 18. | BRCA-2 |
| 19. | Caspase-3 |
| 20. | Cathepsin B |
| 21. | Cathepsin G |
| 22. | Cathepsin L |
| 23. | CD3 |
| 24. | CD9 |
| 25. | CD18 |
| 26. | CD31 |
| 27. | CD44^ |
| 28. | CD68 |
| 29. | CD82/KAI-1 |
| 30. | Cdc25A |
| 31. | Cdc25B |
| 32. | CGA |
| 33. | COX2 |
| 34. | CSF-1 |
| 35. | CSF-1R/fms |
| 36. | cIAP1 |
| 37. | cIAP2 |
| 38. | c-abl |
| 39. | c-kit |
| 40. | c-kit L |
| 41. | c-met |
| 42. | c-myc |
| 43. | cN-1 |
| 44. | cryptochrome1* |
| 45. | c-Src |
| 46. | Cyclin D1 |
| 47. | CYP1B1 |
| 48. | CYP2C9* |
| 49. | Cytokeratin 5^ |
| 50. | Cytokeratin 17^ |
| 51. | Cytokeratin 18^ |
| 52. | DAP-Kinase-1 |
| 53. | DHFR |
| 54. | DIABLO |
| 55. | Dihydropyrimidine dehydrogenase |
| 56. | EGF |
| 57. | ECadherin/CDH1^ |
| 58. | ELF 3* |
| 59. | Endothelin |
| 60. | Epiregulin |
| 61. | ER-alpha^ |
| 62. | ErbB-1 |
| 63. | ErbB-2^ |
| 64. | ErbB-3 |
| 65. | ErbB-4 |
| 66. | ER-Beta |
| 67. | Eukaryotic Translation Initiation Factor 4B*(EIF4B) |
| 68. | E1F4E |
| 69. | farnesyl pyrolophosphate synthetase |
| 70. | FAS (CD95) |
| 71. | FasL |
| 72. | FGF R 1* |
| 73. | FGF2 [bFGF] |
| 74. | 53BP1 |
| 75. | 53BP2 |
| 76. | GALC (galactosylceramidase)* |
| 77. | Gamma-GCS (glutamyl cysteine synthetase) |
| 78. | GATA3^ |
| 79. | geranyl geranyl pyrophosphate synthetase |
| 80. | G-CSF |
| 81. | GPC3 |
| 82. | gravin* [AKAP258] |
| 83. | GRO1 oncogene alpha^ |
| 84. | Grb7 |
| 85. | GST-alpha |
| 86. | GST-pi^ |

TABLE 1-continued

| | |
|---|---|
| 87. | Ha-Ras |
| 88. | HB-EGF |
| 89. | HE4-extracellular Proteinase Inhibitor Homologue* |
| 90. | hepatocyte nuclear factor 3^ |
| 91. | HER-2 |
| 92. | HGF/Scatter factor |
| 93. | hIAP1 |
| 94. | hIAP2 |
| 95. | HIF-1 |
| 96. | human kallikrein 10 |
| 97. | MLH1 |
| 98. | hsp 27 |
| 99. | human chorionic gonadotropin/CGA |
| 100. | Human Extracellular Protein S1-5 |
| 101. | Id-1 |
| 102. | Id-2 |
| 103. | Id-3 |
| 104. | IGF-1 |
| 105. | IGF2 |
| 106. | IGF1R |
| 107. | IGFBP3 |
| 108. | interstitial integrin alpha 7 |
| 109. | IL6 |
| 110. | IL8 |
| 111. | IRF-2* |
| 112. | IRF9 Protein |
| 113. | Kalikrein 5 |
| 114. | Kalikrein 6 |
| 115. | KDR |
| 116. | Ki-67/MiB1 |
| 117. | lipoprotein lipase^ |
| 118. | LIV1 |
| 119. | Lung Resistance Protein/MVP |
| 120. | Lot1 |
| 121. | Maspin |
| 122. | MCM2 |
| 123. | MCM3 |
| 124. | MCM7 |
| 125. | MCP-1 |
| 126. | microtubule-associated protein 4 |
| 127. | MCJ |
| 128. | mdm2 |
| 129. | MDR-1 |
| 130. | microsomal epoxide hydrolase |
| 131. | MMP9 |
| 132. | MRP1 |
| 133. | MRP2 |
| 134. | MRP3 |
| 135. | MRP4 |
| 136. | MSN (Moesin)* |
| 137. | mTOR |
| 138. | Muc1/CA 15-3 |
| 139. | NF-kB |
| 140. | P14ARF |
| 141. | P16INK4a/p14 |
| 142. | p21wAF1/CIP1 |
| 143. | p23 |
| 144. | p27 |
| 145. | p311* |
| 146. | p53 |
| 147. | PAI1 |
| 148. | PCNA |
| 149. | PDGF-A |
| 150. | PDGF-B |
| 151. | PDGF-C |
| 152. | PDGF-D |
| 153. | PDGFR-α |
| 154. | PDGFR-β |
| 155. | PI3K |
| 156. | Pin1 |
| 157. | PKC-ε |
| 158. | Pkc-δ |
| 159. | PLAG1 (pleiomorphic adenoma 1)* |
| 160. | PREP prolyl endopeptidase*PEP |
| 161. | Progesterone receptor |
| 162. | pS2/trefoil factor 1 |
| 163. | PTEN |
| 164. | PTP1b |
| 165. | RAR-alpha |
| 166. | RAR-beta2 |
| 167. | RCP |
| 168. | Reduced Folate Carrier |
| 169. | Retinol binding protein 4^ |
| 170. | STK15/BTAK |
| 171. | Survivin |
| 172. | SXR |
| 173. | Syk |
| 174. | TGD (thymine-DNA glycosylase)* |
| 175. | TGFalpha |
| 176. | Thymidine Kinase |
| 177. | Thymidine phosphorylase |
| 178. | Thymidylate Synthase |
| 179. | Topoisomerase II-α |
| 180. | Topoisomerase II-β |
| 181. | TRAMP |
| 182. | UPA |
| 183. | VEGF |
| 184. | Vimentin |
| 185. | WTH3 |
| 186. | XAF1 |
| 187. | XIAP |
| 188. | XIST |
| 189. | XPA |
| 190. | YB-1 |

*NCI 60 drug Sens./Resist Marker
^In Cluster Defining tumor subclass Jan. 19, 2002

TABLE 2

| Gene | Accession No. | Forward Primer SEQ ID NO. | Reverse Primer SEQ ID NO. | Amplicon SEQ ID NO. |
|---|---|---|---|---|
| ABCB1 | NM_000927 | 1 | 2 | 3 |
| ABCC1 | NM_004996 | 4 | 5 | 6 |
| ABCC2 | NM_000392 | 7 | 8 | 9 |
| ABCC3 | NM_003786 | 10 | 11 | 12 |
| ABCC4 | NM_005845 | 13 | 14 | 15 |
| ABL1 | NM_005157 | 16 | 17 | 18 |
| ABL2 | NM_005158 | 19 | 20 | 21 |
| ACTB | NM_001101 | 22 | 23 | 24 |
| AKT1 | NM_005163 | 25 | 26 | 27 |
| AKT3 | NM_005465 | 28 | 29 | 30 |
| ALDH1 | NM_000689 | 31 | 32 | 33 |
| ALDH1A3 | NM_000693 | 34 | 35 | 36 |
| APC | NM_000038 | 37 | 38 | 39 |
| AREG | NM_001657 | 40 | 41 | 42 |
| B2M | NM_004048 | 43 | 44 | 45 |
| BAK1 | NM_001188 | 46 | 47 | 48 |
| BAX | NM_004324 | 49 | 50 | 51 |
| BCL2 | NM_000633 | 52 | 53 | 54 |
| BCL2L1 | NM_001191 | 55 | 56 | 57 |
| BIRC3 | NM_001165 | 58 | 59 | 60 |
| BIRC4 | NM_001167 | 61 | 62 | 63 |
| BIRC5 | NM_001168 | 64 | 65 | 66 |
| BRCA1 | NM_007295 | 67 | 68 | 69 |
| BRCA2 | NM_000059 | 70 | 71 | 72 |
| CCND1 | NM_001758 | 73 | 74 | 75 |
| CD3Z | NM_000734 | 76 | 77 | 78 |
| CD68 | NM_001251 | 79 | 80 | 81 |
| CDC25A | NM_001789 | 82 | 83 | 84 |
| CDH1 | NM_004360 | 85 | 86 | 87 |
| CDKN1A | NM_000389 | 88 | 89 | 90 |
| CDKN1B | NM_004064 | 91 | 92 | 93 |
| CDKN2A | NM_000077 | 94 | 95 | 96 |

TABLE 2-continued

| Gene | Accession No. | Forward Primer SEQ ID NO. | Reverse Primer SEQ ID NO. | Amplicon SEQ ID NO. |
|---|---|---|---|---|
| CYP1B1 | NM_000104 | 97 | 98 | 99 |
| DHFR | NM_000791 | 100 | 101 | 102 |
| DPYD | NM_000110 | 103 | 104 | 105 |
| ECGF1 | NM_001953 | 106 | 107 | 108 |
| EGFR | NM_005228 | 109 | 110 | 111 |
| EIF4E | NM_001968 | 112 | 113 | 114 |
| ERBB2 | NM_004448 | 115 | 116 | 117 |
| ERBB3 | NM_001982 | 118 | 119 | 120 |
| ESR1 | NM_000125 | 121 | 122 | 123 |
| ESR2 | NM_001437 | 124 | 125 | 126 |
| GAPD | NM_002046 | 127 | 128 | 129 |
| GATA3 | NM_002051 | 130 | 131 | 132 |
| GRB7 | NM_005310 | 133 | 134 | 135 |
| GRO1 | NM_001511 | 136 | 137 | 138 |
| GSTP1 | NM_000852 | 139 | 140 | 141 |
| GUSB | NM_000181 | 142 | 143 | 144 |
| hHGF | M29145 | 145 | 146 | 147 |
| HNF3A | NM_004496 | 148 | 149 | 150 |
| ID2 | NM_002166 | 151 | 152 | 153 |
| IGF1 | NM_000618 | 154 | 155 | 156 |
| IGFBP3 | NM_000598 | 157 | 158 | 159 |
| ITGA7 | NM_002206 | 160 | 161 | 162 |
| ITGB2 | NM_000211 | 163 | 164 | 165 |
| KDR | NM_002253 | 166 | 167 | 168 |
| KIT | NM_000222 | 169 | 170 | 171 |
| KITLG | NM_000899 | 172 | 173 | 174 |
| KRT17 | NM_000422 | 175 | 176 | 177 |
| KRT5 | NM_000424 | 178 | 179 | 180 |
| LPL | NM_000237 | 181 | 182 | 183 |
| MET | NM_000245 | 184 | 185 | 186 |
| MKI67 | NM_002417 | 187 | 188 | 189 |
| MVP | NM_017458 | 190 | 191 | 192 |
| MYC | NM_002467 | 193 | 194 | 195 |
| PDGFA | NM_002607 | 196 | 197 | 198 |
| PDGFB | NM_002608 | 199 | 200 | 201 |
| PDGFC | NM_016205 | 202 | 203 | 204 |
| PDGFRA | NM_006206 | 205 | 206 | 207 |
| PDGFRB | NM_002609 | 208 | 209 | 210 |
| PGK1 | NM_000291 | 211 | 212 | 213 |
| PGR | NM_000926 | 214 | 215 | 216 |
| PIN1 | NM_006221 | 217 | 218 | 219 |
| PLAU | NM_002658 | 220 | 221 | 222 |
| PPIH | NM_006347 | 223 | 224 | 225 |
| PTEN | NM_000314 | 226 | 227 | 228 |
| PTGS2 | NM_000963 | 229 | 230 | 231 |
| RBP4 | NM_006744 | 232 | 233 | 234 |
| RELA | NM_021975 | 235 | 236 | 237 |
| RPL19 | NM_000981 | 238 | 239 | 240 |
| RPLP0 | NM_001002 | 241 | 242 | 243 |
| SCDGF-B | NM_025208 | 244 | 245 | 246 |
| SERPINE1 | NM_000602 | 247 | 248 | 249 |
| SLC19A1 | NM_003056 | 250 | 251 | 252 |
| TBP | NM_003194 | 253 | 254 | 255 |
| TFF1 | NM_003225 | 256 | 257 | 258 |
| TFRC | NM_003234 | 259 | 260 | 261 |
| TK1 | NM_003258 | 262 | 263 | 264 |
| TNFRSF6 | NM_000043 | 265 | 266 | 267 |
| TNFSF6 | NM_000639 | 268 | 269 | 270 |
| TOP2A | NM_001067 | 271 | 272 | 273 |
| TOP2B | NM_001068 | 274 | 275 | 276 |
| TP53 | NM_000546 | 277 | 278 | 279 |
| TYMS | NM_001071 | 280 | 281 | 282 |
| VEGF | NM_003376 | 283 | 284 | 285 |

TABLE 3

| GENE | ACCESSION NO. | SEQ ID NO: |
|---|---|---|
| AK055699 | AK055699 | 286 |
| BAG1 | NM_004323 | 287 |
| BBC3 | NM_014417 | 288 |
| Bcl2 | NM_000633 | 289 |
| BRCA2 | NM_000059 | 290 |
| CA9 | NM_001216 | 291 |
| CCNB1 | NM_031966 | 292 |
| CDC25B | NM_021874 | 293 |
| CEGP1 | NM_020974 | 294 |
| Chk1 | NM_001274 | 295 |
| Chk2 | NM_007194 | 296 |
| CYP3A4 | NM_017460 | 297 |
| DIABLO | NM_019887 | 298 |
| DPYD | NM_000110 | 299 |
| EGFR | NM_005228 | 300 |
| EpCAM | NM_002354 | 301 |
| EPHX1 | NM_000120 | 302 |
| ESR1 | NM_000125 | 303 |
| FOXM1 | NM_021953 | 304 |
| GATA3 | NM_002051 | 305 |
| GSTM1 | NM_000561 | 306 |
| GSTM3 | NM_000849 | 307 |
| hENT1 | NM_004955 | 308 |
| HIF1A | NM_001530 | 309 |
| HNF3A | NM_004496 | 310 |
| ID1 | NM_002165 | 311 |
| IGF1R | NM_000875 | 312 |
| Ki-67 | NM_002417 | 313 |
| NFKBp65 | NM_021975 | 314 |
| NME1 | NM_000269 | 315 |
| p27 | NM_004064 | 316 |
| PI3KC2A | NM_002645 | 317 |
| PR | NM_000926 | 318 |
| PRAME | NM_006115 | 319 |
| pS2 | NM_003225 | 320 |
| RPS6KB1 | NM_003161 | 321 |
| Src | NM_004383 | 322 |
| STK15 | NM_003600 | 323 |
| BIRC5 | NM_001168 | 324 |
| TFRC | NM_003234 | 325 |
| TGFB3 | NM_003239 | 326 |
| TK1 | NM_003258 | 327 |
| VDR | NM_000376 | 328 |
| VEGFC | NM_005429 | 329 |
| WISP1 | NM_003882 | 330 |
| XIAP | NM_001167 | 331 |
| YB-1 | NM_004559 | 332 |
| ITGA7 | NM_002206 | 333 |
| PDGFB | NM_002608 | 334 |
| Upa | NM_002658 | 335 |
| TBP | NM_003194 | 336 |
| PDGFRa | NM_006206 | 337 |
| Pin1 | NM_006221 | 338 |
| CYP | NM_006347 | 339 |
| RBP4 | NM_006744 | 340 |
| BRCA1 | NM_007295 | 341 |
| APC | NM_000038 | 342 |
| GUS | NM_000181 | 343 |
| CD18 | NM_000211 | 344 |
| PTEN | NM_000314 | 345 |
| P53 | NM_000546 | 346 |
| ALDH1A3 | NM_000693 | 347 |
| GSTp | NM_000852 | 348 |
| TOP2B | NM_001068 | 349 |
| TS | NM_001071 | 350 |
| Bclx | NM_001191 | 351 |
| AREG | NM_001657 | 352 |
| TP | NM_001953 | 353 |
| EIF4E | NM_001968 | 354 |
| ErbB3 | NM_001982 | 355 |
| EREG | NM_001432 | 356 |
| GCLC | NM_001498 | 357 |
| CD9 | NM_001769 | 358 |
| HB-EGF | NM_001945 | 359 |
| IGFBP2 | NM_000597 | 360 |
| CTSL | NM_001912 | 361 |
| PREP | NM_002726 | 362 |
| CYP3A4 | NM_017460 | 363 |
| ILT-2 | NM_006669 | 364 |
| MCM3 | NM_002388 | 365 |
| KRT19 | NM_002276 | 366 |

TABLE 3-continued

| GENE | ACCESSION NO. | SEQ ID NO: |
|---|---|---|
| KRT18 | NM_000224 | 367 |
| TIMP2 | NM_003255 | 368 |
| BAD | NM_004322 | 369 |
| CYP2C8 | NM_030878 | 370 |
| DCR3 | NM_016434 | 371 |
| PLAUR | NM_002659 | 372 |
| PI3KC2A | NM_002645 | 373 |
| FGF2 | NM_002006 | 374 |
| HLA-G | NM_002127 | 375 |
| AIB1 | NM_006534 | 376 |

TABLE 3-continued

| GENE | ACCESSION NO. | SEQ ID NO: |
|---|---|---|
| MCP1 | NM_002982 | 377 |
| Contig46653 | Contig46653 | 378 |
| RhoC | NM_005167 | 379 |
| DR5 | NM_003842 | 380 |
| RAD51C | NM_058216 | 381 |
| BIN1 | NM_004305 | 382 |
| VDR | NM_000376 | 383 |
| TERC | U86046 | 384 |

What is claimed is:

1. A method for predicting the likelihood of long-term survival without recurrence of breast cancer comprising:

assaying a level of a RNA transcript of BIRC5 in a tissue sample obtained from a primary ductal or lobular breast tumor of a human patient;

normalizing said level against a level of at least one reference RNA transcript in said tissue sample to provide a normalized BIRC5 RNA level; and predicting the likelihood of long-term survival of said patient without recurrence of breast cancer by comparing said normalized BIRC5 RNA level to BIRC5 expression data obtained from reference breast cancer samples, wherein an increased normalized BIRC5 RNA level is negatively correlated with an increased likelihood of long-term survival without breast cancer recurrence in said patient.

2. The method of claim 1, further comprising
assaying a level of a RNA transcript of one or more genes selected from the group consisting of: STK15, Bcl2, Ki-67, GSTM1, PR, ESR1, CCNB1, and BAG1, in said tissue sample;
normalizing the level of the RNA transcript of the one or more genes against a level of at least one reference RNA transcript in said tissue sample to provide a normalized level of said one or more genes; and
comparing said normalized RNA level of said one or more genes to gene expression data from said one or more genes obtained from reference breast cancer samples,
wherein increased normalized RNA level of one or more of STK15, Ki-67, and CCNB1, negatively correlates with an increased likelihood of long-term survival without breast cancer recurrence, and increased normalized RNA level of one or more of Bcl2, GSTM1, PR, ESR1 and BAG1 positively correlates with an increased likelihood of long-term survival without breast cancer recurrence.

3. The method of claim 1, wherein the breast tumor is an invasive breast tumor, and said method further comprises assaying a level of a RNA transcript of one or more genes selected from the group consisting of: FOXM1, PRAME, Bcl2, STK15, CEGP1, Ki-67, GSTM1, PR, BBC3, NME1, GATA3, TFRC, YB-1, DPYD, CA9, Contig51037, and RPS6K1 and in said tissue sample.

4. The method of claim 1, wherein said breast tumor is an estrogen receptor (ER) positive breast tumor.

5. The method of claim 4, further comprising assaying a level of a RNA transcript of one or more genes selected from the group consisting of: PRAME, Bcl2, FOXM1, DIABLO, EPHX1, HIF1A, VEGFC, Ki-67, IGF1R, VDR, NME1, GSTM3, Contig51037, CDC25B, CTSB, p27, CDH1, and IGFBP3 in said tissue sample.

6. The method of claim 2, wherein levels of 2 or more RNA transcripts of said genes are assayed.

7. The method of claim 1, wherein said tissue sample is a fixed, wax-embedded breast cancer tissue specimen of said patient.

8. The method of claim 1, wherein said tissue sample is from a fine needle biopsy.

9. The method of claim 1, further comprising creating a report based upon the normalized BIRC5 RNA level.

10. The method of claim 9, wherein said report includes a prediction of the likelihood of long term survival of said patient without the recurrence of breast cancer.

11. The method of claim 10, wherein said report comprises information concerning a recommendation for a treatment modality of said patient.

12. The method of claim 1, wherein said BIRC5 expression data is produced using a multivariate analysis using the Cox Proportional Hazards model.

13. The method of claim 1, wherein said assaying is done using RNA obtained from a formalin-fixed paraffin-embedded tissue sample.

14. The method of claim 1, wherein said assaying is done by reverse transcriptase polymerase chain reaction (RT-PCR).

15. The method of claim 1, wherein said assaying is done after a primary ductal carcinoma has been surgically removed from a breast of said patient.

16. The method of claim 15, wherein said primary ductal carcinoma is an invasive ductal carcinoma.

17. The method of claim 1, wherein said assaying is done after a primary lobular carcinoma has been surgically removed from a breast of said patient.

18. The method of claim 17, wherein said primary lobular carcinoma is an invasive lobular carcinoma.

19. The method of claim 1, wherein said comparing is done by calculating a quantitative score indicating the likelihood of long-term survival without the recurrence of breast cancer of the human patient, wherein said quantitative score is calculated using said normalized BIRC5 RNA level of the human patient and the positive correlation between increased normalized BIRC5 RNA level and an increased likelihood of long-term survival without recurrence of breast cancer.

* * * * *

UNITED STATES PATENT AND TRADEMARK OFFICE
CERTIFICATE OF CORRECTION

| | | |
|---|---|---|
| PATENT NO. | : 7,838,224 B2 | Page 1 of 1 |
| APPLICATION NO. | : 11/450962 | |
| DATED | : November 23, 2010 | |
| INVENTOR(S) | : Baker et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 71 days.

Signed and Sealed this
Tenth Day of May, 2011

David J. Kappos
*Director of the United States Patent and Trademark Office*